US012590099B2

(12) United States Patent
Yu et al.

(10) Patent No.: US 12,590,099 B2
(45) Date of Patent: Mar. 31, 2026

(54) INHIBITORS OF HISTONE DEACETYLASE USEFUL FOR THE TREATMENT OR PREVENTION OF HIV INFECTION

(71) Applicant: Merck Sharp & Dohme LLC, Rahway, NJ (US)

(72) Inventors: Wensheng Yu, Edison, NJ (US); Joseph Kozlowski, Princeton, NJ (US); Dane James Clausen, Rahway, NJ (US); Jian Liu, Edison, NJ (US); Younong Yu, East Brunswick, NJ (US); Ming Wang, Belle Mead, NJ (US); Bing Li, Towaco, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 1008 days.

(21) Appl. No.: 17/288,626

(22) PCT Filed: Nov. 4, 2019

(86) PCT No.: PCT/US2019/059582
§ 371 (c)(1),
(2) Date: Apr. 26, 2021

(87) PCT Pub. No.: WO2020/096916
PCT Pub. Date: May 14, 2020

(65) Prior Publication Data

US 2021/0403479 A1 Dec. 30, 2021

Related U.S. Application Data

(60) Provisional application No. 62/757,422, filed on Nov. 8, 2018.

(51) Int. Cl.

| | |
|---|---|
| ***C07D 487/10*** | (2006.01) |
| ***A61K 45/06*** | (2006.01) |
| ***C07D 401/12*** | (2006.01) |
| ***C07D 401/14*** | (2006.01) |
| ***C07D 403/12*** | (2006.01) |
| ***C07D 405/14*** | (2006.01) |
| ***C07D 413/14*** | (2006.01) |
| ***C07D 417/14*** | (2006.01) |
| ***C07D 471/04*** | (2006.01) |
| ***C07D 498/10*** | (2006.01) |

(52) U.S. Cl.
CPC ............ *C07D 487/10* (2013.01); *A61K 45/06* (2013.01); *C07D 401/12* (2013.01); *C07D 401/14* (2013.01); *C07D 403/12* (2013.01); *C07D 405/14* (2013.01); *C07D 413/14* (2013.01); *C07D 417/14* (2013.01); *C07D 471/04* (2013.01); *C07D 498/10* (2013.01)

(58) Field of Classification Search
CPC .. C07D 487/10; C07D 401/12; C07D 401/14; C07D 403/12; C07D 405/14; C07D 413/14; C07D 417/14; C07D 471/04; C07D 498/10; A61K 45/06
See application file for complete search history.

(56) References Cited

U.S. PATENT DOCUMENTS

| | | | |
|---|---|---|---|
| 7,863,294 B2 | 1/2011 | Attenni et al. | |
| 8,026,265 B2 | 9/2011 | Jones et al. | |
| 8,686,020 B2 | 4/2014 | Hamblett et al. | |
| 9,371,295 B2 * | 6/2016 | Altamura ............. | A61K 31/454 |
| 2008/0221157 A1 | 9/2008 | Chakravarty et al. | |
| 2014/0128391 A1 | 5/2014 | Van Duzer et al. | |
| 2017/0042898 A1 | 2/2017 | Berenson et al. | |
| 2018/0194769 A1 | 7/2018 | Jefson et al. | |

FOREIGN PATENT DOCUMENTS

| | | |
|---|---|---|
| WO | 2009042646 A1 | 4/2009 |
| WO | 2016126725 A1 | 8/2016 |
| WO | 2020028150 A1 | 2/2020 |
| WO | 2020150091 A1 | 7/2020 |
| WO | 2020190827 A1 | 9/2020 |

OTHER PUBLICATIONS

Ngayo MO, Okalebo FA, Bulimo WD, Mwachari C, Guantai AN, et al. (2016) Impact of First Line Antiretroviral Therapy on Clinical Outcomes Among HIV-1 Infected Adults Attending One of the Largest HIV Care and Treatment Program in Nairobi Kenya. J AIDS Clin Res 7: 615. (Year: 2016).*

Shirakawa K, Chavez L, Hakre S, Calvanese V, Verdin E. Reactivation of latent HIV by histone deacetylase inhibitors. Trends Microbiol. Jun. 2013;21(6):277-85. (Year: 2013).*

Gao, X., Liu, D., Song, Z., & Dai, K. (2017c). Isosteric design of friction-reduction and anti-wear lubricant additives with less sulfur content. Friction, 6(2), 164-182. (Year: 2017).*

Agrawal, N., & Mishra, P. (2018). The synthetic and therapeutic expedition of isoxazole and its analogs. Medicinal Chemistry Research, 27(5), 1309-1344. (Year: 2018).*

(Continued)

*Primary Examiner* — James H Alstrum-Acevedo
*Assistant Examiner* — Pierre Paul Eleniste
(74) *Attorney, Agent, or Firm* — Eric Greenwald; John C. Todaro

(57) ABSTRACT

The present invention relates to Compounds of Formula I: and pharmaceutically acceptable salts or prodrug thereof, wherein $R^1$, $R^2$, $R^3$, $R^4$ and A are as defined herein. The present invention also relates to compositions comprising at least one compound of Formula I, and methods of using the compounds of Formula I for treating or preventing HIV infection in a subject.

I

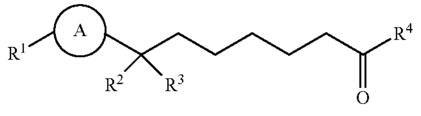

4 Claims, No Drawings

(56) References Cited

OTHER PUBLICATIONS

Wermuth et al., Comprehensive Medicinal Chemistry II, vol. 2, p. 649-711, Available online Apr. 2, 2007. (Year: 2007).*

Attenni, Barbara et al., Histone deacetylase inhibitors with a primary amide zinc binding group display antitumor activity in xenograft model, Bioorganic & Medicinal Chemistry Letters, 2009, 3081-3084, 19.

Jones, Philip et al., A Novel Series of Potent and Selective Ketone Histone Deacetylase Inhibitors with Antitumor Activity in Vivo, J. Med. Chem., 2008, 2350-2353, 51(8).

Kinzel, Olaf et al., Discovery of a Potent Class I Selective Ketone Histone Deacetylase Inhibitor with Antitumor Activity in Vivo and Optimized Pharmacokinetic Properties, J. Med. Chem., 2009, 3453-3456, 52.

Moradei, Oscar et al., Histone Deacetylase Inhibitors in Cancer Therapy: New Compounds and Clinical Update of Benzamide-Type Agents, Current Topics in Medicinal Chemistry, 2008, 841-858, 8.

Pescatore, Giovanna et al., Optimization of a series of potent and selective ketone histone deacetylase inhibitors, Bioorganic & Medicinal Chemistry Letters, 2008, 5528-5532, 18.

* cited by examiner

INHIBITORS OF HISTONE DEACETYLASE USEFUL FOR THE TREATMENT OR PREVENTION OF HIV INFECTION

CROSS REFERENCE TO RELATED APPLICATIONS

This application is a U.S. National Phase application under 35 U.S.C. § 371 of PCT Application No. PCT/US2019/059582 filed Nov. 4, 2019, which claims priority to U.S. Ser. No. 62/757,422 filed Nov. 8, 2018.

FIELD OF THE INVENTION

The present invention relates to inhibitors of histone deacetylase, compositions comprising at least one inhibitor of histone deacetylase, and methods of using the inhibitors of histone deacetylase for treating or preventing HIV infection in a subject.

BACKGROUND OF THE INVENTION

DNA in the nucleus of the cell exists as a hierarchy of compacted chromatin structures. The basic repeating unit in chromatin is the nucleosome, which consists of a histone octamer of proteins in the nucleus of the cell around which DNA is wrapped twice. The orderly packaging of DNA in the nucleus plays an important role in the functional aspects of gene regulation. Covalent modifications of the histones have a key role in altering chromatin higher order structure and function, and ultimately, gene expression. The covalent modification of histones, such as acetylation, occurs by enzymatically mediated process.

Regulation of gene expression through the inhibition of the nuclear enzyme histone deacetylase (HDAC) is one of the several possible regulatory mechanisms whereby chromatin actively can be affected. The dynamic homeostasis of the nuclear acetylation of histone can be regulated by the opposing activity of the enzymes histone acetyl transferase (HAT) and histone deacetylase (HDAC). Transcriptionally silent chromatin can be characterized by nucleosomes with low levels of acetylated histones. Acetylation reduces the positive charge of histones, thereby expanding the structure of the nucleosome and facilitating the interaction of transcription factors with the DNA. Removal of the acetyl group restores the positive charge, condensing the structure of the nucleosome. While histone acetylation can activate DNA transcription, enhancing gene expression, histone deacetylase can reverse the process and can serve to repress gene expression. Inhibition of the histone deacetylase (HDAC inhibition) can also increase the activation of DNA transcription. See, for example, Grunstein, Nature, 389, 349-352 (1997); Pazin et al., Cell 89, 325-328 (1997); Wade et al., Trends Biochem Sci. 22, 128-132 (1997); and Wolffe, Science 272, 371-372 (1996).

With the introduction of combination antiretroviral therapy (ART), HIV became a controllable chronic disease. The combination of ART (cART) targets specific stages of the viral life cycle, and is effective at combatting active viral load down to undetectable levels. However, HIV persists within the body of infected individuals undergoing therapy, and cessation of ART leads to a viral rebound within 3-4 weeks. The HIV can persist in resting memory and naïve CD4+ T cells and other long-lived cells, such as infected astrocytes and cells of macrophage lineage. HIV can persist in these resting cells by establishing a latent or "silent" infection. In these cells, virus is integrated into the host genome, but viral production does not occur as a result of inhibition of both viral transcriptions from proteins. However, these latently infected cells still do contain replication competent virus, and once cART is stopped, rebound in plasma HIV RNA is observed in nearly all patients.

One approach currently being explored to eliminate latently infected CD4+ T cells is to activate viral production from these cells in the presence of cART, when the production of the virus should kill the infected cells. Histone deacetylase inhibitors have shown promise in vitro in activating virus production from latent infected cells, and therefore this class of drugs is being studied as part of a strategy aimed at a cure of HIV.

Eleven members of the HDAC family has been identified in humans, which share a conserved catalytic domain and are grouped into two classes: class I (1,2,3,8), homologous to yeast Rpd3; and class IIa (4,5,7,9) and IIb (6, 10), homologous to yeast Hdal. HDAC 11 shares homology with both classes, but is at the same time distinct from all the other ten subtypes. The first generation of HDAC inhibitors (HDACi) are promising therapeutic agents against cancer and other diseases, and showed in vitro activation of virus production from latent infected cells. However, due to their poor selectivity, those that entered clinical trials, all show similar adverse effects. The poorly selective HDACi's are not suitable for healthy HIV patents on cART, thus the interest is high for the discovery and development of novel and subtype selective HDAC inhibitors.

SUMMARY OF THE INVENTION

In one aspect, the present invention provides Compounds of Formula I:

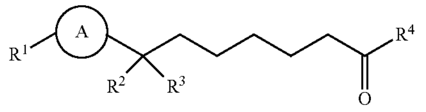

wherein 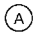 is a five-membered heteroaryl ring which is optionally substituted with halo, cyano, $R^5$, $R^6$, $(C{=}O)N(R^5)_2$, $NR^5(C{=}O)N(R^5)_2$, $(C{=}O)R^6$ or $(C_{1-3}$ alkyl$)O(C{=}O)R^5$;

$R^1$ is phenyl, bicyclic aryl, tricyclic aryl or heteroaryl, which may be monocyclic, bicyclic or tricyclic, wherein said phenyl and heteroaryl groups are optionally substituted with one to four groups independently selected from the group consisting of halo, oxo, cyano, $C_{2-3}$ alkenyl, $R^5$, $R^6$, $OR^5$, $N(R^5)_2$, $(C{=}O)NHR^6$, $NR^5(C{=}O)N(R^5)_2$, $NR^5(C{=}NR^5)N(R^5)_2$, $SO_2R^5$, $SO_2N(R^5)_2$, $NR^5SO_2R^5$, and $NR^5SO_2N(R^5)_2$;

$R^2$ is selected from the group consisting of hydrogen, $N(R^5)_2$, $NR^5(C{=}O)R^5$, $NR^5(C{=}O)N(R^5)_2$, $NR^5(C{=}NR^5)N(R^5)_2$, $NR^5(C{=}O)R^6$, $NR^5(C_{1-3}alkyl)R^6$ and $NR^5(C{=}O)(C_{1-3}alkyl)R^6$; $R^3$ is selected from hydrogen, $C_{1-6}$ alkyl or $CH_2OR^5$;

$R^4$ is $C_{1-6}$ alkyl, or $C_{3-6}$ cycloalkyl, which is optionally substituted with one to three substituents independently selected from the group consisting of halo and hydroxyl, or $C_{3-6}$ cycloalkyl; each $R^5$ is independently hydrogen, cyano, or $C_{1-6}$ alkyl, which is optionally substituted with $NH_2$, $N(CH_3)_2$, $NH(CH_3)_2$, $N(CH_2CH_3)_2$, or one to three halo;

$R^6$ is (a) heterocyclyl, which may be monocyclic, bicyclic or tricyclic, (b) $C_{3-6}$ cycloalkyl, (c) phenyl, or (d) heteroaryl, which may be monocyclic, bicyclic or tricyclic, wherein said heterocyclyl, cycloalkyl, phenyl and heteroaryl groups are optionally substituted with one to four groups independently selected from the group consisting of halo, cyano, oxo, $R^5$, $OR^5$, $(C{=}O)R^5$, $(C{=}O)OR^5$, $N(R^5)_2$, $(C{=}O)N(R^5)_2$, $NR^5(C{=}O)R^5$, $NR^5(C{=}O)N(R^5)_2$, $NR^5(C{=}NR^5)N(R^5)_2$, $SO_2R^5$; $SO_2N(R^5)_2$, $NR^5SO_2R^5$, $NR^5SO_2N(R^5)_2$, $C_{2-3}$ alkenyl, benzyl, benzyl-$OR^5$, $CH_2(C_{3-6}$ cycloalkyl), $CH_2$(heteroaryl), heteroaryl, heterocyclyl and $C_{3-6}$ cycloalkyl.

The Compounds of Formula I and pharmaceutically acceptable salts or prodrugs thereof may be useful, for example, for activating HIV latency for potential complete cure of HIV infection alone or in combination with cART and/or other HIV treatments.

Accordingly, the present invention provides methods for treating or preventing HIV infection in a subject, comprising administering to the subject an effective amount of at least one compound of Formula I.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes to inhibitors of histone deacetylase, compositions comprising at least one inhibitor of histone deacetylase, and methods of using the inhibitors of histone deacetylase for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Tricyclic Heterocycle Compound and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The terms "treating" or "treatment" as used herein with respect to an HIV viral infection or AIDS, includes inhibiting the severity of HIV infection or AIDS, i.e., arresting or reducing the development of the HIV infection or AIDS or its clinical symptoms; or relieving the HIV infection or AIDS, i.e., causing regression of the severity of HIV infection or AIDS or its clinical symptoms.

The terms "preventing," or "prophylaxis," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "alkenyl, as used herein, refers to an aliphatic hydrocarbon group having at least one carbon to carbon double bond. An alkenyl group may be straight or branched and contain from about 2 to about 10 carbon atoms. In one embodiment, an alkenyl group contains from about 2 to about 6 carbon atoms. In different embodiments, an alkenyl group contains from 2 to 3 carbon atoms ($C_{2-3}$ alkyl). Non-limiting examples of alkenyl groups include ethenyl, propenyl, butenyl, pentenyl and hexenyl. In one embodiment, an alkenyl group is linear. In another embodiment, an alkenyl group is branched. Unless otherwise indicated, an alkenyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include $—CH_2F$, $—CHF_2$, $—CF_3$, $—CH_2Cl$ and $—CCl_3$. The term "$C_1$-$C_6$ haloalkyl" refers to a haloalkyl group having from 1 to 6 carbon atoms.

The term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on. Bicyclic cycloalkyl ring systems include fused ring systems, where two rings share two atoms, and spiro ring systems, where two rings share one atom.

The term "aryl", as used herein, represents a stable bicyclic or tricyclic ring system of up to 10 atoms in each ring, wherein at least one ring is aromatic, and all of the ring atoms are carbon. Bicyclic and tricyclic ring systems include fused ring systems, where two rings share two atoms, and spiro ring systems, where two rings share one atom.

The term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrazolopyrimidinyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, dihydrobenzodioxinyl, dihydropyrazoloxazinyl, dihydropyrazolyothiazinedioxidyl, methylenedioxybenzene, benzothiazolyl, benzothienyl, quinolinyl, isoquinolinyl, oxazolyl, tetra-hydroquinoline and 3-oxo-3, 4dihydro-2N-benzo[b][1,4]thiazine. If the heteroaryl contains nitrogen atoms, it is understood that the corresponding N-oxides thereof are also encompassed by this definition.

The term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: azaspirononanyl, azaspirooctanyl, azetidinyl, dioxanyl, oxadiazaspirodecenyl, oxaspirooctanyl, oxazolidinonyl, piperazinyl, piperidinyl, pyrrolidinyl, morpholinyl, thiomorpholinyl, tetrahydrofuranyl, tetrahydropyranyl, dihydropiperidinyl, tetrahydrothiophenyl and the like. If the heterocycle contains a nitrogen, it is understood that the corresponding N-oxides thereof are also encompassed by this definition.

"Celite®" (Fluka) diatomite is diatomaceous earth, and can be referred to as "celite".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $R^4$) occurs more than one time in any constituent or in Formula I, its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a compound of Formula I or a pharmaceutically acceptable salt of the compound. The transformation may occur by various mechanisms (e.g., by metabolic or chemical processes), such as, for example, through hydrolysis in blood. For example, if a compound of Formula I or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula I contains an alcohol functional group, a prodrug can be formed by the replacement of one or more of the hydrogen atoms of the alcohol groups with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1$-

$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a compound of Formula I incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$) alkyl, ($C_3$-$C_7$) cycloalkyl, benzyl, a natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$) alkyl; carboxy ($C_1$-$C_6$)alkyl; amino($C_1$-$C_4$)alkyl or mono-N- or di-N,N—($C_1$-$C_6$)alkylaminoalkyl; —C($Y^4$)$Y^5$ wherein $Y^4$ is H or methyl and $Y^5$ is mono-N- or di-N,N—($C_1$-$C_6$) alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.,* 93(3, 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.,* 5(1), article 12 (2004); and A. L. Bingham et al, *Chem. Commun.,* 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The compound of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), *Academic Press*, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Also, some of the compound of Formula I may be atropisomers (e.g., substituted biaryls) and are considered as part of this invention. Enantiomers can also be directly separated using chiral chromatographic techniques.

It is also possible that the compound of Formula I may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound of Formula I incorporates a double bond or a fused ring, both the cis- and trans-forms, as well as mixtures, are embraced within the scope of the invention.

When a substituent on a chiral carbon atom is depicted without specific stereochemistry (by using a straight line bond to a chiral center), it is to be understood that both the alpha and beta configurations of said substituent group are to be considered part of the present invention. For example, the compound of the present invention, which is drawn as follows:

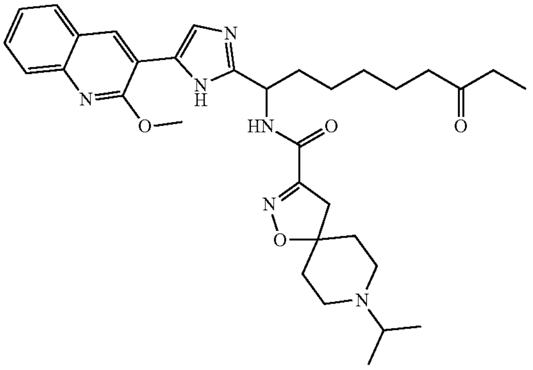

, is understood to encompass both stereoisomers at the indicated chiral center, the structures of which are as follows:

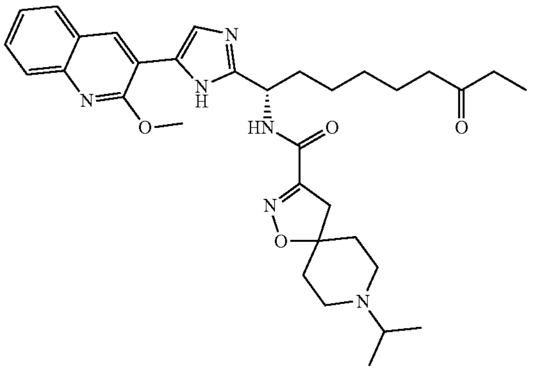

and

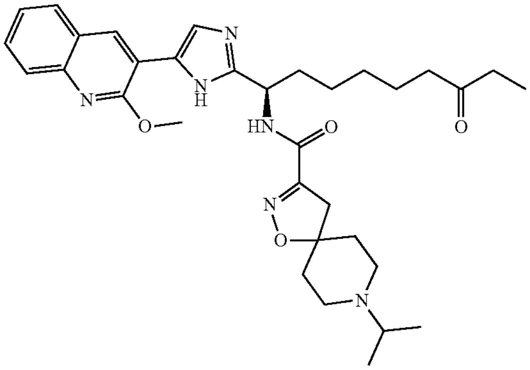

.

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula I can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula I has one or more of its hydrogen atoms replaced with deuterium.

The compounds of Formula I may be useful in human and veterinary medicine for treating or preventing HIV infection in a subject. In one embodiment, the compounds of Formula I can be inhibitors of HIV viral replication. In a specific embodiment, the compound of Formula I are inhibitors of HIV-1. Accordingly, the compounds of Formula I may be useful for treating HIV infections and AIDS. In accordance with the invention, the compounds of Formula I can be administered to a subject in need of treatment or prevention of HIV infection.

Accordingly, in one embodiment, the invention provides methods for treating HIV infection in a subject comprising administering to the subject an effective amount of at least one compound of Formula I or a pharmaceutically acceptable salt thereof. In a specific embodiment, the present invention provides methods for treating AIDS in a subject comprising administering to the subject an effective amount of at least one compound of Formula I or a pharmaceutically acceptable salt thereof.

The Compounds of Formula I

The present invention provides Compounds of Formula I:

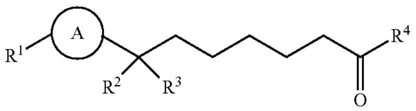

wherein Ⓐ is a five-membered heteroaryl ring which is optionally substituted with halo, cyano, $R^5$, $R^6$, (C═O)$N(R^5)_2$, $NR^5$(C═O)$N(R^5)_2$, (C═O)$R^6$ or ($C_{1-3}$ alkyl)O(C═O)$R^5$;

$R^1$ is phenyl, bicyclic aryl, tricyclic aryl or heteroaryl, which may be monocyclic, bicyclic or tricyclic, wherein said phenyl and heteroaryl groups are optionally substituted with one to four groups independently selected from the group consisting of halo, oxo, cyano, $C_{2-3}$ alkenyl, $R^5$, $R^6$, $OR^5$, $N(R^5)_2$, (C═O)$NHR^6$, $NR^5$(C═O)$N(R^5)_2$, $NR^5$(C═$NR^5$)$N(R^5)_2$, $SO_2R^5$, $SO_2N(R^5)_2$, $NR^5SO_2R^5$, and $NR^5SO_2N(R^5)_2$;

$R^2$ is selected from the group consisting of hydrogen, $N(R^5)_2$, $NR^5$(C═O)$R^5$, $NR^5$(C═O)$N(R^5)_2$, $NR^5$(C═$NR^5$)$N(R^5)_2$, $NR^5$(C═O)$R^6$, $NR^5$($C_{1-3}$alkyl)$R^6$ and $NR^5$(C═O)($C_{1-3}$alkyl)$R^6$;

$R^3$ is selected from hydrogen, $C_{1-6}$ alkyl or $CH_2OR^5$;

$R^4$ is $C_{1-6}$ alkyl, or $C_{3-6}$ cycloalkyl, which is optionally substituted with one to three substituents independently selected from the group consisting of halo and hydroxyl, or $C_{3-6}$ cycloalkyl;

each $R^5$ is independently hydrogen, cyano, or $C_{1-6}$ alkyl, which is optionally substituted with $NH_2$, $N(CH_3)_2$, $NH(CH_3)_2$, $N(CH_2CH_3)_2$, or one to three halo;

$R^6$ is (a) heterocyclyl, which may be monocyclic, bicyclic or tricyclic, (b) $C_{3-6}$ cycloalkyl, (c) phenyl, or (d) heteroaryl, which may be monocyclic, bicyclic or tricyclic, wherein said heterocyclyl, cycloalkyl, phenyl and heteroaryl groups are optionally substituted with one to four groups independently selected from the group consisting of halo, cyano, oxo, $R^5$, $OR^5$, (C═O)$R^5$, (C═O)$OR^5$, $N(R^5)_2$, (C═O)$N(R^5)_2$, $NR^5$(C═O)$R^5$, $NR^5$(C═O)$N(R^5)_2$, $NR^5$(C═$NR^5$)$N(R^5)_2$, $SO_2R^5$; $SO_2N(R^5)_2$, $NR^5SO_2R^5$, $NR^5SO_2N(R^5)_2$, $C_{2-3}$ alkenyl, benzyl, benzyl-$OR^5$, $CH_2$($C_{3-6}$ cycloalkyl), $CH_2$(heteroaryl), heteroaryl, heterocyclyl and $C_{3-6}$ cycloalkyl; or a pharmaceutically acceptable salt thereof.

In an embodiment of the invention, Ⓐ is selected from imidazolyl, oxazolyl, oxadiazolyl or triazolyl, wherein said groups are optionally substituted with halo, cyano or $C_{1-3}$ alkyl. In a class of the embodiment, Ⓐ is selected from imidazolyl. In another embodiment of the invention, Ⓐ is oxazolyl. In another class of the embodiment, Ⓐ is oxadiazolyl. In another class of the embodiment, Ⓐ is triazolyl.

In an embodiment of the invention, $R^1$ is azaindazolyl, benzoxazolyl, benzothiazolyl, carbazolyl, chromenyl, cinnolinyl, dihydroisoquinolinyl, imidazolyl, imidazopyridinyl, indazolyl, isoquinolinyl, naphthalenyl, naphthyridinyl, phenyl, pyridinyl, pyrimidinyl, quinolinyl, quinoxalinyl, or tetrahydroepaminonaphthalenyl, tetrahydromethanonaphthalenyl, wherein said groups are optionally substituted with one to three groups optionally selected from the group consisting of halo, oxo, cyano, $C_{2-3}$ alkenyl, $R^5$, $R^6$, $OR^5$, $N(R^5)_2$, (C═O)$NHR^6$ and $SO_2R^5$.

In an embodiment of the invention, $R^2$ is NH(C═O)$R^6$ or NH(C═O)($C_{1-3}$alkyl)$R^6$, and $R^6$ is selected from the group consisting of azaspirobicyclooctanecyclopropanyl, azetidinyl, azaspirohepatnyl, azaspirohexanyl, azaspirononanyl, azaspirooctanyl, diazaspirooctanyl, dihydropyrroloindolyl, dihydroethanoquinolinyl, isoxazolyl, oxadiazaspirodecenyl, oxaspirooctanyl, quinuclidine, spirooctanyl, spirocyclohexanefuropyridinyl, tetrahydrocyclopentaindolyl, tetrahydropyranyl and thiazolyl, wherein said groups are optionally substituted with one or two groups independently selected from the group consisting of halo, oxo, $R^5$, $OR^5$, (C═O)$N(R^5)_2$, $C_{2-3}$ alkenyl, benzyl, benzyl-$OR^5$, $CH_2$($C_{3-6}$ cycloalkyl), $CH_2$(heteroaryl), heteroaryl and $C_{3-6}$ cycloalkyl.

In an embodiment of the invention, $R^3$ is hydrogen.

In an embodiment of the invention, $R^4$ is ethyl.

In another embodiment, the Compounds of Formula I are in substantially purified form.

It is to be understood that any of the aforementioned embodiments may be combined with one or more separate embodiments.

Other embodiments of the present invention include the following:

(a) A pharmaceutical composition comprising an effective amount of a Compound of Formula I, and a pharmaceutically acceptable carrier.

(b) The pharmaceutical composition of (a), further comprising a second therapeutic agent selected from the group consisting of HIV antiviral agents, immunomodulators, anti-infective agents, vaccines, and antibodies.

(c) The pharmaceutical composition of (b), wherein the HIV antiviral agent is an antiviral selected from the group consisting of HIV protease inhibitors, HIV integrase inhibitors and HIV NNRTI inhibitors.

(d) A pharmaceutical combination that is (i) a Compound of Formula I and (ii) a second therapeutic agent selected from the group consisting of HIV antiviral agents, immunomodulators, and anti-infective agents, vaccines, and antibodies; wherein the Compound of Formula I and the second therapeutic agent are each employed in an amount that renders the combination effective for inhibiting HIV replication, or for treating HIV infection and/or reducing the likelihood or severity of symptoms of HIV infection, and eradicates HIV infection.

(e) The combination of (d), wherein the HIV antiviral agent is an antiviral selected from the group consisting of HIV protease inhibitors, HIV integrase inhibitors and HIV NNRTI inhibitors.

(f) A method of inhibiting HIV replication in a subject in need thereof which comprises administering to the subject an effective amount of a Compound of Formula I.

(g) A method of treating HIV infection and/or reducing the likelihood or severity of symptoms of HIV infection in a subject in need thereof which comprises administering to the subject an effective amount of a Compound of Formula I.

(h) The method of (g), wherein the Compound of Formula I is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors and HIV NNRTI inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

Additional embodiments of the present invention include the following:

(l) A pharmaceutical composition comprising an effective amount of a pharmaceutically acceptable salt of a Compound of Formula I, and a pharmaceutically acceptable carrier.

(m) The pharmaceutical composition of (l), further comprising a second therapeutic agent selected from the group consisting of HIV antiviral agents, immunomodulators, anti-infective agents, vaccines and antibodies.

(n) The pharmaceutical composition of (m), wherein the HIV antiviral agent is an antiviral selected from the group consisting of HIV protease inhibitors and HIV NNRTI inhibitors.

(o) A pharmaceutical combination that is (i) a pharmaceutically acceptable salt of a Compound of Formula I and (ii) a second therapeutic agent selected from the group consisting of HIV antiviral agents, immunomodulators, and anti-infective agents; wherein the pharmaceutically acceptable salt of the Compound of Formula I and the second therapeutic agent are each employed in an amount that renders the combination effective for inhibiting HIV replication, or for treating HIV infection and/or reducing the likelihood or severity of symptoms of HIV infection.

(p) The combination of (o), wherein the HIV antiviral agent is an antiviral selected from the group consisting of HIV protease inhibitors and HIV NNRTI inhibitors.

(q) A method of inhibiting HIV replication in a subject in need thereof which comprises administering to the subject an effective amount of a pharmaceutically acceptable salt of a Compound of Formula I.

(r) A method of treating HIV infection and/or reducing the likelihood or severity of symptoms of HIV infection in a subject in need thereof which comprises administering to the subject an effective amount of a pharmaceutically acceptable salt of a Compound of Formula I.

(s) The method of (r), wherein the pharmaceutically acceptable salt of the Compound of Formula I is administered in combination with an effective amount of at least one second therapeutic agent selected from the group consisting of HIV antiviral agents, immunomodulators, and anti-infective agents.

(t) The method of (s), wherein the HIV antiviral agent is an antiviral selected from the group consisting of HIV protease inhibitors and HIV NS5B polymerase inhibitors.

(u) A method of inhibiting HIV replication in a subject in need thereof which comprises administering to the subject the pharmaceutical composition of (l), (m) or (n) or the combination of (o) or (p).

(v) A method of treating HIV infection and/or reducing the likelihood or severity of symptoms of HIV infection in a subject in need thereof which comprises administering to the subject the pharmaceutical composition of (l), (m) or (n) or the combination of (o) or (p).

Further embodiments of the present invention include the following:

(w) A pharmaceutical composition comprising an effective amount of a Compound of Formula I or a pharmaceutically acceptable salt thereof, and a pharmaceutically acceptable carrier.

(x) The pharmaceutical composition of (w), further comprising a second therapeutic agent selected from the group consisting of HIV antiviral agents, immunomodulators, and anti-infective agents.

(y) The pharmaceutical composition of (x), wherein the HIV antiviral agent is an antiviral selected from the group consisting of HIV protease inhibitors and HIV NNRTI inhibitors.

(z) A pharmaceutical combination that is (i) a Compound of Formula I and (ii) or a pharmaceutically acceptable salt thereof, a second therapeutic agent selected from the group consisting of HIV antiviral agents, immunomodulators, and anti-infective agents; wherein the Compound of Formula I and the second therapeutic agent are each employed in an amount that renders the combination effective for inhibiting HIV replication, or for treating HIV infection and/or reducing the likelihood or severity of symptoms of HIV infection.

(aa) The combination of (z), wherein the HIV antiviral agent is an antiviral selected from the group consisting of HIV protease inhibitors and HIV NNRTI inhibitors.

(bb) A method of inhibiting HIV replication in a subject in need thereof which comprises administering to the subject an effective amount of a Compound of Formula I or a pharmaceutically acceptable salt thereof.

(cc) A method of treating HIV infection and/or reducing the likelihood or severity of symptoms of HIV infection in a subject in need thereof which comprises administering to the subject an effective amount of a Compound of Formula I or a pharmaceutically acceptable salt thereof.

(dd) The method of (cc), wherein the Compound of Formula I or pharmaceutically acceptable salt thereof, is administered in combination with an effective amount of at least one second therapeutic agent selected from the group consisting of HIV antiviral agents, immunomodulators, and anti-infective agents.

(ee) The method of (dd), wherein the HIV antiviral agent is an antiviral selected from the group consisting of HIV protease inhibitors and HIV NNRTI inhibitors.

(ff) A method of inhibiting HIV replication in a subject in need thereof which comprises administering to the subject the pharmaceutical composition of (w), (x) or (y) or the combination of (z) or (aa).

(gg) A method of treating HIV infection and/or reducing the likelihood or severity of symptoms of HIV infection in a subject in need thereof which comprises administering to the subject the pharmaceutical composition of (w), (x) or (y) or the combination of (z) or (aa).

The present invention also includes a compound of the present invention for use I in, (ii) as a medicament for, or (iii) in the preparation of a medicament for: (a) medicine; (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(gg) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (gg) above are understood to include all embodiments of the compounds, including such embodiments as result from combinations of embodiments.

Non-limiting examples of the Compounds of Formula I include compounds 1-196 as set forth in the Examples below, and pharmaceutically acceptable salts thereof.

Methods for Making the Compounds of Formula I

The Compounds of Formula I may be prepared from known or readily prepared starting materials, following methods known to one skilled in the art of organic synthesis. Methods useful for making the Compounds of Formula I are set forth in the Examples below and generalized in the Schemes below. Alternative synthetic pathways and analogous structures will be apparent to those skilled in the art of organic synthesis.

General List of Abbreviations

Abbreviations and acronyms employed herein include the following:

| | |
|---|---|
| Ac | Acetyl |
| Aq | Aqueous |
| ACN | Acetonitrile |
| AIBN | Azobisisobutyronitrile |
| AUC | Area under the curve |
| BAST | Bis(2-methoxyethyl)aminosulfur trifluoride |
| BOC | tert-butyloxycarbonyl |
| BPD | 3-(1,3-Benzodioxol-5-yl)-4-phenyl-2,5-furandione |
| Brettphos | 2-(Dicyclohexylphosphino)3,6-dimethoxy-2',4',6'-triisopropyl-1,1'-biphenyl |
| Bu | Butyl |
| Burgess reagent | Methyl N-(triethylammoniosulfonyl)carbamate |
| Bz | Benzoyl |
| CDI | Carbonyldiimidazole |
| DBDMH | 1,3-Dibromo-5,5-dimethylhydantoin |
| DBU | 2,3,4,6,7,8,9,10-Octahydropyrimidol[1,2-a]azepine |
| DCM | Dichloromethane |
| DCE | 1,2-Dichloroethane |
| DEAD | 1,2-Ethoxycarbonyl diazene solution |
| DHP | 3,4-dihydro-2H-pyran |
| DIBAL-H | Diisobutylaluminium hydride |
| DIEA, DIPEA or Hünig's base | N,N-diisopropylethylamine |
| DMA | N,N-Dimethylacetamide |
| DMAP | 4-dimethylaminopyridine |
| DME | Dimethyoxyethane |
| DMF | Dimethylformamide |
| DMP | Dess-Martin periodinane |
| Dppf | 1,1'-Bis(diphenylphosphino)ferrocene |
| DMSO | dimethyl sulfoxide |
| DTBPF | 1,1'-bis(di-tert-butylphosphino)ferrocene |
| EA | Ethyl Acetate |
| EDCI | N-ethyl-N'-(3-dimethylaminopropyl)carbodiimide hydrochloride |
| Et | Ethyl |
| EtOH | Ethanol |
| EtOAc | ethyl acetate |
| G | Grams |
| GI | Gastrointenstinal |
| H | Hour |

-continued

| | |
|---|---|
| HATU | 1-[Bis(dimethylamino)methylene]-1H-1,2,3-triazolo[4,5-b]pyridinium 3-oxide hexafluorophosphate |
| HCHO | Formaldehyde |
| HIV | human immunodeficiency virus |
| HOBT, HOBt | 1-Hydroxybenzotriazole hydrate |
| HPBCD | hydroxypropyl β-cyclodextrin |
| HPLC | high-performance liquid chromatography |
| mCPBA, CPBA | meta-Chloroperoxybenzoic |
| Hz | Hertz |
| IPA | Isopropanol |
| IV | Intravenous |
| iPr | Isopropyl |
| $Ir[dF(CF_3)ppy]_2(dtbpy)PF_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| L | Liter |
| LC | liquid chromatography |
| LC/MS | liquid chromatography mass spectrometry |
| LDA | Lithium diisopropylamide |
| LED | light-emitting diode |
| LiHMDS | lithium bis(trimethylsilyl)amide |
| Me | Methyl |
| MeOH | Methanol |
| Mg | Milligrams |
| MHz | Megahertz |
| Min | Minute |
| μL | Microliters |
| mL | Milliliters |
| Mmol | Millimoles |
| MOM-Cl | chloromethyl methyl ether |
| MPLC | medium pressure liquid chromatography |
| MS | mass spectrometry |
| NBS | N-Bromosuccinimide |
| NCS | N-Chlorosuccinimide |
| NHS | normal human serum |
| NIS | N-Iodosuccinimide |
| NMO | 4-methylmorpholine N-oxide |
| NMR | nuclear magnetic resonance spectroscopy |
| PBMC | peripheral blood mononuclear cell |
| $Pd_2(dba)_3$ | Tris(dibenzylideneacetone)dipalladium(0) |
| Ph | Phenyl |
| P.O. | Oral |
| PPTS | Pyridinium p-toluenesulfonate |
| PTSA | para-toluenesulfonic acid |
| Pr | Propyl |
| Rpm | revolutions per minute |
| RT or rt | room temperature (ambient, about 25° C.) |
| sat or sat'd | Saturated |
| SelectFluor | 1-Chloromethyl-4-fluoro-1,4-diazoniabicyclo[2.2.2]octane bis(tetrafluoroborate) |
| SEMCl | 2-Chloromethoxyethyl)trimethylsilane |
| SFC | supercritical fluid chromatography |
| T3P, $T_3P$ | 1-Propanephosphonic anhydride solution |
| TBAF | Tetra-n-butylammonium fluoride |
| TBDPSCl | tert-Butyldiphenylchlorosilane |
| TBSCl | tert-Butyldimethylsilyl chloride |
| tBu | tert-butyl |
| TCP | 2,3,5-Trichloro-6-hydroxypyridine |
| TEA | triethylamine ($Et_3N$) |
| TEMED | Tetramethylethylenediamine |
| TFA | trifluoroacetic acid |
| TFV | Tenofovir |
| TFV-MP | Tenofovir monophosphoate |
| TFV-DP | Tenofovir diphosphate |
| THF | Tetrahydrofuran |
| TMS | Tetramethylsilane |
| TosMIC | Toluenesulfonylmethyl isocyanide |
| TPAP | Tetrapropylammonium perruthenate |
| Ts | Tosyl |
| UPLC | ultrahigh pressure liquid chromatography |
| UV | Ultraviolet |
| UV/VIS | ultraviolet/visible |
| W | Watt |
| XPhos | 2-Dicyclohexylphosphino-2',4',6'-triisopropylbiphenyl |
| XPhos-Pd-G2 | Chloro(2-dicyclohexylphosphino-2',4',6'-triisopropyl-1,1'-biphenyl)[2-(2'-amino-1,1'-biphenyl)]palladium(II) |

General Procedures

Starting materials and intermediates are purchased or are made using known procedures, or as otherwise illustrated. The general route applied to the synthesis of compounds of Formula I is described in the Schemes that follows. In some cases the order of carrying out the reaction steps in the schemes may be varied to facilitate the reaction or to avoid unwanted reaction products.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC/MS).

Typically the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 μm or a Waters Acquity UPLC® BEH C18 1.0×50 mm, 1.7 μm. The flow rate was 1 mL/min, and the injection volume was 10 μL. UV detection was in the range 210-400 nm. The mobile phase consisted of solvent A (water plus 0.05% TFA) and solvent B (MeCN plus 0.05% TFA) with a gradient of 100% solvent A for 0.7 min changing to 100% solvent B over 3.75 min, maintained for 1.1 min, then reverting to 100% solvent A over 0.2 min. Alternatively, the column was commonly a Waters Acquity UPLC® BEH C18 1.0×50 mm, 1.7 μm. The flow rate was 0.3 mL/min, and the injection volume was 0.5 μL. UV detection was 215 or 254 nm. Either the mobile phase consisted of solvent A (water plus 0.05% TFA) and solvent B (MeCN plus 0.05% TFA) with a gradient of 90% solvent A changing to 99% solvent B over 1.6 min, maintained for 0.4 min, then reverting to 90% solvent A over 0.1 min or the mobile phase consisted of solvent A (water plus 0.05% TFA) and solvent B (MeCN plus 0.05% TFA) with a gradient of 97% solvent A changing to 4% then 50% solvent B over 0.5 min and 0.9 min, 50%-99% solvent B over 0.2 min, maintained for 0.4 min, then reverting to 90% solvent A over 0.1 min.

Preparative HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. An alternate preparative HPLC system used was a Gilson Workstation consisting of: Gilson GX-281 Injector/Collector, Gilson UV/VIS-155 Detector, Gilson 322, 333, and 334 Pumps, and a Phenomenex Gemini-NX C-18 5 micron, 50 mm (id)×250 mm column, a Waters XBridge™ C-18 5 micron OBD™, 30 mm (id)×250 mm column, or a Waters SUNFIRE™ C-18 OBD™ 10 micron, 30 mm (id)×150 mm column. The mobile phases consisted of mixtures of acetonitrile (0-90%) in water containing 0.1% or 0.05% TFA. Flow rates were maintained at 50 mL/min for the Waters Xbridge™ column, 90 mL/min for the Phenomenex Gemini column, and 30 mL/min for the Waters SUNFIRE™ column. The injection volume ranged from 1000-8000 μL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Reactions performed using photon irradiation were normally carried out using either a second generation Merck photoreactor or a Kessil 34 W blue LED lamp. Concentration of solutions was carried out on a rotary evaporator under reduced pressure. Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 microns, 60 Å pore size) in pre-packed cartridges of the size noted. $^1H$ NMR spectra were acquired at 500 MHz spectrometers in $CDCl_3$ solutions unless otherwise noted. Chemical shifts were reported in parts per million (ppm). Tetramethylsilane (TMS) was used as internal reference in $CDCl_3$ solutions, and residual $CH_3OH$ peak or TMS was used as internal reference in $CD_3OD$ solutions. Coupling constants (J) were reported in hertz (Hz). Chiral analytical chromatography was most commonly performed on one of CHIRALPAK® AS, CHIRALPAK® AD, CHIRALCEL® OD, CHIRALCEL® IA, or CHIRALCEL® OJ columns (250×4.6 mm) (Daicel Chemical Industries, Ltd.) with noted percentage of ethanol in hexane (% EtOH/Hex), isopropanol in heptane (% IPA/Hep), ethanol in carbon dioxide (% $EtOH/CO_2$), or isopropanol in carbon dioxide (% $IPA/CO_2$) as isocratic solvent systems. Chiral preparative chromatography was conducted on one of CHIRALPAK AS, of CHIRALPAK AD, CHIRALCEL® OD, CHIRALCEL® IA, CHIRALCEL® OJ columns (20×250 mm) (Daicel Chemical Industries, Ltd.) with desired isocratic solvent systems identified on chiral analytical chromatography or by supercritical fluid (SFC) conditions.

Several catalysts are used in the following procedures. "UMICORE M71 SIPR" is also known as Umicore Hoveyda Grubbs Catalyst M71 SIPr" and [1,3-Bis(2,6-diisopropylphenyl)-2-imidazolidinylidene]dichloro[(2-isopropoxy)(5-trifluoroacetamido)benzylidene]ruthenium(II). It is available from Umicore Precious Metals Chemistry USA, LLC, 1305 Main Parkway Catoosa, OK 74015. "Zhan's catalyst" is available from Sigma Aldrich.

Several methods for preparing the compounds of this invention are also described in the Examples. Starting materials and intermediates were purchased commercially from common catalog sources or were made using known procedures, or as otherwise illustrated.

Example 1

Preparation of Intermediate A1

A1

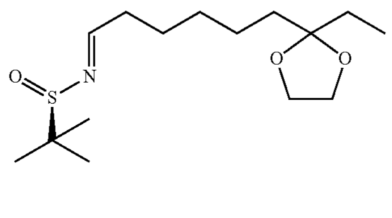

Intermediate A1 was prepared by the procedures described in Tetrahedron, 2009, 65 (45),9487-9493.

Example 2

Preparation of Intermediate A2

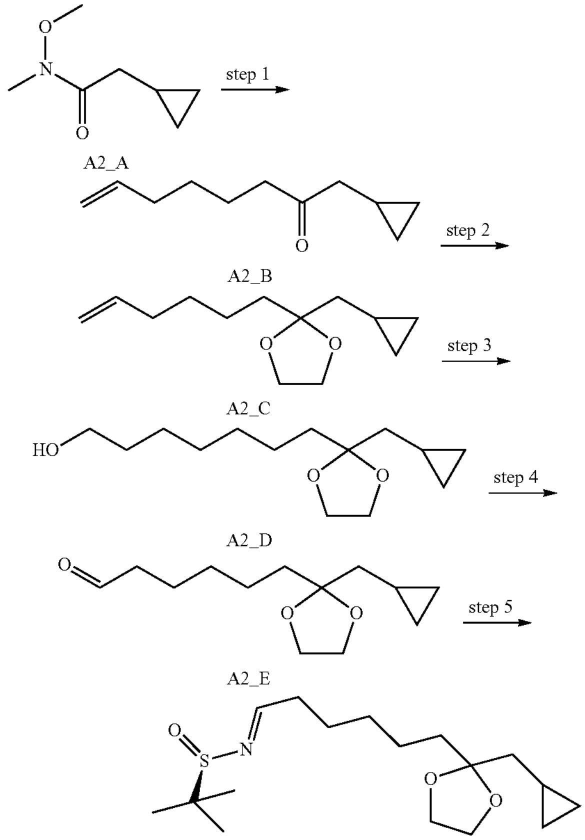

A2_A
A2_B
A2_C
A2_D
A2_E
A2

Step 1: Preparation of 1-cyclopropyloct-7-en-2-one (A2_B): Hex-5-en-1-ylmagnesium bromide (37.9 g, 202 mmol) in anhydrous THF (150 mL) was added to a stirred mixture of 2-cyclopropyl-N-methoxy-N-methylacetamide (A2_A, 20 g, 140 mmol) in THF (100 mL) at 0° C. and the mixture was stirred at room temperature for 2 h. The mixture was cooled to 0° C., hydrochloric acid (1 M, 30 mL) was added and the mixture was extracted with ethyl acetate (3×100 mL). The combined organic fractions were washed with brine (saturated, 2×50 mL), dried ($Na_2SO_4$), filtered and the solvent was evaporated under reduced pressure. The residue was purified by silica gel column flash chromatography, eluting with EtOAc/petroleum ether=0-10% to give 1-cyclopropyloct-7-en-2-one (A2_B). $^1$H NMR (400 MHz, $CDCl_3$) δ 5.76-5.83 (m, 1H), 4.88-5.08 (m, 2H), 2.46 (t, J=7.4 Hz, 2H), 2.28 (d, J=7.0 Hz, 2H), 2.05-2.12 (m, 2H), 1.56-1.64 (m, 2H), 1.34-1.45 (m, 2H), 0.93-1.04 (m, 1H), 0.50-0.60 (m, 2H), 0.06-0.17 (m, 2H).

Step 2: Preparation of 2-(cyclopropylmethyl)-2-(hex-5-en-1-yl)-1,3-dioxolane (A2_C): Ts-OH (1.4 g, 7.36 mmol) was added to a stirred mixture of ethane-1,2-diol (32 mL, 575 mmol), and 1-cyclopropyloct-7-en-2-one (A2_B, 31.7 g, 191 mmol) in toluene (100 mL) at room temperature and the mixture was stirred at 135° C. for 12 h. The mixture was cooled to room temperature, aqueous sodium hydrogen carbonate (saturated, 50 mL) was added and the mixture was extracted with ethyl acetate (3×50 mL). The combined organic fractions were washed with brine (saturated, 2×100 mL), dried ($Na_2SO_4$), filtered and the solvent was evaporated under reduced pressure to afford 2-(cyclopropylmethyl)-2-(hex-5-en-1-yl)-1,3-dioxolane (A2_C) which was used to the next step without further purification. $^1$H NMR (400 MHz, $CDCl_3$) δ 5.86-5.94 (m, 1H), 4.98-5.13 (m, 2H), 4.04 (s, 4H), 2.12-2.17 (m, 2H), 1.78-1.83 (m, 2H), 1.60 (d, J=6.8 Hz, 2H), 1.48-1.49 (m, 4H), 0.77-0.91 (m, 1H), 0.51-0.59 (m, 2H), 0.16-0.20 (m, 2H).

Step 3: Preparation of 6-(2-(cyclopropylmethyl)-1,3-dioxolan-2-yl)hexan-1-ol (A2_D): $BH_3$. THF (1.0 M, 160 mL, 160 mmol) was added to a stirred mixture of 2-(cyclopropylmethyl)-2-(hex-5-en-1-yl)-1,3-dioxolane (A2_C, 15 g, 71.3 mmol) in THF (50 mL) at room temperature and the mixture was stirred at room temperature for 2 h. NaOH (3 g, 75 mmol) in $H_2O_2$ (30%, 60 mL, 685 mmol) was drop-wise added in the mixture at 0° C. carefully, then aq $Na_2SO_3$ (saturated, 50 mL) was added and the mixture was extracted with ethyl acetate (3×100 mL). The combined organic fractions were washed with brine (saturated, 2×100 mL), dried ($Na_2SO_4$), filtered and the solvent was evaporated under reduced pressure. The residue was purified by silica gel column flash chromatography, eluting with EtOAc/petroleum ether=0-40% to give 6-(2-(cyclopropylmethyl)-1,3-dioxolan-2-yl)hexan-1-ol (A2_D). $^1$H NMR (400 MHz, $CDCl_3$) δ 3.92-4.01 (m, 4H), 3.65 (t, J=6.6 Hz, 2H), 1.68-1.78 (m, 2H), 1.47-1.63 (m, 5H), 1.32-1.43 (m, 7H), 0.71-0.81 (m, 1H), 0.44-0.50 (m, 2H), 0.08-0.13 (m, 2H).

Step 4: Preparation of 6-(2-(cyclopropylmethyl)-1,3-dioxolan-2-yl)hexanal (A2_E): Pyridine sulfur trioxide (105 mg, 0.657 mmol), and DIEA (0.153 mL, 0.876 mmol) was added to a stirred mixture of 6-(2-(cyclopropylmethyl)-1,3-dioxolan-2-yl)hexan-1-ol (A2_D, 100 mg, 0.438 mmol) in DCM (5 mL)/DMSO (1 mL) at room temperature and the mixture was stirred at room temperature for 12 h. The mixture was then stirred at 40° C. for 12 h. The mixture was cooled, diluted with ethyl acetate (10 mL), washed with brine (saturated, 3×10 mL), dried ($Na_2SO_4$), filtered and the solvent was evaporated under reduced pressure. The residue was purified by silica gel column flash chromatography, eluting with EtOAc/petroleum ether=0-30% to give 6-(2-(cyclopropylmethyl)-1,3-dioxolan-2-yl)hexanal (A2_E). $^1$H NMR (400 MHz, $CDCl_3$) δ 9.76 (s, 1H), 3.87-4.04 (m, 4H), 2.36-2.49 (m, 2H), 1.69-1.76 (m, 2H), 1.61-1.66 (m, 2H), 1.51 (d, J=6.7 Hz, 2H), 1.31-1.44 (m, 4H), 0.68-0.79 (m, 1H), 0.42-0.50 (m, 2H), 0.09 (d, J=4.7 Hz, 2H).

Step 5: Preparation of (R,E)-N-(6-(2-(cyclopropylmethyl)-1,3-dioxolan-2-yl)hexylidene)-2-methylpropane-2-sulfinamide (A2): Copper(II) sulfate (30 g, 188 mmol), and (R)-2-methylpropane-2-sulfinamide (3.00 g, 24.79 mmol) were added to a stirred mixture of 6-(2-(cyclopropylmethyl)-1,3-dioxolan-2-yl)hexanal (A2_E, 5.1 g, 22.54 mmol) in DCM (50 mL) at room temperature and the mixture was stirred at room temperature for 48 h. The mixture was filtered, washed with ethyl acetate, the residue was purified by silica gel column flash chromatography, eluting with EtOAc/petroleum ether=0-40% to give (R,E)-N-(6-(2-(cyclopropylmethyl)-1,3-dioxolan-2-yl)hexylidene)-2-methylpropane-2-sulfinamide (A2). $^1$HNMR (400 MHz, $CDCl_3$) δ 8.07 (t, J=4.8 Hz, 1H), 3.94-4.00 (m, 4H), 2.50-2.55 (m, 2H), 1.69-1.76 (m, 2H), 1.62-1.67 (m, 2H), 1.52 (d, J=6.8

Hz, 2H), 1.35-1.42 (m, 4H), 1.20 (s, 9H), 0.70-0.79 (m, 1H), 0.41-0.50 (m, 2H), 0.07-0.14 (m, 2H).

Example 3

Preparation of Intermediate A3

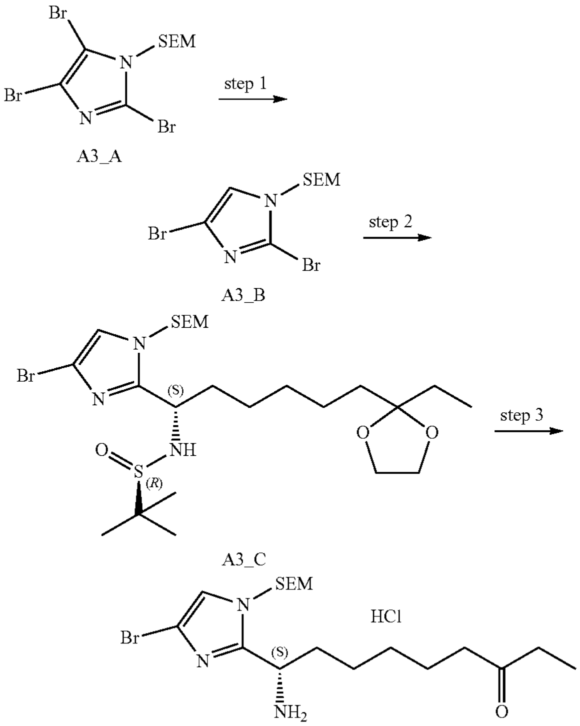

A3_A

A3_B

A3_C

A3

Step 1: Preparation of 2,4-dibromo-1-((2-(trimethylsilyl)ethoxy)methyl)-1H-imidazole (A3_B): Into a 10-L 3-necked round-bottom flask purged and maintained with an inert atmosphere of nitrogen, was placed a solution of 2,4,5-tribromo-1-[[2-(trimethylsilyl)ethoxy]methyl]-1H-imidazole (A3_A, 420 g, 965.46 mmol) in tetrahydrofuran (4000 mL). This was followed by the addition of n-BuLi (783 mL, 2.02 equiv) dropwise with stirring at −78° C. The mixture was stirred at −78° C. for 10 min. To this was added water (17.4 g, 966.67 mmol) at −78° C. The mixture was slowly warmed to −50° C. over 1 h. To the mixture was added $Br_2$ (170 g, 1.06 mol, 1.20 equiv) at −78° C. The mixture was stirred at −78° C. for 30 min. The reaction was then quenched by the addition of 2 L of water. The resulting solution was extracted with 3×2 L of ethyl acetate and the organic layers combined. The resulting mixture was washed with 1×1 L of brine. The mixture was dried over anhydrous sodium sulfate and concentrated under vacuum. The residue was applied onto a silica gel column with ethyl acetate/petroleum ether (1:30) to afford 2,4-dibromo-1-[[2-(trimethylsilyl)ethoxy]methyl]-1H-imidazole (A3_B).

Step 2: Preparation of (R)—N—((S)-1-(4-bromo-1-((2-(trimethylsilyl)ethoxy)methyl)-1H-imidazol-2-yl)-6-(2-ethyl-1,3-dioxolan-2-yl)hexyl)-2-methylpropane-2-sulfinamide (A3_C): Into a 5-L 3-necked round-bottom flask purged and maintained with an inert atmosphere of nitrogen, was placed a solution of 2,4-dibromo-1-[[2-(trimethylsilyl)ethoxy]methyl]-1H-imidazole (A3_B, 120 g, 336.96 mmol) in tetrahydrofuran (1200 mL). This was followed by the addition of n-BuLi (138 g, 2.15 mol, 1.02 equiv) dropwise with stirring at −78° C. To this was added (R)—N-[(1E)-6-(2-ethyl-1,3-dioxolan-2-yl)hexylidene]-2-methylpropane-2-sulfinamide (A1, 102 g, 336.12 mmol) at −78° C. The resulting solution was stirred for 30 min at −30° C. in a liquid nitrogen bath. The reaction was then quenched by the addition of 1 L of water. The resulting solution was extracted with 3×1 L of ethyl acetate and the organic layers combined. The resulting mixture was washed with 1×500 mL of brine. The mixture was dried over anhydrous sodium sulfate and concentrated under vacuum. The crude product (200 g) was purified by Flash-Prep-HPLC with the following conditions (IntelFlash-1): Column, silica gel; mobile phase, ACN/water $NH_4HCO_3$=50% increasing to ACN/water $NH_4HCO_3$=70% within 20 min; Detector, UV 254 nm. 130 g product was obtained. The crude product was purified by Chiral-Prep-HPLC with the following conditions (Prep SFC 350): Column, CHIRALPAK IA-SFC-025 cm*25 cm Chiral-P(IA) 011S90IA0SCY-SL-001; mobile phase, CO2:80, MeOH; Detector, uv 220 nm. This resulted in (R)—N-[(1S)-1-(4-bromo-1-[[2-(trimethylsilyl)ethoxy]methyl]-1H-imidazol-2-yl)-6-(2-ethyl-1,3-dioxolan-2-yl)hexyl]-2-methylpropane-2-sulfinamide (A3_C).

Step 3: Preparation of (S)-9-amino-9-(4-bromo-1-((2-(trimethylsilyl)ethoxy)methyl)-1H-imidazol-2-yl)nonan-3-one (A3): Into a 3-L 3-necked round-bottom flask purged and maintained with an inert atmosphere of nitrogen, was placed a solution of (R)—N-[(1S)-1-(4-bromo-1-[[2-(trimethylsilyl)ethoxy]methyl]-1H-imidazol-2-yl)-6-(2-ethyl-1,3-dioxolan-2-yl)hexyl]-2-methylpropane-2-sulfinamide (A3_C, 130 g, 223.87 mmol) in tetrahydrofuran (1300 mL). This was followed by the addition of hydrogen chloride (24 g, 1.10 equiv) dropwise with stirring at 0-5° C. The resulting solution was stirred at room temperature for 8 h. The resulting solution was diluted with 1000 mL of ice-water. The resulting solution was extracted with 3×500 mL of ethyl acetate and the organic layers combined. The resulting mixture was washed with 1×500 mL of brine. The mixture was dried over anhydrous sodium sulfate and concentrated under vacuum. The residue was applied onto a silica gel column with DCM/EtOH (30/1). The product was diluted with DCM 500 mL and washed with $Na_2CO_3$, followed by brine, and mixed with HCl conc. (16 g in EtOAc 100 mL). The mixture was washed with brine, dried over $Na_2SO_4$, and concentrated to afford (9S)-9-amino-9-(4-bromo-1-[[2-(trimethylsilyl)ethoxy]methyl]-1H-imidazol-2-yl)nonan-3-one hydro chloride (A3). LCMS (ESI) calc'd for $C_{18}H_{34}BrN_3O_2Si$ $[M+H]^+$: 432.2, found: 434.0. H NMR (300 MHz, DMSO) δ 8.29 (brs, 3H), 7.51 (s, 1H), 5.54 (d, J=11.1 Hz, 1H), 5.23 (d, J=11.2 Hz, 1H), 4.40 (t, J=6.9 Hz, 1H), 3.44 (m, 2H), 2.41-2.26 (m, 4H), 1.84 (brs, 2H), 1.36 (m, 2H), 1.11 (m, 5H), 0.94-0.68 (m, 5H), −0.06 (s, 9H).

Example 4

Preparation of Intermediate A4

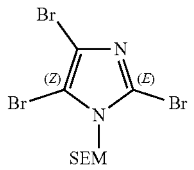

+

-continued

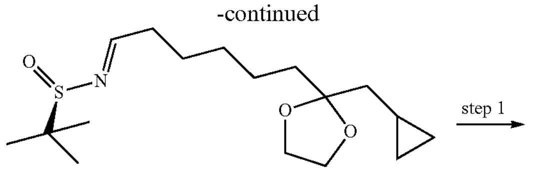

A2

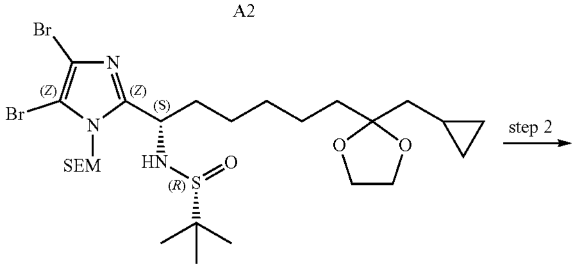

A4_A

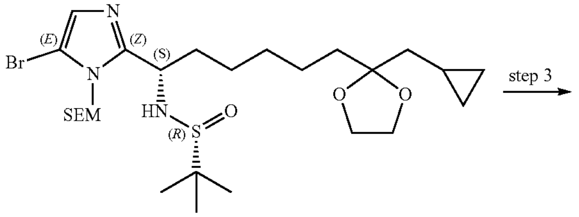

A4_B

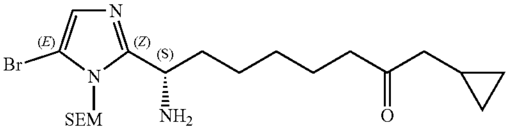

A4

Step 1: Preparation of (S)—N—((S)-6-(2-(cyclopropylmethyl)-1,3-dioxolan-2-yl)-1-(4,5-dibromo-1-((2-(trimethylsilyl)ethoxy)methyl)-1H-imidazol-2-yl)hexyl)-2-methylpropane-2-sulfinamide (A4_A): nBuLi (1.8 mL, 4.50 mmol) was added to a stirred mixture of 2,4,5-tribromo-1-((2-(trimethylsilyl)ethoxy)methyl)-1H-imidazole (1.954 g, 4.49 mmol) in THF (20 mL) at −78° C. and the mixture was stirred at −78° C. for 30 min. (R,E)-N-(6-(2-(cyclopropylmethyl)-1,3-dioxolan-2-yl)hexylidene)-2-methylpropane-2-sulfinamide (A2, 1 g, 3.03 mmol) in THF (2 mL) was added dropwise. Then the mixture was stirred at −78° C. for 2 h. Aqueous ammonium chloride (saturated, 15 mL), water (20 mL) was added at −78° C. and the mixture was extracted with ethyl acetate (3×20 mL). The combined organic fractions were washed with brine (saturated, 2×20 mL), dried ($Na_2SO_4$), filtered and the solvent was evaporated under reduced pressure. The residue was purified by silica gel column flash chromatography, eluting with EtOAc/petroleum ether=0-50% to give (S)—N—((S)-6-(2-(cyclopropylmethyl)-1,3-dioxolan-2-yl)-1-(4,5-dibromo-1-((2-(trimethylsilyl)ethoxy)methyl)-1H-imidazol-2-yl)hexyl)-2-methylpropane-2-sulfinamide (A4_A). LCMS (ESI) calc'd for $C_{26}H_{47}Br_2N_3O_4SSi$ $[M+H]^+$: 684.1, found: 686.2. $^1H$ NMR (400 MHz, $CDCl_3$) δ 5.48 (d, J=11.2 Hz, 1H), 5.27 (d, J=11.3 Hz, 1H), 4.51-4.59 (m, 1H), 3.89-4.00 (m, 4H), 3.68-3.77 (m, 1H), 3.56 (t, J=8.3 Hz, 2H), 2.08-2.18 (m, 1H), 1.94-2.04 (m, 1H), 1.59-1.71 (m, 3H), 1.50 (d, J=6.8 Hz, 2H), 1.33 (brs, 3H), 1.17 (s, 9H), 0.88-0.97 (m, 2H), 0.74 (m, 1H), 0.42-0.49 (m, 2H), 0.07-0.12 (m, 2H), 0.02 (s, 9H).

Step 2: Preparation of (S)—N—((S)-1-(5-bromo-1-((2-(trimethylsilyl)ethoxy)methyl)-1H-imidazol-2-yl)-6-(2-(cyclopropylmethyl)-1,3-dioxolan-2-yl)hexyl)-2-methylpropane-2-sulfinamide (A4 B): nBuLi (2.5 M, 0.45 mL, 1.125 mmol) was added to a stirred mixture of (S)—N—((S)-6-(2-(cyclopropylmethyl)-1,3-dioxolan-2-yl)-1-(4,5-dibromo-1-((2-(trimethylsilyl)ethoxy)methyl)-1H-imidazol-2-yl) hexyl)-2-methylpropane-2-sulfinamide (A4_A, 500 mg, 0.729 mmol) in THF (5 mL) at −78° C. and the mixture was stirred at −78° C. for 30 min. i-PrOH (0.3 mL, 3.89 mmol) was added, and the mixture was stirred at −78° C. for 20 min. Aqueous ammonium chloride (saturated, 10 mL) was added and the mixture was extracted with ethyl acetate (3×10 mL). The combined organic fractions were washed with brine (saturated, 2×15 mL), dried ($Na_2SO_4$), filtered and the solvent was evaporated under reduced pressure. The residue was purified by silica gel column flash chromatography, eluting with EtOAc/petroleum ether=0-50% to give (S)—N—((S)-1-(5-bromo-1-((2-(trimethylsilyl)ethoxy) methyl)-1H-imidazol-2-yl)-6-(2-(cyclopropylmethyl)-1,3-dioxolan-2-yl)hexyl)-2-methylpropane-2-sulfinamide (A4_B). LCMS (ESI) calc'd for $C_{26}H_{48}BrN_3O_4SSi$ $[M+H]^+$: 606.2, found: 606.3. $^1H$ NMR (400 MHz, $CDCl_3$) δ 6.89 (s, 1H), 5.40 (d, J=11.0 Hz, 1H), 5.14 (d, J=10.8 Hz, 1H), 4.47-4.54 (m, 1H), 3.90-3.98 (m, 4H), 3.50 (t, J=8.3 Hz, 2H), 2.13 (d, J=9.0 Hz, 1H), 1.97-2.04 (m, 1H), 1.59-1.72 (m, 4H), 1.49 (d, J=6.8 Hz, 2H), 1.33 (brs, 4H), 1.16 (s, 9H), 0.88-0.95 (m, 2H), 0.68-0.78 (m, 1H), 0.42-0.49 (m, 2H), 0.07-0.11 (m, 2H), 0.01 (s, 9H).

Step 3: Preparation of (S)-8-amino-8-(5-bromo-1-((2-(trimethylsilyl)ethoxy)methyl)-1H-imidazol-2-yl)-1-cyclopropyloctan-2-one hydrochloride (A4): HCl/MeOH (0.25 mL, 1.000 mmol) was added to a stirred mixture of (S)—N—((S)-1-(5-bromo-1-((2-(trimethylsilyl)ethoxy)methyl)-1H-imidazol-2-yl)-6-(2-(cyclopropylmethyl)-1,3-dioxolan-2-yl)hexyl)-2-methylpropane-2-sulfinamide (A4_B, 150 mg, 0.247 mmol) in MeOH (2 mL) at room temperature and the mixture was stirred at room temperature for 2 h. Most of the MeOH was removed, and it was concentrated to give (S)-8-amino-8-(5-bromo-1-((2-(trimethylsilyl)ethoxy) methyl)-1H-imidazol-2-yl)-1-cyclopropyloctan-2-one hydrochloride (A4) which was used to the next step without further purification. LCMS (ESI) calc'd for $C_{20}H_{36}BrN_3O_2Si$ $[M+H]^+$: 458.2, found: 460.1.

Example 5

Preparation of Intermediate A5

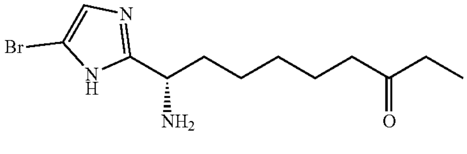 [SMILES: CCC(=O)CCCCC[C@H](N)c1ncc(Br)[nH]1]

Hydrogen chloride in EtOAc (4 M, 20.0 mL, 80.0 mmol) was added to a stirred mixture of (S)-9-amino-9-(5-bromo-1-((2-(trimethylsilyl)ethoxy)methyl)-1H-imidazol-2-yl) nonan-3-one hydrochloride (A2, 2.50 g, 5.33 mmol) in ethyl acetate (20 mL) at room temperature and the mixture was stirred at room temperature for 12 h. The mixture was quenched with aqueous $NaHCO_3$(saturated, 30 mL) and the mixture was extracted with DCM (3×30 mL). The combined organic fractions were washed with brine (30 mL), dried ($Na_2SO_4$), filtered and the solvent was evaporated under reduced pressure. The residue was purified by silica gel column flash chromatography, eluting with DCM/MeOH=10:1 to give (S)-9-amino-9-(5-bromo-1H-imidazol-2-yl)nonan-3-one (A3). LCMS (ESI) calc'd for $C_{12}H_{20}BrN_3O$ [M+H]$^+$: 302.1, found: 304.0.

Example 6

Preparation of Intermediate A6

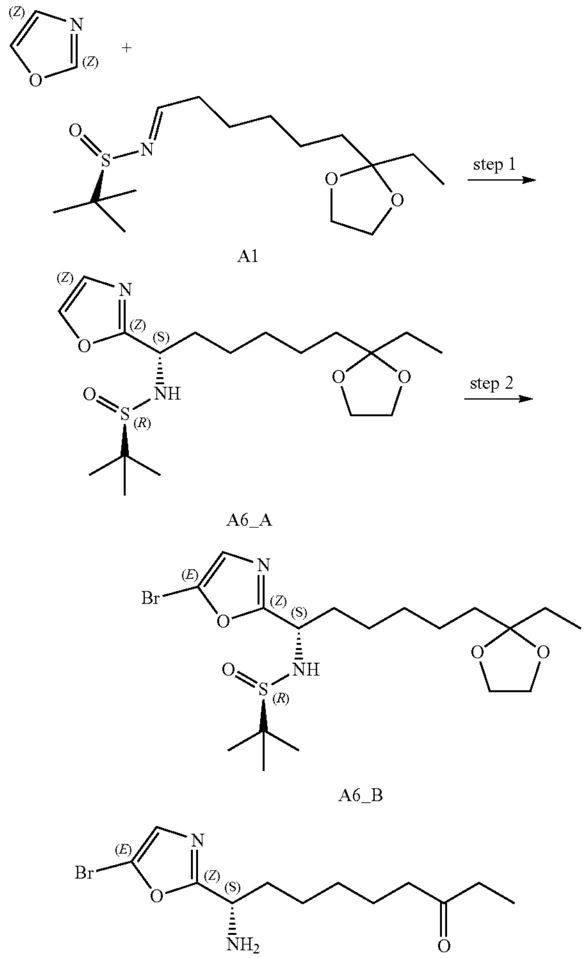

A1

A6_A

A6_B

A6

Step 1: (R)—N—((S)-6-(2-ethyl-1,3-dioxolan-2-yl)-1-(oxazol-2-yl) hexyl)-2-methylpropane-2-sulfinamide (A6_A): $BH_3$·THF (1.0 M, 1.8 mL, 1.800 mmol) was added to a stirred mixture of oxazole (148 mg, 2.142 mmol) in THF (5 mL) at rt and the mixture was stirred at rt for 1 h under $N_2$. The reaction mixture was cooled to −78° C., and then n-butyllithium (2.5 M, 0.7 mL, 1.750 mmol) was added to the mixture slowly under $N_2$. The mixture was stirred at −78° C. for 1 h. (R,E)-N-(6-(2-ethyl-1,3-dioxolan-2-yl)hexylidene)-2-methylpropane-2-sulfinamide (A1, 500 mg, 1.648 mmol) in THF (1 mL) was added to the mixture slowly at −78° C. and the mixture was stirred at −78° C. for 2 h. Aqueous $NH_4Cl$ (saturated, 0.2 mL) was added to the mixture. The mixture was extracted with ethyl acetate (3×10 mL). The combined organic fractions were washed with brine (5 mL), dried ($Na_2SO_4$), filtered and the solvent was evaporated under reduced pressure. The residue was purified by silica gel flash chromatography (ISCORF75; Sepa flash column), eluting with DCM/MeOH=10/1 to give (R)—N—((S)-6-(2-ethyl-1,3-dioxolan-2-yl)-1-(oxazol-2-yl)hexyl)-2-methylpropane-2-sulfinamide (A6_A). LCMS (ESI) calc'd for $C_{18}H_{32}N_2O_4S$ [M+H]$^+$: 373.2, found: 373.1.

Step 2: Preparation of (R)—N—((S)-1-(5-bromooxazol-2-yl)-6-(2-ethyl-1,3-dioxolan-2-yl)hexyl)-2-methylpropane-2-sulfinamide (A6_B): Tert-butyllithium (1.3 M, 3.3 mL, 4.29 mmol) was added to a stirred mixture of (R)—N—((S)-6-(2-ethyl-1,3-dioxolan-2-yl)-1-(oxazol-2-yl) hexyl)-2-methylpropane-2-sulfinamide (A6_A, 400 mg, 1.074 mmol) in THF (4 mL) at −78° C. and the mixture was stirred at −78° C. for 1 h under $N_2$. Then $CBr_4$ (1068 mg, 3.22 mmol) in THF (0.5 mL) was added to the mixture slowly at −78° C. and the mixture was stirred at −78° C. for 1 h. Aqueous $NH_4Cl$ (saturated, 2 mL) was added and the mixture was extracted with DCM (3×6 mL). The combined organic fractions were washed with brine (5 mL), dried ($Na_2SO_4$), filtered and the solvent was evaporated under reduced pressure. The residue was purified by silica gel flash chromatography (ISCORF75; Sepa flash column), eluting with petroleum ether/EtOAc=1/1~0/1 to give (R)—N—((S)-1-(5-bromooxazol-2-yl)-6-(2-ethyl-1,3-dioxolan-2-yl) hexyl)-2-methylpropane-2-sulfinamide (A6_B). LCMS (ESI) calc'd for $C_{15}H_{31}BrN_2O_4S$ [M+H]$^+$: 451.1, found: 453.1.

Step 3: Preparation of (S)-9-amino-9-(5-bromooxazol-2-yl)nonan-3-one (A6): HCl (~4 Min MeOH, 0.1 mL, 0.400 mmol) was added to a stirred mixture of (R)—N—((S)-1-(5-bromooxazol-2-yl)-6-(2-ethyl-1,3-dioxolan-2-yl)hexyl)-2-methylpropane-2-sulfinamide (A6_B, 91 mg, 0.202 mmol) in MeOH (1 mL) at rt and the mixture was stirred at rt for 5 min. Aqueous $NaHCO_3$ (saturated, 1 mL) was added and the mixture was extracted with ethyl acetate (3×3 mL). The combined organic fractions were washed with brine (saturated, 2 mL), dried ($Na_2SO_4$), filtered and the filtrate was concentrated to give (S)-9-amino-9-(5-bromooxazol-2-yl)nonan-3-one (A6) which was used without further purification. LCMS (ESI) calc'd for $C_{12}H_{19}BrN_2O_2$ [M+H]$^+$: 303.1, found: 303.0.

The following intermediate was prepared using similar procedures as described for intermediate A6

| Intermediate ID | Structures | Observed [M + H]$^+$ |
|---|---|---|
| A7 | 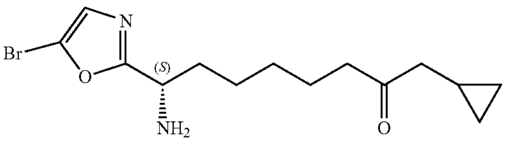 | 329.1 |

Example 7

Preparation of Intermediate A8 (209)

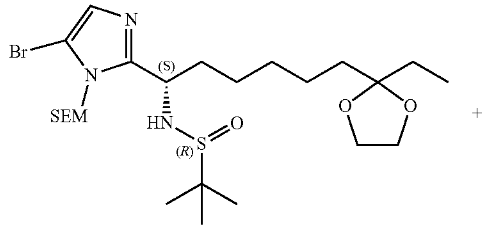

A3_C

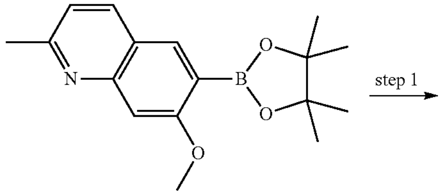

C1

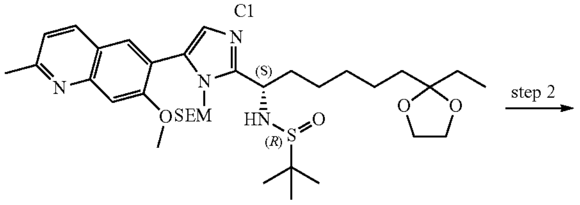

A8_A

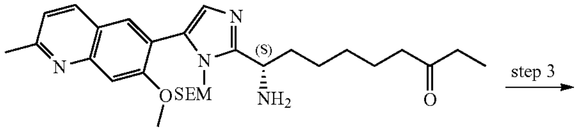

A8_B

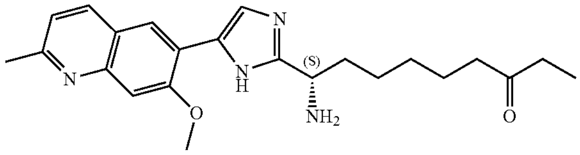

A8

Step 1: (R)—N—((S)-6-(2-ethyl-1,3-dioxolan-2-yl)-1-(5-(7-methoxy-2-methylquinolin-6-yl)-1-((2-(trimethylsilyl)ethoxy)methyl)-1H-imidazol-2-yl)hexyl)-2-methylpropane-2-sulfinamide (A8_A): $PdCl_2$(DTBPF) (20 mg, 0.031 mmol) was added to a mixture of (R)—N—((S)-1-(5-bromo-1-((2-(trimethylsilyl)ethoxy)methyl)-1H-imidazol-2-yl)-6-(2-ethyl-1,3-dioxolan-2-yl)hexyl)-2-methylpropane-2-sulfinamide (A3_C, 152 mg, 0.262 mmol), 7-methoxy-2-methyl-6-(4,4,5,5-tetramethyl-1,3,2-dioxaborolan-2-yl)quinoline (C1, 90 mg, 0.301 mmol) and $K_3PO_4$ (220 mg, 1.036 mmol) in co-solvents of THF (2 mL) and water (0.2 mL) and the mixture was stirred at 80° C. for 3 h. The mixture was diluted with water (15 mL), extracted with DCM (3×10 mL). The combined organic fractions were washed with brine (saturated, 10 mL), dried ($Na_2SO_4$), filtered and the solvent was evaporated under reduced pressure. The residue was purified by silica gel column flash chromatography, eluting with DCM/MeOH=0~6% to give (R)—N—((S)-6-(2-ethyl-1,3-dioxolan-2-yl)-1-(5-(7-methoxy-2-methylquinolin-6-yl)-1-((2-(trimethylsilyl)ethoxy)methyl)-1H-imidazol-2-yl)hexyl)-2-methylpropane-2-sulfinamide (A8_A). LCMS (ESI) calc'd for $C_{35}H_{56}N_4O_5SSi$ $[M+H]^+$: 673.4, found: 673.4.

Step 2: (S)-9-amino-9-(5-(7-methoxy-2-methylquinolin-6-yl)-1-((2-(trimethylsilyl)ethoxy)methyl)-1H-imidazol-2-yl)nonan-3-one (A8_B): HCl (3 mL, 12.00 mmol) (MeOH solution) was added to (R)—N—((S)-6-(2-ethyl-1,3-dioxolan-2-yl)-1-(5-(7-methoxy-2-methylquinolin-6-yl)-1-((2-(trimethylsilyl)ethoxy)methyl)-1H-imidazol-2-yl)hexyl)-2-methylpropane-2-sulfinamide (A8_A, 146 mg, 0.217 mmol) and the mixture was stirred at 26° C. for 30 mins. The solvent was evaporated under reduced pressure to give (S)-9-amino-9-(5-(7-methoxy-2-methylquinolin-6-yl)-1-((2-(trimethylsilyl)ethoxy)methyl)-1H-imidazol-2-yl)nonan-3-one (A8_B), which was used to the next step without further purification. LCMS (ESI) calc'd for $C_{29}H_{44}N_4O_3Si$ $[M+H]^+$: 525.3, found: 525.3.

Step 3: (S)-9-amino-9-(5-(7-methoxy-2-methylquinolin-6-yl)-1H-imidazol-2-yl)nonan-3-one (A8): TFA (2 mL, 26.0 mmol) was added to (S)-9-amino-9-(5-(7-methoxy-2-methylquinolin-6-yl)-1-((2-(trimethylsilyl)ethoxy)methyl)-1H-imidazol-2-yl)nonan-3-one (A8_B, 152 mg, 0.290 mmol) and the mixture was stirred at 26° C. for 3 h. The solvent was evaporated under reduced pressure and pH was adjusted to 7 with $Et_3N$ (0.2 mL). The residue was purified by preparative HPLC (reverse phase C-18 column), eluting with acetonitrile/water+0.05% $NH_3 \cdot H_2O$, to give (S)-9-amino-9-(5-(7-methoxy-2-methylquinolin-6-yl)-1H-imidazol-2-yl)nonan-3-one (A8). LCMS (ESI) calc'd for $C_{23}H_{30}N_4O_2$ $[M+H]^+$: 395.2, found: 395.2.

The following intermediates were prepared using similar procedures as described for intermediate A8

| Intermediate ID | Structures | Observed $[M + H]^+$ |
| --- | --- | --- |
| A9 | 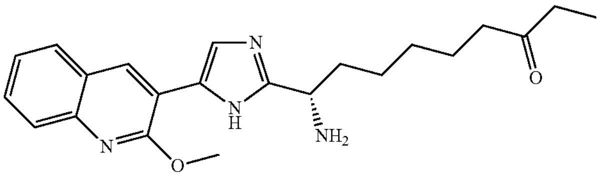 | 381.2 |
| A10 (178) | 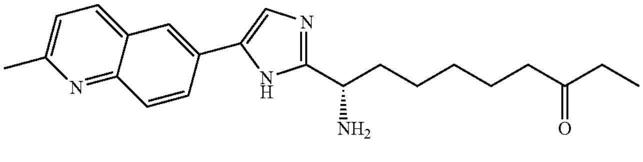 [SMILES: CCC(=O)CCCCC[C@H](N)c1ncc(-c2ccc3nc(C)ccc3c2)[nH]1] | 365.2 |

-continued

| Intermediate ID | Structures | Observed $[M + H]^+$ |
|---|---|---|
| A11 | 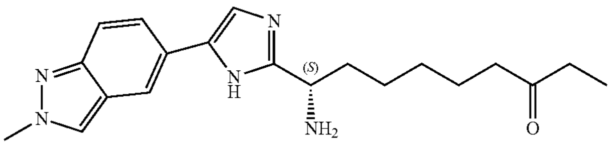 | 354.1 |

Example 8

Preparation of Intermediate A12

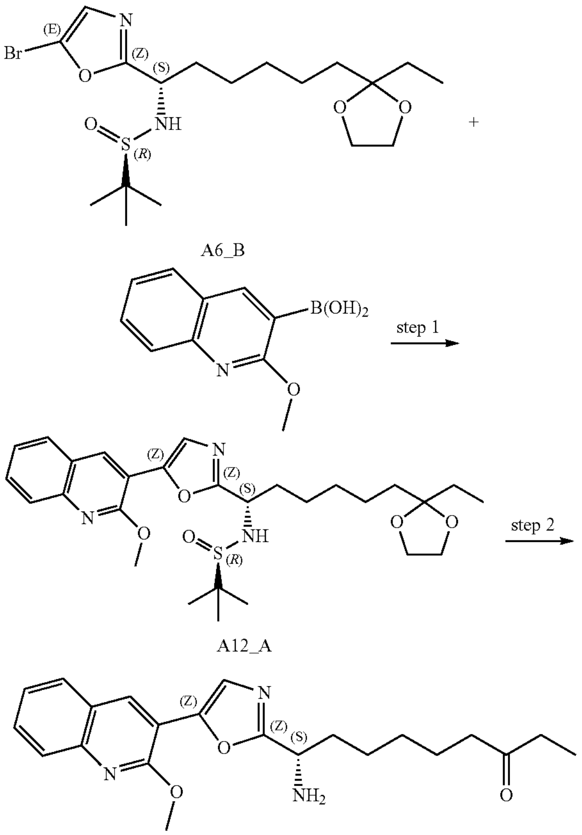

A6_B

A12_A

A12

Step 1: Preparation of (R)—N—((S)-6-(2-ethyl-1,3-dioxolan-2-yl)-1-(5-(2-methoxyquinolin-3-yl)oxazol-2-yl)hexyl)-2-methylpropane-2-sulfinamide (A12_A): $PdCl_2$ (DTBPF) (0.144 g, 0.222 mmol) was added to a stirred mixture of $K_2CO_3$ (0.918 g, 6.65 mmol), (2-methoxyquinolin-3-yl)boronic acid (0.450 g, 2.215 mmol) and (R)—N—((S)-1-(5-bromooxazol-2-yl)-6-(2-ethyl-1,3-dioxolan-2-yl)hexyl)-2-methylpropane-2-sulfinamide (A6_B, 1.0 g, 2.215 mmol) in THF (10 mL) and Water (1 mL) at room temperature and the mixture was heated with stirring at 80° C. for 18 h under $N_2$ protection. The mixture was cooled to room temperature, water (10 mL) was added and the mixture was extracted with ethyl acetate (3×15 mL). The combined organic fractions were washed with brine (saturated, 15 mL), dried ($Na_2SO_4$), filtered and the solvent was evaporated under reduced pressure. The residue was purified by silica gel flash chromatography (ISCORF75; Sepa flash column), eluting with petroleum ether/EtOAc=1/1-0/1 to give (R)—N—((S)-6-(2-ethyl-1,3-dioxolan-2-yl)-1-(5-(2-methoxyquinolin-3-yl)oxazol-2-yl)hexyl)-2-methylpropane-2-sulfinamide (A12_A). LCMS (ESI) calc'd for $C_{28}H_{39}N_3O_5S$ $[M+H]^+$: 530.3, found: 530.3.

Step 2: Preparation of (S)-9-amino-9-(5-(2-methoxyquinolin-3-yl)oxazol-2-yl)nonan-3-one (A12): HCl/MeOH (0.2 mL, 0.800 mmol) was added to a stirred mixture of (R)—N—((S)-6-(2-ethyl-1,3-dioxolan-2-yl)-1-(5-(2-methoxyquinolin-3-yl)oxazol-2-yl)hexyl)-2-methylpropane-2-sulfinamide (A12_A, 247 mg, 0.466 mmol) in MeOH (2 mL) at room temperature and the mixture was stirred at room temperature for 30 min. The mixture was cooled to room temperature, aqueous $NaHCO_3$(saturated, 5 mL) was added and the mixture was extracted with ethyl acetate (3×5 mL). The combined organic fractions were washed with brine (saturated, 5 mL), dried ($Na_2SO_4$), filtered and concentrated to give (S)-9-amino-9-(5-(2-methoxyquinolin-3-yl)oxazol-2-yl)nonan-3-one (A12), which was used to next step without further purification. LCMS (ESI) calc'd for $C_{22}H_{27}N_3O_3$ $[M+H]^+$: 382.2, found: 382.2.

The following intermediates were prepared using similar procedures as described for intermediate A12

| Intermediate ID | Structures | Observed $[M + H]^+$ |
|---|---|---|
| A13 (224) | 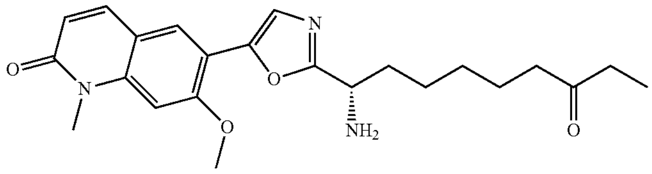 [SMILES: CCC(=O)CCCCC[C@H](N)c1ncc(-c2cc3ccc(=O)n(C)c3cc2OC)o1] | 412.1 |

-continued

| Intermediate ID | Structures | Observed [M + H]+ |
|---|---|---|
| A14 | 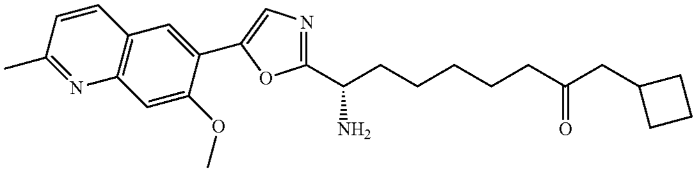 [SMILES: COc1cc2nc(C)ccc2cc1-c1cnc([C@@H](N)CCCCCC(=O)CC2CCC2)o1] | 436.3 |
| A15 | 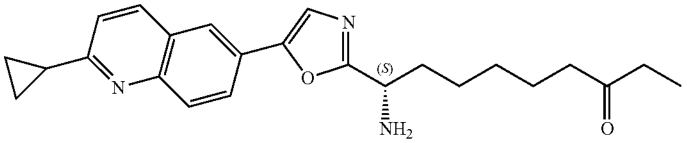 | 392.2 |
| A16 | 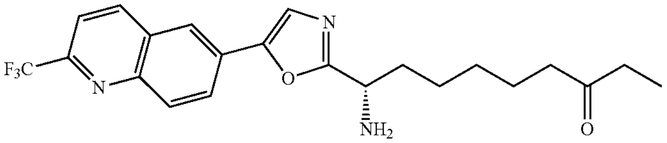 [SMILES: CCC(=O)CCCCC[C@H](N)c1ncc(-c2ccc3nc(C(F)(F)F)ccc3c2)o1] | 420.2 |

Example 9

Preparation of Intermediate A17

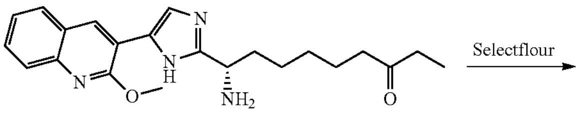

A9

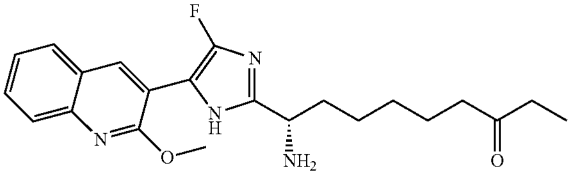

A17

To the solution of (S)-9-amino-9-(5-(2-methoxyquinolin-3-yl)-1H-imidazol-2-yl)nonan-3-one (A9, 0.5 g, 1.04 mmol) in 5.0 mL DMF and 0.5 mL $H_2O$, SelectFluor (0.55 g, 1.56 mmol) was added. The mixture was stirred at rt for 16 h. 10 mL water was added, the mixture was extracted with ethyl acetate. The organic phase was washed with brine and dried with anhydrous $Na_2SO_4$. After concentration it was purified by silica gel chromatography (10% MeOH in DCM) to give the title compound mixed with chloride. $^1H$ NMR (400 MHz, $CDCl_3$) δ 0.95 (t, J=7.43 Hz, 3H), 1.16-1.39 (m, 5H), 1.40-1.54 (m, 2H), 1.78-1.91 (m, 1H), 1.91-2.01 (m, 1H), 2.22-2.38 (m, 4H), 4.05-4.24 (m, 3H), 4.36 (q, J=7.30 Hz, 1H), 7.27-7.36 (m, 1H), 7.47-7.67 (m, 2H), 7.68-7.78 (m, 1H), 8.15-8.23 (m, 0.5H), 8.50-8.59 (m, 0.5H). LCMS (ESI) calc'd for $C_{35}H_{46}FN_5O_5$ $[M+K]^+$: 437.2, found: 437.0.

Example 10

Preparation of Intermediate A18

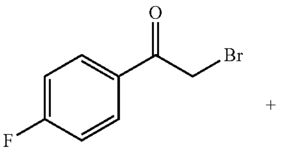

A18_A

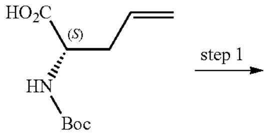

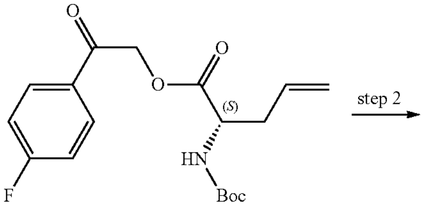

A18_B

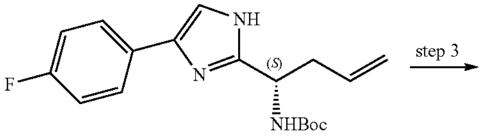

A18_C

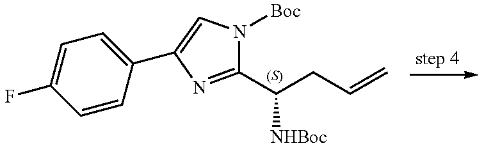

A18_D

-continued

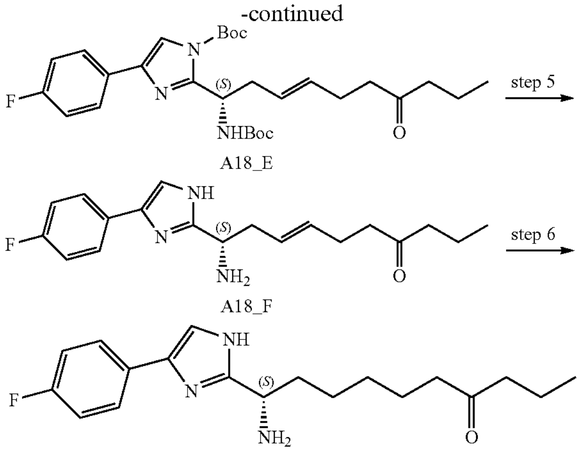

A18_E

A18_F

A18

Step 1: Preparation of (S)-2-(4-fluorophenyl)-2-oxoethyl 2-((tert-butoxycarbonyl) amino)pent-4-enoate (A18_B): To the solution of (S)-2-((tert-butoxycarbonyl)amino)pent-4-enoic acid (0.5 g, 2.32 mmol) in 5.0 mL DMF, 2-bromo-1-(4-fluorophenyl)ethanone (A18_A, 0.48 g, 2.21 mmol) was added. DIEA (0.57 g, 4.42 mmol) was then added dropwise. The mixture was stirred at rt for 1 h. 10 mL water was added and it was extracted with EtOAc three times. The combined organic phase was washed with brine and dried with anhydrous $Na_2SO_4$. It was concentrated to give the title compound (A18_B). $^1$H NMR (400 MHz, $CDCl_3$) δ 1.44 (s, 9H), 2.68 (brs, 2H), 4.46-4.58 (m, 1H), 4.95-5.09 (m, 1H), 5.12-5.29 (m, 3H), 5.43-5.58 (m, 1H), 5.77-5.95 (m, 1H), 7.10-7.22 (m, 2H), 7.84-8.00 (m, 2H); LCMS (ESI) calc'd for $C_{18}H_{22}FNO_5$ $[M+H]^+$: 352.1, found: 352.1.

Step 2: Preparation of (S)-tert-butyl (1-(4-(4-fluorophenyl)-1H-imidazol-2-yl) but-3-en-1-yl)carbamate (A18_C): To the solution of (S)-2-(4-fluorophenyl)-2-oxoethyl 2-((tert-butoxycarbonyl)amino) pent-4-enoate (A18_B, 0.6 g, 1.7 mmol) in 15 mL toluene, $NH_4OAc$ (1.3 g, 17.0 mmol) was added. The mixture was heated to 130° C. (to make toluene flux) with stirring at 130° C. for 16 h. The crude product, after evaporation, was purified by silica gel chromatography to give the target compound (A18_C). $^1$H NMR (400 MHz, $CDCl_3$) δ 1.43 (s, 9H), 2.01-2.07 (m, 1H), 2.71-2.84 (m, 2H), 4.77 (d, J=6.3 Hz, 1H), 5.05-5.20 (m, 2H), 5.53 (brs, 1H), 5.74-5.91 (m, 1H), 7.02 (s, 2H), 7.07-7.16 (m, 1H), 7.40-7.76 (m, 2H); LCMS (ESI) calc'd for $C_{18}H_{22}FN_3O_2$ $[M+H]^+$: 332.2, found: 332.2.

Step 3: Preparation of (S)-tert-butyl 2-(1-((tert-butoxycarbonyl)amino) but-3-en-1-yl)-4-(4-fluorophenyl)-1H-imidazole-1-carboxylate (A18_D): (S)-tert-butyl (1-(4-(4-fluorophenyl)-1H-imidazol-2-yl)but-3-en-1-yl)carbamate (A18_C, 0.5 g, 1.51 mmol) was dissolved in 8.0 mL DCM, then the solution was cooled down to 0° C., then the solution of $(Boc)_2O$ (0.35 mL, 1.51 mmol) in 2.0 DCM was dropwise added. Subsequently DMAP (20 mg, 0.16 mmol) was added. The mixture was stirred at 0° C. for 1 h. 5 ml water was added, and it was extracted with EtOAc. The organic phase was washed with brine and dried with anhydrous $Na_2SO_4$. The crude product obtained after concentration was purified by silica gel chromatography (10% EtOAc in petroleum ether) to give the target compound (A18_D). $^1$H NMR (400 MHz, $CDCl_3$) δ 1.21 (s, 9H), 1.41 (s, 9H), 2.19-2.32 (m, 1H), 2.37-2.50 (m, 1H), 4.81 (s, 2H) 5.26-5.36 (m, 1H) 5.41-5.60 (m, 2H), 6.77-6.89 (m, 2H), 7.02 (s, 1H), 7.43-7.57 (m, 2H); LCMS (ESI) calc'd for $C_{23}H_{30}FN_3O_4$ $[M+H]^+$: 432.1, found: 432.1.

Step 4: Preparation of (S,E)-tert-butyl 2-(1-((tert-butoxycarbonyl)amino)-7-oxodec-3-en-1-yl)-4-(4-fluorophenyl)-1H-imidazole-1-carboxylate (A18_E): (S)-tert-butyl2-(1-((tert-butoxycarbonyl)amino)but-3-en-1-yl)-4-(4-fluorophenyl)-1H-imidazole-1-carboxylate (A18_D, 300 mg, 0.7 mmol) and oct-7-en-4-one (175 mg, 1.39 mmol) were dissolved in 7 mL degassed toluene, then Zhan's catalyst (25.5 mg, 34.76 μmol) was added under $N_2$. The mixture was stirred at 60° C. for 16 h. The solvent was removed by evaporator and the crude product was purified by silica gel chromatography (5% EtOAc in petroleum ether) to afford a mixture of mono-Boc and di-Boc product (A18_E) which was used directly for the next step without further purification. LCMS (ESI) calc'd for $C_{29}H_{40}FN_3O_5$ $[M+H]^+$: 530.3, found: 530.2.

Step 5: Preparation of (S,E)-10-amino-10-(4-(4-fluorophenyl)-1H-imidazol-2-yl)dec-7-en-4-one (A18_F): (S,E)-tert-butyl 2-(1-((tert-butoxycarbonyl)amino)-7-oxodec-3-en-1-yl)-4-(4-fluorophenyl)-1H-imidazole-1-carboxylate and its de-Boc product (mixture, 150 mg) were dissolved in 3.0 mL DCM, then 0.3 mL TFA was added dropwise. The mixture was stirred at 25° C. for 5 h. Afterwards it was quenched with saturated $NaHCO_3$ at 0° C., and extracted with DCM three times. The combined organic phase was washed with brine and dried with anhydrous $Na_2SO_4$. The solvent was removed by evaporator to give the crude product (A18_F). LCMS (ESI) calc'd for $C_{19}H_{24}FN_3O$ $[M+H]^+$: 330.2, found: 330.1.

Step 6: Preparation of (S)-10-amino-10-(4-(4-fluorophenyl)-1H-imidazol-2-yl)decan-4-one (A18): The crude (S,E)-10-amino-10-(4-(4-fluorophenyl)-1H-imidazol-2-yl)dec-7-en-4-one (A18_F, 100 mg) was dissolved in 3.0 mL MeOH, then 10% Pd/C (10 mg) was added. The mixture was stirred under $H_2$ at 25° C. for 16 h. Afterwards it was filtered on diatomite and the filtrate was concentrated to give the target product (A18) which was directly used for the next step without further purification. LCMS (ESI) calc'd for $C_{19}H_{26}FN_3O$ $[M+H]^+$: 332.2, found: 332.2.

The following intermediates were prepared using similar procedures as described for intermediate A16

| Intermediate ID | Structures | Observed $[M + H]^+$ |
| --- | --- | --- |
| A19 | 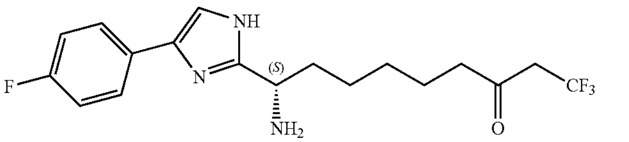 | 372.2 |

-continued

| Intermediate ID | Structures | Observed [M + H]$^+$ |
| --- | --- | --- |
| A20 | 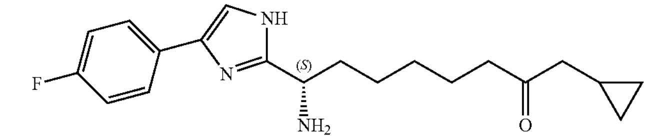 | 344.1 |
| A30 | 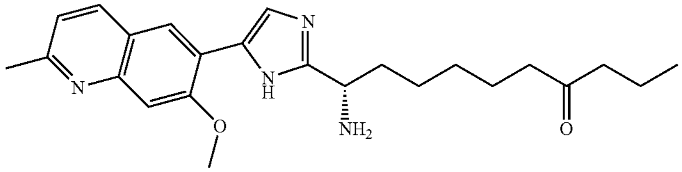 [SMILES: CCCC(=O)CCCCC[C@H](N)c1ncc(-c2cc3ccc(C)nc3cc2OC)[nH]1] | 409.2 |

Example 11

Preparation of Intermediate A21

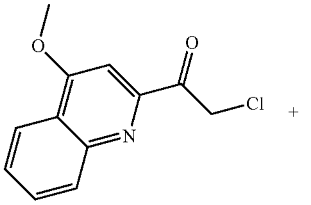

A21_A

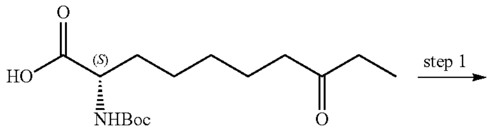

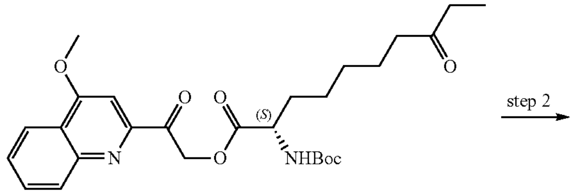

A21_B

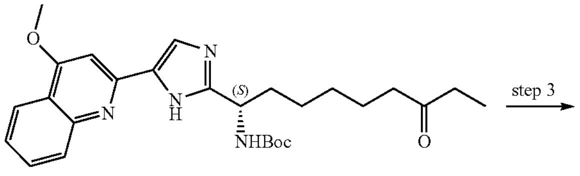

A21_C

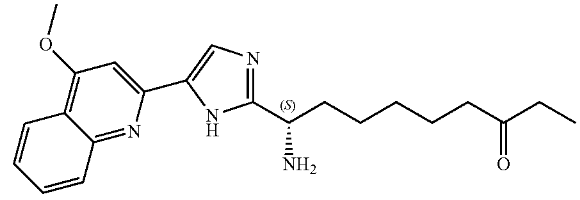

A21

Step 1: Preparation of (S)-2-(4-methoxyquinolin-2-yl)-2-oxoethyl 2-((tert-butoxycarbonyl)amino)-8-oxodecanoate (A21_B): 2-chloro-1-(4-methoxyquinolin-2-yl)ethanone (A21_A, 496 mg, 2.105 mmol) was added to a stirred mixture of (S)-2-((tert-butoxycarbonyl)amino)-8-oxodecanoic acid (Synthesis, 2006, 12, 2069-2073, 692 mg, 2.296 mmol) and DIPEA (1.2 mL, 6.87 mmol) in DMF (5 mL) at rt and the mixture was stirred at 60° C. for 3 h. The mixture was diluted with water (20 mL), extracted with ethyl acetate (3×20 mL). The combined organic fractions were washed with water (3×8 mL) and brine (saturated, 10 mL), dried ($Na_2SO_4$), filtered and the solvent was evaporated under reduced pressure. The residue was purified by preparative TLC on silica gel, eluting with petroleum ether/EtOAc=3:1 to give (S)-2-(4-methoxyquinolin-2-yl)-2-oxoethyl 2-((tert-butoxycarbonyl)amino)-8-oxodecanoate (A21_B). LCMS (ESI) calc'd for $C_{27}H_{36}N_2O_7$ [M+H]$^+$: 501.5, found: 501.3.

Step 2: Preparation of (S)-tert-butyl (1-(5-(4-methoxyquinolin-2-yl)-1H-imidazol-2-yl)-7-oxononyl)carbamate (A21_C): A mixture of (S)-2-(4-methoxyquinolin-2-yl)-2-oxoethyl 2-((tert-butoxycarbonyl)amino)-8-oxodecanoate (A21_B, 330 mg, 0.659 mmol) and ammonium acetate (780 mg, 10.12 mmol) in xylene (18 mL) was stirred at 140° C. for 2 h. The mixture was concentrated in vacuo. The residue was purified by preparative TLC on silica gel, eluting with DCM/MeOH=10:1 to give (S)-tert-butyl (1-(5-(4-methoxyquinolin-2-yl)-1H-imidazol-2-yl)-7-oxononyl)carbamate (A21_C). LCMS (ESI) calc'd for $C_{27}H_{36}N_4O_4$ [M+H]$^+$: 481.5, found: 481.3.

$^1$H NMR (400 MHz, $CDCl_3$) δ 8.07 (d, J=8.22 Hz, 1H), 7.88 (brs, 1H), 7.55-7.64 (m, 1H), 7.37 (d, J=7.43 Hz, 1H), 6.92 (d, J=10.56 Hz, 1H), 5.05 (brs, 1H), 4.05 (brs, 2H), 2.28-2.39 (m, 3H), 1.75-1.91 (m, 2H), 1.53 (d, J=8.61 Hz, 4H), 1.29-1.44 (m, 12H), 0.97 (t, J=7.24 Hz, 2H).

Step 3: Preparation of (S)-9-amino-9-(5-(4-methoxyquinolin-2-yl)-1H-imidazol-2-yl)nonan-3-one (A21): TFA (0.5 ml, 6.49 mmol) was added to a mixture of (S)-tert-butyl (1-(5-(4-methoxyquinolin-2-yl)-1H-imidazol-2-yl)-7-oxononyl)carbamate (A21_C, 180 mg, 0.375 mmol) in DCM (5 ml) at rt and the mixture was stirred at rt for 3 h. The solvent was evaporated under reduced pressure to give (S)-9-amino-9-(5-(4-methoxyquinolin-2-yl)-1H-imidazol-2-yl)nonan-3-one, TFA salt (A21) which was used to the next step without further purification. LCMS (ESI) calc'd for $C_{22}H_{28}N_4O_2$ [M+H]$^+$: 381.4, found: 381.2.

Example 12

Preparation of Intermediate A22

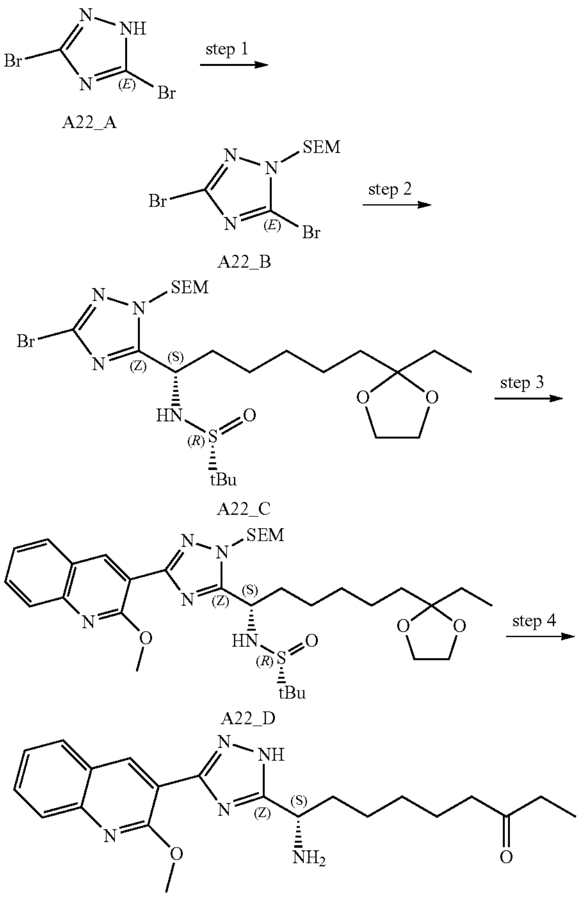

A22

Step 1: Preparation of 3,5-dibromo-1-((2-(trimethylsilyl)ethoxy)methyl)-1H-1,2,4-triazole (A22_B): NaH (1.058 g, 26.4 mmol) was added to a stirred mixture of 3,5-dibromo-1H-1,2,4-triazole (A22_A, 5.0 g, 22.04 mmol) in DMF (30.0 mL) at 0-5° C. and the mixture was stirred at 0-5° C. for 30 min. SEM-Cl (4.10 mL, 23.14 mmol) was added. The mixture was stirred at 0° C.-rt for 12 h. The mixture was cooled to 0-5° C., aqueous $NH_4Cl$ (saturated, 60 mL) was added and the mixture was extracted with ethyl acetate (3×50 mL). The combined organic fractions were washed with water (3×50 mL), brine (saturated, 60 mL), dried ($Na_2SO_4$), filtered and the solvent was evaporated under reduced pressure. The residue was purified by silica gel column flash chromatography, eluting with petroleum ether/EtOAc=100:1-5:1 to give 3,5-dibromo-1-((2-(trimethylsilyl)ethoxy)methyl)-1H-1,2,4-triazole (A22_B). LCMS (ESI) calc'd for $C_8H_{15}Br_2N_3OSi$ $[M+H]^+$: 355.9, found: 357.9. $^1H$ NMR (400 MHz, $CDCl_3$) δ 5.46 (s, 2H), 3.62-3.74 (m, 2H), 0.88-1.00 (m, 2H), 0.01 (s, 9H).

Step 2: Preparation of (R)—N—((S)-1-(3-bromo-1-((2-(trimethylsilyl)ethoxy)methyl)-1H-1,2,4-triazol-5-yl)-6-(2-ethyl-1,3-dioxolan-2-yl)hexyl)-2-methylpropane-2-sulfinamide (A22_C): nButyllithium (1.1 ml, 2.75 mmol) was added to a stirred mixture of 3,5-dibromo-1-((2-(trimethylsilyl)ethoxy)methyl)-1H-1,2,4-triazole (A22_B, 900 mg, 2.52 mmol) in THF (10 mL) at −78° C. and the mixture was stirred at −78° C. for 1 h under $N_2$. Then (R,E)-N-(6-(2-ethyl-1,3-dioxolan-2-yl) hexylidene)-2-methylpropane-2-sulfinamide (A1, 700 mg, 2.307 mmol) in THF (1 mL) was added to the mixture and the mixture was stirred at −78° C. for 2 h. The mixture was concentrated. The residue was purified by silica gel column flash chromatography, eluting with petroleum ether/EtOAc=100:1-2:1 to give (R)—N—((S)-1-(3-bromo-1-((2-(trimethylsilyl)ethoxy)methyl)-1H-1,2,4-triazol-5-yl)-6-(2-ethyl-1,3-dioxolan-2-yl)hexyl)-2-methylpropane-2-sulfinamide (A22_C), and (R)—N—((R)-1-(3-bromo-1-((2-(trimethylsilyl)ethoxy)methyl)-1H-1,2,4-triazol-5-yl)-6-(2-ethyl-1,3-dioxolan-2-yl)hexyl)-2-methylpropane-2-sulfinamide. LCMS (ESI) calc'd for $C_{23}H_{45}BrN_4O_4SSi$ $[M+H]^+$: 581.2, found: 583.1.

Step 3: Preparation of (R)—N—((S)-6-(2-ethyl-1,3-dioxolan-2-yl)-1-(3-(2-methoxyquinolin-3-yl)-1-((2-(trimethylsilyl)ethoxy)methyl)-1H-1,2,4-triazol-5-yl)hexyl)-2-methylpropane-2-sulfinamide (A22_D): $PdCl_2$(DTBPF) (16 mg, 0.025 mmol) was added to a stirred mixture of (2-methoxyquinolin-3-yl)boronic acid (100 mg, 0.493 mmol), (R)—N—((S)-1-(3-bromo-1-((2-(trimethylsilyl)ethoxy)methyl)-1H-1,2,4-triazol-5-yl)-6-(2-ethyl-1,3-dioxolan-2-yl)hexyl)-2-methylpropane-2-sulfinamide (A22_C, 300 mg, 0.516 mmol) and $K_3PO_4$ (314 mg, 1.478 mmol) in THF (6.0 mL) and water (0.5 mL) at room temperature. The mixture was stirred at 65° C. for 12 h under $N_2$. The mixture was concentrated, the residue was purified by silica gel column flash chromatography, eluting with petroleum ether/EtOAc=1:1 to give (R)—N—((S)-6-(2-ethyl-1,3-dioxolan-2-yl)-1-(3-(2-methoxyquinolin-3-yl)-1-((2-(trimethylsilyl)ethoxy)methyl)-1H-1,2,4-triazol-5-yl)hexyl)-2-methylpropane-2-sulfinamide (A22_D). LCMS (ESI) calc'd for $C_{33}H_{53}N_5O_5SSi$ $[M+H]^+$: 660.4, found: 660.1.

Step 4: Preparation of (S)-9-amino-9-(3-(2-methoxyquinolin-3-yl)-1H-1,2,4-triazol-5-yl) nonan-3-one (A22): HCl/MeOH (4M, 0.7 ml, 2.80 mmol) was added to a stirred mixture of (R)—N—((S)-6-(2-ethyl-1,3-dioxolan-2-yl)-1-(3-(2-methoxyquinolin-3-yl)-1-((2-(trimethylsilyl)ethoxy)methyl)-1H-1,2,4-triazol-5-yl)hexyl)-2-methylpropane-2-sulfinamide (A22_D, 300 mg, 0.455 mmol) in MeOH (10.0 mL) at room temperature and the mixture was stirred at room temperature for 2 h. The mixture was stirred at room temperature for another 3 h. The mixture was quenched with aqueous $NaHCO_3$(saturated, 20 mL) and the mixture was extracted with ethyl acetate (3×25 mL). The combined organic fractions were washed with brine (saturated, 25 mL), dried ($Na_2SO_4$), filtered and the solvent was evaporated under reduced pressure to give crude (S)-9-amino-9-(3-(2-methoxyquinolin-3-yl)-1H-1,2,4-triazol-5-yl) nonan-3-one (A22) which was used to the next step without further purification. LCMS (ESI) calc'd for $C_{21}H_{27}N_5O_2$ $[M+H]^+$: 382.2, found: 382.2.

Example 13

Preparation of Intermediate A23

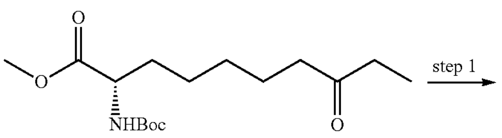

A23_A

-continued

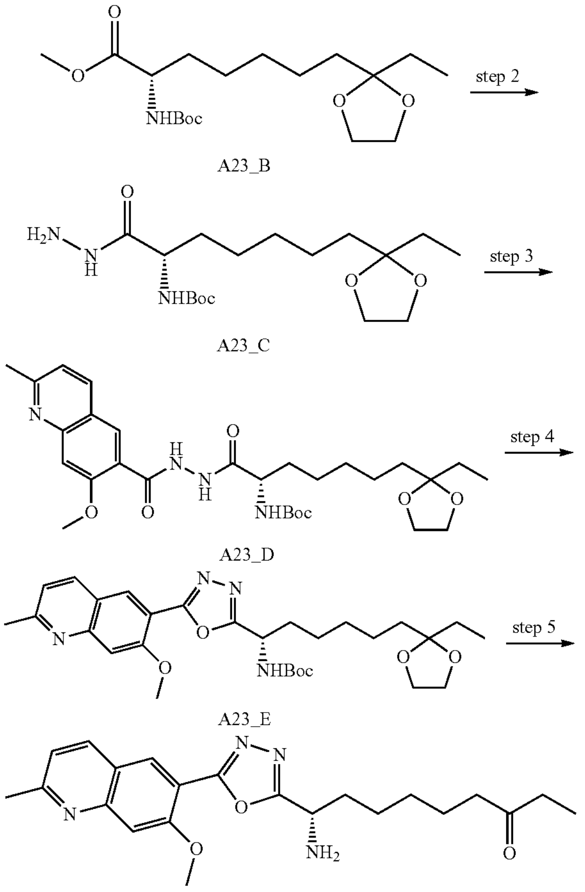

A23

Step 1: Preparation of (S)-methyl 2-((tert-butoxycarbonyl)amino)-7-(2-ethyl-1,3-dioxolan-2-yl)heptanoate (A23_B): TsOH (0.055 g, 0.317 mmol)) and ethane-1,2-diol (3.94 g, 63.4 mmol) were added to a stirred mixture of (S)-methyl 2-((tert-butoxycarbonyl)amino)-8-oxodecanoate (A23_A, 2 g, 6.34 mmol) in toluene (50 mL) at room temperature and the mixture was heated with stirring at 130° C. for 18 h. The mixture was cooled to room temperature, aqueous $NaHCO_3$ (saturated, 20 mL) was added, and the mixture was extracted with ethyl acetate (2×20 mL). The combined organic fractions were washed with brine (saturated, 2×20 mL), dried ($Na_2SO_4$), filtered and the solvent was evaporated under reduced pressure. The residue was purified by silica gel column flash chromatography, eluting with petroleum ether/EtOAc=80:20 to give (S)-methyl 2-((tert-butoxycarbonyl)amino)-7-(2-ethyl-1,3-dioxolan-2-yl)heptanoate (A23-B). $^1$H NMR (400 MHz, $CDCl_3$) δ 4.99 (d, J=7.7 Hz, 1H), 4.29 (d, J=5.1 Hz, 1H), 3.93 (s, 4H), 3.74 (s, 3H), 2.45-2.38 (m, 1H), 1.84-1.73 (m, 0.5H), 1.66-1.55 (m, 6H), 1.45 (s, 9H), 1.42-1.25 (m, 7H), 1.05 (t, J=7.4 Hz, 0.5H), 0.90 (t, J=7.5 Hz, 3H).

Step 2: Preparation of (S)-tert-butyl (7-(2-ethyl-1,3-dioxolan-2-yl)-1-hydrazinyl-1-oxoheptan-2-yl)carbamate (A23_C): Hydrazine (1.468 g, 38.9 mmol) was added to a stirred mixture of (S)-methyl 2-((tert-butoxycarbonyl)amino)-7-(2-ethyl-1,3-dioxolan-2-yl)heptanoate (A23_B, 1.4 g, 3.89 mmol) in MeOH (15 mL) at room temperature and the mixture was heated with stirring at 60° C. overnight. The mixture was cooled to room temperature. Water (50 mL) was added and the mixture was extracted with ethyl acetate (2×50 mL). The combined organic fractions were washed with water (2×50 mL), dried ($Na_2SO_4$), filtered and the solvent was evaporated under reduced pressure. The residue was purified by silica gel column flash chromatography, eluting with DCM/MeOH=40:1 to give (S)-tert-butyl (7-(2-ethyl-1,3-dioxolan-2-yl)-1-hydrazinyl-1-oxoheptan-2-yl) carbamate (A23_C). $^1$H NMR (400 MHz, $CDCl_3$) δ 7.40 (brs, 1H), 5.29 (s, 1H), 4.80 (s, 1H), 3.92 (s, 4H), 1.80 (m, 1H), 1.55-1.63 (m, 5H), 1.43 (s, 9H), 1.32 (brs, 5H), 0.88 (t, J=7.2 Hz, 3H).

Step 3: Preparation of (S)-tert-butyl (7-(2-ethyl-1,3-dioxolan-2-yl)-1-(2-(7-methoxy-2-methylquinoline-6-carbonyl)hydrazinyl)-1-oxoheptan-2-yl)carbamate (A23_D): HATU (473 mg, 1.243 mmol) and DIEA (0.434 ml, 2.486 mmol) were added to a stirred mixture of 7-methoxy-2-methylquinoline-6-carboxylic acid (180 mg, 0.829 mmol) in DMF (4 mL) at room temperature and the mixture was stirred at rt for 10 min. Then (S)-tert-butyl (7-(2-ethyl-1,3-dioxolan-2-yl)-1-hydrazinyl-1-oxoheptan-2-yl)carbamate (A21_C, 298 mg, 0.829 mmol) was added and the mixture was stirred at rt for 1 h. The mixture was added to water (20 mL) and was extracted with ethyl acetate (40 mL). The combined organic fractions were washed with brine (2×20 mL), dried ($Na_2SO_4$), filtered and the solvent was evaporated under reduced pressure. The residue was purified by silica gel column flash chromatography, eluting with petroleum ether/EtOAc=1:3 to give (S)-tert-butyl (7-(2-ethyl-1,3-dioxolan-2-yl)-1-(2-(7-methoxy-2-methylquinoline-6-carbonyl)hydrazinyl)-1-oxoheptan-2-yl)carbamate (A23_D). LCMS (ESI) calc'd for $C_{29}H_{42}N_4O_7$ $[M+H]^+$: 559.3, found: 559.3.

Step 4: Preparation of (S)-tert-butyl (6-(2-ethyl-1,3-dioxolan-2-yl)-1-(5-(7-methoxy-2-methylquinolin-6-yl)-1,3,4-oxadiazol-2-yl)hexyl)carbamate (A23_E): Burgess reagent (308 mg, 1.289 mmol) was added to a stirred mixture of (S)-tert-butyl (7-(2-ethyl-1,3-dioxolan-2-yl)-1-(2-(7-methoxy-2-methylquinoline-6-carbonyl)hydrazinyl)-1-oxoheptan-2-yl)carbamate (A23_D, 360 mg, 0.644 mmol) in THF (5 mL). The mixture was heated at 50° C. for 2 h, and the mixture was stirred overnight at room temperature. The mixture was filtered and the filter cake was washed with DCM (20 mL). The filtrate was concentrated to dryness. The residue was purified by silica gel column flash chromatography, eluting with DCM:EtOAc=3:1 to give (S)-tert-butyl (6-(2-ethyl-1,3-dioxolan-2-yl)-1-(5-(7-methoxy-2-methylquinolin-6-yl)-1,3,4-oxadiazol-2-yl)hexyl)carbamate (A23_E). LCMS (ESI) calc'd for $C_{29}H_{40}N_4O_6$ $[M+H]^+$: 541.3, found: 541.3.

Step 5: Preparation of (S)-9-amino-9-(5-(7-methoxy-2-methylquinolin-6-yl)-1,3,4-oxadiazol-2-yl)nonan-3-one (A23): HCl/MeOH (4M, 0.139 mL, 0.555 mmol) was added to a stirred mixture of (S)-tert-butyl (6-(2-ethyl-1,3-dioxolan-2-yl)-1-(5-(7-methoxy-2-methylquinolin-6-yl)-1,3,4-oxadiazol-2-yl)hexyl)carbamate (A23_E, 50 mg, 0.092 mmol) in MeOH (1 mL) and the mixture was stirred at rt for 0.5 h. The solution was concentrated to give crude compound which was used to the next step without further purification. LCMS (ESI) calc'd for $C_{22}H_{28}N_4O_3$ $[M+H]^+$: 397.2, found: 397.2.

The following intermediate was prepared using similar procedures as described for intermediate A23.

| Intermediate ID | Structures | Observed $[M + H]^+$ |
|---|---|---|
| A29 | 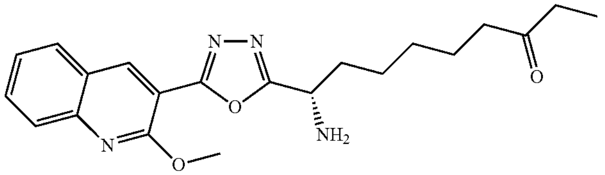 [SMILES: CCC(=O)CCCCC[C@H](N)c1nnc(-c2cc3ccccc3nc2OC)o1] | 383.3 |

Example 14

Preparation of Intermediate A24

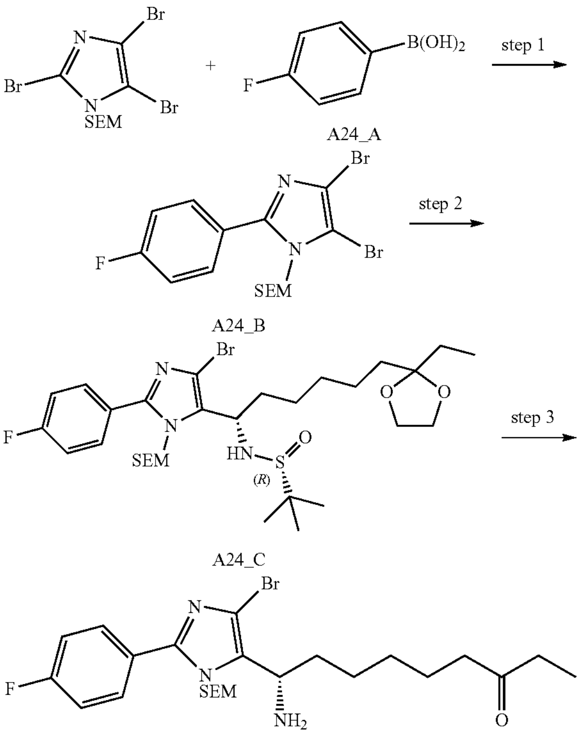

A24

Step 1: Preparation of 4,5-dibromo-2-(4-fluorophenyl)-1-((2-(trimethylsilyl)ethoxy)methyl)-1H-imidazole (A24_B): $Pd(PPh_3)_4$ (0.133 g, 0.115 mmol) was added to a stirred mixture of potassium carbonate (0.635 g, 4.60 mmol), (4-fluorophenyl)boronic acid (0.354 g, 2.53 mmol), 2,4,5-tribromo-1-((2-(trimethylsilyl)ethoxy)methyl)-1H-imidazole (A24_A, 1.00 g, 2.299 mmol) in toluene (10 mL) and MeOH (2 mL) at room temperature and the mixture was stirred at 65° C. for 24 h under $N_2$. The mixture was cooled to room temperature, water (50 mL) was added and the mixture was extracted with ethyl acetate (3×40 mL). The combined organic fractions were washed with brine (saturated, 3×20 mL), dried ($Na_2SO_4$), filtered and the solvent was evaporated under reduced pressure. The residue was purified by silica gel column flash chromatography, eluting with pet.ether/EtOAc=1/0~10/1 to give 4,5-dibromo-2-(4-fluorophenyl)-1-((2-(trimethylsilyl)ethoxy)methyl)-1H-imidazole (A24_B). $^1H$ NMR (400 MHz, $CDCl_3$) δ 7.81 (dd, J=5.40, 8.49 Hz, 2H), 7.15 (t, J=8.60 Hz, 2H), 5.28 (s, 2H), 3.70 (t, J=8.16 Hz, 2H), 0.97 (t, J=8.27 Hz, 2H), 0.02 (s, 9H).

Step 2: Preparation of (R)—N—((S)-1-(4-bromo-2-(4-fluorophenyl)-1-((2-(trimethylsilyl)ethoxy)methyl)-1H-imidazol-5-yl)-6-(2-ethyl-1,3-dioxolan-2-yl)hexyl)-2-methylpropane-2-sulfinamide (A24_C): $BF_3 \cdot OEt_2$ (3.10 mL, 24.43 mmol) was added to a stirred mixture of 4,5-dibromo-2-(4-fluorophenyl)-1-((2-(trimethylsilyl)ethoxy)methyl)-1H-imidazole (A24_B, 10.0 g, 22.21 mmol) in THF (100 mL) at −78° C. and nbutyllithium (11.55 mL, 28.9 mmol) was added to the mixture slowly under $N_2$. The mixture was stirred at −78° C. for 1 h. Then (R,E)-N-(6-(2-ethyl-1,3-dioxolan-2-yl)hexylidene)-2-methyl propane-2-sulfinamide (A1, 7.41 g, 24.43 mmol) in THF (10 mL) was added to the mixture slowly and the mixture was stirred at −78° C. for 2 h. Aqueous $NH_4Cl$ (saturated, 50 mL) and water (50 mL) was added and the mixture was extracted with ethyl acetate (3×75 mL). The combined organic fractions were washed with brine (saturated, 50 mL), dried ($Na_2SO_4$), filtered and the solvent was evaporated under reduced pressure. The residue was purified by silica gel flash chromatography (ISCORF75; Sepa flash column), eluting with petroleum ether/EtOAc=10/1~3/1 to give and (R)—N—((S)-1-(4-bromo-2-(4-fluorophenyl)-1-((2-(trimethylsilyl)ethoxy)methyl)-1H-imidazol-5-yl)-6-(2-ethyl-1,3-dioxolan-2-yl)hexyl)-2-methylpropane-2-sulfinamide (7.0 g, crude). The crude product was purified by preparative HPLC (reverse phase C-18 column), eluting with acetonitrile/water, to give (R)—N—((S)-1-(4-bromo-2-(4-fluorophenyl)-1-((2-(trimethylsilyl)ethoxy)methyl)-1H-imidazol-5-yl)-6-(2-ethyl-1,3-dioxolan-2-yl)hexyl)-2-methylpropane-2-sulfinamide (A24_C). LCMS (ESI) calc'd for $C_{30}H_{49}BrFN_3O_4SSi$ $[M+H]^+$: 674.2, found: 676.3.

Step 3: Preparation of (S)-9-amino-9-(4-bromo-2-(4-fluorophenyl)-1-((2-(trimethylsilyl)ethoxy)methyl)-1H-imidazol-5-yl)nonan-3-one (A24): HCl/MeOH (0.608 mL, 7.41 mmol) was added to a stirred mixture of (R)—N—((S)-1-(4-bromo-2-(4-fluorophenyl)-1-((2-(trimethylsilyl)ethoxy)methyl)-1H-imidazol-5-yl)-6-(2-ethyl-1,3-dioxolan-2-yl)hexyl)-2-methylpropane-2-sulfinamide (A24_C, 5.0 g, 7.41 mmol) in MeOH (50 mL) at 30° C. and the mixture was stirred at 30° C. for 10 min. Aqueous $NaHCO_3$(saturated, 10 mL) was added and the mixture was extracted with DCM (3×50 mL). The combined organic fractions were washed with brine (50 mL), dried ($Na_2SO_4$), filtered and the solvent was evaporated under reduced pressure. The residue was purified by silica gel flash chromatography (ISCORF75; Sepa flash column), eluting with petroleum ether/EtOAc=3/1~1/1 to give (S)-9-amino-9-(4-bromo-2-(4-fluorophenyl)-1-((2-(trimethylsilyl)ethoxy)methyl)-1H-imidazol-5-yl)nonan-3-one (A24). LCMS (ESI) calc'd for $C_{24}H_{37}BrFN_3O_2Si$ $[M+H]^+$: 526.3, found: 528.3. $^1H$ NMR (400 MHz, $CDCl_3$) δ 7.62-7.67 (m, 2H), 7.11-7.17 (m, 2H), 5.14-5.50 (m, 2H), 4.09-4.19 (m, 1H), 3.42-3.48 (m, 2H), 2.36-2.44 (m, 4H), 1.80-2.03 (m, 2H), 1.55-1.60 (m, 2H), 1.23-1.38 (m, 5H), 1.01-1.06 (m, 3H), 0.87-0.92 (m, 2H), −0.02-0.00 (m, 9H).

Example 15

Preparation of Intermediate A25

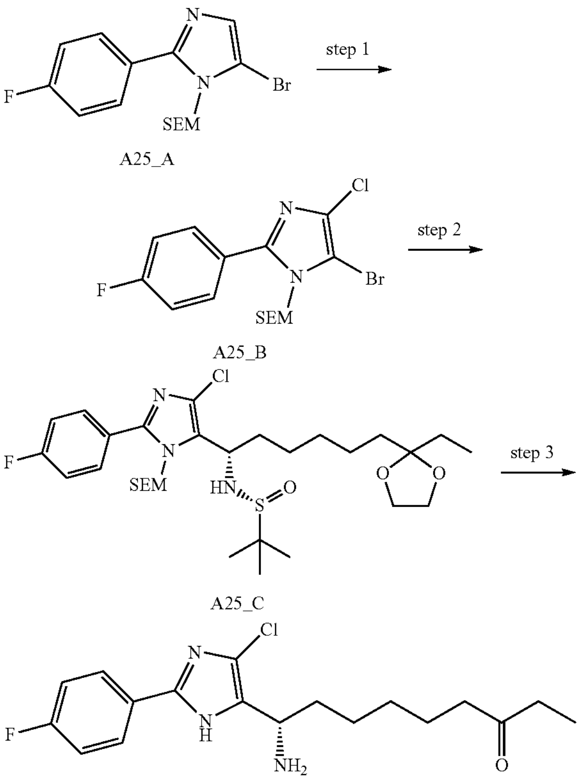

A25_A

A25_B

A25_C

A25

Step 1: Preparation of 5-bromo-4-chloro-2-(4-fluorophenyl)-1-((2-(trimethylsilyl)ethoxy) methyl)-1H-imidazole (A25_B): NCS (281 mg, 2.101 mmol) was added to a stirred mixture of 5-bromo-2-(4-fluorophenyl)-1-((2-(trimethylsilyl)ethoxy)methyl)-1H-imidazole (A25_A, 600 mg, 1.616 mmol) in THF (15 mL) at rt and the resulting mixture was stirred at rt for 4 h. The solvent was evaporated under reduced pressure. The residue was purified by silica gel flash chromatography (ISCORF75; Sepa flash column), eluting with petroleum ether/EtOAc=0~10% to give the title compound (A25_B). LCMS (ESI) calc'd for $C_{15}H_{19}BrClFN_2OSi$ $[M+H]^+$: 405.0, found: 407.0.

Step 2: Preparation of (R)—N—((S)-1-(4-chloro-2-(4-fluorophenyl)-1-((2-(trimethylsilyl) ethoxy)methyl)-1H-imidazol-5-yl)-6-(2-ethyl-1,3-dioxolan-2-yl)hexyl)-2-methylpropane-2-sulfinamide (A25_C): n-BuLi (0.71 mL, 1.775 mmol) was added dropwise to a stirred mixture of 5-bromo-4-chloro-2-(4-fluorophenyl)-1-((2-(trimethylsilyl)ethoxy) methyl)-1H-imidazole (A25_B, 550 mg, 1.355 mmol) in THF (10 mL) at −78° C. under $N_2$. The mixture was stirred at −78° C. for 1 h. Then a solution of (R,E)-N-(6-(2-ethyl-1,3-dioxolan-2-yl)hexylidene)-2-methylpropane-2-sulfinamide (A1, 452 mg, 1.491 mmol) in THF (5 mL) was added slowly and the mixture was stirred at −78° C. for 2 h. Aqueous $NH_4Cl$ (saturated, 20 mL) was added and the mixture was extracted with ethyl acetate (3×30 mL). The combined organic fractions were washed with brine (saturated, 30 mL), dried ($Na_2SO_4$), filtered and the solvent was evaporated under reduced pressure. The residue was purified by silica gel flash chromatography (ISCORF75; Sepa flash column), eluting with petroleum ether/EtOAc=10/1~1/1 to give the title compound (A25_C). LCMS (ESI) calc'd for $C_{30}H_{49}ClFN_3O_4SSi$ $[M+H]^+$: 630.3, found: 630.3.

Step 3: Preparation of (S)-9-amino-9-(4-chloro-2-(4-fluorophenyl)-1H-imidazol-5-yl)nonan-3-one hydrochloride (A25): The mixture of (R)—N—((S)-1-(4-chloro-2-(4-fluorophenyl)-1-((2-(trimethylsilyl)ethoxy)methyl)-1H-imidazol-5-yl)-6-(2-ethyl-1,3-dioxolan-2-yl)hexyl)-2-methylpropane-2-sulfinamide (A25_C, 350 mg, 0.555 mmol) and HCl/MeOH (10 mL, 40.0 mmol) was stirred at rt for 4 h. The mixture was concentrated under reduced pressure to give HCl salt of the title compound (A25) which was used to the next step without further purification. LCMS (ESI) calc'd for $C_{18}H_{23}ClFN_3O$ $[M+H]^+$: 352.2, found: 352.1.

Example 16

Preparation of Intermediate A26

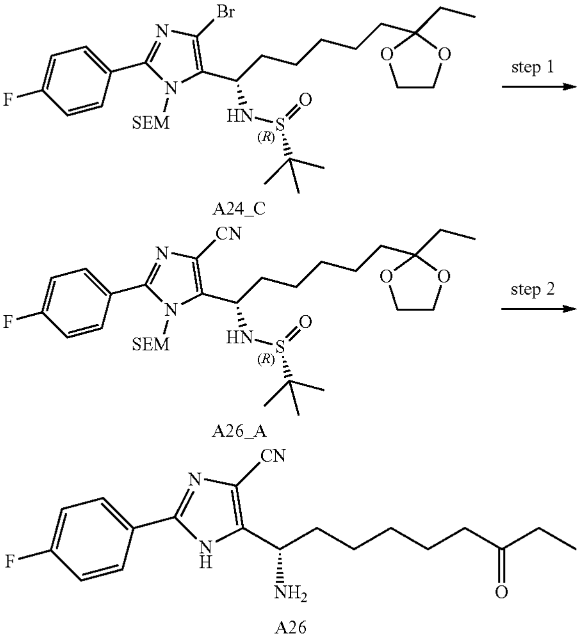

A24_C

A26_A

A26

Step 1: Preparation of (R)—N—((S)-1-(4-cyano-2-(4-fluorophenyl)-1-((2-(trimethylsilyl)ethoxy)methyl)-1H-imidazol-5-yl)-6-(2-ethyl-1,3-dioxolan-2-yl)hexyl)-2-methylpropane-2-sulfinamide (A26_A): Brettphos (16 mg, 0.030 mmol) was added to a stirred mixture of potassium ferrocyanide trihydrate (69 mg, 0.163 mmol), allylpalladium chloride dimer (5 mg, 0.014 mmol), (R)—N—((S)-1-(4-bromo-2-(4-fluorophenyl)-1-((2-(trimethylsilyl)ethoxy) methyl)-1H-imidazol-5-yl)-6-(2-ethyl-1,3-dioxolan-2-yl) hexyl)-2-methylpropane-2-sulfinamide (A24_C, 200 mg, 0.296 mmol) in DMA (2 mL) and water (1 mL), the mixture was stirred at 100° C. for 18 h under $N_2$. The mixture was cooled to room temperature, water (5 mL) was added and the mixture was extracted with DCM (3×5 mL). The combined organic fractions were washed with brine (saturated, 5 mL), dried ($Na_2SO_4$), filtered and the solvent was evaporated under reduced pressure. The residue was purified by silica gel flash chromatography (ISCORF75; Sepa flash column), eluting with petroleum ether/EtOAc=1/2 to give (R)—N—((S)-1-(4-cyano-2-(4-fluorophenyl)-1-((2-(trimethylsilyl)ethoxy)methyl)-1H-imidazol-5-yl)-6-(2-ethyl-1,3-dioxolan-2-yl)hexyl)-2-methylpropane-2-sulfinamide (A26_A). LCMS (ESI) calc'd for $C_{31}H_{49}FN_4O_4SSi$ $[M+H]^+$: 621.3, found: 621.3. $^1H$ NMR (400 MHz, $CDCl_3$) δ 7.66 (dd, J=5.28, 8.41 Hz, 2H), 7.19 (t, J=8.61 Hz, 2H), 5.11-5.38 (m, 2H), 4.62 (d, J=3.13 Hz, 1H), 3.92 (s, 4H), 3.72 (d, J=2.74 Hz, 1H), 3.49 (t, J=8.41 Hz, 2H), 2.16 (d, J=6.65 Hz, 1H), 2.04 (brs, 1H), 1.36 (brs, 6H), 1.19-1.28 (m, 10H), 0.85-1.00 (m, 5H), 0.00 (s, 9H).

Step 2: Preparation of (S)-5-(1-amino-7-oxononyl)-2-(4-fluorophenyl)-1-((2-(trimethylsilyl)ethoxy)methyl)-1H-imidazole-4-carbonitrile (A26): Hydrogen chloride in MeOH (0.05 mL, 0.200 mmol) was added to a stirred mixture of (R)—N—((S)-1-(4-cyano-2-(4-fluorophenyl)-1-((2-(trimethylsilyl)ethoxy)methyl)-1H-imidazol-5-yl)-6-(2-ethyl-1,3-dioxolan-2-yl)hexyl)-2-methylpropane-2-sulfinamide (A26_A, 132 mg, 0.213 mmol) in MeOH (1 mL) at room temperature and the mixture was stirred at 30° C. for 3 h. The reaction mixture was concentrated and another batch of hydrogen chloride/MeOH (0.05 mL, 0.200 mmol) was added, and the mixture was stirred at 30° C. for 3 h. The reaction mixture was concentrated to give crude (S)-5-(1-amino-7-oxononyl)-2-(4-fluorophenyl)-1H-imidazole-4-carbonitrile which was used to next step without further purification. LCMS (ESI) calc'd for $C_{19}H_{23}FN_4O$ $[M+H]^+$: 343.2, found: 343.2.

Example 17

Preparation of Intermediate A27

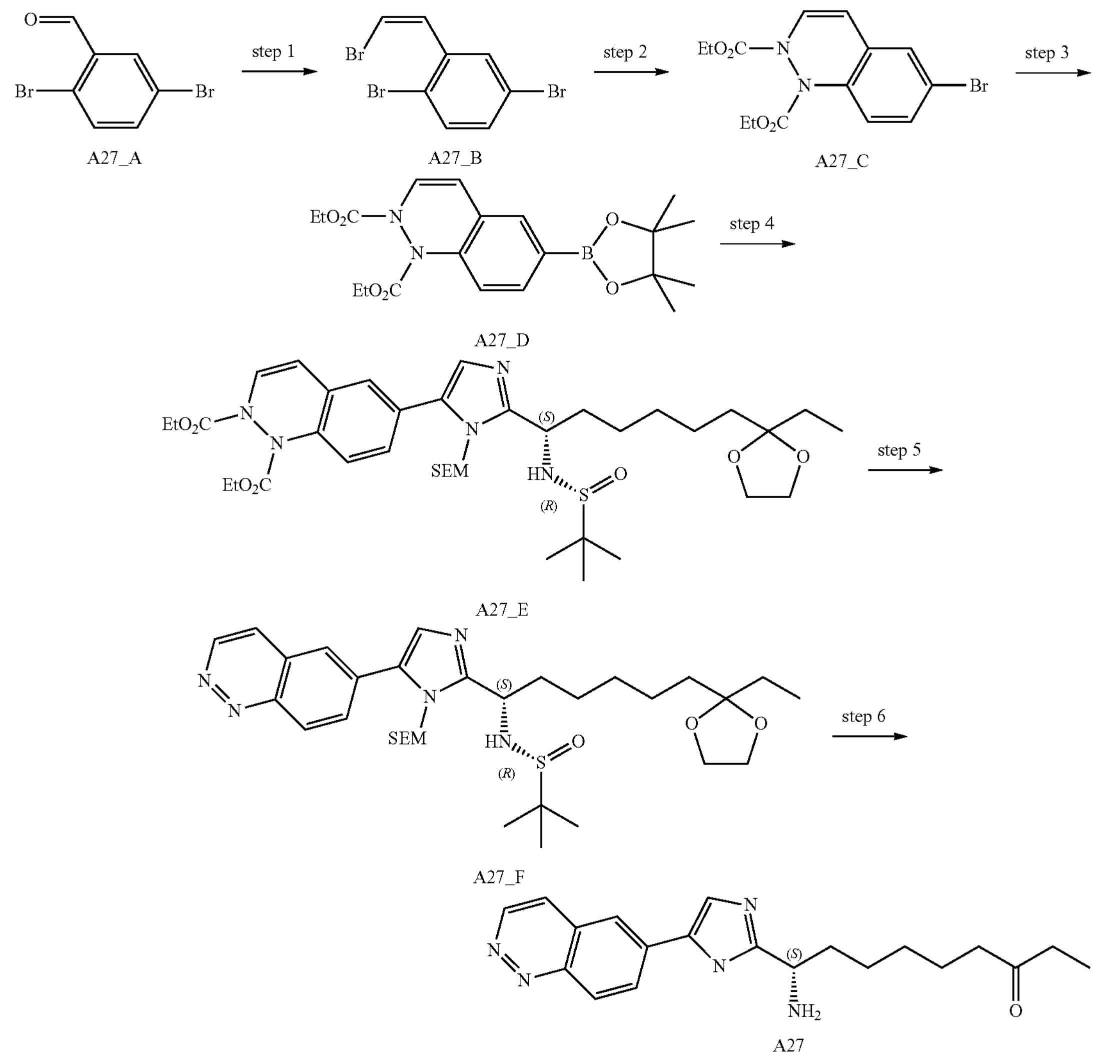

A27_A A27_B A27_C A27_D A27_E A27_F A27

Step 1: (Z)-1,4-dibromo-2-(2-bromovinyl)benzene (A27_B): t-BuOK (0.510 g, 4.55 mmol) was added to a solution of (bromomethyl)triphenylphosphonium bromide (1.983 g, 4.55 mmol) in THF (30 mL) at −78° C. The mixture was stirred for 1 h. Then 2,5-dibromobenzaldehyde (A27_A, 1 g, 3.79 mmol) was added at −78° C. and the reaction was stirred at rt for another 12 h. Aqueous $NH_4Cl$ (saturated, 10 mL) was added and the mixture was extracted with ethyl acetate (20×3 mL). The combined organic fractions were washed with brine (saturated, 10 mL), dried ($Na_2SO_4$), filtered and the solvent was evaporated under reduced pressure. The residue was purified by silica gel column flash chromatography (ISCO®; 12 g SepaFlash® Silica Flash Column, eluent of 0% EtOAc/Petro. Ether gradient @ 40 mL/min) to give (Z)-1,4-dibromo-2-(2-bromovinyl)benzene (A27_B). $^1H$ NMR (400 MHz, $CDCl_3$) δ 7.90 (d, J=1.8 Hz, 1H), 7.45 (d, J=8.6 Hz, 1H), 7.34-7.28 (m, 1H), 7.12 (s, 1H), 6.64 (d, J=8.2 Hz, 1H).

Step 2: diethyl 6-bromocinnoline-1,2-dicarboxylate (A27_C): Diethyl hydrazine-1,2-dicarboxylate (0.517 g, 2.93 mmol) was added to a stirred mixture of copper(I) iodide (0.028 g, 0.147 mmol), $K_2CO_3$ (0.507 g, 3.67 mmol), $N_1$,$N_2$-dimethylethane-1,2-diamine (0.026 g, 0.293 mmol) and (Z)-1,4-dibromo-2-(2-bromovinyl)benzene (A27_B, 0.5 g, 1.467 mmol) in dioxane (5 mL) and water (1 mL), the mixture was degassed and backfilled with $N_2$ three times. The mixture was heated to 90° C. for 10 h. The mixture was cooled and filtered, the filter cake was washed with ethyl acetate (50 mL). The filtrate was concentrated to dryness. The crude product was purified by silica gel column flash chromatography (ISCO®; 12 g SepaFlash® Silica Flash Column, eluent of 0~20% EtOAc/Petro. Ether gradient @ 40 mL/min) to give diethyl 6-bromocinnoline-1,2-dicarboxylate (A27_C). LCMS (ESI) calc'd for $C_{14}H_{15}BrN_2O_4$ $[M+H]^+$: 355.0, 357.0, found: 354.9, 356.9.

Step 3: diethyl 6-(4,4,5,5-tetramethyl-1,3,2-dioxaborolan-2-yl)cinnoline-1,2-dicarboxylate (A27_D): Diethyl 6-bromocinnoline-1,2-dicarboxylate (A27_C, 150 mg, 0.422 mmol) was added to a stirred mixture of Pd(DPPF)$Cl_2$ (30.9 mg, 0.042 mmol), potassium acetate (104 mg, 1.056 mmol) and 4,4,4',4',5,5,5',5'-octamethyl-2,2'-bi(1,3,2-dioxaborolane) (139 mg, 0.549 mmol) in dioxane (5 mL) and water (1 mL), the mixture was degassed and backfilled with $N_2$ three times. The mixture was heated to 90° C. for 10 h. The mixture was cooled and filtered, the filter cake was washed with ethyl acetate (50 mL). The filtrate was concentrated to dryness. The crude product was purified by silica gel column flash chromatography (ISCO®; 12 g SepaFlash® Silica Flash Column, eluent of 0~50% EtOAc/Petro. Ether gradient @ 40 mL/min) to give diethyl 6-(4,4,5,5-tetramethyl-1,3,2-dioxaborolan-2-yl)cinnoline-1,2-dicarboxylate (A27_D). LCMS (ESI) calc'd for $C_{20}H_{27}BN_2O_6$ $[M+H]^+$: 403.2, found: 403.2. $^1H$ NMR (400 MHz, $CDCl_3$) δ 7.74-7.66 (m, 1H), 7.59-7.52 (m, 1H), 7.47-7.37 (m, 1H), 7.29-7.20 (m, 1H), 6.22-6.01 (m, 1H), 4.39-4.06 (m, 4H), 1.32 (s, 12H), 1.26-1.21 (m, 9H).

Step 4: diethyl 6-(2-((S)-1-((R)-1,1-dimethylethylsulfinamido)-6-(2-ethyl-1,3-dioxolan-2-yl)hexyl)-1-((2-(trimethylsilyl)ethoxy)methyl)-1H-imidazol-5-yl)cinnoline-1,2-dicarboxylate (A27_E): A mixture of diethyl 6-(4,4,5,5-tetramethyl-1,3,2-dioxaborolan-2-yl)cinnoline-1,2-dicarboxylate (A27_D, 130 mg, 0.323 mmol), (R)—N—((S)-1-(5-bromo-1-((2-(trimethylsilyl)ethoxy)methyl)-1H-imidazol-2-yl)-6-(2-ethyl-1,3-dioxolan-2-yl)hexyl)-2-methylpropane-2-sulfinamide (A3_C, 225 mg, 0.388 mmol), $K_3PO_4$ (206 mg, 0.970 mmol) and Pd(DTBPF)$Cl_2$ (21 mg, 0.032 mmol) in THF (10 mL) and water (1 mL) was degassed and backfilled with $N_2$ (three times). The mixture was heated to 80° C. for 12 h. The mixture was concentrated to dryness. The crude product was purified by silica gel column flash chromatography (ISCO®; 4 g SepaFlash® Silica Flash Column, eluent of 0~100% EtOAc/Petro. Ether gradient @ 40 mL/min) to give diethyl 6-(2-((S)-1-((R)-1,1-dimethylethylsulfinamido)-6-(2-ethyl-1,3-dioxolan-2-yl)hexyl)-1-((2-(trimethylsilyl)ethoxy)methyl)-1H-imidazol-5-yl)cinnoline-1,2-dicarboxylate (A27_E). LCMS (ESI) calc'd for $C_{38}H_{61}N_5OSSSi$ $[M+H]^+$: 776.4, found: 776.3.

Step 5: (R)—N—((S)-1-(5-(cinnolin-6-yl)-1-((2-(trimethylsilyl)ethoxy)methyl)-1H-imidazol-2-yl)-6-(2-ethyl-1,3-dioxolan-2-yl)hexyl)-2-methylpropane-2-sulfinamide (A27_F): A open mixture of diethyl 6-(2-((S)-1-((R)-1,1-dimethylethylsulfinamido)-6-(2-ethyl-1,3-dioxolan-2-yl)hexyl)-1-((2-(trimethylsilyl)ethoxy)methyl)-1H-imidazol-5-yl)cinnoline-1,2-dicarboxylate (A27_E, 120 mg, 0.155 mmol), NaOH (0.2 mL, 1.000 mmol) in EtOH (2 mL) was heated at 70° C. for 12 h. After cooling to rt, the mixture was cooled, diluted with DCM (20 mL), washed with water (10 mL), dried ($Na_2SO_4$), filtered and the solvent was evaporated under reduced pressure to give (R)—N—((S)-1-(5-(cinnolin-6-yl)-1-((2-(trimethylsilyl)ethoxy)methyl)-1H-imidazol-2-yl)-6-(2-ethyl-1,3-dioxolan-2-yl)hexyl)-2-methylpropane-2-sulfinamide (A27_F) which used directly in next step. LCMS (ESI) calc'd for $C_{32}H_{51}N_5O_4SSi$ $[M+H]^+$: 630.3, found: 630.3.

Step 6: (S)-9-amino-9-(5-(cinnolin-6-yl)-1H-imidazol-2-yl)nonan-3-one (A27): TFA (2 mL, 26.0 mmol) was added to a stirred mixture of (R)—N—((S)-1-(5-(cinnolin-6-yl)-1-((2-(trimethylsilyl)ethoxy)methyl)-1H-imidazol-2-yl)-6-(2-ethyl-1,3-dioxolan-2-yl)hexyl)-2-methylpropane-2-sulfinamide (A27_F, 100 mg, 0.159 mmol) in DCM (2 mL) at rt and the mixture was stirred at room temperature for 1 h. The solvent was evaporated under reduced pressure to give (S)-9-amino-9-(5-(cinnolin-6-yl)-1H-imidazol-2-yl)nonan-3-one (A27) which was used directly in next step. LCMS (ESI) calc'd for $C_{20}H_{25}N_5O$ $[M+H]^+$: 352.2, found: 352.1.

Example 18

Preparation of Intermediate A28

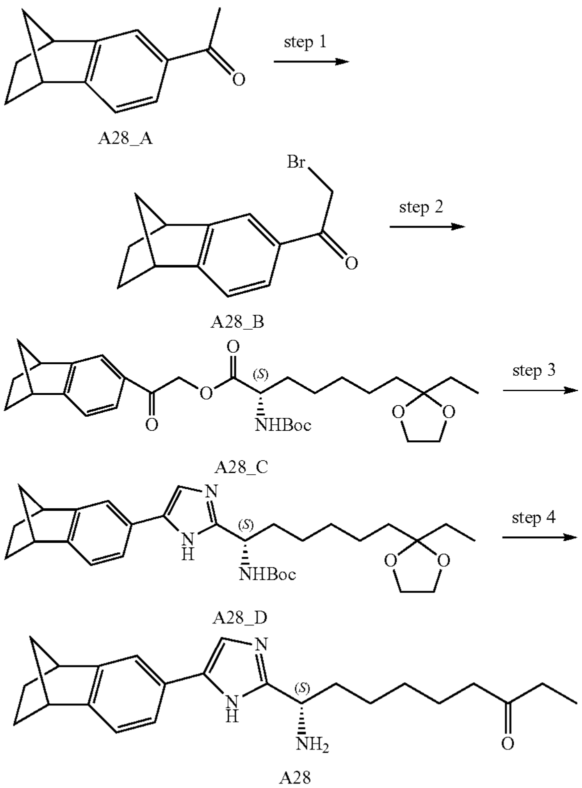

A28_A, A28_B, A28_C, A28_D, A28

Step 1: Preparation of 2-bromo-1-((1S,4R)-1,2,3,4-tetrahydro-1,4-methanonaphthalen-6-yl)ethanone (A28_B): The mixture of 1-((1S,4R)-1,2,3,4-tetrahydro-1,4-methanonaphthalen-6-yl)ethanone (prepared according to Journal of Medicinal Chemistry, 1984, 27, 1516-1531) (A28_A, 420 mg, 2.255 mmol) and phenyltrimethylammonium tribromide (1.30 g, 3.46 mmol) in THF (15 mL) was stirred at rt for 2 h under nitrogen atmosphere. The mixture was diluted with EtOAc (20 mL), washed with brine (2×10 mL), dried ($Na_2SO_4$), filtered and the solvent was evaporated under reduced pressure to give the title compound (A28_B) which was used to the next step without further purification.

Step 2: Preparation of (2S)-2-oxo-2-(1,2,3,4-tetrahydro-1,4-methanonaphthalen-6-yl)ethyl 2-((tert-butoxycarbonyl)amino)-7-(2-ethyl-1,3-dioxolan-2-yl)heptanoate (A28_C): The mixture of 2-bromo-1-((1S,4R)-1,2,3,4-tetrahydro-1,4-methanonaphthalen-6-yl)ethanone (A28_B, 600 mg, 2.263 mmol), (S)-2-((tert-butoxycarbonyl)amino)-7-(2-ethyl-1,3-dioxolan-2-yl)heptanoic acid (782 mg, 2.263 mmol) and DIPEA (1.2 mL, 6.87 mmol) in THF (10 mL) was stirred at rt for 16 h under nitrogen atmosphere. The mixture was concentrated to dryness and the residue was purified by silica gel column flash chromatography, eluting with EtOAc in petroleum ether=0~35% to give the title compound (A28_C). LCMS (ESI) calc'd for $C_{30}H_{43}NO_7$ $[M+H]^+$: 530.3, found: 552.1 (M+23).

Step 3: Preparation of tert-butyl ((S)-6-(2-ethyl-1,3-dioxolan-2-yl)-1-(5-((1R,4S)-1,2,3,4-tetrahydro-1,4-methanonaphthalen-6-yl)-1H-imidazol-2-yl)hexyl)carbamate (A28_D): The mixture of (2S)-2-oxo-2-(1,2,3,4-tetrahydro-1,4-methanonaphthalen-6-yl)ethyl 2-((tert-butoxycarbonyl)amino)-7-(2-ethyl-1,3-dioxolan-2-yl)heptanoate (A28_C, 760 mg, 1.435 mmol) and ammonium acetate (1.10 g, 14.27 mmol) in xylene (15 mL) was stirred at 120° C. for 4 h under nitrogen atmosphere. The mixture was concentrated to remove xylene and the residue was triturated with EtOAc (30 mL), washed with brine (2×10 mL), dried ($Na_2SO_4$), filtered and the solvent was evaporated under reduced pressure. The residue was purified by silica gel column flash chromatography, eluting with EtOAc in petroleum ether=0~35% to give the mixture of tert-butyl ((S)-6-(2-ethyl-1,3-dioxolan-2-yl)-1-(5-((1R,4S)-1,2,3,4-tetrahydro-1,4-methanonaphthalen-6-yl)-1H-imidazol-2-yl)hexyl)carbamate (73D) and tert-butyl ((S)-7-oxo-1-(5-((1R,4S)-1,2,3,4-tetrahydro-1,4-methanonaphthalen-6-yl)-1H-imidazol-2-yl)nonyl)carbamate. LCMS (ESI) calc'd for $C_{30}H_{43}N_3O_4$ $[M+H]^+$: 509.3, found: 510.2. LCMS (ESI) calc'd for $C_{28}H_{39}N_3O_3$ $[M+H]^+$: 465.3, found: 466.2.

Step 4: Preparation of (S)-9-amino-9-(5-((1R,4S)-1,2,3,4-tetrahydro-1,4-methanonaphthalen-6-yl)-1H-imidazol-2-yl)nonan-3-one hydrochloride (A28): The mixture of tert-butyl ((S)-7-oxo-1-(5-((1R,4S)-1,2,3,4-tetrahydro-1,4-methanonaphthalen-6-yl)-1H-imidazol-2-yl)nonyl) carbamate (A28_D) and tert-butyl ((S)-6-(2-ethyl-1,3-dioxolan-2-yl)-1-(5-((1R,4S)-1,2,3,4-tetrahydro-1,4-methanonaphthalen-6-yl)-1H-imidazol-2-yl)hexyl) carbamate (400 mg mixture) in HCl (5 mL, 4 M)/EtOAc (10 mL) was stirred at rt for 4 h. The mixture was concentrated in vacuo to give the title compound (A28) which was used to the next step without further purification. LCMS (ESI) calc'd for $C_{23}H_{31}N_3O$ $[M+H]^+$: 366.2, found: 366.1.

Example 19

Preparation of Intermediate B1

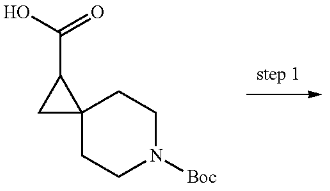

B1_A

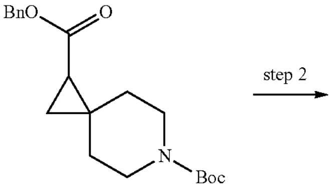

B1_B

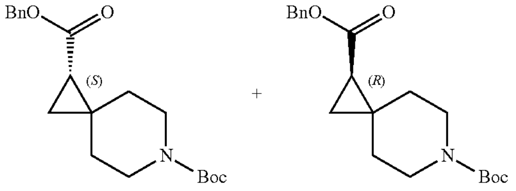

B1

Step 1: 1-benzyl 6-tert-butyl 6-azaspiro[2.5]octane-1,6-dicarboxylate (B1_A): Two reactions were carried out in parallel.

DBU (235 g, 1.55 mol, 233 mL) was added in one portion to a solution of 6-(tert-butoxycarbonyl)-6-azaspiro[2.5]octane-1-carboxylic acid (B1_A, 330 g, 1.29 mol) in $CH_3CN$ (3.3 L) at 20° C. Benzyl bromide (242 g, 1.42 mol, 168 mL) was added to the suspension in one portion at 20° C. The suspension was stirred at 20° C. for 4 h. The two reactions were combined and concentrated. Ethyl acetate (5.5 L) was added to dissolve the residual, and precipitate appeared. The precipitate was filtered and then washed with ethyl acetate (300 mL*3). The organic phase was washed with citric acid (10% w/w, 3 L*2), sat.$NaHCO_3$ aqueous (3 L*2), water (2 L) and brine (2 L) in sequence. The organic phase was dried over $Na_2SO_4$. It was filtered and the filtrate was concentrated to give the crude product.

The crude product was dissolved with petroleum ether (7 L) and it was put in a dry ice-acetone bath for 12 h. A solid appeared; the solution was removed and the solid was grinded with petroleum ether (600 mL) for 1 hour. The suspension was filtered, and the filter cake was washed with petroleum ether (30 mL*2).

The mother solutions were concentrated in vacuo to yield 1-benzyl 6-tert-butyl 6-azaspiro[2.5]octane-1,6-dicarboxylate (B1_B). $^1H$ NMR (400 MHz, $CDCl_3$) δ 7.41-7.31 (m, 5H), 5.19-5.07 (m, 2H), 3.55-3.36 (m, 3H), 3.28-3.17 (m, 1H), 1.77-1.61 (m, 3H), 1.49-1.37 (m, 11H), 1.21 (t, J=4.9 Hz, 1H), 0.96 (dd, J=4.5, 7.6 Hz, 1H).

Step 2: (S)-1-benzyl 6-tert-butyl 6-azaspiro[2.5]octane-1,6-dicarboxylate (B1): Racemic 1-benzyl 6-tert-butyl 6-azaspiro[2.5]octane-1,6-dicarboxylate (B1_B) was resolved on a ChiralPak AD column (300×50 mm) under supercritical fluid chromatography (SFC) conditions on a Thar 200 preparative SFC instrument. The racemate was dissolved isopropanol/DCM. The separation was accomplished using 20% MeOH/$CO_2$, flow rate 200 mL/min, 100 bar, 38° C. The $2^{nd}$ peak is the S one.

Alternatively, the resolution could also be achieved using a mobile phase of 20% 1:1 heptane: ethanol/$CO_2$ on ChiralPak AY column (300×50 mm) with a flow rate of 200 mL/min. In that case the sample was prepared by dissolving in MeCN/ethanol. After separation, the fractions were dried off via rotary evaporator at bath temperature 40° C.

$^1$H NMR-P1 (400 MHz, $CDCl_3$) δ 7.42-7.29 (m, 5H), 5.19-5.06 (m, 2H), 3.55-3.35 (m, 3H), 3.26-3.16 (m, 1H), 1.75-1.59 (m, 3H), 1.53-1.33 (m, 11H), 1.21 (t, J=4.9 Hz, 1H), 0.96 (dd, J=4.6, 7.7 Hz, 1H).

$^1$H NMR-P2 (400 MHz, $CDCl_3$) δ 7.43-7.29 (m, 5H), 5.18-5.07 (m, 2H), 3.54-3.36 (m, 3H), 3.26-3.16 (m, 1H), 1.73-1.60 (m, 3H), 1.53-1.34 (m, 11H), 1.21 (t, J=5.1 Hz, 1H), 0.96 (dd, J=4.4, 7.9 Hz, 1H).

Example 20

Preparation of Intermediate B2

B2

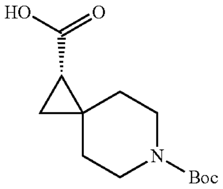

A mixture of (S)-1-benzyl 6-tert-butyl 6-azaspiro[2.5]octane-1,6-dicarboxylate (B1, 5 g, 14.47 mmol), 10% Pd/C (0.154 g, 1.447 mmol) in MeOH (30 mL) was hydrogenated under $H_2$ (20 psi) at room temperature for 18 h. The mixture was filtered and the filter cake was washed with MeOH (30×3 mL). The filtrate was concentrated to dryness to give (S)-6-(tert-butoxycarbonyl)-6-azaspiro[2.5]octane-1-carboxylic acid (B2) which was used without further purification. LCMS (ESI) calc'd for $C_{13}H_{21}NO_4$ $[M+H]^+$: 256.2, found: 200.1 (M-55).

Example 21

Preparation of Intermediate B3

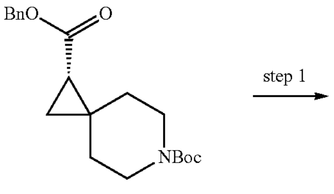

B1

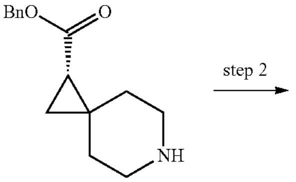

B3_A

-continued

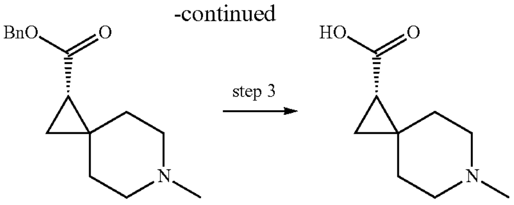

B3_B B3

Step 1: (S)-benzyl 6-azaspiro[2.5]octane-1-carboxylate (B3_A): TFA (15 mL, 202 mmol) was added to a stirred mixture of (S)-1-benzyl 6-tert-butyl 6-azaspiro[2.5]octane-1,6-dicarboxylate (B1, 10.02 g, 29.0 mmol) in DCM (100 mL) at 0-5° C. and the mixture was stirred at room temperature for 4 h. All the volatiles were removed by evaporator to give crude (S)-benzyl 6-azaspiro[2.5]octane-1-carboxylate (B3_A) which was used without further purification. LCMS (ESI) calc'd for $C_{15}H_{19}NO_2$ $[M+H]^+$: 246.3, found: 246.1.

Step 2: (S)-benzyl 6-methyl-6-azaspiro[2.5]octane-1-carboxylate (B3_B): Formaldehyde (18.77 g, 231 mmol) was added to a stirred mixture of (S)-benzyl 6-azaspiro[2.5]octane-1-carboxylate (B3_A, 9.9 g, 28.9 mmol) in MeOH (100 mL) at room temperature and the mixture was stirred at room temperature for 2 h. Sodium triacetoxyhydroborate (18.39 g, 87 mmol) was added to the stirred mixture and the mixture was stirred at room temperature for 1 h. The solvent was removed by evaporator, then water (100 mL) was added and the mixture was extracted with ethyl acetate (50 mL) three times. The combined organic fractions were washed with aqueous $NaHCO_3$(saturated, 50 mL), dried ($Na_2SO_4$), filtered and the solvent was evaporated under reduced pressure. The residue was purified by silica gel column flash chromatography, eluting with DCM/MeOH=10/1 to give (S)-benzyl 6-methyl-6-azaspiro[2.5]octane-1-carboxylate (B3_B). LCMS (ESI) calc'd for $C_{16}H_{21}NO_2$ $[M+H]^+$: 260.3, found: 260.1.

Step 3: (S)-6-methyl-6-azaspiro[2.5]octane-1-carboxylic acid (B3): A solution of (S)-benzyl 6-methyl-6-azaspiro[2.5]octane-1-carboxylate (B3_B, 7.5 g, 28.9 mmol) in MeOH (75 mL) was added to 100 mL three-necked bottle and then Pd/C (520 mg, 0.489 mmol) (10%, wet) was added under Ar. The suspension was degassed under vacuum and purged with $N_2$ several times. The mixture was then stirred under $H_2$ (15 psi) at 24° C. for 90 min. The mixture was filtered and the filter cake was washed with MeOH (20 mL×2). The filtrate was concentrated to dryness to give as (S)-6-methyl-6-azaspiro[2.5]octane-1-carboxylic acid (B3). $^1$H NMR (400 MHz, DMSO-$d_6$) δ 2.95 (brs, 2H), 2.60 (s, 3H), 1.77-1.89 (m, 2H), 1.58 (t, J=6.6 Hz, 1H), 0.91-0.99 (m, 2H).

Example 22

Preparation of Intermediate B4

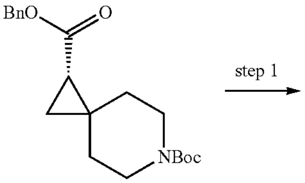

B1

-continued

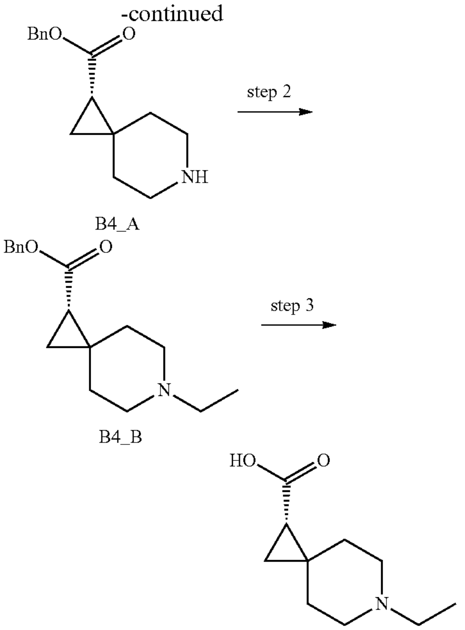

B4_A

B4_B

B4

Step 1: Preparation of (S)-benzyl 6-azaspiro[2.5]octane-1-carboxylate 2,2,2-trifluoroacetate (B4_A): TFA (4.5 ml, 60.6 mmol) was added to a stirred mixture of (S)-1-benzyl 6-tert-butyl 6-azaspiro[2.5]octane-1,6-dicarboxylate (B1, 3.0 g, 8.68 mmol) in DCM (30 mL) at rt and the mixture was stirred at room temperature for 4 h. All the volatiles were removed by evaporator to give crude (S)-benzyl 6-azaspiro[2.5]octane-1-carboxylate (B4_A, 3.1 g) which was used directly for the next step without further purification treatment. LCMS (ESI) calc'd for $C_{15}H_{19}NO_2$ $[M+H]^+$: 246.1, found: 246.1.

Step 2: Preparation of (S)-benzyl 6-ethyl-6-azaspiro[2.5]octane-1-carboxylate (B4_B): Acetaldehyde (21 ml, 149 mmol) was added to a stirred mixture of (S)-benzyl 6-azaspiro[2.5]octane-1-carboxylate (B4_A, 6.2 g, 18.11 mmol) in MeOH (60 mL) at room temperature and the mixture was stirred at 30° C. for 16 h. Then another batch of acetaldehyde (4.0 mL) was added and it was stirred at 30° C. for further 16 h. Sodium triacetoxyhydroborate (11.52 g, 54.3 mmol) was added then the mixture was stirred at 30° C. for 16 h. Most of the MeOH was removed by evaporator. Water (50 mL) was added and the mixture was extracted with ethyl acetate (3x35 mL). The combined organic fractions were washed with aqueous $NaHCO_3$(saturated, 2x35 mL) then brine (2x35 mL), dried ($Na_2SO_4$), filtered and the solvent was evaporated under reduced pressure. The residue was purified by silica gel flash chromatography (ISCORF75; Sepa flash column), eluting with DCM/MeOH=0~10/1 to give (S)-benzyl 6-ethyl-6-azaspiro[2.5]octane-1-carboxylate (B4_B). LCMS (ESI) calc'd for $C_{17}H_{23}NO_2$ $[M+H]^+$: 274.2, found: 274.1.

Step 3: Preparation of (S)-6-ethyl-6-azaspiro[2.5]octane-1-carboxylic acid (B4): To a solution of (S)-benzyl 6-ethyl-6-azaspiro[2.5]octane-1-carboxylate (B4_B, 4.5 g, 16.46 mmol) in MeOH (45 mL) was added Pd/C (300 mg, 0.282 mmol) (10%, wet) under Ar. The suspension was degassed under vacuum and purged with $N_2$ several times. The mixture was then stirred under $H_2$ (15 psi) at 18° C. for 2 h. The mixture was filtered and the filter cake was washed with MeOH (3x15 mL). The filtrate was concentrated to dryness to give (S)-6-ethyl-6-azaspiro[2.5]octane-1-carboxylic acid (B4) which was used as crude. $^1$H NMR (400 MHz, DMSO-$d_6$) δ 2.60-2.71 (m, 2H), 2.54-2.60 (m, 2H), 2.50 (brs, 2H), 1.65-1.78 (m, 2H), 1.48 (dd, J=5.6, 7.4 Hz, 3H), 1.06 (t, J=7.2 Hz, 3H), 0.87-0.92 (m, 1H), 0.81-0.87 (m, 1H).

Example 23

Preparation of Intermediate B5

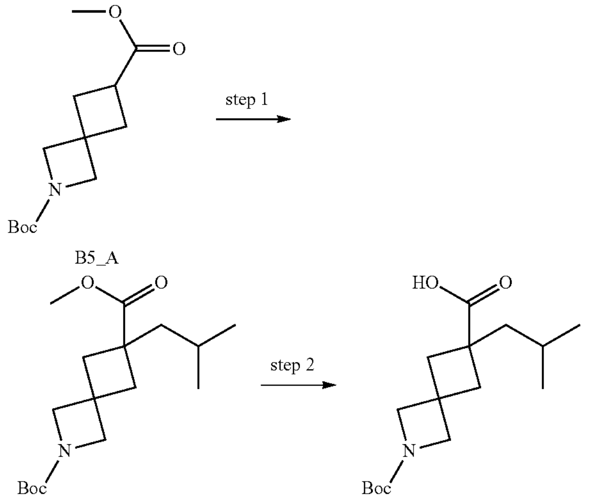

B5_A

B5_B

B5

Step 2: preparation of 2-tert-butyl 6-methyl 6-isobutyl-2-azaspiro[3.3]heptane-2,6-dicarboxylate (B5_B): LDA (0.58 mL, 1.160 mmol) was added to a stirred mixture of 1-iodo-2-methylpropane (360 mg, 1.958 mmol) and 2-tert-butyl 6-methyl 2-azaspiro[3.3]heptane-2,6-dicarboxylate (B5_A, 100 mg, 0.392 mmol) in THF (3 mL) at −78° C., and the mixture was stirred at −78° C. for 3 h, then at rt for 10 h. The mixture was quenched with $NH_4Cl$ (10 mL), extracted with EtOAc (10 mL*3), the combined organic layers were washed with brine (10 mL), dried over $Na_2SO_4$, filtered and concentrated. The residue was purified by flash silica gel chromatography (ISCO®; 4 g SepaFlash® Silica Flash Column, Eluent of 0~10% EtOAc/Petro. Ether gradient @ 40 mL/min) to give 2-tert-butyl 6-methyl 6-isobutyl-2-azaspiro[3.3]heptane-2,6-dicarboxylate (B5_B). $^1$H NMR (400 MHz, $CDCl_3$) δ 3.87 (d, J=3.1 Hz, 4H), 3.69 (s, 3H), 2.68-2.58 (m, 1H), 2.18-2.09 (m, 1H), 1.67-1.61 (m, 3H), 1.59-1.48 (m, 1H), 1.42 (s, 9H), 0.83 (d, J=6.7 Hz, 6H).

Step 3: preparation of 2-(tert-butoxycarbonyl)-6-isobutyl-2-azaspiro[3.3]heptane-6-carboxylic acid (B5): NaOH aq (2 M, 2 mL, 4.00 mmol) was added to a stirred mixture of 2-tert-butyl 6-methyl 6-isobutyl-2-azaspiro[3.3]heptane-2,6-dicarboxylate (B5_B, 250 mg, 0.803 mmol) in MeOH (4 mL) at rt and the mixture was stirred at 50° C. for 15 h. The mixture was cooled, extracted with EtOAc (5 mL), the aqueous layers was adjusted to pH2 with HCl (2 M), and then extracted with EtOAc (5 mL*3), the combined organic layers were washed with brine (10 mL), dried over $Na_2SO_4$, filtered and concentrated to get 2-(tert-butoxycarbonyl)-6-isobutyl-2-azaspiro[3.3]heptane-6-carboxylic acid (B5). $^1$H NMR (400 MHz, $CDCl_3$) δ 3.99-3.78 (m, 4H), 2.74-2.59 (m, 1H), 2.22-2.08 (m, 1H), 1.64 (brs, 2H), 1.40 (s, 5H), 0.84 (brs, 3H).

Example 24

Preparation of Intermediate B6

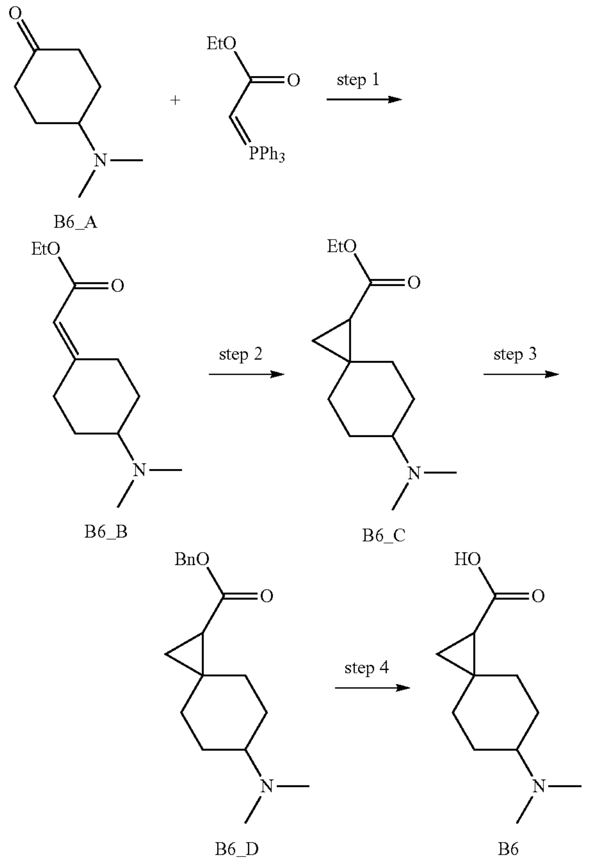

Step 1: Preparation of ethyl 2-(4-(dimethylamino)cyclohexylidene)acetate (B6_B): Ethyl 2-(triphenylphosphoranylidene)acetate (4.934 g, 14.16 mmol) was added to the solution of 4-(dimethylamino)cyclohexanone (B6_A, 1.000 g, 7.08 mmol) in xylene (30 mL), and the resultant mixture was stirred at 135° C. for 30 h. The mixture was concentrated to dryness. The residue was purified by silica gel flash chromatography (ISCORF75; Sepa flash column), eluting with DCM/MeOH=10:0-10:1 to give ethyl 2-(4-(dimethylamino)cyclohexylidene)acetate (B6_B). LCMS (ESI) calc'd for $C_{12}H_{21}NO_2$ $[M+H]^+$: 212.1, found: 212.1.

Step 2: Preparation of ethyl 6-(dimethylamino)spiro[2.5]octane-1-carboxylate (B6_C): $Pd(OAc)_2$ (0.179 g, 0.795 mmol) and a solution of diazomethane (50.0 mL, 25.00 mmol) in ether was added sequentially in 5 portions to the solution of ethyl 2-(4-(dimethylamino)cyclohexylidene)acetate (B6_B, 1.68 g, 7.95 mmol) in DCM (5 mL) at 0° C. with an interval of 20 min. The resultant mixture was stirred at 0° C. for additional 1 h while the $N_2$ bubble stopped. The mixture was quenched with AcOH. The mixture was filtered and the filter cake was washed with MeOH (3*20 mL). The filtrate was concentrated to dryness to give ethyl 6-(dimethylamino)spiro[2.5]octane-1-carboxylate (B6_C) which is a mixture including starting material and used to the next step without purification. LCMS (ESI) calc'd for $C_{13}H_{23}NO_2$ $[M+H]^+$: 226.2, found: 226.2.

Step 3: Preparation of benzyl 6-(dimethylamino)spiro[2.5]octane-1-carboxylate (B6_D): Titanium(iv) isopropoxide (3.51 mL, 11.98 mmol) and molecular sieve (4A, 3.0 g) was added to the solution of ethyl 6-(dimethylamino)spiro[2.5]octane-1-carboxylate (127C, 900 mg, 3.99 mmol) in BnOH (10.0 g, 92 mmol), and the resultant mixture was stirred at 120° C. for 50 h. The reaction mixture was filtered and concentrated in vacuo to remove excess phenylmethanol. The residue was purified by silica gel column flash chromatography, eluting with DCM/MeOH=10:0-4:1 to give benzyl 6-(dimethylamino)spiro[2.5]octane-1-carboxylate (B6_D). LCMS (ESI) calc'd for $C_{18}H_{25}NO_2$ $[M+H]^+$: 288.2, found: 288.2.

Step 4: Preparation of 6-(dimethylamino)spiro[2.5]octane-1-carboxylic acid (B61_A solution of benzyl 6-(dimethylamino)spiro[2.5]octane-1-carboxylate (B6_D, 180 mg, 0.626 mmol) in MeOH (10 mL) was added to 100 mL bottle and then Pd—C (20 mg, 0.188 mmol) (10%, wet) was added under $N_2$. The suspension was degassed under vacuum and purged with $H_2$ several times. The mixture was then stirred under $H_2$ (Pressure: 1 atm) at 35° C. for 18 h. The mixture was filtered through Celite and the filter cake was washed with THF (3*30 mL). The filtrate was concentrated to dryness to give 6-(dimethylamino)spiro[2.5]octane-1-carboxylic acid (B6) which was used without further purification. LCMS (ESI) calc'd for $C_{11}H_{19}NO_2$ $[M+H]^+$: 198.1, found: 198.1.

Example 25

Preparation of Intermediate B7

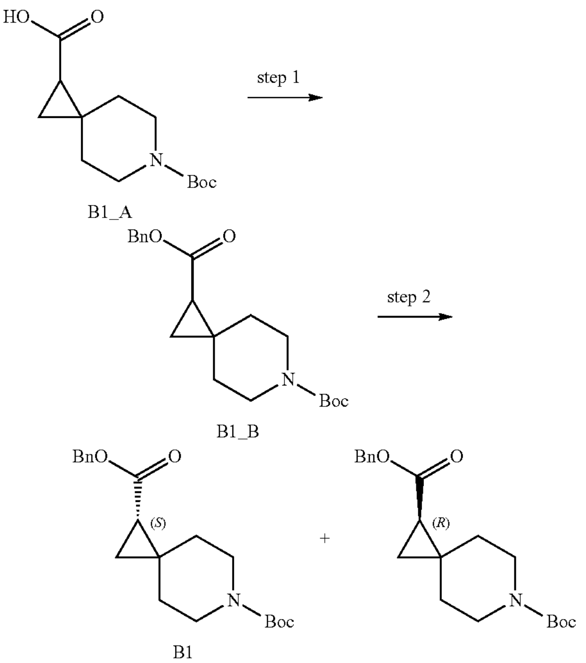

Step 1: Preparation of tert-butyl 3-methylene-8-azabicyclo[3.2.1]octane-8-carboxylate (B7_B) Butyllithium (9 mL, 22.50 mmol) was added to a stirred mixture of methyltriphenylphosphonium bromide (8 g, 22.39 mmol) in THF (20 mL) at 0° C. and the mixture was stirred at 0° C. for 10 min under $N_2$ atmosphere. Tert-butyl 3-oxo-8-azabicyclo[3.2.1]octane-8-carboxylate (B7_A, 2 g, 8.88 mmol) in THF (30 mL) was then added dropwise. The mixture was stirred at 0-5° C. for 45 min. The mixture was diluted with ethyl acetate (200 mL), washed with aqueous $Na_2CO_3$ (saturated, 1×50 mL), dried ($Na_2SO_4$), filtered and the solvent was evaporated under reduced pressure. The residue was purified by silica gel column (Petro. Ether:EtOAc=20:1) to give tert-butyl 3-methylene-8-azabicyclo[3.2.1]octane-8-carboxylate (B7_B). LCMS (ESI) calc'd for $C_{17}H_{23}BN_2O_2$ $[M+H]^+$: 224.2, found: 167.8 $[M-55]^+$.

Step 2: Preparation of 8-tert-butyl 2'-ethyl 8-azaspiro[bicyclo[3.2.1]octane-3,1'-cyclopropane]-2',8-dicarboxylate (B7_C): Ethyl 2-diazoacetate (1.022 g, 8.96 mmol) in DCM (5 mL) was added drop-wise carefully to a stirred mixture of diacetoxyrhodium (0.198 g, 0.448 mmol), and tert-butyl 3-methylene-8-azabicyclo[3.2.1]octane-8-carboxylate (B7_B, 1.0 g, 4.48 mmol) in DCM (5 mL) at room temperature and the mixture was stirred at room temperature for 12 h. AcOH (a drop) in water (10 mL) was added and the mixture was extracted with DCM (3×15 mL). The combined organic fractions were washed with brine (saturated, 3×15 mL), dried ($Na_2SO_4$), filtered and the solvent was evaporated under reduced pressure. The residue was purified by silica gel column flash chromatography, eluting with EtOAc/petroleum ether=0-10% to give 8-tert-butyl 2'-ethyl 8-azaspiro[bicyclo[3.2.1]octane-3,1'-cyclopropane]-2',8-dicarboxylate (B7_C). LCMS (ESI) calc'd for $C_{17}H_{27}NO_4$ $[M+H]^+$: 310.2, found: 254.1 (M-55).

Step 3: Preparation of 8-(tert-butoxycarbonyl)-8-azaspiro[bicyclo[3.2.1]octane-3,1'-cyclopropane]-2'-carboxylic acid (B7): LiOH $H_2O$ (0.326 g, 7.76 mmol) was added to a stirred mixture of 8-tert-butyl 2'-ethyl 8-azaspiro[bicyclo[3.2.1]octane-3,1'-cyclopropane]-2',8-dicarboxylate (B7_C, 1.2 g, 3.88 mmol) in water (1 mL)/MeOH (10 mL) at room temperature and the mixture was stirred at 40° C. for 12 h. The residue was concentrated to give 8-(tert-butoxycarbonyl)-8-azaspiro[bicyclo[3.2.1]octane-3,1'-cyclopropane]-2'-carboxylic acid (B7). LCMS (ESI) calc'd for $C_{15}H_{23}NO_4$ $[M+H]^+$: 282.2, found: 226.1 (M-55).

Example 26

Preparation of Intermediate B8

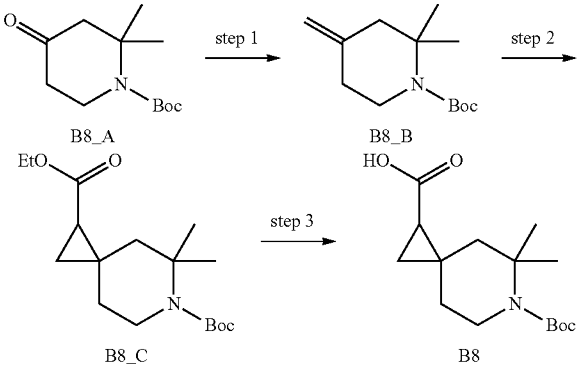

B8_A B8_B B8_C B8

Step 1: Preparation of tert-butyl 2,2-dimethyl-4-methylenepiperidine-1-carboxylate (B8_B): nBuLi (1.214 mL, 3.04 mmol) was added to a stirred mixture of $PPh_3MeBr$ (1.179 g, 3.30 mmol) in THF (6.0 mL) at 0-5° C. and the mixture was stirred at 0-5° C. for 10 min under $N_2$ atmosphere. Tert-butyl 2,2-dimethyl-4-oxopiperidine-1-carboxylate (B8_A, 300 mg, 1.320 mmol) in 1 mL of THF was then added dropwise. The mixture was stirred at rt for 16 h. The mixture was diluted with ethyl acetate (15 mL), washed with aqueous $Na_2CO_3$ (saturated, 1×10 mL), dried ($Na_2SO_4$), filtered and the solvent was evaporated under reduced pressure. The residue was purified by silica gel column flash chromatography, eluting with petroleum ether/EtOAc=10:1 to give tert-butyl 2,2-dimethyl-4-methylenepiperidine-1-carboxylate (B8_B). LCMS (ESI) calc'd for $C_{13}H_{23}NO_2$ $[M+H]^+$: 226.2, found: 170.1 (M-55). $^1H$ NMR (400 MHz, $CDCl_3$) δ 4.82 (brs, 2H), 3.56 (t, J=6.17 Hz, 2H), 2.38 (t, J=5.95 Hz, 2H), 2.28 (s, 2H), 1.47 (s, 9H), 1.38 (s, 6H).

Step 2: Preparation of 6-tert-butyl 1-ethyl 5,5-dimethyl-6-azaspiro[2.5]octane-1,6-dicarboxylate (B8_C): $Rh_2(OAc)_4$ (29.4 mg, 0.067 mmol) was added to a stirred mixture of tert-butyl 2,2-dimethyl-4-methylenepiperidine-1-carboxylate (150 mg, 0.666 mmol) in DCM (8.0 mL) at room temperature and ethyl diazoacetate (152 mg, 1.331 mmol) in 1 mL of DCM was added dropwise, and the mixture was stirred at rt for 5 h. Then, $Rh_2(OAc)_4$ (29.4 mg, 0.067 mmol) and ethyl diazoacetate (152 mg, 1.331 mmol) was added to above solution and stirred for another 5 h, then quenched with 1 MAcOH (3 mL), and the mixture was extracted with ethyl acetate (15 mL). The combined organic fractions were washed with brine (saturated, 8 mL), dried ($Na_2SO_4$), filtered and the solvent was evaporated under reduced pressure. The residue was purified by preparative TLC on silica gel, eluting with petroleum ether/EtOAc=5:1 and further purified by preparative HPLC (reverse phase C-18 column), eluting with acetonitrile/water+0.225% HCOOH, to give 6-tert-butyl 1-ethyl 5,5-dimethyl-6-azaspiro[2.5]octane-1,6-dicarboxylate (B8_C). LCMS (ESI) calc'd for $C_{17}H_{29}NO_4$ $[M+H]^+$: 312.2, found: 312.1. $^1H$ NMR (400 MHz, $CDCl_3$) δ 4.04-4.17 (m, 2H), 3.37-3.57 (m, 2H), 1.70-1.77 (m, 2H), 1.56 (brs, 2H), 1.39-1.47 (m, 15H), 1.24 (t, J=7.04 Hz, 3H), 1.11-1.18 (m, 1H), 0.87-0.97 (m, 1H).

Step 3: Preparation of 6-(tert-butoxycarbonyl)-5,5-dimethyl-6-azaspiro[2.5]octane-1-carboxylic acid (B8): LiOH $H_2O$ (27 mg, 0.643 mmol) was added to a stirred mixture of 6-tert-butyl 1-ethyl 5,5-dimethyl-6-azaspiro[2.5]octane-1,6-dicarboxylate (B8_C, 100 mg, 0.321 mmol) in MeOH (2.0 mL) and water (0.5 mL) at room temperature and the mixture was heated to 45° C. and stirred for 16 h, concentrated, the mixture was adjusted to pH 7 with hydrochloric acid (0.2 M solution) and the mixture was extracted with ethyl acetate (10 mL). The combined organic fractions were washed with brine (saturated, 5 mL), dried ($Na_2SO_4$), filtered and the solvent was evaporated under reduced pressure to afford 6-(tert-butoxycarbonyl)-5,5-dimethyl-6-azaspiro[2.5]octane-1-carboxylic acid (B8) without further purification. LCMS (ESI) calc'd for $C_{15}H_{25}NO_4$ $[M+H]^+$: 284.2, found: 228.1.

Example 27

Preparation of Intermediate B9

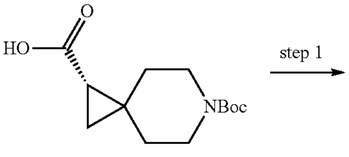

B2

-continued

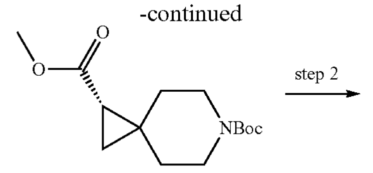

B9_A

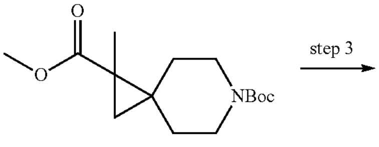

B9_B

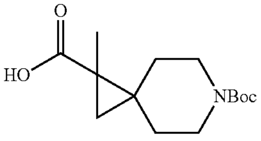

B9

Step 1: Preparation of (R)-6-tert-butyl 1-methyl 6-azaspiro[2.5]octane-1,6-dicarboxylate (B9_A): (Diazomethyl)trimethylsilane (4.90 mL, 9.79 mmol) was added to a stirred mixture of 6-(tert-butoxycarbonyl)-6-azaspiro[2.5] octane-1-carboxylic acid (B2, 500 mg, 1.958 mmol) in MeOH (10 mL) at 0° C., and the mixture was stirred at 20° C. for 15h. The solvent was removed under reduced pressure. The crude product was purified by flash silica gel chromatography (ISCO®; 12 g SepaFlash® Silica Flash Column, Eluent of 0~10% EtOAc/Petro.Ether gradient @30 mL/min) to give 6-tert-butyl 1-methyl 6-azaspiro[2.5]octane-1,6-dicarboxylate (B9_A. LCMS (ESI) calc'd for $C_{14}H_{23}NO_4$ $[M+H]^+$: 270.2, found: 213.9 (M-55).

Step 2: Preparation of (R)-6-tert-butyl 1-methyl 1-methyl-6-azaspiro[2.5]octane-1,6-dicarboxylate (B9_B): LDA (0.557 mL, 1.114 mmol) was added to a stirred mixture of 6-tert-butyl 1-methyl 6-azaspiro[2.5]octane-1,6-dicarboxylate (B9_A, 100 mg, 0.371 mmol) and MeI (0.116 mL, 1.856 mmol) in THF (2 mL) at −78° C. and the mixture was stirred at −78° C. for 3 h and then at rt for 15 h. The mixture was quenched with $NH_4Cl$ (10 mL), extracted with EtOAc (10 mL*3), the combined organic layers were washed with brine (10 mL), dried over $Na_2SO_4$, filtered and concentrated to get the crude. The residue was purified by prep-HPLC (TFA) to give 6-tert-butyl 1-methyl 1-methyl-6-azaspiro[2.5]octane-1,6-dicarboxylate (B9_B). LCMS (ESI) calc'd for $C_{15}H_{25}NO_4$ $[M+H]^+$: 284.2, found: 306.1 (M+Na+).

Step 3: Preparation of (R)-6-(tert-butoxycarbonyl)-1-methyl-6-azaspiro[2.5]octane-1-carboxylic acid (B9): Sodium hydroxide aq (2M, 0.4 mL, 0.800 mmol) was added to a stirred mixture of 6-tert-butyl 1-methyl 1-methyl-6-azaspiro[2.5]octane-1,6-dicarboxylate (B9_B, 52 mg, 0.184 mmol) in MeOH (3 mL) at 25° C., and the mixture was stirred at 50° C. for 6 h. The mixture was concentrated and the aqueous layer was adjust to pH=2 with HCl aq (2 M), and extracted with EtOAc (10 mL*3). The combined organic layers were washed with brine (10 mL), dried over $Na_2SO_4$, filtered and concentrated to give 6-(tert-butoxycarbonyl)-1-methyl-6-azaspiro[2.5]octane-1-carboxylic acid (B9).

Example 28

Preparation of Intermediate C1

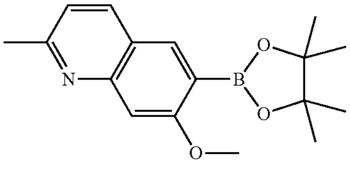

Step 1: 6-bromo-7-methoxy-2-methylquinoline (C1_A): A suspension of 4-bromo-3-methoxyaniline (15.00 g, 74.2 mmol) and HCl (52.5 mL, 639 mmol) in water (60 mL) was heated to 110° C. (E)-but-2-enal (8.23 g, 117 mmol) was added dropwise into the above mixture over 30 min. Then the reaction mixture was stirred at 110° C. for another 2 h. The reaction mixture was combined with another reaction with the same scale. The combined mixture was cooled to rt, aqueous ammonia (28%, 300 mL) was added and the mixture was extracted with ethyl acetate (200×3 mL). The combined organic fractions were washed with brine (400 mL), dried ($Na_2SO_4$), filtered and the solvent was evaporated under reduced pressure. The residue was purified by silica gel column flash chromatography, eluting with petroleum ether/EtOAc=10%-40% to give 6-bromo-7-methoxy-2-methylquinoline (C1_A). LCMS (ESI) calc'd for $C_{11}H_{10}BrNO$ $[M+H]^+$: 252.0, found: 251.9.

Step 2: 7-methoxy-2-methyl-6-(4,4,5,5-tetramethyl-1,3,2-dioxaborolan-2-yl)quinoline (C1): $PdCl_2$(dppf) (85 mg, 0.116 mmol) was added to a stirred mixture of potassium acetate (405 mg, 4.13 mmol), BPD (786 mg, 3.09 mmol) and 6-bromo-7-methoxy-2-methylquinoline (C1_A, 520 mg, 2.063 mmol) in 1,4-dioxane (8 mL) at room temperature and the mixture was stirred at 80° C. for 12 h under $N_2$ protection. The mixture was concentrated and the residue was purified by silica gel column flash chromatography, eluting with petroleum ether/EtOAc=1:1 to give 7-methoxy-2-methyl-6-(4,4,5,5-tetramethyl-1,3,2-dioxaborolan-2-yl) quinoline (C1). LCMS (ESI) calc'd for $C_{17}H_{22}BNO_3$ $[M+H]^+$: 300.2, found: 300.2. $^1H$ NMR (400 MHz, $CDCl_3$) δ 8.12 (s, 1H), 7.98 (d, J=8.22 Hz, 1H), 7.34 (s, 1H), 7.14 (d, J=8.22 Hz, 1H), 3.97 (s, 3H), 2.72 (s, 3H), 1.41 (s, 12H).

Example 29

Preparation of Intermediate C2

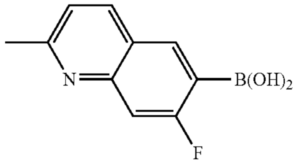

Step 1: 6-bromo-7-fluoro-2-methylquinoline (C2_A): 4-bromo-3-fluoroaniline (500 mg, 2.63 mmol) was added to a stirred mixture of p-chloranil (0.776 g, 3.16 mmol) in BuOH (5.0 mL)/HCl (5 mL, 60.9 mmol) at room temperature and the mixture was stirred at 120° C., and then (E)-but-2-enal (9.31 mL, 113 mmol) in BuOH (0.3 mL) was added dropwise. The mixture was stirred at 120° C. for 40 min. After cooling to rt, it was diluted with $H_2O$ (10 mL) and extracted with EtOAc (3×10 mL). The aqueous layer was alkalinized with NaOH (37%) to pH>9, and extracted with EtOAc (3×15 mL). The combined organic fractions were washed with brine (saturated, 20 mL), dried ($Na_2SO_4$), filtered and the solvent was evaporated under reduced pressure. The residue was purified by preparative HPLC (reverse phase C-18 column), eluting with acetonitrile/water+0.225% HCOOH, to give 6-bromo-7-fluoro-2-methylquinoline (C2_A). $^1H$ NMR (400 MHz, MeOD) δ 8.67 (d, J=8.6 Hz, 1H), 8.54 (d, J=7.0 Hz, 1H), 7.85 (d, J=9.0 Hz, 1H), 7.76 (d, J=8.6 Hz, 1H), 2.89 (s, 3H). LCMS (ESI) calc'd for $C_{10}H_7BrFN$ $[M+H]^+$: 240.0, found: 240.0.

Step 2: (7-fluoro-2-methylquinolin-6-yl)boronic acid (C2): nBuLi (1.7 mL, 4.25 mmol) was added to a stirred mixture of 6-bromo-7-fluoro-2-methylquinoline (C2_A, 500 mg, 2.083 mmol) in THF (10 mL) at −78° C., then triisopropyl borate (1 mL, 4.31 mmol) was added and the mixture was stirred at room temperature for 2 h. Aqueous $NH_4Cl$ (saturated, 10 mL) was added and the mixture was extracted with ethyl acetate (3×8 mL). The combined organic fractions were washed with brine (saturated, 15 mL), dried ($Na_2SO_4$), filtered and the solvent was evaporated under reduced pressure. The residue was purified by silica gel column flash chromatography, eluting with MeOH/DCM=0-20% to give (7-fluoro-2-methylquinolin-6-yl)boronic acid (C2). LCMS (ESI) calc'd for $C_{10}H_9BFNO_2$ $[M+H]^+$: 206.1, found: 206.1.

The following intermediates were prepared in a similar manner as described for intermediates $C_1$ and $C_2$ from commercial reagents or reported intermediates.

| ID | Structure | Observed $[M + H]^+$ |
|---|---|---|
| C3 | 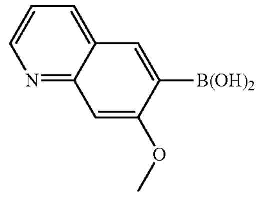 | 204.0 |
| C4 | 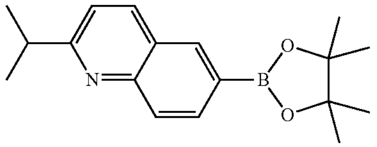 [SMILES: CC(C)c1ccc2cc(B3OC(C)(C)C(C)(C)O3)ccc2n1] | 298.2 |
| C5 | 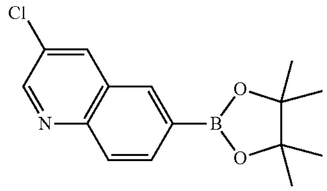 [SMILES: CC1(C)OB(c2ccc3ncc(Cl)cc3c2)OC1(C)C] | 290.0 |
| C6 | 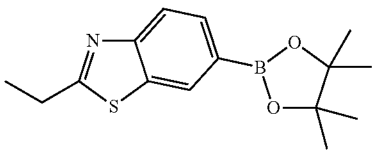 [SMILES: CCc1nc2ccc(B3OC(C)(C)C(C)(C)O3)cc2s1] | 289.9 |

-continued

| ID | Structure | Observed $[M + H]^+$ |
|---|---|---|
| C8 | 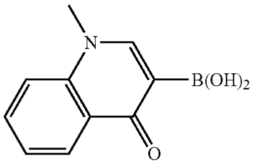 | 204.1 |
| C10 | 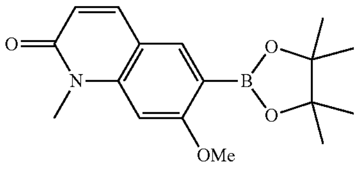 [SMILES: COc1cc2c(ccc(=O)n2C)cc1B1OC(C)(C)C(C)(C)O1] | 316.1 |
| C13 | 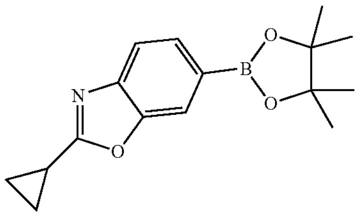 [SMILES: CC1(C)OB(c2ccc3nc(C4CC4)oc3c2)OC1(C)C] | 286.1 |
| C15 | 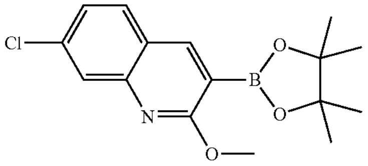 [SMILES: COc1nc2cc(Cl)ccc2cc1B1OC(C)(C)C(C)(C)O1] | 319.9 |
| C16 | 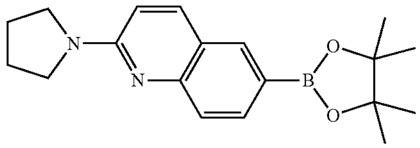 [SMILES: CC1(C)OB(c2ccc3nc(N4CCCC4)ccc3c2)OC1(C)C] | 325.2 |
| C22 | 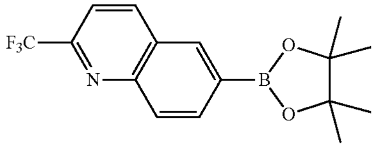 [SMILES: CC1(C)OB(c2ccc3nc(C(F)(F)F)ccc3c2)OC1(C)C] | 324.1 |
| C24 | 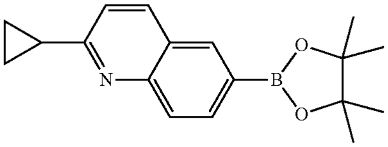 [SMILES: CC1(C)OB(c2ccc3nc(C4CC4)ccc3c2)OC1(C)C] | 296.1 |
| C26 | 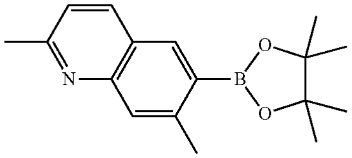 | 283.7 |
| C27 | 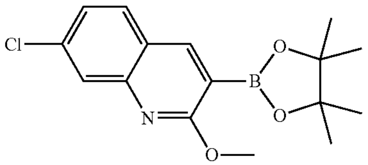 [SMILES: COc1nc2cc(Cl)ccc2cc1B1OC(C)(C)C(C)(C)O1] | 319.9 |

-continued

| ID | Structure | Observed [M + H]+ |
|---|---|---|
| C35 | 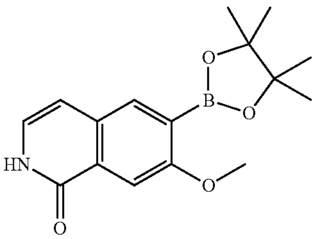 [SMILES: COc1cc2c(=O)[nH]ccc2cc1B1OC(C)(C)C(C)(C)O1] | 302.1 |

Example 30

Preparation of Intermediate C7

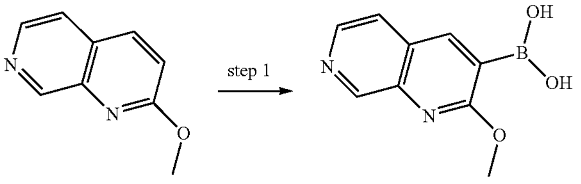

C7_A C7

Step 1: preparation of (2-methoxy-1,7-naphthyridin-3-yl) boronic acid (C7): LDA (1.873 mL, 3.75 mmol) was added to a stirred mixture of 2-methoxy-1,7-naphthyridine ($C_7$_A, 400 mg, 2.497 mmol) and triisopropyl borate (939 mg, 4.99 mmol) in THF (3 mL) at −78° C., and the mixture was stirred at −78° C. for 3 h, followed by stirring at 18° C. for 10 h. The mixture was quenched with $NH_4Cl$ (10 mL), extracted with EtOAc (10 mL*3), the combined organic layers were washed with brine (10 mL), dried over $Na_2SO_4$, filtered and concentrated. The crude product was purified by flash silica gel chromatography (ISCO®; 20 g SepaFlash® Silica Flash Column, Eluent of 0~10% DCM/MeOH gradient @ 40 mL/min) to give (2-methoxy-1,7-naphthyridin-3-yl)boronic acid (C7). $^1$H NMR (400 MHz, MeOD) δ 9.17-9.10 (m, 1H), 8.45-8.39 (m, 1H), 8.30-8.23 (m, 1H), 7.85-7.79 (m, 1H), 4.12 (s, 1H). LCMS (ESI) calc'd for $C_9H_9BN_2O_3$ [M+H]$^+$: 205.1, found: 205.1.

Example 31

Preparation of Intermediate C9

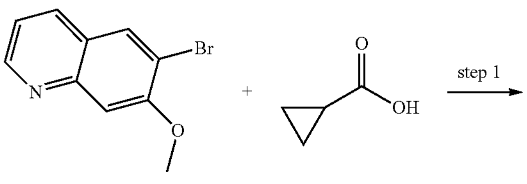

C9_A

-continued

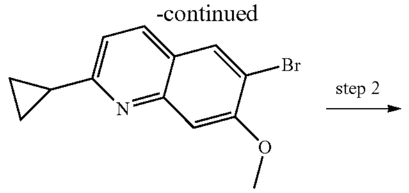

C9_B

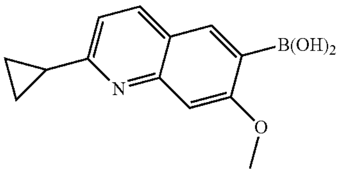

C9

Step 1: Preparation of 6-bromo-2-cyclopropyl-7-methoxyguinoline (C9_B): cAgNO$_3$ (43 mg, 0.253 mmol), cyclopropanecarboxylic acid (37 mg, 0.430 mmol) and 6-bromo-7-methoxyquinoline (C9_A, 100 mg, 0.420 mmol) was added to a stirred mixture of $H_2SO_4$ (0.05 mL, 0.938 mmol) in water (3 mL) at 20° C. and the mixture was warmed to 70° C., and stirred at 70° C. for 6 h. Then $(NH_4)_2S_2O_8$ (288 mg, 1.260 mmol) in water (2 mL) was added drop-wise. After adding, the mixture was cooled to room temperature. Then the mixture was stirred at 70° C. for 12 h. The mixture was cooled, diluted with EtOAc (10 mL), washed with water (3×10 mL), dried ($Na_2SO_4$), filtered and the solvent was evaporated under reduced pressure. The residue was purified by silica gel column flash chromatography, eluting with EtOAc/petroleum ether=0-60% to give 6-bromo-2-cyclopropyl-7-methoxyquinoline (C9_B). LCMS (ESI) calc'd for $C_{13}H_{12}BrNO$ [M+H]$^+$: 278.0, found: 278.0. $^1$H NMR (400 MHz, $CDCl_3$) δ 7.95 (s, 1H), 7.85 (d, J=8.4 Hz, 1H), 7.34 (s, 1H), 7.07 (d, J=8.4 Hz, 1H), 4.03 (s, 3H), 2.16-2.26 (m, 1H), 1.09-1.15 (m, 3H), 0.85 (dd, J=5.7, 19.85 Hz, 1H).

Step 2: Preparation of (2-cyclopropyl-7-methoxyquinolin-6-yl)boronic acid (C9): $PdCl_2$(dppf) (30 mg, 0.041 mmol) was added to a stirred mixture of BPD (110 mg, 0.433 mmol), and 6-bromo-2-cyclopropyl-7-methoxyquinoline (C9_B, 100 mg, 0.360 mmol) in 1,4-dioxane (1 mL) at room temperature and the mixture was stirred at 80° C. for 4 h under $N_2$. The mixture was cooled, diluted with EtOAc (10 mL), washed with brine (saturated, 3×10 mL), dried ($Na_2SO_4$), filtered and the solvent was evaporated under reduced pressure. The residue was purified by silica gel column flash chromatography, eluting with EtOAc/petroleum ether=0-70% to give (2-cyclopropyl-7-methoxyquinolin-6-yl)boronic acid (C9). LCMS (ESI) calc'd for $C_{13}H_{14}BNO_3$ [M+H]$^+$: 244.1, found: 244.1.

Example 32

Preparation of Intermediate C12

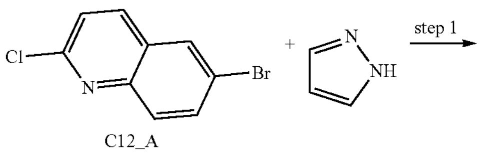

C12_A

-continued

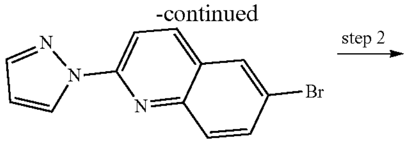

C12_B

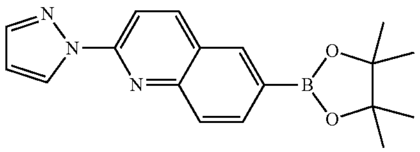

C12

Step 1: Preparation of 6-bromo-2-(1H-pyrazol-1-yl)quinoline (C12_B): A mixture of 6-bromo-2-chloroquinoline (C12_A, 1.00 g, 4.12 mmol), 1H-pyrazole (0.84 g, 12.36 mmol) and $Cs_2CO_3$ (2.69 g, 8.24 mmol) in DMF (30 mL) was stirred at 100° C. for 17 h. The reaction mixture was evaporated in vacuo. To the residue was added water (150 mL) and then it was extracted with EtOAc (60 mL×3). The organic layers were combined, washed with brine (80 mL), dried over anhydrous $Na_2SO_4$, filtered and concentrated. The residue was purified by silica column chromatography (petroleum ether:EtOAc=15:1) to afford 6-bromo-2-(1H-pyrazol-1-yl)quinoline (C12_B). LCMS (ESI) calc'd for $C_{12}H_8BrN_3$ $[M+H]^+$: 274.0, found: 273.9. $^1H$ NMR (400 MHz, $CDCl_3$) δ 6.53 (s, 1H), 7.74-7.82 (m, 2H), 7.83-7.91 (m, 1H), 7.98 (d, J=1.96 Hz, 1H), 8.14-8.28 (m, 2H), 8.77 (d, J=1.96 Hz, 1H).

Step 2: Preparation of 2-(1H-pyrazol-1-yl)-6-(4,4,5,5-tetramethyl-1,3,2-dioxaborolan-2-yl)quinoline (C12): Potassium acetate (1164 mg, 11.86 mmol) was added to the mixture of $PdCl_2$(dppf) (400 mg, 0.547 mmol), 6-bromo-2-(1H-pyrazol-1-yl)quinoline (C12_B, 1300 mg, 4.74 mmol) and BPD (2200 mg, 8.66 mmol) in 1,4-dioxane (30 mL). The resultant mixture was stirred at 70° C. under $N_2$ for 8 h. The mixture was filtered, and the filtrate was concentrated in vacuo. The residue was purified by silica column (petroleum ether:EtOAc=4:1) to afford 2-(1H-pyrazol-1-yl)-6-(4,4,5,5-tetramethyl-1,3,2-dioxaborolan-2-yl)quinoline (C12). LCMS (ESI) calc'd for $C_{18}H_{20}BN_3O_2$ $[M+H]^+$: 322.2, found: 322.0.

Example 33

Preparation of Intermediate C14

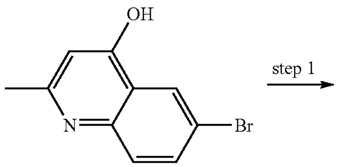

C14_A

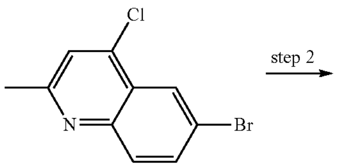

C14_B

-continued

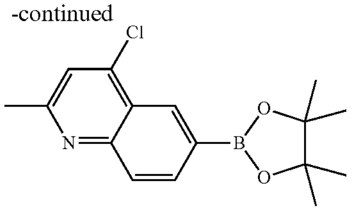

C14

Step 1: Preparation of 6-bromo-4-chloro-2-methylquinoline (C14_B): A suspension of 6-bromo-2-methylquinoline-4-ol ($C_{14}$_A, 1.2 g, 5.06 mmol) in N,N-dimethylaniline (1.3 mL) was treated with phosphorous oxychloride (3.6 mL) and the mixture was heated at 60° C. for 2 h. The mixture was evaporated in vacuo and the residue was taken up with 30 mL water, neutralized with 10 mL saturated aqueous sodium bicarbonate and extracted with EtOAc (3×30 mL). The combined organic fractions were washed with sat. NaCl (30 mL), dried ($Na_2SO_4$), filtered and the solvent was evaporated under reduced pressure. The residue was purified by chromatography on silica gel with ethyl acetate/petroleum ether=1:2 to give 6-bromo-4-chloro-2-methylquinoline (C14_B). LCMS (ESI) calc'd for $C_{10}H_7BrClN$ $[M+H]^+$: 257.9, found: 258.1.

Step 2: Preparation of 4-chloro-2methyl-6-(4,4,5,5-tetramethy-1,3,2-dioxaborolan-2-yl)quinoline (C14): A mixture of 6-bromo-4-chloro-2-methylquinoline (C14_B, 500 mg, 1.96 mmol), BPD (645 mg, 2.53 mmol), KOAc (495 mg, 4.38 mmol) and $PdCl_2$(dppf) (140 mg, 0.19 mmol) in dioxane (20 mL) was degassed and backfilled with $N_2$ three times. The mixture was heated to 90° C. for 2 h. The mixture was filtered and the filtrate was concentrated. The residue was purified by chromatography on silica gel with ethyl acetate/petroleum ether=1:5 to give 4-chloro-2methyl-6-(4,4,5,5-tetramethy-1,3,2-dioxaborolan-2-yl)quinoline (C14). LCMS (ESI) calc'd for $C_{16}H_{19}BrClNO_2$ $[M+H]^+$: 304.1, found: 304.1.

Example 34

Preparation of Intermediate C17

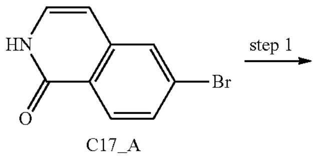

C17_A

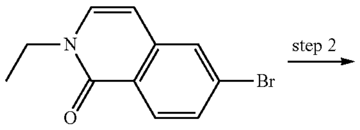

C17_B

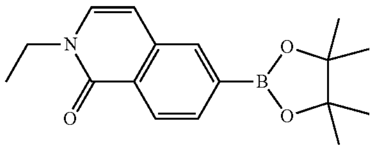

C17

Step 1: Preparation of 6-bromo-2-ethylisoquinolin-1(2H)-one (C17_B): To a solution of 6-bromoisoquinolin-1(2H)-one (C17_A, 500 mg, 2.232 mmol) in DMF (10 mL) was added sodium hydride (214 mg, 5.35 mmol) under $N_2$. After 30 min, iodoethane (1392 mg, 8.93 mmol) was added. The mixture was stirred at 25° C. for 1 h. The mixture was quenched with water (20 mL) and extracted with EtOAc (20 mL*3), the combined oil was concentrated in vacuo. The crude was purified by silica column (petroleum ether:EtOAc=3:1) to afford 6-bromo-2-ethylisoquinolin-1(2H)-one (C17_B).

Step 2: Preparation of 2-ethyl-6-(4,4,5,5-tetramethyl-1,3,2-dioxaborolan-2-yl)isoquinolin-1(2H)-one (C17): Potassium acetate (631 mg, 6.43 mmol) was added to the mixture of $PdCl_2$(dppf) (157 mg, 0.215 mmol), 6-bromo-2-ethylisoquinolin-1(2H)-one (C17_B, 540 mg, 2.142 mmol) and 4,4,4',4',5,5,5',5'-octamethyl-2,2'-bi(1,3,2-dioxaborolane) (1632 mg, 6.43 mmol) in 1,4-dioxane (20 mL). The resultant mixture was stirred at 70° C. under $N_2$ for 8 h. The mixture was filtered, and the filtrate was concentrated in vacuo. The residue was purified by silica column (petroleum ether: EtOAc=3:1) to afford 2-ethyl-6-(4,4,5,5-tetramethyl-1,3,2-dioxaborolan-2-yl)isoquinolin-1(21)-one (C17). LCMS (ESI) calc'd for $C_{17}H_{22}BNO_3$ $[M+H]^+$: 300.2, found: 300.1.

Example 35

Preparation of Intermediate C18

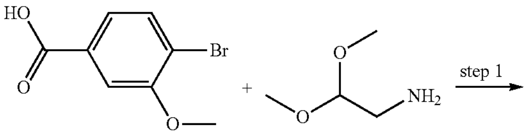

C18_A

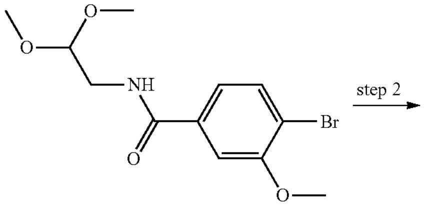

C18_B

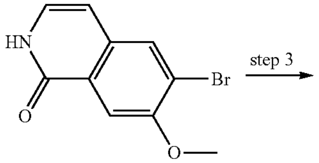

C18_C

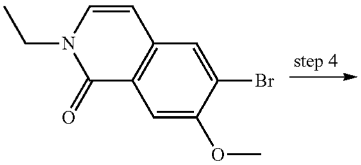

C18_D

-continued

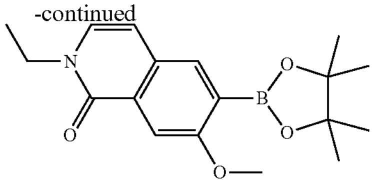

C18

Step 1: Preparation of 4-bromo-N-(2,2-dimethoxyethyl)-3-methoxybenzamide (C18_B): HATU (3.61 g, 9.5 mmol) and TEA (1.042 g, 10.32 mmol) were added to a stirred mixture of 4-bromo-3-methoxybenzoic acid (2 g, 8.6 mmol) in DCM (20 mL) at room temperature and the mixture was stirred at room temperature for 15 min. Then 4-bromo-3-methoxyaniline (C18_A, 997 mg, 9.5 mmol) was added. The solution was stirred for 1 h. Then the solvent was removed to give the title compound ($C_{18}$_B) which was used to the next step without further purification.

Step 2: Preparation of 6-bromo-7-methoxyisoquinolin-1(2H)-one (C18_C): $H_2SO_4$ (20 mL) was added slowly to a stirring round-bottomed flask charged with 4-bromo-N-(2,2-dimethoxyethyl)-3-methoxybenzamide ($C_{18}$_B, 2.72 g crude, 8.6 mmol) at room temperature and the mixture was stirred at room temperature for 2 h. The reaction was poured into ice water, the resulting precipitate was collected by filtration and the filter cake was washed with water (50 mL) and dried to afford the title compound ($C_{18}$_C) which was used directly in the next step.

Step 3: Preparation of 6-bromo-2-ethyl-7-methoxyisoquinolin-1(2H)-one (C18_D): Iodoethane (1.4 g, 8.97 mmol) was added to a stirred mixture of 6-bromo-7-methoxyisoquinolin-1(2H)-one ($C_{18}$_C, 1.52 g, 5.98 mmol) and $Cs_2CO_3$ (2.9 g, 8.97 mmol) in DMF (20 mL) at room temperature and the mixture was stirred at room temperature around for 2 h. The mixture was filtered and the filter cake was washed with DMF (10 mL). The filtrate was poured into water (50 mL) and the precipitate was collected with filtration and the filter cake was washed with water (50 mL) and dried to give 6-bromo-2-ethyl-7-methoxyisoquinolin-1(2H)-one (C18_D). LCMS (ESI) calc'd for $C_{12}H_{12}BrNO_2$ $[M+H]^+$: 282.0, found: 284.0.

Step 4: Preparation of 2-ethyl-7-methoxy-6-(4,4,5,5-tetramethyl-1,3,2-dioxaborolan-2-yl)isoquinolin-1(2H)-one (C18): Potassium acetate (1.660 g, 17 mmol) and BPD (2.16 g, 8.51 mmol) were added to a stirred mixture of 6-bromo-2-ethyl-7-methoxyisoquinolin-1(2H)-one ($C_{18}$_D, 1.6 g, 5.67 mmol) in 1,4-dioxane (20 mL) at room temperature, the mixture was replaced with $N_2$, then $PdCl_2$(dppf) (0.414 g, 0.567 mmol) was added. The mixture was heated with stirring at 80° C. for 18 h. The mixture was cooled to room temperature, filtered and the solvent was evaporated under reduced pressure. The residue was purified by silica gel column flash chromatography, eluting with petroleum ether/EtOAc=30:70 to give 2-ethyl-7-methoxy-6-(4,4,5,5-tetramethyl-1,3,2-dioxaborolan-2-yl)isoquinolin-1(2H)-one (C18). LCMS (ESI) calc'd for $C_{18}H_{24}BNO_4$ $[M+H]^+$: 330.2, found: 330.2.

Example 36

Preparation of Intermediate C19

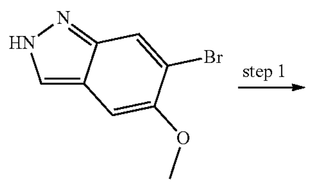

C19_A

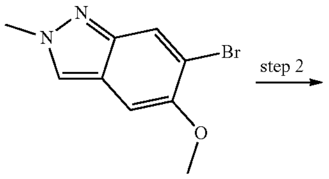

C19_B

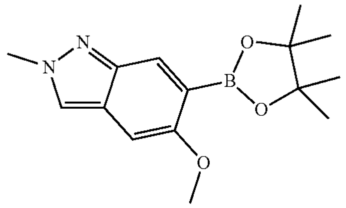

C19

Step 1: Preparation of 6-bromo-5-methoxy-2-methyl-2H-indazole (C19_B): Trimethyloxonium tertafluoroborate (0.782 g, 5.28 mmol) was added to a stirred mixture of 6-bromo-5-methoxy-1H-indazole (C19_A, 1 g, 4.40 mmol) in ethyl acetate (20 mL) at room temperature and the mixture was stirred at room temperature for 2 h. Water (50 mL) was added and the mixture was extracted with ethyl acetate (2×50 mL). The combined organic fractions were washed with brine (saturated, 2×50 mL), dried ($Na_2SO_4$), filtered and the solvent was evaporated under reduced pressure. The residue was purified by silica gel column flash chromatography, eluting with petroleum ether/EtOAc=4:1 to give 6-bromo-5-methoxy-2-methyl-2H-indazole (C19_B). LCMS (ESI) calc'd for $C_9H_9BrN_2O$ $[M+H]^+$: 241.0, found: 242.9. $^1H$ NMR (400 MHz, DMSO-$d_6$) δ 8.22 (s, 1H), 7.90 (s, 1H), 7.19 (s, 1H), 4.11 (s, 3H), 3.83 (s, 3H).

Step 2: Preparation of 5-methoxy-2-methyl-6-(4,4,5,5-tetramethyl-1,3,2-dioxaborolan-2-yl)-2H-indazole (C19): Potassium acetate (855 mg, 8.71 mmol) and BPD (1475 mg, 5.81 mmol) were added to a stirred mixture of 6-bromo-5-methoxy-2-methyl-2H-indazole (C19_B, 700 mg, 2.90 mmol) in 1,4-dioxane (10 mL) at room temperature, the mixture was replaced with $N_2$, and then $PdCl_2$(dppf) (212 mg, 0.290 mmol) was added. The mixture was heated with stirring at 80° C. for 18 h. The mixture was filtered and the filter cake was washed with ethyl acetate (40 mL) and dried under vacuum. The residue was purified by silica gel column flash chromatography, eluting with petroleum ether/EtOAc=3:1 to give 5-methoxy-2-methyl-6-(4,4,5,5-tetramethyl-1,3,2-dioxaborolan-2-yl)-2H-indazole (C19). LCMS (ESI) calc'd for $C_{15}H_{21}BN_2O_3$ $[M+H]^+$: 289.1, found: 289.1.

Example 37

Preparation of Intermediate C20

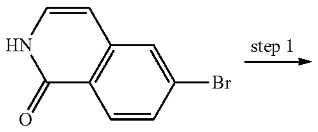

C20_A

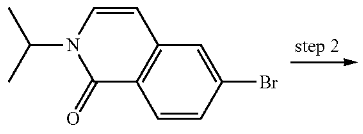

C20_B

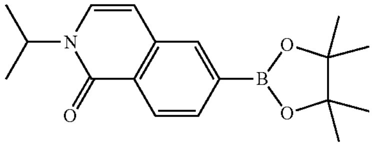

C20

Step 1: Preparation of 6-bromo-2-isopropylisoquinolin-1(2H)-one (C20_B): To a solution of 6-bromoisoquinolin-1(2H)-one (C20_A, 500 mg, 2.232 mmol) in DMF (15 mL) was added NaH (357 mg, 8.93 mmol) at 0° C., the mixture was stirred at 0° C. for 30 min, then 2-iodopropane (1.5 g, 8.82 mmol) was added to the mixture, and the reaction mixture was stirred at room temperature for 16 h. Water (10 mL) was added, it was extracted with EtOAc (25 mL*3), washed with brine (15 mL), dried over $Na_2SO_4$, concentrated, and the residue was purified by prep-TLC ($SiO_2$, petroleum ether:EtOAc=3:1) to give 6-bromo-2-isopropylisoquinolin-1(2H)-one (C20_B). LCMS (ESI) calc'd for $C_{12}H_{10}BrNO$ $[M+H]^+$: 265.9, found: 265.9.

Step 2: Preparation of 2-isopropyl-6-(4,4,5,5-tetramethyl-1,3,2-dioxaborolan-2-yl)isoquinolin-1(2H)-one (C20): Potassium acetate (387 mg, 3.94 mmol) was added to the mixture of BPD (1000 mg, 3.94 mmol) and 6-bromo-2-isopropylisoquinolin-1(2H)-one (C20_B, 350 mg, 1.315 mmol) and $PdCl_2$(dppf) (96 mg, 0.131 mmol) in dioxane (10 mL). The mixture was stirred at 70° C. under $N_2$ for 16 h. The mixture was filtered, water (15 mL) was added to the filtrate, it was extracted with EtOAc (15 mL*3), dried over $Na_2SO_4$, filtered and concentrated, and the residue was purified by prep-TLC ($SiO_2$, petroleum ether:EtOAc=3:1) to give 2-isopropyl-6-(4,4,5,5-tetramethyl-1,3,2-dioxaborolan-2-yl)isoquinolin-1(2H)-one (C20). LCMS (ESI) calc'd for $C_{18}H_{24}BNO_3$ $[M+H]^+$: 314.2, found: 314.2.

Example 38

Preparation of Intermediate C21

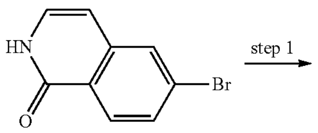

C20_A

-continued

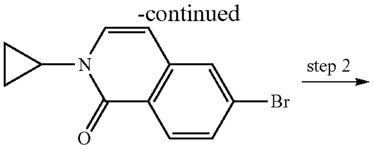

C21_A

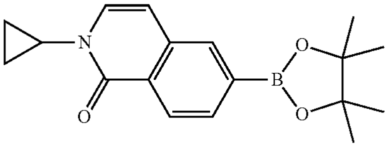

C21

Step 1: Preparation of 6-bromo-2-cyclopropylisoquinolin-1(2H)-one (C21_A): To 6-bromoisoquinolin-1(2H)-one (C20_A, 500 mg, 2.232 mmol) in DCM (30 mL) was added cyclopropylboronic acid (767 mg, 8.93 mmol), diacetoxycopper (405 mg, 2.232 mmol), pyridine (706 mg, 8.93 mmol) and $Et_3N$ (1.244 mL, 8.92 mmol), the mixture was stirred at 20° C. under 02 for 16 h. The mixture was filtered, water (15 mL) was added, it was extracted with DCM (15 mL*3), dried over $Na_2SO_4$, filtrated, concentrated. The residue was purified by prep-TLC ($SiO_2$, petroleum ether: EtOAc=3:1) to give 6-bromo-2-cyclopropylisoquinolin-1 (2H)-one (C21_A). LCMS (ESI) calc'd for $C_{12}H_{10}BrNO$ $[M+H]^+$: 263.9, found: 264.0.

Step 2: Preparation of 2-cyclopropyl-6-(4,4,5,5-tetramethyl-1,3,2-dioxaborolan-2-yl)isoquinolin-1(2H)-one (C21): Potassium acetate (325 mg, 3.31 mmol) was added to the mixture of $PdCl_2(dppf)$ (150 mg, 0.205 mmol), 6-bromo-2-cyclopropylisoquinolin-1(2H)-one (350 mg, 1.325 mmol) and 4,4,4',4',5,5,5',5'-octamethyl-2,2'-bi(1,3,2-dioxaborolane) (606 mg, 2.386 mmol) in 1,4-dioxane (10 mL). The resultant mixture was stirred at 70° C. under $N_2$ for 8 h. The mixture was filtered, and the filtrate was concentrated in vacuo. The residue was purified by silica column (petroleum ether:EtOAc=3:1) to afford 2-cyclopropyl-6-(4,4,5,5-tetramethyl-1,3,2-dioxaborolan-2-yl)isoquinolin-1(2H)-one (C21). LCMS (ESI) calc'd for $C_{18}H_{22}BNO_3$ $[M+H]^+$: 312.2, found: 312.1.

Example 39

Preparation of Intermediate C23

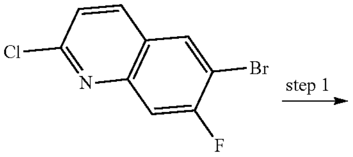

C23_A

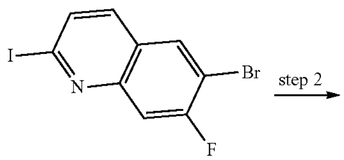

C23_B

-continued

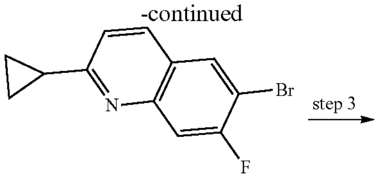

C23_C

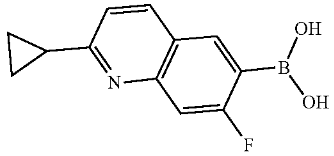

C23

Step 1: Preparation of 6-bromo-7-fluoro-2-iodoquinoline (C23_B): AcCl (0.2 mL, 2.81 mmol) was added to a stirred mixture of 6-bromo-2-chloro-7-fluoroquinoline (C23_A, 0.6 g, 2.303 mmol) and sodium iodide (3.45 g, 23.03 mmol) in acetonitrile (2.5 mL) at 80° C. and the mixture was stirred at 80° C. for 12 h. The mixture was cooled, diluted with ethyl acetate (10 mL), washed with aq $Na_2SO_3$ (3×15 mL), dried ($Na_2SO_4$), filtered and the solvent was evaporated under reduced pressure. The residue was purified by silica gel column flash chromatography, eluting with EtOAc/petroleum ether=0-20% to give 6-bromo-7-fluoro-2-iodoquinoline (C23_B). LCMS (ESI) calc'd for $C_9H_4BrFIN$ $[M+H]^+$: 351.9, found: 351.8. $^1H$ NMR (400 MHz, $CDCl_3$) δ 8.05 (d, J=7.04 Hz, 1H), 7.72-7.78 (m, 2H), 7.66-7.71 (m, 1H).

Step 2: Preparation of 6-bromo-2-cyclopropyl-7-fluoroquinoline (C23_C): Tricyclohexylphosphine (121 mg, 0.432 mmol) and diacetoxypalladium (48 mg, 0.214 mmol) was added to a stirred mixture of $K_3PO_4$ (917 mg, 4.32 mmol), cyclopropylboronic acid (185 mg, 2.159 mmol) and 6-bromo-7-fluoro-2-iodoquinoline (C23_B, 760 mg, 2.159 mmol) in toluene (5 mL) at room temperature and the mixture was stirred at 100° C. for 8 h. The mixture was cooled, diluted with ethyl acetate (10 mL), washed with brine (saturated, 3×15 mL), dried ($Na_2SO_4$), filtered and the solvent was evaporated under reduced pressure. The residue was purified by silica gel column flash chromatography, eluting with EtOAc/petroleum ether=0-10% to give 6-bromo-2-cyclopropyl-7-fluoroquinoline (C23_C). LCMS (ESI) calc'd for $C_{12}H_9BrFN$ $[M+H]^+$: 266.0, found: 267.7.

Step 3: Preparation of (2-cyclopropyl-7-fluoroquinolin-6-yl)boronic acid (C23): nBuLi (2.5 M, 1.5 mL, 3.75 mmol) was added to a stirred mixture of triisopropyl borate (424 mg, 2.255 mmol), and 6-bromo-2-cyclopropyl-7-fluoroquinoline (C23_C, 300 mg, 1.127 mmol) in THF (2 mL) at −78° C. and the mixture was stirred at room temperature for 4 h. Aqueous ammonium chloride (20%, 10 mL) was added and the mixture was extracted with EtOAc (3×10 mL). The combined organic fractions were washed with brine (saturated, 15 mL), dried ($Na_2SO_4$), filtered and the solvent was evaporated under reduced pressure. The residue was purified by silica gel column flash chromatography, eluting with MEOH/DCM=0-20% to give (2-cyclopropyl-7-fluoroquinolin-6-yl)boronic acid (C23). LCMS (ESI) calc'd for $C_{12}H_{11}BFNO_2$ $[M+H]^+$: 232.1, found: 231.7.

Example 40

Preparation of Intermediate C25

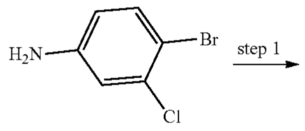

C25_A

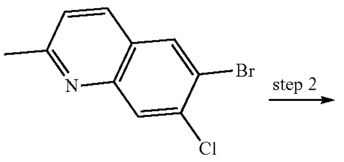

C25_B

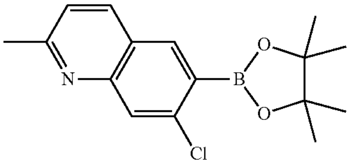

C25

Step 1: Preparation of 6-bromo-7-chloro-2-methylquinoline (C25_B): (E)-but-2-enal (2.03 g, 29.1 mmol) was added dropwise to a stirred mixture of 4-bromo-3-chloroaniline (C25_A, 4 g, 19.37 mmol) and conc. HCl (12.7 mL, 155 mmol) in water (4.0 mL) at 110° C. and the mixture was stirred at 110° C. for 2 h. Then the mixture was neutralized with $NH_{40}H$ until the pH reached 7. The organic phase was extracted with DCM (50 mL*3). The combined organic phases were dried over $MgSO_4$, filtered and concentrated. The crude product was purified by preparative HPLC (reverse phase C-18 column), eluting with acetonitrile/water+0.1 TFA, to give 6-bromo-7-chloro-2-methylquinoline (C25_B). LCMS (ESI) calc'd for $C_{10}H_7BrClN$ $[M+H]^+$: 255.9, found: 258.0.

Step 2: Preparation of 7-chloro-2-methyl-6-(4,4,5,5-tetramethyl-1,3,2-dioxaborolan-2-yl)quinoline (C25): $PdCl_2$ (dppf) (61 mg, 0.084 mmol) was added to a stirred mixture of KOAc (494 mg, 5.03 mmol), BPD (724 mg, 2.85 mmol), and 6-bromo-7-chloro-2-methylquinoline ($C_{25}$_B, 430 mg, 1.676 mmol) in dioxane (10 mL) at room temperature and the mixture was stirred at 70° C. for 1 h under $N_2$. The solvent was evaporated under reduced pressure. The residue was purified by silica gel, eluting with EtOAc/petroleum ether=1/1 to give 7-chloro-2-methyl-6-(4,4,5,5-tetramethyl-1,3,2-dioxaborolan-2-yl)quinoline (C25). LCMS (ESI) calc'd for $C_{16}H_{19}BClNO_2$ $[M+H]^+$: 304.1, found: 304.1.

Example 41

Preparation of Intermediate C28

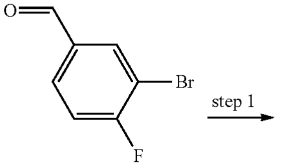

C28_A

-continued

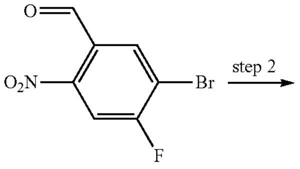

C28_B

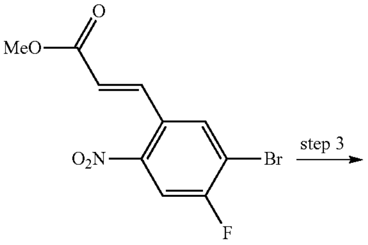

C28_C

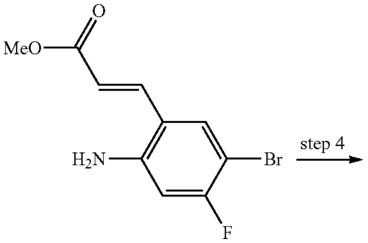

C28_D

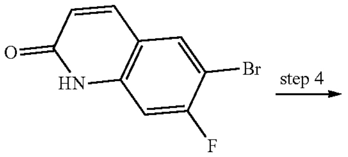

C28_E

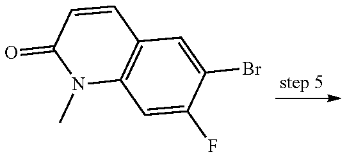

C28_F

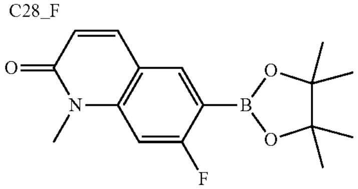

C28

Step 1: Preparation of 5-bromo-4-fluoro-2-nitrobenzaldehyde (C28_B): 3-bromo-4-fluorobenzaldehyde (C28_A, 9.00 g, 44.34 mmol) was added to a stirred solution of concentrated nitric acid (67 percent, 6.0 mL, 88.65 mmol) in concentrated sulfuric acid (54.0 mL) at 0° C. After the addition was complete, the ice bath was removed and the reaction was allowed to stir at room temperature for 5 h. Then the mixture was poured into ice and filtered to give of 5-bromo-4-fluoro-2-nitrobenzaldehyde (C28_B) which was used to the next step without further purification.

Step 2: Preparation of (E)-methyl 3-(5-bromo-4-fluoro-2-nitrophenyl)acrylate (C28_C): 5-bromo-4-fluoro-2-nitrobenzaldehyde (C28_B, 10.00 g, 40.00 mol) and (methoxycarbonylmethylene) triphenylphosphorane (14.80 g, 44.00 mmol) are mixed in toluene (40 mL) and stirred at 120° C. for 30 min. After it was cooled to room temperature, the mixture was diluted with water (200 mL) and extracted with ethyl acetate (200 mL). The organic layer was dried over $Na_2SO_4$, filtered and concentrated in vacuo. The residue was purified by silica chromatography (EtOAc/petroleum ether=1/5 to 1/4) to afford the title compound (C28_C).

Step 3: Preparation of (E)-methyl 3-(2-amino-5-bromo-4-fluorophenyl)acrylate (C28_D): A mixture of (E)-methyl 3-(5-bromo-4-fluoro-2-nitrophenyl)acrylate (C28_C, 6.68 g, 22.00 mmol), Fe power (5.43 g, 96.80 mmol), and $NH_4Cl$ (106 mg, 9.68 mmol) in $EtOH/H_2O$ (80 mL/40 mL) was stirred under reflux conditions under $N_2$ for 2 h. The reaction was cooled to room temperature, filtered through a Celite pad, washed with EtOH, and the resulting elute was concentrated to give (E)-methyl 3-(2-amino-5-bromo-4-fluorophenyl)acrylate (C28_D) which was used in next step without further purification. LCMS (ESI) calc'd for $C_{10}H_{10}BrFNO_2$ [M+Na]*: 274.0, found: 276.0.

Step 4: Preparation of 6-bromo-7-fluoroquinolin-2(1H)-one (C28_E): A mixture of (E)-methyl 3-(2-amino-5-bromo-4-fluorophenyl)acrylate (C28_D, 2.50 g, 9.12 mmol) in THF (10.0 mL) and 3 M hydrochloric acid (10.0 mL) was heated at 65° C. for 18 h. The mixture was cooled to room temperature and the precipitate was filtered, washed with water and dried in vacuo to give 6-bromo-7-fluoroquinolin-2(1H)-one (C28_E). LCMS (ESI) calc'd for $C_{11}H_8BrFN_2O$ $[M+H]^+$: 242.0, found: 242.0. $^1H$ NMR (400 MHz, DMSO-$d_6$) δ 11.89 (s, 1H), 8.07 (d, J=7.50 Hz, 1H), 7.84 (d, J=9.70 Hz, 1H), 7.14 (d, J=9.92 Hz, 1H), 6.48 (d, J=9.70 Hz, 1H).

Step 5: Preparation of 6-bromo-7-fluoro-1-methylquinolin-2(1H)-one (C28_F): NaH (206 mg, 5.14 mmol) was added to a stirred solution of 6-bromo-7-fluoroquinolin-2 (1H)-one (C28_E, 830 mg, 3.43 mmol) at room temperature. Then iodomethane (1660 mg, 11.70 mmol) was added at room temperature and the mixture was stirred at room temperature for 0.5 h. The mixture were poured into ice water (50 mL) and the precipitate was collected with filtration and the filter cake was washed with water (100 mL) and dried to give 6-bromo-7-fluoro-1-methylquinolin-2(1H)-one (C28_F). LCMS (ESI) calc'd for $C_{10}H_7BrFNO$ $[M+H]^+$: 256.0, found: 258.0.

Step 6: Preparation of compound 7-fluoro-1-methyl-6-(4,4,5,5-tetramethyl-1,3,2-dioxaborolan-2-yl)quinolin-2(1H)-one (C28): Potassium acetate (834 mg, 8.49 mmol) and BPD (3451 mg, 13.59 mmol) were added to a stirred mixture of 6-bromo-7-fluoro-1-methylquinolin-2(1H)-one (C28_F, 870 mg, 3.40 mmol) in dioxane (10 mL) at room temperature, the mixture was replaced with $N_2$, then $PdCl_2$(dppf) (124 mg, 0.170 mmol) was added. The mixture was heated with stirring at 100° C. for 24 h. The reaction solution was concentrated and the residue was purified by silica gel column flash chromatography, eluting with petroleum ether/EtOAc=5:1-2:1. The obtained product was washed with petroleum ether (10 mL) to give 7-fluoro-1-methyl-6-(4,4,5,5-tetramethyl-1,3,2-dioxaborolan-2-yl)quinolin-2(1H)-one (C28_F). LCMS (ESI) calc'd for $C_{16}H_{19}BFNO_3$ $[M+H]^+$: 304.1, found: 304.2.

Example 42

Preparation of Intermediates C29 and C30

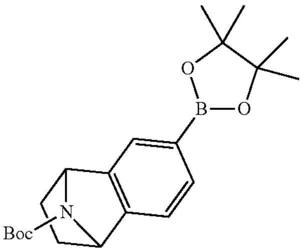

C29

+

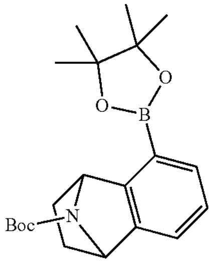

C30

To a degassed solution of tert-butyl 1,2,3,4-tetrahydro-1,4-epiminonaphthalene-9-carboxylate (100 mg, 0.408 mmol), 4,4,4',4',5,5,5',5'-octamethyl-2,2'-bi(1,3,2-dioxaborolane) (311 mg, 1.223 mmol) and (R)-(+)-2,2'-bis[di(3,5-xylyl)phosphino]-6,6'-dimethoxy-1,1'-biphenyl (28.3 mg, 0.041 mmol) in hexane (3.0 mL) was added (1,5-cyclooctadiene)(methoxy)iridium(I) dimer (13.51 mg, 0.020 mmol) under $N_2$. The mixture was stirred at 90° C. for 16 h under $N_2$ and then concentrated. The residue was purified by preparative HPLC (reverse phase C-18 column), eluting with acetonitrile/water+0.225% HCOOH, to give tert-butyl 6-(4,4,5,5-tetramethyl-1,3,2-dioxaborolan-2-yl)-1,2,3,4-tetrahydro-1,4-epiminonaphthalene-9-carboxylate (C29). LCMS (ESI) calc'd for $C_{21}H_{30}BNO_4$ $[M+H]^+$: 372.2, found: 316.1. And tert-butyl 5-(4,4,5,5-tetramethyl-1,3,2-dioxaborolan-2-yl)-1,2,3,4-tetrahydro-1,4-epiminonaphthalene-9-carboxylate (C30). LCMS (ESI) calc'd for $C_{21}H_{30}BNO_4$ $[M+H]^+$: 372.2, found: 272.1.

Example 43

Preparation of Intermediate C31

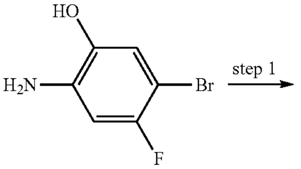

C31_A

-continued

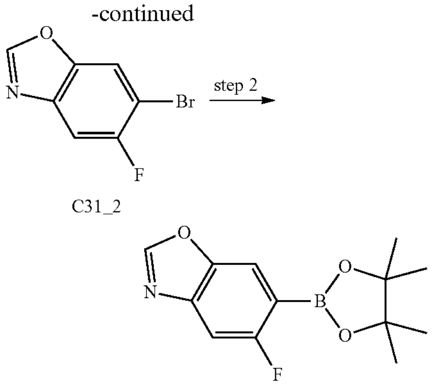

C31_2

C31

Step 1: 6-bromo-5-fluorobenzo[d]oxazole (C31_B): A mixture of 2-amino-5-bromo-4-fluorophenol (C31_A, 1.2 g, 5.82 mmol) and triethoxymethane (10 mL, 60.1 mmol) was stirred at 100° C. for 10 h. The reaction mixture was cooled to room temperature and concentrated. The residue was purified by column chromatography on silica gel using eluent 0-20% ethyl acetate in petroleum ether to give 6-bromo-5-fluorobenzo[d]oxazole (C31_B). LCMS (ESI) calc'd for $C_7H_3BrFNO$ $[M+H]^+$: 215.9, found: 215.5. $^1H$ NMR (400 MHz, $CDCl_3$) δ 8.10 (s, 1H), 7.80 (d, J=5.51 Hz, 1H), 7.54 (d, J=7.94 Hz, 1H).

Step 2: 5-fluoro-6-(4,4,5,5-tetramethyl-1,3,2-dioxaborolan-2-yl)benzo[d]oxazole (C31): Potassium acetate (518 mg, 5.28 mmol) and BPD (536 mg, 2.111 mmol) were added to a stirred mixture of 6-bromo-5-fluorobenzo[d]oxazole (C31_B, 380 mg, 1.759 mmol) in 1,4-dioxane (5 mL) at room temperature, the mixture was replaced with $N_2$, and $PdCl_2$(dppf) (129 mg, 0.176 mmol) was added. The mixture was heated with stirring at 80° C. for 2 h under $N_2$. The mixture was cooled to room temperature, water (10 mL) was added and the mixture was extracted with ethyl acetate (2×10 mL). The combined organic fractions were washed with brine (saturated, 10 mL), dried ($Na_2SO_4$), filtered and the solvent was evaporated under reduced pressure. The residue was purified by silica gel column flash chromatography, eluting with petroleum ether/EtOAc=0-50% to give 5-fluoro-6-(4,4,5,5-tetramethyl-1,3,2-dioxaborolan-2-yl) benzo[d]oxazole (C31). LCMS (ESI) calc'd for $C_{13}H_{15}BFNO_3$ $[M+H]^+$: 264.1, found: 264.0.

Example 44

Preparation of Intermediate C32

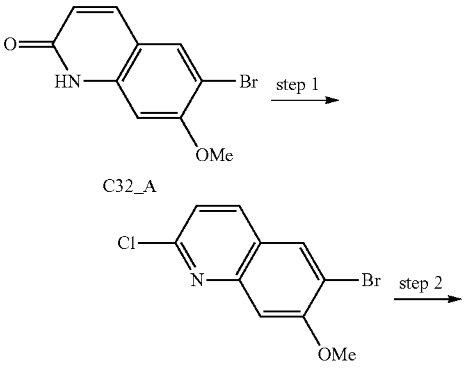

C32_A

C32_B

-continued

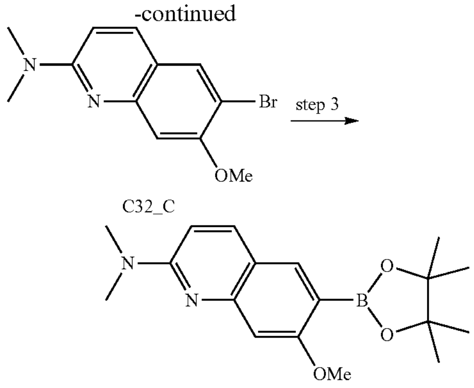

C32_C

C32

Step 1: Preparation of 6-bromo-2-chloro-7-methoxyquinoline (C32_B): 6-Bromo-7-methoxyquinolin-2(1H)-one (C32_A, described in WO2016/34512 A1, 2.47 g, 9.72 mmol) was added to $POCl_3$ (14.8 mL, 159 mmol) slowly in portions at rt and the mixture was stirred at 110° C. for 2.5 h. The mixture was cooled to rt and poured into warm water (200 mL) slowly with vigorous stirring. NaOH (solid) was added to adjust the pH to between 7 and 8 and the mixture was extracted with EtOAc (100 mL×2). The combined organic fractions were washed with brine (saturated, 100 mL), dried ($Na_2SO_4$), filtered and the solvent was evaporated under reduced pressure to give 6-bromo-2-chloro-7-methoxyquinoline (C32_B). LCMS (ESI) calc'd for $C_{10}H_7BrClNO$ $[M+H]^+$: 271.9, found: 273.7. $^1H$ NMR (400 MHz, $CDCl_3$) δ 8.04 (s, 1H), 7.97 (d, J=8.4 Hz, 1H), 7.39 (s, 1H), 7.29 (d, J=8.6 Hz, 1H), 4.03 (s, 3H).

Step 2: Preparation of 6-bromo-7-methoxy-N,N-dimethylquinolin-2-amine (C32_C): A mixture of 6-bromo-2-chloro-7-methoxyquinoline (C32_B, 900 mg, 3.30 mmol), dimethylamine hydrochloride (539 mg, 6.60 mmol) and $Cs_2CO_3$ (3766 mg, 11.56 mmol) in DMF (20 mL) was stirred at 90° C. for 12 h. The combined mixture was cooled to rt, water (250 mL) was added and the mixture was extracted with ethyl acetate (100×2 mL). The combined organic fractions were washed with brine (saturated, 100 mL), dried ($Na_2SO_4$), filtered and the solvent was evaporated under reduced pressure. The residue was purified by silica gel column flash chromatography, eluting with petroleum ether/EtOAc=8:1 to give 6-bromo-7-methoxy-N,N-dimethylquinolin-2-amine (C32_C). LCMS (ESI) calc'd for $C_{12}H_{13}BrN_2O$ $[M+H]^+$: 281.0, found: 281.0. $^1H$ NMR (400 MHz, $CDCl_3$) δ 7.76 (s, 1H), 7.71 (d, J=9.2 Hz, 1H), 7.12 (s, 1H), 6.75 (d, J=9.2 Hz, 1H), 4.00 (s, 3H), 3.22 (s, 6H).

Step 3: Preparation of 7-methoxy-N,N-dimethyl-6-(4,4,5,5-tetramethyl-1,3,2-dioxaborolan-2-yl)quinolin-2-amine (C32): $PdCl_2$(dppf) (195 mg, 0.267 mmol) was added to a stirring mixture of 6-bromo-7-methoxy-N,N-dimethylquinolin-2-amine (C32_C, 750 mg, 2.67 mmol), BPD (1355 mg, 5.34 mmol) and potassium acetate (785 mg, 8.00 mmol) in 1,4-dioxane (25 mL) at rt and the mixture was stirred at 80° C. under $N_2$ atmosphere for 12 h. The combined mixture was cooled to rt and filtered through Celite. The resulting filtrate was concentrated under reduced pressure. The residue was purified by silica gel column flash chromatography, eluting with petroleum ether/EtOAc=33%-67% to give 7-methoxy-N,N-dimethyl-6-(4,4,5,5-tetramethyl-1,3,2-dioxaborolan-2-yl)quinolin-2-amine (C32). LCMS (ESI) calc'd for $C_{18}H_{25}BN_2O_3$ $[M+H]^+$: 329.2, found: 329.2.

Example 45

Preparation of Intermediate D1

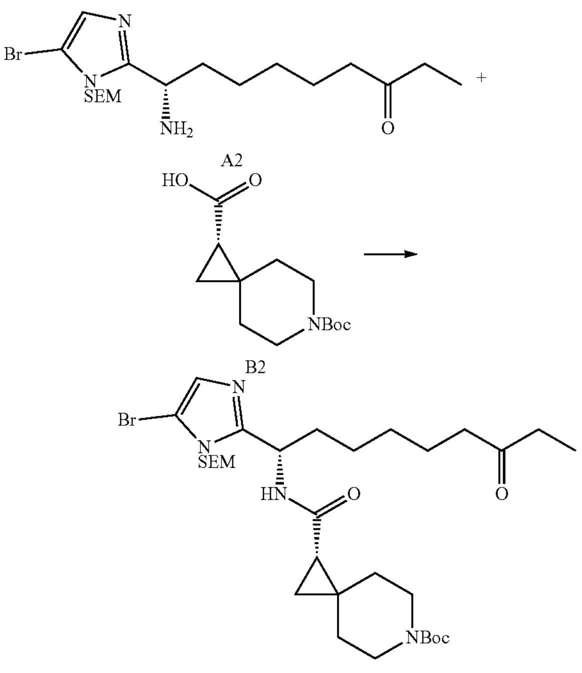

A2

B2

D1

T3P (50% in EtOAc, 14.71 g, 23.12 mmol) was added to a stirred mixture of (S)-9-amino-9-(5-bromo-1-((2-(trimethylsilyl)ethoxy)methyl)-1H-imidazol-2-yl)nonan-3-one (A2, 5 g, 11.56 mmol), (S)-6-(tert-butoxycarbonyl)-6-azaspiro[2.5]octane-1-carboxylic acid (B2, 3.54 g, 13.87 mmol) and DIPEA (6 mL, 34.4 mmol) in THF (50 mL) at room temperature and the mixture was stirred at room temperature for 18 h. The mixture was quenched with water (50 mL) and the mixture was extracted with ethyl acetate (4×50 mL). The combined organic fractions were washed with brine (saturated, 2×40 mL), dried $Na_2SO_4$, filtered and the solvent was evaporated under reduced pressure. The residue, which was combined with another residue from the same reaction starting from 1 g amine, was purified by silica gel column flash chromatography, eluting with petroleum ether/EtOAc=1:1 to give (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (D1). LCMS (ESI) calc'd for $C_{31}H_{53}BrN_4O_5Si$ $[M+H]^+$: 669.3, found: 670.8.

Example 46

Preparation of Intermediate D2

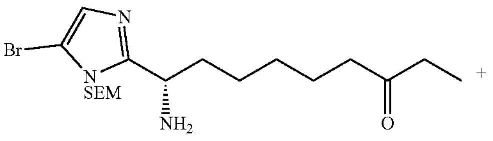

A2

-continued

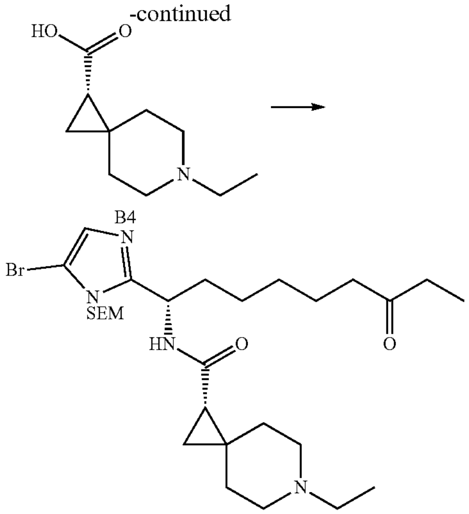

B4

D2

HATU (0.967 g, 2.54 mmol) and $Et_3N$ (1.6 mL, 11.48 mmol) were added to a stirred mixture of (S)-6-ethyl-6-azaspiro[2.5]octane-1-carboxylic acid (B4, 0.466 g, 2.54 mmol) in DMF (15 mL) at room temperature and the mixture was stirred at room temperature for 15 min. Then (S)-9-amino-9-(5-bromo-1-((2-(trimethylsilyl)ethoxy)methyl)-1H-imidazol-2-yl)nonan-3-one (A2, 1.0 g, 2.312 mmol) was added. The mixture was stirred at room temperature for 1 h. Water (10 mL) was added and it was extracted with ethyl acetate (3×10 mL). The combined organic fractions were washed with brine (saturated, lx 10 mL) and dried with $Na_2SO_4$, filtered and the solvent was evaporated under reduced pressure. The residue was purified by silica gel flash chromatography (ISCORF75; Sepa flash column), eluting with DCM/MeOH=1~10/1 to give (S)—N—((S)-1-(5-bromo-1-((2-(trimethylsilyl)ethoxy)methyl)-1H-imidazol-2-yl)-7-oxononyl)-6-ethyl-6-azaspiro[2.5]octane-1-carboxamide (D2). LCMS (ESI) calc'd for $C_{28}H_{49}BrN_4O_3Si$ $[M+H]^+$: 597.3 and 599.3, found: 597.3 and 599.3. $^1H$ NMR (400 MHz, $CDCl_3$) δ 6.87 (s, 1H), 6.15-6.27 (m, 1H), 5.54-5.66 (m, 1H), 5.08-5.17 (m, 1H), 5.01-5.07 (m, 1H), 3.44-3.56 (m, 2H), 2.47-2.56 (m, 1H), 2.27-2.45 (m, 8H), 1.74-2.01 (m, 4H), 1.62-1.73 (m, 1H), 1.44-1.61 (m, 3H), 1.18-1.42 (m, 6H), 1.11-1.17 (m, 1H), 1.06 (s, 6H), 0.83-0.97 (m, 2H), 0.74-0.82 (m, 1H), 0.00 (s, 9H).

Example 47

Preparation of Intermediate D3

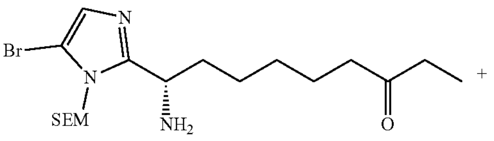

A2

-continued

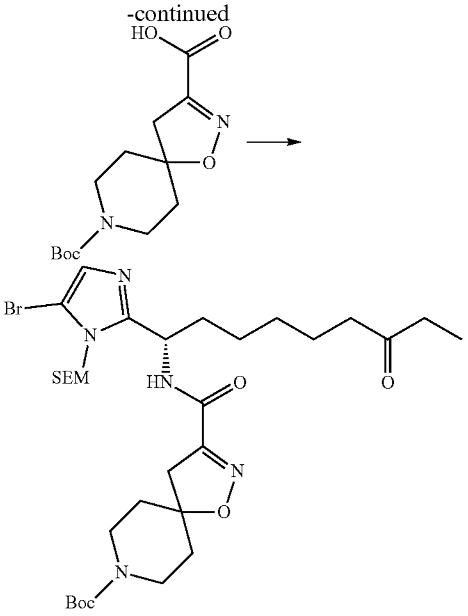

D3

EDCI (1.618 g, 8.44 mmol) and 1H-benzo[d][1,2,3]triazol-1-ol (1.141 g, 8.44 mmol) were added to a stirred mixture of 8-(tert-butoxycarbonyl)-1-oxa-2,8-diazaspiro[4.5]dec-2-ene-3-carboxylic acid (2 g, 7.03 mmol) and DIPEA (1.843 mL, 10.55 mmol) in DMF (20 mL) at room temperature, then (S)-9-amino-9-(5-bromo-1-((2-(trimethylsilyl)ethoxy)methyl)-1H-imidazol-2-yl)nonan-3-one (A2, 3.04 g, 7.03 mmol) was added. The mixture was kept at 20° C. for 1 h. Water (50 mL) was added to the reaction solution and then it was extracted with EtOAc (50 mL×2). The organic phase was washed with brine (50 mL) and the solvent was evaporated under reduced pressure. The residue was purified by flash chromatography on silica gel, eluting with EtOAc: petroleum ether=1:1 to give (S)-tert-butyl 3-((1-(5-bromo-1-((2-(trimethylsilyl)ethoxy)methyl)-1H-imidazol-2-yl)-7-oxononyl)carbamoyl)-1-oxa-2,8-diazaspiro[4.5]dec-2-ene-8-carboxylate (D3). LCMS (ESI) calc'd for $C_{31}H_{52}BrN_5O_6Si$ $[M+H]^+$: 698.3, found: 700.3.

The following intermediates were prepared using similar procedures as described for intermediates D1, D2 and D3

| Intermediate ID | Structures | Observed $[M + H]^+$ |
| --- | --- | --- |
| D4 | 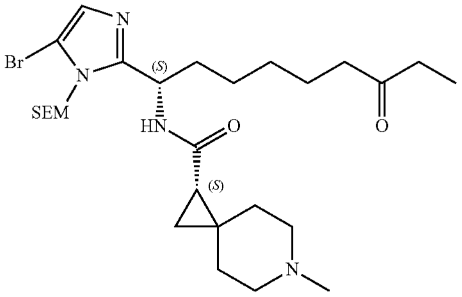 | 583.2 |
| D5 | 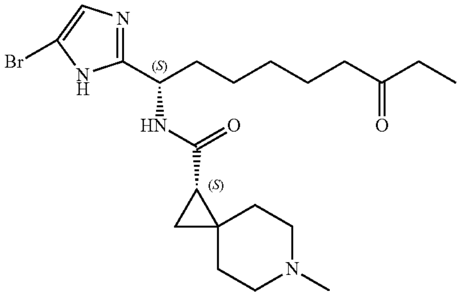 | 455.1 |
| D6 | 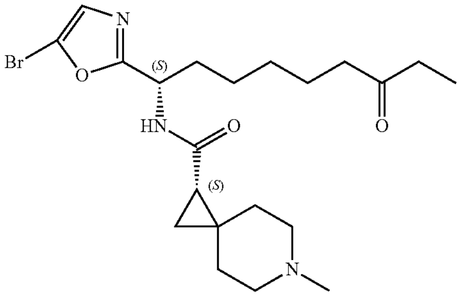 | 456.2 |

-continued
| Intermediate ID | Structures | Observed [M + H]+ |
|---|---|---|
| D7 | 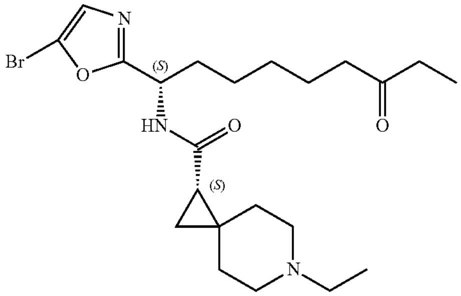 | 470.2 |
| D8 | 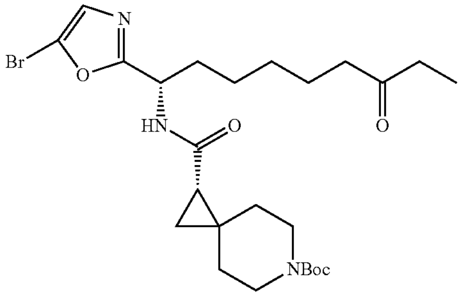 [SMILES: CCC(=O)CCCCC[C@H](NC(=O)[C@H]1CC12CCN(C(=O)OC(C)(C)C)CC2)c1ncc(Br)o1] | 540.2 |
| D9 | 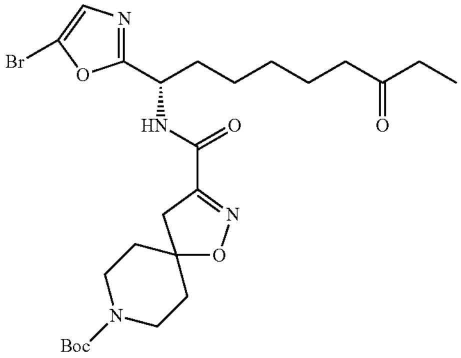 [SMILES: CCC(=O)CCCCC[C@H](NC(=O)C1=NOC2(CCN(C(=O)OC(C)(C)C)CC2)C1)c1ncc(Br)o1] | 571.2 |
| D10 | 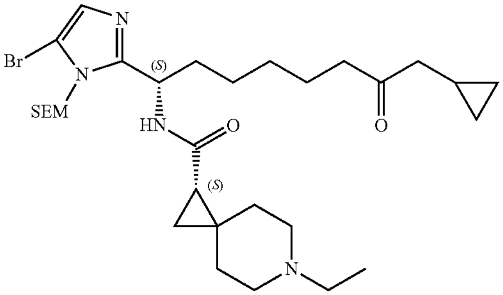 | 623.3 |

-continued

| Intermediate ID | Structures | Observed $[M + H]^+$ |
|---|---|---|
| D11 | 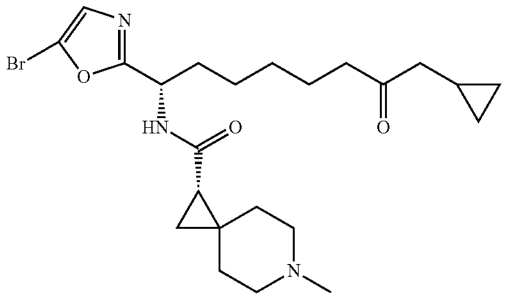 [SMILES: CN1CCC2(CC1)C[C@@H]2C(=O)N[C@@H](CCCCCC(=O)CC1CC1)c1ncc(Br)o1] | 480.2 |
| D12 | 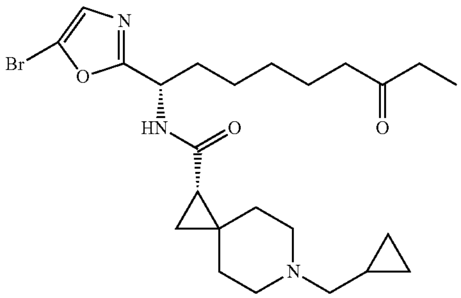 [SMILES: CCC(=O)CCCCC[C@H](NC(=O)[C@H]1CC12CCN(CC1CC1)CC2)c1ncc(Br)o1] | 496.2 |

Example 48

Preparation of Intermediate E1b

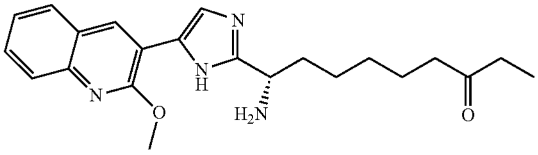

+

A9

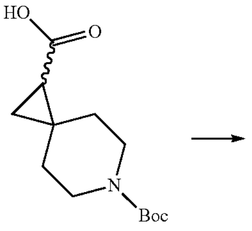

B1_A

-continued

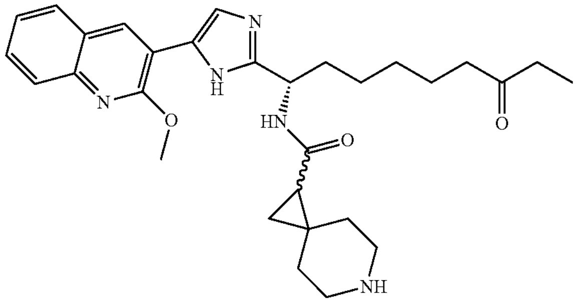

E1b

To a 40 mL pressure vial with pressure release cap was added B1_A (266 mg, 1.041 mmol), HATU (429 mg, 1.128 mmol), A9 (330 mg, 0.867 mmol), DMF (8673 μl), and DIPEA (757 μl, 4.34 mmol). The reaction was stirred at 25° C. for 4 hours. The product was purified by $C_{18}$ chromatography ($CH_3CN$ in water with 0.1% TFA: 0% to 90%) to give tert-butyl 1-(((S)-1-(5-(2-methoxyquinolin-3-yl)-1H-imidazol-2-yl)-7-oxononyl)carbamoyl)-6-azaspiro[2.5]octane-6-carboxylate, TFA. To a 250 flask was added tert-butyl 1-(((S)-1-(5-(2-methoxyquinolin-3-yl)-1H-imidazol-2-yl)-7-oxononyl)carbamoyl)-6-azaspiro[2.5]octane-6-carboxylate (538 mg, 0.871 mmol), $CH_2Cl_2$ (4354 μl), and 2,2,2-trifluoroacetic acid (1334 μl, 17.42 mmol). The reaction was stirred at 25° C. for 2 hours. The reaction mixture was concentrated and dried under vacuum for 16 hours to give E1b). LCMS (ESI) calc'd for $C_{30}H_{39}N_5O_3$: 517.3; found: 518.4 $[M+H]^+$.

The following intermediates were prepared using similar procedures as described for intermediate E1b

| Intermediate ID | Structures | Observed [M + H]$^+$ |
|---|---|---|
| E1a | 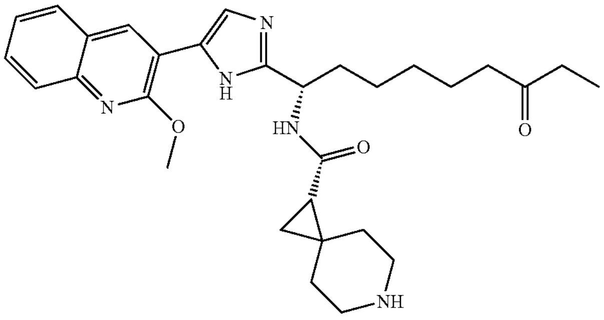 | 518.4 |
| E4 | 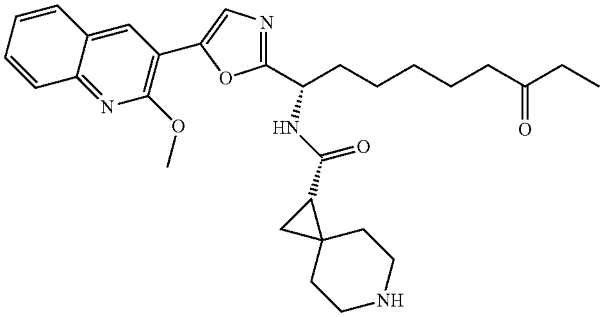 | 519.3 |
| E38 | 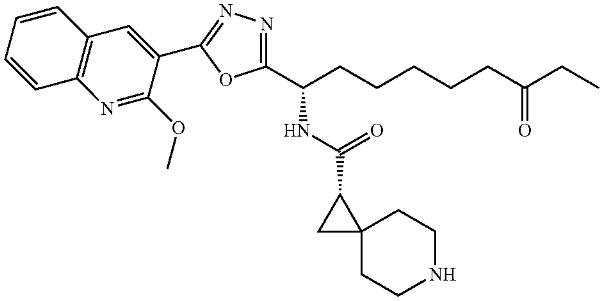 [SMILES: CCC(=O)CCCCC[C@H](NC(=O)[C@H]1CC12CCNCC2)c1nnc(-c2cc3ccccc3nc2OC)o1] | 520.3 |

Example 49

Preparation of Intermediate E2

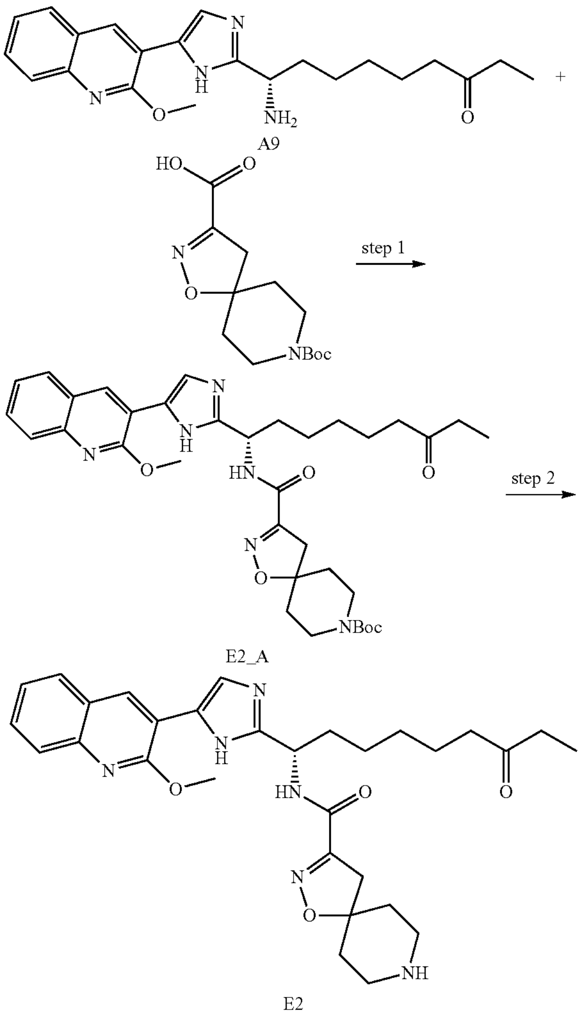

A9

E2_A

E2

Step 1: Preparation of (S)-tert-butyl 3-((1-(5-(2-methoxyuinolin-3-yl)-1H-imidazol-2-yl)-7-oxononyl)carbamoyl)-1-oxa-2,8-diazaspiro[4.5]dec-2-ene-8-carboxylate (E2_A): $Et_3N$ (0.2 mL, 1.435 mmol), and $T_3P$ (301 mg, 0.473 mmol) was added to a stirred mixture of 8-(tert-butoxycarbonyl)-1-oxa-2,8-diazaspiro[4.5]dec-2-ene-3-carboxylic acid (120 mg, 0.422 mmol), and (S)-9-amino-9-(5-(2-methoxyquinolin-3-yl)-1H-imidazol-2-yl)nonan-3-one (A9, 150 mg, 0.394 mmol) in DMF (2 mL) at 20° C. and the mixture was stirred at 20° C. for 12 h. The mixture was diluted with ethyl acetate (15 mL), washed with brine (saturated, 4×10 mL), dried ($Na_2SO_4$), filtered and the solvent was evaporated under reduced pressure. The residue was purified by silica gel column flash chromatography, eluting with petroleum ether/EtOAc=50-100% to give (S)-tert-butyl 3-((1-(5-(2-methoxyquinolin-3-yl)-1H-imidazol-2-yl)-7-oxononyl)carbamoyl)-1-oxa-2,8-diazaspiro[4.5]dec-2-ene-8-carboxylate (E2_A). LCMS (ESI) calc'd for $C_{35}H_{46}N_6O_6$ $[M+H]^+$: 647.3, found: 647.4.

Step 2: Preparation of (S)—N-(1-(5-(2-methoxyuinolin-3-yl)-1H-imidazol-2-yl)-7-oxononyl)-1-oxa-2,8-diazaspiro[4.5]dec-2-ene-3-carboxamide (E2): TFA (0.1 mL, 1.298 mmol) was added to a stirred mixture of (S)-tert-butyl 3-((1-(5-(2-methoxyquinolin-3-yl)-1H-imidazol-2-yl)-7-oxononyl)carbamoyl)-1-oxa-2,8-diazaspiro[4.5]dec-2-ene-8-carboxylate (E2_A, 210 mg, 0.325 mmol) in DCM (2 mL) at 10° C. and the mixture was stirred at 10° C. for 1 h. Most of the DCM was removed, and it was concentrated to give (S)—N-(1-(5-(2-methoxyquinolin-3-yl)-1H-imidazol-2-yl)-7-oxononyl)-1-oxa-2,8-diazaspiro[4.5]dec-2-ene-3-carboxamide (E2) which was used to the next step without further purification. LCMS (ESI) calc'd for $C_{30}H_{38}N_6O_4$ $[M+H]^+$: 547.3, found: 547.3.

Example 50

Preparation of Intermediate E3

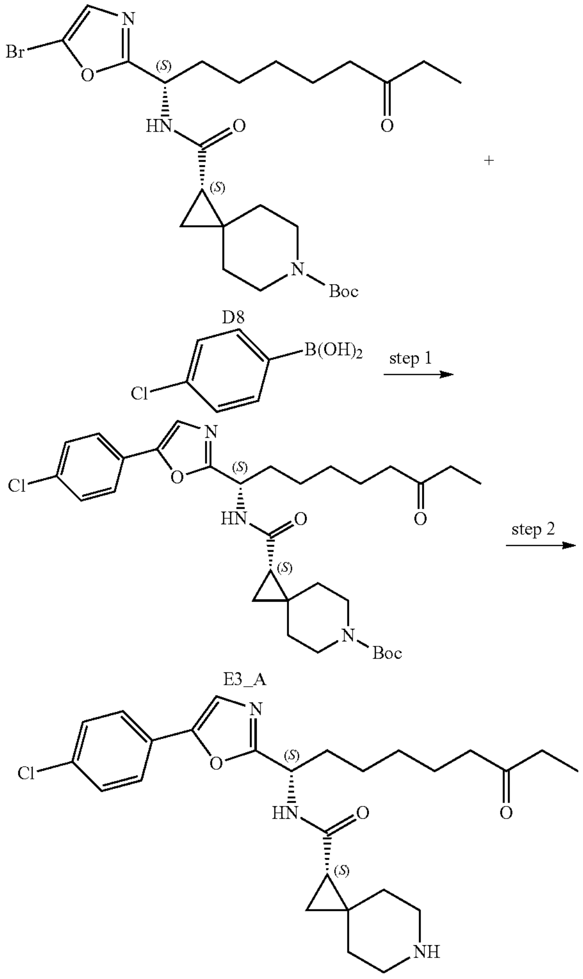

D8

E3_A

E3

Step 1: Preparation of (S)-tert-butyl 1-(((S)-1-(5-(4-chlorophenyl)oxazol-2-yl)-7-oxononyl)carbamoyl)-6-azaspiro[2.5]octane-6-carboxylate (E3_A): $PdCl_2$(DTBPF) (400 mg, 0.614 mmol) was added to a stirred mixture of $K_2CO_3$ (2685 mg, 19.43 mmol), (4-chlorophenyl)boronic acid (1013 mg, 6.48 mmol), and (S)-tert-butyl 1-(((S)-1-(5-bromooxazol-2-yl)-7-oxononyl)carbamoyl)-6-azaspiro[2.5]octane-6-carboxylate (D8, 3.5 g, 6.48 mmol) in THF (15 mL) at room temperature and the mixture was stirred at 70° C. for 6 h. The mixture was cooled, diluted with ethyl acetate (30 mL), washed with water (3×20 mL), dried ($Na_2SO_4$), filtered and the solvent was evaporated under reduced pressure. The residue was purified by silica gel column flash chromatography, eluting with EtOAc/petroleum ether=0-50% to give (S)-tert-butyl 1-(((S)-1-(5-(4-chlorophenyl)oxazol-2-yl)-7-oxononyl)carbamoyl)-6-azaspiro[2.5]octane-6-carboxylate (E3_A). LCMS (ESI) calc'd for $C_{31}H_{42}ClN_3O_5$ $[M+H]^+$: 572.3, found: 572.3. $^1H$ NMR (400 MHz, $CDCl_3$) δ 7.59-7.72 (m, 1H), 7.54 (d, J=8.6 Hz, 2H), 7.37-7.45 (m, 2H), 7.24 (s, 1H), 5.22-5.33 (m, 1H), 3.46 (d, J=3.5 Hz, 2H), 3.34 (brs, 2H), 2.33-2.47 (m, 4H), 1.95-2.03 (m, 1H), 1.79-1.92 (m, 1H), 1.50-1.71 (m, 6H), 1.43 (brs, 9H), 1.26-1.39 (m, 6H), 1.04 (t, J=7.4 Hz, 3H), 0.88 (dd, J=4.5, 7.63 Hz, 1H).

Step 2: Preparation of (S)—N—((S)-1-(5-(4-chlorophenyl)oxazol-2-yl)-7-oxononyl)-6-azaspiro[2.5]octane-1-carboxamide (E3): TFA (5 mL, 64.9 mmol) was added to a stirred mixture of (S)-tert-butyl 1-(((S)-1-(5-(4-chlorophenyl)oxazol-2-yl)-7-oxononyl)carbamoyl)-6-azaspiro[2.5]octane-6-carboxylate (E3_A, 3.0 g, 5.24 mmol) in DCM (15 mL) at room temperature and the mixture was stirred at room temperature for 2 h. Most of the DCM was removed, and it was concentrated to give (S)—N—((S)-1-(5-(4-chlorophenyl)oxazol-2-yl)-7-oxononyl)-6-azaspiro[2.5]octane-1-carboxamide (E3). LCMS (ESI) calc'd for $C_{26}H_{34}ClN_3O_3$ $[M+H]^+$: 472.2, found: 472.2.

The following intermediates were prepared using similar procedures as described for intermediates E1, E2 and E3

| ID | Structure | Observed $[M + H]^+$ |
|---|---|---|
| E5 | 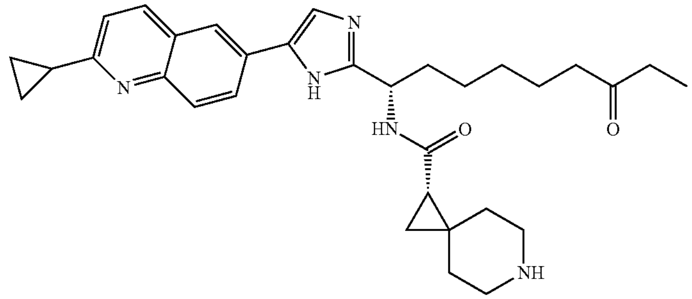 [SMILES: CCC(=O)CCCCC[C@H](NC(=O)[C@H]1CC12CCNCC2)c1ncc(-c2ccc3nc(C4CC4)ccc3c2)[nH]1] | 528.3 |
| E6 | 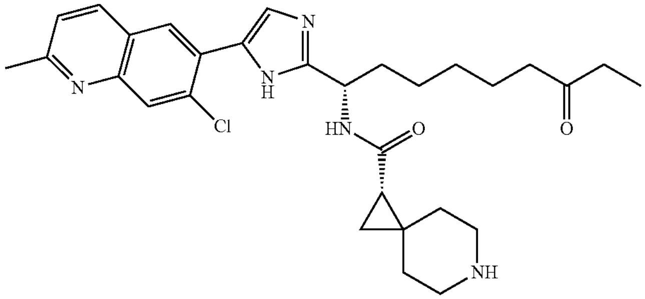 | 536.3 |
| E7 | 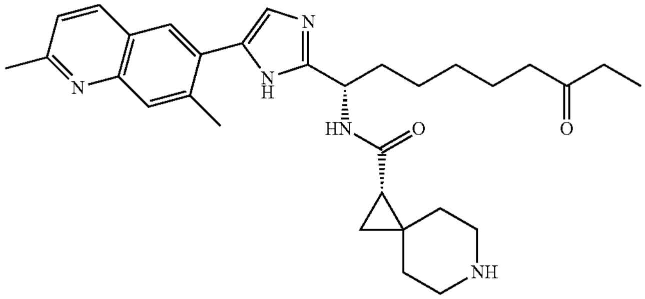 [SMILES: CCC(=O)CCCCC[C@H](NC(=O)[C@H]1CC12CCNCC2)c1ncc(-c2cc3ccc(C)nc3cc2C)[nH]1] | 516.3 |
| E8 | 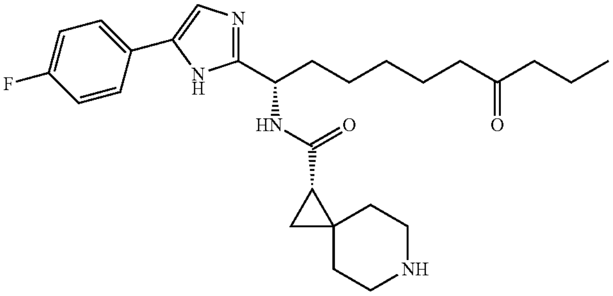 [SMILES: CCCC(=O)CCCCC[C@H](NC(=O)[C@H]1CC12CCNCC2)c1ncc(-c2ccc(F)cc2)[nH]1] | 469.3 |

-continued
| ID | Structure | Observed [M + H]$^+$ |
|---|---|---|
| E9 | 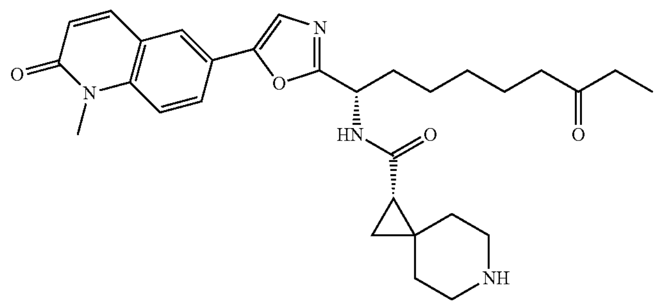 [SMILES: CCC(=O)CCCCC[C@H](NC(=O)[C@H]1CC12CCNCC2)c1ncc(-c2ccc3c(ccc(=O)n3C)c2)o1] | 519.4 |
| E10 | 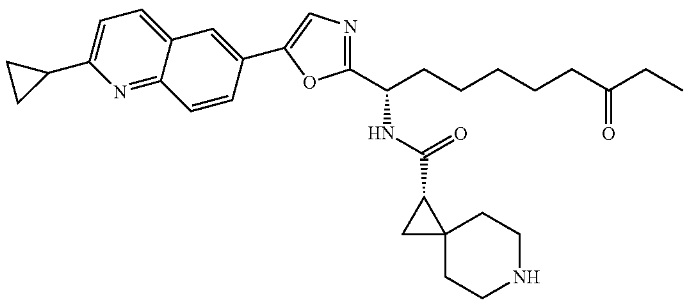 [SMILES: CCC(=O)CCCCC[C@H](NC(=O)[C@H]1CC12CCNCC2)c1ncc(-c2ccc3nc(C4CC4)ccc3c2)o1] | 529.3 |
| E11 | 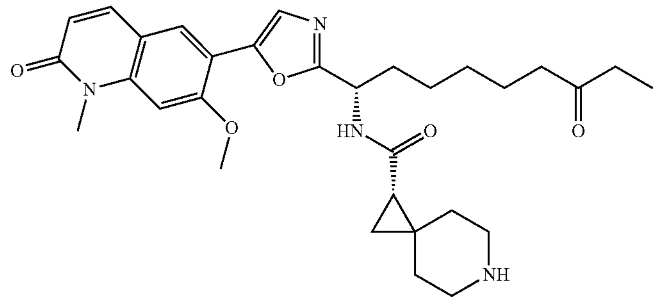 [SMILES: CCC(=O)CCCCC[C@H](NC(=O)[C@H]1CC12CCNCC2)c1ncc(-c2cc3ccc(=O)n(C)c3cc2OC)o1] | 549.3 |
| E12 | 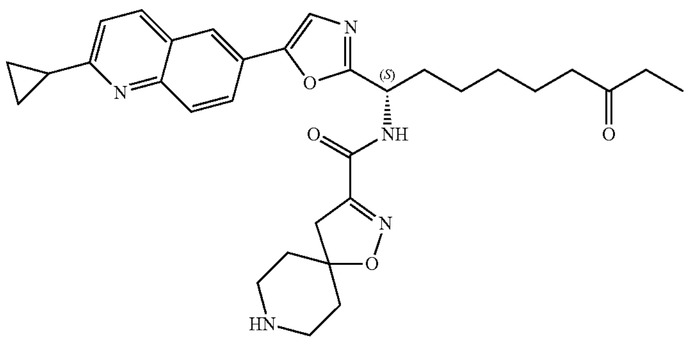 | 558.3 |

-continued
| ID | Structure | Observed [M + H]+ |
|---|---|---|
| E13 | 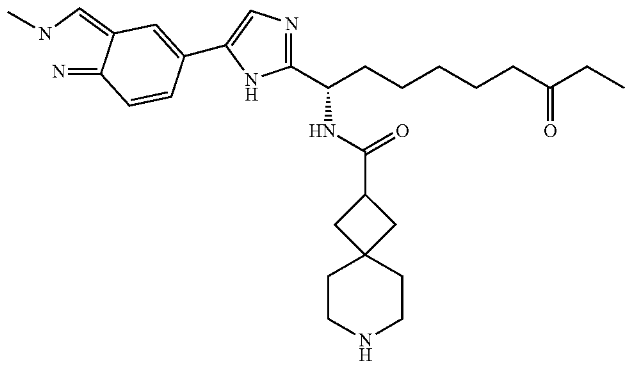 [SMILES: CCC(=O)CCCCC[C@H](NC(=O)C1CC2(CCNCC2)C1)c1ncc(C2=C/C(=C/NC)C(=N)C=C2)[nH]1] | 505.4 |
| E14 | 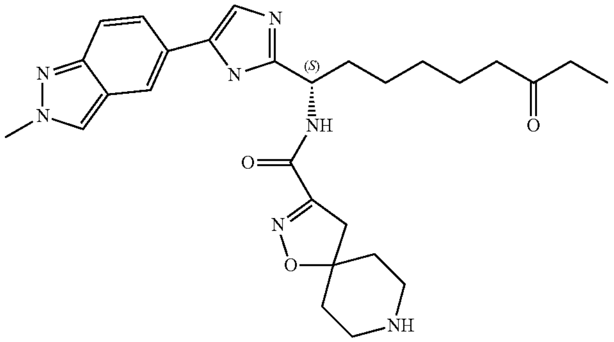 | 520.4 |
| E15 | 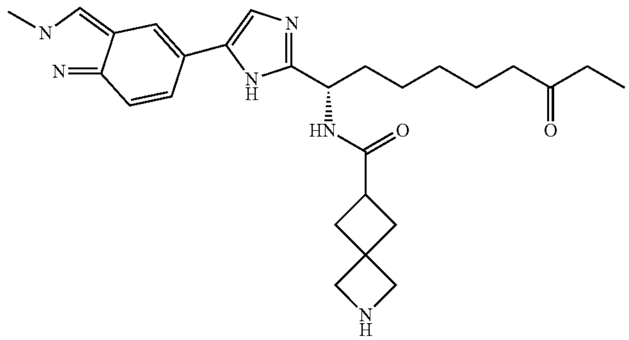 [SMILES: CCC(=O)CCCCC[C@H](NC(=O)C1CC2(CNC2)C1)c1ncc(C2=C/C(=C/NC)C(=N)C=C2)[nH]1] | 477.2 |
| E16 | 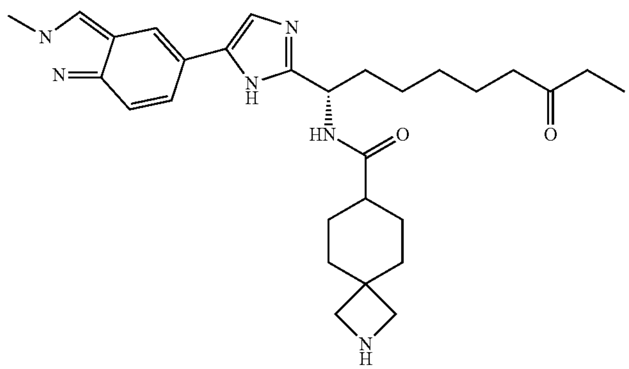 [SMILES: CCC(=O)CCCCC[C@H](NC(=O)C1CCC2(CC1)CNC2)c1ncc(C2=C/C(=C/NC)C(=N)C=C2)[nH]1] | 505.1 |

-continued
| ID | Structure | Observed [M + H]+ |
|---|---|---|
| E17 | 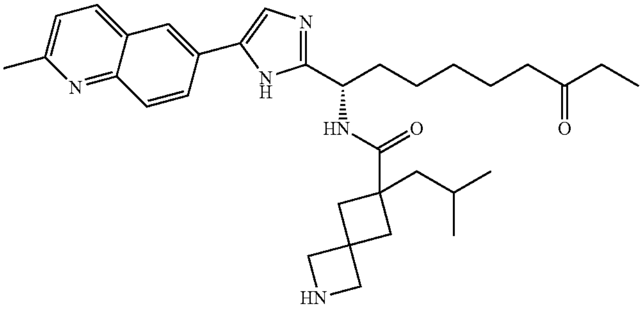 [SMILES: CCC(=O)CCCCC[C@H](NC(=O)C1(CC(C)C)CC2(CNC2)C1)c1ncc(-c2ccc3nc(C)ccc3c2)[nH]1] | 544.4 |
| E18 | 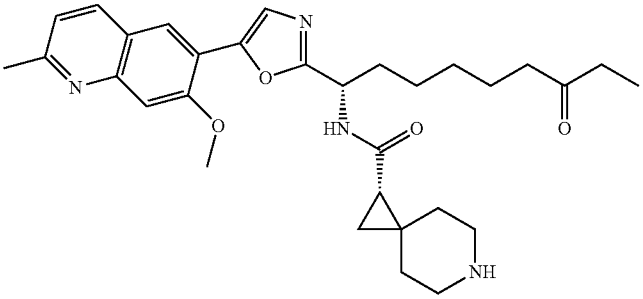 [SMILES: CCC(=O)CCCCC[C@H](NC(=O)[C@H]1CC12CCNCC2)c1ncc(-c2cc3ccc(C)nc3cc2OC)o1] | 533.4 |
| E19 | 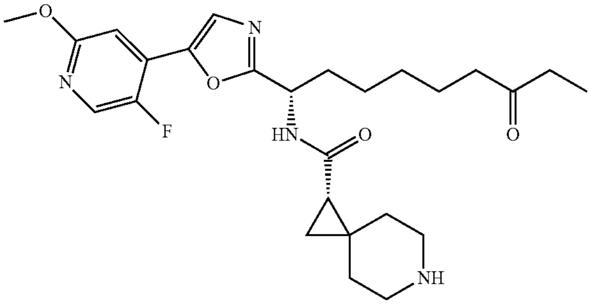 [SMILES: CCC(=O)CCCCC[C@H](NC(=O)[C@H]1CC12CCNCC2)c1ncc(-c2cc(OC)ncc2F)o1] | 487.3 |
| E20 | 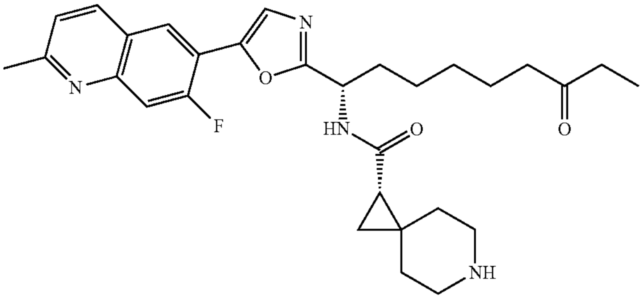 [SMILES: CCC(=O)CCCCC[C@H](NC(=O)[C@H]1CC12CCNCC2)c1ncc(-c2cc3ccc(C)nc3cc2F)o1] | 521.4 |
| E21 | 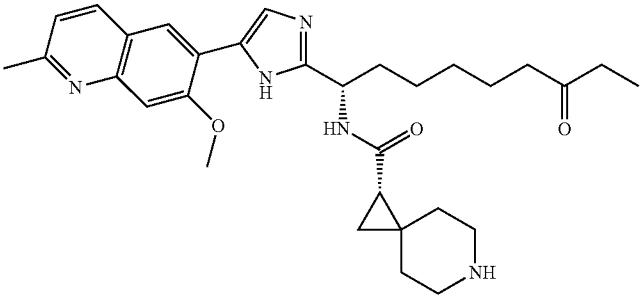 [SMILES: CCC(=O)CCCCC[C@H](NC(=O)[C@H]1CC12CCNCC2)c1ncc(-c2cc3ccc(C)nc3cc2OC)[nH]1] | 532.3 |

-continued
| ID | Structure | Observed [M + H]+ |
| --- | --- | --- |
| E22 | 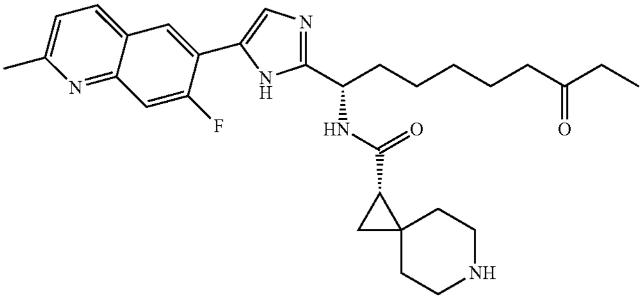 [SMILES: CCC(=O)CCCCC[C@H](NC(=O)[C@H]1CC12CCNCC2)c1ncc(-c2cc3ccc(C)nc3cc2F)[nH]1] | 520.4 |
| E23 | 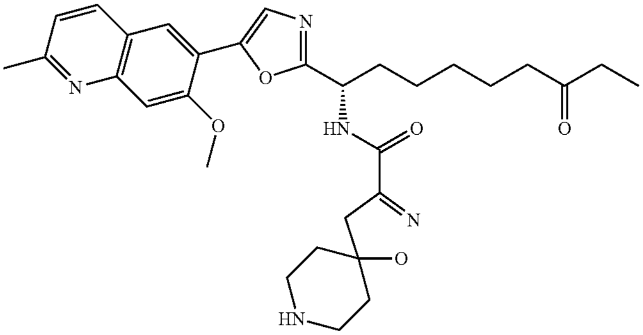 [SMILES: CCC(=O)CCCCC[C@H](NC(=O)C(=N)CC1(O)CCNCC1)c1ncc(-c2cc3ccc(C)nc3cc2OC)o1] | 562.4 |
| E24 | 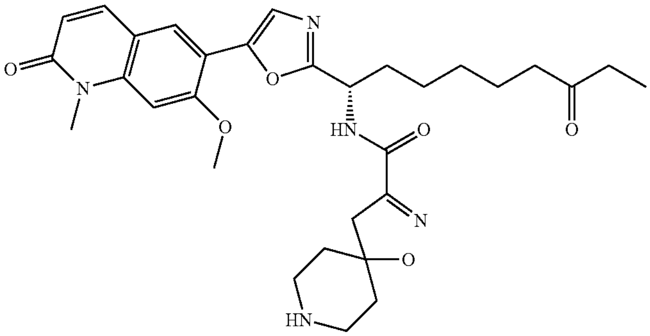 [SMILES: CCC(=O)CCCCC[C@H](NC(=O)C(=N)CC1(O)CCNCC1)c1ncc(-c2cc3ccc(=O)n(C)c3cc2OC)o1] | 578.4 |
| E24 | 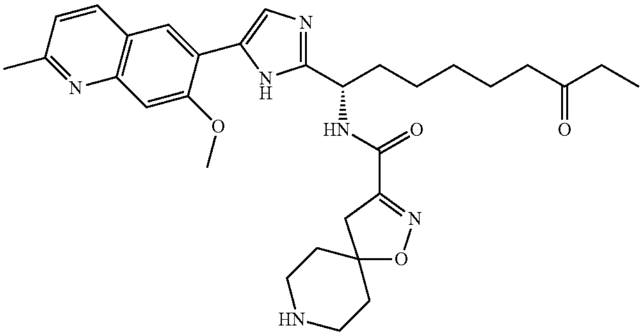 [SMILES: CCC(=O)CCCCC[C@H](NC(=O)C1=NOC2(CCNCC2)C1)c1ncc(-c2cc3ccc(C)nc3cc2OC)[nH]1] | 561.4 |

-continued
| ID | Structure | Observed [M + H]+ |
|---|---|---|
| E25 | 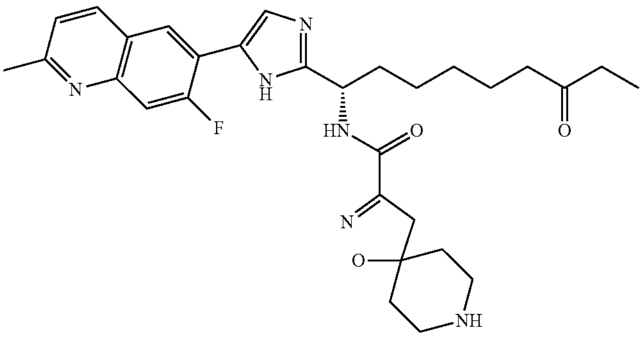 [SMILES: CCC(=O)CCCCC[C@H](NC(=O)C(=N)CC1(O)CCNCC1)c1ncc(-c2cc3ccc(C)nc3cc2F)[nH]1] | 549.3 |
| E26 | 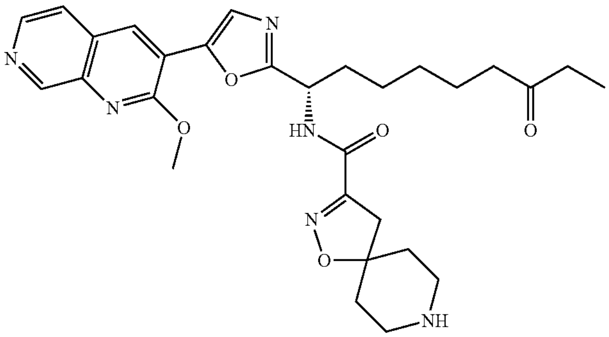 [SMILES: CCC(=O)CCCCC[C@H](NC(=O)C1=NOC2(CCNCC2)C1)c1ncc(-c2cc3ccncc3nc2OC)o1] | 549.3 |
| E27 | 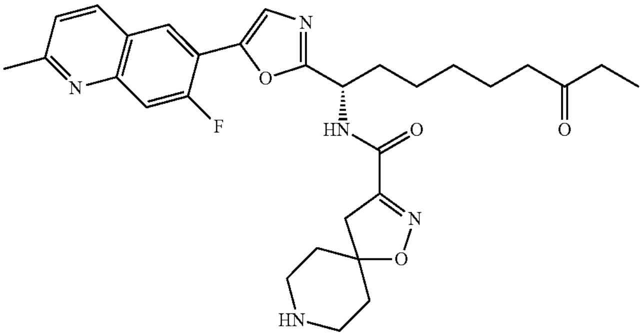 [SMILES: CCC(=O)CCCCC[C@H](NC(=O)C1=NOC2(CCNCC2)C1)c1ncc(-c2cc3ccc(C)nc3cc2F)o1] | 550.3 |
| E28 | 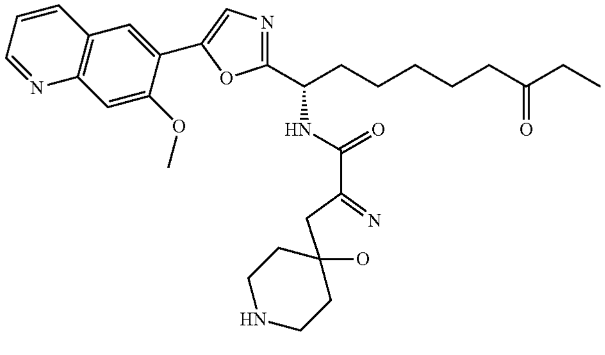 [SMILES: CCC(=O)CCCCC[C@H](NC(=O)C(=N)CC1(O)CCNCC1)c1ncc(-c2cc3cccnc3cc2OC)o1] | 548.1 |

-continued
| ID | Structure | Observed [M + H]+ |
|---|---|---|
| E29 | 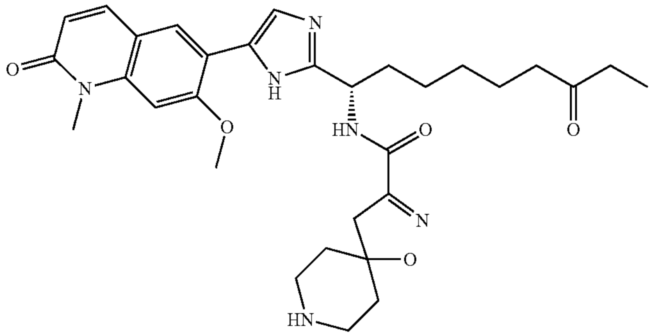 [SMILES: CCC(=O)CCCCC[C@H](NC(=O)C(=N)CC1(O)CCNCC1)c1ncc(-c2cc3ccc(=O)n(C)c3cc2OC)[nH]1] | 577.4 |
| E30 | 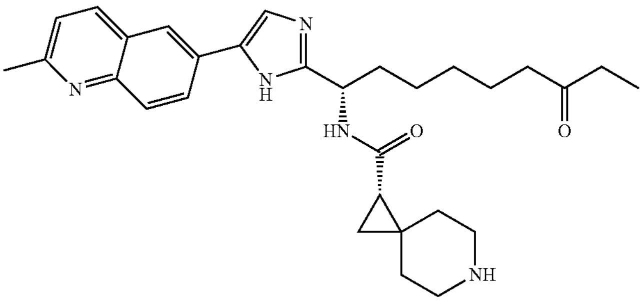 [SMILES: CCC(=O)CCCCC[C@H](NC(=O)[C@H]1CC12CCNCC2)c1ncc(-c2ccc3nc(C)ccc3c2)[nH]1] | 502.3 |
| E31 | 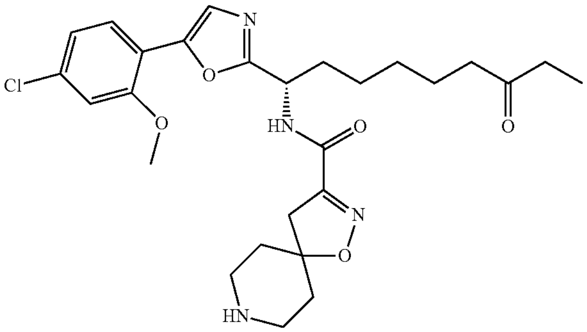 [SMILES: CCC(=O)CCCCC[C@H](NC(=O)C1=NOC2(CCNCC2)C1)c1ncc(-c2ccc(Cl)cc2OC)o1] | 531.3 |
| E32 | 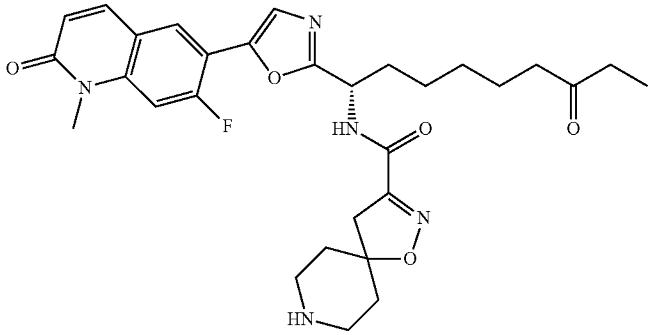 [SMILES: CCC(=O)CCCCC[C@H](NC(=O)C1=NOC2(CCNCC2)C1)c1ncc(-c2cc3ccc(=O)n(C)c3cc2F)o1] | 566.3 |

-continued
| ID | Structure | Observed [M + H]+ |
|---|---|---|
| E33 | 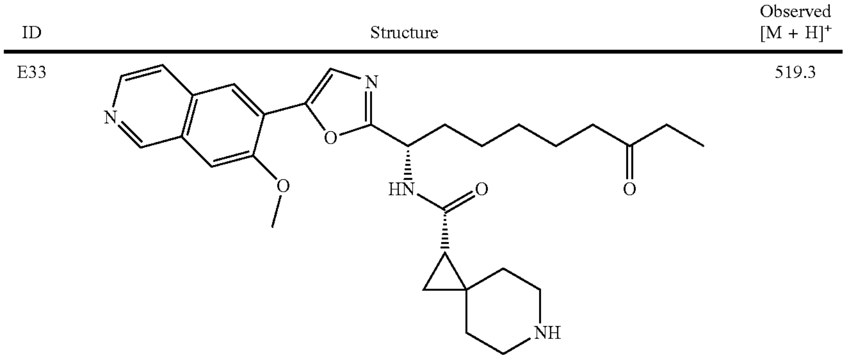 | 519.3 |
| E34 | 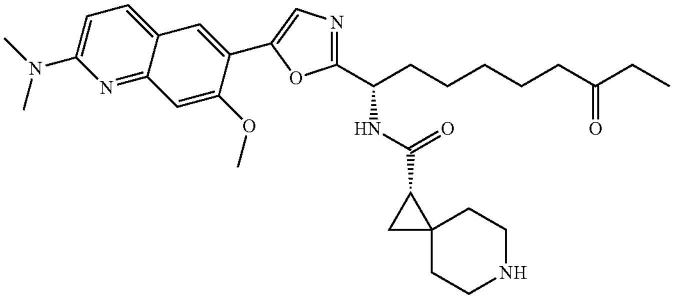 [SMILES: CCC(=O)CCCCC[C@H](NC(=O)[C@H]1CC12CCNCC2)c1ncc(-c2cc3ccc(N(C)C)nc3cc2OC)o1] | 562.4 |
| E35 | 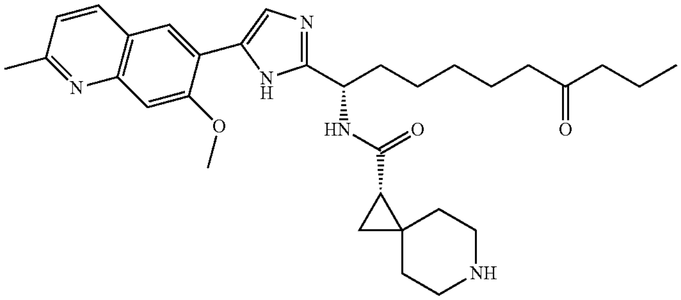 [SMILES: CCCC(=O)CCCCC[C@H](NC(=O)[C@H]1CC12CCNCC2)c1ncc(-c2cc3ccc(C)nc3cc2OC)[nH]1] | 546.3 |
| E37 | 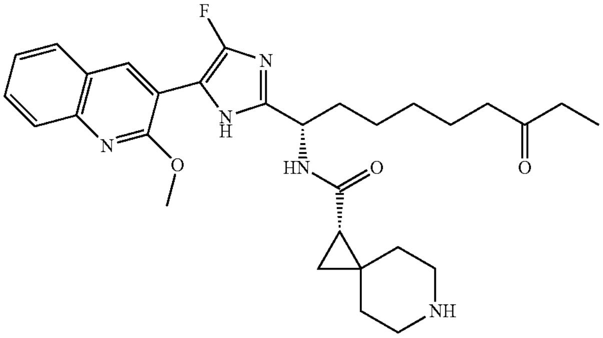 [SMILES: CCC(=O)CCCCC[C@H](NC(=O)[C@H]1CC12CCNCC2)c1nc(F)c(-c2cc3ccccc3nc2OC)[nH]1] | 536.3 |
| E39 | 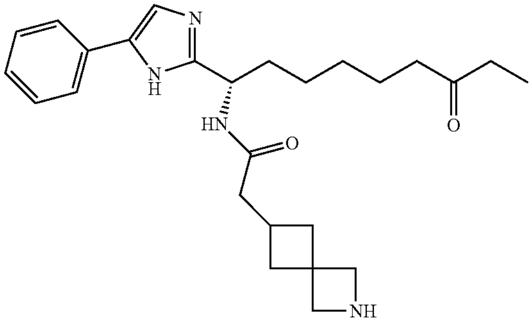 [SMILES: CCC(=O)CCCCC[C@H](NC(=O)CC1CC2(CNC2)C1)c1ncc(-c2ccccc2)[nH]1] | 437.3 |

-continued
| ID | Structure | Observed [M + H]+ |
|---|---|---|
| 297 | 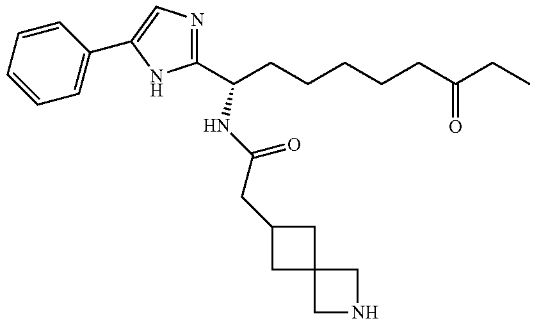 [SMILES: CCC(=O)CCCCC[C@H](NC(=O)CC1CC2(CNC2)C1)c1ncc(-c2ccccc2)[nH]1] | 437.0 |
| 298 | 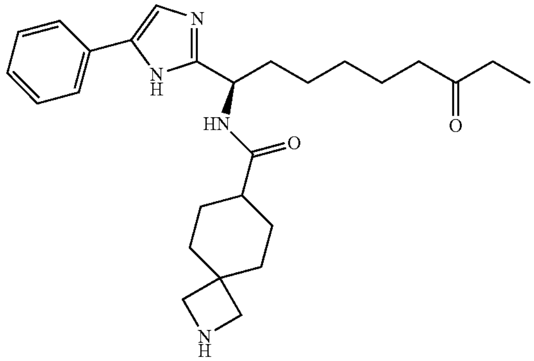 [SMILES: CCC(=O)CCCCC[C@@H](NC(=O)C1CCC2(CC1)CNC2)c1ncc(-c2ccccc2)[nH]1] | 451.4 |
| 299 | 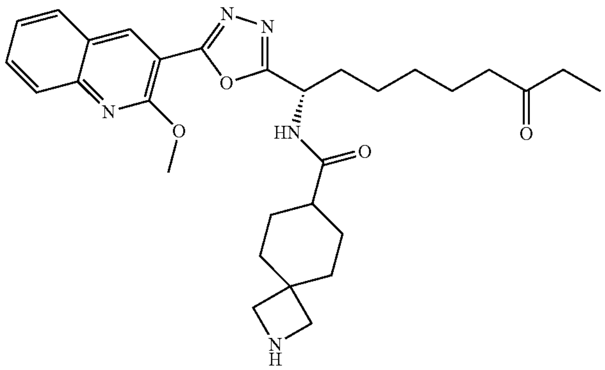 [SMILES: CCC(=O)CCCCC[C@H](NC(=O)C1CCC2(CC1)CNC2)c1nnc(-c2cc3ccccc3nc2OC)o1] | 534.5 |
| 301 | 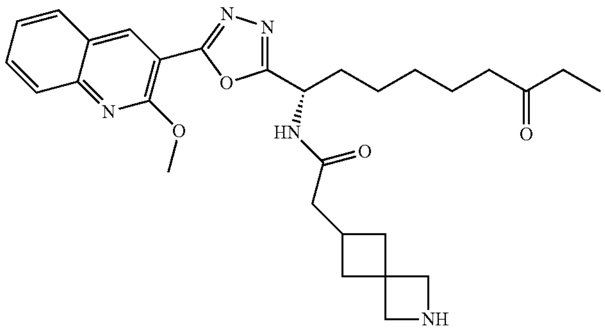 [SMILES: CCC(=O)CCCCC[C@H](NC(=O)CC1CC2(CNC2)C1)c1nnc(-c2cc3ccccc3nc2OC)o1] | 520.4 |

Example 51

Preparation of Intermediate E36

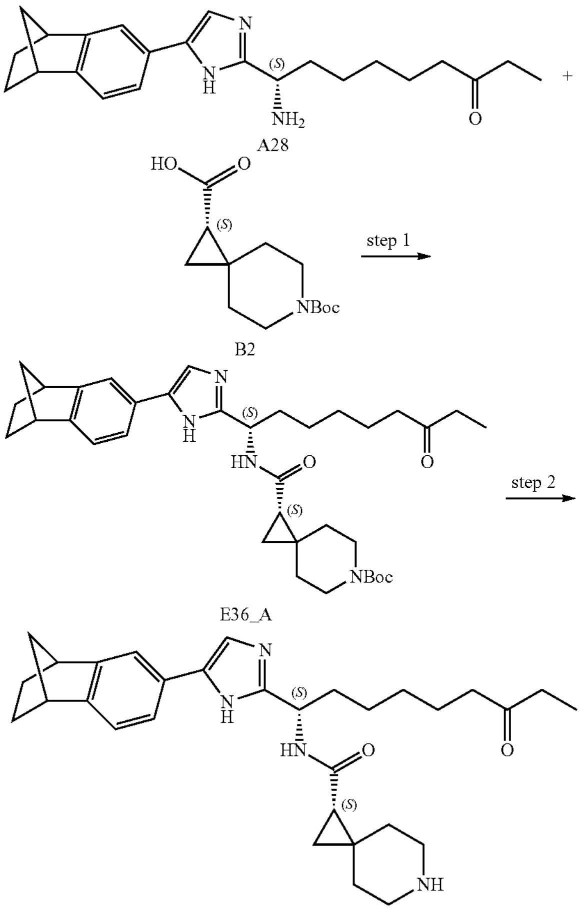

A28 B2 E36_A E36

Step 1: Preparation of (S)-tert-butyl 1-(((S)-7-oxo-1-(5-((R,4S)-1,2,3,4-tetrahydro-1,4-methanonaphthalen-6-yl)-1H-imidazol-2-yl)nonyl)carbamoyl)-6-azaspiro[2.5]octane-6-carboxylate (E36_A): The mixture of (S)-6-(tert-butoxycarbonyl)-6-azaspiro[2.5]octane-1-carboxylic acid (B2, 64 mg, 0.251 mmol), HATU (100 mg, 0.263 mmol) and triethylamine (0.20 mL, 1.435 mmol)) in DMF (10 mL) was stirred at rt for 10 min, then a mixture of (S)-9-amino-9-(5-((1R,4S)-1,2,3,4-tetrahydro-1,4-methanonaphthalen-6-yl)-1H-imidazol-2-yl)nonan-3-one hydrochloride (A28, 100 mg, 0.249 mmol) in DMF (2 mL) was added. The resulting mixture was stirred at rt for 1 h under nitrogen atmosphere. The mixture combined with a same reaction from 50 mg amine was concentrated to remove DMF. The residue was purified by silica gel column flash chromatography, eluting with MeOH in DCM=0~6% to give the title compound (E36_A). LCMS (ESI) calc'd for $C_{36}H_{50}N_4O_4$ $[M+H]^+$: 603.4 found: 603.4.

Step 2: Preparation of (S)—N—((S)-7-oxo-1-(5-((1R,4S)-1,2,3,4-tetrahydro-1,4-methanonaphthalen-6-yl)-1H-imidazol-2-yl)nonyl)-6-azaspiro[2.5]octane-1-carboxamide (E36): The mixture of (S)-tert-butyl 1-(((S)-7-oxo-1-(5-((1R,4S)-1,2,3,4-tetrahydro-1,4-methanonaphthalen-6-yl)-1H-imidazol-2-yl)nonyl)carbamoyl)-6-azaspiro[2.5]octane-6-carboxylate (E36_A, 200 mg, 0.332 mmol) and TFA (0.5 mL, 6.49 mmol) in DCM (5 mL) was stirred at rt for 2 h. The mixture was concentrated to remove solvent, the residue was triturated with EtOAc (20 mL), washed with aqueous $NaHCO_3$(saturated, 2×5 mL), dried ($Na_2SO_4$), filtered and the solvent was evaporated under reduced pressure to give the title compound (E36). LCMS (ESI) calc'd for $C_{31}H_{42}N_4O_2$ $[M+H]^+$: 503.3, found: 525.2 $[M+Na]^+$.

Example 52

N-{(1S)-1-[4-bromo-2-(4-fluorophenyl)-1H-imidazol-5-yl]-7-oxononyl}-1-methylazetidine-3-carboxamide (65)

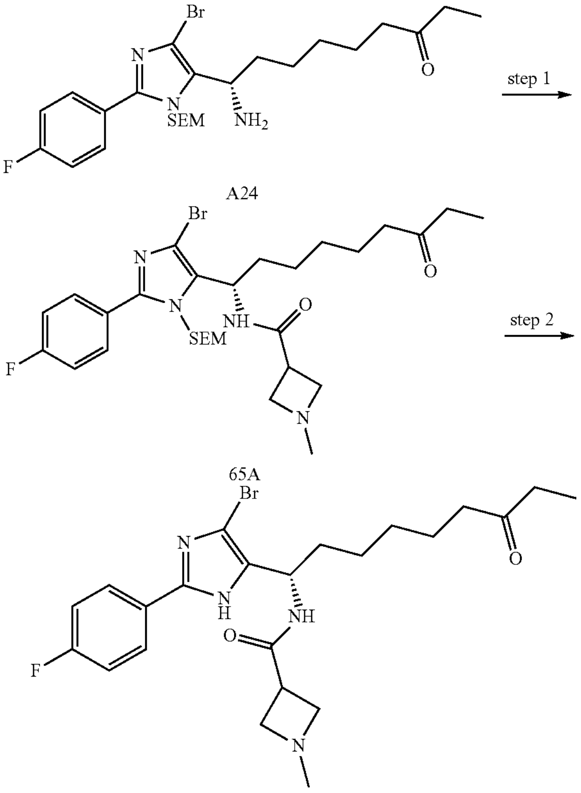

A24 65A 65

Step 1: Preparation of (S)—N-(1-(5-bromo-2-(4-fluorophenyl)-1-((2-(trimethylsilyl)ethoxy)methyl)-1H-imidazol-4-yl)-7-oxononyl)-1-methylazetidine-3-carboxamide (65A): $Et_3N$ (0.349 mL, 2.507 mmol) was added to a stirred mixture of HATU (104 mg, 0.273 mmol), 1-methylazetidine-3-carboxylic acid (29 mg, 0.252 mmol), (S)-9-amino-9-(5-bromo-2-(4-fluorophenyl)-1-((2-(trimethylsilyl)ethoxy)methyl)-1H-imidazol-4-yl)nonan-3-one (A24, 120 mg, 0.228 mmol) in THF (5 mL) at 30° C. and the mixture was stirred at 30° C. for 18 h. The solvent was evaporated under reduced pressure. The residue was purified by silica gel flash chromatography (ISCORF75; Sepa flash column), eluting with DCM/MeOH=10/1 to give (S)—N-(1-(5-bromo-2-(4-fluorophenyl)-1-((2-(trimethylsilyl)ethoxy)methyl)-1H-imidazol-4-yl)-7-oxononyl)-1-methylazetidine-3-carboxamide (65A). LCMS (ESI) calc'd for $C_{29}H_{44}BrFN_4O_3Si$ $[M+H]^+$: 623.2, found: 625.1.

Step 2: Preparation of (S)—N-(1-(4-bromo-2-(4-fluorophenyl)-1H-imidazol-5-yl)-7-oxononyl)-1-methylazetidine-3-carboxamide (65): (S)—N-(1-(4-bromo-2-(4-fluorophenyl)-1-((2-(trimethylsilyl)ethoxy)methyl)-1H-imidazol-5-yl)-7-oxononyl)-1-methylazetidine-3-carboxamide (65A, 110 mg, 0.176 mmol) was dissolved in hydrogen chloride/MeOH (1.00 mL, 4.00 mmol) at 30° C. and the mixture was stirred at 30° C. for 18 h. The solvent was evaporated under reduced pressure at 30° C. The residue was purified by preparative HPLC (reverse phase C-18 column), eluting with ACN/water+0.1% TFA, to give (S)—N-(1-(4-bromo-2-(4-fluorophenyl)-1H-imidazol-5-yl)-7-oxononyl)-1-methylazetidine-3-carboxamide (65). LCMS (ESI) calc'd for $C_{23}H_{30}BrFN_4O_2$ $[M+H]^+$: 493.2, found: 495.1. $^1H$ NMR (400 MHz, $CDCl_3$) δ 11.62 (brs, 1H), 9.40-9.95 (m, 1H), 7.93-8.21 (m, 2H), 7.08-7.24 (m, 2H), 4.94-5.17 (m, 1H), 4.51-4.70 (m, 2H), 3.67-4.07 (m, 5H), 2.39 (quin, J=7.24 Hz, 4H), 1.72-1.96 (m, 2H), 1.51 (d, J=5.09 Hz, 2H), 1.27 (brs, 5H), 1.02 (t, J=7.43 Hz, 3H).

Example 53

(1S)—N-[(1S)-1-{5-[2-(dimethylamino)quinolin-6-yl]-1H-imidazol-2-yl}-7-oxononyl]-6-methyl-6-azaspiro[2.5]octane-1-carboxamide (66)

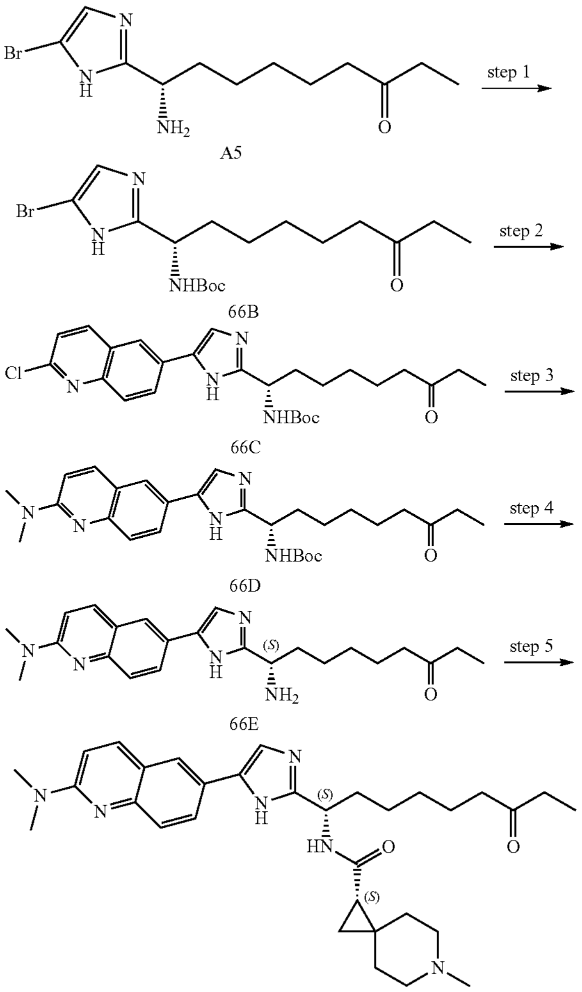

66

Step 1: Preparation of (S)-tert-butyl (1-(5-bromo-1H-imidazol-2-yl)-7-oxononyl) carbamate (66B): $(Boc)_2O$ (3.5 mL, 15.07 mmol) was added to a stirred mixture of (S)-9-amino-9-(5-bromo-1-((2-(trimethylsilyl)ethoxy)methyl)-1H-imidazol-2-yl)nonan-3-one hydrochloride (A5, 5.00 g, 10.66 mmol) and $Et_3N$ (2.3 mL, 16.50 mmol) in DCM (50.0 mL) at room temperature. The mixture was stirred at rt for 3 h. The mixture was concentrated. The residue was purified by silica gel column flash chromatography, eluting with petroleum ether/EtOAc=2:1 to give (S)-tert-butyl (1-(5-bromo-1H-imidazol-2-yl)-7-oxononyl)carbamate (66B). LCMS (ESI) calc'd for $C_{17}H_{28}BrN_3O_3$ $[M+H]^+$: 402.1, found: 403.8.

Step 2: Preparation of (S)-tert-butyl (1-(5-(2-chloroquinolin-6-yl)-1H-imidazol-2-yl)-7-oxononyl) carbamate (66C): $PdCl_2$(DTBPF) (0.16 g, 0.245 mmol) was added to a stirred mixture of (S)-tert-butyl (1-(5-bromo-1H-imidazol-2-yl)-7-oxononyl)carbamate (66B, 1.00 g, 2.486 mmol), (2-chloroquinolin-6-yl)boronic acid (0.67 g, 3.23 mmol) and $K_3PO_4$ (1.58 g, 7.44 mmol) in THF (10.0 mL) and water (0.5 mL) at room temperature and the mixture was stirred at 80° C. for 12 h under $N_2$. The mixture was concentrated. The residue was purified by silica gel column flash chromatography, eluting with petroleum ether/EtOAc=10:1-1:1 to give (S)-tert-butyl (1-(5-(2-chloroquinolin-6-yl)-1H-imidazol-2-yl)-7-oxononyl)carbamate (66C). LCMS (ESI) calc'd for $C_{26}H_{33}ClN_4O_3$ $[M+H]^+$: 485.2, found: 485.0.

Step 3: Preparation of (S)-tert-butyl (1-(5-(2-(dimethylamino)quinolin-6-yl)-1H-imidazol-2-yl)-7-oxononyl)carbamate (66D): Dimethylamine hydrochloride (202 mg, 2.474 mmol) was added to a stirred mixture of $K_2CO_3$ (427 mg, 3.09 mmol) and (S)-tert-butyl (1-(5-(2-chloroquinolin-6-yl)-1H-imidazol-2-yl)-7-oxononyl)carbamate (66C, 150 mg, 0.309 mmol) in DMF (3.0 mL) at room temperature and the mixture was stirred at 70° C. for 48 h. The mixture was filtered and the filter cake was washed with DCM (10 mL). The filtrate was concentrated to dryness. The residue was purified by silica gel column flash chromatography, eluting with petroleum ether/EtOAc=10:1-5:3 to give (S)-tert-butyl (1-(5-(2-(dimethylamino) quinolin-6-yl)-1H-imidazol-2-yl)-7-oxononyl)carbamate (66D). LCMS (ESI) calc'd for $C_{28}H_{39}N_5O_3$ $[M+H]^+$: 494.3, found: 494.2.

Step 4: Preparation of (S)-9-amino-9-(5-(2-(dimethylamino) quinolin-6-yl)-1H-imidazol-2-yl)nonan-3-one (66E): HCl/MeOH (1.0 mL, 4.00 mmol) was added to a stirred mixture of (S)-tert-butyl (1-(5-(2-(dimethylamino) quinolin-6-yl)-1H-imidazol-2-yl)-7-oxononyl) carbamate (66D, 100 mg, 0.203 mmol) in MeOH (2.0 mL) at room temperature and the mixture was stirred at rt for 2 h. The mixture was concentrated to afford crude (S)-9-amino-9-(5-(2-(dimethylamino)quinolin-6-yl)-1H-imidazol-2-yl)nonan-3-one (66E) which was used to the next step without further purification. LCMS (ESI) calc'd for $C_{23}H_{31}N_5O$ $[M+H]^+$: 394.3, found: 394.2.

Step 5: Preparation of (S)—N—((S)-1-(5-(2-(dimethylamino)quinolin-6-yl)-1H-imidazol-2-yl)-7-oxononyl)-6-methyl-6-azaspiro[2.5]octane-1-carboxamide (66): (S)-9-amino-9-(5-(2-(dimethylamino)quinolin-6-yl)-1H-imidazol-2-yl)nonan-3-one hydrochloride (66E, 80 mg, 0.186 mmol) was added to a stirred mixture of HATU (71 mg, 0.187 mmol), (S)-6-methyl-6-azaspiro[2.5]octane-1-carboxylic acid (B3, 30 mg, 0.177 mmol) and $Et_3N$ (0.2 mL, 1.435 mmol) in DMF (2.0 mL) at room temperature. The mixture was stirred at room temperature for 2 h. The residue was purified by preparative HPLC (reverse phase C-18 column), eluting with acetonitrile/water+0.05% $NH_3 \cdot H_2O$, to give (S)—N—((S)-1-(5-(2-(dimethylamino)quinolin-6- yl)-1H-imidazol-2-yl)-7-oxononyl)-6-methyl-6-azaspiro [2.5]octane-1-carboxamide (66). LCMS (ESI) calc'd for $C_{32}H_{44}N_6O_2$ $[M+H]^+$: 545.4, found: 545.3. $^1H$ NMR (400 MHz, MeOD) δ 7.96 (d, J=9.04 Hz, 2H), 7.84 (brs, 1H), 7.65 (d, J=8.60 Hz, 1H), 7.33 (brs, 1H), 7.05 (d, J=9.26 Hz, 1H), 5.01 (t, J=7.50 Hz, 1H), 3.22 (s, 6H), 2.27-2.67 (m, 8H), 2.18 (brs, 3H), 1.97 (d, J=7.94 Hz, 2H), 1.50-1.74 (m, 6H), 1.26-1.48 (m, 5H), 1.11 (t, J=4.63 Hz, 1H), 0.98 (t, J=7.28 Hz, 3H), 0.83 (dd, J=4.41, 7.72 Hz, 1H).
The following compounds were prepared by using similar procedures as described for compound 66.
| ID | Structure | Observed [M + H]$^+$ |
|---|---|---|
| 76 | 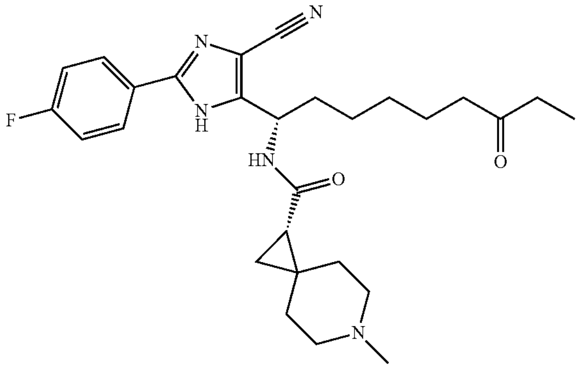 [SMILES: CCC(=O)CCCCC[C@H](NC(=O)[C@H]1CC12CCN(C)CC2)c1[nH]c(-c2ccc(F)cc2)nc1C#N] | 494.1 |
| 91 | 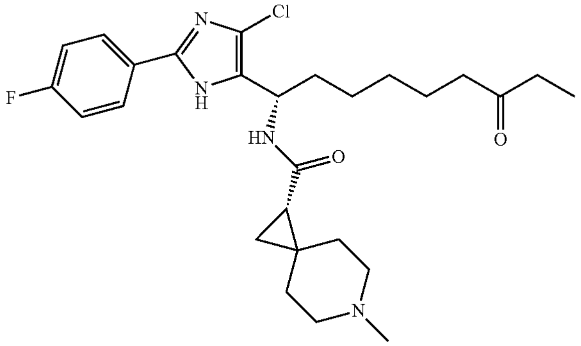 [SMILES: CCC(=O)CCCCC[C@H](NC(=O)[C@H]1CC12CCN(C)CC2)c1[nH]c(-c2ccc(F)cc2)nc1Cl] | 503.2 |
| 240 | 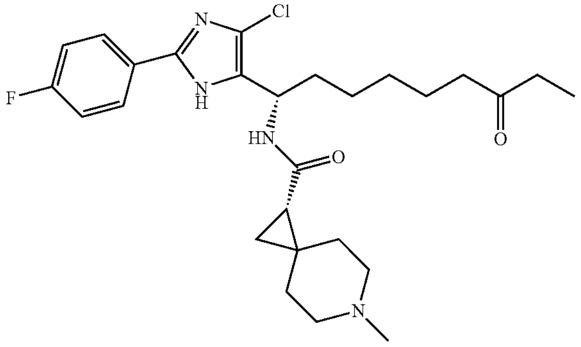 [SMILES: CCC(=O)CCCCC[C@H](NC(=O)[C@H]1CC12CCN(C)CC2)c1[nH]c(-c2ccc(F)cc2)nc1Cl] | 503.2 |

Example 54

(1S)—N-{(1S)-1-[5-(7-fluoro-2-methylquinolin-6-yl)-1H-imidazol-2-yl]-7-oxononyl}-6-methyl-6-azaspiro[2.5]octane-1-carboxamide (71)

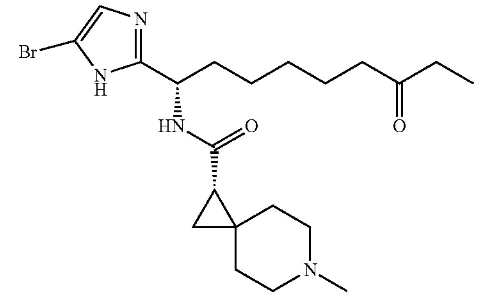

D5

+

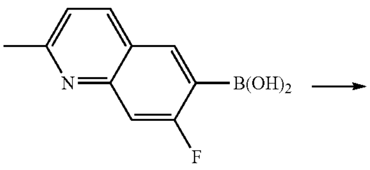

C2

-continued

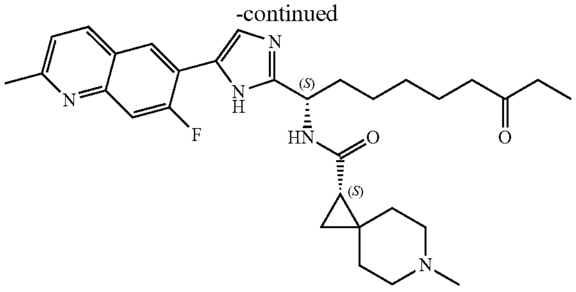

71

$K_3PO_4$ (211 mg, 0.992 mmol), and $PdCl_2$(DTBPF) (5 mg, 7.67 μmol) was added to a stirred mixture of (S)—N—((S)-1-(5-bromo-1H-imidazol-2-yl)-7-oxononyl)-6-methyl-6-azaspiro[2.5]octane-1-carboxamide (D5,150 mg, 0.331 mmol) and (7-fluoro-2-methylquinolin-6-yl)boronic acid (C2, 100 mg, 0.488 mmol) in water (0.5 mL)/THF (2 mL) at rt and the mixture was stirred at 70° C. for 18 h. The mixture was cooled, diluted with ethyl acetate (3 mL), washed with brine (saturated, 3×8 mL), dried ($Na_2SO_4$), filtered and the solvent was evaporated under reduced pressure. The residue was purified by preparative HPLC (reverse phase C-18 column), eluting with acetonitrile/water+0.05% $NH_3H_2O$, to give (S)—N—((S)-1-(5-(7-fluoro-2-methylquinolin-6-yl)-1H-imidazol-2-yl)-7-oxononyl)-6-methyl-6-azaspiro[2.5]octane-1-carboxamide (71). LCMS (ESI) calc'd for $C_{31}H_{40}FN_5O_2$ $[M+H]^+$: 534.3, found: 534.3. $^1H$ NMR (400 MHz, $CDCl_3$) δ 8.46 (brs, 1H), 8.07 (d, J=8.2 Hz, 1H), 7.67 (d, J=12.9 Hz, 1H), 7.47 (d, J=3.9 Hz, 1H), 7.24 (d, J=8.6 Hz, 1H), 6.54 (d, J=7.4 Hz, 1H), 4.97 (q, J=7.4 Hz, 1H), 2.72 (s, 3H), 2.35-2.49 (m, 5H), 2.20-2.34 (m, 3H), 2.17 (s, 3H), 2.04 (d, J=7.8 Hz, 3H), 1.59 (td, J=7.2, 14.48 Hz, 4H), 1.30-1.51 (m, 6H), 1.21 (d, J=4.3 Hz, 1H), 1.03 (t, J=7.4 Hz, 3H), 0.83 (dd, J=4.3, 7.43 Hz, 1H).

The following compounds were prepared using the similar procedures as described for compound 71:

| ID | Structure | Observed $[M + H]^+$ |
|---|---|---|
| 89 | 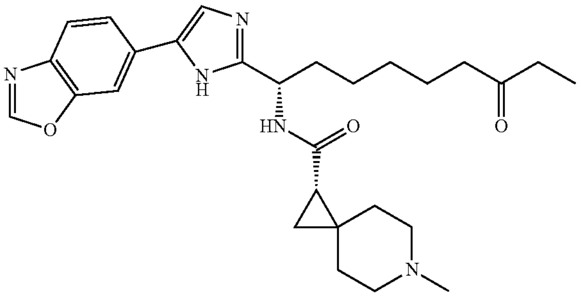 [SMILES: CCC(=O)CCCCC[C@H](NC(=O)[C@H]1CC12CCN(C)CC2)c1ncc(-c2ccc3ncoc3c2)[nH]1] | 492.3 |
| 90 | 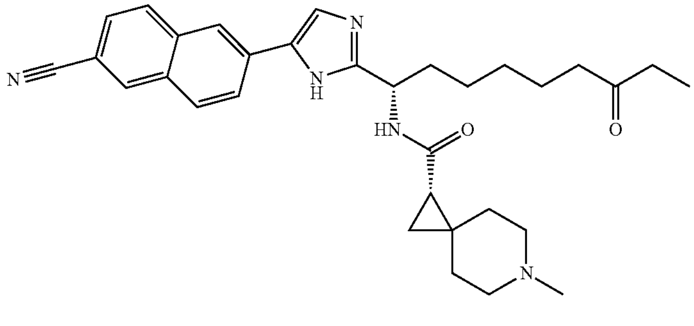 [SMILES: CCC(=O)CCCCC[C@H](NC(=O)[C@H]1CC12CCN(C)CC2)c1ncc(-c2ccc3cc(C#N)ccc3c2)[nH]1] | 526.3 |

-continued
| ID | Structure | Observed [M + H]+ |
|---|---|---|
| 139 | 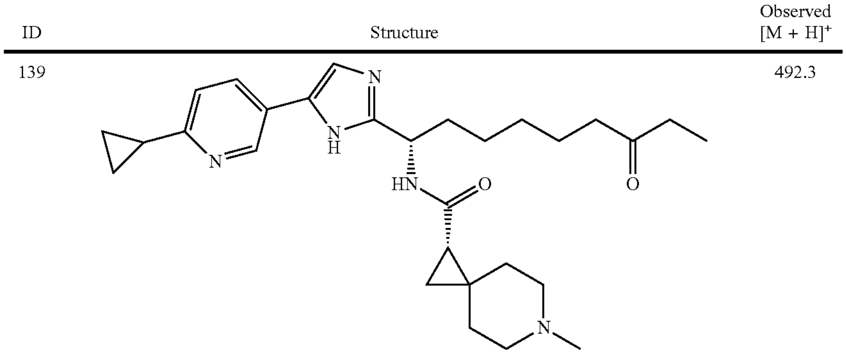 | 492.3 |
| 140 | 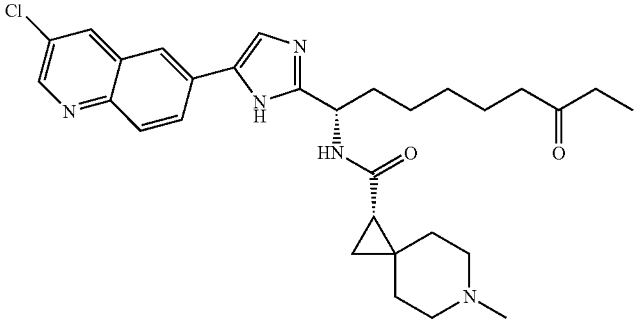 [SMILES: CCC(=O)CCCCC[C@H](NC(=O)[C@H]1CC12CCN(C)CC2)c1ncc(-c2ccc3ncc(Cl)cc3c2)[nH]1] | 536.2 |
| 148 | 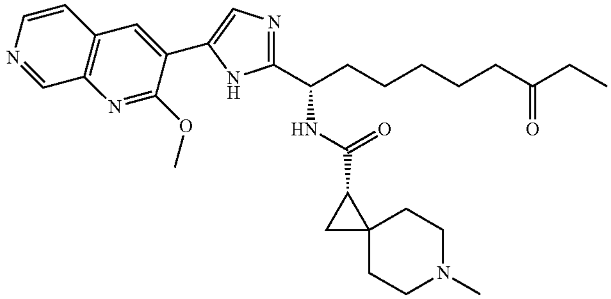 [SMILES: CCC(=O)CCCCC[C@H](NC(=O)[C@H]1CC12CCN(C)CC2)c1ncc(-c2cc3ccncc3nc2OC)[nH]1] | 533.3 |
| 149 | 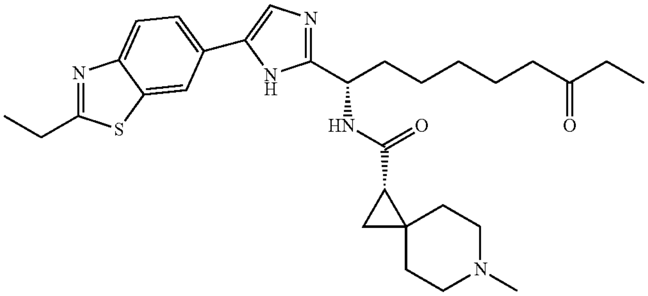 [SMILES: CCC(=O)CCCCC[C@H](NC(=O)[C@H]1CC12CCN(C)CC2)c1ncc(-c2ccc3nc(CC)sc3c2)[nH]1] | 536.3 |
| 243 | 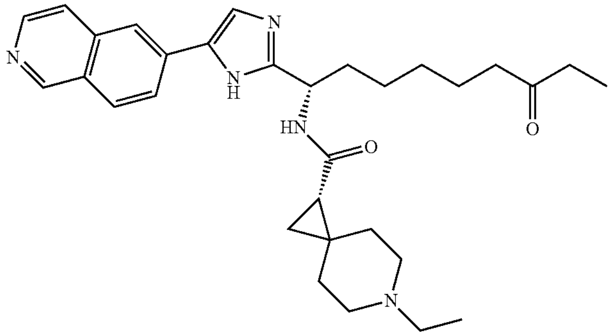 [SMILES: CCC(=O)CCCCC[C@H](NC(=O)[C@H]1CC12CCN(CC)CC2)c1ncc(-c2ccc3cnccc3c2)[nH]1] | 516.3 |

-continued
| ID | Structure | Observed [M + H]+ |
|---|---|---|
| 341 | 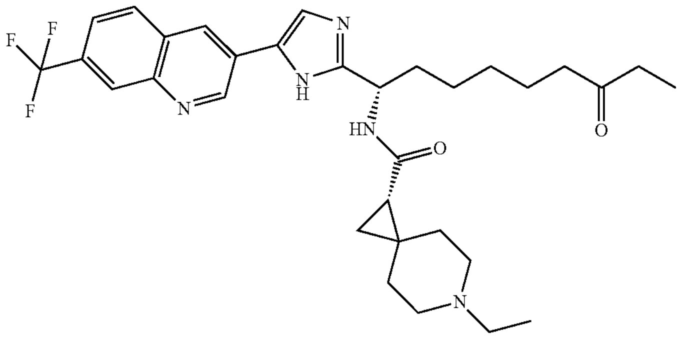 [SMILES: CCC(=O)CCCCC[C@H](NC(=O)[C@H]1CC12CCN(CC)CC2)c1ncc(-c2cnc3cc(C(F)(F)F)ccc3c2)[nH]1] | 584.1 |
| 342 | 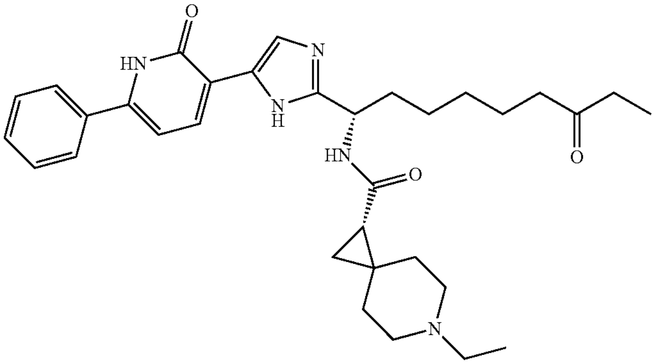 [SMILES: CCC(=O)CCCCC[C@H](NC(=O)[C@H]1CC12CCN(CC)CC2)c1ncc(-c2ccc(-c3ccccc3)[nH]c2=O)[nH]1] | 558.5 |
| 344 | 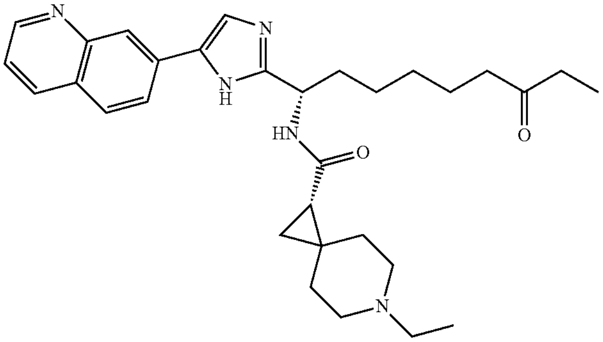 [SMILES: CCC(=O)CCCCC[C@H](NC(=O)[C@H]1CC12CCN(CC)CC2)c1ncc(-c2ccc3cccnc3c2)[nH]1] | 516.4 |
| 345 | 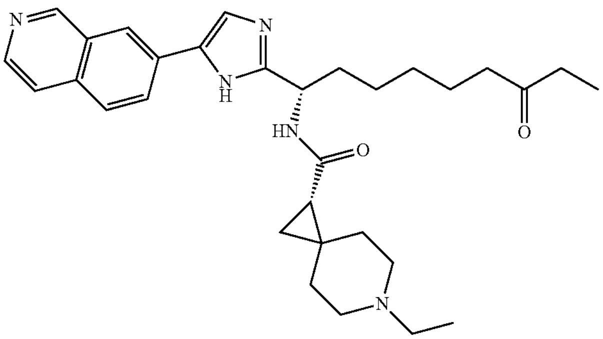 [SMILES: CCC(=O)CCCCC[C@H](NC(=O)[C@H]1CC12CCN(CC)CC2)c1ncc(-c2ccc3ccncc3c2)[nH]1] | 516.4 |

-continued
| ID | Structure | Observed [M + H]+ |
|---|---|---|
| 346 | 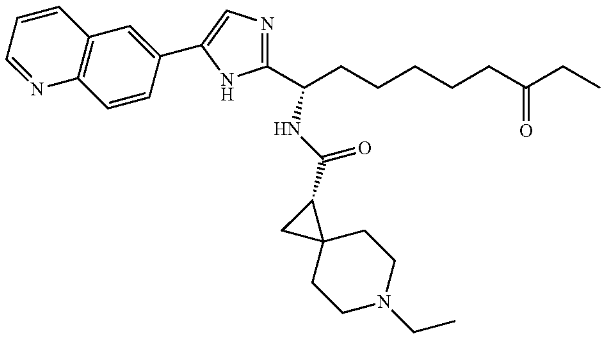 [SMILES: CCC(=O)CCCCC[C@H](NC(=O)[C@H]1CC12CCN(CC)CC2)c1ncc(-c2ccc3ncccc3c2)[nH]1] | 516.4 |
| 347 | 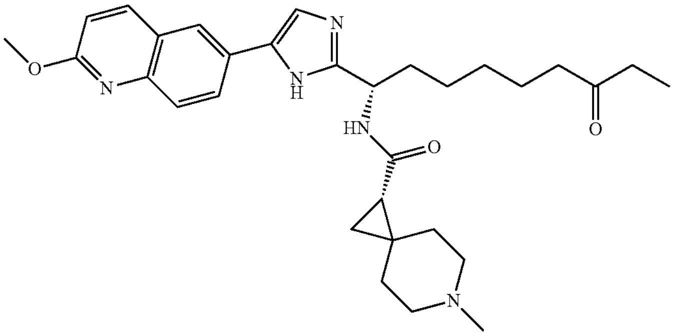 [SMILES: CCC(=O)CCCCC[C@H](NC(=O)[C@H]1CC12CCN(C)CC2)c1ncc(-c2ccc3nc(OC)ccc3c2)[nH]1] | 532.4 |
| 348 | 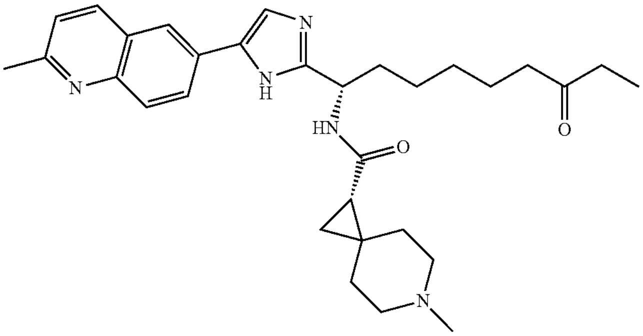 [SMILES: CCC(=O)CCCCC[C@H](NC(=O)[C@H]1CC12CCN(C)CC2)c1ncc(-c2ccc3nc(C)ccc3c2)[nH]1] | 516.4 |
| 349 | 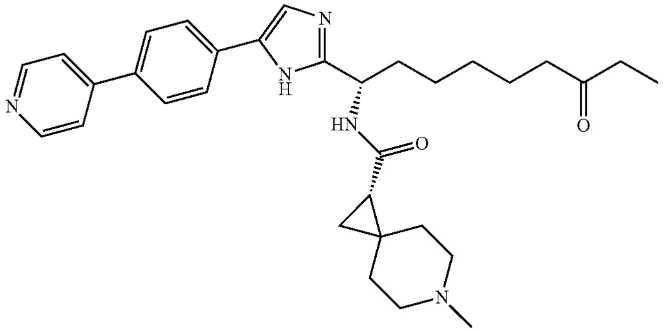 [SMILES: CCC(=O)CCCCC[C@H](NC(=O)[C@H]1CC12CCN(C)CC2)c1ncc(-c2ccc(-c3ccncc3)cc2)[nH]1] | 528.5 |

-continued
| ID | Structure | Observed [M + H]+ |
|---|---|---|
| 350 | 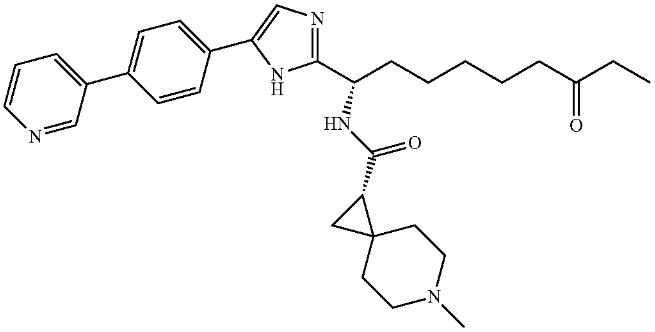 [SMILES: CCC(=O)CCCCC[C@H](NC(=O)[C@H]1CC12CCN(C)CC2)c1ncc(-c2ccc(-c3cccnc3)cc2)[nH]1] | 528.4 |
| 351 | 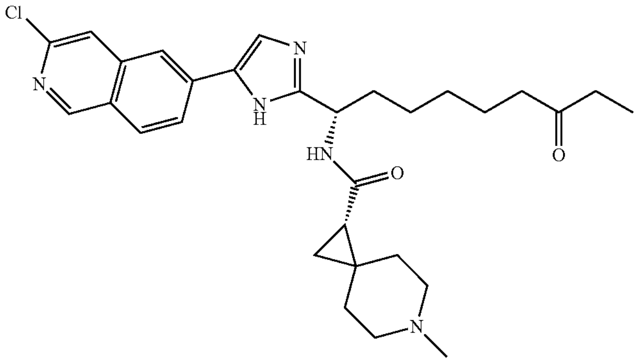 [SMILES: CCC(=O)CCCCC[C@H](NC(=O)[C@H]1CC12CCN(C)CC2)c1ncc(-c2ccc3cnc(Cl)cc3c2)[nH]1] | 536.0 |
| 352 | 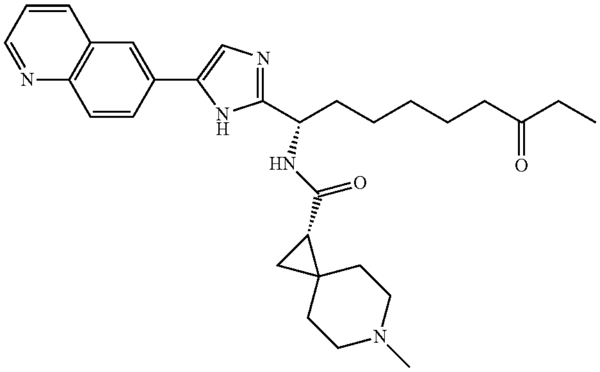 [SMILES: CCC(=O)CCCCC[C@H](NC(=O)[C@H]1CC12CCN(C)CC2)c1ncc(-c2ccc3ncccc3c2)[nH]1] | 502.4 |
| 353 | 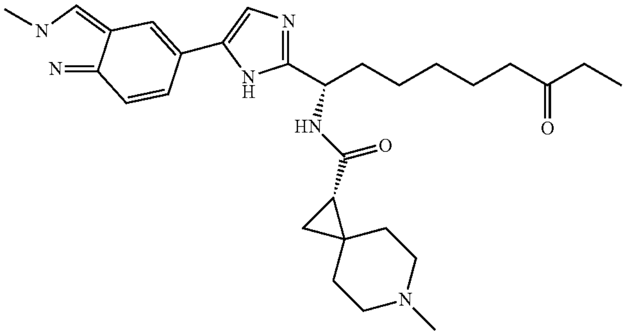 [SMILES: CCC(=O)CCCCC[C@H](NC(=O)[C@H]1CC12CCN(C)CC2)c1ncc(C2=C/C(=C/NC)C(=N)C=C2)[nH]1] | 505.1 |

-continued
| ID | Structure | Observed [M + H]+ |
|---|---|---|
| 354 | 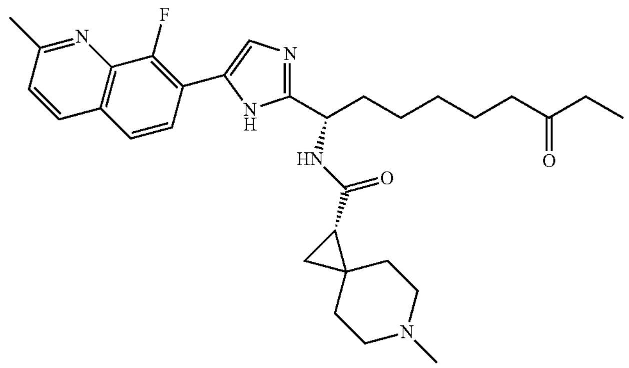 [SMILES: CCC(=O)CCCCC[C@H](NC(=O)[C@H]1CC12CCN(C)CC2)c1ncc(-c2ccc3ccc(C)nc3c2F)[nH]1] | 534.5 |
| 357 | 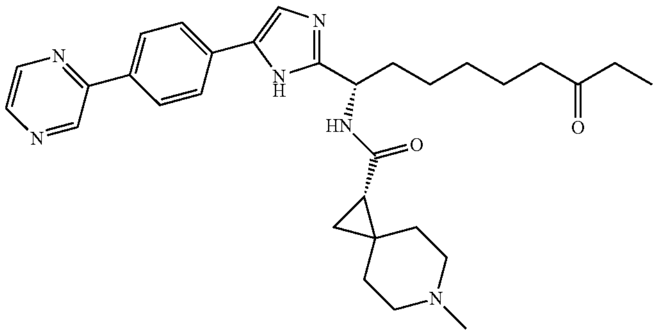 [SMILES: CCC(=O)CCCCC[C@H](NC(=O)[C@H]1CC12CCN(C)CC2)c1ncc(-c2ccc(-c3cnccn3)cc2)[nH]1] | 529.5 |
| 358 | 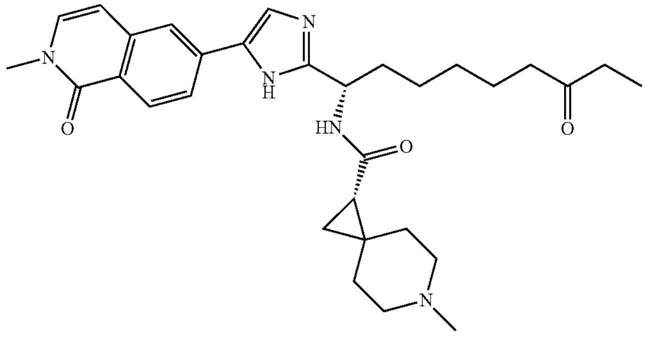 [SMILES: CCC(=O)CCCCC[C@H](NC(=O)[C@H]1CC12CCN(C)CC2)c1ncc(-c2ccc3c(=O)n(C)ccc3c2)[nH]1] | 532.4 |
| 356 | 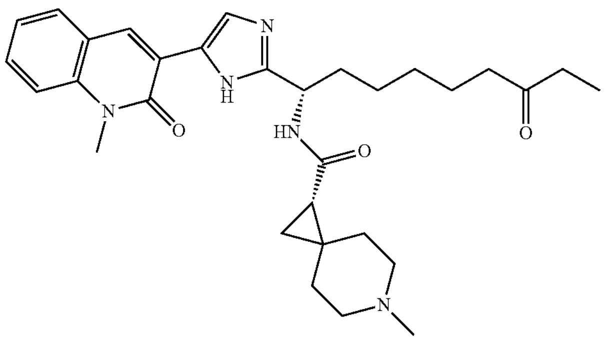 [SMILES: CCC(=O)CCCCC[C@H](NC(=O)[C@H]1CC12CCN(C)CC2)c1ncc(-c2cc3ccccc3n(C)c2=O)[nH]1] | 532.5 |

Example 55

1-methyl-N-{(1S)-7-oxo-1-[5-(1,2,3,4-tetrahydro-1,4-methanonaphthalen-6-yl)-1H-imidazol-2-yl]nonyl}azetidine-3-carboxamide (73)

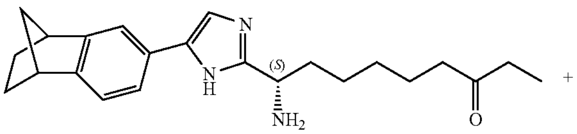

A28

-continued

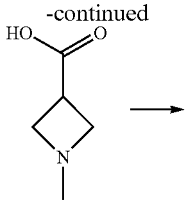

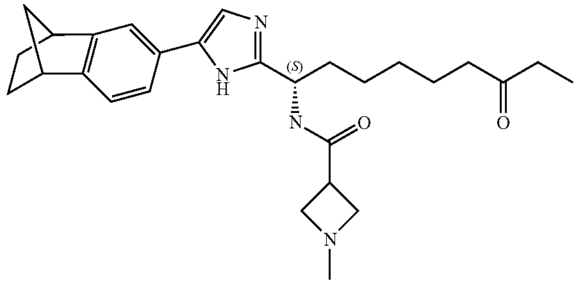

73

The mixture of 1-methylazetidine-3-carboxylic acid (61 mg, 0.530 mmol), HATU (212 mg, 0.557 mmol) and $Et_3N$ (0.30 mL, 2.15 mmol) in DMF (5 mL) was stirred at rt for 10 min, then a mixture of (S)-9-amino-9-(5-((1R,4S)-1,2,3,4-tetrahydro-1,4-methanonaphthalen-6-yl)-1H-imidazol-2-yl)nonan-3-one hydrochloride (73E, 140 mg, 0.348 mmol) in DMF (5 mL) was added. The resulting mixture was stirred at 40° C. for 16 h under nitrogen atmosphere. The mixture was concentrated to remove DMF, the residue was purified by preparative HPLC (reverse phase C-18 column), eluting with acetonitrile/water+0.1% TFA, lyophilized (adding HCl before) to give the title compound (73). LCMS (ESI) calc'd for $C_{28}H_{38}N_4O_2$ $[M+H]^+$: 463.3, found: 463.2. $^1H$ NMR (400 MHz, MeOD) δ 7.69 (s, 1H), 7.50 (s, 1H), 7.40 (d, J=7.5 Hz, 1H), 7.28 (d, J=7.5 Hz, 1H), 5.13 (brs, 1H), 4.54-4.34 (m, 2H), 4.23-4.03 (m, 2H), 3.69 (brs, 1H), 3.60 (q, J=7.1 Hz, 2H), 3.41 (brs, 2H), 2.92 (brs, 3H), 2.47-2.42 (m, 3H), 2.03-1.97 (m, 4H), 1.74 (d, J=8.4 Hz, 1H), 1.63-1.52 (m, 3H), 1.45 (brs, 1H), 1.35 (brs, 3H), 1.17 (t, J=7.1 Hz, 5H), 0.99 (t, J=7.3 Hz, 2H).

The following compound was prepared using similar procedures as described for compound 73:

| ID | Structure | Observed $[M + H]^+$ |
|---|---|---|
| 141 | 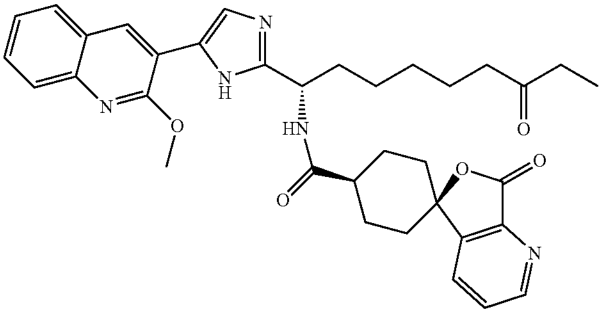 [SMILES: CCC(=O)CCCCC[C@H](NC(=O)[C@H]1CC[C@]2(CC1)OC(=O)c1ncccc12)c1ncc(-c2cc3ccccc3nc2OC)[nH]1] | 610.3 |

Example 56

(1S)-6-methyl-N-[(1S)-7-oxo-1-{5-[2-(trifluoromethyl)quinolin-6-yl]-1,3-oxazol-2-yl}nonyl]-6-azaspiro[2.5]octane-1-carboxamide (78)

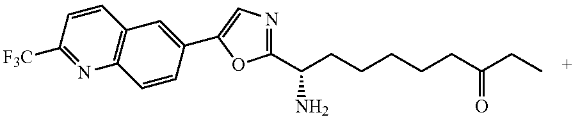

A16

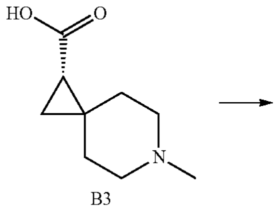

B3

-continued

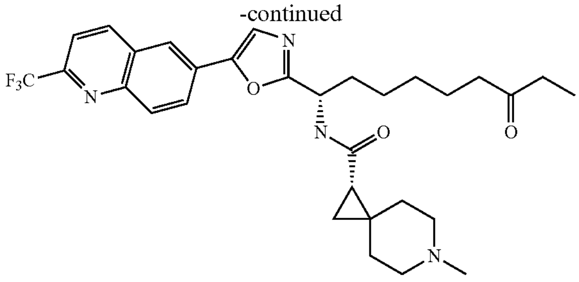

78

(S)-9-amino-9-(5-(2-(trifluoromethyl)quinolin-6-yl)oxazol-2-yl)nonan-3-one (A16, 90 mg, 0.215 mmol) was added to a stirred mixture of $Et_3N$ (0.18 mL, 1.291 mmol), HATU (90 mg, 0.236 mmol), (S)-6-methyl-6-azaspiro[2.5]octane-1-carboxylic acid (B3, 36 mg, 0.213 mmol) in DMF (1 mL) at room temperature and the mixture was stirred at room temperature for 1 h. Water (5 mL) was added and the mixture was extracted with ethyl acetate (3×5 mL). The combined organic fractions were washed with brine (5 mL), dried ($Na_2SO_4$), filtered and the solvent was evaporated under reduced pressure. The residue was purified by preparative HPLC (reverse phase C-18 column), eluting with acetonitrile/water+0.1% TFA, to give (S)-6-methyl-N—((S)-7-oxo-1-(5-(2-(trifluoromethyl)quinolin-6-yl)oxazol-2-yl)nonyl)-6-azaspiro[2.5]octane-1-carboxamide (78). LCMS (ESI) calc'd for $C_{31}H_{37}F_3N_4O_3$ $[M+H]^+$: 571.3, found: 571.2. $^1H$ NMR (400 MHz, $CDCl_3$) δ 11.74-12.17 (m, 1H), 8.41 (dd, J=8.4, 13.9 Hz, 1H), 8.19-8.30 (m, 1H), 8.14 (d, J=10.6 Hz, 1H), 7.99 (d, J=8.6 Hz, 1H), 7.76 (t, J=9.2 Hz, 1H), 7.37-7.51 (m, 1H), 6.87-7.22 (m, 1H), 5.17-5.37 (m, 1H), 3.23-3.64 (m, 2H), 2.56-2.83 (m, 5H), 2.23-2.48 (m, 5H), 0.82-2.12 (m, 17H).

The following compounds were prepared using similar procedures as described for compound 78:

| ID | Structure | Observed $[M + H]^+$ |
|---|---|---|
| 77 | 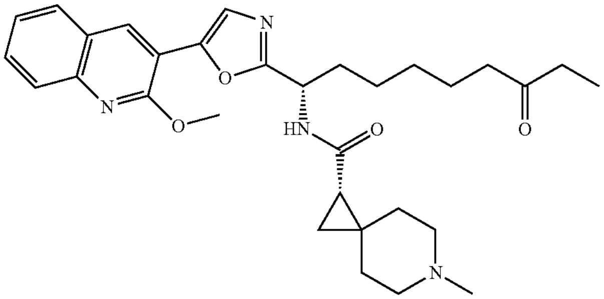 [SMILES: CCC(=O)CCCCC[C@H](NC(=O)[C@H]1CC12CCN(C)CC2)c1ncc(-c2cc3ccccc3nc2OC)o1] | 533.3 |
| 80 | 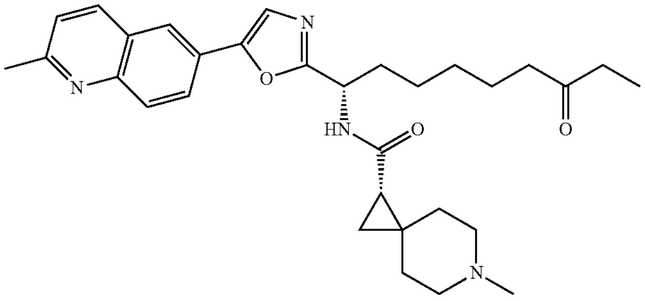 [SMILES: CCC(=O)CCCCC[C@H](NC(=O)[C@H]1CC12CCN(C)CC2)c1ncc(-c2ccc3nc(C)ccc3c2)o1] | 517.2 |
| 122 | 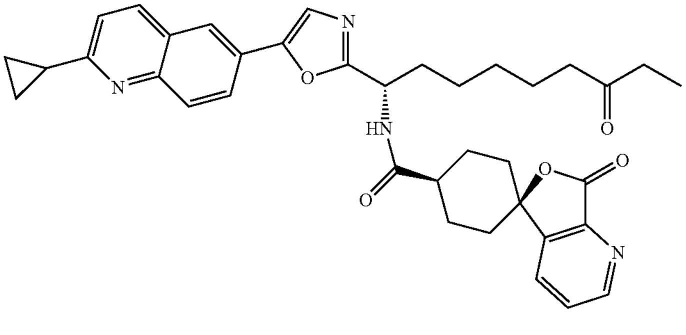 | 621.3 |

-continued
| ID | Structure | Observed [M + H]+ |
| --- | --- | --- |
| 123 | 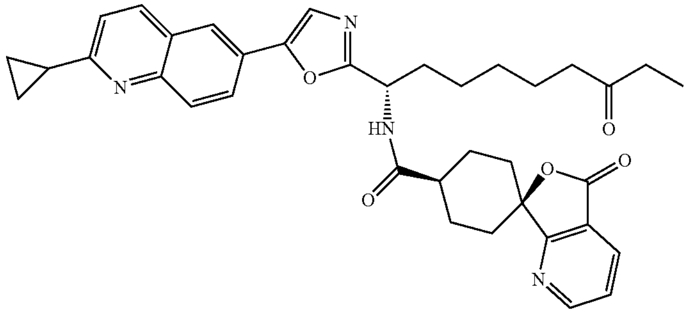 [SMILES: CCC(=O)CCCCC[C@H](NC(=O)[C@H]1CC[C@]2(CC1)OC(=O)c1cccnc12)c1ncc(-c2ccc3nc(C4CC4)ccc3c2)o1] | 621.3 |
| 124 | 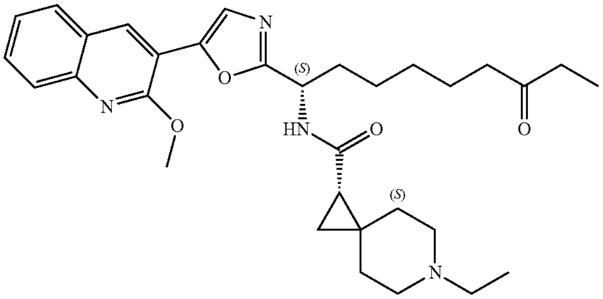 | 547.3 |
| 125 | 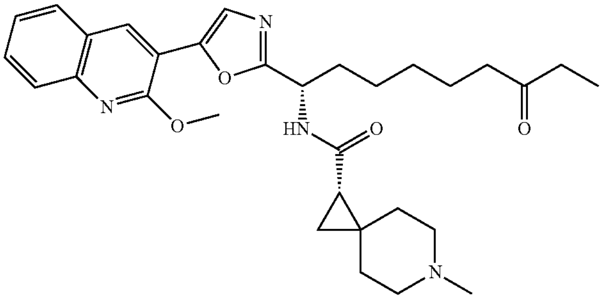 [SMILES: CCC(=O)CCCCC[C@H](NC(=O)[C@H]1CC12CCN(C)CC2)c1ncc(-c2cc3ccccc3nc2OC)o1] | 533.3 |
| 191 | 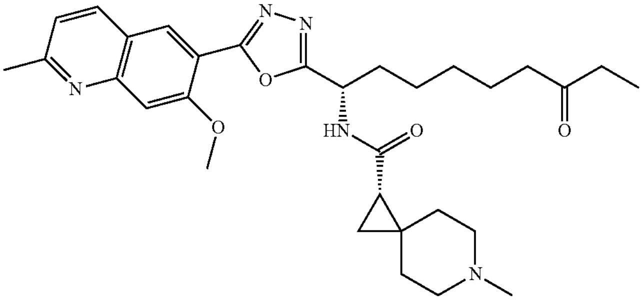 [SMILES: CCC(=O)CCCCC[C@H](NC(=O)[C@H]1CC12CCN(C)CC2)c1nnc(-c2cc3ccc(C)nc3cc2OC)o1] | 548.1 |

Example 57

(1S)—N-{(1S)-1-[4-chloro-5-(2-hydroxyquinolin-3-yl)-1H-imidazol-2-yl]-7-oxononyl}-6-methyl-6-azaspiro[2.5]octane-1-carboxamide (81)

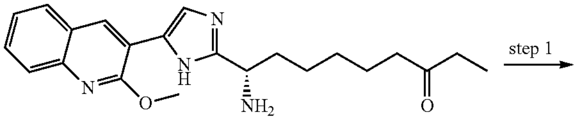

A9

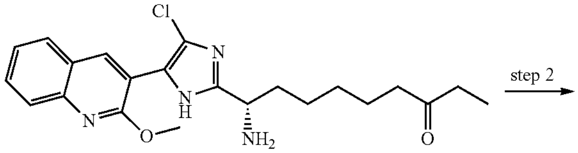

81A

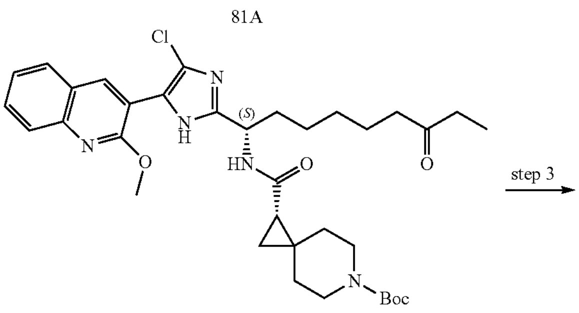

81B

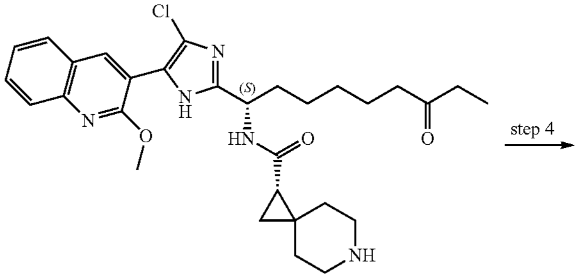

81C

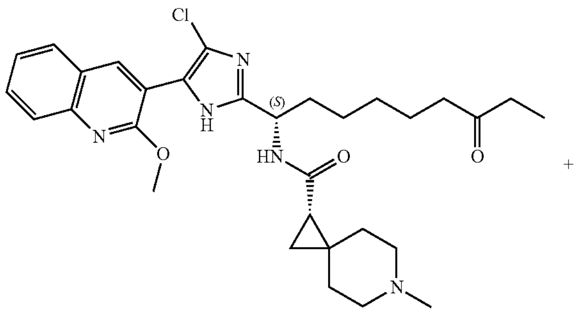

81D

-continued

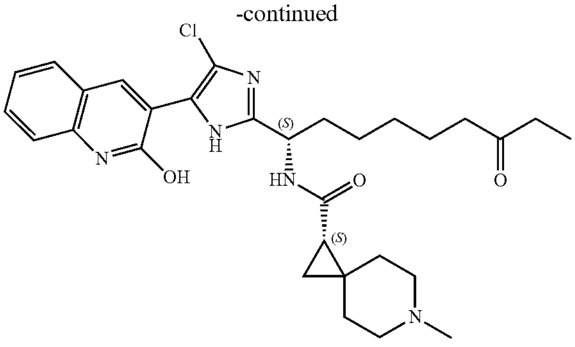

81

Step 1: Preparation of (S)-9-amino-9-(4-chloro-5-(2-methoxyquinolin-3-yl)-1H-imidazol-2-yl)nonan-3-one (81A): NCS (175 mg, 1.314 mmol) was added in portions to a stirred mixture of (S)-9-amino-9-(5-(2-methoxyquinolin-3-yl)-1H-imidazol-2-yl)nonan-3-one (A9, 500 mg, 1.314 mmol) in THF (5 mL) at rt and the mixture was stirred at rt for 8 h. The mixture was quenched with water (10 mL), diluted with EtOAc (20 mL×2), and the solvent was evaporated under reduced pressure. The residue was purified by column chromatography on silica gel, eluting with petroleum ether:EtOAc=5:1-3:1 to give (S)-9-amino-9-(4-chloro-5-(2-methoxyquinolin-3-yl)-1H-imidazol-2-yl)nonan-3-one (81A). LCMS (ESI) calc'd for $C_{22}H_{27}ClN_4O_2$ $[M+H]^+$: 415.1, found: 415.2.

Step 2: Preparation of (S)-tert-butyl 1-(((S)-1-(4-chloro-5-(2-methoxyquinolin-3-yl)-1H-imidazol-2-yl)-7-oxononyl) carbamoyl)-6-azaspiro[2.5]octane-6-carboxylate (81B): (S)-9-amino-9-(4-chloro-5-(2-methoxyquinolin-3-yl)-1H-imidazol-2-yl)nonan-3-one (81A, 80 mg, 0.193 mmol) in THF (1 mL) was added to a stirred mixture of (S)-6-(tert-butoxycarbonyl)-6-azaspiro[2.5]octane-1-carboxylic acid (B2, 49 mg, 0.192 mmol), HATU (73 mg, 0.192 mmol) and triethylamine (0.2 mL, 1.435 mmol) in THF (2 mL) at rt and the mixture was stirred at rt for 3 h. The mixture was diluted with ethyl acetate (2×20 mL), washed with water (10 mL), dried ($Na_2SO_4$), filtered and the solvent was evaporated under reduced pressure. The residue was purified by silica gel column flash chromatography, eluting with DCM/MeOH=15:1-10:1 to give (S)-tert-butyl 1-(((S)-1-(4-chloro-5-(2-methoxyquinolin-3-yl)-1H-imidazol-2-yl)-7-oxononyl)carbamoyl)-6-azaspiro[2.5]octane-6-carboxylate (81B). LCMS (ESI) calc'd for $C_{35}H_{46}ClN_5O_5$ $[M+H]^+$: 652.3, found: 652.4.

Step 3: Preparation of (S)—N—((S)-1-(4-chloro-5-(2-methoxyquinolin-3-yl)-1H-imidazol-2-yl)-7-oxononyl)-6-azaspiro[2.5]octane-1-carboxamide (81C): TFA (0.2 mL, 2.60 mmol) was added to a stirred mixture of (S)-tert-butyl 1-(((S)-1-(4-chloro-5-(2-methoxyquinolin-3-yl)-1H-imidazol-2-yl)-7-oxononyl)carbamoyl)-6-azaspiro[2.5]octane-6-carboxylate (81B, 90 mg, 0.138 mmol) in DCM (5 mL) at room temperature and the mixture was stirred at rt for 2 h. The mixture was extracted with DCM (30×2 mL) and washed with water (10 mL), dried ($Na_2SO_4$) and the solvent was evaporated under reduced pressure to get (S)—N—((S)-1-(4-chloro-5-(2-methoxyquinolin-3-yl)-1H-imidazol-2-yl)-7-oxononyl)-6-azaspiro[2.5]octane-1-carboxamide (81C) which was used in the next step without further purification. LCMS (ESI) calc'd for $C_{30}H_{38}ClN_5O_3$ $[M+H]^+$: 552.2, found: 552.3.

Step 4: Preparation of (S)—N—((S)-1-(4-chloro-5-(2-hydroxyuinolin-3-yl)-1H-imidazol-2-yl)-7-oxononyl)-6- methyl-6-azaspiro[2.5]octane-1-carboxamide (81): Formaldehyde (0.5 mL, 5.02 mmol) and acetic acid (2 drops) were added into a stirred mixture of (S)—N—((S)-1-(4-chloro-5-(2-methoxyquinolin-3-yl)-1H-imidazol-2-yl)-7-oxononyl)-6-azaspiro[2.5]octane-1-carboxamide (81C, 95 mg, 0.172 mmol) in MeOH (5 mL) at rt and the mixture was stirred at rt for 1 h. Then sodium triacetoxyhydroborate (182 mg, 0.860 mmol) was added into the mixture and the mixture was stirred at rt for 1 h. The mixture was quenched with $NH_4Cl$ (2 mL), then evaporated under reduced pressure. The residue was purified by HPLC separation to get (S)—N—((S)-1-(4-chloro-5-(2-methoxyquinolin-3-yl)-1H-imidazol-2-yl)-7-oxononyl)-6-methyl-6-azaspiro[2.5]octane-1-carboxamide (81D) and (S)—N—((S)-1-(4-chloro-5-(2-hydroxyquinolin-3-yl)-1H-imidazol-2-yl)-7-oxononyl)-6-methyl-6-azaspiro[2.5]octane-1-carboxamide (81). LCMS (ESI) calc'd for $C_{30}H_{38}ClN_5O_3$ $[M+H]^+$: 552.3, found: 552.4. $^1H$ NMR (400 MHz, $CDCl_3$) δ 8.58 (s, 1H), 7.47-7.72 (m, 3H), 7.39 (d, J=7.83 Hz, 1H), 7.28-7.33 (m, 1H), 5.51 (brs, 1H), 2.90 (brs, 3H), 2.34 (q, J=7.43 Hz, 7H), 1.92 (brs, 9H), 1.46-1.62 (m, 4H), 1.21-1.37 (m, 5H), 1.06-1.19 (m, 2H), 0.98 (t, J=7.24 Hz, 4H).

Example 58

N-{(1S)-1-[5-(2-methoxyquinolin-3-yl)-1H-imidazol-2-yl]-7-oxononyl}-8-(1-methylethyl)-1-oxa-2,8-diazaspiro[4.5]dec-2-ene-3-carboxamide (106)

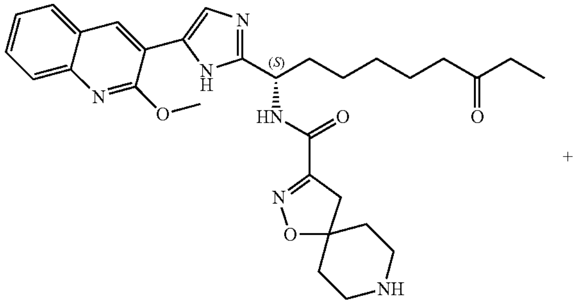

E2

-continued

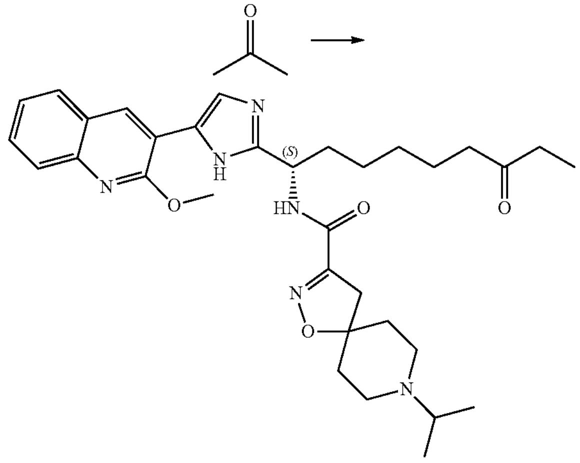

106

(S)—N-(1-(5-(2-methoxyquinolin-3-yl)-1H-imidazol-2-yl)-7-oxononyl)-1-oxa-2,8-diazaspiro[4.5]dec-2-ene-3-carboxamide (E2, 92 mg, 0.168 mmol) was added to acetone (2 ml, 0.168 mmol) at rt and the mixture was stirred at 45° C. for 12 h. Then $NaBH(OAc)_3$ (107 mg, 0.505 mmol) was added at 45° C., and the mixture was stirred at 45° C. for 13 h. The residue was purified by preparative HPLC (reverse phase C-18 column), eluting with acetonitrile/water+0.05% $NH_3{\cdot}H_2O$, to give (S)—N-(1-(5-(2-methoxyquinolin-3-yl)-1H-imidazol-2-yl)-7-oxononyl)-8-methyl-1-oxa-2,8-diazaspiro[4.5]dec-2-ene-3-carboxamide (106). LCMS (ESI) calc'd for $C_{31}H_{40}N_6O_4$ $[M+H]^+$: 589.3, found: 589.3. $^1H$ NMR (400 MHz, $CDCl_3$) δ 8.79 (brs, 1H), 7.84 (d, J=8.2 Hz, 2H), 7.48-7.69 (m, 2H), 7.39 (brs, 1H), 5.05 (brs, 1H), 4.21 (brs, 3H), 2.87-3.05 (m, 2H), 2.61-2.83 (m, 3H), 2.50 (brs, 1H), 2.36-2.44 (m, 4H), 2.28 (d, J=5.7 Hz, 1H), 2.01-2.14 (m, 1H), 1.93 (d, J=15.7 Hz, 2H), 1.80 (brs, 4H), 1.56-1.65 (m, 2H), 1.34-1.51 (m, 4H), 0.99-1.15 (m, 9H).

The following compounds were prepared using similar procedures as described for compound 106.

| ID | Structure | Observed $[M + H]^+$ |
|---|---|---|
| 83 | 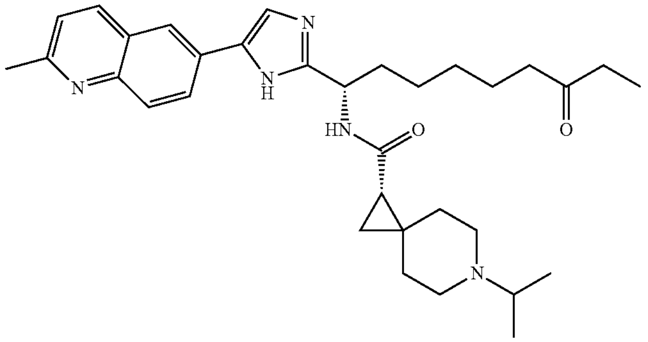 [SMILES: CCC(=O)CCCCC[C@H](NC(=O)[C@H]1CC12CCN(C(C)C)CC2)c1ncc(-c2ccc3nc(C)ccc3c2)[nH]1] | 544.3 |

-continued
| ID | Structure | Observed [M + H]+ |
|---|---|---|
| 96 | 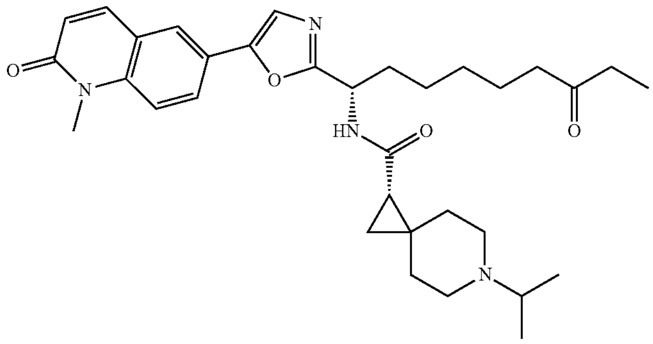 [SMILES: CCC(=O)CCCCC[C@H](NC(=O)[C@H]1CC12CCN(C(C)C)CC2)c1ncc(-c2ccc3c(ccc(=O)n3C)c2)o1] | 561.4 |
| 99 | 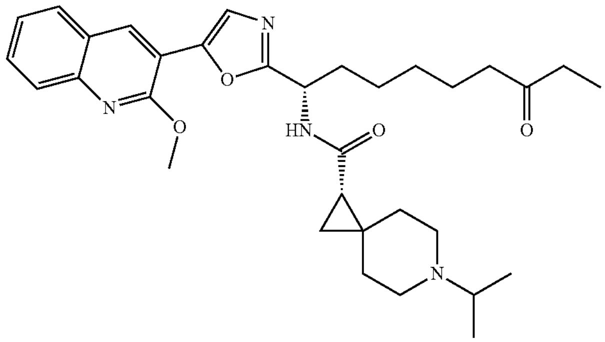 [SMILES: CCC(=O)CCCCC[C@H](NC(=O)[C@H]1CC12CCN(C(C)C)CC2)c1ncc(-c2cc3ccccc3nc2OC)o1] | 561.3 |
| 100 | 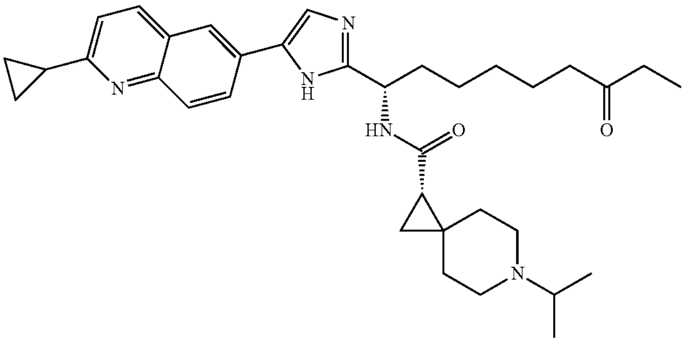 [SMILES: CCC(=O)CCCCC[C@H](NC(=O)[C@H]1CC12CCN(C(C)C)CC2)c1ncc(-c2ccc3nc(C4CC4)ccc3c2)[nH]1] | 570.3 |
| 116 | 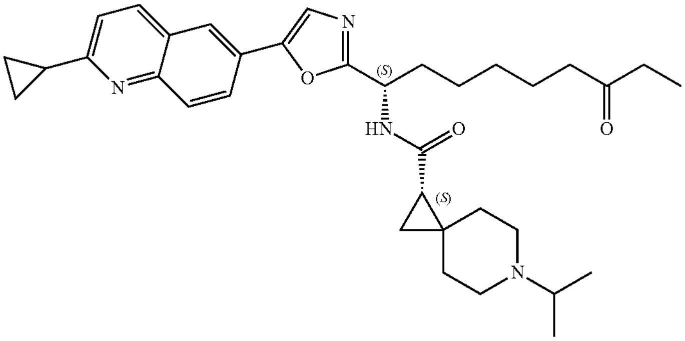 | 571.3 |

-continued
| ID | Structure | Observed $[M + H]^+$ |
|---|---|---|
| 136 | 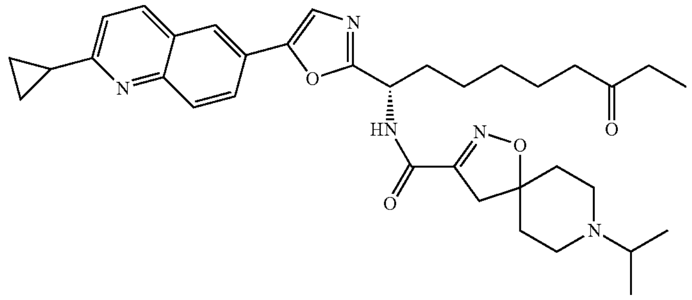 [SMILES: CCC(=O)CCCCC[C@H](NC(=O)C1=NOC2(CCN(C(C)C)CC2)C1)c1ncc(-c2ccc3nc(C4CC4)ccc3c2)o1] | 600.4 |
| 182 | 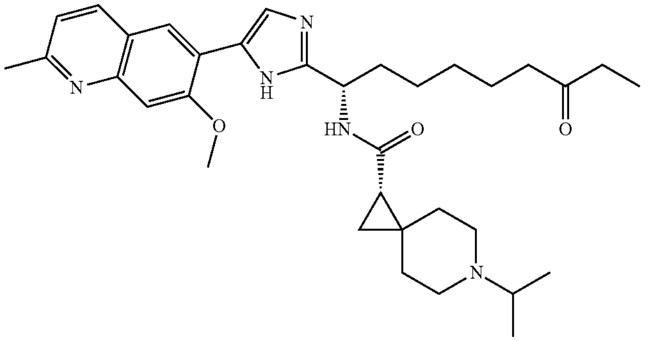 [SMILES: CCC(=O)CCCCC[C@H](NC(=O)[C@H]1CC12CCN(C(C)C)CC2)c1ncc(-c2cc3ccc(C)nc3cc2OC)[nH]1] | 574.1 |
Example 59
(1S)—N-{(1S)-1-[5-(2-cyclopropyl-7-methoxyquinolin-6-yl)-1H-imidazol-2-yl]-7-oxononyl}-6-methyl-6-azaspiro[2.5]octane-1-carboxamide (108)
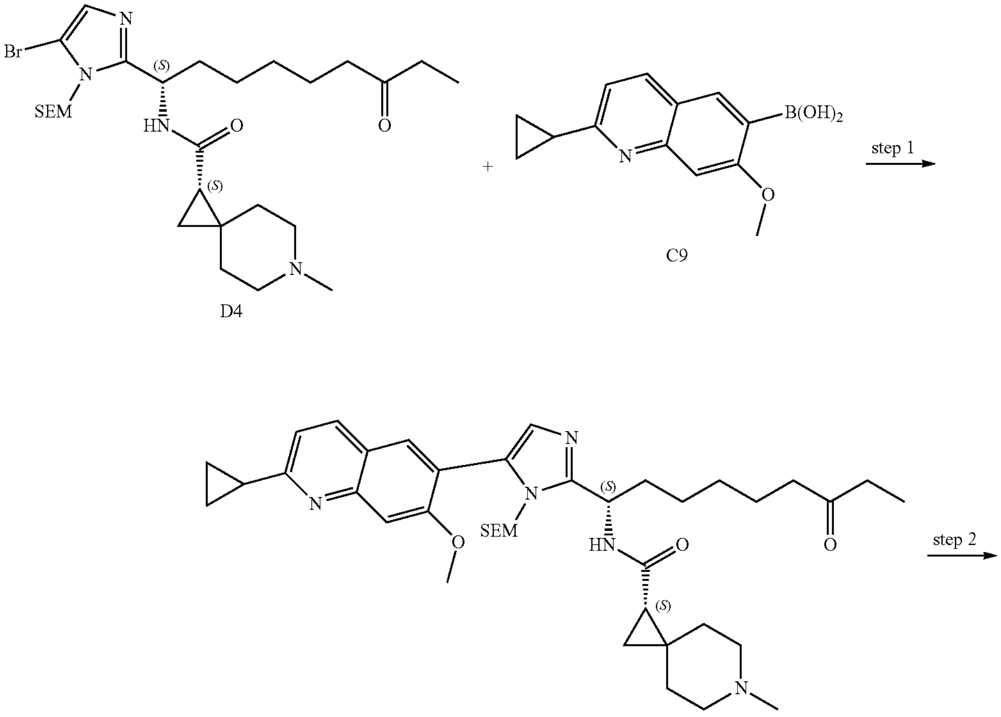
D4
C9
108A -continued

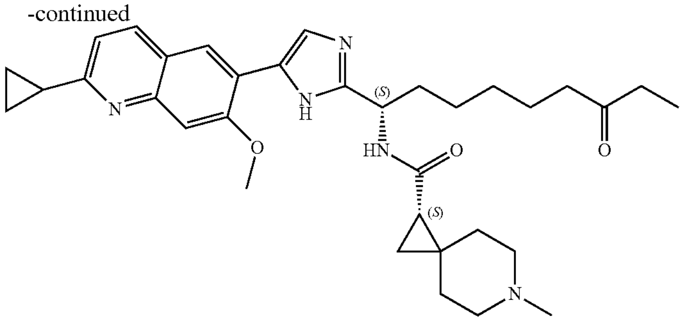

108

Step 1: Preparation of (S)—N—((S)-1-(5-(2-cyclopropyl-7-methoxyquinolin-6-yl)-1-((2-(trimethylsilyl)ethoxy)methyl)-1H-imidazol-2-yl)-7-oxononyl)-6-methyl-6-azaspiro[2.5]octane-1-carboxamide (108A): $PdCl_2$(DTBPF) (15 mg, 0.023 mmol) was added to a stirred mixture of $K_3PO_4$ (105 mg, 0.494 mmol), (S)—N—((S)-1-(5-bromo-1-((2-(trimethylsilyl)ethoxy)methyl)-1H-imidazol-2-yl)-7-oxononyl)-6-methyl-6-azaspiro[2.5]octane-1-carboxamide (D4, 100 mg, 0.171 mmol), (2-cyclopropyl-7-methoxyquinolin-6-yl)boronic acid (C9, 40 mg, 0.165 mmol) in THF (1 mL)/water (0.5 mL) at room temperature and the mixture was stirred at 70° C. for 4 h under $N_2$. The mixture was cooled, diluted with EtOAc (10 mL), washed with water (3×10 mL), dried ($Na_2SO_4$), filtered and the solvent was evaporated under reduced pressure. The residue was purified by silica gel column flash chromatography, eluting with MeOH/DCM=0-30% to give (S)—N—((S)-1-(5-(2-cyclopropyl-7-methoxyquinolin-6-yl)-1-((2-(trimethylsilyl)ethoxy)methyl)-1H-imidazol-2-yl)-7-oxononyl)-6-methyl-6-azaspiro[2.5]octane-1-carboxamide (108A). LCMS (ESI) calc'd for $C_{40}H_{59}N_5O_4Si$ $[M+H]^+$: 702.4, found: 702.5.

Step 2: Preparation of (S)—N—((S)-1-(5-(2-cyclopropyl-7-methoxyquinolin-6-yl)-1H-imidazol-2-yl)-7-oxononyl)-6-methyl-6-azaspiro[2.5]octane-1-carboxamide (108): (S)—N—((S)-1-(5-(2-cyclopropyl-7-methoxyquinolin-6-yl)-1-((2-(trimethylsilyl)ethoxy)methyl)-1H-imidazol-2-yl)-7-oxononyl)-6-methyl-6-azaspiro[2.5]octane-1-carboxamide (108A, 60 mg, 0.085 mmol) was added in TFA (1.5 mL) at room temperature and the mixture was stirred at room temperature for 2 h. Most of the TFA was removed, and the residue was purified by preparative HPLC Reverse phase (C-18), eluting with acetonitrile/water+0.1% TFA, and HCl (0.5 mL, 1M) was added, and lyophilized to give (S)—N—((S)-1-(5-(2-cyclopropyl-7-methoxyquinolin-6-yl)-1H-imidazol-2-yl)-7-oxononyl)-6-methyl-6-azaspiro[2.5]octane-1-carboxamide hydrochloride (108). LCMS (ESI) calc'd for $C_{34}H_{45}N_5O_3$ $[M+H]^+$: 572.4, found: 572.4. $^1H$ NMR (400 MHz, MeOD) δ 8.92 (d, J=8.8 Hz, 1H), 8.81-8.88 (m, 1H), 8.60 (s, 1H), 8.05 and 8.04 (s, 1H), 7.70 (s, 1H), 7.46 (dd, J=2.2, 8.60 Hz, 1H), 5.09 (brs, 1H), 4.24 (d, J=4.2 Hz, 3H), 3.40-3.68 (m, 3H), 2.99-3.25 (m, 2H), 2.82-2.94 (m, 3H), 2.52-2.63 (m, 1H), 2.41-2.52 (m, 4H), 2.05-2.20 (m, 2H), 1.88-1.96 (m, 2H), 1.27-1.68 (m, 11H), 1.13-1.22 (m, 1H), 0.94-1.09 (m, 3H), 0.80 (t, J=7.5 Hz, 1H).

The following compounds were prepared using similar procedures as described for compound 108.

| ID | Structure | Observed $[M + H]^+$ |
|---|---|---|
| 67 | 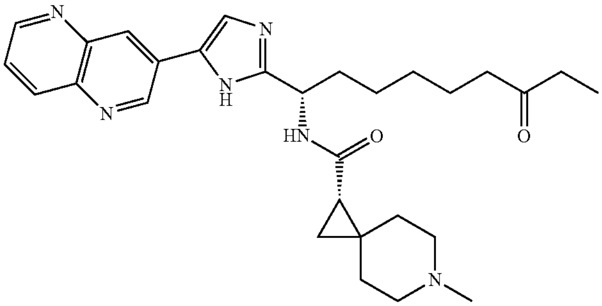 [SMILES: CCC(=O)CCCCC[C@H](NC(=O)[C@H]1CC12CCN(C)CC2)c1ncc(-c2cnc3cccnc3c2)[nH]1] | 503.3 |

-continued
| ID | Structure | Observed $[M + H]^+$ |
|---|---|---|
| 70 | 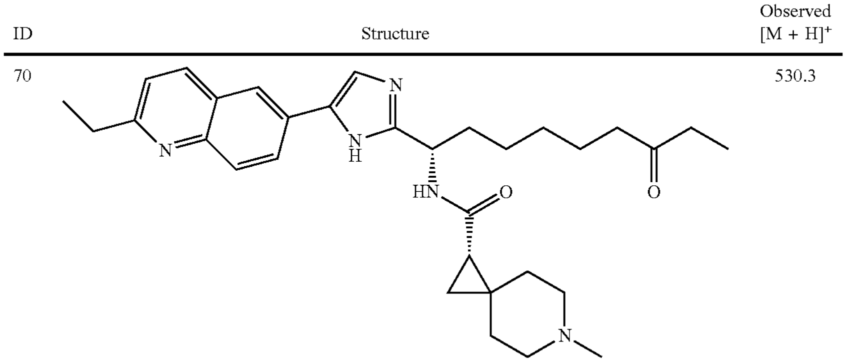 | 530.3 |
| 72 | 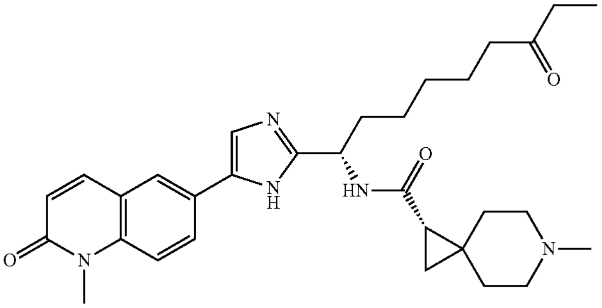 [SMILES: CCC(=O)CCCCC[C@H](NC(=O)[C@H]1CC12CCN(C)CC2)c1ncc(-c2ccc3c(ccc(=O)n3C)c2)[nH]1] | 532.3 |
| 82 | 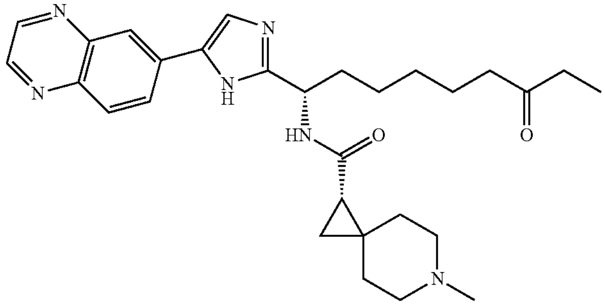 [SMILES: CCC(=O)CCCCC[C@H](NC(=O)[C@H]1CC12CCN(C)CC2)c1ncc(-c2ccc3nccnc3c2)[nH]1] | 503.3 |
| 86 | 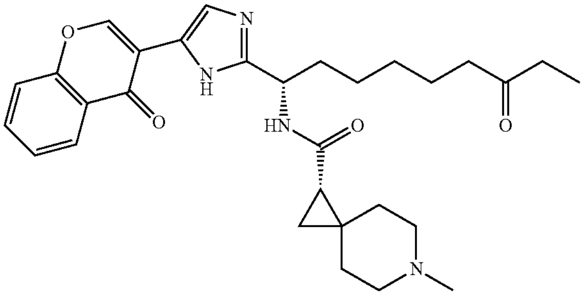 [SMILES: CCC(=O)CCCCC[C@H](NC(=O)[C@H]1CC12CCN(C)CC2)c1ncc(-c2coc3ccccc3c2=O)[nH]1] | 519.3 |
| 92 | 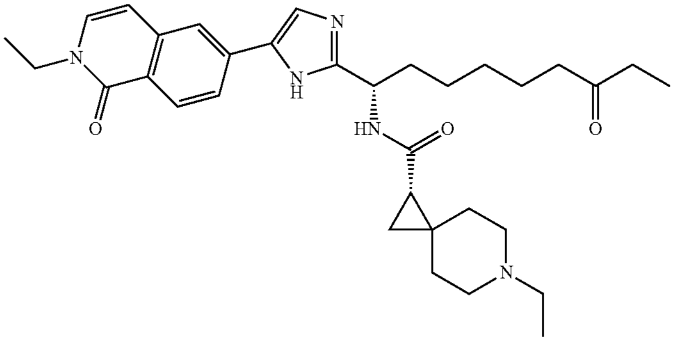 [SMILES: CCC(=O)CCCCC[C@H](NC(=O)[C@H]1CC12CCN(CC)CC2)c1ncc(-c2ccc3c(=O)n(CC)ccc3c2)[nH]1] | 560.4 |

-continued
| ID | Structure | Observed [M + H]+ |
| --- | --- | --- |
| 98 | 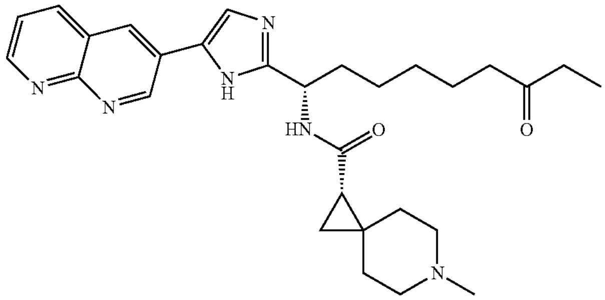 [SMILES: CCC(=O)CCCCC[C@H](NC(=O)[C@H]1CC12CCN(C)CC2)c1ncc(-c2cnc3ncccc3c2)[nH]1] | 503.3 |
| 102 | 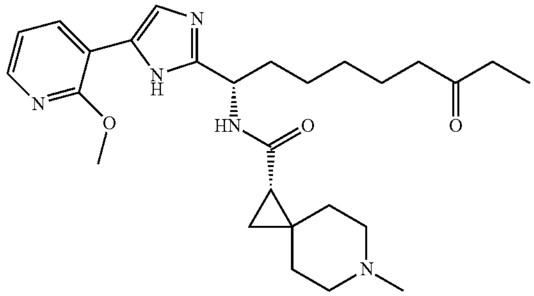 [SMILES: CCC(=O)CCCCC[C@H](NC(=O)[C@H]1CC12CCN(C)CC2)c1ncc(-c2cccnc2OC)[nH]1] | 482.3 |
| 103 | 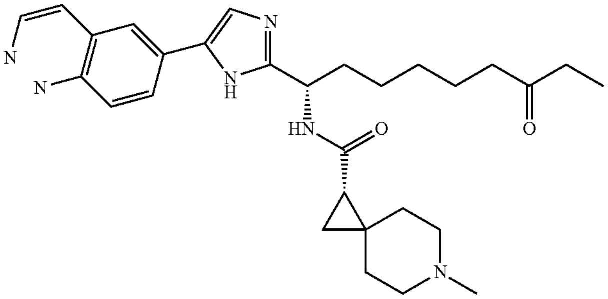 [SMILES: CCC(=O)CCCCC[C@H](NC(=O)[C@H]1CC12CCN(C)CC2)c1ncc(-c2ccc(N)c(/C=C\N)c2)[nH]1] | 503.3 |
| 107 | 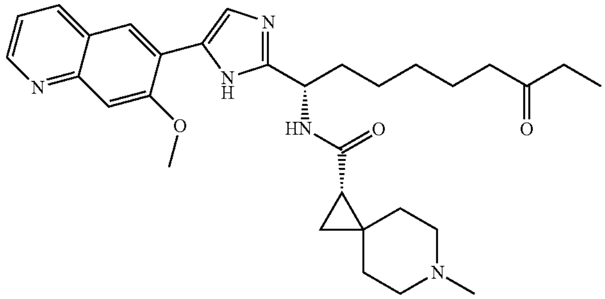 [SMILES: CCC(=O)CCCCC[C@H](NC(=O)[C@H]1CC12CCN(C)CC2)c1ncc(-c2cc3cccnc3cc2OC)[nH]1] | 532.3 |
| 113 | 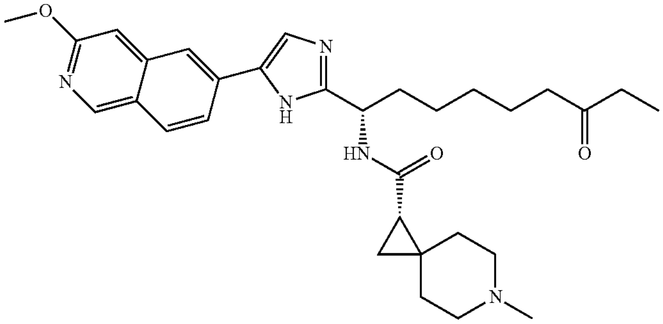 [SMILES: CCC(=O)CCCCC[C@H](NC(=O)[C@H]1CC12CCN(C)CC2)c1ncc(-c2ccc3cnc(OC)cc3c2)[nH]1] | 532.3 |

-continued
| ID | Structure | Observed [M + H]+ |
|---|---|---|
| 119 | 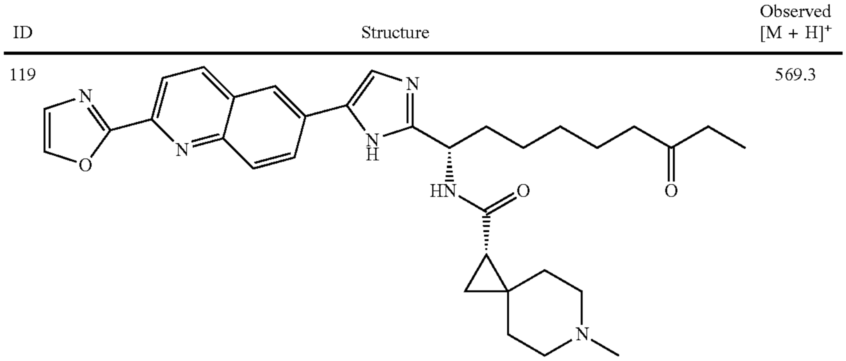 | 569.3 |
| 126 | 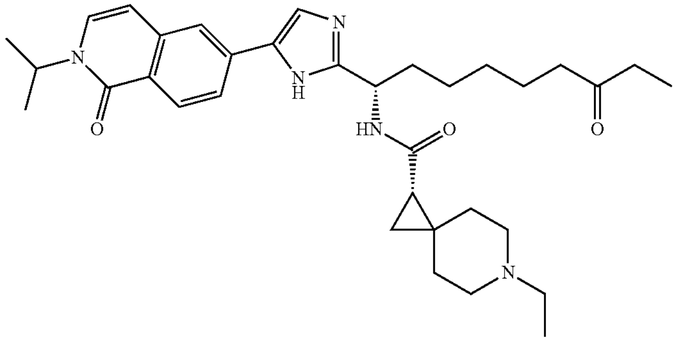 [SMILES: CCC(=O)CCCCC[C@H](NC(=O)[C@H]1CC12CCN(CC)CC2)c1ncc(-c2ccc3c(=O)n(C(C)C)ccc3c2)[nH]1] | 574.4 |
| 138 | 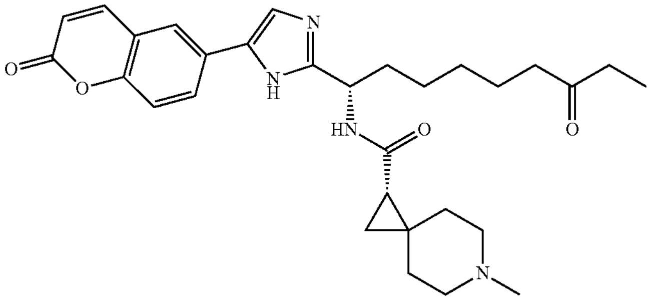 [SMILES: CCC(=O)CCCCC[C@H](NC(=O)[C@H]1CC12CCN(C)CC2)c1ncc(-c2ccc3oc(=O)ccc3c2)[nH]1] | 519.3 |
| 142 | 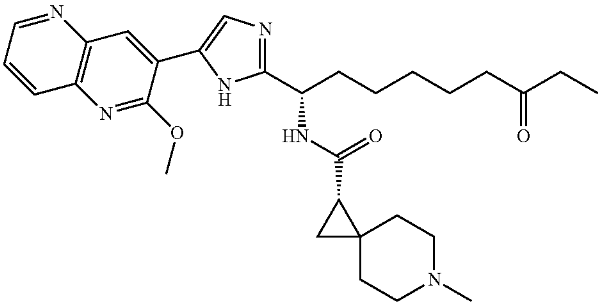 [SMILES: CCC(=O)CCCCC[C@H](NC(=O)[C@H]1CC12CCN(C)CC2)c1ncc(-c2cc3ncccc3nc2OC)[nH]1] | 533.3 |
| 144 | 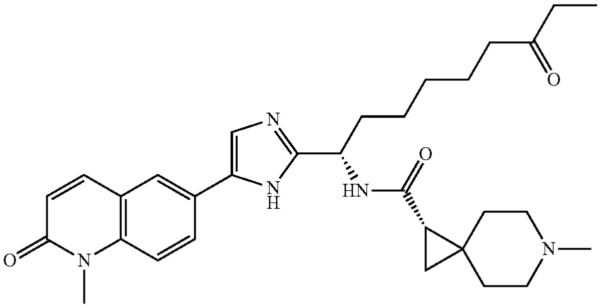 [SMILES: CCC(=O)CCCCC[C@H](NC(=O)[C@H]1CC12CCN(C)CC2)c1ncc(-c2ccc3c(ccc(=O)n3C)c2)[nH]1] | 532.3 |

-continued
| ID | Structure | Observed [M + H]+ |
|---|---|---|
| 146 | 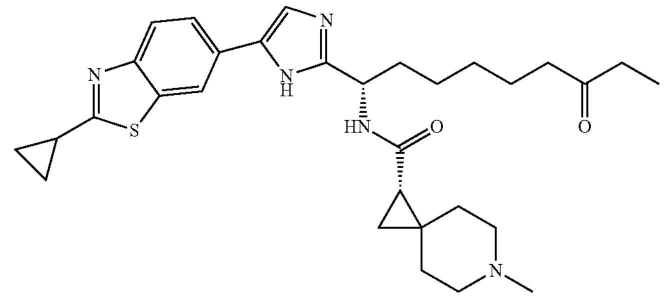 | 548.3 |
| 150 | 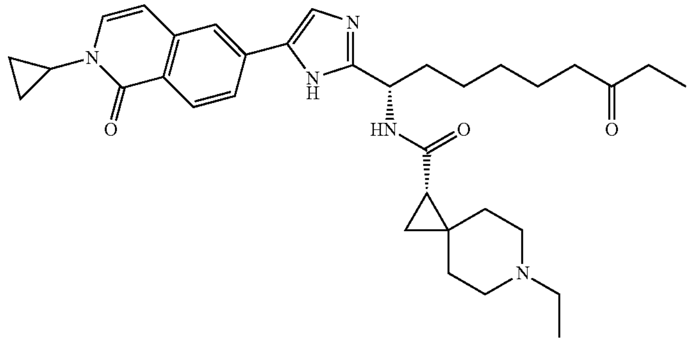 [SMILES: CCC(=O)CCCCC[C@H](NC(=O)[C@H]1CC12CCN(CC)CC2)c1ncc(-c2ccc3c(=O)n(C4CC4)ccc3c2)[nH]1] | 572.4 |
| 158 | 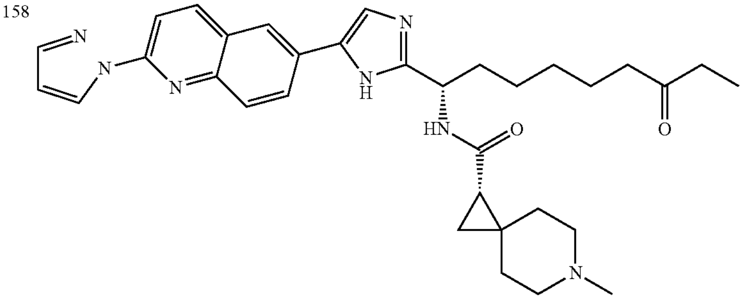 | 568.4 |
| 159 | 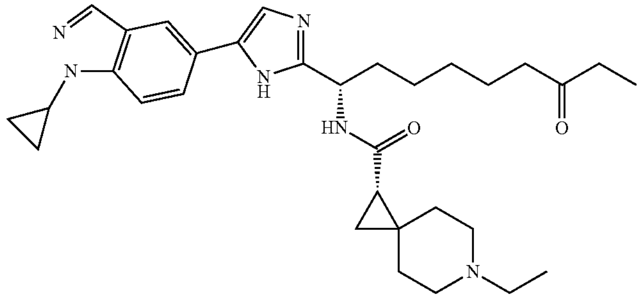 [SMILES: CCC(=O)CCCCC[C@H](NC(=O)[C@H]1CC12CCN(CC)CC2)c1ncc(-c2ccc(NC3CC3)c(C=N)c2)[nH]1] | 545.3 |
| 160 | 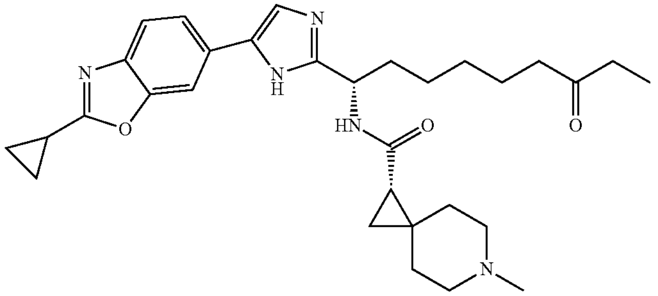 [SMILES: CCC(=O)CCCCC[C@H](NC(=O)[C@H]1CC12CCN(C)CC2)c1ncc(-c2ccc3nc(C4CC4)oc3c2)[nH]1] | 532.4 |

-continued
| ID | Structure | Observed [M + H]+ |
| --- | --- | --- |
| 170 | 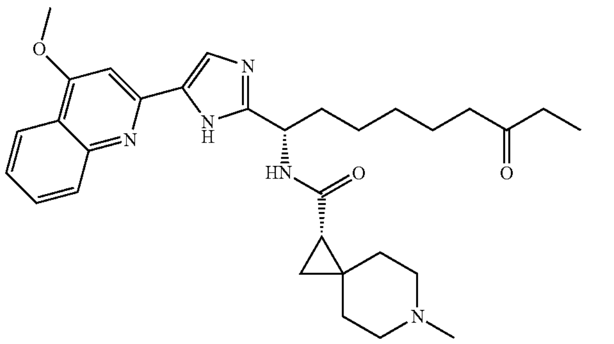 [SMILES: CCC(=O)CCCCC[C@H](NC(=O)[C@H]1CC12CCN(C)CC2)c1ncc(-c2cc(OC)c3ccccc3n2)[nH]1] | 532.1 |
| 172 | 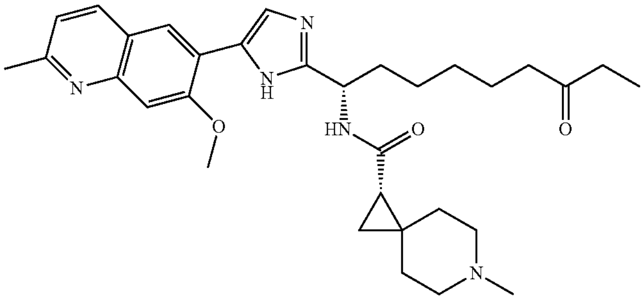 [SMILES: CCC(=O)CCCCC[C@H](NC(=O)[C@H]1CC12CCN(C)CC2)c1ncc(-c2cc3ccc(C)nc3cc2OC)[nH]1] | 546.2 |
| 174 | 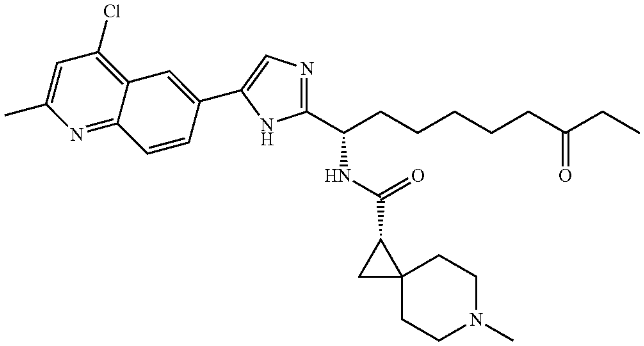 [SMILES: CCC(=O)CCCCC[C@H](NC(=O)[C@H]1CC12CCN(C)CC2)c1ncc(-c2ccc3nc(C)cc(Cl)c3c2)[nH]1] | 550.3 |
| 177 | 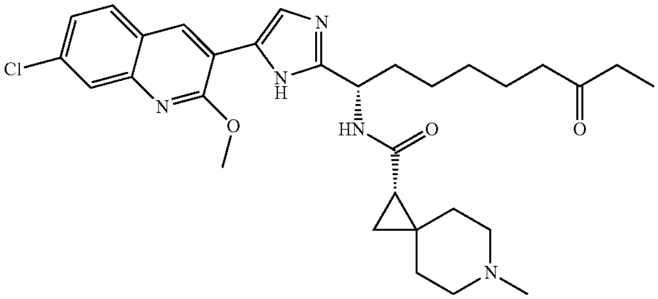 [SMILES: CCC(=O)CCCCC[C@H](NC(=O)[C@H]1CC12CCN(C)CC2)c1ncc(-c2cc3ccc(Cl)cc3nc2OC)[nH]1] | 566.1 |

-continued
| ID | Structure | Observed [M + H]+ |
|---|---|---|
| 181 | 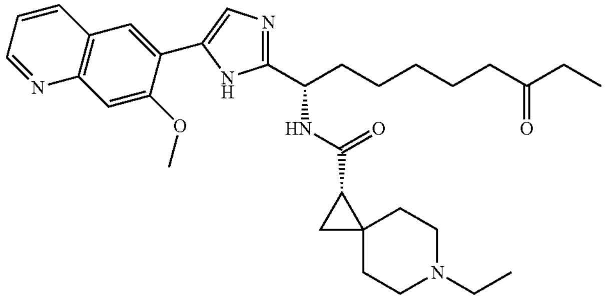 [SMILES: CCC(=O)CCCCC[C@H](NC(=O)[C@H]1CC12CCN(CC)CC2)c1ncc(-c2cc3cccnc3cc2OC)[nH]1] | 546.2 |
| 183 | 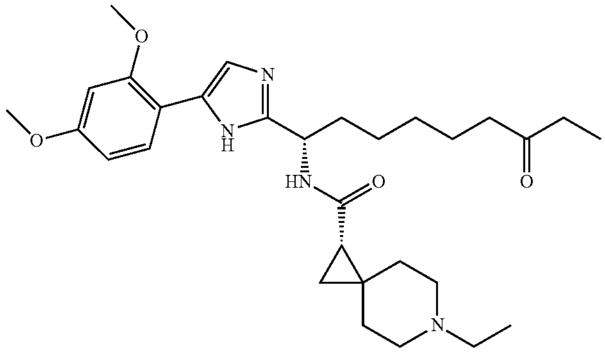 [SMILES: CCC(=O)CCCCC[C@H](NC(=O)[C@H]1CC12CCN(CC)CC2)c1ncc(-c2ccc(OC)cc2OC)[nH]1] | 525.2 |
| 190 | 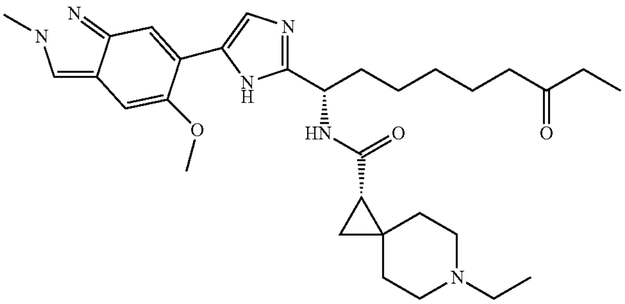 [SMILES: CCC(=O)CCCCC[C@H](NC(=O)[C@H]1CC12CCN(CC)CC2)c1ncc(C2=CC(=N)/C(=C\NC)C=C2OC)[nH]1] | 549.2 |
| 197 | 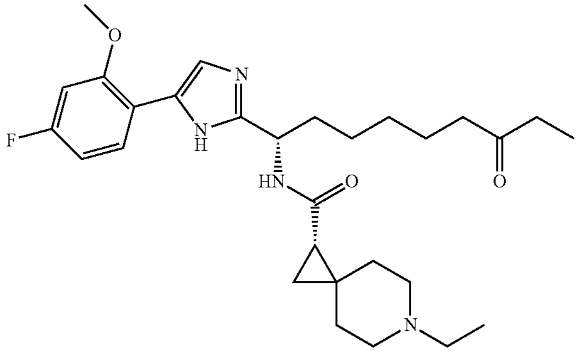 [SMILES: CCC(=O)CCCCC[C@H](NC(=O)[C@H]1CC12CCN(CC)CC2)c1ncc(-c2ccc(F)cc2OC)[nH]1] | 513.1 |

-continued
| ID | Structure | Observed [M + H]+ |
|---|---|---|
| 205 | 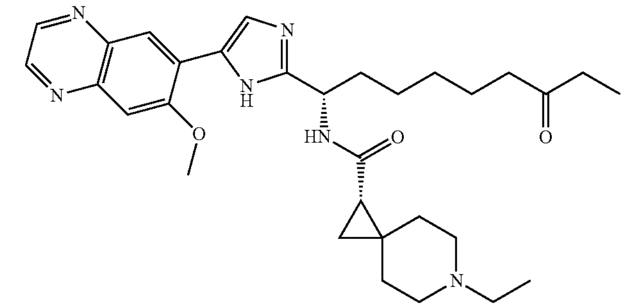 [SMILES: CCC(=O)CCCCC[C@H](NC(=O)[C@H]1CC12CCN(CC)CC2)c1ncc(-c2cc3nccnc3cc2OC)[nH]1] | 547.1 |
| 206 | 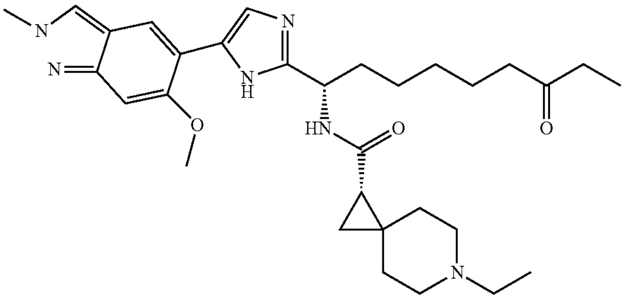 [SMILES: CCC(=O)CCCCC[C@H](NC(=O)[C@H]1CC12CCN(CC)CC2)c1ncc(C2=C/C(=C/NC)C(=N)C=C2OC)[nH]1] | 549.2 |
| 208 | 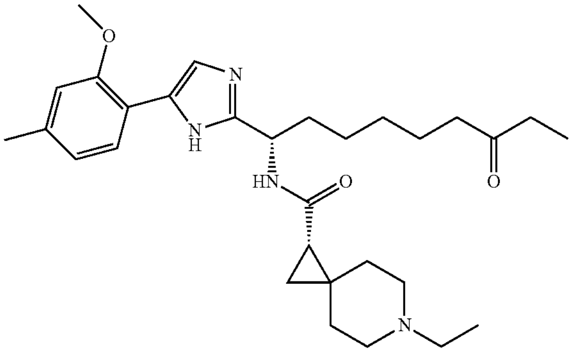 [SMILES: CCC(=O)CCCCC[C@H](NC(=O)[C@H]1CC12CCN(CC)CC2)c1ncc(-c2ccc(C)cc2OC)[nH]1] | 509.2 |
| 211 | 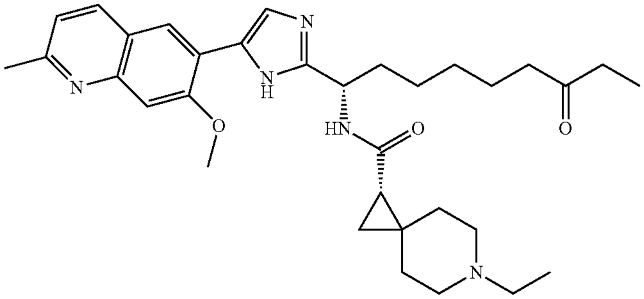 [SMILES: CCC(=O)CCCCC[C@H](NC(=O)[C@H]1CC12CCN(CC)CC2)c1ncc(-c2cc3ccc(C)nc3cc2OC)[nH]1] | 560.3 |

-continued
| ID | Structure | Observed [M + H]+ |
|---|---|---|
| 238 | 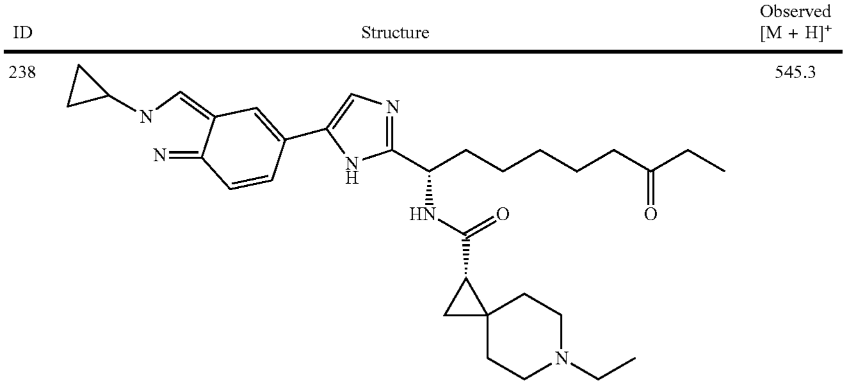 | 545.3 |
| 241 | 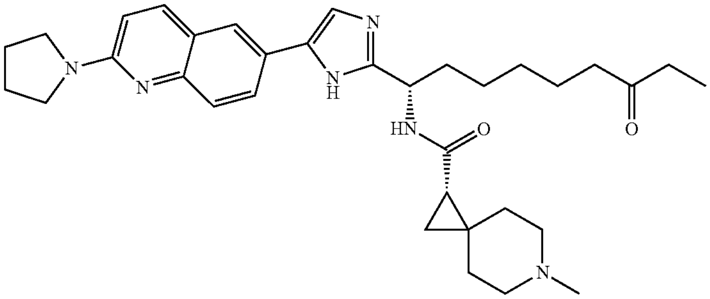 [SMILES: CCC(=O)CCCCC[C@H](NC(=O)[C@H]1CC12CCN(C)CC2)c1ncc(-c2ccc3nc(N4CCCC4)ccc3c2)[nH]1] | 571.4 |
| 244 | 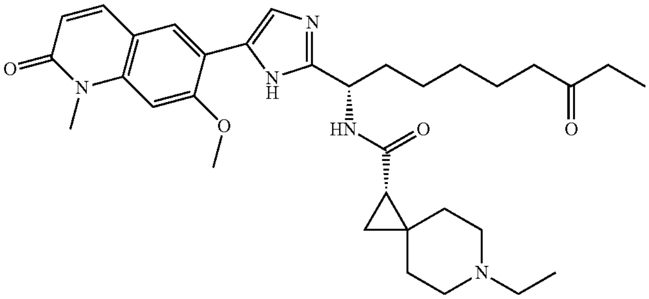 | 576.2 |
| 245 | 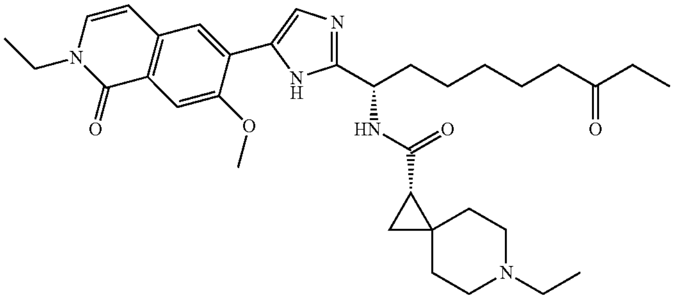 [SMILES: CCC(=O)CCCCC[C@H](NC(=O)[C@H]1CC12CCN(CC)CC2)c1ncc(-c2cc3ccn(CC)c(=O)c3cc2OC)[nH]1] | 590.2 |
| 280 | 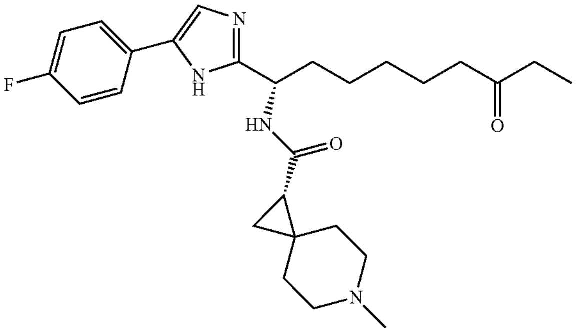 [SMILES: CCC(=O)CCCCC[C@H](NC(=O)[C@H]1CC12CCN(C)CC2)c1ncc(-c2ccc(F)cc2)[nH]1] | 469.4 |

-continued
| ID | Structure | Observed [M + H]+ |
|---|---|---|
| 281 | 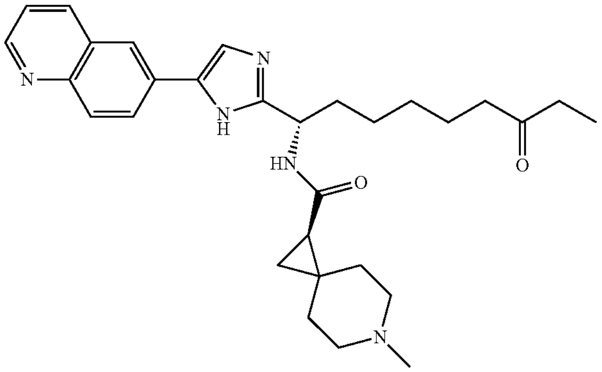 [SMILES: CCC(=O)CCCCC[C@H](NC(=O)[C@@H]1CC12CCN(C)CC2)c1ncc(-c2ccc3ncccc3c2)[nH]1] | 502.3 |
| 282 | 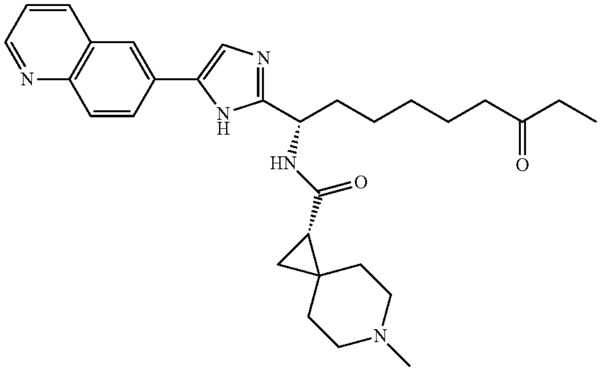 [SMILES: CCC(=O)CCCCC[C@H](NC(=O)[C@H]1CC12CCN(C)CC2)c1ncc(-c2ccc3ncccc3c2)[nH]1] | 502.4 |
| 283 | 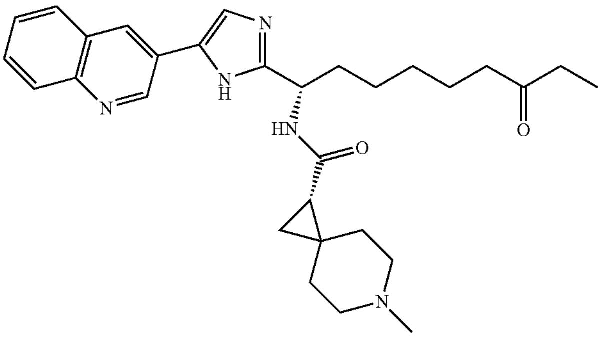 [SMILES: CCC(=O)CCCCC[C@H](NC(=O)[C@H]1CC12CCN(C)CC2)c1ncc(-c2cnc3ccccc3c2)[nH]1] | 502.4 |
| 284 | 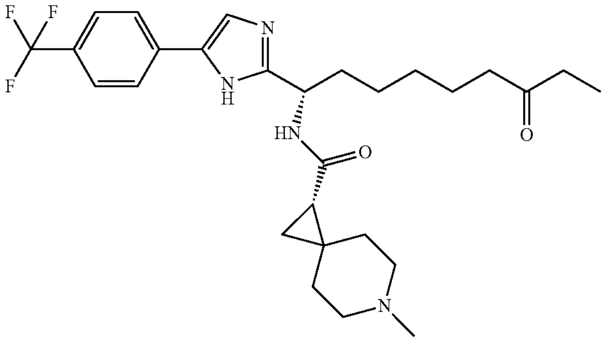 [SMILES: CCC(=O)CCCCC[C@H](NC(=O)[C@H]1CC12CCN(C)CC2)c1ncc(-c2ccc(C(F)(F)F)cc2)[nH]1] | 519.4 |

-continued
| ID | Structure | Observed [M + H]+ |
|---|---|---|
| 289 | 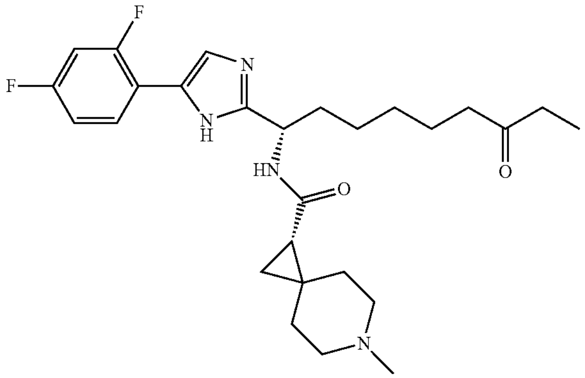 [SMILES: CCC(=O)CCCCC[C@H](NC(=O)[C@H]1CC12CCN(C)CC2)c1ncc(-c2ccc(F)cc2F)[nH]1] | 487.3 |
| 290 | 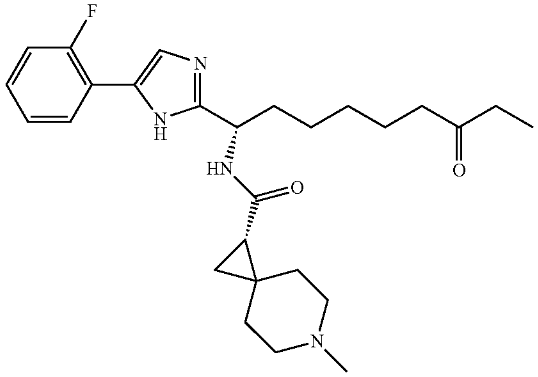 [SMILES: CCC(=O)CCCCC[C@H](NC(=O)[C@H]1CC12CCN(C)CC2)c1ncc(-c2ccccc2F)[nH]1] | 469.4 |
| 307 | 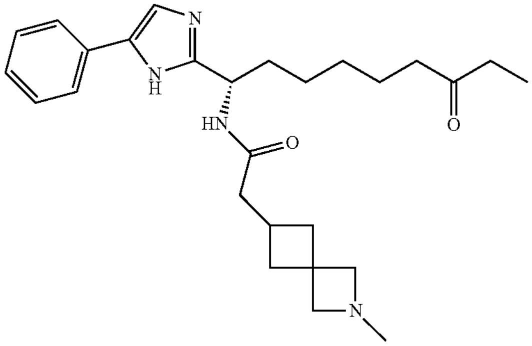 [SMILES: CCC(=O)CCCCC[C@H](NC(=O)CC1CC2(C1)CN(C)C2)c1ncc(-c2ccccc2)[nH]1] | 451.4 |
| 310 | 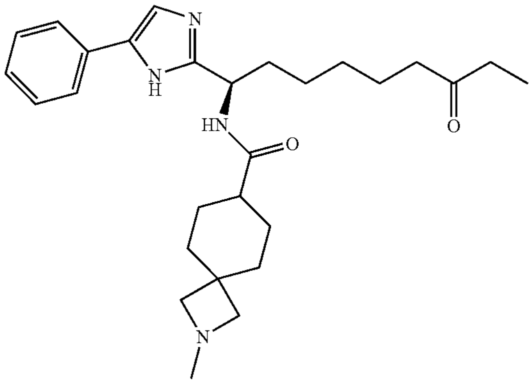 [SMILES: CCC(=O)CCCCC[C@@H](NC(=O)C1CCC2(CC1)CN(C)C2)c1ncc(-c2ccccc2)[nH]1] | 465.4 |

Example 60

(1S)—N-{(1S)-1-[5-(4-chlorophenyl)-1,3-oxazol-2-yl]-7-oxononyl}-6-ethyl-6-azaspiro[2.5]octane-1-carboxamide (110)

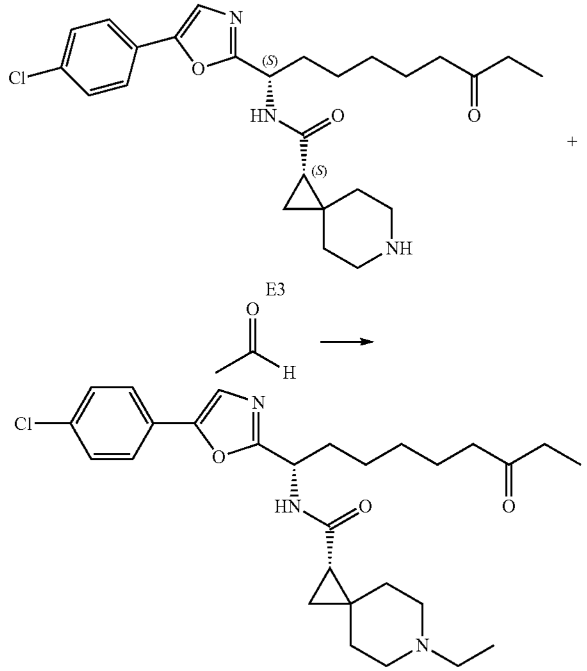

E3

110

Acetaldehyde (5 mL, 5.24 mmol) was added to a stirred mixture of (S)—N—((S)-1-(5-(4-chlorophenyl)oxazol-2-yl)-7-oxononyl)-6-azaspiro[2.5]octane-1-carboxamide (E3, 2.475 g, 5.24 mmol) in MeOH (5 mL) at room temperature and the mixture was stirred at room temperature for 4 h. Then, $NaBH(OAc)_3$ (11.11 g, 52.4 mmol) was added. The mixture was stirred at rt for 1 h. Most of the MeOH was removed, water (15 mL) was added and the mixture was extracted with DCM (3×15 mL). The combined organic fractions were washed with brine (saturated, 2×20 mL), dried ($Na_2SO_4$), filtered and the solvent was evaporated under reduced pressure. The residue was purified by silica gel column flash chromatography, eluting with DCM/MeOH=0-15% and then purified by preparative HPLC, eluting with acetonitrile/water+0.1% TFA, to give (S)—N—((S)-1-(5-(4-chlorophenyl)oxazol-2-yl)-7-oxononyl)-6-ethyl-6-azaspiro[2.5]octane-1-carboxamide (110). LCMS (ESI) calc'd for $C_{28}H_{38}ClN_3O_3$ $[M+H]^+$: 500.3, found: 500.2. $^1H$ NMR (400 MHz, MeOD) δ 7.64-7.74 (m, 2H), 7.43-7.51 (m, 3H), 5.07-5.16 (m, 1H), 3.48-3.64 (m, 2H), 2.98-3.24 (m, 4H), 2.83 (dd, J=9.0, 19.63 Hz, 1H), 2.46 (q, J=7.3 Hz, 3H), 2.23 (d, J=13.0 Hz, 1H), 1.73-2.09 (m, 6H), 1.54-1.62 (m, 2H), 1.18-1.41 (m, 8H), 0.97-1.10 (m, 3H), 0.80 (t, J=7.5 Hz, 1H).

The following compounds were prepared using similar procedures as described for compound 110.

| ID | Structure | Observed $[M + H]^+$ |
|---|---|---|
| 97 | 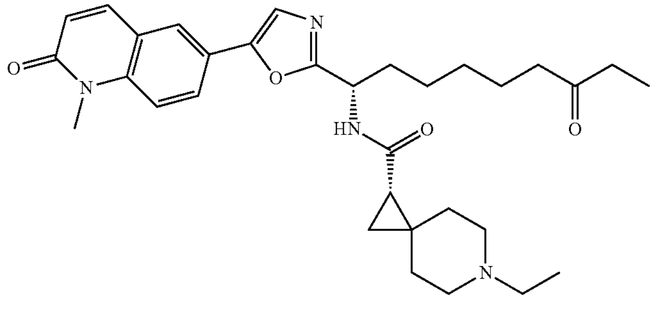 [SMILES: CCC(=O)CCCCC[C@H](NC(=O)[C@H]1CC12CCN(CC)CC2)c1ncc(-c2ccc3c(ccc(=O)n3C)c2)o1] | 547.4 |
| 101 | 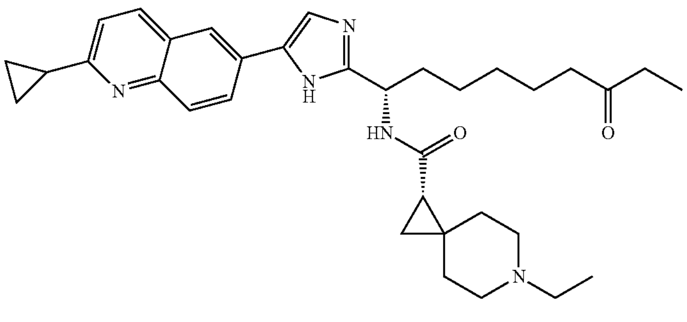 [SMILES: CCC(=O)CCCCC[C@H](NC(=O)[C@H]1CC12CCN(CC)CC2)c1ncc(-c2ccc3nc(C4CC4)ccc3c2)[nH]1] | 556.3 |

-continued
| ID | Structure | Observed [M + H]+ |
|---|---|---|
| 114 | 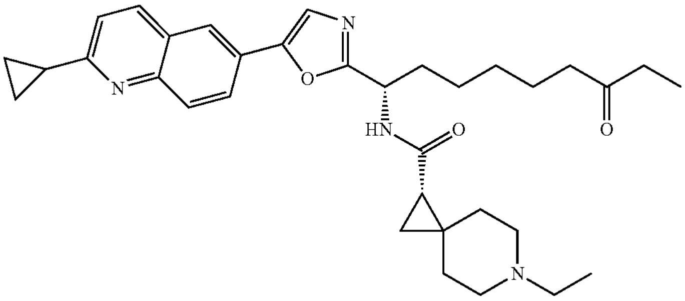 [SMILES: CCC(=O)CCCCC[C@H](NC(=O)[C@H]1CC12CCN(CC)CC2)c1ncc(-c2ccc3nc(C4CC4)ccc3c2)o1] | 557.3 |
| 204 | 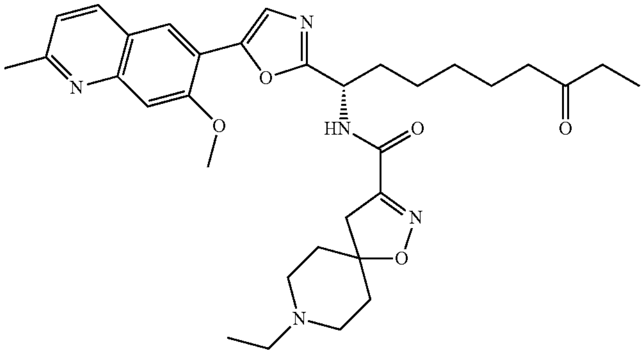 [SMILES: CCC(=O)CCCCC[C@H](NC(=O)C1=NOC2(CCN(CC)CC2)C1)c1ncc(-c2cc3ccc(C)nc3cc2OC)o1] | 590.1 |
| 207 | 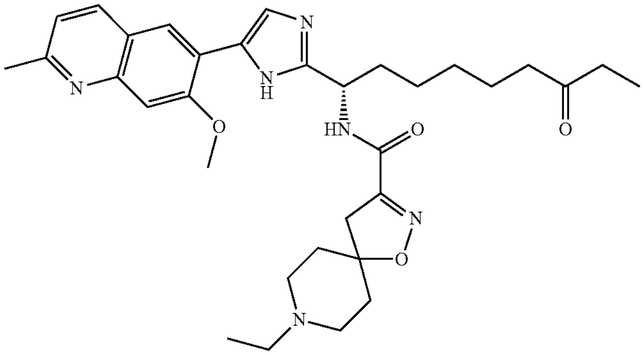 [SMILES: CCC(=O)CCCCC[C@H](NC(=O)C1=NOC2(CCN(CC)CC2)C1)c1ncc(-c2cc3ccc(C)nc3cc2OC)[nH]1] | 589.4 |
| 233 | 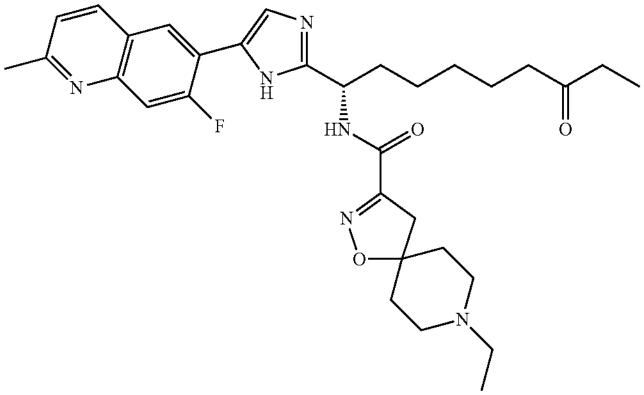 [SMILES: CCC(=O)CCCCC[C@H](NC(=O)C1=NOC2(CCN(CC)CC2)C1)c1ncc(-c2cc3ccc(C)nc3cc2F)[nH]1] | 577.1 |

-continued

| ID | Structure | Observed [M + H]+ |
|---|---|---|
| 235 | 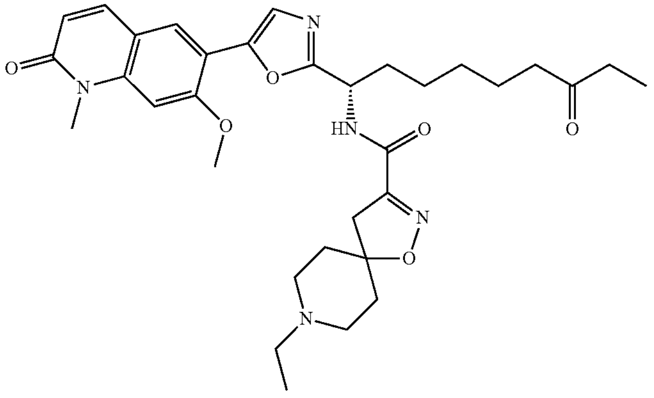 [SMILES: CCC(=O)CCCCC[C@H](NC(=O)C1=NOC2(CCN(CC)CC2)C1)c1ncc(-c2cc3ccc(=O)n(C)c3cc2OC)o1] | 606.1 |
| 243 | 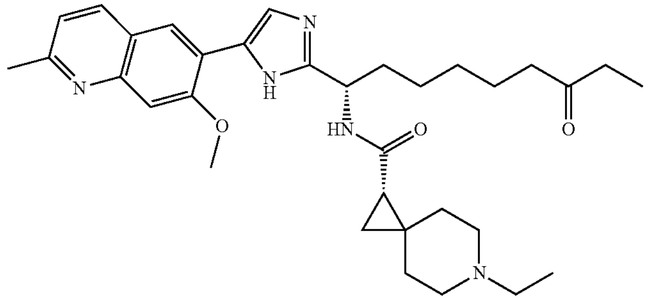 | 560.3 |

Example 61

(1S)—N-[(1S)-1-{5-[4-(2-azetidin-1-ylpyrimidin-5-yl)phenyl]-1,3-oxazol-2-yl}-7-oxononyl]-6-ethyl-6-azaspiro[2.5]octane-1-carboxamide (120)

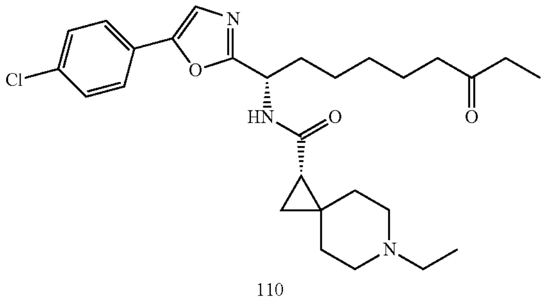

110

+

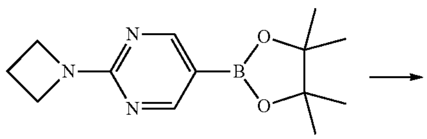

-continued

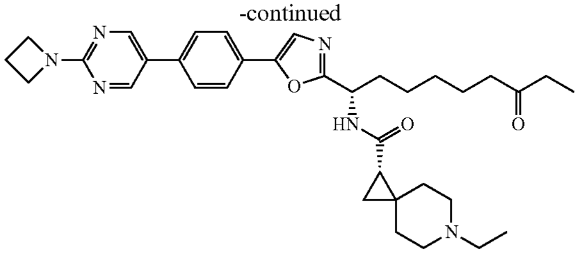

120

$Pd_2(dba)_3$ (9 mg, 9.83 μmol) was added to a stirred mixture of $K_2CO_3$ (83 mg, 0.600 mmol), TCP (7 mg, 0.025 mmol), 2-(azetidin-1-yl)-5-(4,4,5,5-tetramethyl-1,3,2-dioxaborolan-2-yl)pyrimidine (63 mg, 0.241 mmol) and (S)—N—((S)-1-(5-(4-chlorophenyl)oxazol-2-yl)-7-oxononyl)-6-ethyl-6-azaspiro[2.5]octane-1-carboxamide (110, 100 mg, 0.200 mmol) in dioxane (4.0 mL) and water (0.4 mL) at room temperature and the mixture was stirred at 100° C. for 12 h under $N_2$. The residue was purified by preparative HPLC (reverse phase C-18 column), eluting with acetonitrile/water+0.1% TFA, to give (S)—N—((S)-1-(5-(4-(2-(azetidin-1-yl) pyrimidin-5-yl)phenyl)oxazol-2-yl)-7-oxononyl)-6-ethyl-6-azaspiro[2.5]octane-1-carboxamide (120). Hydrogen chloride (0.1 M, 1.4 mL, 0.140 mmol) was added to a stirred mixture of (S)—N—((S)-1-(5-(4-(2-(azetidin-1-yl)pyrimidin-5-yl)phenyl)oxazol-2-yl)-7-oxononyl)-6-ethyl-6-azaspiro[2.5]octane-1-carboxamide (120, 40 mg, 0.067 mmol) in acetonitrile (4 mL) and water (4 mL) at room temperature. The mixture was freeze-dried to give (S)—N—((S)-1-(5-(4-(2-(azetidin-1-yl)pyrimidin-5-yl)phenyl)oxazol-2-yl)-7-oxononyl)-6-ethyl-6-azaspiro[2.5]octane-1-carboxamide hydrochloride. LCMS (ESI) calc'd for $C_{35}H_{46}N_6O_3$ $[M+H]^+$: 599.4, found: 599.4. $^1H$ NMR (400 MHz, MeOD) δ 8.93 (brs, 2H), 7.69-7.93 (m, 4H), 7.56 (brs, 1H), 5.07-5.17 (m, 1H), 4.46 (t, J=7.61 Hz, 3H), 3.52-3.77 (m, 2H), 3.37 (m, 1H), 3.15-3.24 (m, 2H), 2.97-3.09 (m, 1H), 2.88 (d, J=10.58 Hz, 1H), 2.61 (m, 2H), 2.46 (q, J=7.57 Hz, 3H), 2.16-2.37 (m, 2H), 1.79-2.10 (m, 5H), 1.19-1.66 (m, 11H), 0.96-1.09 (m, 3H), 0.81 (t, J=7.50 Hz, 1H).

The following compound was prepared using a similar procedures as described for compound 120.

| ID | Structure | Observed $[M + H]^+$ |
|---|---|---|
| 161 | 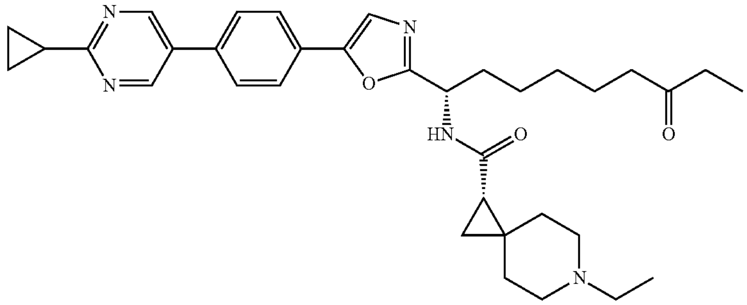 [SMILES: CCC(=O)CCCCC[C@H](NC(=O)[C@H]1CC12CCN(CC)CC2)c1ncc(-c2ccc(-c3cnc(C4CC4)nc3)cc2)o1] | 584.3 |

Example 62

N—((S)-1-(5-(2-methoxyquinolin-3-yl)-1H-imidazol-2-yl)-7-oxononyl)-6-methyl-6-azaspiro[2.5]octane-1-carboxamide (313), (R)—N—((S)-1-(5-(2-methoxyquinolin-3-yl)-1H-imidazol-2-yl)-7-oxononyl)-6-methyl-6-azaspiro[2.5]octane-1-carboxamide (320), and (S)—N—((S)-1-(5-(2-methoxyquinolin-3-yl)-1H-imidazol-2-yl)-7-oxononyl)-6-methyl-6-azaspiro[2.5]octane-1-carboxamide (321)

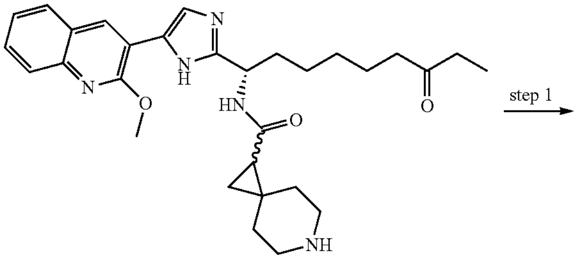

E1b

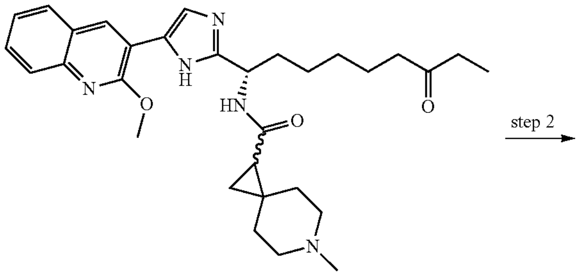

313

-continued

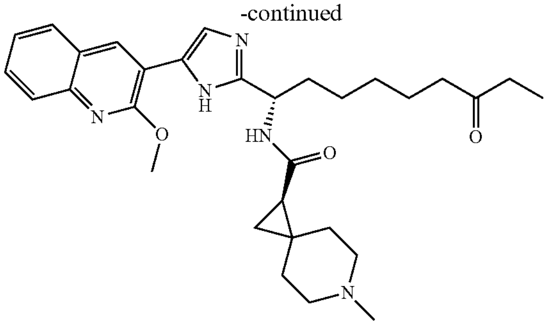

320

+

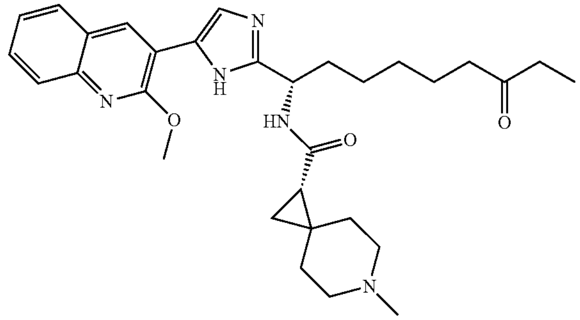

321

Step 1: E1b (150 mg, 0.29 mmol), formaldehyde (141 μl, 1.739 mmol), MeOH (1449 μl), and THF (1449 μl) was added to a 4 mL pressure vial with a pressure release cap. The reaction was stirred at 25° C. for 10 minutes, then sodium triacetoxyborohydride (184 mg, 0.869 mmol) was added. The reaction was stirred 25° C. at 2 hours. The product was purified by $C_{18}$ chromatography (30 g, $CH_3CN$ in water with 0.1% TFA: 0% to 90%) to give 313 (TFA salt). LCMS (ESI) calc'd for $C_{31}H_{42}N_5O_3$ $[M+H]^+$: 532.3, found: 532.4.

Step 2: 313 (TFA salt, 175 mg, 0.27 mmol) was separated by chiral SFC to 320 ($1^{st}$ peak), LCMS (ESI) calc'd for $C_{31}H_{42}N_5O_3$ $[M+H]^+$: 532.3, found: 532.5, and 321 ($2^{nd}$ peak), LCMS (ESI) calc'd for $C_{31}H_{42}N_5O_3$ $[M+H]^+$: 532.3, found: 532.4. SFC conditions: Column: 2.1×25.0 cm Chiralpak AD-H; $CO_2$ co-solvent: isopropanol with 0.25% isopropylamine; Mobile phase:40% co-solvent; flow rate: 80 mL/min, temperature: 25° C.
The following compounds were prepared using similar procedures as described for compound 321.
| ID | Structure | Observed [M + H]+ |
|---|---|---|
| 63 | 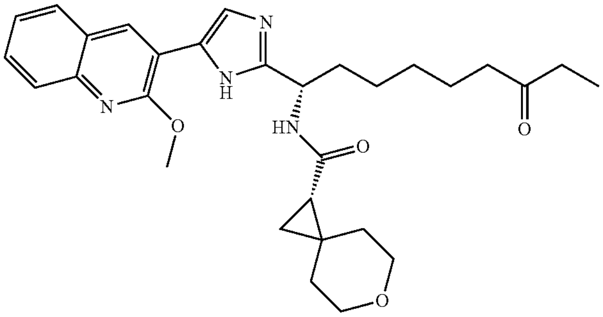 [SMILES: CCC(=O)CCCCC[C@H](NC(=O)[C@H]1CC12CCOCC2)c1ncc(-c2cc3ccccc3nc2OC)[nH]1] | 519.3 |
| 64 | 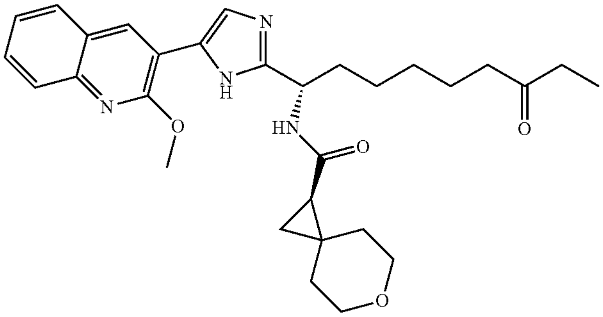 [SMILES: CCC(=O)CCCCC[C@H](NC(=O)[C@@H]1CC12CCOCC2)c1ncc(-c2cc3ccccc3nc2OC)[nH]1] | 519.3 |
| 271 | 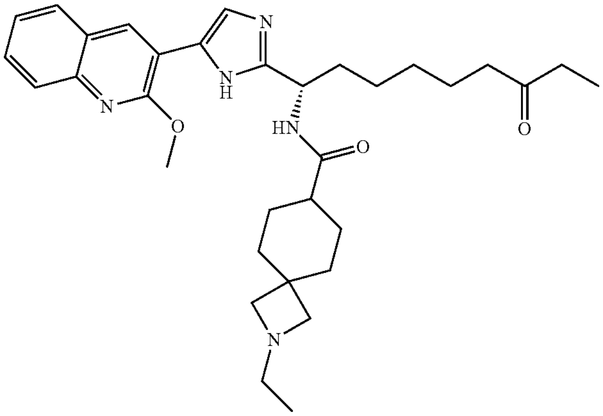 [SMILES: CCC(=O)CCCCC[C@H](NC(=O)C1CCC2(CC1)CN(CC)C2)c1ncc(-c2cc3ccccc3nc2OC)[nH]1] | 560.4 |
| 274 | 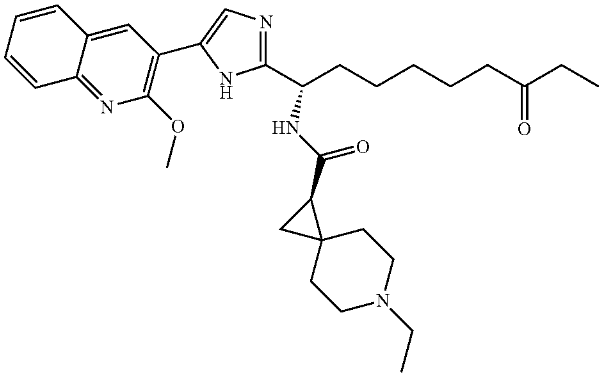 [SMILES: CCC(=O)CCCCC[C@H](NC(=O)[C@@H]1CC12CCN(CC)CC2)c1ncc(-c2cc3ccccc3nc2OC)[nH]1] | 546.5 |

-continued
| ID | Structure | Observed [M + H]+ |
|---|---|---|
| 275 | 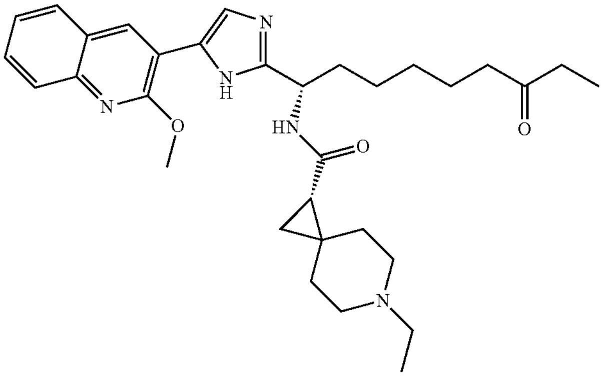 [SMILES: CCC(=O)CCCCC[C@H](NC(=O)[C@H]1CC12CCN(CC)CC2)c1ncc(-c2cc3ccccc3nc2OC)[nH]1] | 546.4 |
| 276 | 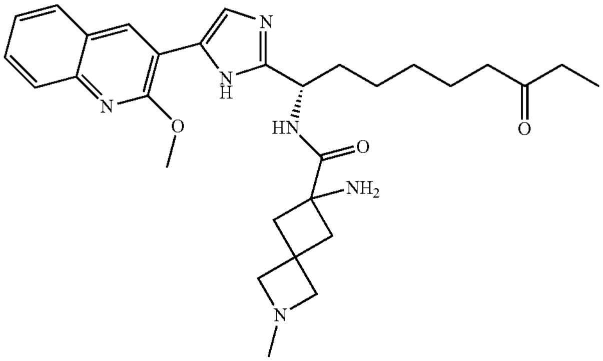 [SMILES: CCC(=O)CCCCC[C@H](NC(=O)C1(N)CC2(CN(C)C2)C1)c1ncc(-c2cc3ccccc3nc2OC)[nH]1] | 533.4 |
| 277 | 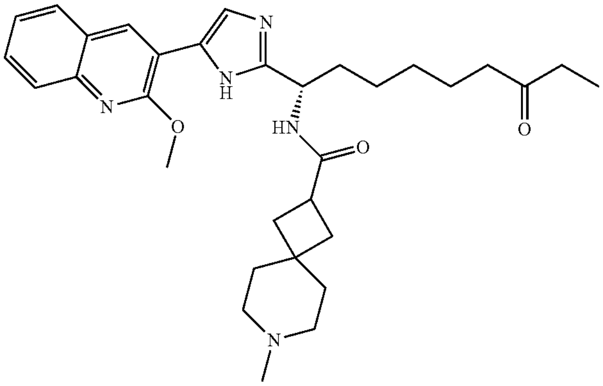 [SMILES: CCC(=O)CCCCC[C@H](NC(=O)C1CC2(CCN(C)CC2)C1)c1ncc(-c2cc3ccccc3nc2OC)[nH]1] | 546.5 |
| 278 | 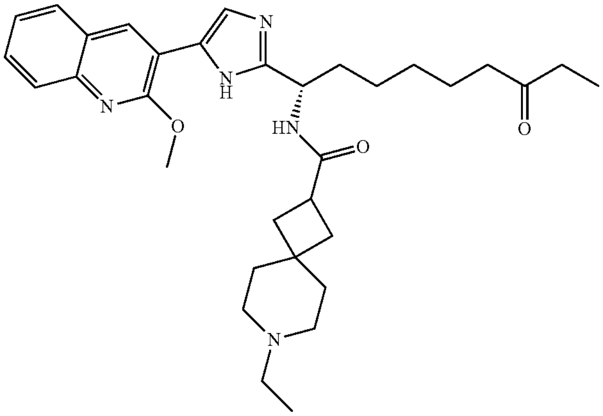 [SMILES: CCC(=O)CCCCC[C@H](NC(=O)C1CC2(CCN(CC)CC2)C1)c1ncc(-c2cc3ccccc3nc2OC)[nH]1] | 560.5 |

-continued
| ID | Structure | Observed [M + H]$^+$ |
|---|---|---|
| 279 | 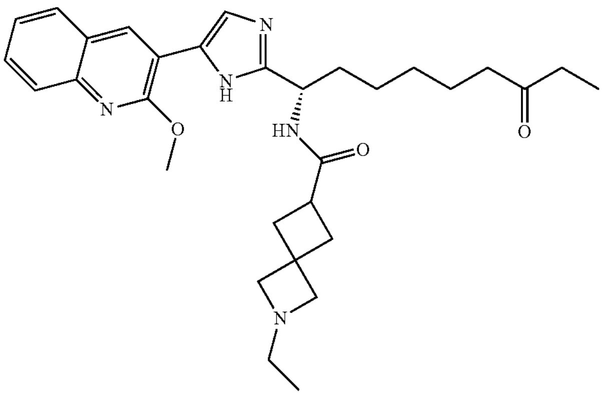 [SMILES: CCC(=O)CCCCC[C@H](NC(=O)C1CC2(C1)CN(CC)C2)c1ncc(-c2cc3ccccc3nc2OC)[nH]1] | 532.5 |
| 285 | 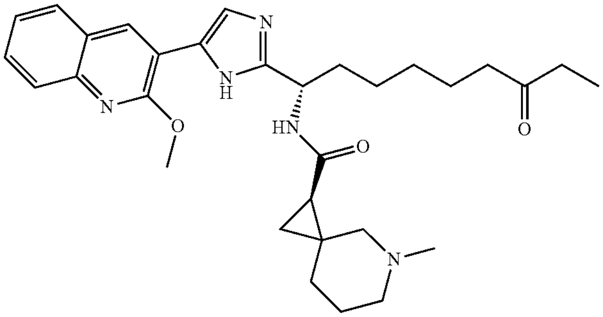 [SMILES: CCC(=O)CCCCC[C@H](NC(=O)[C@@H]1CC12CCCN(C)C2)c1ncc(-c2cc3ccccc3nc2OC)[nH]1] | 532.4 |
| 286 | 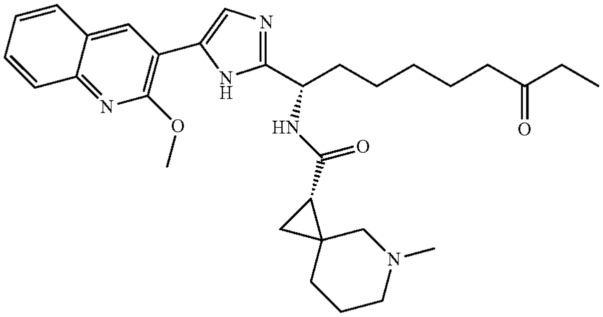 [SMILES: CCC(=O)CCCCC[C@H](NC(=O)[C@H]1CC12CCCN(C)C2)c1ncc(-c2cc3ccccc3nc2OC)[nH]1] | 532.4 |
| 287 | 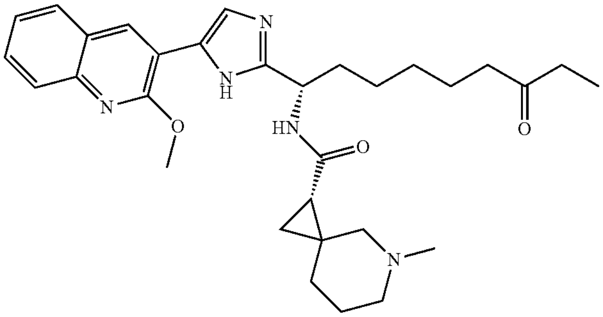 [SMILES: CCC(=O)CCCCC[C@H](NC(=O)[C@H]1CC12CCCN(C)C2)c1ncc(-c2cc3ccccc3nc2OC)[nH]1] | 532.4 |

-continued
| ID | Structure | Observed [M + H]+ |
|---|---|---|
| 288 | 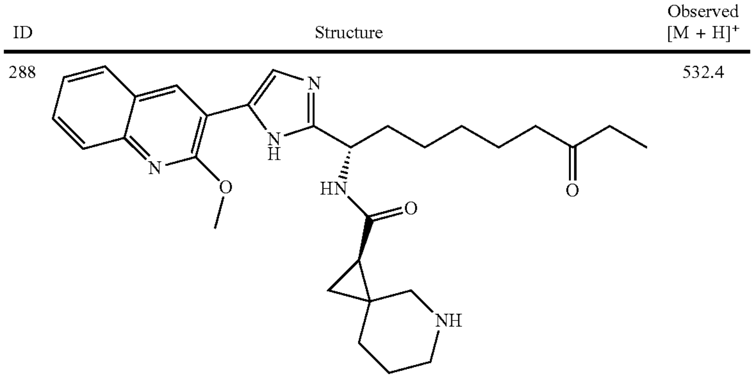 | 532.4 |
| 302 | 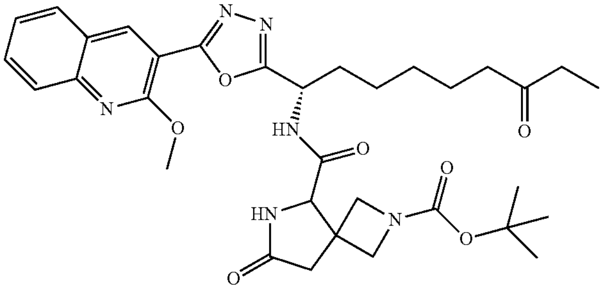 [SMILES: CCC(=O)CCCCC[C@H](NC(=O)C1NC(=O)CC12CN(C(=O)OC(C)(C)C)C2)c1nnc(-c2cc3ccccc3nc2OC)o1] | 635.5 |
| 303 | 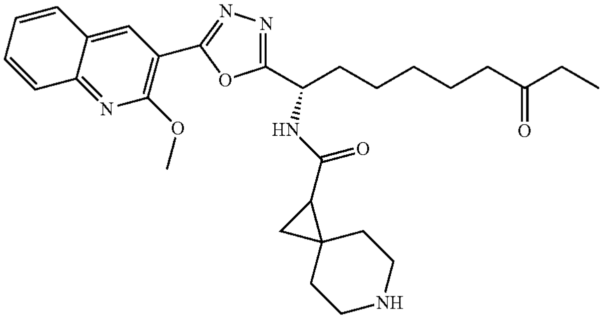 [SMILES: CCC(=O)CCCCC[C@H](NC(=O)C1CC12CCNCC2)c1nnc(-c2cc3ccccc3nc2OC)o1] | 520.4 |
| 304 | 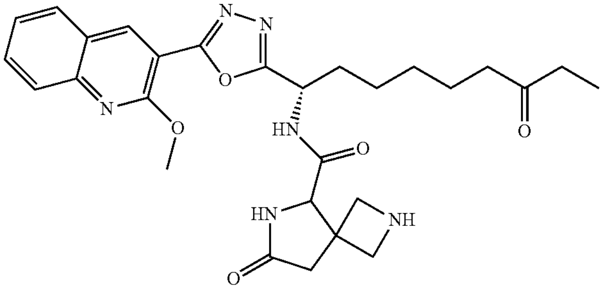 [SMILES: CCC(=O)CCCCC[C@H](NC(=O)C1NC(=O)CC12CNC2)c1nnc(-c2cc3ccccc3nc2OC)o1] | 535.4 |
| 305 | 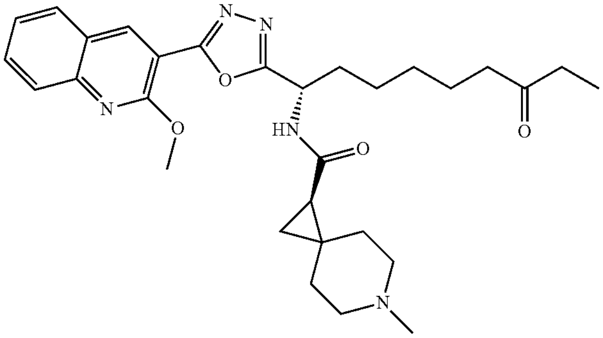 [SMILES: CCC(=O)CCCCC[C@H](NC(=O)[C@@H]1CC12CCN(C)CC2)c1nnc(-c2cc3ccccc3nc2OC)o1] | 534.4 |

-continued
| ID | Structure | Observed [M + H]+ |
| --- | --- | --- |
| 306 | 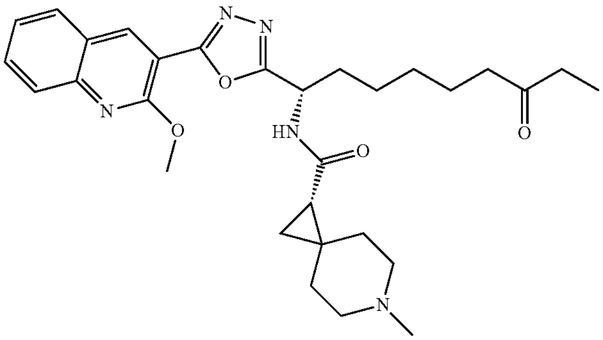 [SMILES: CCC(=O)CCCCC[C@H](NC(=O)[C@H]1CC12CCN(C)CC2)c1nnc(-c2cc3ccccc3nc2OC)o1] | 534.4 |
| 308 | 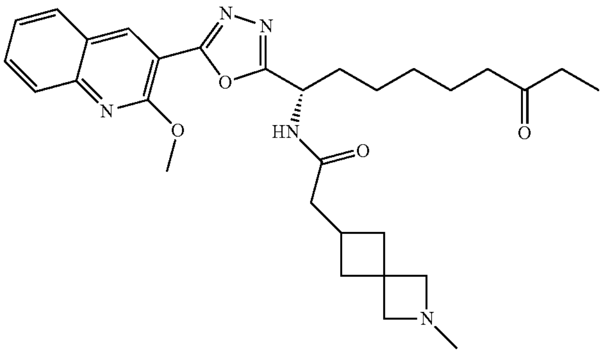 [SMILES: CCC(=O)CCCCC[C@H](NC(=O)CC1CC2(C1)CN(C)C2)c1nnc(-c2cc3ccccc3nc2OC)o1] | 534.4 |
| 309 | 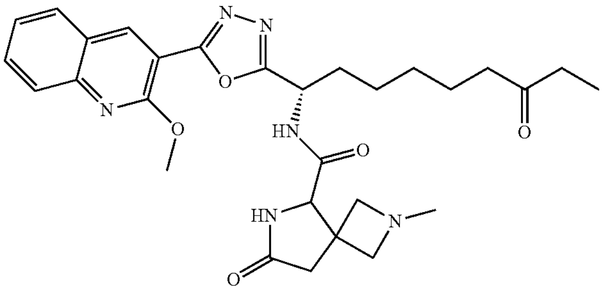 [SMILES: CCC(=O)CCCCC[C@H](NC(=O)C1NC(=O)CC12CN(C)C2)c1nnc(-c2cc3ccccc3nc2OC)o1] | 549.3 |
| 311 | 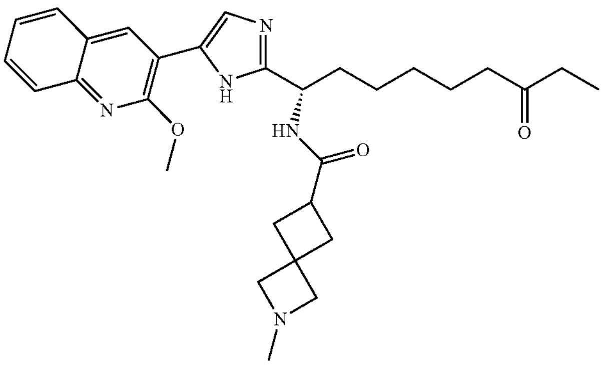 [SMILES: CCC(=O)CCCCC[C@H](NC(=O)C1CC2(C1)CN(C)C2)c1ncc(-c2cc3ccccc3nc2OC)[nH]1] | 518.4 |

-continued
| ID | Structure | Observed [M + H]+ |
|---|---|---|
| 312 | 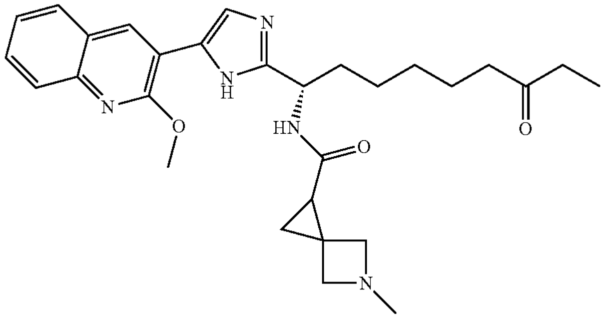 [SMILES: CCC(=O)CCCCC[C@H](NC(=O)C1CC12CN(C)C2)c1ncc(-c2cc3ccccc3nc2OC)[nH]1] | 504.4 |
| 313 | 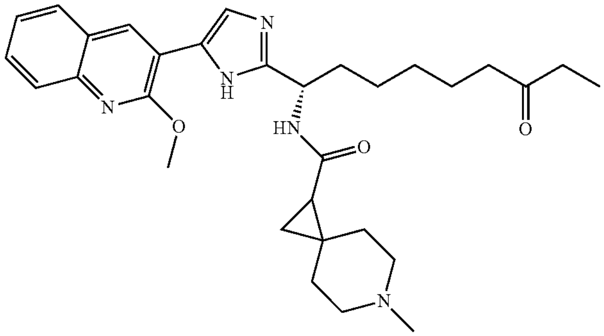 [SMILES: CCC(=O)CCCCC[C@H](NC(=O)C1CC12CCN(C)CC2)c1ncc(-c2cc3ccccc3nc2OC)[nH]1] | 532.4 |
| 314 | 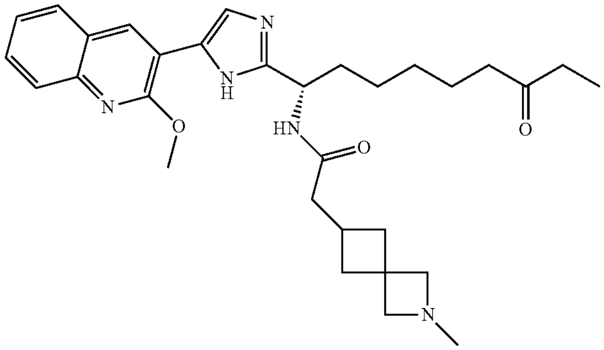 [SMILES: CCC(=O)CCCCC[C@H](NC(=O)CC1CC2(C1)CN(C)C2)c1ncc(-c2cc3ccccc3nc2OC)[nH]1] | 532.1 |
| 315 | 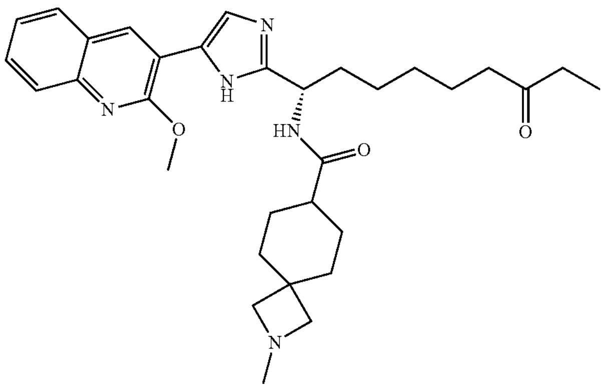 [SMILES: CCC(=O)CCCCC[C@H](NC(=O)C1CCC2(CC1)CN(C)C2)c1ncc(-c2cc3ccccc3nc2OC)[nH]1] | 546.4 |

-continued
| ID | Structure | Observed [M + H]+ |
|---|---|---|
| 316 | 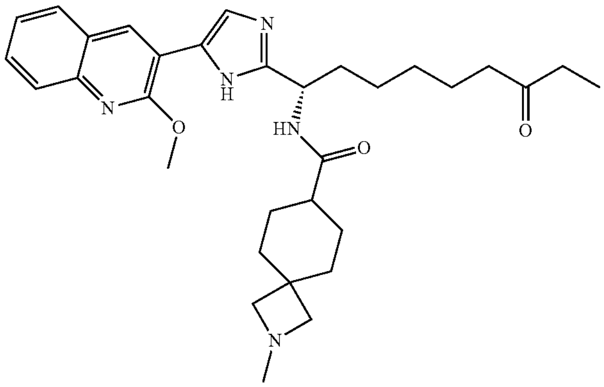 [SMILES: CCC(=O)CCCCC[C@H](NC(=O)C1CCC2(CC1)CN(C)C2)c1ncc(-c2cc3ccccc3nc2OC)[nH]1] | |
| 317 | 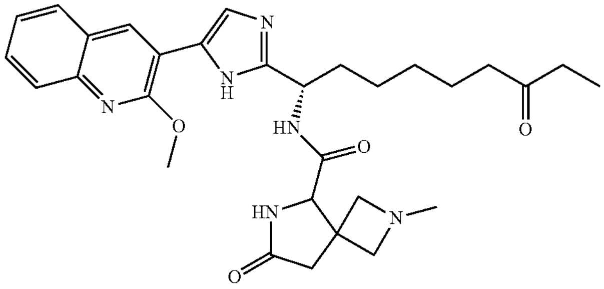 [SMILES: CCC(=O)CCCCC[C@H](NC(=O)C1NC(=O)CC12CN(C)C2)c1ncc(-c2cc3ccccc3nc2OC)[nH]1] | 547.2 |
| 322 | 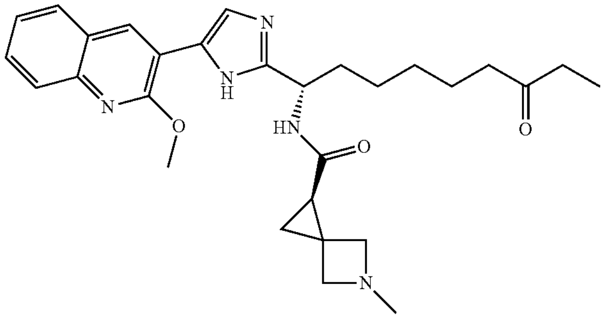 [SMILES: CCC(=O)CCCCC[C@H](NC(=O)[C@@H]1CC12CN(C)C2)c1ncc(-c2cc3ccccc3nc2OC)[nH]1] | 504.3 |
| 323 | 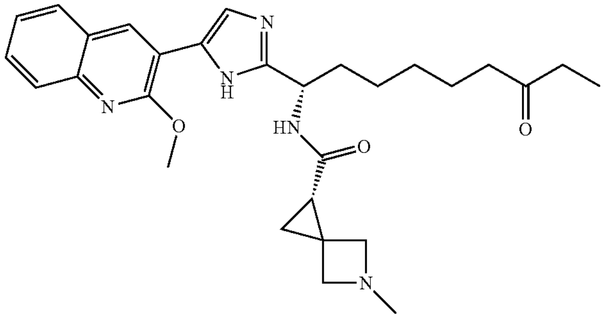 [SMILES: CCC(=O)CCCCC[C@H](NC(=O)[C@H]1CC12CN(C)C2)c1ncc(-c2cc3ccccc3nc2OC)[nH]1] | 504.3 |

-continued
| ID | Structure | Observed [M + H]+ |
|---|---|---|
| 327 | 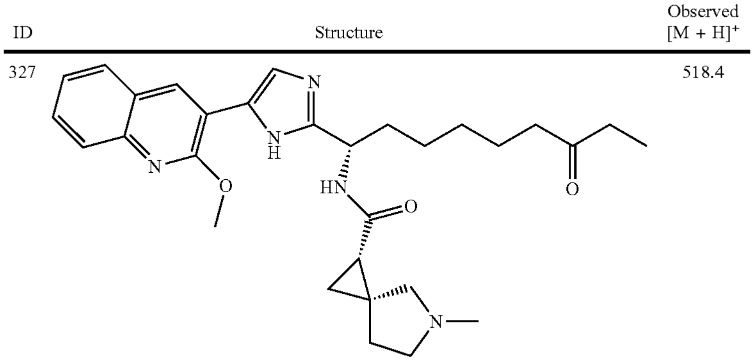 | 518.4 |
| 328 | 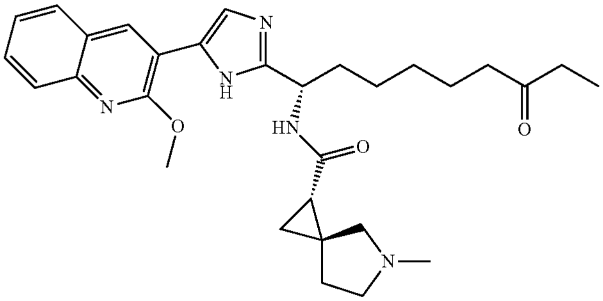 [SMILES: CCC(=O)CCCCC[C@H](NC(=O)[C@H]1C[C@@]12CCN(C)C2)c1ncc(-c2cc3ccccc3nc2OC)[nH]1] | 518.3 |
| 329 | 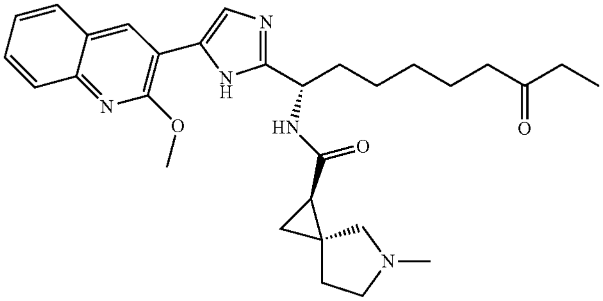 [SMILES: CCC(=O)CCCCC[C@H](NC(=O)[C@@H]1C[C@]12CCN(C)C2)c1ncc(-c2cc3ccccc3nc2OC)[nH]1] | 518.4 |
| 330 | 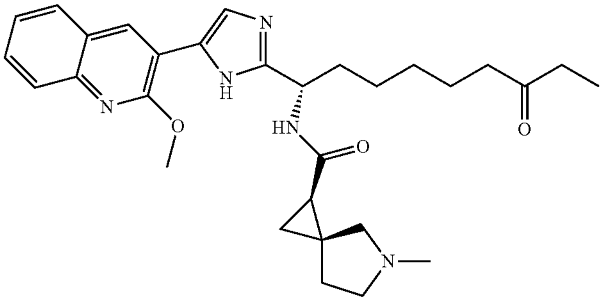 [SMILES: CCC(=O)CCCCC[C@H](NC(=O)[C@@H]1C[C@@]12CCN(C)C2)c1ncc(-c2cc3ccccc3nc2OC)[nH]1] | 518.4 |
| 338 | 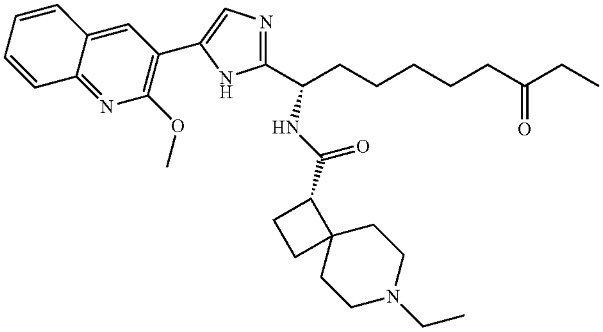 [SMILES: CCC(=O)CCCCC[C@H](NC(=O)[C@H]1CCC12CCN(CC)CC2)c1ncc(-c2cc3ccccc3nc2OC)[nH]1] | 560.2 |

Example 63

6-(dimethylamino)-N-{(1S)-1-[5-(2-methoxyquinolin-3-yl)-1H-imidazol-2-yl]-7-oxononyl}spiro[2.5]octane-1-carboxamide (127&128)

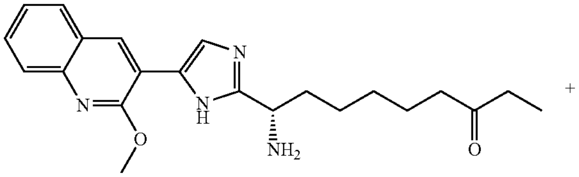

A9

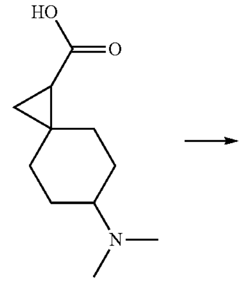

B6

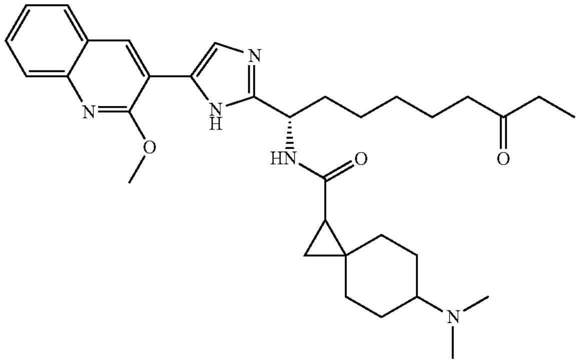

127&128

Step 5: Preparation of 6-(dimethylamino)-N—((S)-1-(5-(2-methoxycuinolin-3-yl)-1H-imidazol-2-yl)-7-oxononyl)spiro[2.5]octane-1-carboxamide (127 & 128): (S)-9-amino-9-(5-(2-methoxyquinolin-3-yl)-1H-imidazol-2-yl)nonan-3-one (A9, 174 mg, 0.456 mmol) was added to the stirred mixture of DIPEA (0.159 mL, 0.912 mmol), $T_3P$ (435 mg, 0.684 mmol) and 6-(dimethylamino)spiro[2.5]octane-1-carboxylic acid (B6, 90 mg, 0.456 mmol) in DMF (1.5 mL), and the resultant mixture was stirred at 20° C. for 2 h. The mixture was quenched with water (10 mL), and the mixture was extracted with ethyl acetate (2×20 mL). The combined organic fractions were washed with brine (saturated, 10 mL), dried ($Na_2SO_4$), filtered and the solvent was evaporated under reduced pressure. The residue was purified by preparative TLC on silica gel, eluting with DCM/MeOH=10:1 (with 2% $NH_{40}H$) to give 6-(dimethylamino)-N—((S)-1-(5-(2-methoxyquinolin-3-yl)-1H-imidazol-2-yl)-7-oxononyl)spiro[2.5]octane-1-carboxamide (mixture of 4 isomers). LCMS (ESI) calc'd for $C_{33}H_{45}N_5O_3$ $[M+H]^+$: 560.4, found: 560.4. The mixture was further separated by Chiral SFC on Chiralpak AD column, eluent with 5% to 40% ethanol in $CO_2$ (0.05% DEA) to give the title compounds 127 (first eluent, contained second eluent) and 128 (the third eluent, contained the fourth eluent).

For 127, $^1H$ NMR (400 MHz, MeOD) δ 8.50-8.67 (m, 1H), 7.73-7.85 (m, 2H), 7.51-7.64 (m, 2H), 7.33-7.44 (m, 1H), 5.03-5.16 (m, 1H), 4.16 (s, 3H), 2.74 (brs, 1H), 2.42 (q, J=7.04 Hz, 4H), 2.29 (brs, 1H), 1.90-2.10 (m, 7H), 1.68-1.85 (m, 3H), 1.30-1.63 (m, 11H), 1.08-1.19 (m, 1H), 0.92-1.03 (m, 4H), 0.65-0.88 (m, 2H). For 128, $^1H$ NMR (400 MHz, MeOD) δ 8.40-8.83 (m, 1H), 7.79 (t, J=7.24 Hz, 2H), 7.49-7.66 (m, 2H), 7.38 (t, J=7.43 Hz, 1H), 4.99-5.14 (m, 1H), 4.10-4.24 (m, 3H), 3.01-3.16 (m, 1H), 2.26-2.49 (m, 9H), 1.71-2.08 (m, 6H), 1.25-1.65 (m, 9H), 0.72-1.22 (m, 7H).

Example 64

(1S)—N-[(1S)-1-{5-[4-(5-cyclopropylpyrazin-2-yl)phenyl]-1,3-oxazol-2-yl}-7-oxononyl]-6-ethyl-6-azaspiro[2.5]octane-1-carboxamide (129)

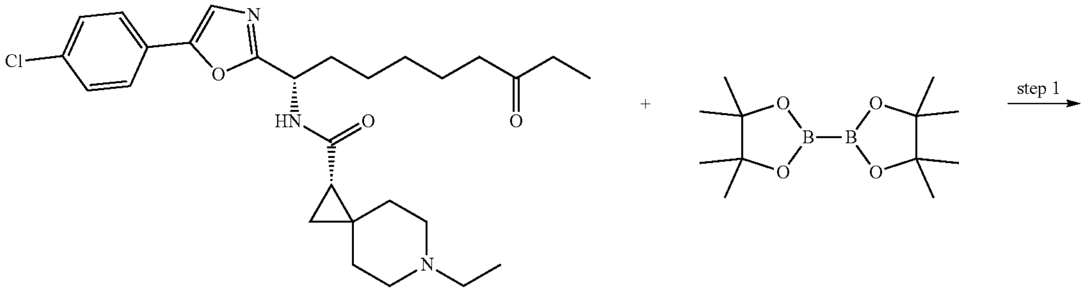

110

-continued

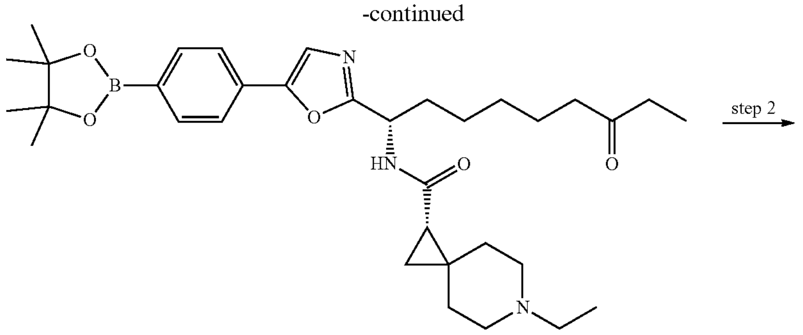

129A

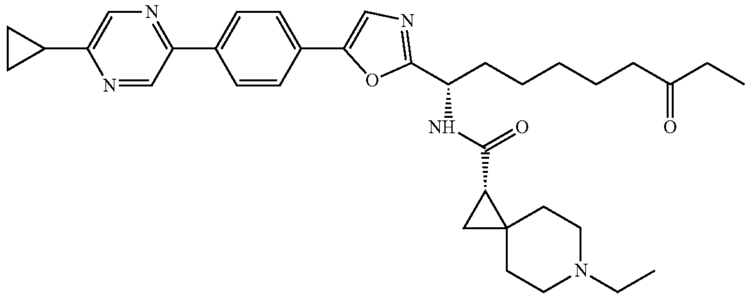

129

Step 1: Preparation of (S)-6-ethyl-N—((S)-7-oxo-1-(5-(4-(4,4,5,5-tetramethyl-1,3,2-dioxaborolan-2-yl)phenyl)oxazol-2-yl)nonyl)-6-azaspiro[2.5]octane-1-carboxamide (129A): Potassium acetate (40 mg, 0.408 mmol) and $Pd_2(dba)_3$ (8 mg, 8.74 μmol) was added to the mixture of BPD (76 mg, 0.300 mmol) and XPhos (20 mg, 0.042 mmol) and (S)—N—((S)-1-(5-(4-chlorophenyl)oxazol-2-yl)-7-oxononyl)-6-ethyl-6-azaspiro[2.5]octane-1-carboxamide (110, 100 mg, 0.200 mmol) in dioxane (1.5 mL). The resultant mixture was stirred at 80° C. under $N_2$ overnight. The mixture was concentrated in vacuo. The residue was combined with a same reaction from 100 mg of chloride and purified by silica gel flash chromatography (ISCORF75; Sepa flash column), eluting with DCM/MeOH/$NH_3$(Aq.)=10:1.5:0.02 to give (S)-6-ethyl-N—((S)-7-oxo-1-(5-(4-(4,4,5,5-tetramethyl-1,3,2-dioxaborolan-2-yl)phenyl)oxazol-2-yl)nonyl)-6-azaspiro[2.5]octane-1-carboxamide (129A). LCMS (ESI) calc'd for $C_{34}H_{50}BN_3O_5$ $[M+H]^+$: 592.4, found: 592.4.

Step 2: Preparation of (S)—N—((S)-1-(5-(4-(5-cyclopropylpyrazin-2-yl)phenyl)oxazol-2-yl)-7-oxononyl)-6-ethyl-6-azaspiro[2.5]octane-1-carboxamide (129): $K_2CO_3$ (98 mg, 0.710 mmol) and $PdCl_2$(DTBPF) (20 mg, 0.031 mmol) was added to the solution of (S)-6-ethyl-N—((S)-7-oxo-1-(5-(4-(4,4,5,5-tetramethyl-1,3,2-dioxaborolan-2-yl)phenyl)oxazol-2-yl)nonyl)-6-azaspiro[2.5]octane-1-carboxamide (129A, 210 mg, 0.355 mmol) and 2-bromo-5-cyclopropylpyrazine (75 mg, 0.377 mmol) in dioxane (2 mL) and water (0.3 mL), and the resultant mixture was stirred at 70° C. for 16 h. The mixture was filtered and the filter cake was washed with MeOH (10 mL). The filtrate was concentrated to dryness. The residue was purified by preparative HPLC (reverse phase C-18 column), eluting with acetonitrile/water+0.1% TFA, to give (S)—N—((S)-1-(5-(4-(5-cyclopropylpyrazin-2-yl)phenyl)oxazol-2-yl)-7-oxononyl)-6-ethyl-6-azaspiro[2.5]octane-1-carboxamide hydrochloride (129). LCMS (ESI) calc'd for $C_{35}H_{45}N_5O_3$ $[M+H]^+$: 584.4, found: 584.4. $^1H$ NMR (400 MHz, MeOD) δ 9.06-9.18 (m, 1H), 8.82 (s, 1H), 8.14-8.28 (m, 2H), 7.90 (d, J=7.94 Hz, 2H), 7.60-7.74 (m, 1H), 5.07-5.20 (m, 1H), 3.48-3.65 (m, 1H), 3.35 (m, 1H), 2.77-3.25 (m, 4H), 2.21-2.53 (m, 5H), 1.78-2.13 (m, 5H), 1.16-1.66 (m, 16H), 0.75-1.10 (m, 4H).

The following compounds were prepared using similar procedures as described for compound 129.

| ID | Structure | Observed [M + H]+ |
|---|---|---|
| 143 | 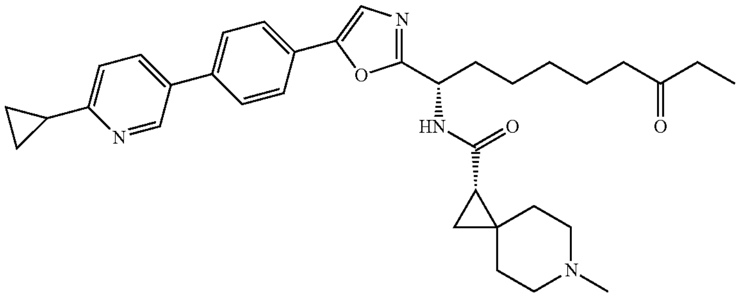 [SMILES: CCC(=O)CCCCC[C@H](NC(=O)[C@H]1CC12CCN(C)CC2)c1ncc(-c2ccc(-c3ccc(C4CC4)nc3)cc2)o1] | 569.3 |
| 391 | 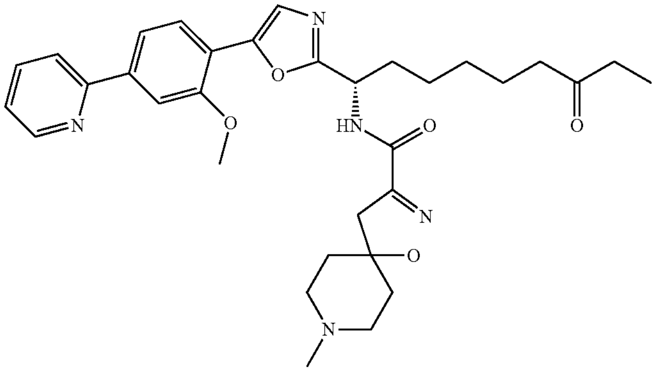 [SMILES: CCC(=O)CCCCC[C@H](NC(=O)C(=N)CC1(O)CCN(C)CC1)c1ncc(-c2ccc(-c3ccccn3)cc2OC)o1] | 588.1 |
Example 65
5,5,6-trimethyl-N-{(1S)-1-[5-(2-methylquinolin-6-yl)-1H-imidazol-2-yl]-7-oxononyl}-6-azaspiro[2.5]octane-1-carboxamide (130, 131, 132 &133)
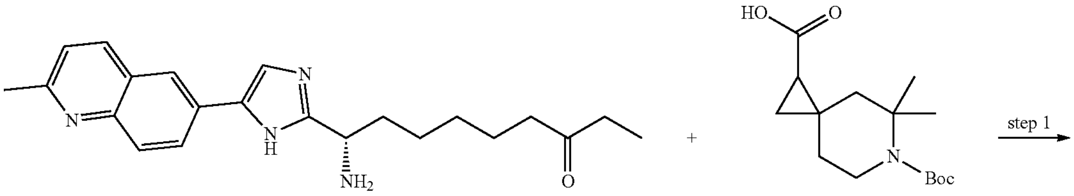
A10 B8
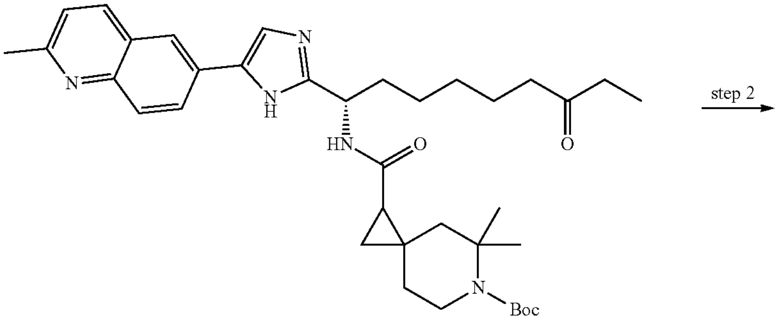
130A -continued

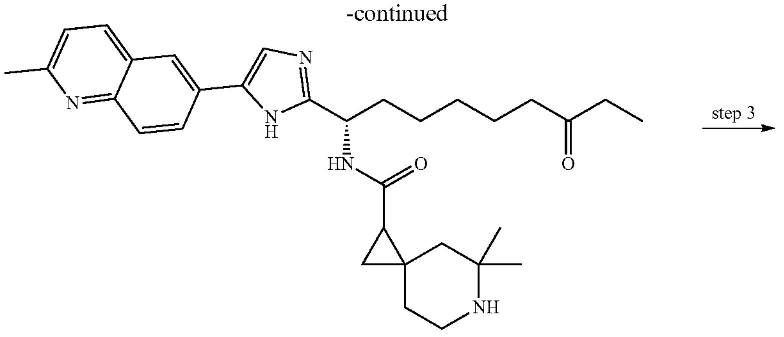

130B

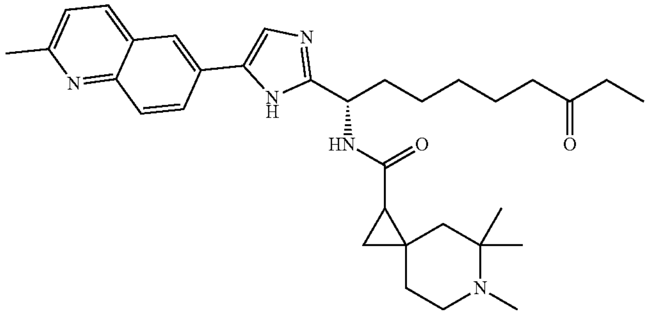

130, 131, 132 & 133

Step 1: Preparation of tert-butyl 5,5-dimethyl-1-(((S)-1-(5-(2-methylquinolin-6-yl)-1H-imidazol-2-yl)-7-oxononyl) carbamoyl)-6-azaspiro[2.5]octane-6-carboxylate (130_A): $T_3P$ (404 mg, 0.635 mmol) was added to a stirred mixture of (S)-9-amino-9-(5-(2-methylquinolin-6-yl)-1H-imidazol-2-yl)nonan-3-one (A10, 127 mg, 0.349 mmol), 6-(tert-butoxycarbonyl)-5,5-dimethyl-6-azaspiro[2.5]octane-1-carboxylic acid (B8, 90 mg, 0.318 mmol) and DIPEA (0.166 mL, 0.953 mmol) in DMF (2.0 mL) at room temperature and the mixture was stirred at rt for 3 h. The mixture was cooled, diluted with ethyl acetate (20 mL) and $H_2O$ (8 mL), washed with brine (saturated, 10 mL), dried ($Na_2SO_4$), filtered and the solvent was evaporated under reduced pressure. The residue was purified by preparative TLC on silica gel, eluting with DCM:MeOH=10:1 to give tert-butyl 5,5-dimethyl-1-(((S)-1-(5-(2-methylquinolin-6-yl)-1H-imidazol-2-yl)-7-oxononyl)carbamoyl)-6-azaspiro[2.5]octane-6-carboxylate (130A). LCMS (ESI) calc'd for $C_{37}H_{51}N_5O_4$ $[M+H]^+$: 630.4, found: 630.4.

Step 2: Preparation of 5,5-dimethyl-N—((S)-1-(5-(2-methylquinolin-6-yl)-1H-imidazol-2-yl)-7-oxononyl)-6-azaspiro[2.5]octane-1-carboxamide (130B): TFA (0.5 mL, 6.49 mmol) was added to a stirred mixture of tert-butyl 5,5-dimethyl-1-(((S)-1-(5-(2-methylquinolin-6-yl)-1H-imidazol-2-yl)-7-oxononyl)carbamoyl)-6-azaspiro[2.5]octane-6-carboxylate (130A, 135 mg, 0.214 mmol) in DCM (2.0 mL) at room temperature and the mixture was stirred at rt for 2 h. The mixture was concentrated to afford 5,5-dimethyl-N—((S)-1-(5-(2-methylquinolin-6-yl)-1H-imidazol-2-yl)-7-oxononyl)-6-azaspiro[2.5]octane-1-carboxamide (130B) without further purification. LCMS (ESI) calc'd for $C_{32}H_{43}N_5O_2$ $[M+H]^+$: 530.3, found: 530.4.

Step 3: Preparation of 5,5,6-trimethyl-N—((S)-1-(5-(2-methylquinolin-6-yl)-1H-imidazol-2-yl)-7-oxononyl)-6-azaspiro[2.5]octane-1-carboxamide (130, 131, 132, 133): HCHO solution (0.1 mL) was added to a stirred mixture of 5,5-dimethyl-N—((S)-1-(5-(2-methylquinolin-6-yl)-1H-imidazol-2-yl)-7-oxononyl)-6-azaspiro[2.5]octane-1-carboxamide (130B, 110 mg, 0.208 mmol) in MeOH (3.0 mL) at room temperature and the mixture was stirred at rt for 18 h. $NaBH(OAc)_3$ (440 mg, 2.077 mmol) was added to the above mixture solution, and it was stirred at rt for 2 h, and then concentrated. The residue was purified by preparative HPLC (reverse phase C-18 column), eluting with acetonitrile/water+0.10% TFA and then separated by chiral SFC on Chiralpak AD column, eluent 5% to 40% ethanol in $CO_2$ (0.05% DEA) to afford the title compounds.

130. Fast eluent on HPLC and second eluent on SFC, LCMS (ESI) calc'd for $C_{33}H_{45}N_5O_2$ $[M+H]^+$: 544.4, found: 544.4, $^1H$ NMR (400 MHz, MeOD) δ8.88 (d, J=8.60 Hz, 1H), 8.60 (d, J=5.73 Hz, 1H), 8.36-8.45 (m, 1H), 8.22 (d, J=9.04 Hz, 1H), 8.06 (s, 1H), 7.91 (d, J=8.60 Hz, 1H), 5.14-5.26 (m, 1H), 3.33-3.42 (m, 2H), 3.01-3.10 (m, 1H), 2.98 (s, 3H), 2.79-2.88 (m, 3H), 2.41-2.51 (m, 4H), 1.71-2.32 (m, 6H), 1.71-1.78 (m, 1H), 1.22-1.64 (m, 16H), 1.04-1.15 (m, 1H), 0.99 (t, J=7.28 Hz, 3H).

131. Second eluent on HPLC and second eluent on SFC, LCMS (ESI) calc'd for $C_{33}H_{45}N_5O_2$ $[M+H]^+$: 544.4, found: 544.4, $^1H$ NMR (400 MHz, MeOD) δ 8.91 (d, J=8.60 Hz, 1H), 8.57-8.68 (m, 1H), 8.41 (d, J=8.60 Hz, 1H), 8.24 (d, J=8.82 Hz, 1H), 8.04-8.12 (m, 1H), 7.93 (d, J=8.60 Hz, 1H), 5.10 (t, J=7.50 Hz, 1H), 3.32-3.44 (m, 1H), 3.11-3.29 (m, 2H), 2.99 (s, 3H), 2.71-2.86 (m, 3H), 2.22-2.58 (m, 5H), 1.77-2.21 (m, 5H), 1.05-1.74 (m, 16H), 0.75-1.03 (m, 3H).

132. Fast eluent on HPLC and first eluent on SFC, LCMS (ESI) calc'd for $C_{33}H_{45}N_5O_2$ $[M+H]^+$: 544.4, found: 544.4, $^1H$ NMR (400 MHz, MeOD) δ 8.81 (dd, J=2.32, 8.49 Hz, 1H), 8.55 (brs, 1H), 8.36 (d, J=8.82 Hz, 1H), 8.19 (d, J=8.82 Hz, 1H), 8.03 (s, 1H), 7.86 (d, J=8.60 Hz, 1H), 5.05-5.24 (m, 1H), 3.32-3.56 (m, 3H), 2.95 (s, 3H), 2.84 (d, J=8.60 Hz, 3H), 2.40-2.54 (m, 4H), 1.65-2.37 (m, 6H), 1.22-1.63 (m, 15H), 0.87-1.19 (m, 4H).

133. Second eluent on HPLC and first eluent on SFC, LCMS (ESI) calc'd for $C_{33}H_{45}N_5O_2$ $[M+H]^+$: 544.4, found: 544.4, $^1H$ NMR (400 MHz, MeOD) δ 8.80 (d, J=8.60 Hz, 1H), 8.55 (d, J=9.92 Hz, 1H), 8.30-8.41 (m, 1H), 8.18 (d, J=8.82 Hz, 1H), 8.01 (d, J=4.85 Hz, 1H), 7.85 (d, J=8.60 Hz, 1H), 5.02-5.18 (m, 1H), 3.21-3.29 (m, 1H), 2.94 (s, 3H), 2.66-2.81 (m, 3H), 2.40-2.52 (m, 4H), 1.68-2.32 (m, 7H), 1.20-1.63 (m, 14H), 0.84-1.19 (m, 6H).
Example 66
(1S)—N-{(1S)-1-[4-(4-fluorophenyl)-1H-imidazol-2-yl]-8-hydroxy-7-oxononyl}-6-methyl-6-azaspiro[2.5]octane-1-carboxamide (134)
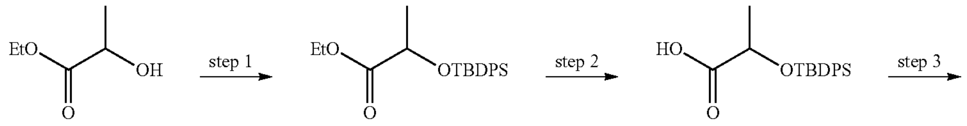
134A 134B 134C
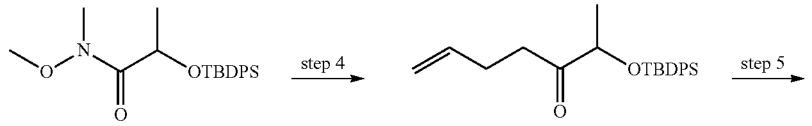
134D 134E
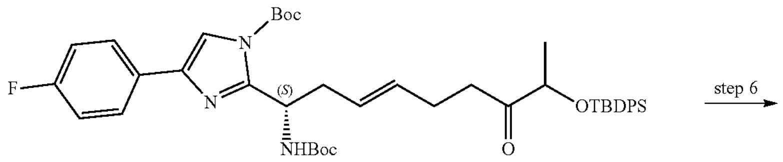
134F
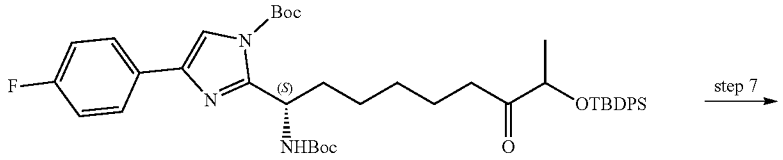
134G
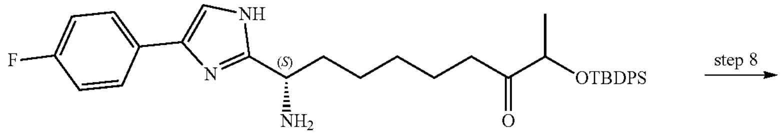
134H
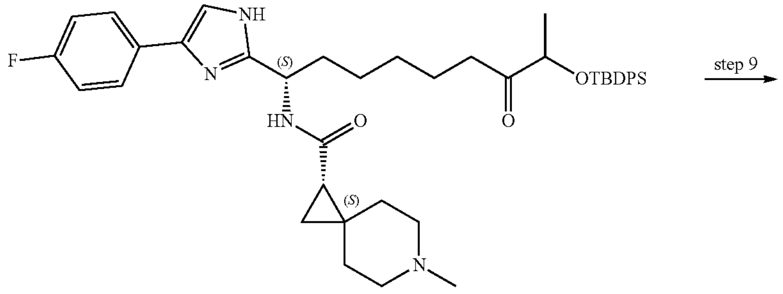
134I -continued

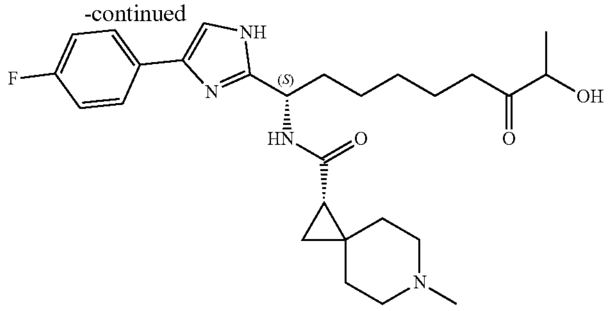

134

Step 1: Preparation of ethyl 2-((tert-butyldiphenylsilyl)oxy)propanoate (134B): TBDPSCl (3.3 mL, 12.85 mmol) and imidazole (0.576 g, 8.47 mmol) were added to a stirred mixture of ethyl 2-hydroxypropanoate (134A, 1 g, 8.47 mmol) in THF (10 mL) at 0° C. and the mixture was stirred at rt for 18 h. The mixture was extracted with ethyl acetate (100 mL*2). The combined organic fractions were washed with water (50 mL), dried ($Na_2SO_4$), filtered and the solvent was evaporated under reduced pressure. The residue was purified by silica gel column flash chromatography, eluting with petroleum ether/EtOAc=0-30% to give ethyl 2-((tert-butyldiphenylsilyl)oxy) propanoate (134B). $^1H$ NMR (400 MHz, $CDCl_3$) δ 7.69 (t, J=7.94 Hz, 4H), 7.30-7.52 (m, 6H), 4.28 (q, J=6.84 Hz, 1H), 4.03 (q, J=6.98 Hz, 2H), 1.38 (d, J=6.62 Hz, 3H), 1.16 (t, J=7.06 Hz, 3H), 1.11 (s, 9H).

Step 2: Preparation of 2-((tert-butyldiphenylsilyl)oxy) propanoic acid (134C): Lithium hydroxide hydrate (0.377 g, 8.98 mmol) was added to a stirred mixture of ethyl 2-((tert-butyldiphenylsilyl)oxy)propanoate (134B, 1.6 g, 4.49 mmol) in THF (5 mL), MeOH (5 mL), water (2 mL) at 25° C. and the mixture was stirred at 25° C. for 1 h. The mixture was acidified by 1 M HCl to pH=5-6 then extracted with ethyl acetate (50 mL*2). The combined organic fractions were washed with water (20 mL), dried ($Na_2SO_4$), filtered and the solvent was evaporated under reduced pressure to afford 2-((tert-butyldiphenylsilyl)oxy) propanoic acid (134C) which was used to next step without further purification. $^1H$ NMR (400 MHz, $CDCl_3$) δ 7.59-7.69 (m, 5H), 7.33-7.45 (m, 7H), 4.34 (q, J=6.84 Hz, 1H), 1.32 (d, J=6.84 Hz, 3H), 1.13 (s, 9H).

Step 3: Preparation of 2-((tert-butyldiphenylsilyl)oxy)-N-methoxy-N-methyl propanamide (134D): Oxalyl dichloride (0.3 mL, 3.42 mmol) was added to a stirred mixture of 2-((tert-butyldiphenylsilyl)oxy)propanoic acid (134C, 1 g, 3.04 mmol) in DCM (10 mL) at 25° C. and followed by N,N-dimethylformamide (two drops), and the mixture was stirred at 25° C. for 1 h. The mixture was added to a stirred mixture of N,O-dimethylhydroxylamine hydrochloride (1.45 g, 15.3 mmol) in water (20 mL) which was basified by $NaHCO_3$(0.25 g, 3.05 mmol) to pH=7-8 at 0° C. and the mixture was stirred at 0° C. for 1 h. The mixture was extracted with DCM (25 mL*2), and washed with water (20 mL). The combined organic fractions were dried ($Na_2SO_4$), filtered and the solvent was evaporated under reduced pressure to afford 2-((tert-butyldiphenylsilyl)oxy)-N-methoxy-N-methyl propanamide (134D) which was used to next step without further purification. $^1H$ NMR (400 MHz, $CDCl_3$) δ 7.71 (d, J=6.26 Hz, 4H), 7.31-7.48 (m, 6H), 4.53 (q, J=6.65 Hz, 1H), 2.95-3.20 (m, 6H), 1.38 (d, J=6.26 Hz, 3H), 1.09 (s, 9H).

Step 4: Preparation of 2-((tert-butyldiphenylsilyl)oxy)hept-6-en-3-one (134E): 12 (164 mg, 0.646 mmol) and magnesium (314 mg, 12.92 mmol) were added to a stirred mixture of 4-bromobut-1-ene (872 mg, 6.46 mmol) in THF (5 mL) at 25° C. under $N_2$ atmosphere. The exothermic reaction was complete when the temperature returned to room temperature. The mixture was used into next step without further purification. But-3-en-1-ylmagnesium bromide solution was added to a stirred mixture of 2-((tert-butyldiphenylsilyl)oxy)-N-methoxy-N-methylpropanamide (134D, 800 mg, 2.153 mmol) in THF (5 mL) at 0° C. and the mixture was stirred at 0° C. for 3 h. The mixture was quenched with $NH_4Cl$ aq and the mixture was extracted with ethyl acetate (50 mL*2) and washed with water. The combined organic fractions were evaporated under reduced pressure. The residue was purified by silica gel column flash chromatography, eluting with petroleum ether/EtOAc=0-30% to give 2-((tert-butyldiphenylsilyl)oxy)hept-6-en-3-one (134E). $^1H$ NMR (400 MHz, $CDCl_3$) δ 7.59-7.70 (m, 4H), 7.33-7.49 (m, 6H), 5.78 (m, 1H), 4.91-5.06 (m, 2H), 4.22 (q, J=6.91 Hz, 1H), 2.66 (dt, J=2.74, 7.24 Hz, 2H), 2.24 (q, J=7.04 Hz, 2H), 1.20 (d, J=6.65 Hz, 3H), 1.12 (s, 9H).

Step 5: Preparation of tert-butyl 4-(4-fluorophenyl)-2-((12S,E)-2,2,5,16,16-penta methyl-6,14-dioxo-3,3-diphenyl-4,15-dioxa-13-aza-3-silaheptadec-9-en-12-yl)-1H-imidazole-1-carboxylate (134F): (1,3-dimesitylimidazolidin-2-ylidene)(5-(N,N-dimethylsulfamoyl)-2-isopropoxybenzylidene)ruthenium(VI) chloride (17 mg, 0.023 mmol) and 2-((tert-butyldiphenylsilyl)oxy)hept-6-en-3-one (134E, 187 mg, 0.510 mmol) were added to a stirred mixture of (S)-tert-butyl 2-(1-((tert-butoxycarbonyl)amino)but-3-en-1-yl)-4-(4-fluorophenyl)-1H-imidazole-1-carboxylate (200 mg, 0.463 mmol) in toluene (5 mL) at 25° C. and the mixture was stirred at 60° C. for 15 h under $N_2$ atmosphere. The mixture was cooled, diluted with ethyl acetate (30 mL*2), washed with water (10 mL), dried ($Na_2SO_4$), filtered and the solvent was evaporated under reduced pressure. The residue was purified by silica gel column flash chromatography, eluting with petroleum ether/EtOAc=0-30% to give tert-butyl 4-(4-fluorophenyl)-2-((12S,E)-2,2,5,16,16-pentamethyl-6,14-dioxo-3,3-diphenyl-4,15-dioxa-13-aza-3-silaheptadec-9-en-12-yl)-1H-imidazole-1-carboxylate (134F). LCMS (ESI) calc'd for $C_{44}H_{56}FN_3O_6Si$ $[M+H]^+$: 770.3, found: 670.4.

Step 6: Preparation of tert-butyl 4-(4-fluorophenyl)-2-((12S)-2,2,5,16,16-penta methyl-6,14-dioxo-3,3-diphenyl-4,15-dioxa-13-aza-3-silaheptadecan-12-yl)-1H-imidazole-1-carboxylate (134G): Pd/C (10%, 10 mg, 0.094 mmol) was added to a stirred mixture of tert-butyl 4-(4-fluorophenyl)-2-((12S,E)-2,2,5,16,16-pentamethyl-6,14-dioxo-3,3-diphenyl-4,15-dioxa-13-aza-3-silaheptadec-9-en-12-yl)-1H-imidazole-1-carboxylate (134F, 100 mg, 0.130 mmol) in MeOH (1 mL) at 25° C. and the mixture was stirred at 25° C. under $H_2$ at 1 atm for 3 h. The mixture was filtered through Celite and the filter cake was washed with MeOH (2×20 mL). The filtrate was concentrated to dryness to give tert-butyl 4-(4-fluorophenyl)-2-((12S)-2,2,5,16,16-pentamethyl-6,14-dioxo-3,3-diphenyl-4,15-dioxa-13-aza-3-silaheptadecan-12-yl)-1H-imidazole-1-carboxylate (134G. LCMS showed the target was de-Boc. LCMS (ESI) calc'd for $C_{44}H_5SFN_3O_6Si$ $[M+H]^+$: 772.4, found: 672.1.

Step 7: Preparation of (9S)-9-amino-2-((tert-butldiphenylsilyl)oxy)-9-(4-(4-fluorophenyl)-1H-imidazol-2-yl) nonan-3-one (134H): TFA (0.1 mL, 1.298 mmol) was added to a stirred mixture of tert-butyl 4-(4-fluorophenyl)-2-((12S)-2,2,5,16,16-pentamethyl-6,14-dioxo-3,3-diphenyl-4,15-dioxa-13-aza-3-silaheptadecan-12-yl)-1H-imidazole-1-carboxylate (134G, 90 mg, 0.117 mmol) in DCM (2 mL) at 25° C. and the mixture was stirred at 25° C. for 3 h. The mixture was evaporated under reduced pressure to give (9S)-9-amino-2-((tert-butyldiphenyl silyl)oxy)-9-(4-(4-fluorophenyl)-1H-imidazol-2-yl)nonan-3-one (134H) which was used to the next step without further purification. LCMS (ESI) calc'd for $C_{34}H_{42}FN_3O_2Si$ $[M+H]^+$: 572.3, found: 572.3.

Step 8: Preparation of (1S)—N-((1S)-8-((tert-butyldiphenylsilyl)oxy)-1-(4-(4-fluorophenyl)-1H-imidazol-2-yl)-7-oxononyl)-6-methyl-6-azaspiro[2.5]octane-1-carboxamide (134I): HATU (33 mg, 0.087 mmol), triethylamine (0.1 mL, 0.717 mmol), (S)-6-(tert-butoxycarbonyl)-6-azaspiro[2.5] octane-1-carboxylic acid (B3, 23 mg, 0.090 mmol) were added to a stirred mixture of (9S)-9-amino-2-((tert-butyldiphenylsilyl)oxy)-9-(4-(4-fluorophenyl)-1H-imidazol-2-yl) nonan-3-one (134H, 50 mg, 0.087 mmol) in DCM (2 mL) at 25° C. and the mixture was stirred at 25° C. for 6 h. The mixture was extracted with ethyl acetate (5 mL) and washed with water (2 mL). The organic fractions were filtered and the solvent was evaporated under reduced pressure. The residue was purified by preparative TLC on silica gel, eluting with petroleum ether/EtOAc=2:1 to give (1S)-tert-butyl 1-(((1S)-8-((tert-butyldiphenylsilyl)oxy)-1-(4-(4-fluoro phenyl)-1H-imidazol-2-yl)-7-oxononyl)carbamoyl)-6-azaspiro[2.5]octane-6-carboxylate (134I). LCMS (ESI) calc'd for $C_{43}H_{55}FN_4O_3Si$ $[M+H]^+$: 809.4, found: 809.5.

Step 9: Preparation of (1S)—N-((1S)-1-(4-(4-fluorophenyl)-1H-imidazol-2-yl)-8-hydroxy-7-oxononyl)-6-methyl-6-azaspiro[2.5]octane-1-carboxamide (134): TBAF (3 mg, 0.011 mmol) was added to a stirred mixture of (1R)—N-((1S)-8-((tert-butyldiphenylsilyl)oxy)-1-(4-(4-fluorophenyl)-1H-imidazol-2-yl)-7-oxononyl)-6-methyl-6-azaspiro [2.5]octane-1-carboxamide (134I, 5 mg, 6.92 μmol) in THF (2 mL) at 30° C. and the mixture was stirred at rt for 18 h. The mixture was evaporated under pressure and purified by HPLC to get (1R)—N-((1S)-1-(4-(4-fluorophenyl)-1H-imidazol-2-yl)-8-hydroxy-7-oxononyl)-6-methyl-6-azaspiro [2.5]octane-1-carboxamide hydrochloride (134). LCMS (ESI) calc'd for $C_{27}H_{37}FN_4O_3$ $[M+H]^+$: 485.3, found: 485.3. $^1$H NMR (400 MHz, MeOD) δ 7.74 (dd, J=5.28, 10.76 Hz, 2H), 7.67 (d, J=7.43 Hz, 1H), 7.42-7.48 (m, 1H), 7.29-7.37 (m, 2H), 7.22 (d, J=4.70 Hz, 2H), 4.99 (t, J=7.43 Hz, 1H), 4.14 (q, J=6.78 Hz, 1H), 2.83 (d, J=5.87 Hz, 3H), 2.55 (t, J=7.04 Hz, 2H), 2.11-2.34 (m, 1H), 1.92-2.07 (m, 3H), 1.74-1.92 (m, 3H), 1.49-1.66 (m, 3H), 1.35 (brs, 4H), 1.26 (d, J=7.04 Hz, 5H), 0.82-1.07 (m, 1H).

Example 67

(1S or 1R)-1-methyl-6-(1-methylethyl)-N-{(1S)-1-[5-(2-methylquinolin-6-yl)-1H-imidazol-2-yl]-7-oxononyl}-6-azaspiro[2.5]octane-1-carboxamide (151 & 152)

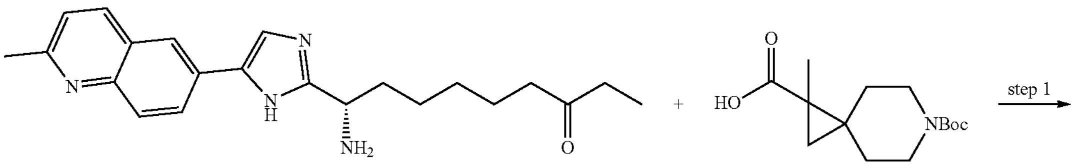

A10 B9

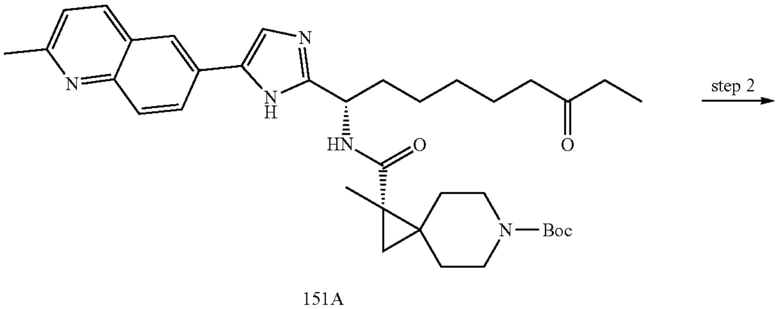

151A

-continued

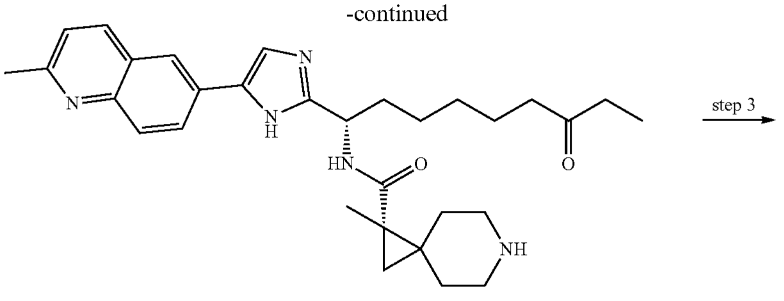

151B

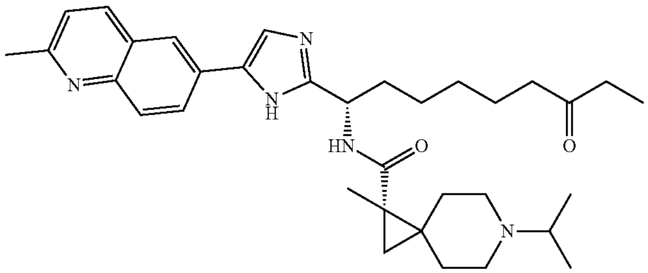

and

151

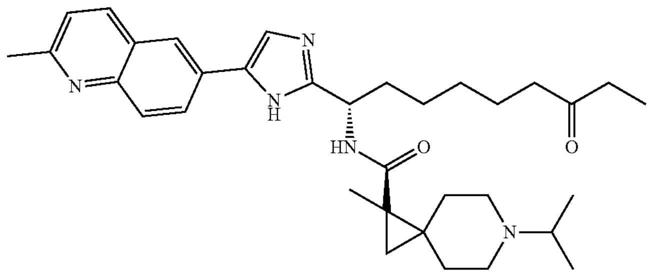

152

Step 1: Preparation of (R)-tert-butyl 1-methyl-1-(((S)-1-(5-(2-methylquinolin-6-yl)-1H-imidazol-2-yl)-7-oxononyl) carbamoyl)-6-azaspiro[2.5]octane-6-carboxylate (151A): HATU (313 mg, 0.823 mmol) was added to a stirred mixture of 6-(tert-butoxycarbonyl)-1-methyl-6-azaspiro[2.5]octane-1-carboxylic acid (B9, 122 mg, 0.453 mmol) and $Et_3N$ (0.172 mL, 1.235 mmol) in DMF (2 mL) at 18° C., and the mixture was stirred at 18° C. for 30 min. Then (S)-9-amino-9-(5-(2-methylquinolin-6-yl)-1H-imidazol-2-yl)nonan-3-one (A10, 150 mg, 0.412 mmol) was added, and the resulting mixture was stirred at 18° C. until LCMS showed completion of the reaction. The mixture was quenched with water (10 mL), extracted with EtOAc (10 mL*3), the combined organic layers were washed with brine (10 mL), dried over $Na_2SO_4$, filtered and concentrated. The crude was purified by prep-HPLC (TFA) to give tert-butyl 1-methyl-1-(((S)-1-(5-(2-methylquinolin-6-yl)-1H-imidazol-2-yl)-7-oxononyl)carbamoyl)-6-azaspiro[2.5]octane-6-carboxylate (151A) which was further separated by chiral SFC on AD column to afford two single isomers. LCMS (ESI) calc'd for $C_{36}H_{49}N_5O_4$ $[M+H]^+$: 616.4, found: 616.4. (first peak); LCMS (ESI) calc'd for $C_{36}H_{49}N_5O_4$ $[M+H]^+$: 616.4, found: 616.4. (second peak).

Step 2: Preparation of (R)-tert-butyl 1-methyl-1-(((S)-1-(5-(2-methylquinolin-6-yl)-1H-imidazol-2-yl)-7-oxononyl) carbamoyl)-6-azaspiro[2.5]octane-6-carboxylate (151B): HCl/MeOH (2 mL, 8.00 mmol) was added to a stirred mixture of tert-butyl 1-methyl-1-(((S)-1-(5-(2-methylquinolin-6-yl)-1H-imidazol-2-yl)-7-oxononyl)carbamoyl)-6-azaspiro[2.5]octane-6-carboxylate (151A, first peak in SFC) in MeOH (1 mL) at 15° C. and the mixture was stirred at 15° C. for 4 h. The mixture was quenched with $NaHCO_3$(10 mL), extracted with EtOAc (10 mL*3), the combined organic layers were washed with brine (10 mL), dried over $Na_2SO_4$, filtered and concentrated to get 1-methyl-N—((S)-1-(5-(2-methylquinolin-6-yl)-1H-imidazol-2-yl)-7-oxononyl)-6-azaspiro[2.5]octane-1-carboxamide (151B) which was used in the next step directly without purification. LCMS (ESI) calc'd for $C_{31}H_{41}N_5O_2$ $[M+H]^+$: 516.3, found: 516.3.

Step 3: Preparation of (R)-tert-butyl 1-methyl-1-(((S)-1-(5-(2-methylquinolin-6-yl)-1H-imidazol-2-yl)-7-oxononyl) carbamoyl)-6-azaspiro[2.5]octane-6-carboxylate (151): A mixture of 1-methyl-N—((S)-1-(5-(2-methylquinolin-6-yl)-1H-imidazol-2-yl)-7-oxononyl)-6-azaspiro[2.5]octane-1-carboxamide (151B, 21 mg, 0.041 mmol) in acetone (3 mL) was heated at 50° C. for 1 h, then sodium triacetoxyborohydride (104 mg, 0.489 mmol) was added to the mixture. The mixture was stirred at the same temperature for 48 h. The mixture was quenched with $NaHCO_3$(10 mL), extracted with EtOAc (10 mL*3), the combined organic layers were washed with brine (10 mL), dried over $Na_2SO_4$, filtered and concentrated. The crude was purified by prep-HPLC (TFA) to give 6-isopropyl-1-methyl-N—((S)-1-(5-(2-methylquinolin-6-yl)-1H-imidazol-2-yl)-7-oxononyl)-6-azaspiro[2.5]octane-1-carboxamide (151). HCl (10 μL, 0.122 mmol) was added to a mixture of 6-isopropyl-1-methyl-N—((S)-1-(5-(2-methylquinolin-6-yl)-1H-imidazol-2-yl)-7-oxononyl)-6-azaspiro[2.5]octane-1-carboxamide (151, 15 mg, 0.027 mmol) in MeCN (5 mL) and water (5 mL) at rt, then the mixture was stirred at rt for 30 min, and the resulting mixture was lyophilized to give 6-isopropyl-1-methyl-N—((S)-1-(5-(2-methylquinolin-6-yl)-1H-imidazol-2-yl)-7-oxononyl)-6-azaspiro[2.5]octane-1-carboxamide hydrochloride. LCMS (ESI) calc'd for $C_{34}H_{47}N_5O_2$ $[M+H]^+$: 558.4, found: 558.5. $^1H$ NMR (400 MHz, MeOD-d) δ 9.12 (d, J=8.8 Hz, 1H), 8.76 (d, J=8.8 Hz, 1H), 8.51 (d, J=8.4 Hz, 1H), 8.28 (d, J=10.0 Hz, 1H), 8.7 (s, 1H), 8.2 (d, J=8.4 Hz, 1H), 5.3 (t, 1H), 3.2 (m, 4H), 3.1 (s, 5H), 2.5 (m, 4H), 2.3 (m, 4H), 1.5 (m, 5H), 1.4 (s, 3H), 1.3 (m, 13H), 1.0 (t, 3H), 0.6 (s, 1H). 152 was prepared using a similar method as 151 from the second peak from step 1; the absolute configuration was not confirmed. LCMS (ESI) calc'd for $C_{34}H_{47}N_5O_2$ $[M+H]^+$: 558.4, found: 558.5.

The following compounds were prepared using similar procedures as described for compounds 151 and 152.

| ID | Structure | Observed $[M + H]^+$ |
|---|---|---|
| 272 | 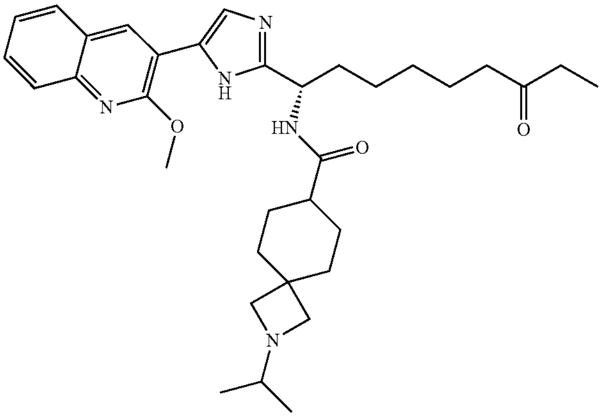 [SMILES: CCC(=O)CCCCC[C@H](NC(=O)C1CCC2(CC1)CN(C(C)C)C2)c1ncc(-c2cc3ccccc3nc2OC)[nH]1] | 574.6 |
| 273 | 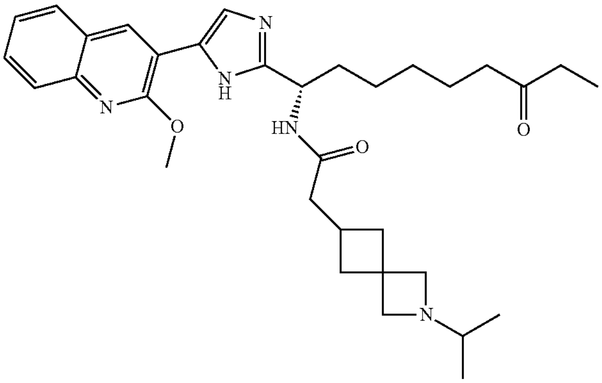 [SMILES: CCC(=O)CCCCC[C@H](NC(=O)CC1CC2(C1)CN(C(C)C)C2)c1ncc(-c2cc3ccccc3nc2OC)[nH]1] | 560.4 |

Example 68

(1S)—N-{(1S)-1-[5-(7-methoxy-2-methylquinolin-6-yl)-1,3-oxazol-2-yl]-7-oxononyl}-6-methyl-6-azaspiro[2.5]octane-1-carboxamide (163)

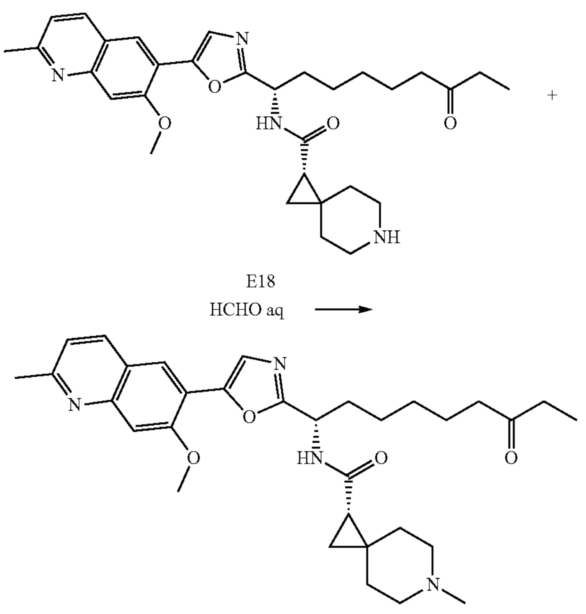

163

Formaldehyde (0.1 mL, 1.232 mmol) was added to a stirred mixture of (S)—N—((S)-1-(5-(7-methoxy-2-methylquinolin-6-yl)oxazol-2-yl)-7-oxononyl)-6-azaspiro[2.5]octane-1-carboxamide (E18, 250 mg, 0.469 mmol) in MeOH (3 mL) at room temperature and the mixture was stirred at rt for 23 h. Then triacetoxyhydroborate (532 mg, 2.82 mmol) was added into the mixture at room temperature and the mixture was stirred at rt for 3 h. The mixture was extracted with ethyl acetate (100 mL×2) and washed with water (100 mL), dried ($Na_2SO_4$), filtered and the solvent was evaporated under reduced pressure. The residue was purified by silica gel column flash chromatography, eluting with DCM/MeOH=0-10% to give (S)—N—((S)-1-(5-(7-methoxy-2-methylquinolin-6-yl)oxazol-2-yl)-7-oxononyl)-6-methyl-6-azaspiro[2.5]octane-1-carboxamide (163).

L-(+)-tartaric acid (55 mg, 0.366 mmol) was added to a stirred mixture of (S)—N—((S)-1-(5-(7-methoxy-2-methylquinolin-6-yl)oxazol-2-yl)-7-oxononyl)-6-methyl-6-azaspiro[2.5]octane-1-carboxamide (163, 200 mg, 0.366 mmol) in MeCN (2 mL) water (2 mL) at room temperature and the mixture was dried to give (S)—N—((S)-1-(5-(7-methoxy-2-methyl quinolin-6-yl)oxazol-2-yl)-7-oxononyl)-6-methyl-6-azaspiro[2.5]octane-1-carboxamide (2R,3R)-2,3-dihydroxysuccinate. LCMS (ESI) calc'd for $C_{32}H_{42}N_4O_4$ $[M+H]^+$: 547.3, found: 547.3. $^1H$ NMR (400 MHz, MeOD) δ 8.62 (d, J=8.22 Hz, 1H), 8.39-8.47 (m, 1H), 7.68 (brs, 1H), 7.53-7.59 (m, 2H), 5.17 (dd, J=5.87, 8.61 Hz, 1H), 4.54 (s, 3H), 4.19 (s, 2H), 4.16-4.21 (m, 1H), 3.42-3.62 (m, 1H), 2.93-3.15 (m, 1H), 2.88 (s, 3H), 2.84 (s, 3H), 2.42-2.50 (m, 4H), 2.28 (brs, 1H), 1.90-2.14 (m, 4H), 1.83 (brs, 1H), 1.60 (brs, 2H), 1.35-1.54 (m, 4H), 1.18-1.33 (m, 3H), 0.96-1.10 (m, 4H).

The following compounds were prepared using similar procedures as described for compound 163.

| ID | Structure | Observed $[M + H]^+$ |
|---|---|---|
| 74 | 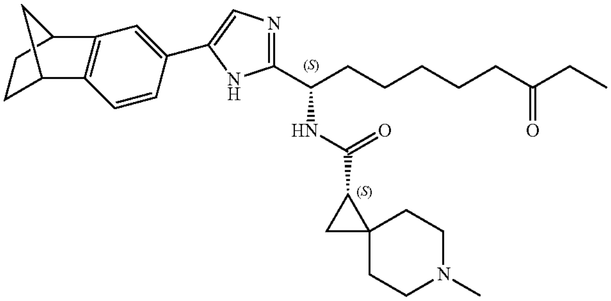 | 517.3 |
| 75 | 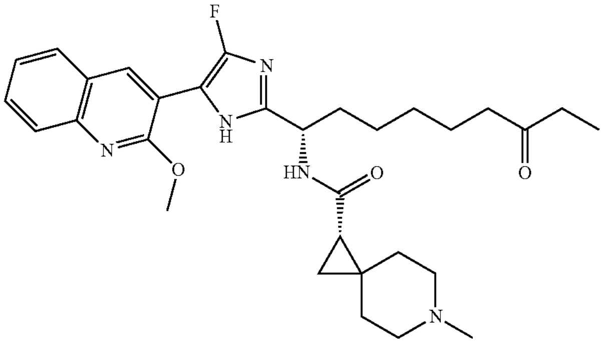 [SMILES: CCC(=O)CCCCC[C@H](NC(=O)[C@H]1CC12CCN(C)CC2)c1nc(F)c(-c2cc3ccccc3nc2OC)[nH]1] | 550.1 |

-continued
| ID | Structure | Observed [M + H]+ |
|---|---|---|
| 105 | 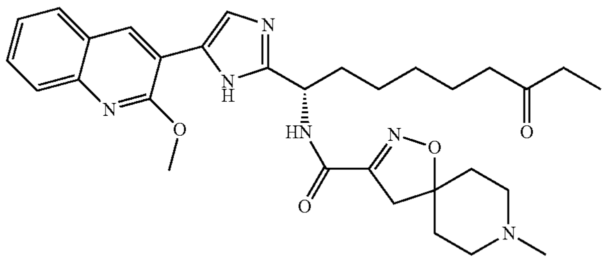 [SMILES: CCC(=O)CCCCC[C@H](NC(=O)C1=NOC2(CCN(C)CC2)C1)c1ncc(-c2cc3ccccc3nc2OC)[nH]1] | 561.3 |
| 112 | 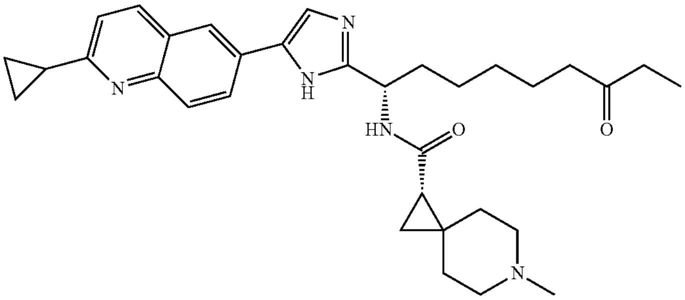 [SMILES: CCC(=O)CCCCC[C@H](NC(=O)[C@H]1CC12CCN(C)CC2)c1ncc(-c2ccc3nc(C4CC4)ccc3c2)[nH]1] | 542.2 |
| 135 | 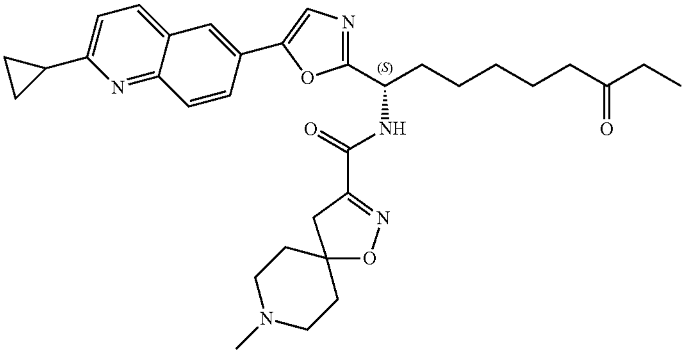 | 572.2 |
| 145 | 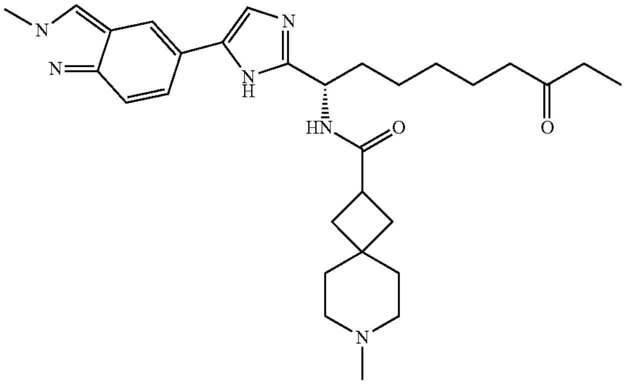 [SMILES: CCC(=O)CCCCC[C@H](NC(=O)C1CC2(CCN(C)CC2)C1)c1ncc(C2=C/C(=C/NC)C(=N)C=C2)[nH]1] | 519.4 |

-continued
| ID | Structure | Observed [M + H]$^+$ |
|---|---|---|
| 147 | 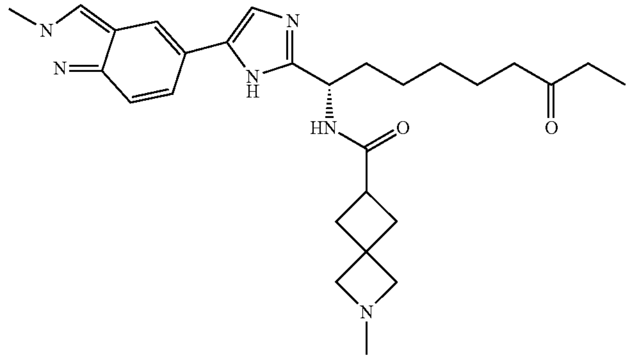 [SMILES: CCC(=O)CCCCC[C@H](NC(=O)C1CC2(C1)CN(C)C2)c1ncc(C2=C/C(=C/NC)C(=N)C=C2)[nH]1] | 491.4 |
| 154 | 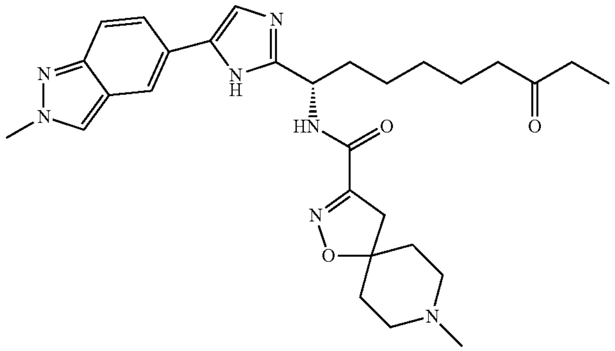 [SMILES: CCC(=O)CCCCC[C@H](NC(=O)C1=NOC2(CCN(C)CC2)C1)c1ncc(-c2ccc3nn(C)cc3c2)[nH]1] | 534.3 |
| 156 | 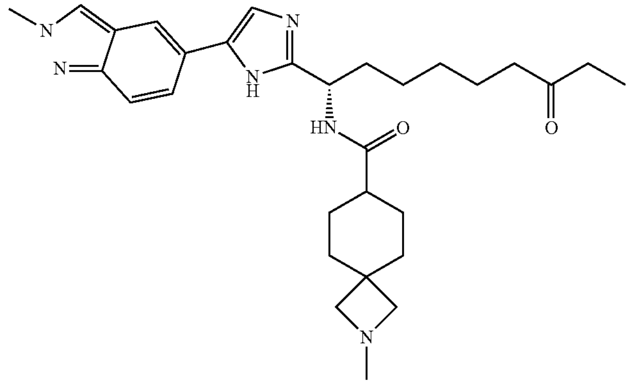 [SMILES: CCC(=O)CCCCC[C@H](NC(=O)C1CCC2(CC1)CN(C)C2)c1ncc(C2=C/C(=C/NC)C(=N)C=C2)[nH]1] | 519.4 |
| 157 | 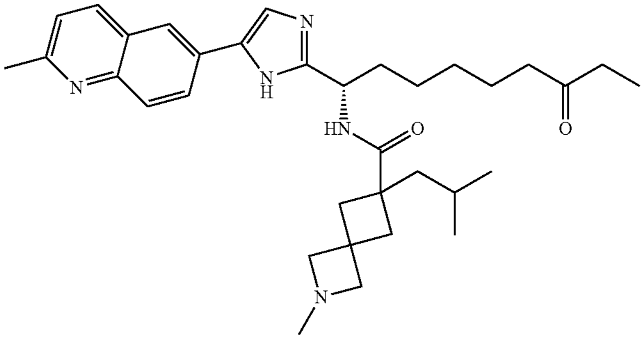 [SMILES: CCC(=O)CCCCC[C@H](NC(=O)C1(CC(C)C)CC2(CN(C)C2)C1)c1ncc(-c2ccc3nc(C)ccc3c2)[nH]1] | 558.3 |

-continued
| ID | Structure | Observed [M + H]+ |
|---|---|---|
| 188 | 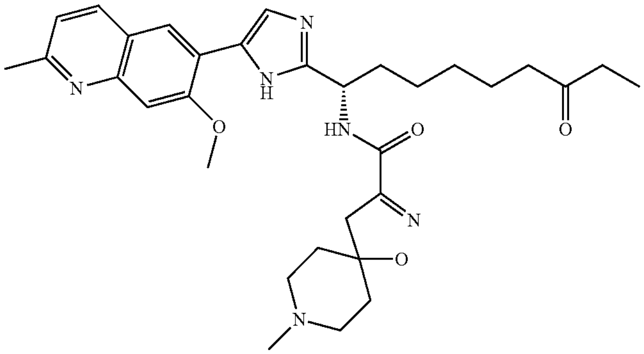 [SMILES: CCC(=O)CCCCC[C@H](NC(=O)C(=N)CC1(O)CCN(C)CC1)c1ncc(-c2cc3ccc(C)nc3cc2OC)[nH]1] | 561.4 |
| 193 | 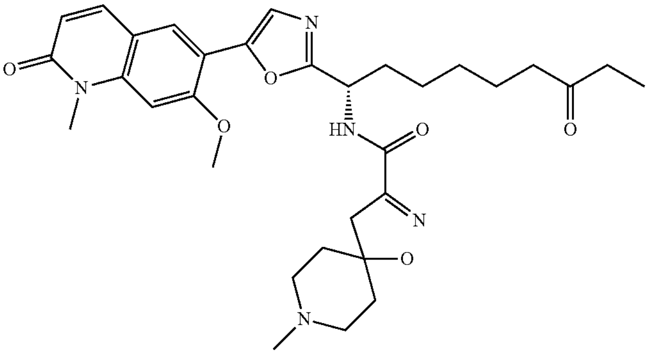 [SMILES: CCC(=O)CCCCC[C@H](NC(=O)C(=N)CC1(O)CCN(C)CC1)c1ncc(-c2cc3ccc(=O)n(C)c3cc2OC)o1] | 592.1 |
| 196 | 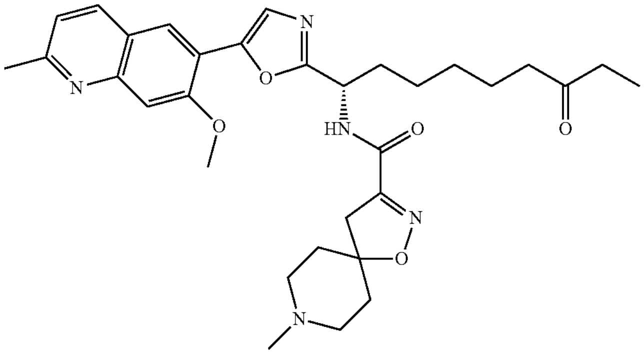 [SMILES: CCC(=O)CCCCC[C@H](NC(=O)C1=NOC2(CCN(C)CC2)C1)c1ncc(-c2cc3ccc(C)nc3cc2OC)o1] | 576.3 |
| 198 | 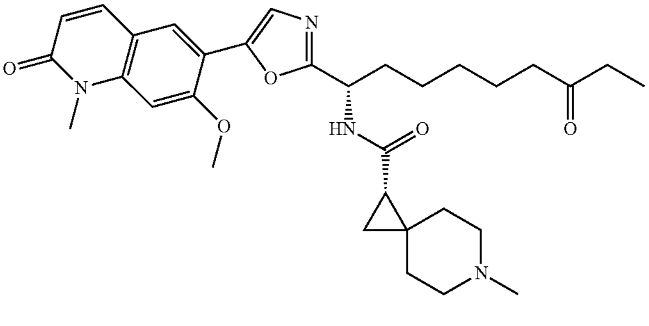 [SMILES: CCC(=O)CCCCC[C@H](NC(=O)[C@H]1CC12CCN(C)CC2)c1ncc(-c2cc3ccc(=O)n(C)c3cc2OC)o1] | 563.1 |

-continued
| ID | Structure | Observed [M + H]+ |
|---|---|---|
| 200 | 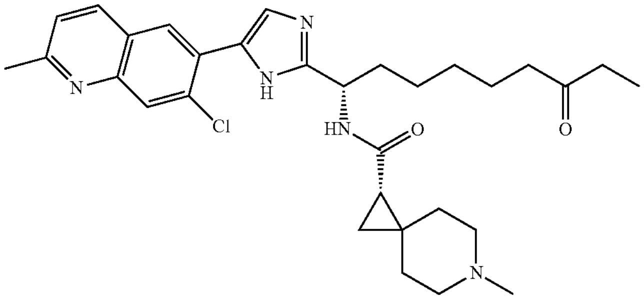 [SMILES: CCC(=O)CCCCC[C@H](NC(=O)[C@H]1CC12CCN(C)CC2)c1ncc(-c2cc3ccc(C)nc3cc2Cl)[nH]1] | 550.1 |
| 216 | 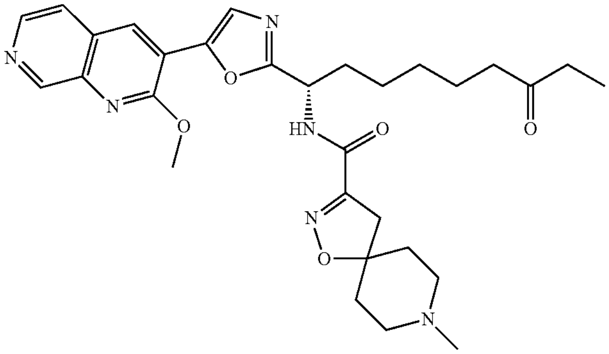 [SMILES: CCC(=O)CCCCC[C@H](NC(=O)C1=NOC2(CCN(C)CC2)C1)c1ncc(-c2cc3ccncc3nc2OC)o1] | 563.0 |
| 218 | 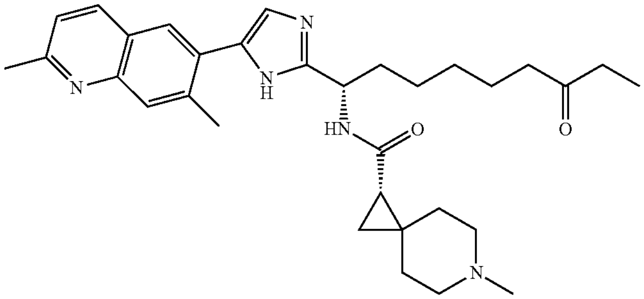 | 530.2 |
| 220 | 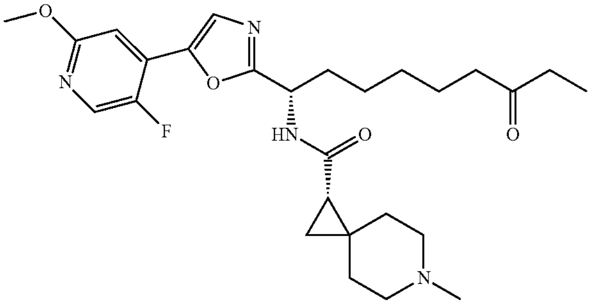 [SMILES: CCC(=O)CCCCC[C@H](NC(=O)[C@H]1CC12CCN(C)CC2)c1ncc(-c2cc(OC)ncc2F)o1] | 501.1 |

-continued
| ID | Structure | Observed [M + H]+ |
|---|---|---|
| 221 | 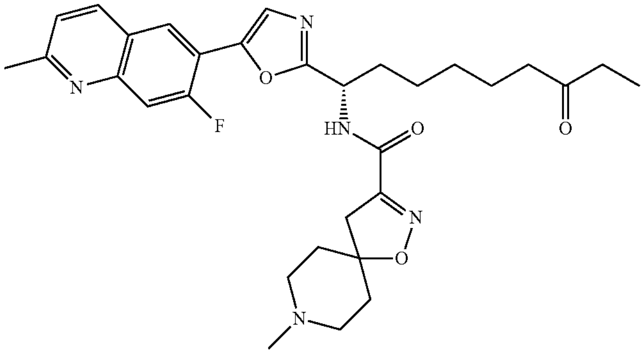 [SMILES: CCC(=O)CCCCC[C@H](NC(=O)C1=NOC2(CCN(C)CC2)C1)c1ncc(-c2cc3ccc(C)nc3cc2F)o1] | 564.0 |
| 223 | 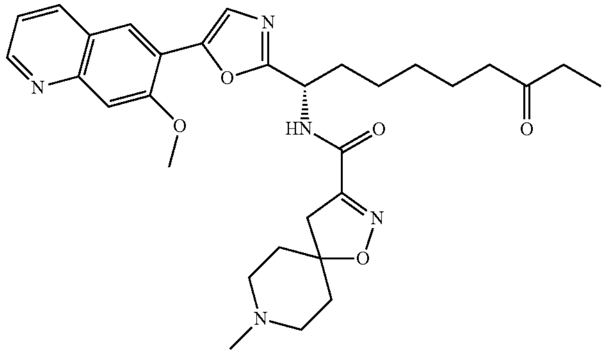 [SMILES: CCC(=O)CCCCC[C@H](NC(=O)C1=NOC2(CCN(C)CC2)C1)c1ncc(-c2cc3cccnc3cc2OC)o1] | 562.0 |
| 226 | 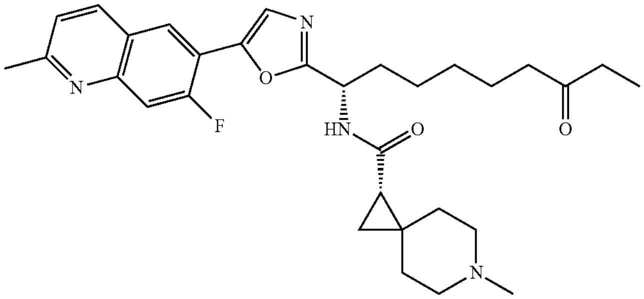 [SMILES: CCC(=O)CCCCC[C@H](NC(=O)[C@H]1CC12CCN(C)CC2)c1ncc(-c2cc3ccc(C)nc3cc2F)o1] | 535.1 |
| 232 | 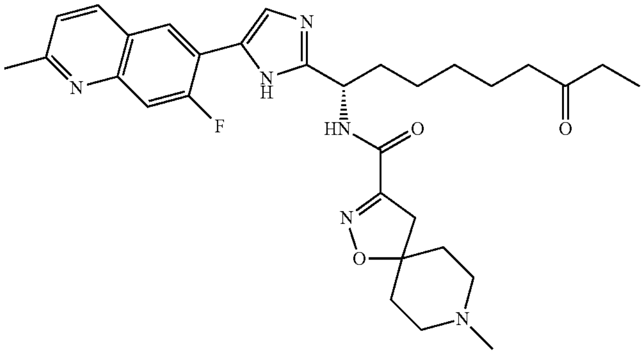 [SMILES: CCC(=O)CCCCC[C@H](NC(=O)C1=NOC2(CCN(C)CC2)C1)c1ncc(-c2cc3ccc(C)nc3cc2F)[nH]1] | 563.0 |

-continued
| ID | Structure | Observed [M + H]+ |
|---|---|---|
| 239 | 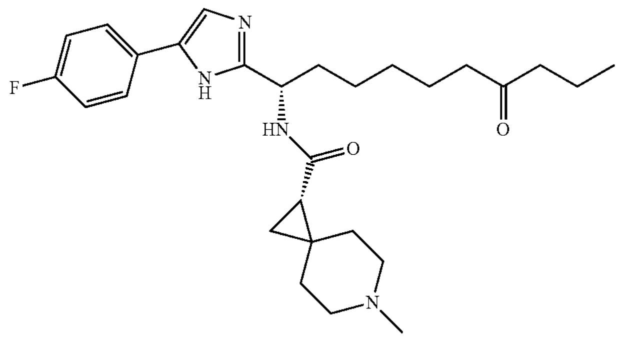 [SMILES: CCCC(=O)CCCCC[C@H](NC(=O)[C@H]1CC12CCN(C)CC2)c1ncc(-c2ccc(F)cc2)[nH]1] | 483.4 |
| 386 | 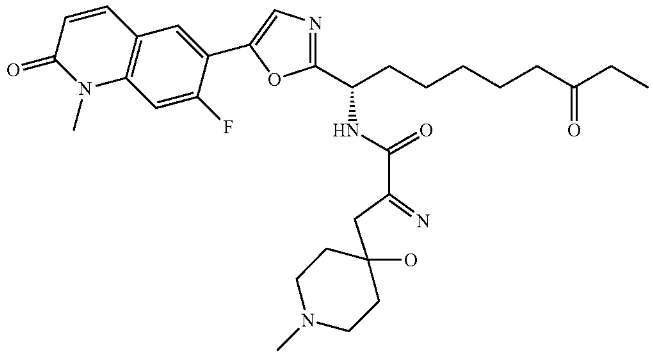 [SMILES: CCC(=O)CCCCC[C@H](NC(=O)C(=N)CC1(O)CCN(C)CC1)c1ncc(-c2cc3ccc(=O)n(C)c3cc2F)o1] | 580.3 |
| 390 | 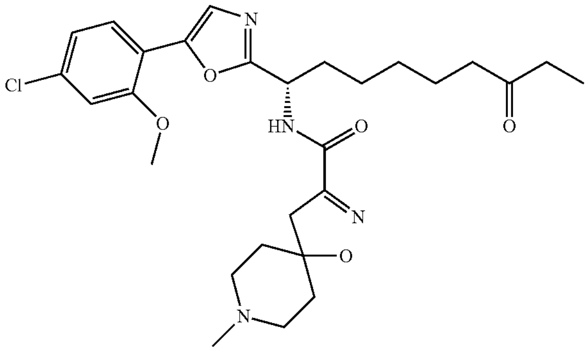 [SMILES: CCC(=O)CCCCC[C@H](NC(=O)C(=N)CC1(O)CCN(C)CC1)c1ncc(-c2ccc(Cl)cc2OC)o1] | 545.1 |
| 405 | 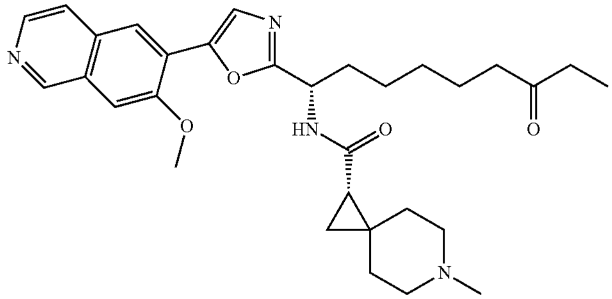 [SMILES: CCC(=O)CCCCC[C@H](NC(=O)[C@H]1CC12CCN(C)CC2)c1ncc(-c2cc3ccncc3cc2OC)o1] | 533.1 |

-continued

| ID | Structure | Observed $[M + H]^+$ |
|---|---|---|
| 406 | 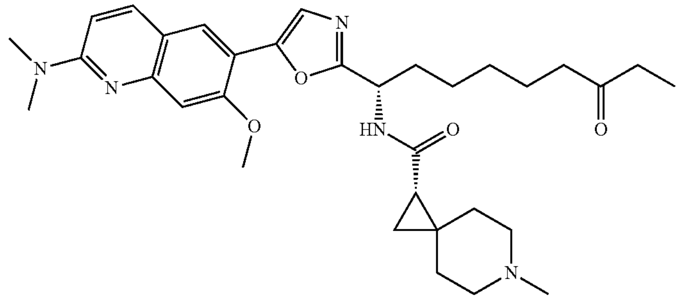 [SMILES: CCC(=O)CCCCC[C@H](NC(=O)[C@H]1CC12CCN(C)CC2)c1ncc(-c2cc3ccc(N(C)C)nc3cc2OC)o1] | 576.1 |

Example 69

(1S)-6-(cyclopropylmethyl)-N-{(1S)-1-[5-(7-methoxy-2-methylquinolin-6-yl)-1H-imidazol-2-yl]-7-oxononyl}-6-azaspiro[2.5]octane-1-carboxamide (187)

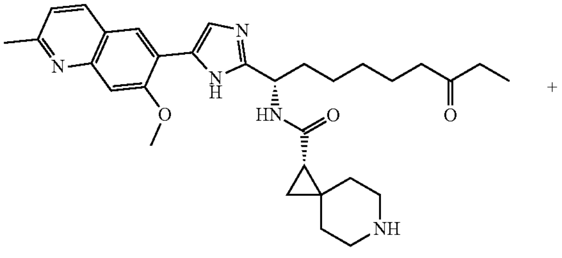

E21

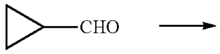

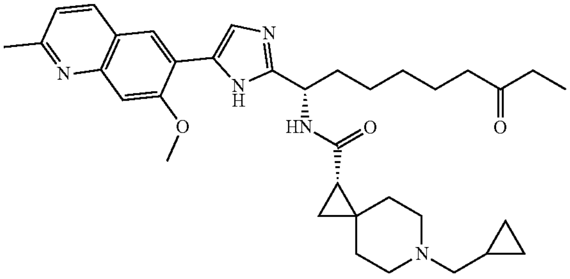

187

Cyclopropanecarbaldehyde (25 mg, 0.357 mmol) was added to a stirred mixture of (S)—N—((S)-1-(5-(7-methoxy-2-methylquinolin-6-yl)-1H-imidazol-2-yl)-7-oxononyl)-6-azaspiro[2.5]octane-1-carboxamide 2,2,2-trifluoroacetate (E21, 125 mg, 0.194 mmol) in MeOH (2 mL) and the mixture was stirred at room temperature for 1 h. Then, $NaBH(OAc)_3$ (123 mg, 0.581 mmol) was added and it was stirred at rt for 24 h. Water (5 mL) was added and the mixture was extracted with ethyl acetate (3×5 mL). The combined organic fractions were washed with aqueous $NaHCO_3$(saturated, 1×5 mL), dried ($Na_2SO_4$), filtered and the solvent was evaporated under reduced pressure. The residue was purified by preparative HPLC (reverse phase C-18 column), eluting with acetonitrile/water+0.05% $NH_3 \cdot H_2O$, to give (S)-6-(cyclopropylmethyl)-N—((S)-1-(5-(7-methoxy-2-methylquinolin-6-yl)-1H-imidazol-2-yl)-7-oxononyl)-6-azaspiro[2.5]octane-1-carboxamide (187).

L-(+)-tartaric acid (10 mg, 0.067 mmol) was added to a stirred mixture of (S)-6-(cyclopropylmethyl)-N—((S)-1-(5-(7-methoxy-2-methylquinolin-6-yl)-1H-imidazol-2-yl)-7-oxononyl)-6-azaspiro[2.5]octane-1-carboxamide (187, 50 mg, 0.085 mmol) in acetonitrile (2 mL) and water (2 mL) at room temperature and the mixture was made dry by lyophilization to give (S)-6-(cyclopropylmethyl)-N—((S)-1-(5-(7-methoxy-2-methylquinolin-6-yl)-1H-imidazol-2-yl)-7-oxononyl)-6-azaspiro[2.5]octane-1-carboxamide (2R,3R)-2,3-dihydroxysuccinate. LCMS (ESI) calc'd for $C_{35}H_{47}N_5O_3$ $[M+H]^+$: 586.4, found: 586.1. $^1H$ NMR (400 MHz, MeOD) δ 8.40 (brs, 1H), 8.23 (d, J=8.2 Hz, 1H), 7.65 (s, 1H), 7.43 (s, 1H), 7.34 (d, J=8.2 Hz, 1H), 5.07 (t, J=7.6 Hz, 1H), 4.45 (s, 2H), 4.10 (s, 3H), 3.50 (brs, 3H), 3.13 (brs, 2H), 2.71 (s, 4H), 2.38-2.50 (m, 4H), 1.73-2.35 (m, 6H), 1.08-1.68 (m, 9H), 0.98 (t, J=7.2 Hz, 4H), 0.72 (brs, 1H), 0.43 (brs, 2H), −0.03 (br s, 1H).

The following compounds were prepared using similar procedures as described for compound 187.

| ID | Structure | Observed [M + H]+ |
|---|---|---|
| 104 | 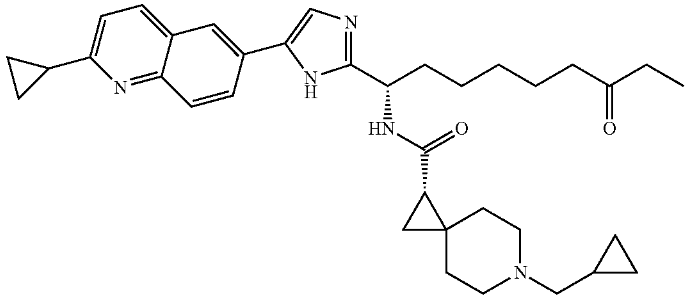 [SMILES: CCC(=O)CCCCC[C@H](NC(=O)[C@H]1CC12CCN(CC1CC1)CC2)c1ncc(-c2ccc3nc(C4CC4)ccc3c2)[nH]1] | 582.3 |
| 115 | 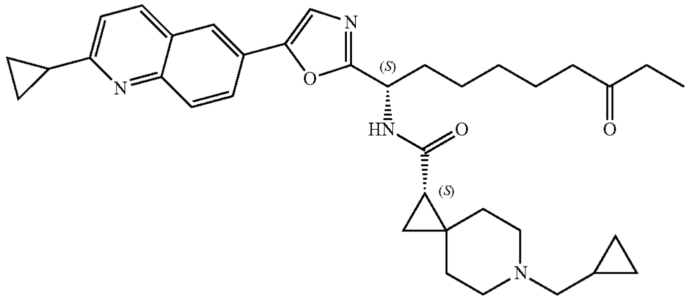 | 583.3 |
| 192 | 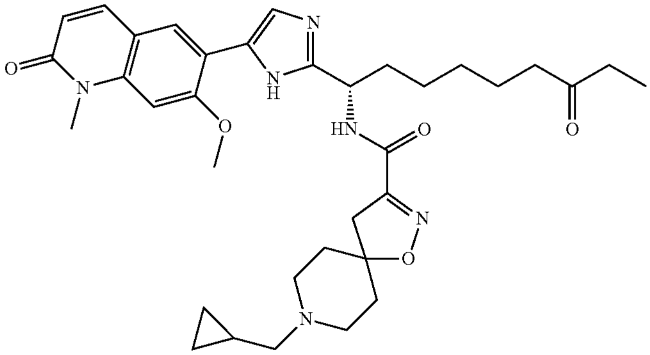 [SMILES: CCC(=O)CCCCC[C@H](NC(=O)C1=NOC2(CCN(CC3CC3)CC2)C1)c1ncc(-c2cc3ccc(=O)n(C)c3cc2OC)[nH]1] | 577.4 |
| 199 | 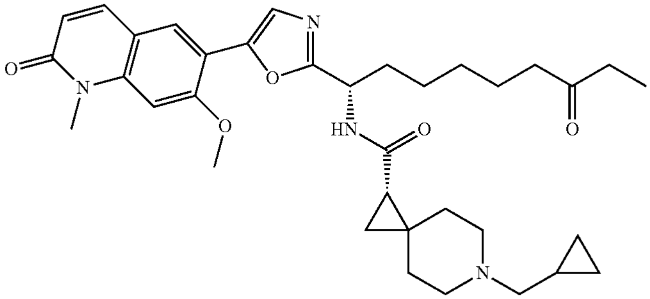 [SMILES: CCC(=O)CCCCC[C@H](NC(=O)[C@H]1CC12CCN(CC1CC1)CC2)c1ncc(-c2cc3ccc(=O)n(C)c3cc2OC)o1] | 603.1 |

-continued
| ID | Structure | Observed [M + H]+ |
|---|---|---|
| 219 | 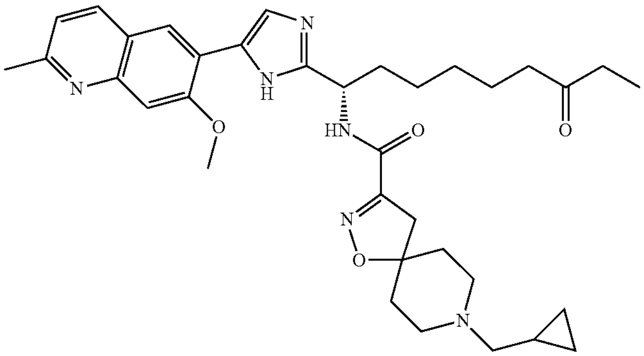 [SMILES: CCC(=O)CCCCC[C@H](NC(=O)C1=NOC2(CCN(CC3CC3)CC2)C1)c1ncc(-c2cc3ccc(C)nc3cc2OC)[nH]1] | 615.1 |
| 225 | 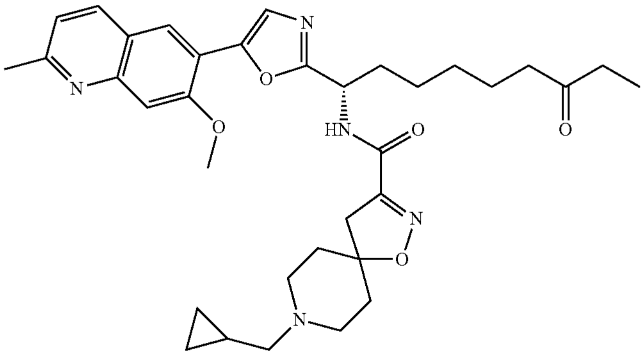 [SMILES: CCC(=O)CCCCC[C@H](NC(=O)C1=NOC2(CCN(CC3CC3)CC2)C1)c1ncc(-c2cc3ccc(C)nc3cc2OC)o1] | 616.4 |
| 228 | 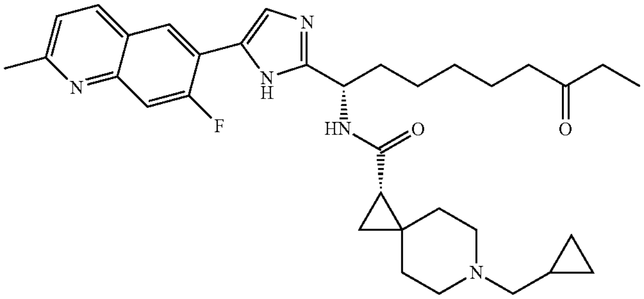 [SMILES: CCC(=O)CCCCC[C@H](NC(=O)[C@H]1CC12CCN(CC1CC1)CC2)c1ncc(-c2cc3ccc(C)nc3cc2F)[nH]1] | 574.1 |
| 229 | 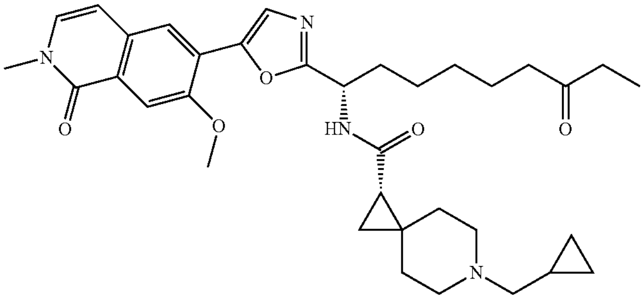 [SMILES: CCC(=O)CCCCC[C@H](NC(=O)[C@H]1CC12CCN(CC1CC1)CC2)c1ncc(-c2cc3ccn(C)c(=O)c3cc2OC)o1] | 603.2 |

-continued
| ID | Structure | Observed [M + H]+ |
| --- | --- | --- |
| 234 | 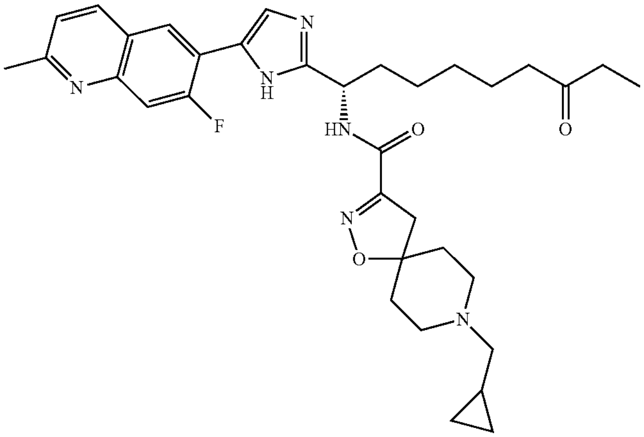 [SMILES: CCC(=O)CCCCC[C@H](NC(=O)C1=NOC2(CCN(CC3CC3)CC2)C1)c1ncc(-c2cc3ccc(C)nc3cc2F)[nH]1] | 603.1 |
| 236 | 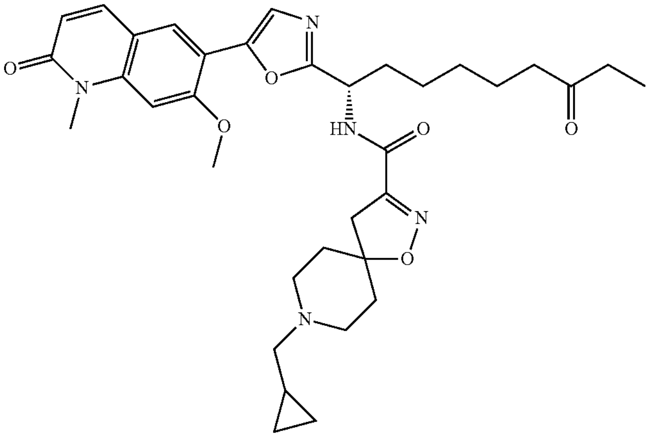 [SMILES: CCC(=O)CCCCC[C@H](NC(=O)C1=NOC2(CCN(CC3CC3)CC2)C1)c1ncc(-c2cc3ccc(=O)n(C)c3cc2OC)o1] | 632.1 |
| 387 | 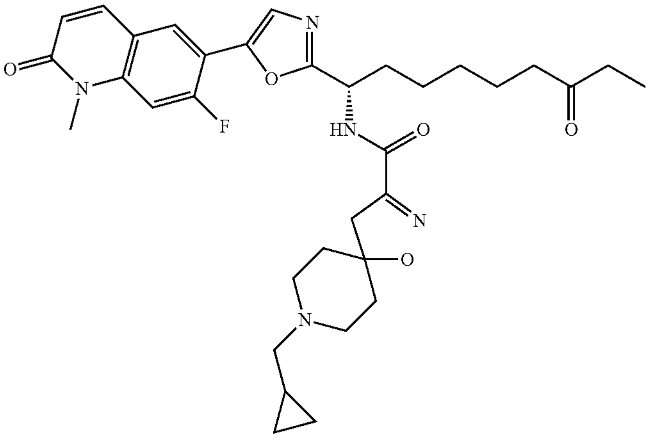 [SMILES: CCC(=O)CCCCC[C@H](NC(=O)C(=N)CC1(O)CCN(CC2CC2)CC1)c1ncc(-c2cc3ccc(=O)n(C)c3cc2F)o1] | 620.1 |

-continued
| ID | Structure | Observed [M + H]⁺ |
|---|---|---|
| 393 | 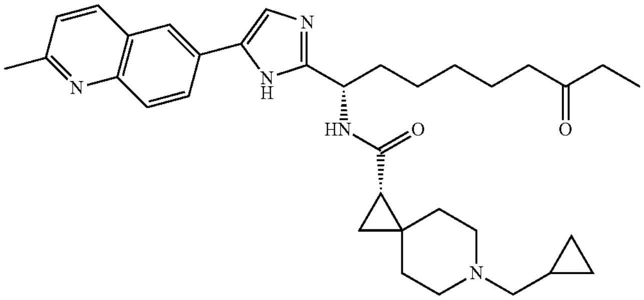 [SMILES: CCC(=O)CCCCC[C@H](NC(=O)[C@H]1CC12CCN(CC1CC1)CC2)c1ncc(-c2ccc3nc(C)ccc3c2)[nH]1] | 556.1 |
| 394 | 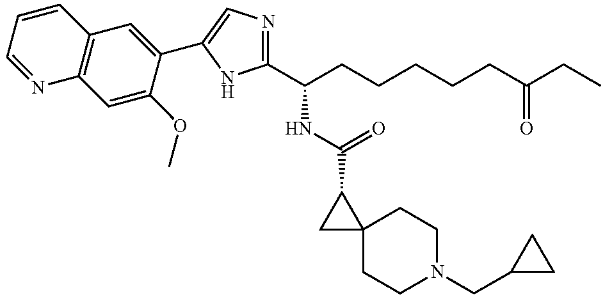 [SMILES: CCC(=O)CCCCC[C@H](NC(=O)[C@H]1CC12CCN(CC1CC1)CC2)c1ncc(-c2cc3cccnc3cc2OC)[nH]1] | 572.2 |
| 400 | 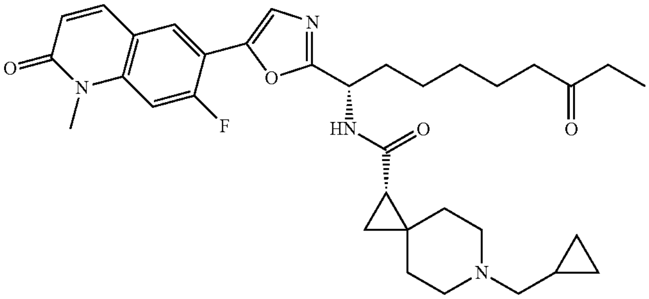 [SMILES: CCC(=O)CCCCC[C@H](NC(=O)[C@H]1CC12CCN(CC1CC1)CC2)c1ncc(-c2cc3ccc(=O)n(C)c3cc2F)o1] | 591.1 |
| 416 | 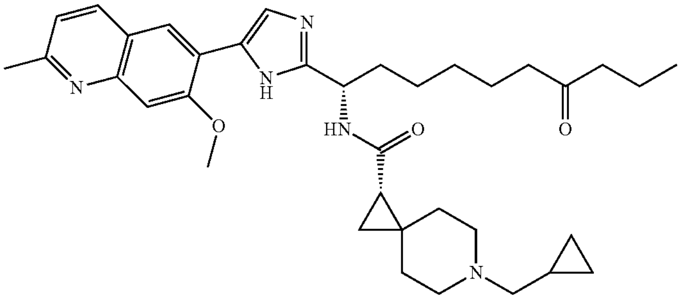 [SMILES: CCCC(=O)CCCCC[C@H](NC(=O)[C@H]1CC12CCN(CC1CC1)CC2)c1ncc(-c2cc3ccc(C)nc3cc2OC)[nH]1] | 600.4 |
| 422 | 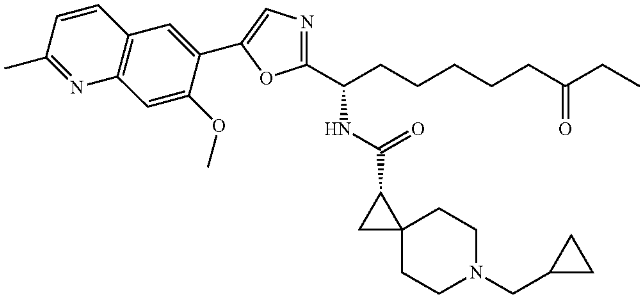 [SMILES: CCC(=O)CCCCC[C@H](NC(=O)[C@H]1CC12CCN(CC1CC1)CC2)c1ncc(-c2cc3ccc(C)nc3cc2OC)o1] | 587.1 |

-continued
| ID | Structure | Observed [M + H]+ |
|---|---|---|
| 293 | 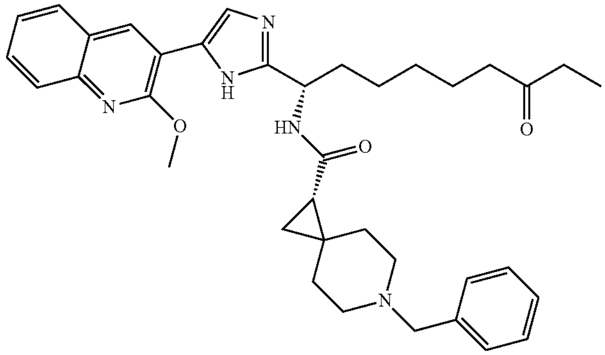 [SMILES: CCC(=O)CCCCC[C@H](NC(=O)[C@H]1CC12CCN(Cc1ccccc1)CC2)c1ncc(-c2cc3ccccc3nc2OC)[nH]1] | 608.4 |
| 294 | 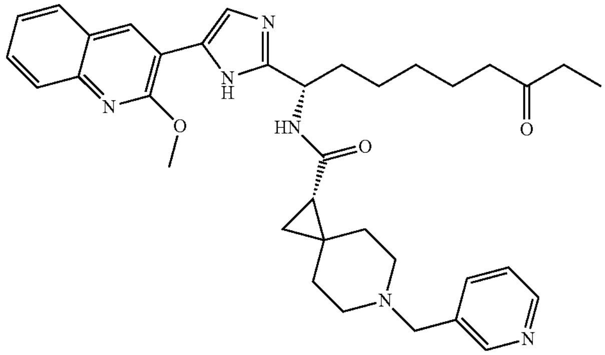 [SMILES: CCC(=O)CCCCC[C@H](NC(=O)[C@H]1CC12CCN(Cc1cccnc1)CC2)c1ncc(-c2cc3ccccc3nc2OC)[nH]1] | 609.4 |
| 295 | 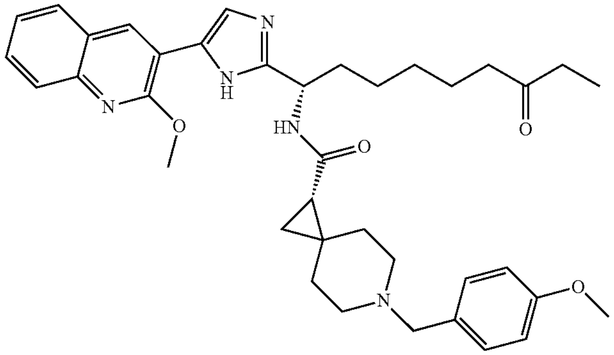 [SMILES: CCC(=O)CCCCC[C@H](NC(=O)[C@H]1CC12CCN(Cc1ccc(OC)cc1)CC2)c1ncc(-c2cc3ccccc3nc2OC)[nH]1] | 638.5 |
| 331 | 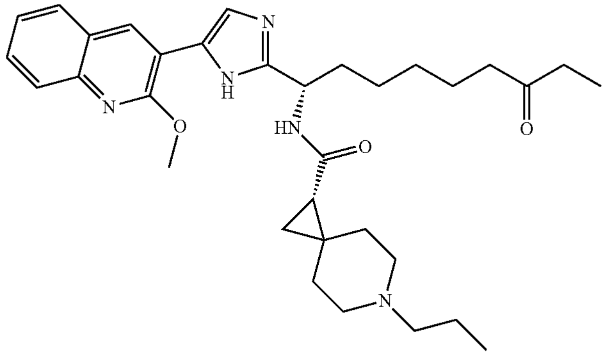 [SMILES: CCCN1CCC2(CC1)C[C@@H]2C(=O)N[C@@H](CCCCCC(=O)CC)c1ncc(-c2cc3ccccc3nc2OC)[nH]1] | 560.5 |

-continued
| ID | Structure | Observed [M + H]+ |
|---|---|---|
| 332 | 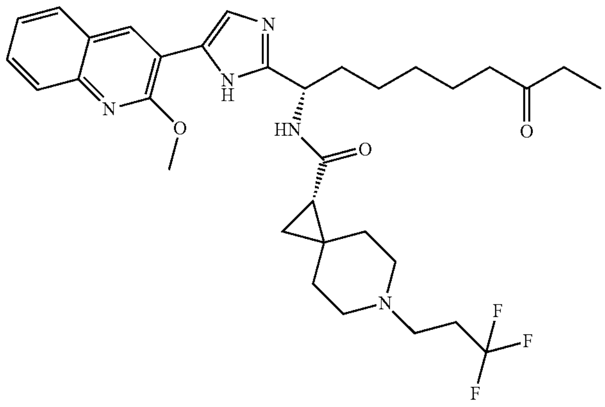 [SMILES: CCC(=O)CCCCC[C@H](NC(=O)[C@H]1CC12CCN(CCC(F)(F)F)CC2)c1ncc(-c2cc3ccccc3nc2OC)[nH]1] | 614.4 |
| 333 | 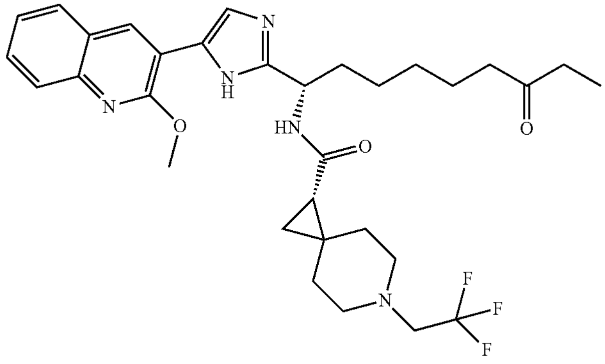 [SMILES: CCC(=O)CCCCC[C@H](NC(=O)[C@H]1CC12CCN(CC(F)(F)F)CC2)c1ncc(-c2cc3ccccc3nc2OC)[nH]1] | 600.5 |
| 335 | 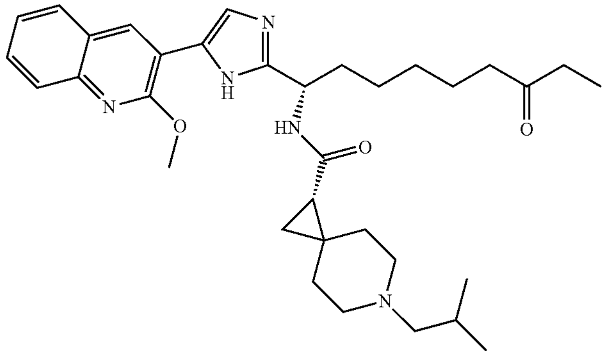 [SMILES: CCC(=O)CCCCC[C@H](NC(=O)[C@H]1CC12CCN(CC(C)C)CC2)c1ncc(-c2cc3ccccc3nc2OC)[nH]1] | 574.5 |
| 336 | 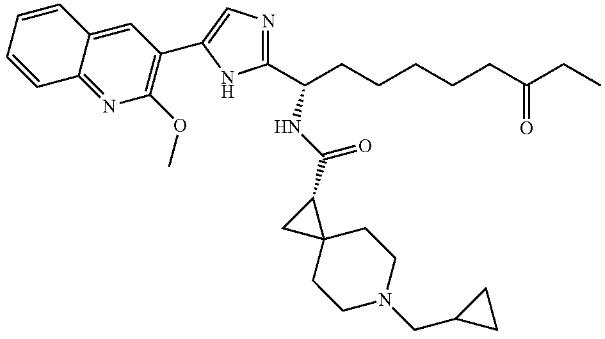 [SMILES: CCC(=O)CCCCC[C@H](NC(=O)[C@H]1CC12CCN(CC1CC1)CC2)c1ncc(-c2cc3ccccc3nc2OC)[nH]1] | 572.5 |

-continued
| ID | Structure | Observed [M + H]+ |
|---|---|---|
| 337 | 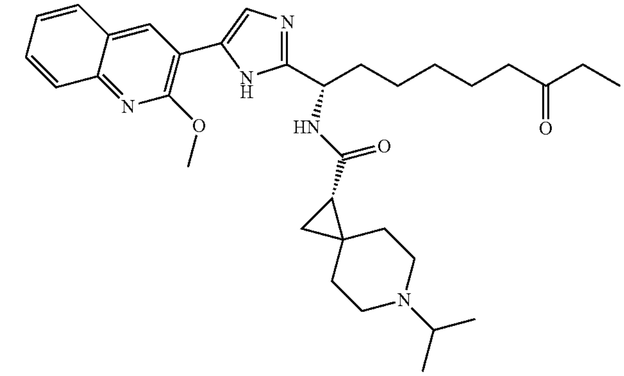 [SMILES: CCC(=O)CCCCC[C@H](NC(=O)[C@H]1CC12CCN(C(C)C)CC2)c1ncc(-c2cc3ccccc3nc2OC)[nH]1] | 560.2 |
| 359 | 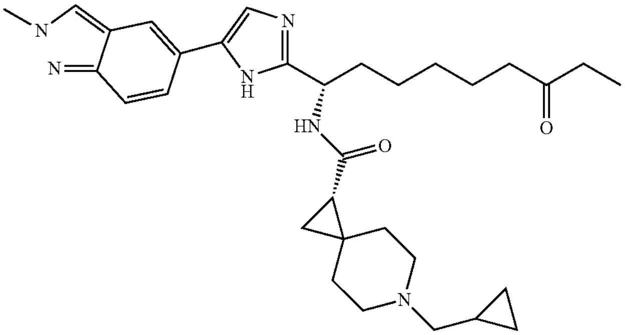 [SMILES: CCC(=O)CCCCC[C@H](NC(=O)[C@H]1CC12CCN(CC1CC1)CC2)c1ncc(C2=C/C(=C/NC)C(=N)C=C2)[nH]1] | 359 |
| 360 | 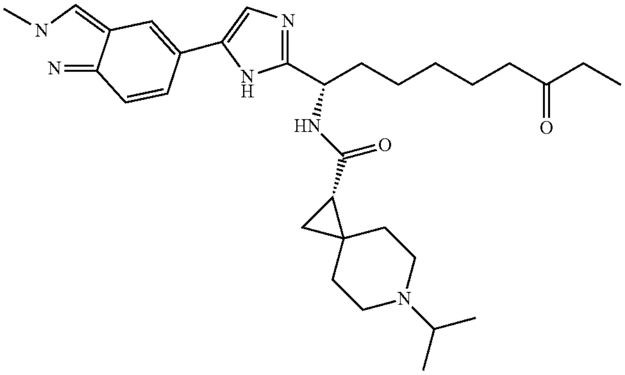 [SMILES: CCC(=O)CCCCC[C@H](NC(=O)[C@H]1CC12CCN(C(C)C)CC2)c1ncc(C2=C/C(=C/NC)C(=N)C=C2)[nH]1] | 360 |
| 361 | 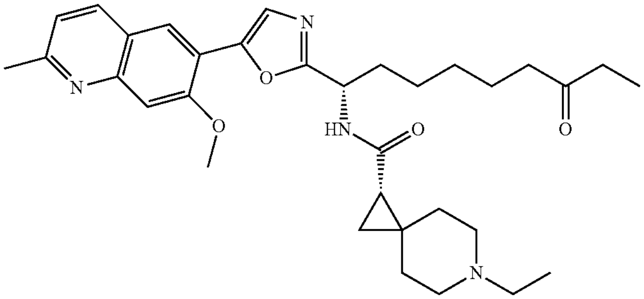 [SMILES: CCC(=O)CCCCC[C@H](NC(=O)[C@H]1CC12CCN(CC)CC2)c1ncc(-c2cc3ccc(C)nc3cc2OC)o1] | 361 |

Example 70

(1S)—N-{(1S)-8-cyclopropyl-1-[5-(7-methoxy-2-methylquinolin-6-yl)-1,3-oxazol-2-yl]-7-oxooctyl}-6-methyl-6-azaspiro[2.5]octane-1-carboxamide (195)

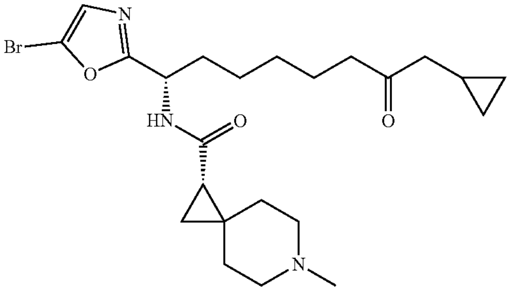

+

D11

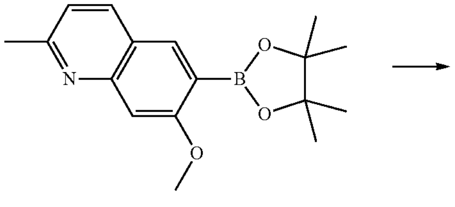

C1

-continued

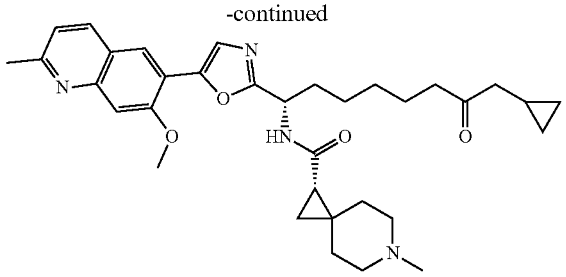

195

Potassium phosphate tribasic (60 mg, 0.283 mmol) and $PdCl_2$(DTBPF) (10 mg, 0.015 mmol) was added to the solution of (S)—N—((S)-1-(5-bromooxazol-2-yl)-8-cyclopropyl-7-oxooctyl)-6-methyl-6-azaspiro[2.5]octane-1-carboxamide (D11, 60 mg, 0.125 mmol) and 7-methoxy-2-methyl-6-(4,4,5,5-tetramethyl-1,3,2-dioxaborolan-2-yl) quinoline (C1, 50 mg, 0.167 mmol) in THF (1.5 mL) and water (0.1 mL), and the resultant mixture was stirred at 70° C. for 2 h. The reaction mixture was concentrated in vacuo. The residue was purified by preparative HPLC (reverse phase C-18 column), eluting with acetonitrile/water+0.05% $NH_3·H_2O$, to give (S)—N—((S)-8-cyclopropyl-1-(5-(7-methoxy-2-methylquinolin-6-yl)oxazol-2-yl)-7-oxooctyl)-6-methyl-6-azaspiro[2.5]octane-1-carboxamide (195).

The free base was dissolved in water (2 mL) and MeCN (1 mL), L-tartaric acid (7 mg) was added to the solution and the resultant mixture was lyophilized to give the tartaric salt. LCMS (ESI) calc'd for $C_{34}H_{44}N_4O_4$ $[M+H]^+$: 573.3, found: 573.1. $^1H$ NMR (400 MHz, MeOD) δ 8.15-8.28 (m, 2H), 7.55 (s, 1H), 7.40 (s, 1H), 7.30 (d, J=8.41 Hz, 1H), 5.05-5.17 (m, 1H), 5.05-5.16 (m, 1H), 4.41 (s, 4H), 4.07 (s, 3H), 2.78 (brs, 3H), 2.66 (s, 3H), 2.46 (t, J=7.04 Hz, 2H), 2.23 (d, J=7.04 Hz, 2H), 1.70-2.08 (m, 6H), 1.12-1.62 (m, 10H), 0.78-1.04 (m, 3H), 0.37-0.50 (m, 2H), −0.11-0.08 (m, 3H).

The following compounds were prepared using similar procedures as described for compound 195.

| ID | Structure | Observed $[M + H]^+$ |
|---|---|---|
| 77 | 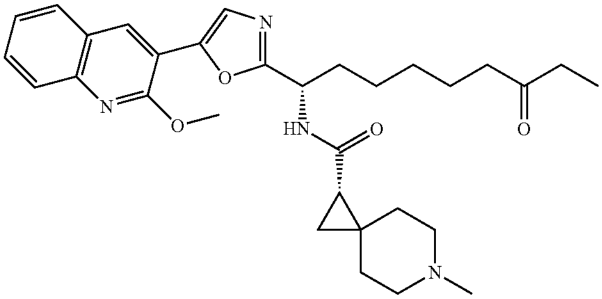 [SMILES: CCC(=O)CCCCC[C@H](NC(=O)[C@H]1CC12CCN(C)CC2)c1ncc(-c2cc3ccccc3nc2OC)o1] | 533.3 |
| 79 | 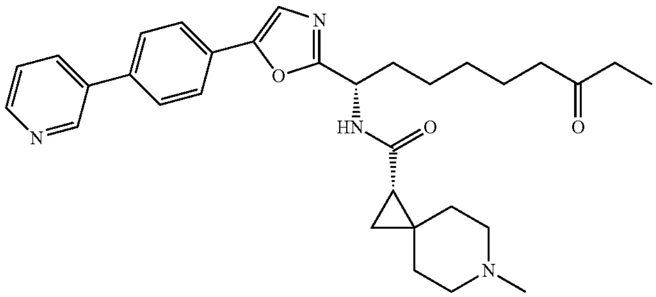 [SMILES: CCC(=O)CCCCC[C@H](NC(=O)[C@H]1CC12CCN(C)CC2)c1ncc(-c2ccc(-c3cccnc3)cc2)o1] | 529.3 |

-continued
| ID | Structure | Observed [M + H]+ |
|---|---|---|
| 93 | 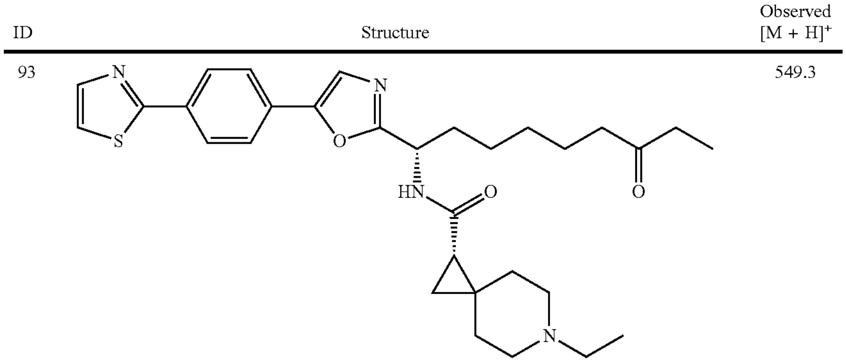 | 549.3 |
| 94 | 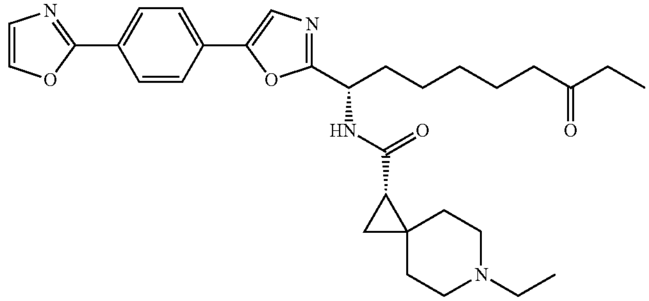 [SMILES: CCC(=O)CCCCC[C@H](NC(=O)[C@H]1CC12CCN(CC)CC2)c1ncc(-c2ccc(-c3nccs3)cc2)o1] | 533.3 |
| 95 | 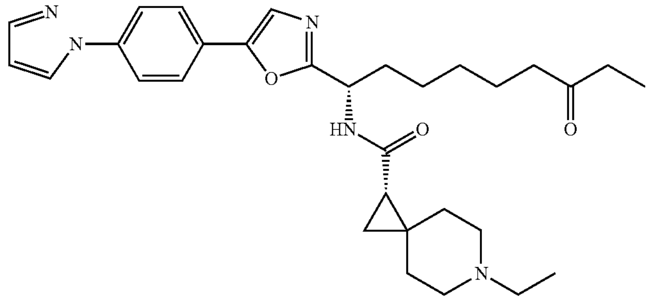 [SMILES: CCC(=O)CCCCC[C@H](NC(=O)[C@H]1CC12CCN(CC)CC2)c1ncc(-c2ccc(N/C=C\C=N)cc2)o1] | 532.3 |
| 109 | 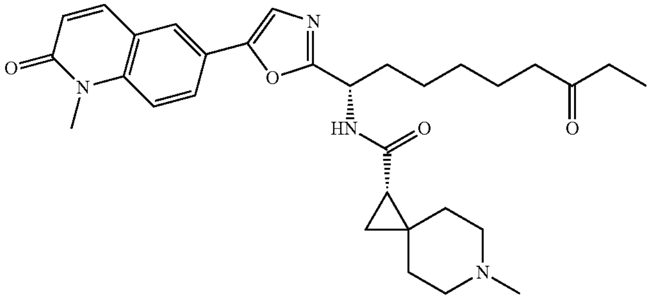 [SMILES: CCC(=O)CCCCC[C@H](NC(=O)[C@H]1CC12CCN(C)CC2)c1ncc(-c2ccc3c(ccc(=O)n3C)c2)o1] | 533.3 |
| 111 | 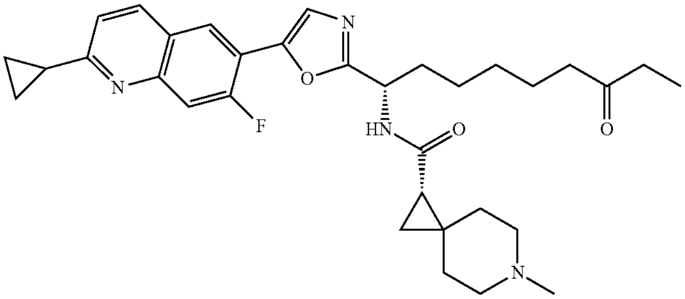 [SMILES: CCC(=O)CCCCC[C@H](NC(=O)[C@H]1CC12CCN(C)CC2)c1ncc(-c2cc3ccc(C4CC4)nc3cc2F)o1] | 561.3 |

-continued
| ID | Structure | Observed $[M + H]^+$ |
|---|---|---|
| 121 | 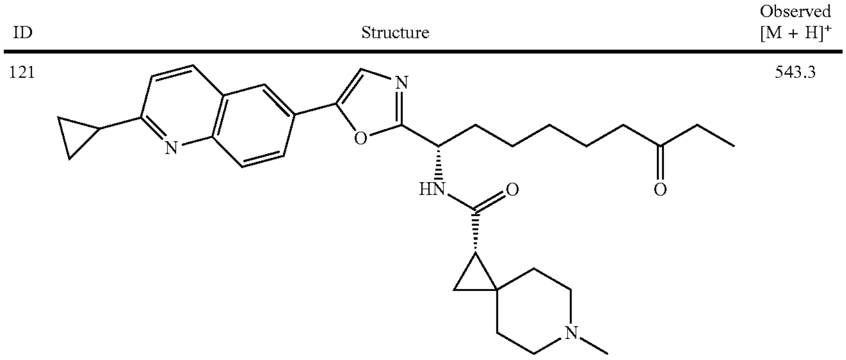 | 543.3 |
| 153 | 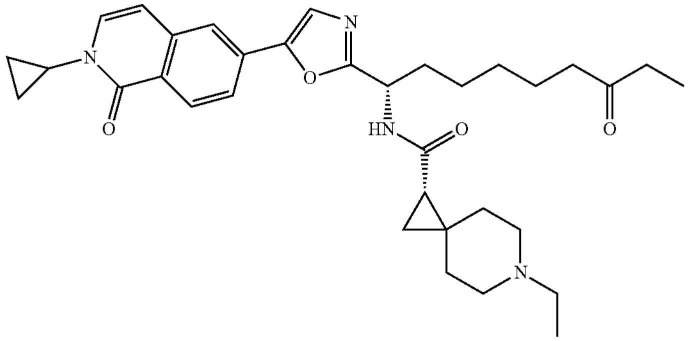 [SMILES: CCC(=O)CCCCC[C@H](NC(=O)[C@H]1CC12CCN(CC)CC2)c1ncc(-c2ccc3c(=O)n(C4CC4)ccc3c2)o1] | 573.4 |
| 162 | 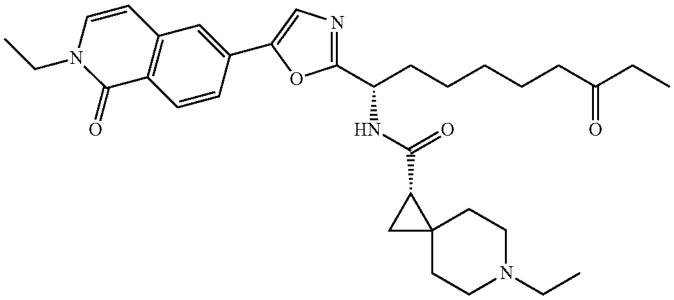 [SMILES: CCC(=O)CCCCC[C@H](NC(=O)[C@H]1CC12CCN(CC)CC2)c1ncc(-c2ccc3c(=O)n(CC)ccc3c2)o1] | 561.4 |
| 164 | 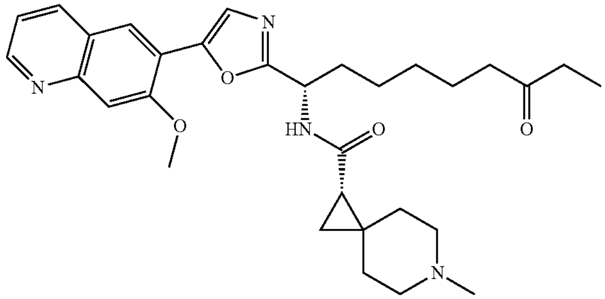 [SMILES: CCC(=O)CCCCC[C@H](NC(=O)[C@H]1CC12CCN(C)CC2)c1ncc(-c2cc3cccnc3cc2OC)o1] | 533.1 |
| 167 | 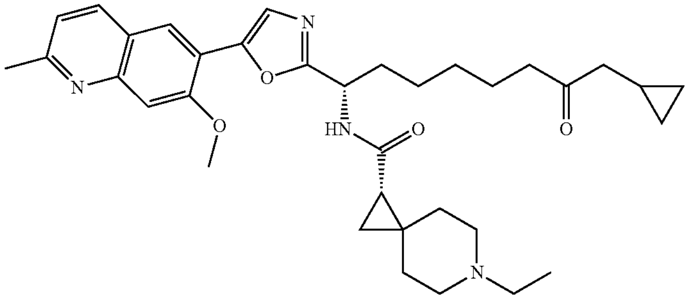 [SMILES: CCN1CCC2(CC1)C[C@@H]2C(=O)N[C@@H](CCCCCC(=O)CC1CC1)c1ncc(-c2cc3ccc(C)nc3cc2OC)o1] | 587.3 |

-continued
| ID | Structure | Observed [M + H]+ |
|---|---|---|
| 168 | 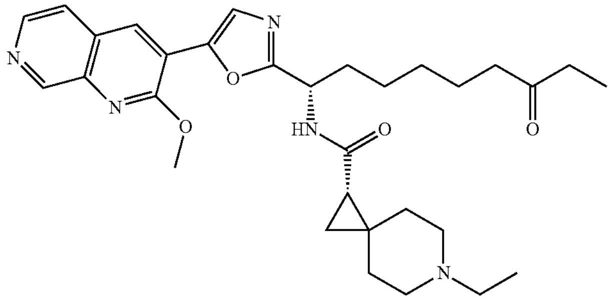 [SMILES: CCC(=O)CCCCC[C@H](NC(=O)[C@H]1CC12CCN(CC)CC2)c1ncc(-c2cc3ccncc3nc2OC)o1] | 548.1 |
| 169 | 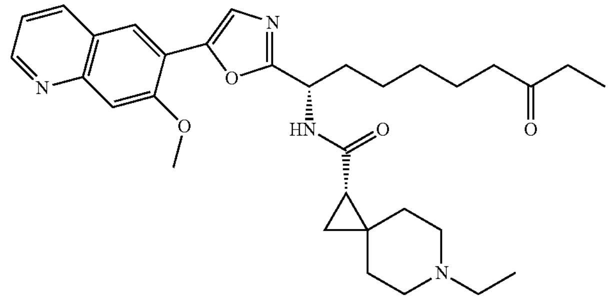 [SMILES: CCC(=O)CCCCC[C@H](NC(=O)[C@H]1CC12CCN(CC)CC2)c1ncc(-c2cc3cccnc3cc2OC)o1] | 547.4 |
| 171 | 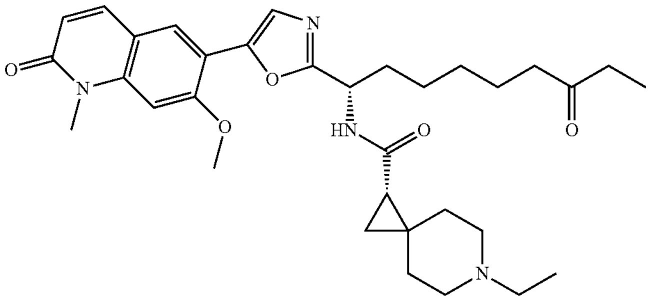 [SMILES: CCC(=O)CCCCC[C@H](NC(=O)[C@H]1CC12CCN(CC)CC2)c1ncc(-c2cc3ccc(=O)n(C)c3cc2OC)o1] | 577.3 |
| 173 | 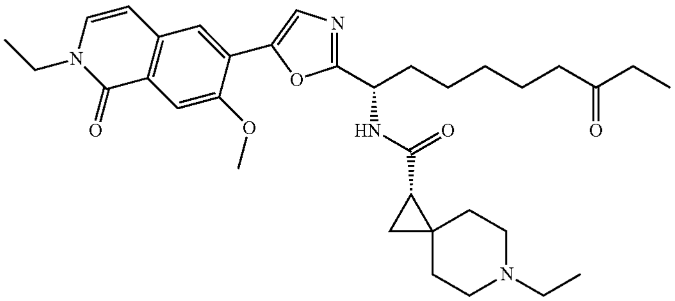 [SMILES: CCC(=O)CCCCC[C@H](NC(=O)[C@H]1CC12CCN(CC)CC2)c1ncc(-c2cc3ccn(CC)c(=O)c3cc2OC)o1] | 591.2 |
| 189 | 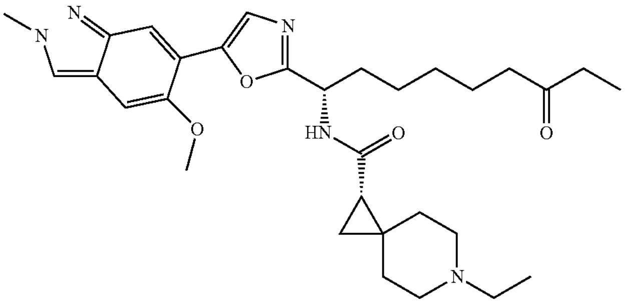 [SMILES: CCC(=O)CCCCC[C@H](NC(=O)[C@H]1CC12CCN(CC)CC2)c1ncc(C2=CC(=N)/C(=C\NC)C=C2OC)o1] | 550.1 |

-continued
| ID | Structure | Observed [M + H]+ |
|---|---|---|
| 389 | 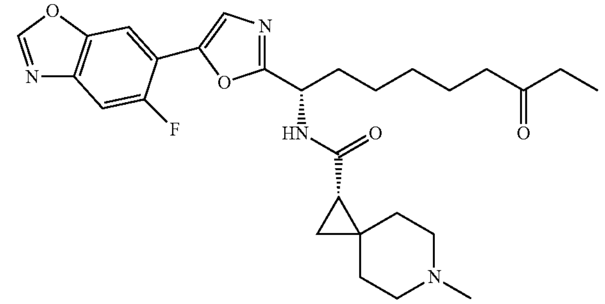 [SMILES: CCC(=O)CCCCC[C@H](NC(=O)[C@H]1CC12CCN(C)CC2)c1ncc(-c2cc3ocnc3cc2F)o1] | 511.2 |
| 397 | 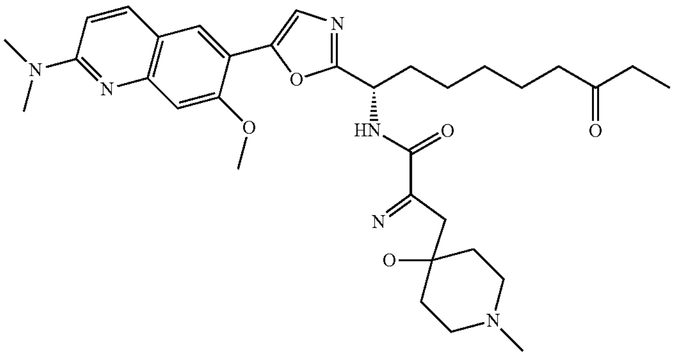 [SMILES: CCC(=O)CCCCC[C@H](NC(=O)C(=N)CC1(O)CCN(C)CC1)c1ncc(-c2cc3ccc(N(C)C)nc3cc2OC)o1] | 605.1 |
| 408 | 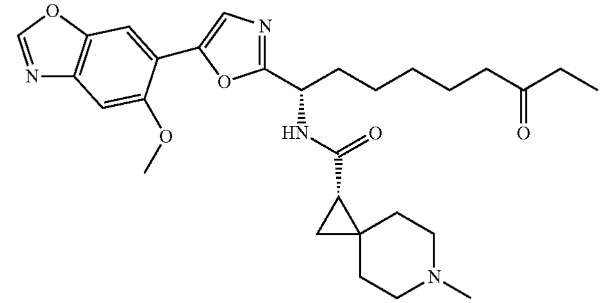 [SMILES: CCC(=O)CCCCC[C@H](NC(=O)[C@H]1CC12CCN(C)CC2)c1ncc(-c2cc3ocnc3cc2OC)o1] | 523.1 |
| 415 | 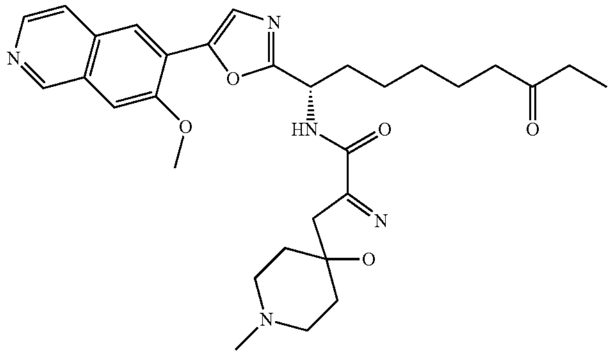 [SMILES: CCC(=O)CCCCC[C@H](NC(=O)C(=N)CC1(O)CCN(C)CC1)c1ncc(-c2cc3ccncc3cc2OC)o1] | 562.1 |

Example 71

8-methyl-N-[(1S)-7-oxo-1-(5-quinolin-6-yl-1H-imidazol-2-yl)nonyl]-8-azaspiro[bicyclo[3.2.1]octane-3,1'-cyclopropane]-2'-carboxamide (166 & 242)

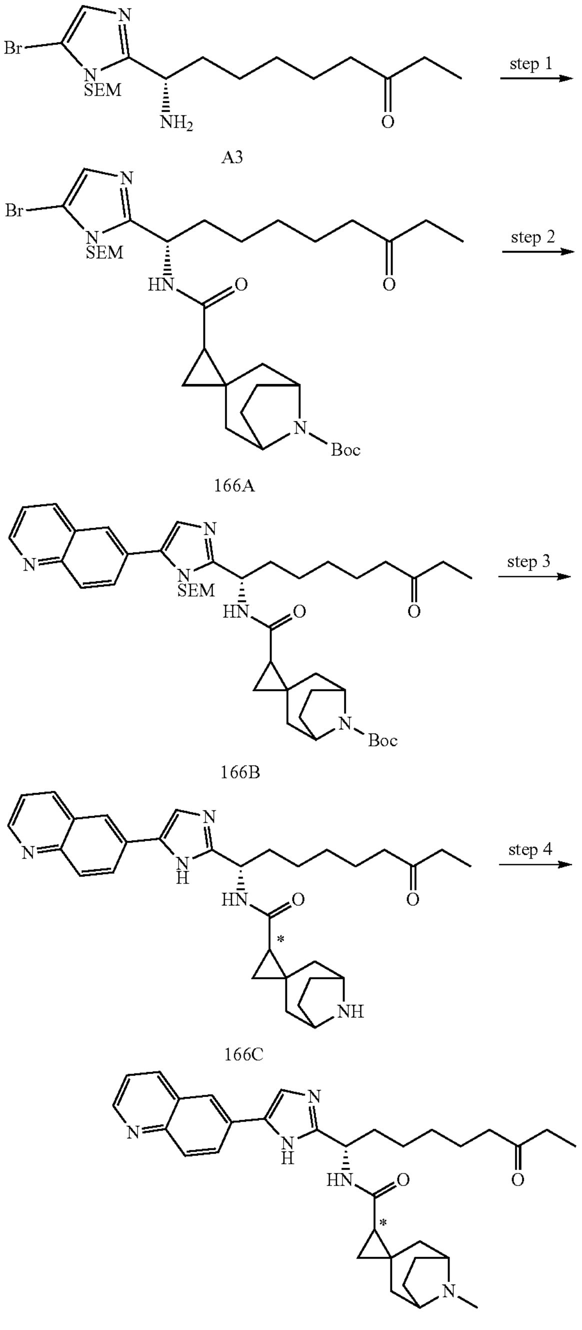

Step 1: Preparation of tert-butyl 2'-(((S)-1-(5-bromo-1-((2-(trimethylsilyl)ethoxy)methyl)-1H-imidazol-2-yl)-7-oxononyl)carbamoyl)-8-azaspiro[bicyclo[3.2.1]octane-3,1'-cyclopropane]-8-carboxylate (166A): $T_3P$ (3.70 g, 5.82 mmol) was added to a stirred mixture of (S)-9-amino-9-(5-bromo-1-((2-(trimethylsilyl)ethoxy)methyl)-1H-imidazol-2-yl)nonan-3-one (A3, 1.677 g, 3.88 mmol), DIPEA (2.0 mL, 11.45 mmol), and 8-(tert-butoxycarbonyl)-8-azaspiro[bicyclo[3.2.1]octane-3,1'-cyclopropane]-2'-carboxylic acid (B7, 1.091 g, 3.88 mmol) in DMF (10 mL) at room temperature and the mixture was stirred at room temperature for 12 h. The mixture was diluted with ethyl acetate (20 mL), washed with brine (saturated, 3×20 mL), dried ($Na_2SO_4$), filtered and the solvent was evaporated under reduced pressure. The residue was purified by silica gel column flash chromatography, eluting with EtOAc/petroleum ether=0-50% to give tert-butyl 2'-(((S)-1-(5-bromo-1-((2-(trimethylsilyl)ethoxy)methyl)-1H-imidazol-2-yl)-7-oxononyl)carbamoyl)-8-azaspiro[bicyclo[3.2.1]octane-3,1'-cyclopropane]-8-carboxylate (166A). LCMS (ESI) calc'd for $C_{33}H_{55}BrN_4O_5Si$ $[M+H]^+$: 695.3, found: 697.4. $^1H$ NMR (400 MHz, $CDCl_3$) δ 6.90 (d, J=5.5 Hz, 1H), 5.50-5.71 (m, 2H), 5.03-5.15 (m, 2H), 4.26 (brs, 2H), 3.42-3.61 (m, 3H), 2.30-2.53 (m, 5H), 1.71-1.99 (m, 7H), 1.55 (brs, 2H), 1.46 (d, J=13.3 Hz, 8H), 1.27 (t, J=7.2 Hz, 5H), 1.04 (t, J=7.2 Hz, 4H), 0.72-0.96 (m, 4H), −0.13-0.09 (m, 9H).

Step 2: Preparation of tert-butyl 2'-(((S)-7-oxo-1-(5-(quinolin-6-yl)-1-((2-(trimethylsilyl)ethoxy)methyl)-1H-imidazol-2-yl)nonyl)carbamoyl)-8-azaspiro[bicyclo[3.2.1]octane-3,1'-cyclopropane]-8-carboxylate (166B): $PdCl_2$ (DTBPF) (0.141 g, 0.216 mmol) was added to a stirred mixture of $K_3PO_4$ (1.373 g, 6.47 mmol), 6-(4,4,5,5-tetramethyl-1,3,2-dioxaborolan-2-yl)quinoline (0.6 g, 2.352 mmol), and tert-butyl 2'-(((S)-1-(5-bromo-1-((2-(trimethylsilyl)ethoxy)methyl)-1H-imidazol-2-yl)-7-oxononyl)carbamoyl)-8-azaspiro[bicyclo[3.2.1]octane-3,1'-cyclopropane]-8-carboxylate (166A, 1.5 g, 2.156 mmol) in water (2 mL)/THF (10 mL) at room temperature and the mixture was stirred at 70° C. for 8 h under $N_2$. The mixture was cooled, diluted with ethyl acetate (20 mL), washed with brine (saturated, 3×15 mL), dried ($Na_2SO_4$), filtered and the solvent was evaporated under reduced pressure. The residue was purified by preparative HPLC, eluting with acetonitrile/water+0.1% TFA, to give tert-butyl 2'-(((S)-7-oxo-1-(5-(quinolin-6-yl)-1-((2-(trimethylsilyl)ethoxy)methyl)-1H-imidazol-2-yl)nonyl)carbamoyl)-8-azaspiro[bicyclo[3.2.1]octane-3,1'-cyclopropane]-8-carboxylate (166B). LCMS (ESI) calc'd for $C_{42}H_{61}N_5O_5Si$ $[M+H]^+$: 744.4, found: 744.4.

Step 3: Preparation of N—((S)-7-oxo-1-(5-(quinolin-6-yl)-1H-imidazol-2-yl)nonyl)-8-azaspiro[bicyclo[3.2.1]octane-3,1'-cyclopropane]-2'-carboxamide (166C): TFA (5 mL, 64.9 mmol) was added to a stirred mixture of tert-butyl 2'-(((S)-7-oxo-1-(5-(quinolin-6-yl)-1-((2-(trimethylsilyl)ethoxy)methyl)-1H-imidazol-2-yl)nonyl)carbamoyl)-8-azaspiro[bicyclo[3.2.1]octane-3,1'-cyclopropane]-8-carboxylate (166B, 1.05 g, 1.411 mmol) in DCM (5 mL) at room temperature and the mixture was stirred at room temperature for 13 h. Most of the DCM was removed, and the residue was purified by preparative HPLC, eluting with acetonitrile/water+0.1% TFA, to give N—((S)-7-oxo-1-(5-(quinolin-6-yl)-1H-imidazol-2-yl)nonyl)-8-azaspiro[bicyclo[3.2.1]octane-3,1'-cyclopropane]-2'-carboxamide (166C, two isomers). LCMS (ESI) calc'd for $C_{37}H_{53}N_5O_3Si$ $[M+H]^+$: 514.3, found: 514.4.

Step 4: Preparation of 8-methyl-N—((S)-7-oxo-1-(5-(quinolin-6-yl)-1H-imidazol-2-yl)nonyl)-8-azaspiro[bicyclo[3.2.1]octane-3,1'-cyclopropane]-2'-carboxamide (166): Formaldehyde (1.0 mL, 13.43 mmol) was added to the solution of N—((S)-7-oxo-1-(5-(quinolin-6-yl)-1H-imidazol-2-yl)nonyl)-8-azaspiro[bicyclo[3.2.1]octane-3,1'-cyclopropane]-2'-carboxamide (166C, second peak on HPLC, 190 mg, 0.370 mmol) in MeOH (5 mL) and stirred at 20° C. for 2 h, then sodium triacetoxyborohydride (78 mg, 0.370 mmol) was added to the reaction mixture, stirred at 20° C. for 1 h. The mixture was quenched with aqueous $NaHCO_3$ (saturated, 20 mL), and the mixture was extracted with ethyl acetate (2×30 mL). The combined organic fractions were washed with brine (saturated, 10 mL), dried ($Na_2SO_4$), filtered and the solvent was evaporated under reduced pressure. The residue was purified by preparative HPLC (reverse phase C-18 column), eluting with acetonitrile/water+0.05% $NH_3 \cdot H_2O$, to give 8-methyl-N—((S)-7-oxo-1-(5-(quinolin-6-yl)-1H-imidazol-2-yl)nonyl)-8-azaspiro[bicyclo[3.2.1]octane-3,1'-cyclopropane]-2'-carboxamide (166). $^1H$ NMR (400 MHz, MeOD) δ 8.74-8.81 (m, 1H), 8.77 (brs, 1H), 8.77 (dd, J=1.65, 4.30 Hz, 1H), 8.37 (d, J=7.94 Hz, 1H), 8.32-8.41 (m, 1H), 8.24 (s, 1H), 8.14 (dd, J=1.76, 8.82 Hz, 1H), 8.01 (d, J=8.82 Hz, 1H), 7.49-7.57 (m, 2H), 5.02 (t, J=7.50 Hz, 1H), 3.22 (brs, 2H), 2.36-2.47 (m, 2H), 2.28 (s, 3H), 1.71-2.09 (m, 6H), 1.50-1.61 (m, 2H), 1.24-1.47 (m, 6H), 0.87-1.11 (m, 4H).

Compound 242 was prepared using the same procedures as above, but using the compound from first peak in HPLC. $^1H$ NMR (400 MHz, MeOD) δ 8.77 (d, J=2.87 Hz, 1H), 8.36 (d, J=8.16 Hz, 1H), 8.25 (s, 1H), 8.13 (d, J=9.04 Hz, 1H), 8.00 (d, J=8.82 Hz, 1H), 7.48-7.58 (m, 2H), 5.04 (t, J=7.39 Hz, 1H), 3.48-3.68 (m, 1H), 3.14-3.25 (m, 1H), 2.44 (tt, J=3.64, 7.28 Hz, 4H), 2.31 (s, 3H), 1.78-2.12 (m, 7H), 1.57 (t, J=6.84 Hz, 2H), 1.27-1.50 (m, 7H), 0.90-1.08 (m, 5H).

Example 72

(1S)—N-[(1S)-1-{5-[2-methoxy-7-(1,3-oxazol-2-yl)quinolin-3-yl]-1H-imidazol-2-yl}-7-oxononyl]-6-methyl-6-azaspiro[2.5]octane-1-carboxamide (175)

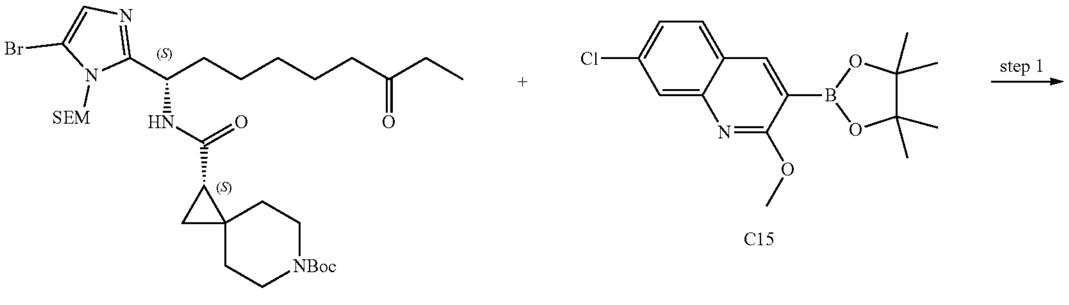

D1

C15

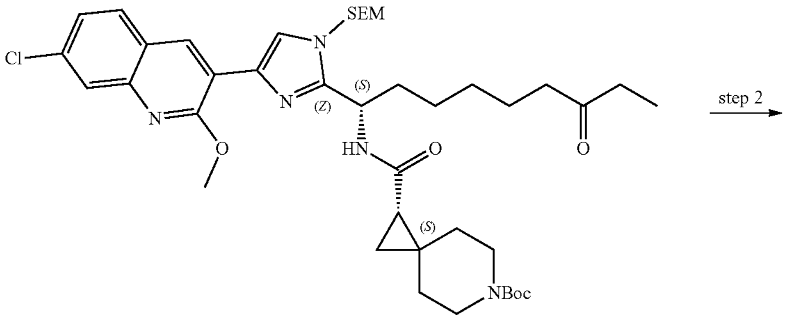

175A

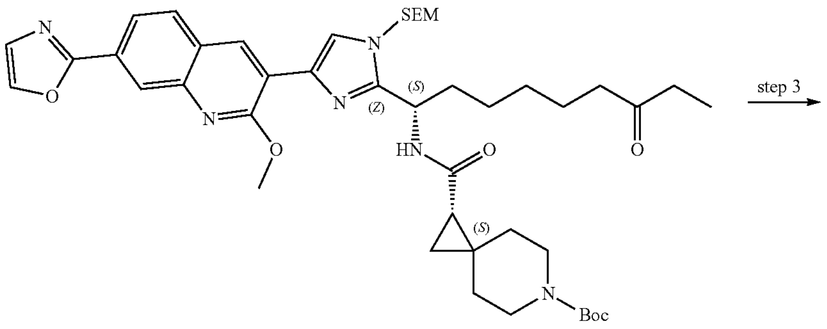

175B

-continued

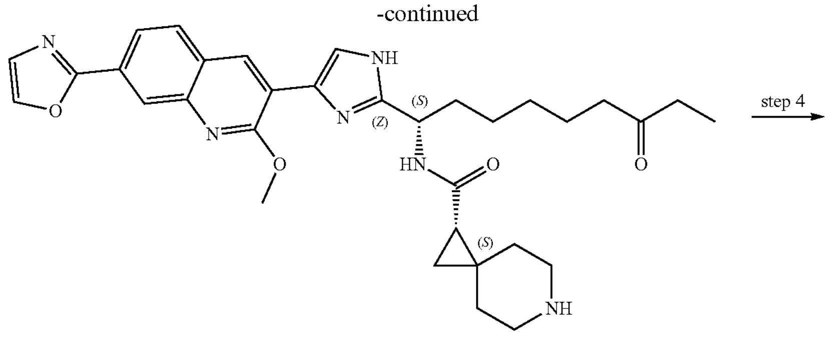

175D

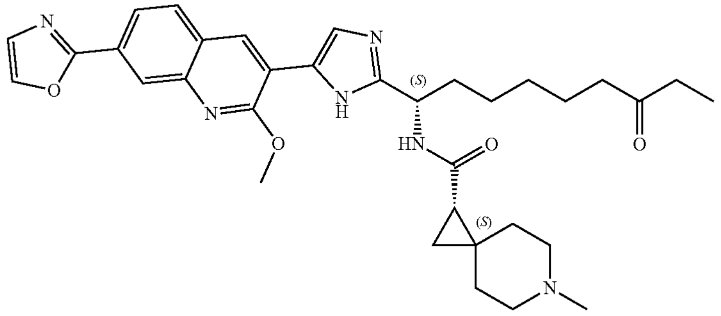

175

Step 1: Preparation of (S)-tert-butyl 1-(((S)-1-(4-(7-chloro-2-methoxyquinolin-3-yl)-1-((2-(trimethylsilyl)ethoxy)methyl)-1H-imidazol-2-yl)-7-oxononyl)carbamoyl)-6-azaspiro[2.5]octane-6-carboxylate (175A): A mixture of Pd(DTBPF)$Cl_2$ (0.109 g, 2.06 mmol), $K_3PO_4$ (0.996 g, 4.70 mmol), 7-chloro-2-methoxy-3-(4,4,5,5-tetramethyl-1,3,2-dioxaborolan-2-yl)quinoline (C15, 0.900 g 2.82 mmol) and (S)-tert-butyl 1-(((S)-1-(4-bromo-1-((2-(trimethylsilyl)ethoxy)methyl)-1H-imidazol-2-yl)-7-oxononyl)carbamoyl)-6-azaspiro[2.5]octane-6-carboxylate (D1, 1.380 g, 2.06 mmol) in toluene/water was degassed and backfilled with $N_2$. The mixture was heated to 80° C. and stirred for 3 h. The precipitate was filtered off, the filtrate was concentrated, and the residue was purified by chromatography on silica gel with petroleum ether/EtOAc=5:1 to obtain (S)-tert-butyl 1-(((S)-1-(4-(7-chloro-2-methoxyquinolin-3-yl)-1-((2-(trimethylsilyl)ethoxy)methyl)-1H-imidazol-2-yl)-7-oxononyl)carbamoyl)-6-azaspiro[2.5]octane-6-carboxylate (175A). LCMS (ESI) calc'd for $C_{41}H_{60}ClN_5O_6Si$ $[M+H]^+$: 782.5, found: 782.5.

Step 2: Preparation of (S)-tert-butyl 1-(((S)-1-(5-(2-methoxy-7-(oxazol-2-yl)quinolin-3-yl)-1-((2-(trimethylsilyl)ethoxy)methyl)-1H-imidazol-2-yl)-7-oxononyl)carbamoyl)-6-azaspiro[2.5]octane-6-carboxylate (175B): A mixture of (S)-tert-butyl 1-(((S)-1-(4-(7-chloro-2-methoxyquinolin-3-yl)-1-((2-(trimethylsilyl)ethoxy)methyl)-1H-imidazol-2-yl)-7-oxononyl)carbamoyl)-6-azaspiro[2.5]octane-6-carboxylate (175A, 300 mg, 0.383 mmol), 2-(tributylstannyl)oxazole (165 mg, 0.460 mmol), $K_3PO_4$ (163 mg, 0.767 mmol) and XPhos-Pd-G2 (31 mg, 0.039 mmol) in toluene (4 mL) was degassed and backfilled with $N_2$ three times. The mixture was heated at 85° C. for 18 h. The mixture was filtered and the filter cake was washed with ethyl acetate (20 mL). The filtrate was concentrated to dryness. The residue was purified by silica gel flash chromatography (ISCORF75; Sepa flash column), eluting with DCM/MeOH=100:1-9:1 to give (S)-tert-butyl 1-(((S)-1-(5-(2-methoxy-7-(oxazol-2-yl)quinolin-3-yl)-1-((2-(trimethylsilyl)ethoxy)methyl)-1H-imidazol-2-yl)-7-oxononyl)carbamoyl)-6-azaspiro[2.5]octane-6-carboxylate (175B). LCMS (ESI) calc'd for $C_{44}H_{62}N_6O_7Si$ $[M+H]^+$: 815.4, found: 815.5.

Step 3: Preparation of (S)—N—((S)-1-(4-(2-methoxy-7-(oxazol-2-yl)quinolin-3-yl)-1H-imidazol-2-yl)-7-oxononyl)-6-azaspiro[2.5]octane-1-carboxamide (175C): A mixture of (S)-tert-butyl 1-(((5)-1-(4-(2-methoxy-7-(oxazol-2-yl)quinolin-3-yl)-1-((2-(trimethylsilyl)ethoxy)methyl)-1H-imidazol-2-yl)-7-oxononyl)carbamoyl)-6-azaspiro[2.5]octane-6-carboxylate (175B, 100 mg, 0.123 mmol) in TFA (2 mL, 26.9 mmol) at rt was stirred at room temperature for 1 h. The mixture was concentrated to give (S)—N—((S)-1-(4-(2-methoxy-7-(oxazol-2-yl)quinolin-3-yl)-1H-imidazol-2-yl)-7-oxononyl)-6-azaspiro[2.5]octane-1-carboxamide (175C) which was used directly to next step. LCMS (ESI) calc'd for $C_{33}H_{40}N_6O_4$ $[M+H]^+$: 585.3, found: 585.4.

Step 4: Preparation of (S)—N—((S)-1-(5-(2-methoxy-7-(oxazol-2-yl)quinolin-3-yl)-1H-imidazol-2-yl)-7-oxononyl)-6-methyl-6-azaspiro[2.5]octane-1-carboxamide (175): Formaldehyde (103 mg, 1.368 mmol) was added to a stirred mixture of (S)—N—((S)-1-(4-(2-methoxy-7-(oxazol-2-yl)quinolin-3-yl)-1H-imidazol-2-yl)-7-oxononyl)-6-azaspiro[2.5]octane-1-carboxamide (175C, 80 mg, 0.137 mmol) in MeOH (5 mL) at rt and the mixture was stirred at room temperature for 10 min. Then, sodium triacetoxyhydroborate (87 mg, 0.410 mmol) was added. The mixture was stirred at rt for 30 min. Aqueous $NaHCO_3$(saturated, 2 mL) was added and the mixture was extracted with ethyl acetate (3x3 mL). The combined organic fractions were washed with brine (saturated, 1x3 mL), dried ($Na_2SO_4$), filtered and the residue was purified by preparative HPLC (reverse phase C-18 column), eluting with acetonitrile/water+0.1% TFA, to give (S)—N—((S)-1-(5-(2-methoxy-7-(oxazol-2-yl)quinolin-3-yl)-1H-imidazol-2-yl)-7-oxononyl)-6-methyl-6-azaspiro[2.5]octane-1-carboxamide (175). LCMS (ESI) calc'd for $C_{34}H_{42}N_6O_4$ $[M+H]^+$: 599.3, found: 599.4. $^1H$ NMR (400 MHz, MeOD) δ 8.59-8.77 (m, 1H), 8.42-8.51 (m, 1H), 8.03-8.15 (m, 2H), 7.88-8.02 (m, 2H), 7.36-7.42 (m, 1H), 4.98-5.19 (m, 1H), 4.19-4.28 (m, 3H), 3.37-3.55 (m, 2H), 2.98-3.26 (m, 3H), 2.71-2.88 (m, 1H), 2.71-2.88

(m, 3H), 2.35-2.51 (m, 4H), 1.97-2.27 (m, 3H), 1.74-1.95 (m, 3H), 1.49-1.62 (m, 3H), 1.15-1.42 (m, 5H), 0.93-1.06 (m, 4H).
Example 73
(1S)—N-[(1S)-1-{5-[2-methoxy-7-(1H-pyrazol-1-yl)quinolin-3-yl]-1H-imidazol-2-yl}-7-oxononyl]-6-methyl-6-azaspiro[2.5]octane-1-carboxamide (176)
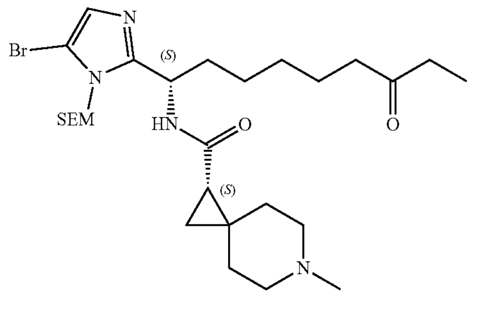
D4
+
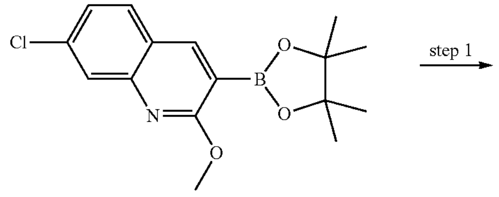
C15
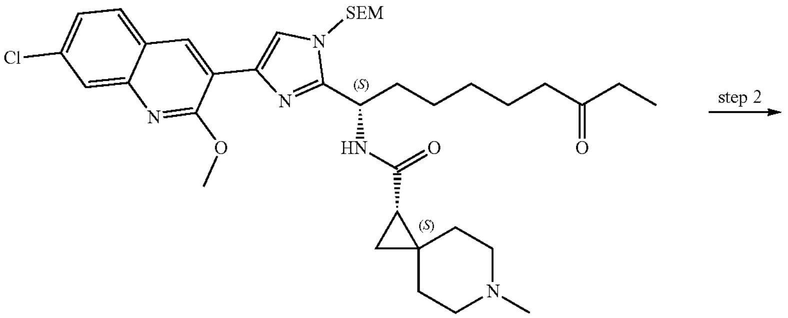
176A
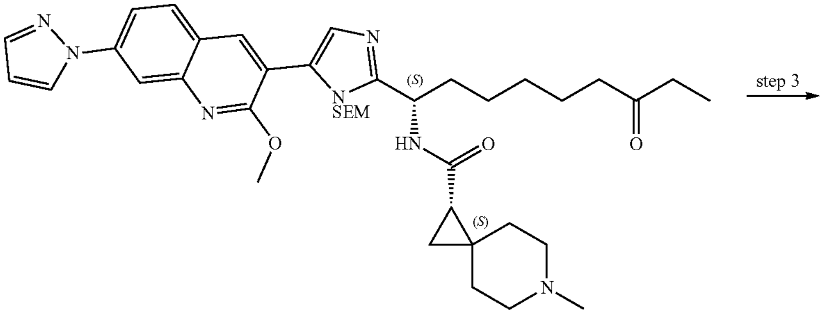
176B
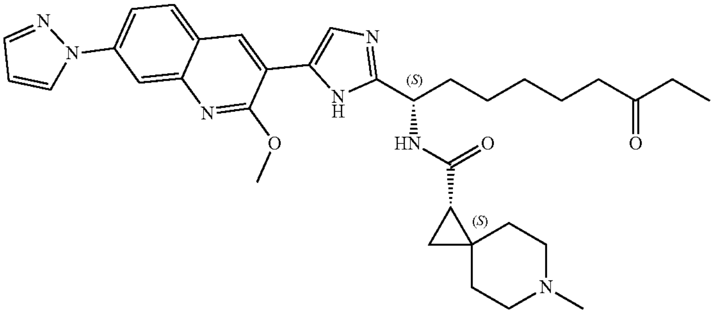
176

Step 1: Preparation of (S)—N—((S)-1-(4-(7-chloro-2-methoxyquinolin-3-yl)-1-((2-(trimethylsilyl) ethoxy) methyl)-1H-imidazol-2-yl)-7-oxononyl)-6-methyl-6-azaspiro[2.5]octane-1-carboxamide (176A): A mixture of 7-chloro-2-methoxy-3-(4,4,5,5-tetramethyl-1,3,2-dioxaborolan-2-yl)quinoline (C15, 600 mg, 1.877 mmol), (S)—N—((S)-1-(5-bromo-1-((2-(trimethylsilyl)ethoxy)methyl)-1H-imidazol-2-yl)-7-oxononyl)-6-methyl-6-azaspiro[2.5] octane-1-carboxamide (D4, 1.205 g, 2.065 mmol), $K_3PO_4$ (996 mg, 4.69 mmol) and $PdCl_2$(DTBPF) (122 mg, 0.188 mmol) in THF (5 mL) and water (0.5 mL) was degassed and backfilled with $N_2$ three times. The mixture was heated at 80° C. for 10 h. The mixture was cooled to rt, water (10 mL) was added and the mixture was extracted with ethyl acetate (3×10 mL). The combined organic fractions were washed with brine (saturated, 10 mL), dried ($Na_2SO_4$), filtered and the solvent was evaporated under reduced pressure. The residue was purified by preparative HPLC (reverse phase C-18 column), eluting with acetonitrile/water+0.1% TFA, to give (S)—N—((S)-1-(4-(7-chloro-2-methoxyquinolin-3-yl)-1-((2-(trimethylsilyl)ethoxy)methyl)-1H-imidazol-2-yl)-7-oxononyl)-6-methyl-6-azaspiro[2.5]octane-1-carboxamide (176A). LCMS (ESI) calc'd for $C_{37}H_{54}ClN_5O_4Si$ $[M+H]^+$: 696.3, found: 696.1. $^1H$ NMR (400 MHz, $CDCl_3$) δ 9.06-9.25 (m, 1H), 7.77-7.89 (m, 1H), 7.69-7.77 (m, 1H), 7.60-7.69 (m, 1H), 7.35-7.42 (m, 1H), 5.89-6.02 (m, 1H), 5.34-5.43 (m, 1H), 4.95-5.07 (m, 1H), 4.14-4.27 (m, 3H), 3.61-3.72 (m, 2H), 3.22-3.32 (m, 1H), 2.69-2.79 (m, 1H), 2.28-2.46 (m, 6H), 2.16-2.28 (m, 3H), 1.91-2.04 (m, 2H), 1.50-1.69 (m, 1H), 1.18-1.43 (m, 6H), 0.86-1.09 (m, 8H), −0.01-0.02 (m, 9H).

Step 2: Preparation of (S)—N—((S)-1-(4-(2-methoxy-7-(1H-pyrazol-1-yl)quinolin-3-yl)-1-((2-(trimethylsilyl) ethoxy)methyl)-1H-imidazol-2-yl)-7-oxononyl)-6-methyl-6-azaspiro[2.5]octane-1-carboxamide (176B): A mixture of (S)—N—((S)-1-(4-(7-chloro-2-methoxyquinolin-3-yl)-1-((2-(trimethylsilyl)ethoxy)methyl)-1H-imidazol-2-yl)-7-oxononyl)-6-methyl-6-azaspiro[2.5]octane-1-carboxamide (176A, 110 mg, 0.158 mmol), tBuXPhos-Pd-G1 (10.85 mg, 0.016 mmol), $Cs_2CO_3$ (154 mg, 0.474 mmol) and 1H-pyrazole (22 mg, 0.323 mmol) in dioxane (2 mL) was degassed and backfilled with $N_2$ three times. The mixture was heated at 100° C. for 22 h. The residue was purified by preparative HPLC (reverse phase C-18 column), eluting with acetonitrile/water+0.1% TFA, to give (S)—N—((S)-1-(4-(2-methoxy-7-(1H-pyrazol-1-yl)quinolin-3-yl)-1-((2-(trimethylsilyl)ethoxy)methyl)-1H-imidazol-2-yl)-7-oxononyl)-6-methyl-6-azaspiro[2.5]octane-1-carboxamide (176B). LCMS (ESI) calc'd for $C_{40}H_{57}N_7O_4Si$ $[M+H]^+$: 728.4, found: 728.3.

Step 3: Preparation of (S)—N—((S)-1-(5-(2-methoxy-7-(1H-pyrazol-1-yl)quinolin-3-yl)-1H-imidazol-2-yl)-7-oxononyl)-6-methyl-6-azaspiro[2.5]octane-1-carboxamide (176): A stirred mixture of (S)—N—((S)-1-(5-(2-methoxy-7-(1H-pyrazol-1-yl)quinolin-3-yl)-1-((2-(trimethylsilyl) ethoxy)methyl)-1H-imidazol-2-yl)-7-oxononyl)-6-methyl-6-azaspiro[2.5]octane-1-carboxamide (176B, 20 mg, 0.027 mmol) in TFA (1 mL) was stirred at room temperature for 1 h. The residue was concentrated and purified by preparative HPLC (reverse phase C-18 column), eluting with acetonitrile/water+0.1% TFA, to give (S)—N—((S)-1-(5-(2-methoxy-7-(1H-pyrazol-1-yl)quinolin-3-yl)-1H-imidazol-2-yl)-7-oxononyl)-6-methyl-6-azaspiro[2.5]octane-1-carboxamide (176). LCMS (ESI) calc'd for $C_{34}H_{43}N_7O_3$ $[M+H]^+$: 598.3, found: 598.4. $^1H$ NMR (400 MHz, MeOD) δ 8.57-8.73 (m, 1H), 8.40-8.51 (m, 1H), 8.10-8.24 (m, 1H), 7.87-8.01 (m, 3H), 7.75-7.82 (m, 1H), 6.54-6.63 (m, 1H), 5.03-5.14 (m, 1H), 4.16-4.30 (m, 3H), 3.37-3.53 (m, 2H), 2.98-3.26 (m, 3H), 2.72-2.89 (m, 3H), 2.36-2.49 (m, 4H), 1.97-2.28 (m, 3H), 1.76-1.94 (m, 3H), 1.51-1.63 (m, 3H), 1.18-1.40 (m, 5H), 0.92-1.09 (m, 4H).

Example 74

(1S)—N-{(1S)-7-oxo-1-[5-(9-prop-2-en-1-yl-1,2,3,4-tetrahydro-1,4-epiminonaphthalen-6-yl)-1H-imidazol-2-yl]nonyl}-6-prop-2-en-1-yl-6-azaspiro[2.5]octane-1-carboxamide (179)

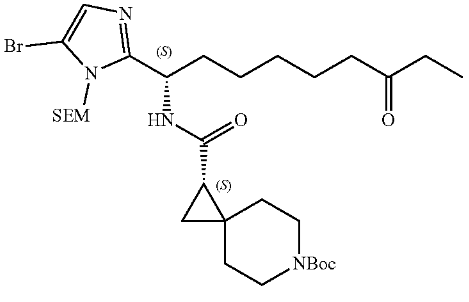

D1

+

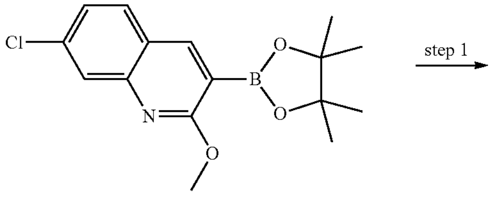

C15

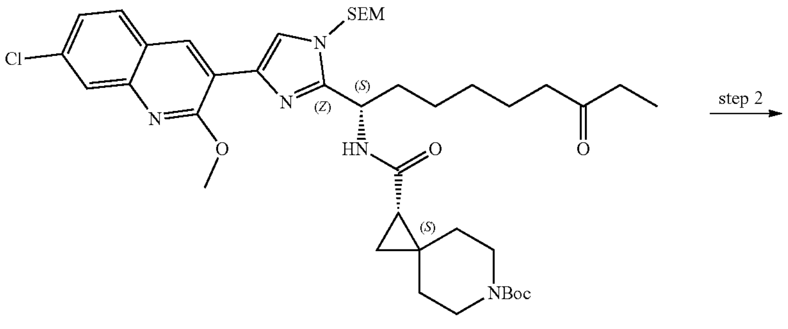

175A

-continued

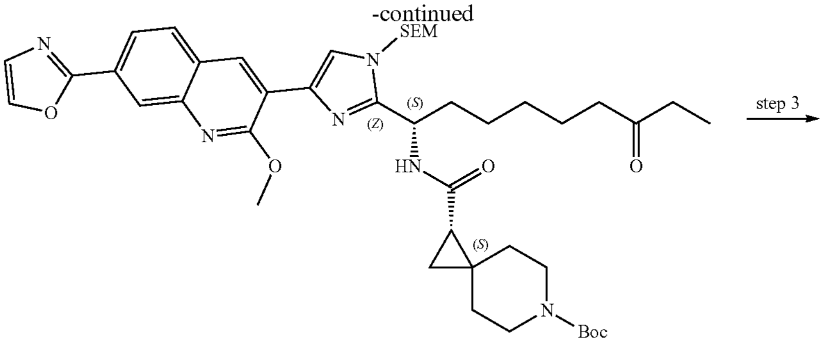

175B

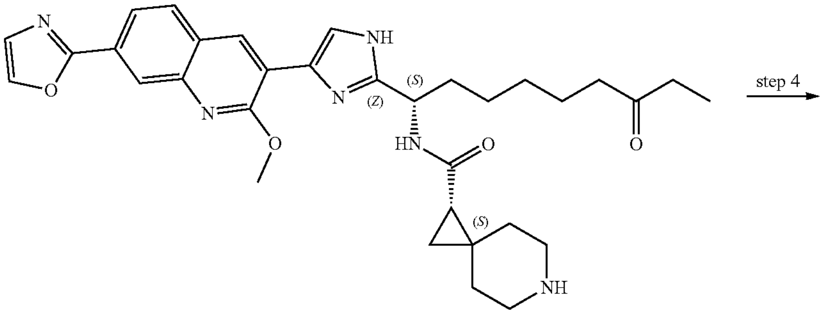

175D

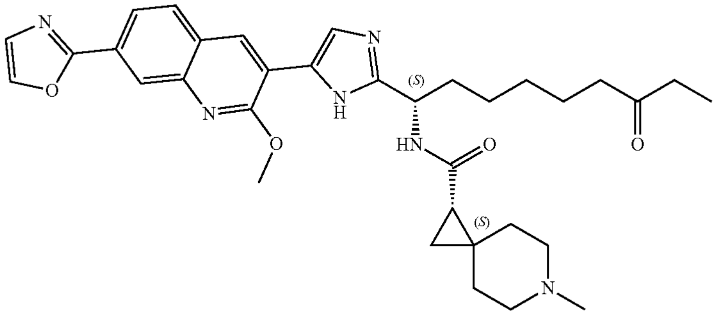

175

Step 1: Preparation of tert-butyl 6-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (179A): $PdCl_2$(DTBPF) (36.0 mg, 0.055 mmol) was added to a stirred mixture of (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (D1, 370 mg, 0.552 mmol), tert-butyl 6-(4,4,5,5-tetramethyl-1,3,2-dioxaborolan-2-yl)-1,2,3,4-tetrahydro-1,4-epiminonaphthalene-9-carboxylate (C29, 220 mg, 0.593 mmol) and $K_2CO_3$ (229 mg, 1.657 mmol) in THF (5.0 mL) and water (0.5 mL) at room temperature under $N_2$ atmosphere and the mixture was stirred at 65° C. for 16 h, then cooled to room temperature and concentrated. The residue was purified by silica gel column flash chromatography, eluting with petroleum ether:EtOAc=1.5:1 to give tert-butyl 6-(2-((S)-1-((S)-6-(tert-butoxy carbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (179A). LCMS (ESI) calc'd for $C_{46}H_{71}N_5O_7Si$ $[M+H]^+$: 834.5, found: 834.7.

Step 2: Preparation of (1S)—N-((1S)-7-oxo-1-(5-(1,2,3,4-tetrahydro-1,4-epiminonaphthalen-6-yl)-1-((2-(trimethylsilyl)ethoxy)methyl)-1H-imidazol-2-yl)nonyl)-6-azaspiro[2.5]octane-1-carboxamide (179B): HCl/MeOH (2.0 mL, 8.00 mmol) was added to a stirred mixture of tert-butyl 6-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (179A, 380 mg, 0.456 mmol) in MeOH (5.0 mL) at room temperature and the mixture was stirred at rt for 1 h. Then the mixture was concentrated at room temperature, adjusted to pH 9 with $NaHCO_3$ solution, and the mixture was extracted with ethyl acetate (2x20 mL). The combined organic fractions were washed with brine (saturated, 10 mL), dried ($Na_2SO_4$), filtered and the solvent was evaporated under reduced pressure to give (1S)—N-((1S)-7-oxo-1-(5-(1,2,3,4-tetrahydro-1,4-epiminonaphthalen-6-yl)-1-((2-(trimethylsilyl)ethoxy)methyl)-1H-imidazol-2-yl)nonyl)-6-azaspiro[2.5]octane-1-carboxamide (179B). LCMS (ESI) calc'd for $C_{36}H_{55}N_5O_3Si$ $[M+H]^+$: 634.4, found: 634.5.

Step 3: Preparation of (1S)-6-allyl-N-((1S)-1-(5-(9-allyl-1,2,3,4-tetrahydro-1,4-epiminonaphthalen-6-yl)-1-((2-(trimethylsilyl)ethoxy)methyl)-1H-imidazol-2-yl)-7-oxononyl)-6-azaspiro[2.5]octane-1-carboxamide (179C):

DIEA (0.207 ml, 1.183 mmol) was added to a stirred mixture of (1S)—N-((1S)-7-oxo-1-(5-(1,2,3,4-tetrahydro-1,4-epiminonaphthalen-6-yl)-1-((2-(trimethylsilyl)ethoxy)methyl)-1H-imidazol-2-yl)nonyl)-6-azaspiro[2.5]octane-1-carboxamide (179B, 250 mg, 0.394 mmol) and 3-bromoprop-1-ene (95 mg, 0.789 mmol) in acetonitrile (10 mL) at room temperature and the mixture was stirred at rt for 2 h, then water (10 mL) was added and the mixture was extracted with ethyl acetate (20 mL). The combined organic fractions were washed with brine (saturated, 10 mL), dried ($Na_2SO_4$), filtered and the solvent was evaporated under reduced pressure. The residue was purified by preparative TLC on silica gel, eluting with DCM/MeOH=10:1 to give (1S)-6-allyl-N-((1S)-1-(5-(9-allyl-1,2,3,4-tetrahydro-1,4-epiminonaphthalen-6-yl)-1-((2-(trimethylsilyl)ethoxy)methyl)-1H-imidazol-2-yl)-7-oxononyl)-6-azaspiro[2.5]octane-1-carboxamide (179C). LCMS (ESI) calc'd for $C_{42}H_{63}N_5O_3Si$ $[M+H]^+$: 714.5, found: 714.5.

Step 4: Preparation of (1S)-6-allyl-N-((1S)-1-(5-(9-allyl-1,2,3,4-tetrahydro-1,4-epiminonaphthalen-6-yl)-1H-imidazol-2-yl)-7-oxononyl)-6-azaspiro[2.5]octane-1-carboxamide (179): TFA (1.0 mL, 12.98 mmol) was added to a stirred mixture of (1S)-6-allyl-N-((1S)-1-(5-(9-allyl-1,2,3,4-tetrahydro-1,4-epiminonaphthalen-6-yl)-1-((2-(trimethylsilyl)ethoxy)methyl)-1H-imidazol-2-yl)-7-oxononyl)-6-azaspiro[2.5]octane-1-carboxamide (179C, 10 mg, 0.014 mmol) in DCM (1.0 mL) under $N_2$ atmosphere at room temperature and the mixture was stirred at rt for 2 h, then left to stand overnight. The mixture was concentrated and the residue was purified by preparative HPLC (reverse phase C-18 column), eluting with acetonitrile/water+0.1% TFA, to give (1S)-6-allyl-N-((1S)-1-(5-(9-allyl-1,2,3,4-tetrahydro-1,4-epiminonaphthalen-6-yl)-1H-imidazol-2-yl)-7-oxononyl)-6-azaspiro[2.5]octane-1-carboxamide (179). LCMS (ESI) calc'd for $C_{36}H_{49}N_5O_2$ $[M+H]^+$: 584.4, found: 584.1. $^1H$ NMR (400 MHz, MeOD) δ 7.73-7.98 (m, 3H), 7.57-7.69 (m, 1H), 5.78-6.06 (m, 2H), 5.42-5.72 (m, 3H), 5.16-5.38 (m, 2H), 5.06 (brs, 1H), 3.62-3.84 (m, 3H), 3.51 (brs, 1H), 3.42 (d, J=7.06 Hz, 1H), 2.94-3.23 (m, 2H), 2.37-2.60 (m, 6H), 2.13-2.36 (m, 1H), 1.74-2.12 (m, 5H), 1.13-1.73 (m, 11H), 0.99 (t, J=7.39 Hz, 4H).

Example 75

(1S)—N-{(1S)-7-oxo-1-[5-(9-prop-2-en-1-yl-1,2,3,4-tetrahydro-1,4-epiminonaphthalen-5-yl)-1H-imidazol-2-yl]nonyl}-6-prop-2-en-1-yl-6-azaspiro[2.5]octane-1-carboxamide (180)

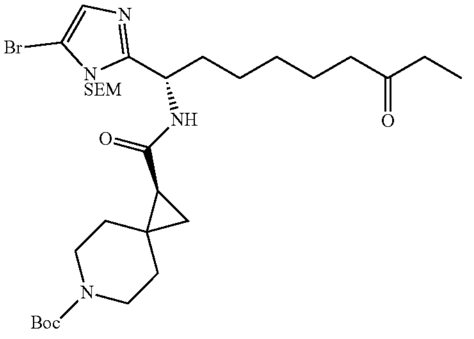

D1

+

-continued

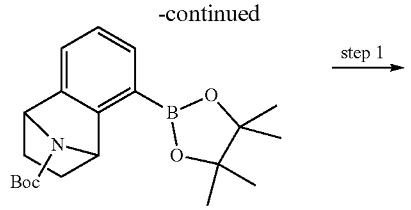

C30

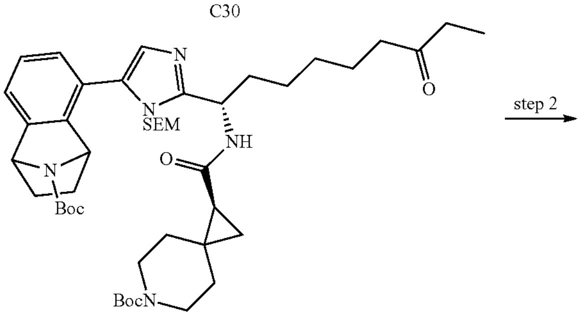

180A

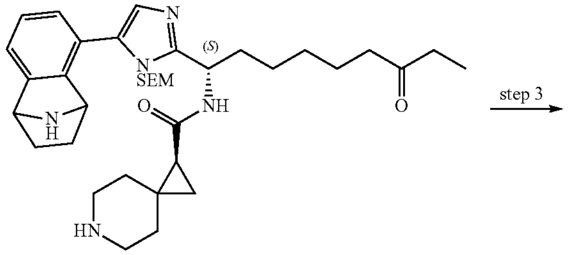

180B

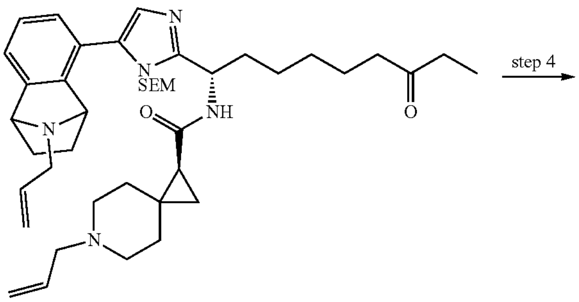

180C

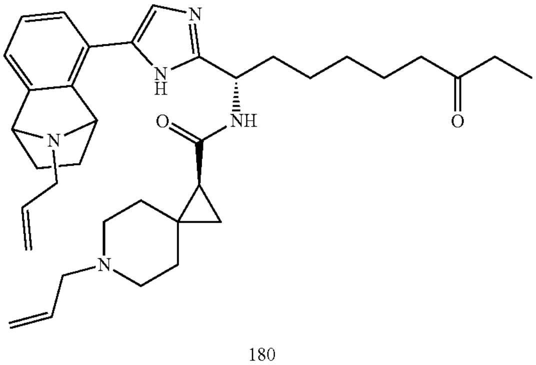

180

Step 1: Preparation of tert-butyl 5-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (180A): $PdCl_2(DTBPF)$ (15 mg, 0.023 mmol) was added to a stirred mixture of (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (D1, 250 mg, 0.373 mmol), tert-butyl 5-(4,4,5,5-tetramethyl-1,3,2-dioxaborolan-2-yl)-1,2,3,4-tetrahydro-1,4-epiminonaphthalene-9-carboxylate (C30, 150 mg, 0.404 mmol) and $K_2CO_3$ (155 mg, 1.120 mmol) in THF (5.0 mL) and water (0.5 mL) at room temperature under $N_2$ atmosphere and the mixture was stirred at 60° C. for 16 h, then cooled to room temperature and concentrated. The residue was purified by silica gel column flash chromatography, eluting with petroleum ether:EtOAc=1.5:1 to give tert-butyl 5-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (180A). LCMS (ESI) calc'd for $C_{46}H_{71}N_5O_7Si$ $[M+H]^+$: 834.5, found: 834.6.

Step 2: Preparation of (1S)—N-((1S)-7-oxo-1-(5-(1,2,3,4-tetrahydro-1,4-epiminonaphthalen-5-yl)-1-((2-(trimethylsilyl)ethoxy)methyl)-1H-imidazol-2-yl)nonyl)-6-azaspiro[2.5]octane-1-carboxamide (180B): HCl/MeOH (2.0 mL, 8.00 mmol) was added to a stirred mixture of tert-butyl 5-(2-((S)-1-((S)-6-(tert-butoxycarbonyl)-6-azaspiro[2.5]octane-1-carboxamido)-7-oxononyl)-1-((2-(trimethylsilyl)ethoxy)methyl)-1H-imidazol-5-yl)-1,2,3,4-tetrahydro-1,4-epiminonaphthalene-9-carboxylate (180A, 250 mg, 0.300 mmol) in MeOH (5.0 mL) at room temperature and the mixture was stirred at rt for 4 h, then adjusted to pH 8 with $NaHCO_3$ solution, extracted with EtOAc (10 mL*2), washed with brine (10 mL), dried over $Na_2SO_4$, filtered and concentrated to afford (1S)—N-((1S)-7-oxo-1-(5-(1,2,3,4-tetrahydro-1,4-epiminonaphthalen-5-yl)-1-((2-(trimethylsilyl)ethoxy)methyl)-1H-imidazol-2-yl)nonyl)-6-azaspiro[2.5]octane-1-carboxamide (180B) without further purification. LCMS (ESI) calc'd for $C_{36}H_{55}N_5O_3Si$ $[M+H]^+$: 634.4, found: 634.4.

Step 3: Preparation of (1S)-6-allyl-N-((1S)-1-(5-(9-allyl-1,2,3,4-tetrahydro-1,4-epiminonaphthalen-5-yl)-1-((2-(trimethylsilyl)ethoxy)methyl)-1H-imidazol-2-yl)-7-oxononyl)-6-azaspiro[2.5]octane-1-carboxamide (180C): 3-bromoprop-1-ene (67 mg, 0.554 mmol) was added to a stirred mixture of (1S)—N-((1S)-7-oxo-1-(5-(1,2,3,4-tetrahydro-1,4-epiminonaphthalen-5-yl)-1-((2-(trimethylsilyl)ethoxy)methyl)-1H-imidazol-2-yl)nonyl)-6-azaspiro[2.5]octane-1-carboxamide (180B, 170 mg, 0.268 mmol) and DIPEA (0.141 mL, 0.804 mmol) in MeCN (3.0 mL) at room temperature and the mixture was stirred at rt for 4 h. The mixture was diluted with ethyl acetate (10 mL), washed with brine (saturated, 5 mL), dried ($Na_2SO_4$), filtered and the solvent was evaporated under reduced pressure. The residue was purified by preparative TLC on silica gel, eluting with DCM:MeOH=10:1 to give (1S)-6-allyl-N-((1S)-1-(5-(9-allyl-1,2,3,4-tetrahydro-1,4-epiminonaphthalen-5-yl)-1-((2-(trimethylsilyl)ethoxy)methyl)-1H-imidazol-2-yl)-7-oxononyl)-6-azaspiro[2.5]octane-1-carboxamide (180C). LCMS (ESI) calc'd for $C_{42}H_{63}N_5O_3Si$ $[M+H]^+$: 714.5, found: 714.5.

Step 4: Preparation of (1S)-6-allyl-N-((1S)-1-(5-(9-allyl-1,2,3,4-tetrahydro-1,4-epiminonaphthalen-5-yl)-1H-imidazol-2-yl)-7-oxononyl)-6-azaspiro[2.5]octane-1-carboxamide (180): TFA (1.0 mL, 12.98 mmol) was added to a stirred mixture of (1S)-6-allyl-N-((1S)-1-(5-(9-allyl-1,2,3,4-tetrahydro-1,4-epiminonaphthalen-5-yl)-1-((2-(trimethylsilyl)ethoxy)methyl)-1H-imidazol-2-yl)-7-oxononyl)-6-azaspiro[2.5]octane-1-carboxamide (180C, 10 mg, 0.014 mmol) in DCM (0.2 mL) under $N_2$ atmosphere at room temperature and the mixture was stirred at rt for 2 h, then left to stand overnight. The mixture was concentrated. The residue was purified by preparative HPLC (reverse phase C-18 column), eluting with acetonitrile/water+0.1% TFA, to give (1S)-6-allyl-N-((1S)-1-(5-(9-allyl-1,2,3,4-tetrahydro-1,4-epiminonaphthalen-5-yl)-1H-imidazol-2-yl)-7-oxononyl)-6-azaspiro[2.5]octane-1-carboxamide (180). LCMS (ESI) calc'd for $C_{36}H_{49}N_5O_2$ $[M+H]^+$: 584.4, found: 584.1. $^1H$ NMR (400 MHz, MeOD) δ 7.69 (brs, 1H), 7.38-7.58 (m, 3H), 5.91 (brs, 2H), 5.40-5.71 (m, 4H), 5.15-5.31 (m, 1H), 5.02 (t, J=7.24 Hz, 1H), 3.75 (brs, 3H), 3.37-3.58 (m, 1H), 3.35-3.43 (m, 1H), 2.86-3.20 (m, 2H), 2.38-2.62 (m, 6H), 2.21 (brs, 1H), 1.98 (brs, 4H), 1.65-1.85 (m, 3H), 1.40-1.59 (m, 3H), 1.10-1.39 (m, 6H), 0.98 (t, J=7.34 Hz, 4H).

Example 76

(1S)-6-cyclobutyl-N-{(1S)-1-[5-(7-methoxy-2-methylquinolin-6-yl)-1H-imidazol-2-yl]-7-oxononyl}-6-azaspiro[2.5]octane-1-carboxamide (186)

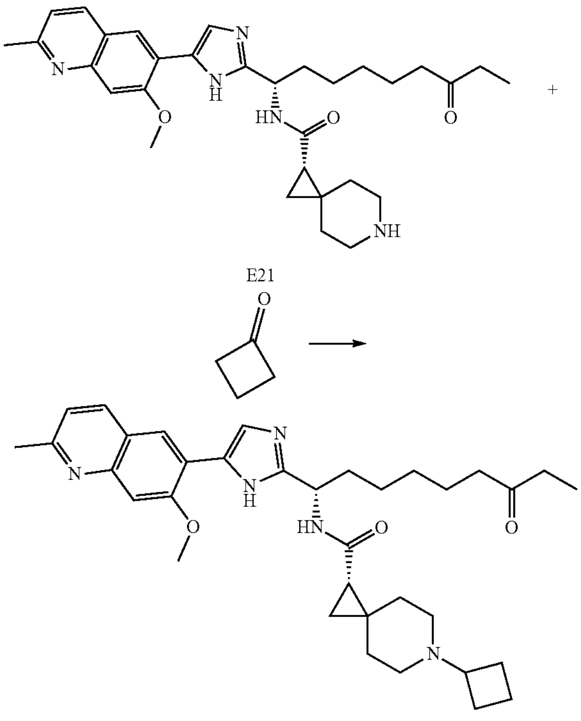

E21

186

Cyclobutanone (25 mg, 0.357 mmol) was added to a stirred mixture of (S)—N—((S)-1-(5-(7-methoxy-2-methylquinolin-6-yl)-1H-imidazol-2-yl)-7-oxononyl)-6-azaspiro[2.5]octane-1-carboxamide 2,2,2-trifluoroacetate (E21, 125 mg, 0.194 mmol) in MeOH (2 mL) at room temperature for 1 h. Then $NaBH(OAc)_3$ (123 mg, 0.581 mmol) was added. It was stirred at rt for 24 h. Water (5 mL) was added and the mixture was extracted with ethyl acetate (3×5 mL). The combined organic fractions were washed with aqueous $NaHCO_3$(saturated, 1×5 mL), dried ($Na_2SO_4$), filtered and the solvent was evaporated under reduced pressure. The residue was purified by preparative HPLC (reverse phase C-18 column), eluting with acetonitrile/water+0.05% $NH_3 \cdot H_2O$, to give (S)-6-cyclobutyl-N—((S)-1-(5-(7-methoxy-2-methylquinolin-6-yl)-1H-imidazol-2-yl)-7-oxononyl)-6-azaspiro[2.5]octane-1-carboxamide (186).

L-(+)-tartaric acid (11 mg, 0.073 mmol) was added to a stirred mixture of (S)-6-cyclobutyl-N—((S)-1-(5-(7-methoxy-2-methylquinolin-6-yl)-1H-imidazol-2-yl)-7-oxononyl)-6-azaspiro[2.5]octane-1-carboxamide (186, 40 mg, 0.068 mmol) in acetonitrile (2 mL) and water (2 mL) at room temperature and the mixture was made dry by lyophilization to give (S)-6-cyclobutyl-N—((S)-1-(5-(7-methoxy-2-methylquinolin-6-yl)-1H-imidazol-2-yl)-7-oxononyl)-6-azaspiro[2.5]octane-1-carboxamide (2R,3R)-2,3-dihydroxysuccinate. $^1$H NMR (400 MHz, MeOD) δ 8.45-8.59 (m, 1H), 8.25-8.36 (m, 1H), 7.63-7.77 (m, 1H), 7.45 (s, 1H), 7.32-

7.41 (m, 1H), 5.01-5.16 (m, 1H), 4.48 (s, 2H), 4.11 (s, 3H), 2.88 (brs, 2H), 2.72 (s, 3H), 2.44 (d, J=6.7 Hz, 5H), 1.67-2.35 (m, 11H), 1.16-1.64 (m, 10H), 0.98 (t, J=7.0 Hz, 5H). LCMS (ESI) calc'd for $C_{27}H_{29}N_5O_4$ $[M+H]^+$: 586.4, found: 586.1.

Example 77

(1S)—N-{(1S)-1-[5-(7-ethyl-2-methylquinolin-6-yl)-1H-imidazol-2-yl]-7-oxononyl}-6-methyl-6-azaspiro[2.5]octane-1-carboxamide (210)

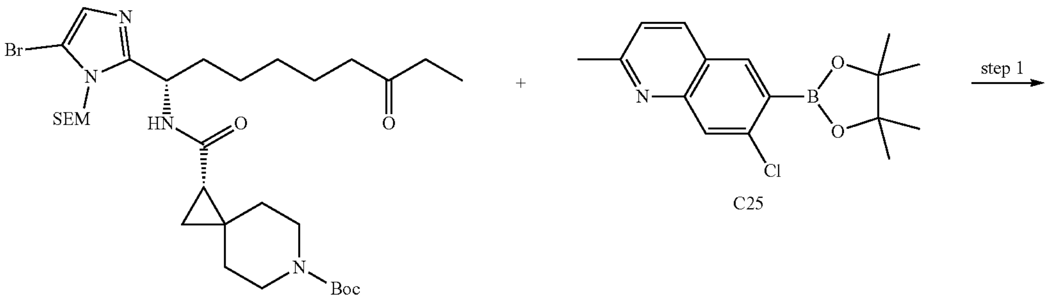

D1

C25

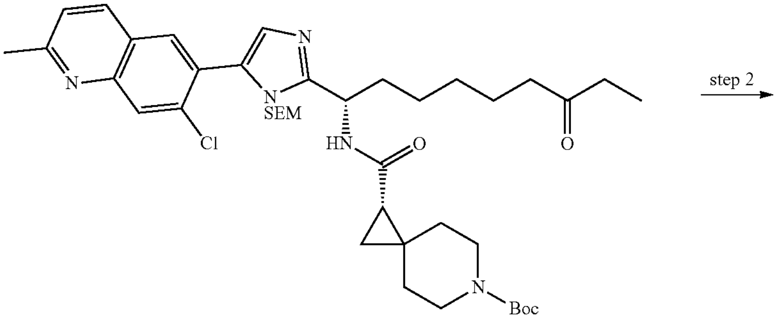

210A

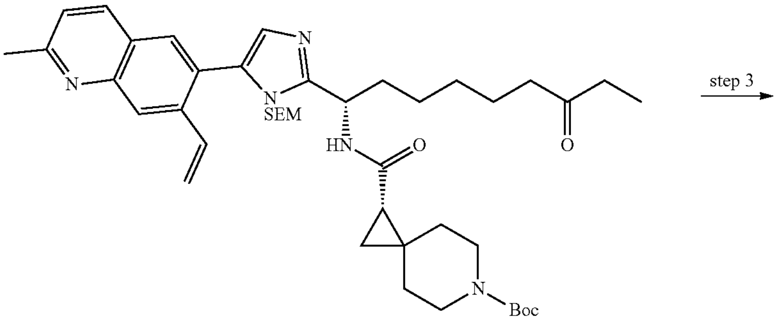

210B

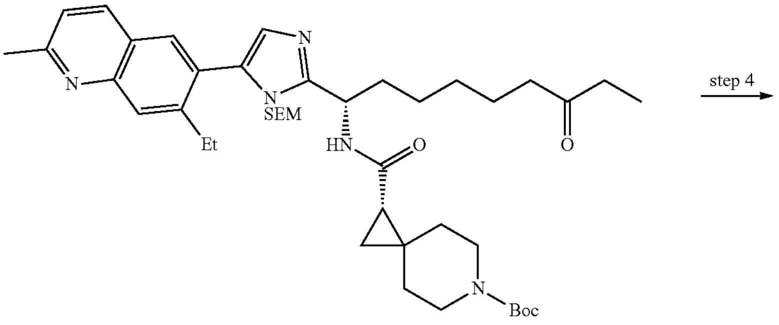

210C

-continued

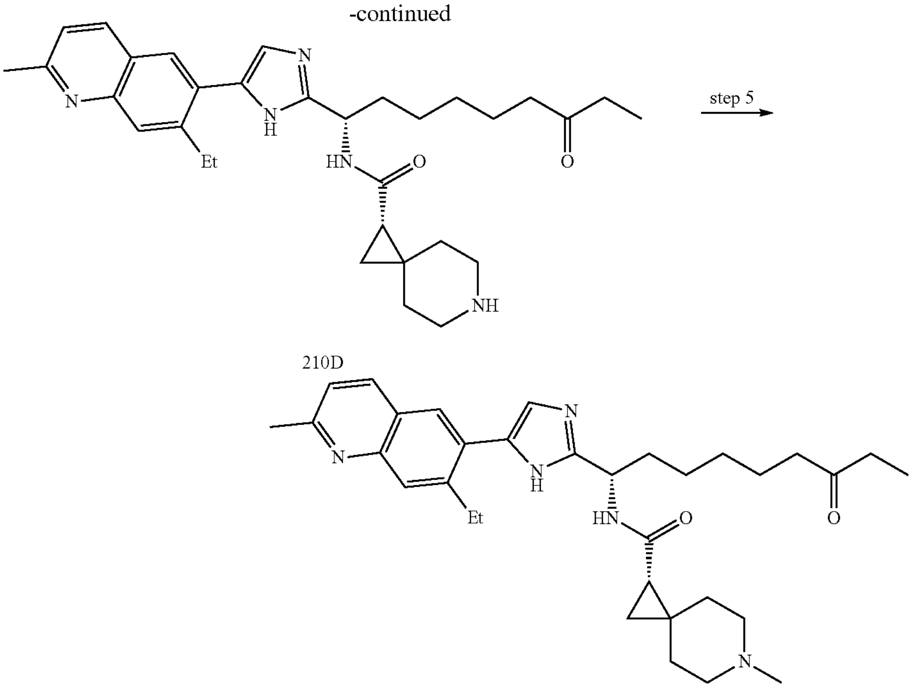

210D

210

Step 1: Preparation of (S)-tert-butyl 1-(((S)-1-(5-(7-chloro-2-methylquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (210A): $PdCl_2$(DTBPF) (52 mg, 0.081 mmol) was added to a stirring mixture of (S)-tert-butyl 1-(((S)-1-(5-bromo-1-((2-(trimethylsilyl)ethoxy)methyl)-1H-imidazol-2-yl)-7-oxononyl)carbamoyl)-6-azaspiro[2.5]octane-6-carboxylate (D1, 600 mg, 0.896 mmol), 7-chloro-2-methyl-6-(4,4,5,5-tetramethyl-1,3,2-dioxaborolan-2-yl)quinoline (C25, 408 mg, 1.344 mmol) and $K_3PO_4$ (570 mg, 2.69 mmol) in dioxane (12.0 mL) and water (0.5 mL). Then, the mixture was heated with stirring at 70° C. under $N_2$ atmosphere for 4 h. The combined mixture was cooled to rt and filtered through Celite. The resulting filtrate was concentrated under reduced pressure and the residue was purified by silica gel column flash chromatography, eluting with petroleum ether/EtOAc to give (S)-tert-butyl 1-(((S)-1-(5-(7-chloro-2-methylquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (210A). LCMS (ESI) calc'd for $C_{41}H_{60}ClN_5O_5Si$ $[M+H]^+$: 766.4, found: 766.5.

Step 2: (S)-tert-butyl 1-(((S)-1-(5-(2-methyl-7-vinylquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (210B): $PdCl_2$(DTBPF) (33 mg, 0.051 mmol) was added to a mixture of (S)-tert-butyl 1-(((S)-1-(5-(7-chloro-2-methylquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (210A, 203 mg, 0.265 mmol), 4,4,5,5-tetramethyl-2-vinyl-1,3,2-dioxaborolane (210 mg, 1.364 mmol) and $K_3PO_4$ (189 mg, 0.890 mmol) in co-solvents of THF (3 mL) and water (0.3 mL) at rt and the mixture was stirred at 80° C. for 6 h. To the mixture was added another 4,4,5,5-tetramethyl-2-vinyl-1,3,2-dioxaborolane (200 mg), $K_3PO_4$ (190 mg), $PdCl_2$(DTBPF) (30 mg) and bubbled with $N_2$, then it was stirred at 80° C. for 9 h. To the mixture was added another 4,4,5,5-tetramethyl-2-vinyl-1,3,2-dioxaborolane (180 mg), $K_3PO_4$ (190 mg), $PdCl_2$ (DTBPF) (33 mg) and it was bubbled with $N_2$, then stirred at 80° C. for another 20 h. The mixture was diluted with water (30 mL) and extracted with DCM (3×15 mL). The combined organic fractions were washed with brine (saturated, 15 mL), dried ($Na_2SO_4$), filtered and the solvent was evaporated under reduced pressure. The residue was purified by silica gel column flash chromatography, eluting with MeOH/DCM=0~10% and then purified by preparative HPLC (reverse phase C-18 column), eluting with acetonitrile/water+0.1% TFA, to give (S)-tert-butyl 1-(((S)-1-(5-(2-methyl-7-vinylquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (210B). LCMS (ESI) calc'd for $C_{43}H_{63}N_5O_5Si$ $[M+H]^+$: 758.5, found: 758.4.

Step 3: (S)-tert-butyl 1-(((S)-1-(5-(7-ethyl-2-methylquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (210C): 10% Pd—C (80 mg, 0.075 mmol) was added to a stirred mixture of (S)-tert-butyl 1-(((S)-1-(5-(2-methyl-7-vinylquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (210B, 70 mg, 0.092 mmol) in MeOH (15 mL) at rt and the mixture was stirred at rt for 2 h under $H_2$ (15 psi). The mixture was filtered and the filter cake was washed with MeOH (30 mL). The filtrate was concentrated to give (S)-tert-butyl 1-(((S)-1-(5-(7-ethyl-2-methylquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (210C) which was used to the next step without purification. LCMS (ESI) calc'd for $C_{43}H_{65}N_5O_5Si$ $[M+H]^+$: 760.5, found: 760.5.

Step 4: (S)—N—((S)-1-(5-(7-ethyl-2-methylquinolin-6-yl)-1H-imidazol-2-yl)-7-oxononyl)-6-azaspiro[2.5]octane- 1-carboxamide (210D): TFA (4 mL, 51.9 mmol) was added to (S)-tert-butyl 1-(((S)-1-(5-(7-ethyl-2-methylquinolin-6-yl)-1-((2-(trimethylsilyl)ethoxy)methyl)-1H-imidazol-2-yl)-7-oxononyl)carbamoyl)-6-azaspiro[2.5]octane-6-carboxylate (210C, 65 mg, 0.086 mmol) and the mixture was stirred at rt for 3 h. TFA was evaporated under reduced pressure to give (S)—N—((S)-1-(5-(7-ethyl-2-methylquinolin-6-yl)-1H-imidazol-2-yl)-7-oxononyl)-6-azaspiro[2.5]octane-1-carboxamide (210D) which was used in the next step without purification. LCMS (ESI) calc'd for $C_{32}H_{43}N_5O_2$ $[M+H]^+$: 530.3, found: 530.4.

Step 5: (S)—N—((S)-1-(5-(7-ethyl-2-methylquinolin-6-yl)-1H-imidazol-2-yl)-7-oxononyl)-6-methyl-6-azaspiro[2.5]octane-1-carboxamide (210): A mixture of (S)—N—((S)-1-(5-(7-ethyl-2-methylquinolin-6-yl)-1H-imidazol-2-yl)-7-oxononyl)-6-azaspiro[2.5]octane-1-carboxamide (210D, 45 mg, 0.085 mmol) and formaldehyde (0.5 mL, 6.72 mmol) in MeOH (2 mL) was stirred at rt for 8 h, then NaBH(OAc) (103 mg, 0.486 mmol) was added portionwise and the mixture was stirred at rt for 1 h. The mixture was diluted with DMF (3 mL). The residue was purified by preparative HPLC (reverse phase C-18 column), eluting with acetonitrile/water+0.1% TFA, to give (S)—N—((S)-1-(5-(7-ethyl-2-methylquinolin-6-yl)-1H-imidazol-2-yl)-7-oxononyl)-6-methyl-6-azaspiro[2.5]octane-1-carboxamide (20 mg).

(S)—N—((S)-1-(5-(7-ethyl-2-methylquinolin-6-yl)-1H-imidazol-2-yl)-7-oxononyl)-6-methyl-6-azaspiro[2.5]octane-1-carboxamide (20 mg, 0.037 mmol) was purified by preparative HPLC (reverse phase C-18 column), eluting with acetonitrile/water+0.05% $NH_3 \cdot H_2O$, to give (S)—N—((S)-1-(5-(7-ethyl-2-methylquinolin-6-yl)-1H-imidazol-2-yl)-7-oxononyl)-6-methyl-6-azaspiro[2.5]octane-1-carboxamide (210). LCMS (ESI) calc'd for $C_{33}H_{45}N_5O_2$ $[M+H]^+$: 544.4, found: 544.4. $^1H$ NMR (400 MHz, MeOD) δ 8.19 (d, J=8.22 Hz, 1H), 7.92 (brs, 1H), 7.85 (s, 1H), 7.37 (d, J=8.61 Hz, 1H), 7.15 (brs, 1H), 5.02 (t, J=7.63 Hz, 1H), 2.98 (d, J=6.65 Hz, 2H), 2.71 (s, 3H), 2.40-2.56 (m, 6H), 2.34 (brs, 1H), 2.17 (s, 3H), 1.88-2.05 (m, 2H), 1.67 (brs, 2H), 1.51-1.62 (m, 4H), 1.43 (d, J=6.26 Hz, 1H), 1.29-1.41 (m, 4H), 1.24 (t, J=7.63 Hz, 3H), 1.11 (t, J=4.89 Hz, 1H), 1.07-1.14 (m, 1H), 0.99 (t, J=7.24 Hz, 3H), 0.79-0.86 (m, 1H), 0.82 (dd, J=4.50, 8.02 Hz, 1H).

Example 78

{2-[(1S)-1-({[(1S)-6-ethyl-6-azaspiro[2.5]oct-1-yl]carbonyl}amino)-7-oxononyl]-4-(7-methoxy-2-methylquinolin-6-yl)-1H-imidazol-1-yl}methyl 2,2-dimethylpropanoate (215)

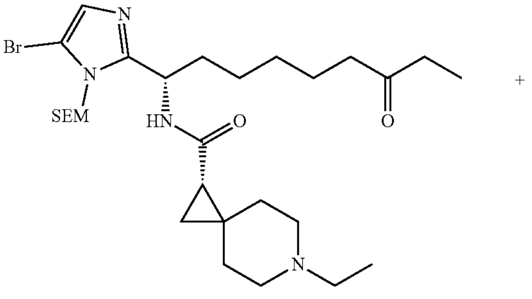

D2

-continued

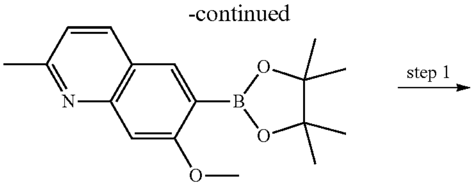

C1

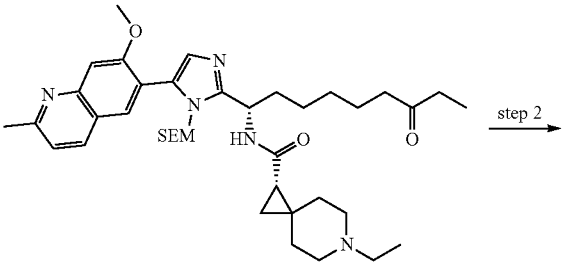

215A

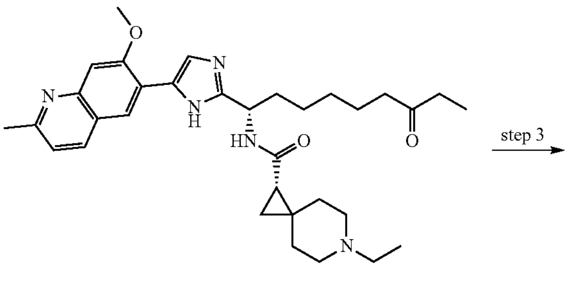

215B

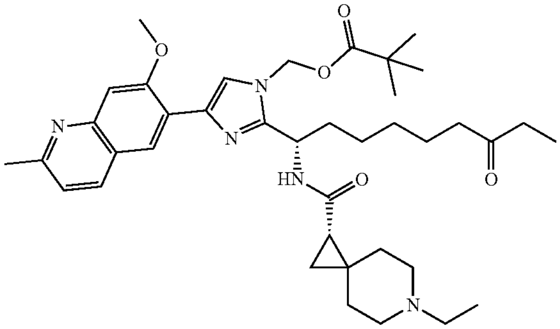

215

Step 1: Preparation of (S)-6-ethyl-N—((S)-1-(5-(7-methoxy-2-methylquinolin-6-yl)-1-((2-(trimethylsilyl)ethoxy)methyl)-1H-imidazol-2-yl)-7-oxononyl)-6-azaspiro[2.5]octane-1-carboxamide (215A): $PdCl_2$(DTBPF) (27 mg, 0.041 mmol) was added to a mixture of (S)—N—((S)-1-(5-bromo-1-((2-(trimethylsilyl)ethoxy)methyl)-1H-imidazol-2-yl)-7-oxononyl)-6-ethyl-6-azaspiro[2.5]octane-1-carboxamide (D2, 250 mg, 0.418 mmol), 7-methoxy-2-methyl-6-(4,4,5,5-tetramethyl-1,3,2-dioxaborolan-2-yl)quinoline (C1, 128 mg, 0.427 mmol) and $K_3PO_4$ (266 mg, 1.255 mmol) in co-solvents of THF (3 mL) and water (0.3 mL) at room temperature and the mixture was stirred at 70° C. for 2 h. The mixture was diluted with water (15 mL), and extracted with ethyl acetate (3×10 mL). The combined organic fractions were washed with brine (saturated, 10 mL), dried ($Na_2SO_4$), filtered and the solvent was evaporated under reduced pressure. The residue was purified by silica gel column flash chromatography, eluting with DCM/MeOH=0~30% to give (S)-6-ethyl-N—((S)-1-(5-(7-methoxy-2-methylquinolin-6-yl)-1-((2-(trimethylsilyl)

ethoxy)methyl)-1H-imidazol-2-yl)-7-oxononyl)-6-azaspiro[2.5]octane-1-carboxamide (215A). LCMS (ESI) calc'd for $C_{39}H_{59}N_5O_4Si$ $[M+H]^+$: 690.4, found: 690.4.

Step 2: Preparation of (S)-6-ethyl-N—((S)-1-(5-(7-methoxy-2-methylquinolin-6-yl)-1H-imidazol-2-yl)-7-oxononyl)-6-azaspiro[2.5]octane-1-carboxamide (215B): TFA (4 mL, 51.9 mmol) was added to a stirred mixture of (S)-6-ethyl-N—((S)-1-(5-(7-methoxy-2-methylquinolin-6-yl)-1-((2-(trimethylsilyl)ethoxy)methyl)-1H-imidazol-2-yl)-7-oxononyl)-6-azaspiro[2.5]octane-1-carboxamide (215A, 250 mg, 0.362 mmol) at room temperature and the mixture was stirred at room temperature for 2 h. All the volatiles were removed by evaporator to give (S)-6-ethyl-N—((S)-1-(5-(7-methoxy-2-methylquinolin-6-yl)-1H-imidazol-2-yl)-7-oxononyl)-6-azaspiro[2.5]octane-1-carboxamide (215B) which was used to the next step without further purification. LCMS (ESI) calc'd for $C_{33}H_{45}N_5O_3$ $[M+H]^+$: 560.4, found: 560.4.

Step 3: Preparation of (2-((S)-1-((S)-6-ethyl-6-azaspiro[2.5]octane-1-carboxamido)-7-oxononyl)-4-(7-methoxy-2-methylquinolin-6-yl)-1H-imidazol-1-yl)methyl pivalate (215): Chloromethyl pivalate (89 mg, 0.594 mmol) was added to a stirred mixture of (S)-6-ethyl-N—((S)-1-(5-(7-methoxy-2-methylquinolin-6-yl)-1H-imidazol-2-yl)-7-oxononyl)-6-azaspiro[2.5]octane-1-carboxamide 2,2,2-trifluoroacetate (215B, 160 mg, 0.237 mmol) and DIPEA (0.25 mL, 1.431 mmol) in DMF (2 mL) at rt and the mixture was stirred at rt for 7 d. The mixture was purified by preparative HPLC (reverse phase C-18 column), eluting with acetonitrile/water+0.05% $NH_3 \cdot H_2O$, to give (2-((S)-1-((S)-6-ethyl-6-azaspiro[2.5]octane-1-carboxamido)-7-oxononyl)-4-(7-methoxy-2-methylquinolin-6-yl)-1H-imidazol-1-yl)methyl pivalate (215). LCMS (ESI) calc'd for $C_{39}H_{55}N_5O_5$ $[M+H]^+$: 674.4, found: 674.1. $^1H$ NMR (400 MHz, MeOD) δ 8.51 (s, 1H), 8.14 (d, J=8.4 Hz, 1H), 7.73 (s, 1H), 7.38 (s, 1H), 7.27 (d, J=8.2 Hz, 1H), 6.35 (d, J=10.9 Hz, 1H), 6.00 (d, J=11.2 Hz, 1H), 5.19 (t, J=7.5 Hz, 1H), 4.08 (s, 3H), 2.67 (s, 3H), 2.62 (brs, 1H), 2.35-2.47 (m, 5H), 2.32 (d, J=6.9 Hz, 1H), 1.95-2.22 (m, 4H), 1.25-1.74 (m, 10H), 1.18 (s, 10H), 1.05-1.12 (m, 2H), 0.94 (t, J=7.3 Hz, 3H), 0.79 (dd, J=4.5, 7.8 Hz, 1H), 0.64 (brs, 3H).

Example 79

(9S)-9-{[2-(dimethylamino)ethyl]amino}-9-[5-(7-methoxy-2-methylquinolin-6-yl)-1H-imidazol-2-yl]nonan-3-one (217)

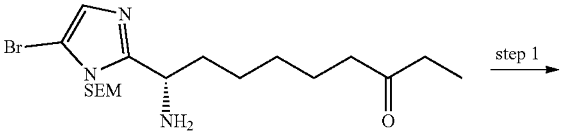

A3

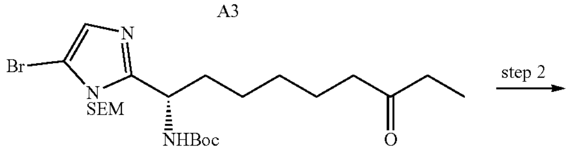

217A

-continued

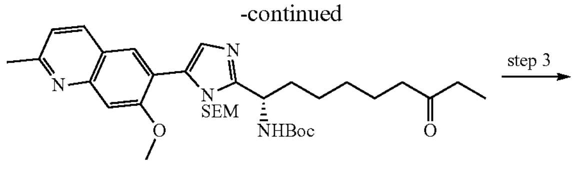

217B

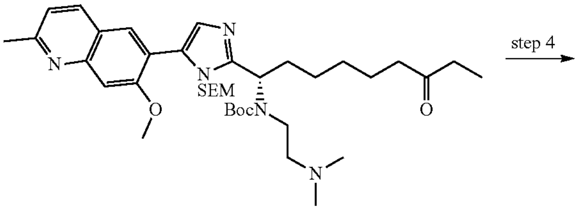

217C

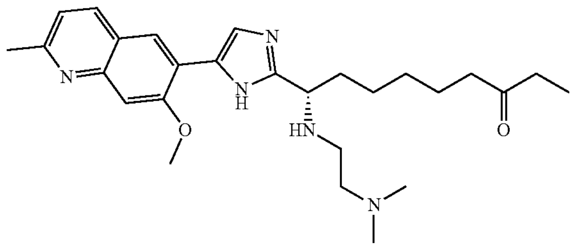

217

Step 1: Preparation of (S)-tert-butyl (1-(5-bromo-1-((2-(trimethylsilyl) (1-(5-bromo-1-((2-(trimethylsilyl)ethoxy)methyl)-1H-imidazol-2-yl)-7-oxononyl)carbamate (217A): To a stirred solution of (S)-9-amino-9-(5-bromo-1-((2-(trimethylsilyl)ethoxy)methyl)-1H-imidazol-2-yl)nonan-3-one (A3, 1.00 g, 2.31 mmol) in DCM (10 mL) was added $Boc_2O$ (760 mg, 3.47 mmol) and TEA (702 mg, 6.94 mmol). The resulting mixture was stirred at room temperature for 16 h. The mixture was diluted with water (50 mL), extracted with DCM (50 mL*2), dried over $Na_2SO_4$, filtered and concentrated in vacuo to give the title product (217A) which was used to the next step without further purification. LCMS (ESI) calc'd for $C_{23}H_{43}BrN_3O_4Si$ $[M+H]^+$. 532.2, found: 532.3.

Step 2: Preparation of (S)-tert-butyl(1-(5-(7-methoxy-2-methylquinolin-6-yl)-1-((2-(trimethylsilyl)ethoxy)methyl)-1H-imidazol-2-yl)-7-oxononyl)carbamate (217B): To a stirred solution of (S)-tert-butyl (1-(5-bromo-1-((2-(trimethylsilyl)ethoxy)methyl)-1H-imidazol-2-yl)-7-oxononyl)carbamate (217A, 1.10 g, 2.07 mmol) in a mixture of dioxane (12 mL) and $H_2O$ (2 mL) was added 7-methoxy-2-methyl-6-(4,4,5,5-tetramethyl-1,3,2-dioxaborolan-2-yl)quinoline (C1, 741 mg, 2.48 mmol), $PdCl_2$(DTBPF) (135 mg, 0.21 mmol) and $K_3PO_4$ (1.32 g, 6.20 mmol). The reaction mixture was allowed to stir at 70° C. for 2 h under $N_2$ atmosphere. After it cooled to room temperature, the mixture was diluted with water (40 mL), extracted with EtOAc (50 mL*2), dried over $Na_2SO_4$, filtered and concentrated in vacuo. The residue was purified by silica gel column flash chromatography, eluting with EtOAc: petroleum ether=1:2 to give (S)-tert-butyl(1-(5-(7-methoxy-2-methylquinolin-6-yl)-1-((2-(trimethylsilyl)ethoxy)methyl)-1H-imidazol-2-yl)-7-oxononyl)carbamate (217B). LCMS (ESI) calc'd for $C_{34}H_{53}N_4O_5Si$ $[M+H]^+$: 625.4, found: 625.4. $^1H$ NMR (400 MHz, $CDCl_3$) δ 8.54 (s, 1H), 8.07 (d, J=8.16 Hz, 1H), 7.61 (s, 1H), 7.43 (s, 1H), 7.16 (d, J=8.38 Hz, 1H), 5.57 (d, J=10.58 Hz, 1H), 5.32 (d, J=9.48 Hz, 1H), 5.23 (d, J=11.03 Hz, 1H), 4.93 (q, J=7.94 Hz, 1H), 4.07 (s, 3H), 3.49-3.65 (m, 2H), 2.72 (s, 3H), 2.30-2.44 (m, 4H), 1.90-2.00 (m, 2H), 1.52-1.58 (m, 2H), 1.43 (s, 9H), 1.35 (dd, J=7.28, 14.11 Hz, 3H), 1.01 (t, J=7.28 Hz, 3H), 0.89-0.97 (m, 2H), 0.00 (s, 9H).

Step 3: Preparation of (S)-tert-butyl (2-(dimethylamino) ethyl)(1-(5-(7-methoxy-2-methylquinolin-6-yl)-1-((2-(trimethylsilyl)ethoxy)methyl)-1H-imidazol-2-yl)-7-oxononyl) carbamate (217C): NaH (30 mg, 0.750 mmol) was added to a stirred mixture of (S)-tert-butyl (1-(5-(7-methoxy-2-methylquinolin-6-yl)-1-((2-(trimethylsilyl)ethoxy)methyl)-1H-imidazol-2-yl)-7-oxononyl)carbamate (217B, 150 mg, 0.240 mmol) in THF (2 mL), then 2-bromo-N,N-dimethylethanamine hydrobromide (80 mg, 0.343 mmol) was added at room temperature and the mixture was stirred at room temperature for 18 h. Water (5 mL) was added and the mixture was extracted with ethyl acetate (3×5 mL). The combined organic fractions were washed with brine (saturated, 1×5 mL), dried ($Na_2SO_4$), filtered and the solvent was evaporated under reduced pressure to give (S)-tert-butyl (2-(dimethylamino)ethyl)(1-(5-(7-methoxy-2-methylquinolin-6-yl)-1-((2-(trimethylsilyl)ethoxy)methyl)-1H-imidazol-2-yl)-7-oxononyl)carbamate (217C) which was directly used for next step. LCMS (ESI) calc'd for $C_{38}H_{61}N_5O_5Si$ $[M+H]^+$: 696.4, found: 696.5.

Step 4: Preparation of (S)-9-((2-(dimethylamino)ethyl) amino)-9-(5-(7-methoxy-2-methylquinolin-6-yl)-1H-imidazol-2-yl)nonan-3-one (217): TFA (2 mL, 26.0 mmol) was added to a stirred mixture of (S)-tert-butyl (2-(dimethylamino)ethyl)(1-(5-(7-methoxy-2-methylquinolin-6-yl)-1-((2-(trimethylsilyl)ethoxy)methyl)-1H-imidazol-2-yl)-7-oxononyl)carbamate (217C, 150 mg, 0.216 mmol) at room temperature and the mixture was stirred at room temperature for 1 h. Most of the TFA was removed by evaporator, then the residue was dissolved in MeOH and neutralized with $NaHCO_3$(sat.). The mixture was purified by preparative HPLC (reverse phase C-18 column), eluting with acetonitrile/water+0.05% $NH_3 \cdot H_2O$, to give (S)-9-((2-(dimethylamino)ethyl)amino)-9-(5-(7-methoxy-2-methylquinolin-6-yl)-1H-imidazol-2-yl)nonan-3-one (217). LCMS (ESI) calc'd for $C_{27}H_{39}N_5O_2$ $[M+H]^+$: 466.3, found: 466.3.

L-(+)-tartaric acid (32 mg, 0.213 mmol) was added to a stirred mixture of (S)-9-((2-(dimethylamino)ethyl)amino)-9-(5-(7-methoxy-2-methylquinolin-6-yl)-1H-imidazol-2-yl) nonan-3-one (217, 98 mg, 0.210 mmol) in acetonitrile (2 mL) and water (2 mL) at room temperature and the mixture was made dry by lyophilization to give (S)-9-((2-(dimethylamino)ethyl)amino)-9-(5-(7-methoxy-2-methylquinolin-6-yl)-1H-imidazol-2-yl)nonan-3-one (2R,3R)-2,3-dihydroxysuccinate. LCMS (ESI) calc'd for $C_{27}H_{39}N_5O_2$ $[M+H]^+$: 466.3, found: 466.2. $^1H$ NMR (400 MHz, MeOD) δ 8.39 (s, 1H), 8.25 (d, J=8.2 Hz, 1H), 7.75 (s, 1H), 7.42 (s, 1H), 7.32 (d, J=8.2 Hz, 1H), 4.47 (s, 2H), 4.10 (s, 3H), 4.02-4.07 (m, 1H), 2.97-3.27 (m, 3H), 2.83-2.89 (m, 1H), 2.81 (s, 6H), 2.71 (s, 3H), 2.37-2.41 (m, 4H), 1.91-2.02 (m, 2H), 1.52 (q, J=7.3 Hz, 2H), 1.18-1.44 (m, 4H), 0.95 (t, J=7.2 Hz, 3H).

Example 80

N-{(1S)-1-[5-(2-methoxy-4-pyridin-3-ylphenyl)-1,3-oxazol-2-yl]-7-oxononyl}-8-methyl-1-oxa-2,8-diazaspiro[4.5]dec-2-ene-3-carboxamide (222)

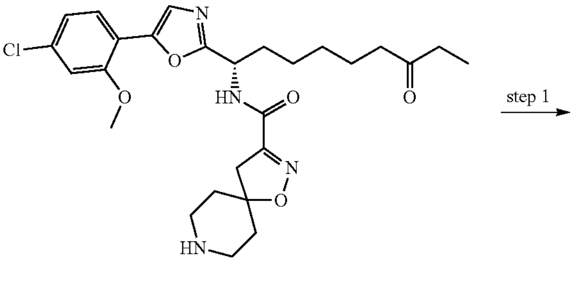

E31

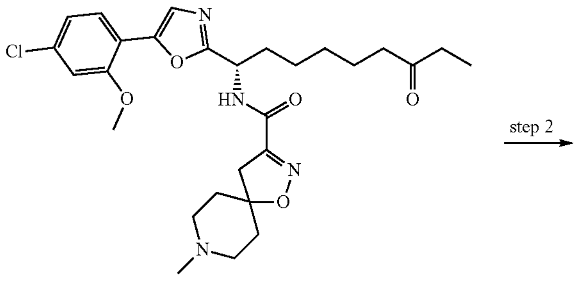

222A

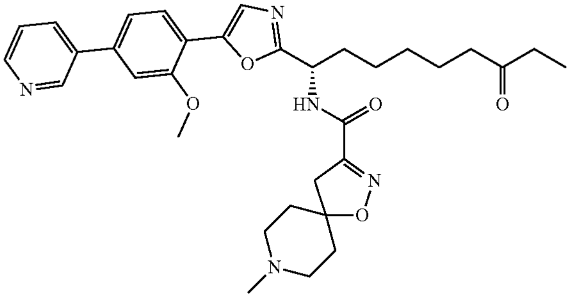

222

Step 1: Preparation of (S)—N-(1-(5-(4-chloro-2-methoxyphenyl)oxazol-2-yl)-7-oxononyl)-8-methyl-1-oxa-2,8-diazaspiro[4.5]dec-2-ene-3-carboxamide (222A): Formaldehyde (0.80 mL, 10.75 mmol) was added to a stirred mixture of (S)—N-(1-(5-(4-chloro-2-methoxyphenyl)oxazol-2-yl)-7-oxononyl)-1-oxa-2,8-diazaspiro[4.5]dec-2-ene-3-carboxamide (E31, 589 mg, 1.109 mmol) in methanol (10 mL) at room temperature and the mixture was stirred at room temperature for 30 min. Then $NaBH(OAc)_3$ (2.351 g, 11.09 mmol) was added and stirred for 1 h. $NaHCO_3$ (saturated, 30 mL) was added and the mixture was extracted with ethyl acetate (2×50 mL). The combined organic fractions were washed with brine (saturated, 50 mL), dried ($Na_2SO_4$), filtered and the solvent was evaporated under reduced pressure to afford (S)—N-(1-(5-(4-chloro-2-methoxyphenyl)oxazol-2-yl)-7-oxononyl)-8-methyl-1-oxa-2,8-diazaspiro [4.5]dec-2-ene-3-carboxamide (222A) which was used to the next step without further purification. LCMS (ESI) calc'd for $C_{28}H_{37}ClN_4O_5$ $[M+H]^+$: 545.2, found: 545.3.

Step 2: Preparation of compound (S)—N-(1-(5-(2-methoxy-4-(pyridin-3-yl)phenyl)oxazol-2-yl)-7-oxononyl)-

8-methyl-1-oxa-2,8-diazaspiro[4.5]dec-2-ene-3-carboxamide (222): (S)—N-(1-(5-(4-chloro-2-methoxyphenyl)oxazol-2-yl)-7-oxononyl)-8-methyl-1-oxa-2,8-diazaspiro[4.5]dec-2-ene-3-carboxamide (222A, 100 mg, 0.183 mmol) and $K_3PO_4$ (117 mg, 0.550 mmol) were added to a stirred mixture of pyridin-3-ylboronic acid (27 mg, 0.220 mmol) in dioxane (2 mL) and water (0.5 mL). The mixture was replaced with $N_2$. Then, $PdCl_2$(DTBPF) (12 mg, 0.018 mmol) was added at room temperature and the mixture was heated with stirring at 70° C. for 2 h. Then $Pd_2(dba)_3$ (17 mg, 0.019 mmol) and XPhos (18 mg, 0.038 mmol) were added to the reaction solution and it was heated to 100° C. and stirred overnight. The mixture was cooled to room temperature. Water (10 mL) was added and the mixture was extracted with ethyl acetate (2×10 mL). The combined organic fractions were washed with brine (2×10 mL), dried ($Na_2SO_4$), filtered and the solvent was evaporated under reduced pressure and the residue was purified by preparative HPLC (reverse phase C-18 column), eluting with acetonitrile/water+0.05% $NH_3 \cdot H_2O$, to give (S)—N-(1-(5-(2-methoxy-4-(pyridin-3-yl)phenyl)oxazol-2-yl)-7-oxononyl)-8-methyl-1-oxa-2,8-diazaspiro[4.5]dec-2-ene-3-carboxamide (222).

L-(+)-tartaric acid (6 mg, 0.040 mmol) was added to a stirred mixture of (S)—N-(1-(5-(2-methoxy-4-(pyridin-3-yl)phenyl)oxazol-2-yl)-7-oxononyl)-8-methyl-1-oxa-2,8-diazaspiro[4.5]dec-2-ene-3-carboxamide (222, 23 mg, 0.039 mmol) in acetonitrile (5 mL) and water (2 mL) at room temperature. Then, it was made dry by lyophilization to give (S)—N-(1-(5-(2-methoxy-4-(pyridin-3-yl)phenyl)oxazol-2-yl)-7-oxononyl)-8-methyl-1-oxa-2,8-diazaspiro[4.5]dec-2-ene-3-carboxamide (2R,3R)-2,3-dihydroxysuccinate. LCMS (ESI) calc'd for $C_{33}H_{41}N_5O_5$ $[M+H]^+$: 588.3, found: 588.1. $^1H$ NMR (400 MHz, MeOD) δ 8.88 (brs, 1H), 8.55 (d, J=2.35 Hz, 1H), 8.18 (d, J=7.83 Hz, 1H), 7.87 (d, J=8.22 Hz, 1H), 7.50-7.58 (m, 2H), 7.34-7.42 (m, 2H), 5.23-5.28 (m, 1H), 4.48 (s, 5H), 4.08 (s, 3H), 3.33-3.51 (m, 4H), 3.16 (s, 2H), 2.90 (s, 3H), 2.42-2.50 (m, 4H), 2.06-2.23 (m, 5H), 2.01 (d, J=9.00 Hz, 1H), 1.52-1.65 (m, 2H), 1.33-1.51 (m, 4H), 0.99 (t, J=7.24 Hz, 3H).

The following compound was prepared using similar procedures as described for compound 222.

| ID | Structure | Observed $[M + H]^+$ |
|---|---|---|
| 395 | 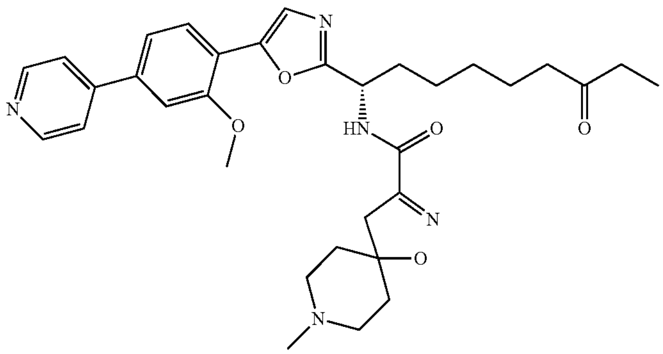 [SMILES: CCC(=O)CCCCC[C@H](NC(=O)C(=N)CC1(O)CCN(C)CC1)c1ncc(-c2ccc(-c3ccncc3)cc2OC)o1] | 588.1 |

Example 81

(S)—N—((S)-1-(5-(7-methoxy-2-methylquinolin-6-yl)oxazol-2-yl)-7-oxononyl)-5-methyl-5-azaspiro[2.3]hexane-1-carboxamide (230) and (R)—N—((S)-1-(5-(7-methoxy-2-methylquinolin-6-yl)oxazol-2-yl)-7-oxononyl)-5-methyl-5-azaspiro[2.3]hexane-1-carboxamide (231)

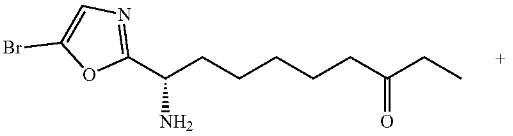

A6

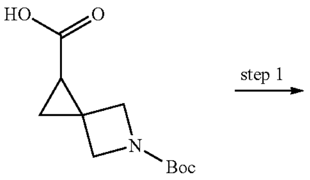

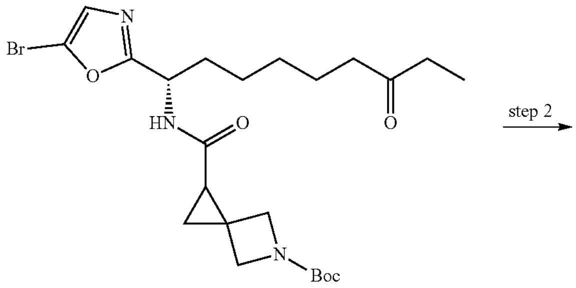

231A

-continued

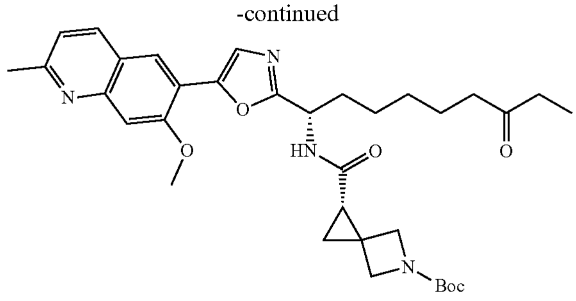

230B

-continued

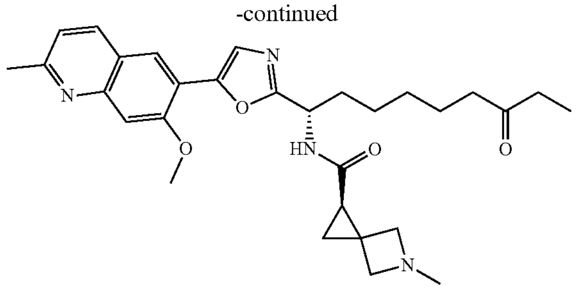

231

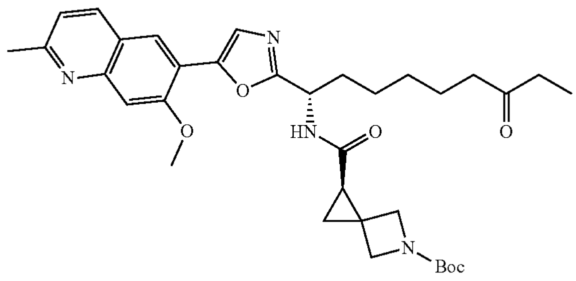

231B

230B

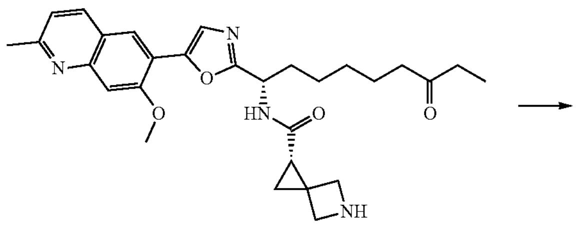

230C

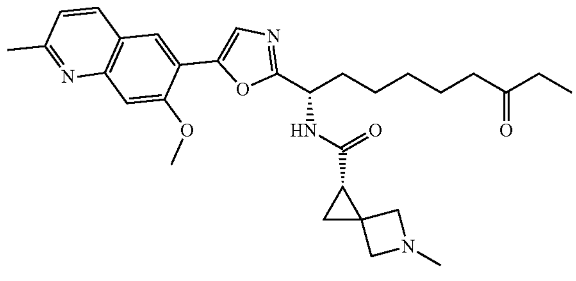

230

231B step 3

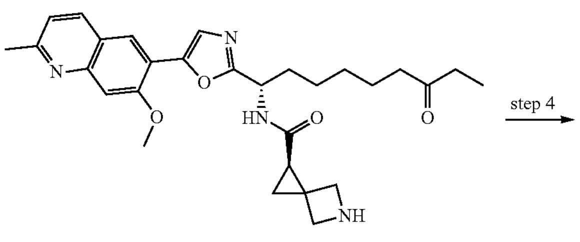

231C

Step 1: Preparation of tert-butyl 1-(((S)-1-(5-bromooxazol-2-yl)-7-oxononyl)carbamoyl)-5-azaspiro[2.3]hexane-5-carboxylate (231A): T3P (4.20 g, 6.60 mmol) was added to a stirred mixture of (S)-9-amino-9-(5-bromooxazol-2-yl) nonan-3-one (A6, 1 g, 3.30 mmol), 5-(tert-butoxycarbonyl)-5-azaspiro[2.3]hexane-1-carboxylic acid (0.899 g, 3.96 mmol) and DIEA (1.8 mL, 10.11 mmol) in DMF (15 mL) at room temperature and the mixture was stirred at room temperature for 18 h. The mixture was extracted with ethyl acetate (3×100 mL). The combined organic fractions were washed with brine (saturated, 2×50 mL), dried ($Na_2SO_4$), filtered and the solvent was evaporated under reduced pressure. The residue was purified by silica gel column flash chromatography, eluting with petroleum ether/EtOAc=1:1 to give tert-butyl 1-(((S)-1-(5-bromooxazol-2-yl)-7-oxononyl)carbamoyl)-5-azaspiro[2.3]hexane-5-carboxylate (231A). LCMS (ESI) calc'd for $C_{23}H_{34}BrN_3O_5$ $[M+H]^+$: 512.2, found: 512.2.

Step 2: Preparation of tert-butyl 1-(((S)-1-(5-(7-methoxy-2-methylquinolin-6-yl)oxazol-2-yl)-7-oxononyl)carbamoyl)-5-azaspiro[2.3]hexane-5-carboxylate (231B): $PdCl_2$ (DTBPF) (0.124 g, 0.190 mmol) was added to a stirred mixture of 7-methoxy-2-methyl-6-(4,4,5,5-tetramethyl-1,3,2-dioxaborolan-2-yl)quinoline (C1, 0.683 g, 2.283 mmol), tert-butyl 1-(((S)-1-(5-bromooxazol-2-yl)-7-oxononyl)carbamoyl)-5-azaspiro[2.3]hexane-5-carboxylate (231A, 1.3 g, 1.903 mmol) and $K_3PO_4$ (1.212 g, 5.71 mmol) in THF (10 mL)/water (2 mL) at room temperature and the mixture was stirred at 70° C. for 3 h. The mixture was diluted with ethyl acetate (50 mL), washed with water (20 mL) and brine (saturated 20 mL), dried ($Na_2SO_4$), filtered and the solvent was evaporated under reduced pressure. The mixture was purified by preparative HPLC (reverse phase C-18 column), eluting with acetonitrile/water+0.1% TFA, to give tert-butyl 1-(((S)-1-(5-(7-methoxy-2-methylquinolin-6-yl)oxazol-2-yl)-7-oxononyl)carbamoyl)-5-azaspiro[2.3]hexane-5-carboxylate (231B, first peak on HPLC). LCMS (ESI) calc'd for $C_{34}H_{44}N_4O_6$ $[M+H]^+$: 605.3, found: 605.3. tert-butyl 1-(((S)-1-(5-(7-methoxy-2-methylquinolin-6-yl)oxazol-2-yl)-7-oxononyl)carbamoyl)-5-azaspiro[2.3]hexane-5-carboxylate (second peak on HPLC). LCMS (ESI) calc'd for $C_{34}H_{44}N_4O_6$ $[M+H]^+$: 605.3, found: 605.4.

Step 3: Preparation of N—((S)-1-(5-(7-methoxy-2-methylquinolin-6-yl)oxazol-2-yl)-7-oxononyl)-5-azaspiro[2.3]hexane-1-carboxamide (231C): TFA (0.1 mL, 1.298 mmol) was added to tert-butyl 1-(((S)-1-(5-(7-methoxy-2-methylquinolin-6-yl)oxazol-2-yl)-7-oxononyl)carbamoyl)-5-azaspiro[2.3]hexane-5-carboxylate (231B, first peak on HPLC, 80 mg, 0.132 mmol) in DCM (1 mL) at room temperature for 1 h. The mixture was evaporated under pressure to remove TFA to give N—((S)-1-(5-(7-methoxy-2-methylquinolin-6-yl)oxazol-2-yl)-7-oxononyl)-5-azaspiro[2.3]hexane-1-carboxamide (231C) which was used to next step without further purification. LCMS (ESI) calc'd for $C_{29}H_{36}N_4O_4$ $[M+H]^+$: 505.3, found: 505.3.

Step 4: Preparation of N—((S)-1-(5-(7-methoxy-2-methylquinolin-6-yl)oxazol-2-yl)-7-oxononyl)-5-methyl-5-azaspiro[2.3]hexane-1-carboxamide (231): Formaldehyde (22 mg, 0.733 mmol) was added to a stirred mixture of N—((S)-1-(5-(7-methoxy-2-methylquinolin-6-yl)oxazol-2-yl)-7-oxononyl)-5-azaspiro[2.3]hexane-1-carboxamide (231C, 60 mg, 0.119 mmol) in MeOH (3 mL) at room temperature and the mixture was stirred at room temperature for 1 h. Sodium triacetoxyhydroborate (227 mg, 1.070 mmol) was added into the mixture at room temperature and the mixture was stirred at room temperature for 1 h. The mixture was neutralized by $NaHCO_3$(2 mL), extracted with ethyl acetate (2*20 mL) and washed with water (10 mL), dried ($Na_2SO_4$), filtered and the solvent was evaporated under reduced pressure. The residue was purified by preparative HPLC (reverse phase C-18 column), eluting with acetonitrile/water+0.05% $NH_3 \cdot H_2O$, to give N—((S)-1-(5-(7-methoxy-2-methylquinolin-6-yl)oxazol-2-yl)-7-oxononyl)-5-methyl-5-azaspiro[2.3]hexane-1-carboxamide (231. LCMS (ESI) calc'd for $C_{30}H_{38}N_4O_4$ $[M+H]^+$: 519.3, found: 519.1. $^1H$ NMR (400 MHz, MeOD) δ 8.41 (d, J=8.22 Hz, 1H), 8.32 (s, 1H), 7.62 (s, 1H), 7.41-7.49 (m, 2H), 5.18 (t, J=7.43 Hz, 1H), 4.15 (s, 3H), 3.03 (s, 2H), 2.99-3.09 (m, 1H), 2.77 (s, 3H), 2.42-2.51 (m, 4H), 1.60 (quin, J=7.34 Hz, 2H), 1.27-1.44 (m, 5H), 0.99 (t, J=7.24 Hz, 3H).

Compound 230 was prepared from second peak in step 2. The absolute configuration was not confirmed. LCMS (ESI) calc'd for $C_{30}H_{38}N_4O_4$ $[M+H]^+$: 519.3, found: 519.1. $^1H$ NMR (400 MHz, MeOD) δ 9.04 (t, J=9.00 Hz, 1H), 8.69 (d, J=7.43 Hz, 1H), 7.74-7.82 (m, 2H), 7.64 (s, 1H), 5.11-5.23 (m, 1H), 4.28 (s, 3H), 2.96-3.03 (m, 6H), 2.46 (q, J=7.56 Hz, 5H), 1.94-2.16 (m, 4H), 1.59 (d, J=4.70 Hz, 4H), 1.29 (brs, 6H), 1.00 (t, J=7.43 Hz, 3H), 0.85-0.93 (m, 2H).

The following compounds were prepared using similar procedures as described for compounds 230 and 231.

| ID | Structure | Observed $[M + H]^+$ |
| --- | --- | --- |
| 68 | 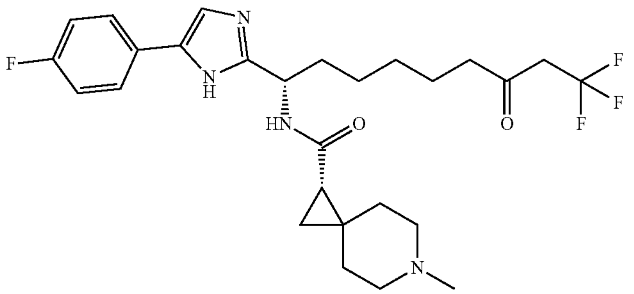 [SMILES: CN1CCC2(CC1)C[C@@H]2C(=O)N[C@@H](CCCCCC(=O)CC(F)(F)F)c1ncc(-c2ccc(F)cc2)[nH]1] | 523.2 |
| 84 | 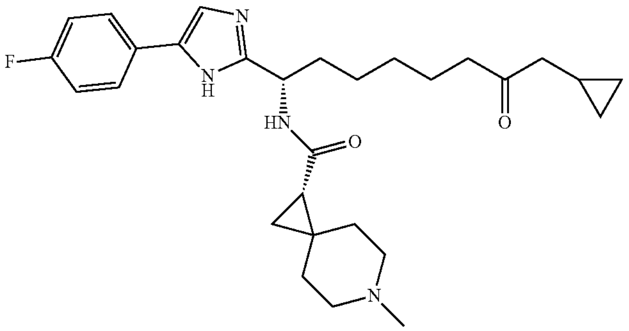 [SMILES: CN1CCC2(CC1)C[C@@H]2C(=O)N[C@@H](CCCCCC(=O)CC1CC1)c1ncc(-c2ccc(F)cc2)[nH]1] | 495.1 |
| 137 | 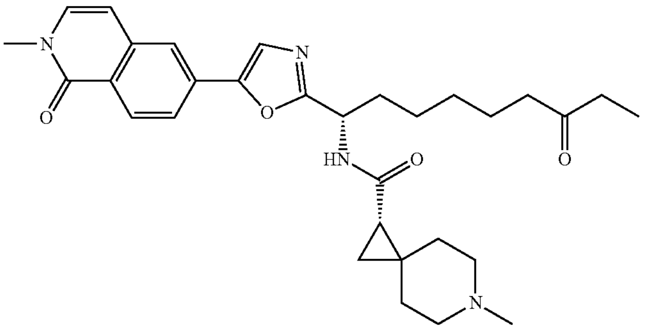 [SMILES: CCC(=O)CCCCC[C@H](NC(=O)[C@H]1CC12CCN(C)CC2)c1ncc(-c2ccc3c(=O)n(C)ccc3c2)o1] | 533.3 |

-continued
| ID | Structure | Observed [M + H]+ |
|---|---|---|
| 155 | 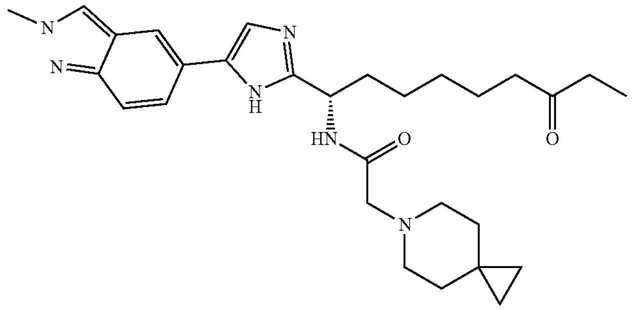 [SMILES: CCC(=O)CCCCC[C@H](NC(=O)CN1CCC2(CC1)CC2)c1ncc(C2=C/C(=C/NC)C(=N)C=C2)[nH]1] | 505.3 |
| 165 | 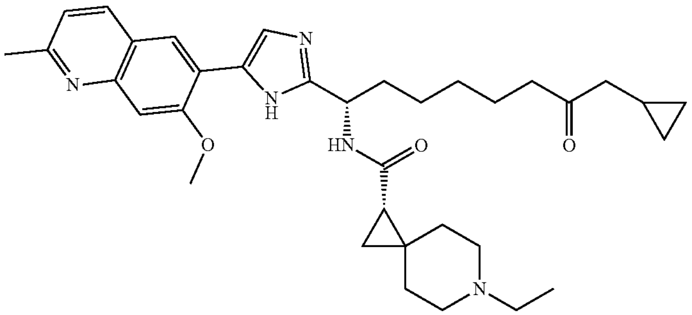 [SMILES: CCN1CCC2(CC1)C[C@@H]2C(=O)N[C@@H](CCCCCC(=O)CC1CC1)c1ncc(-c2cc3ccc(C)nc3cc2OC)[nH]1] | 586.1 |
| 184 | 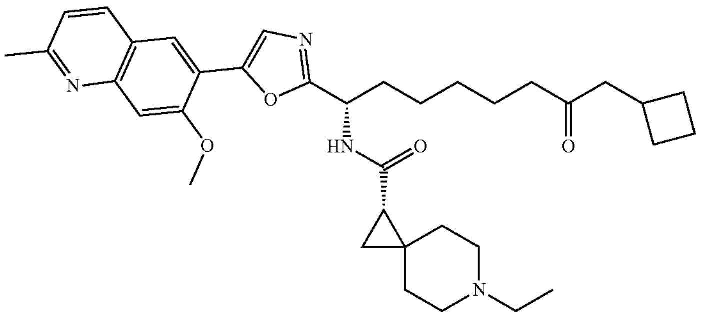 [SMILES: CCN1CCC2(CC1)C[C@@H]2C(=O)N[C@@H](CCCCCC(=O)CC1CCC1)c1ncc(-c2cc3ccc(C)nc3cc2OC)o1] | 601.2 |
| 185 | 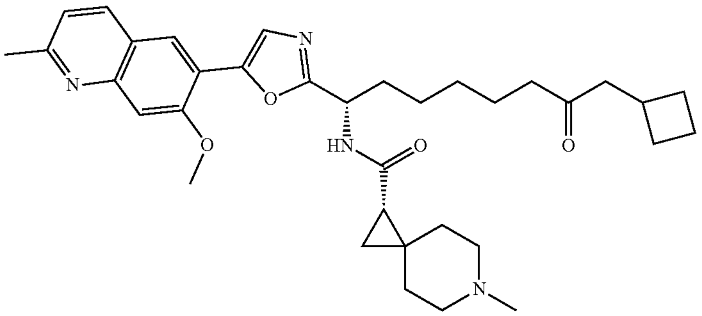 [SMILES: COc1cc2nc(C)ccc2cc1-c1cnc([C@H](CCCCCC(=O)CC2CCC2)NC(=O)[C@H]2CC23CCN(C)CC3)o1] | 587.2 |
| 201 | 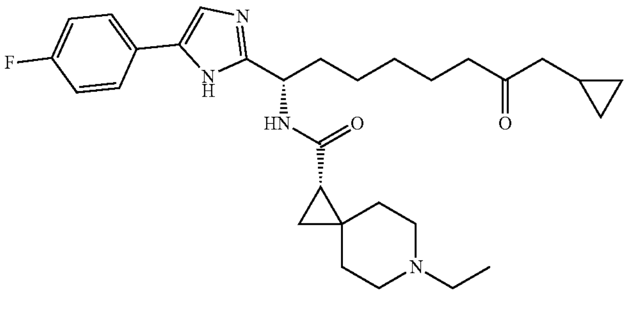 [SMILES: CCN1CCC2(CC1)C[C@@H]2C(=O)N[C@@H](CCCCCC(=O)CC1CC1)c1ncc(-c2ccc(F)cc2)[nH]1] | 509.1 |

-continued

| ID | Structure | Observed $[M + H]^+$ |
|---|---|---|
| 202 | 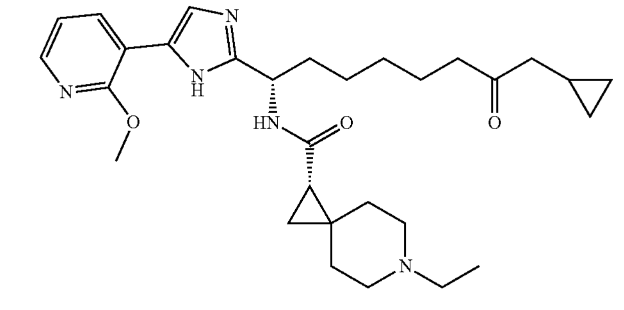 [SMILES: CCN1CCC2(CC1)C[C@@H]2C(=O)N[C@@H](CCCCCC(=O)CC1CC1)c1ncc(-c2cccnc2OC)[nH]1] | 522.2 |
| 269 | 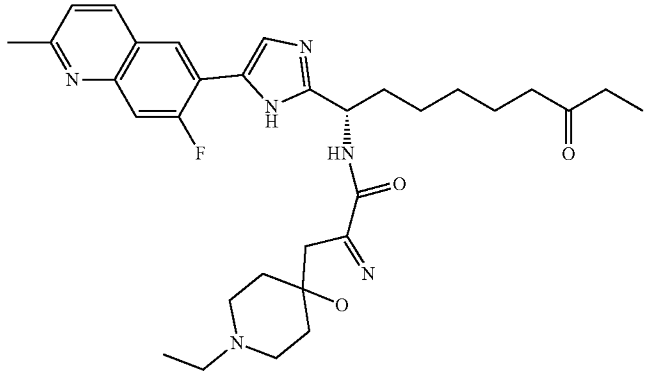 [SMILES: CCC(=O)CCCCC[C@H](NC(=O)C(=N)CC1(O)CCN(CC)CC1)c1ncc(-c2cc3ccc(C)nc3cc2F)[nH]1] | 578.4 |

Example 82

N-{(1S)-1-[5-(2-methoxy-4-pyrazin-2-ylphenyl)-1,3-oxazol-2-yl]-7-oxononyl}-8-methyl-1-oxa-2,8-diazaspiro[4.5]dec-2-ene-3-carboxamide (237)

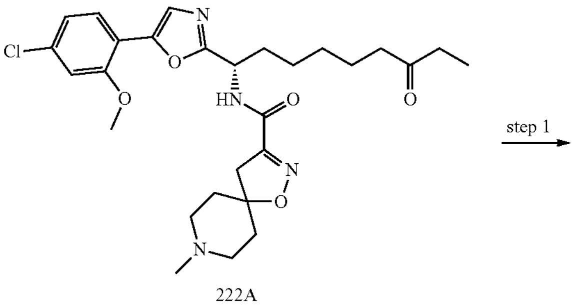

222A

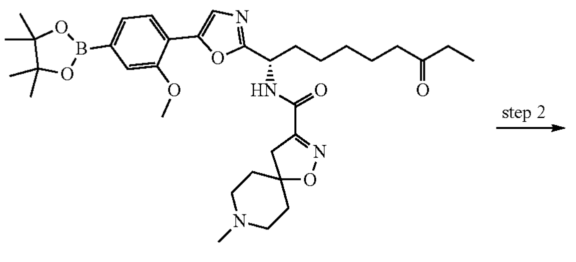

237A

-continued

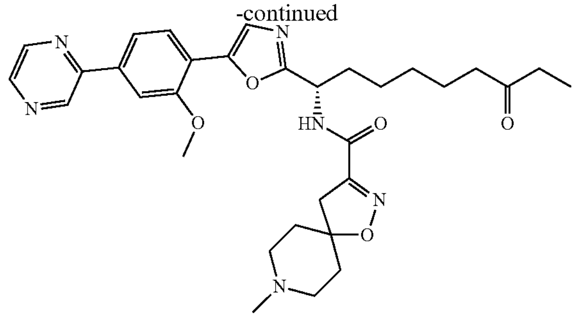

237

Step 1: Preparation of (S)—N-(1-(5-(2-methoxy-4-(4,4,5,5-tetramethyl-1,3,2-dioxaborolan-2-yl)phenyl)oxazol-2-yl)-7-oxononyl)-8-methyl-1-oxa-2,8-diazaspiro[4.5]dec-2-ene-3-carboxamide (237A): Potassium acetate (45 mg, 0.459 mmol) and $Pd_2(dba)_3$ (25 mg, 0.027 mmol) were added to the mixture of BPD (70 mg, 0.276 mmol) and XPhos (30 mg, 0.063 mmol) and (S)—N-(1-(5-(4-chloro-2-methoxyphenyl)oxazol-2-yl)-7-oxononyl)-8-methyl-1-oxa-2,8-diazaspiro[4.5]dec-2-ene-3-carboxamide (222A, 100 mg, 0.183 mmol) in dioxane (2 mL). The resultant mixture was stirred at 80° C. under $N_2$ for 16 h. The mixture was concentrated in vacuo. The residue was purified together with a same reaction from 30 mg 222A by silica gel flash chromatography (ISCORF75; Sepa flash column), eluting with DCM/MeOH=30:1-10:1 to give (S)—N-(1-(5-(2-methoxy-4-(4,4,5,5-tetramethyl-1,3,2-dioxaborolan-2-yl)phenyl)oxazol-2-yl)-7-oxononyl)-8-methyl-1-oxa-2,8-diazaspiro[4.5]dec-2-ene-3-carboxamide (237A). LCMS (ESI) calc'd for $C_{34}H_{49}BN_4O_7$ $[M+H]^+$: 637.4, found: 637.4.

Step 2: Preparation of (S)—N-(1-(5-(2-methoxy-4-(pyrazin-2-yl)phenyl)oxazol-2-yl)-7-oxononyl)-8-methyl-1-oxa-2,8-diazaspiro[4.5]dec-2-ene-3-carboxamide (237): Potassium phosphate tribasic (65 mg, 0.306 mmol) and XPhos (22 mg, 0.046 mmol) and $Pd_2(dba)_3$ (22 mg, 0.024 mmol) were added to the solution of 2-bromopyrazine (40 mg, 0.252 mmol) and (S)—N-(1-(5-(2-methoxy-4-(4,4,5,5-tetramethyl-1,3,2-dioxaborolan-2-yl)phenyl)oxazol-2-yl)-7-oxononyl)-8-methyl-1-oxa-2,8-diazaspiro[4.5]dec-2-ene-3-carboxamide (237A, 100 mg, 0.157 mmol) in dioxane (2 mL) and water (0.2 mL), the resultant mixture was stirred at 70° C. for 4 h. The reaction mixture was extracted with EtOAc (2*20 mL) and the combined organic layer was dried over $Na_2SO_4$, filtered and concentrated in vacuo. The residue was purified by silica gel flash chromatography (ISCORF75; Sepa flash column), eluting with DCM/MeOH/$NH_3$(Aq.)=20:1:0.01 to give a crude product. The crude product was purified by preparative HPLC (reverse phase C-18 column), eluting with acetonitrile/water+0.05% $NH_3 \cdot H_2O$, to give (S)—N-(1-(5-(2-methoxy-4-(pyrazin-2-yl)phenyl)oxazol-2-yl)-7-oxononyl)-8-methyl-1-oxa-2,8-diazaspiro[4.5]dec-2-ene-3-carboxamide (237).

L-(+)-tartaric acid (9 mg, 0.060 mmol) was added to the solution of (S)—N-(1-(5-(2-methoxy-4-(pyrazin-2-yl)phenyl)oxazol-2-yl)-7-oxononyl)-8-methyl-1-oxa-2,8-diazaspiro[4.5]dec-2-ene-3-carboxamide (237, 32 mg, 0.054 mmol) in MeOH (3 mL) and water (10 mL), and the resultant solution was lyophilized to give (S)—N-(1-(5-(2-methoxy-4-(pyrazin-2-yl)phenyl)oxazol-2-yl)-7-oxononyl)-8-methyl-1-oxa-2,8-diazaspiro[4.5]dec-2-ene-3-carboxamide (2R,3R)-2,3-dihydroxysuccinate. LCMS (ESI) calc'd for $C_{32}H_{40}N_6O_5$ $[M+H]^+$: 589.3, found: 589.1. $^1H$ NMR (400 MHz, MeOD) δ 9.19 (s, 1H), 8.69 (s, 1H), 8.55 (d, J=1.96 Hz, 1H), 7.75-7.93 (m, 3H), 7.54 (s, 1H), 5.20-5.32 (m, 1H), 4.48 (s, 3H), 4.09 (s, 3H), 3.35-3.52 (m, 1H), 3.34-3.52 (m, 1H), 3.16 (brs, 2H), 2.89 (brs, 3H), 2.40-2.51 (m, 4H), 1.93-2.28 (m, 6H), 1.31-1.64 (m, 6H), 0.99 (t, J=7.24 Hz, 3H).

Example 83

Synthesis of Compounds 246-254 (Library Synthesis)

To boronic acid monomer (0.101 mmol) and XPhos Pd G3 (2.447 mg, 2.89 μmol), a solution of (S)—N—((S)-1-(4-bromo-2-(4-fluorophenyl)-1-((2-(trimethylsilyl)ethoxy)methyl)-1H-imidazol-5-yl)-7-oxononyl)-6-ethyl-6-azaspiro[2.5]octane-1-carboxamide (40 mg, 0.058 mmol) in dioxane (1.5 ml) at ambient temperature was added, followed by $K_3PO_4$ (30.7 mg, 0.145 mmol) in water (100 μl). The reaction mixture was heated to 100° C. overnight for 16 hr. The reaction mixture was cooled and extracted with DCM and washed by water and brine, and dried by sodium sulfate. The crude was obtained after filtering and concentrating. The resulting residue was assumed to have the corresponding product and was used directly without further purification. The crude was dissolved in DCM (1 ml), and TFA (0.103 ml, 1.334 mmol) was added. The reaction mixture was reacted at 50° C. for 2 hr. The reaction mixture was concentrated down via GeneVac. The residue was dissolved in DMSO (1.75 ml) and filtered. The plate was submitted to HTP for further purification and registration.

The following compounds were prepared by the above library synthesis:

| ID | Structure | Observed $[M + H]^+$ |
|---|---|---|
| 246 | 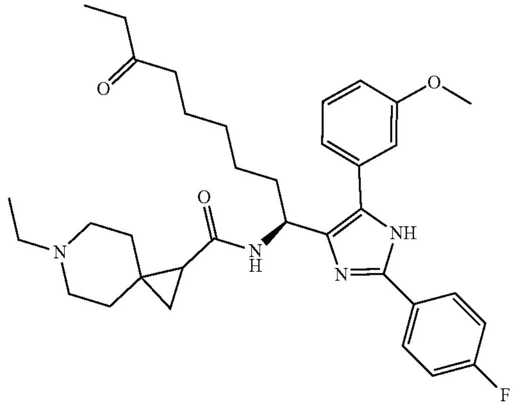 [SMILES: CCC(=O)CCCCC[C@H](NC(=O)C1CC12CCN(CC)CC2)c1nc(-c2ccc(F)cc2)[nH]c1-c1cccc(OC)c1] | 589.308 |
| 247 | 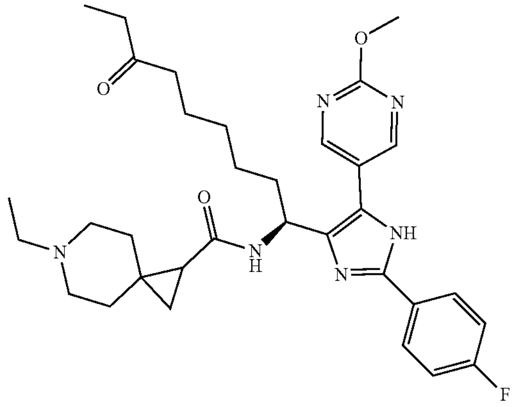 [SMILES: CCC(=O)CCCCC[C@H](NC(=O)C1CC12CCN(CC)CC2)c1nc(-c2ccc(F)cc2)[nH]c1-c1cnc(OC)nc1] | 591.308 |

-continued
| ID | Structure | Observed [M + H]+ |
|---|---|---|
| 248 | 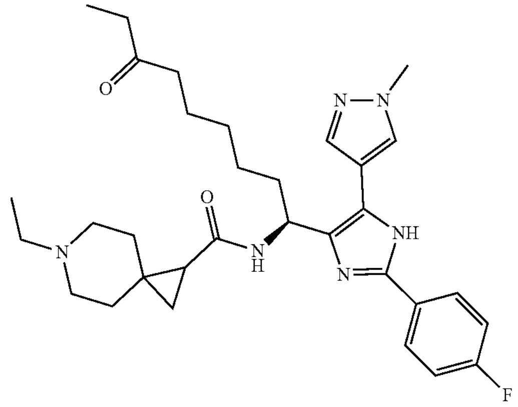 [SMILES: CCC(=O)CCCCC[C@H](NC(=O)C1CC12CCN(CC)CC2)c1nc(-c2ccc(F)cc2)[nH]c1-c1cnn(C)c1] | 563.308 |
| 249 | 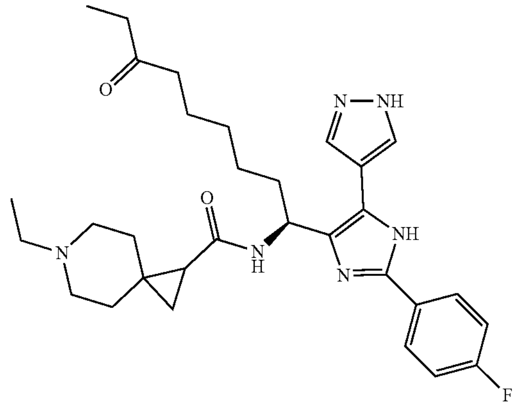 [SMILES: CCC(=O)CCCCC[C@H](NC(=O)C1CC12CCN(CC)CC2)c1nc(-c2ccc(F)cc2)[nH]c1-c1cn[nH]c1] | 549.308 |
| 250 | 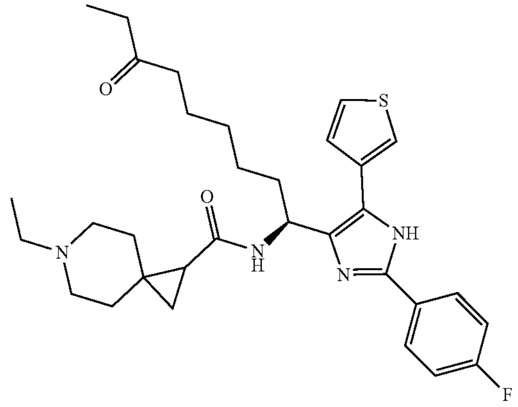 [SMILES: CCC(=O)CCCCC[C@H](NC(=O)C1CC12CCN(CC)CC2)c1nc(-c2ccc(F)cc2)[nH]c1-c1ccsc1] | 565.308 |

-continued
| ID | Structure | Observed [M + H]+ |
|---|---|---|
| 251 | 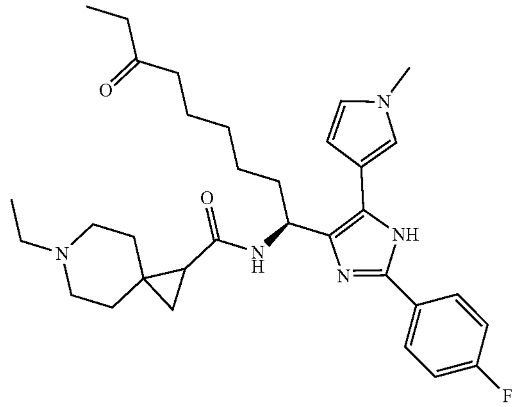 [SMILES: CCC(=O)CCCCC[C@H](NC(=O)C1CC12CCN(CC)CC2)c1nc(-c2ccc(F)cc2)[nH]c1-c1ccn(C)c1] | 562.308 |
| 252 | 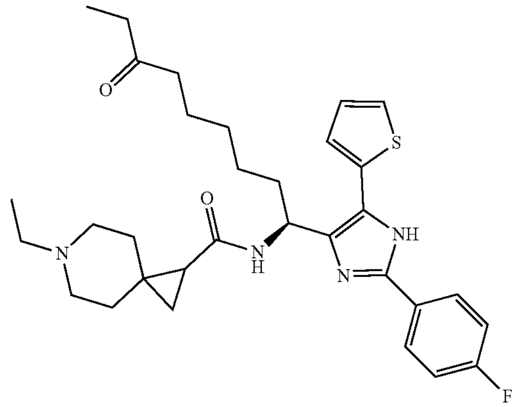 [SMILES: CCC(=O)CCCCC[C@H](NC(=O)C1CC12CCN(CC)CC2)c1nc(-c2ccc(F)cc2)[nH]c1-c1cccs1] | 565.308 |
| 253 | 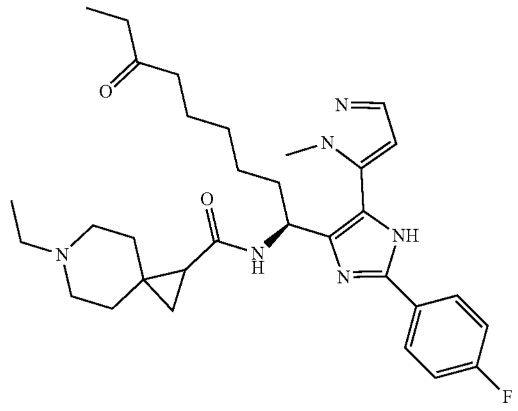 [SMILES: CCC(=O)CCCCC[C@H](NC(=O)C1CC12CCN(CC)CC2)c1nc(-c2ccc(F)cc2)[nH]c1/C(=C/C=N)NC] | 563.308 |

-continued

| ID | Structure | Observed [M + H]+ |
|---|---|---|
| 254 | 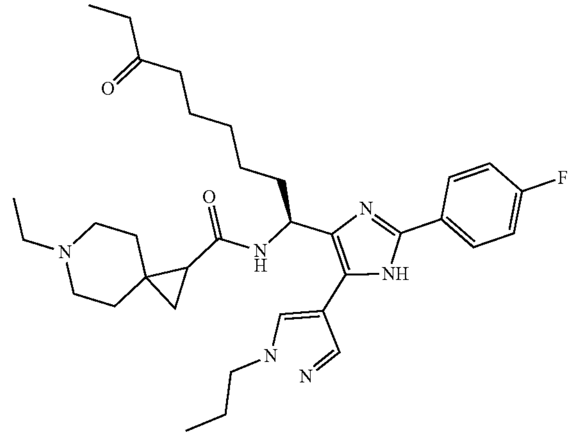 [SMILES: CCCN/C=C(\C=N)c1[nH]c(-c2ccc(F)cc2)nc1[C@H](CCCCCC(=O)CC)NC(=O)C1CC12CCN(CC)CC2] | 591.408 |

Example 84

Synthesis of compounds 255-268 (library synthesis)

To a 8 mL pressure vial with a pressure release cap was added $PdCl_2(dppf)-CH_2Cl_2$Adduct (9.36 mg, 0.011 mmol), (S)—N—((S)-1-(5-bromo-1-((2-(trimethylsilyl)ethoxy) methyl)-1H-imidazol-2-yl)-7-oxononyl)-6-methyl-6-azaspiro[2.5]octane-1-carboxamide, TFA (40 mg, 0.057 mmol) and the boronic acid monomer (0.100 mmol). The flask was degassed by vacuum and re-filled with $N_2$. 1,4-Dioxane (1.5 ml) and potassium carbonate (0.172 ml, 0.344 mmol) were added. The reaction was stirred at 100° C. for 16 hours. The reaction mixture was diluted with EtOAc (4 mL) was washed with water. The organic layer was concentrated down via GeneVac. The resulting crude was dissolved in DCM (2 ml), and treated with TFA (0.439 ml, 5.70 mmol). The reaction was stirred at 50° C. for 3 hours. The reaction mixture was reacted at 50° C. for 2 hr. The reaction mixture was concentrated down via GeneVac. The residue was dissolved in DMSO (1.75 ml) and filtered. The plate was submitted to HTP for further purification and registration.

The following compounds were prepared by the above library synthesis:

| ID | Structure | Observed [M + H]+ |
|---|---|---|
| 255 | 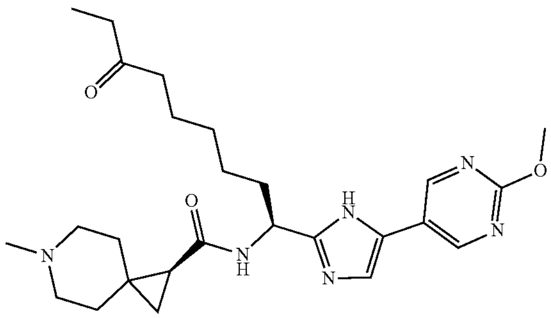 | 482.30 |
| 256 | 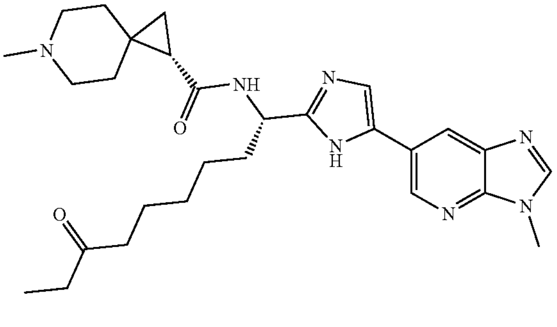 [SMILES: CCC(=O)CCCCC[C@H](NC(=O)[C@H]1CC12CCN(C)CC2)c1ncc(-c2cnc3c(c2)ncn3C)[nH]1] | 506.14 |

-continued
| ID | Structure | Observed [M + H]+ |
|---|---|---|
| 257 | 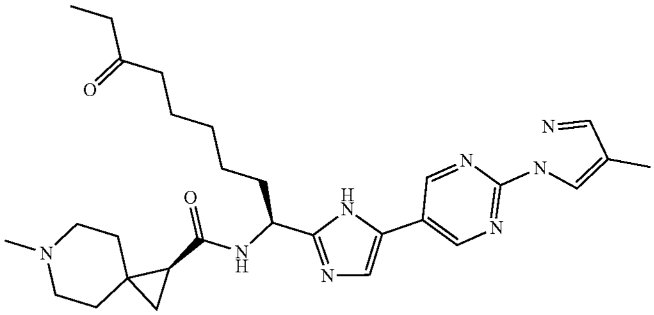 [SMILES: CCC(=O)CCCCC[C@H](NC(=O)[C@H]1CC12CCN(C)CC2)c1ncc(-c2cnc(N/C=C(/C)C=N)nc2)[nH]1] | 533.3349 |
| 258 | 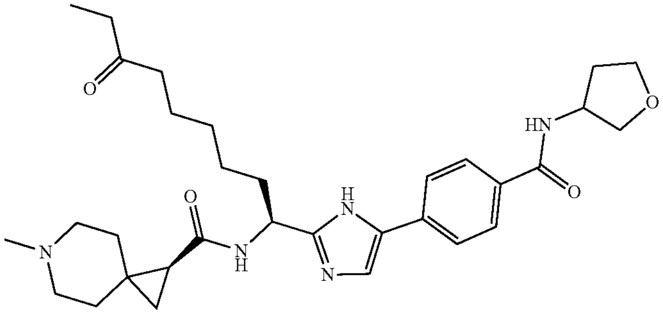 [SMILES: CCC(=O)CCCCC[C@H](NC(=O)[C@H]1CC12CCN(C)CC2)c1ncc(-c2ccc(C(=O)NC3CCOC3)cc2)[nH]1] | 564.3549 |
| 259 | 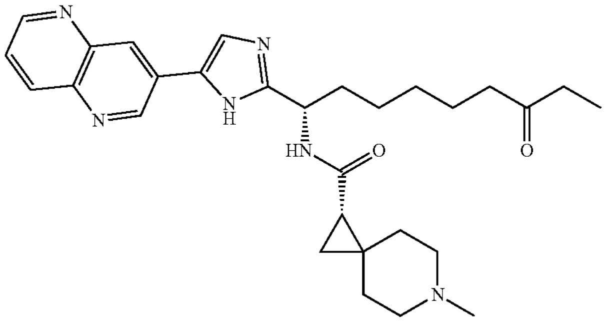 [SMILES: CCC(=O)CCCCC[C@H](NC(=O)[C@H]1CC12CCN(C)CC2)c1ncc(-c2cnc3cccnc3c2)[nH]1] | 503.3139 |
| 260 | 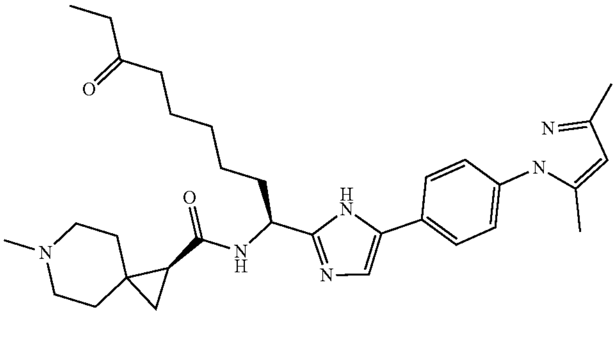 [SMILES: CCC(=O)CCCCC[C@H](NC(=O)[C@H]1CC12CCN(C)CC2)c1ncc(-c2ccc(N/C(C)=C\C(C)=N)cc2)[nH]1] | 545.3609 |

-continued
| ID | Structure | Observed [M + H]+ |
|---|---|---|
| 261 | 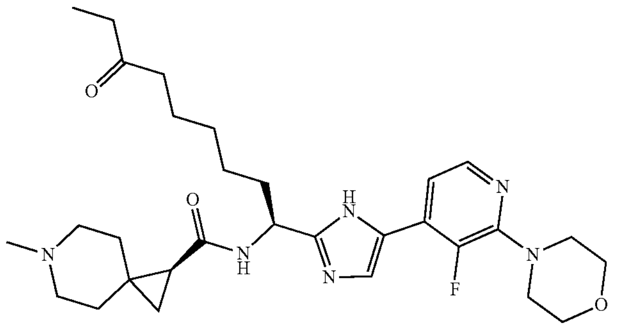 [SMILES: CCC(=O)CCCCC[C@H](NC(=O)[C@H]1CC12CCN(C)CC2)c1ncc(-c2ccnc(N3CCOCC3)c2F)[nH]1] | 555.3459 |
| 262 | 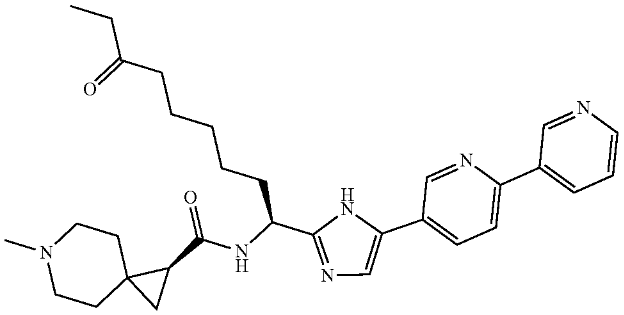 [SMILES: CCC(=O)CCCCC[C@H](NC(=O)[C@H]1CC12CCN(C)CC2)c1ncc(-c2ccc(-c3cccnc3)nc2)[nH]1] | 529.3289 |
| 263 | 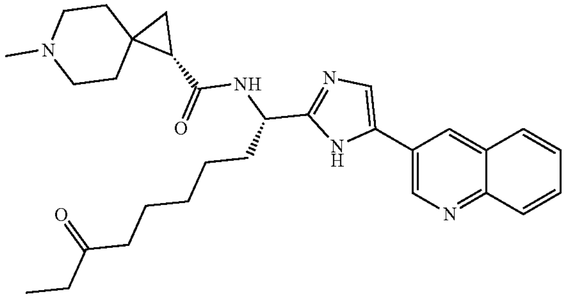 [SMILES: CCC(=O)CCCCC[C@H](NC(=O)[C@H]1CC12CCN(C)CC2)c1ncc(-c2cnc3ccccc3c2)[nH]1] | 502.3179 |
| 264 | 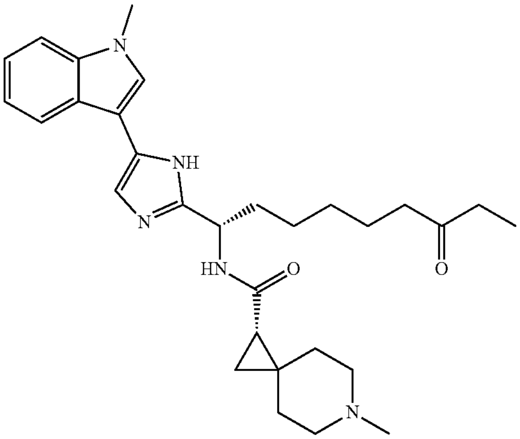 [SMILES: CCC(=O)CCCCC[C@H](NC(=O)[C@H]1CC12CCN(C)CC2)c1ncc(-c2cn(C)c3ccccc23)[nH]1] | 504.3339 |

-continued
| ID | Structure | Observed [M + H]+ |
|---|---|---|
| 265 | 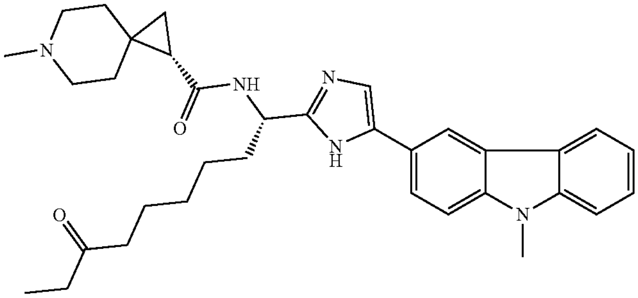 [SMILES: CCC(=O)CCCCC[C@H](NC(=O)[C@H]1CC12CCN(C)CC2)c1ncc(-c2ccc3c(c2)c2ccccc2n3C)[nH]1] | 554.3499 |
| 266 | 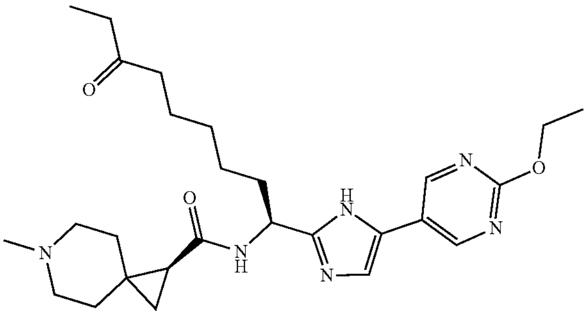 [SMILES: CCOc1ncc(-c2cnc([C@H](CCCCCC(=O)CC)NC(=O)[C@H]3CC34CCN(C)CC4)[nH]2)cn1] | 497.3239 |
| 267 | 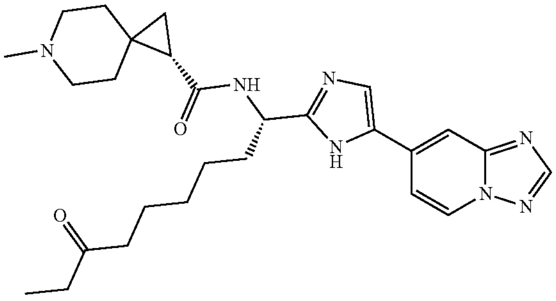 [SMILES: CCC(=O)CCCCC[C@H](NC(=O)[C@H]1CC12CCN(C)CC2)c1ncc(-c2ccn3ncnc3c2)[nH]1] | 492.3089 |
| 268 | 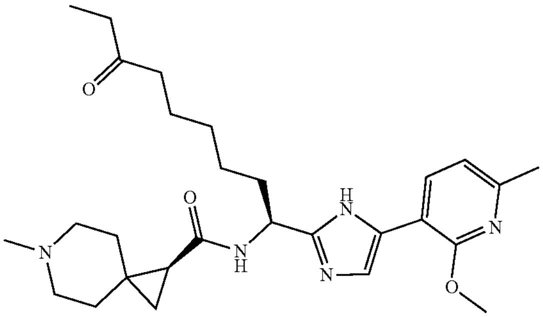 | 496.3289 |

Example 85

(S)-2-(2-acetyl-2-azaspiro[3.3]heptan-6-yl)-N-(7-oxo-1-(5-phenyl-1H-imidazol-2-yl)nonyl)acetamide (300)

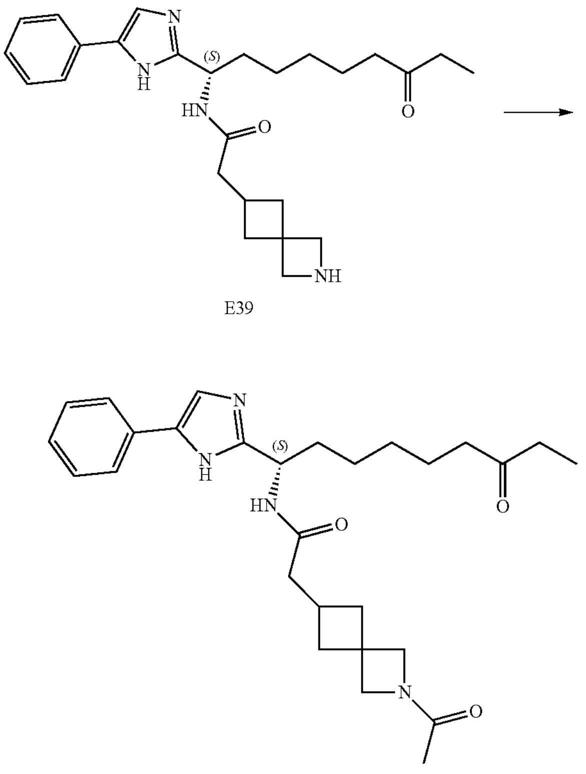

E39

300

To a 4 mL pressure vial with pressure release cap (S)—N-(7-oxo-1-(5-phenyl-1H-imidazol-2-yl)nonyl)-2-(2-azaspiro[3.3]heptan-6-yl)acetamide (E39, 12 mg, 0.027 mmol), acetic acid (3.30 mg, 0.055 mmol), HATU (15.68 mg, 0.041 mmol), DMF (275 μl), and DIPEA (48.0 μl, 0.275 mmol) were added. The reaction was stirred with DMF (275 μl) for 2 hours. The product was purified by C18 HPLC (Gilson, $CH_3CN$ in water with 0.1% TFA: 0% to 70%) to give (S)-2-(2-acetyl-2-azaspiro[3.3]heptan-6-yl)-N-(7-oxo-1-(5-phenyl-1H-imidazol-2-yl)nonyl)acetamide, TFA (300) LCMS (ESI) calc'd for $C_{28}H_{39}N_4O_3$ $[M+H]^+$: 479.3, found: 479.3.

Example 86

Synthesis of Compounds 363-384 (Library Synthesis)

The amine monomer (0.1 mmol), the corresponding acid (0.100 mmol), and DIPEA (0.3 mmol) were mixed in DMF (1 ml), and treated with HATU (0.130 mmol). The reaction mixtures were stirred at rt for 20 minutes, 0.1 mL of water was added, and the mixture was stirred for 5 minutes, then filtered. The plate was sent to HTP for library purification.

The following compounds were prepared by the above library synthesis:

| ID | Structure | Observed $[M + H]^+$ |
|---|---|---|
| 363 | 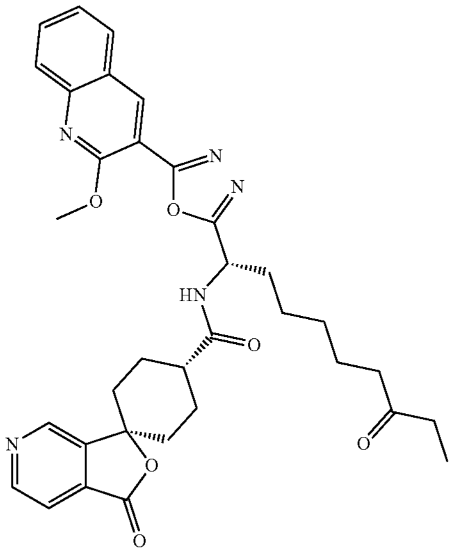 [SMILES: CCC(=O)CCCCC[C@H](NC(=O)[C@H]1CC[C@@]2(CC1)OC(=O)c1ccncc12)C(=N)OC(=N)c1cc2ccccc2nc1OC] | 612.35 |

-continued
| ID | Structure | Observed [M + H]+ |
|---|---|---|
| 364 | 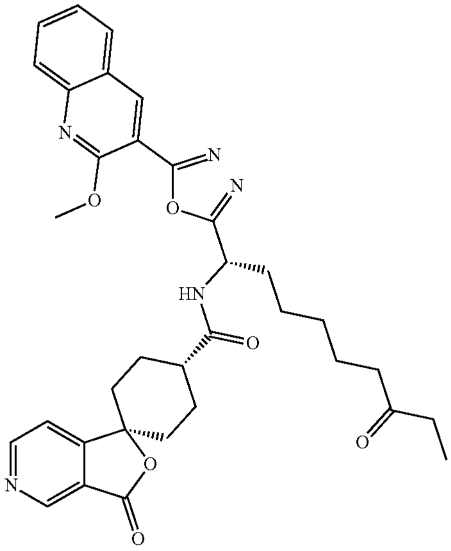 [SMILES: CCC(=O)CCCCC[C@H](NC(=O)[C@H]1CC[C@@]2(CC1)OC(=O)c1cnccc12)C(=N)OC(=N)c1cc2ccccc2nc1OC] | 612.36 |
| 365 | 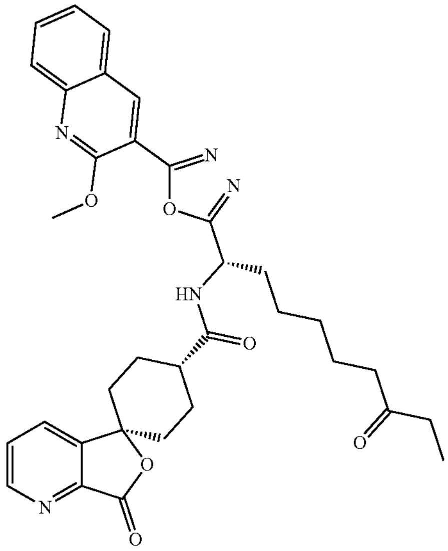 [SMILES: CCC(=O)CCCCC[C@H](NC(=O)[C@H]1CC[C@@]2(CC1)OC(=O)c1ncccc12)C(=N)OC(=N)c1cc2ccccc2nc1OC] | 612.37 |

-continued
| ID | Structure | Observed [M + H]+ |
|---|---|---|
| 366 | 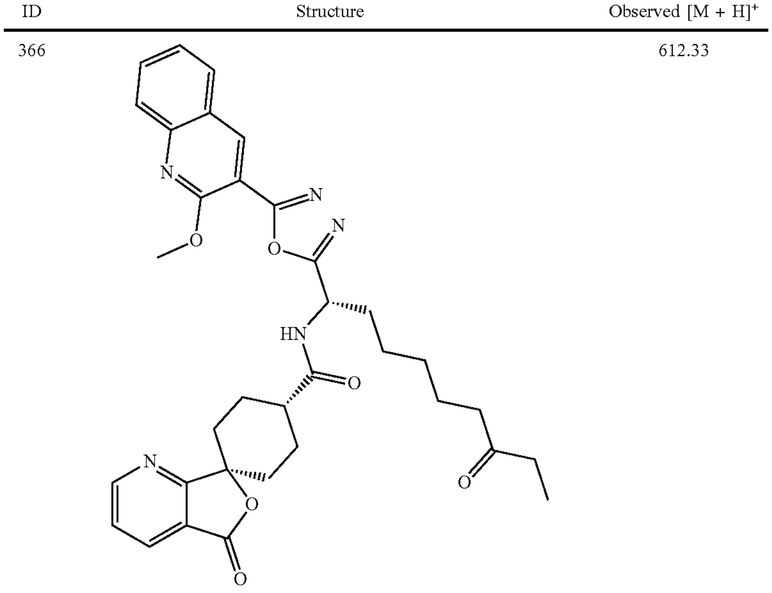 | 612.33 |
| 367 | 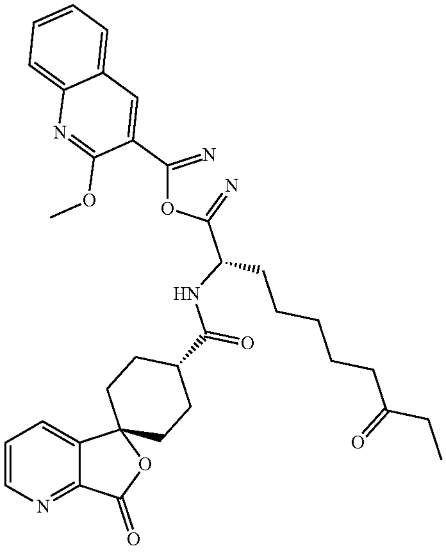 [SMILES: CCC(=O)CCCCC[C@H](NC(=O)[C@H]1CC[C@]2(CC1)OC(=O)c1ncccc12)C(=N)OC(=N)c1cc2ccccc2nc1OC] | 612.42 |

-continued
| ID | Structure | Observed [M + H]+ |
|---|---|---|
| 368 | 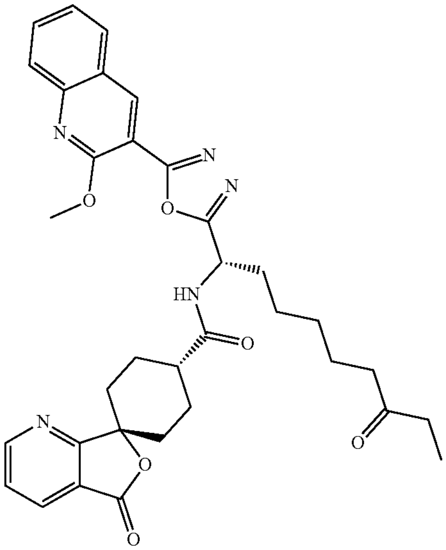 [SMILES: CCC(=O)CCCCC[C@H](NC(=O)[C@H]1CC[C@]2(CC1)OC(=O)c1cccnc12)C(=N)OC(=N)c1cc2ccccc2nc1OC] | 612.35 |
| 369 | 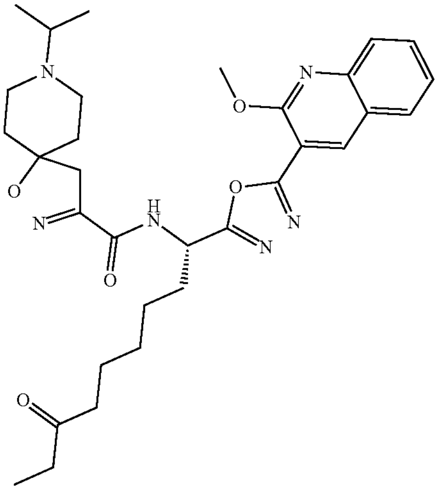 [SMILES: CCC(=O)CCCCC[C@H](NC(=O)C(=N)CC1(O)CCN(C(C)C)CC1)C(=N)OC(=N)c1cc2ccccc2nc1OC] | 591.4 |
| 370 | 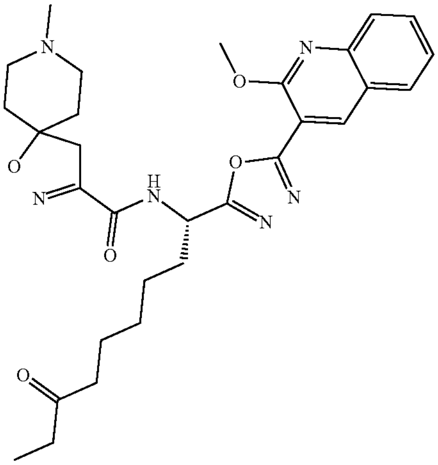 [SMILES: CCC(=O)CCCCC[C@H](NC(=O)C(=N)CC1(O)CCN(C)CC1)C(=N)OC(=N)c1cc2ccccc2nc1OC] | 563.41 |

-continued
| ID | Structure | Observed [M + H]+ |
|---|---|---|
| 371 | 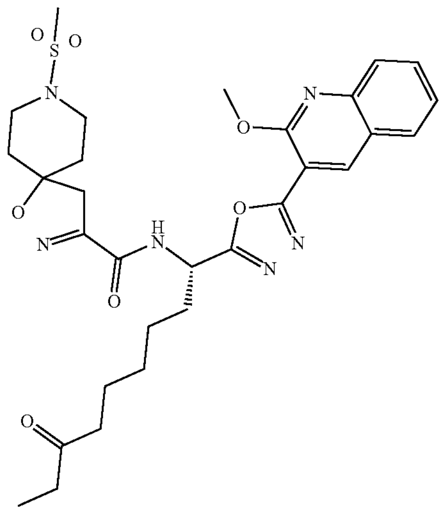 | 627.39 |
| 372 | 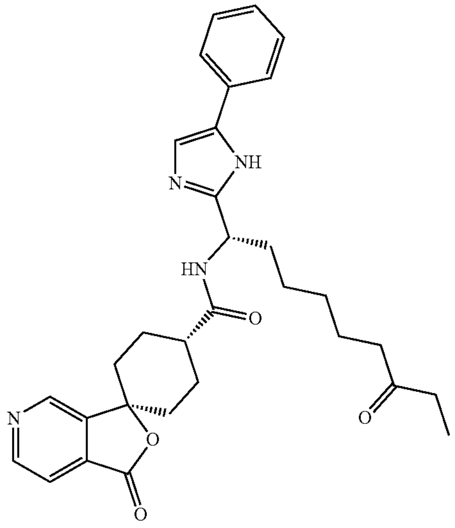 [SMILES: CCC(=O)CCCCC[C@H](NC(=O)[C@H]1CC[C@@]2(CC1)OC(=O)c1ccncc12)c1ncc(-c2ccccc2)[nH]1] | 529.32 |
| 373 | 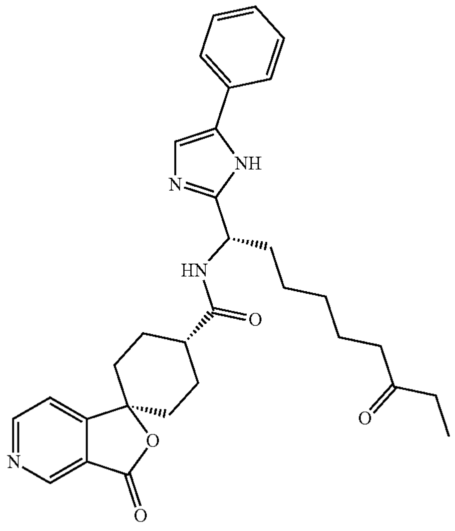 [SMILES: CCC(=O)CCCCC[C@H](NC(=O)[C@H]1CC[C@@]2(CC1)OC(=O)c1cnccc12)c1ncc(-c2ccccc2)[nH]1] | 529.28 |

-continued
| ID | Structure | Observed [M + H]+ |
|---|---|---|
| 374 | 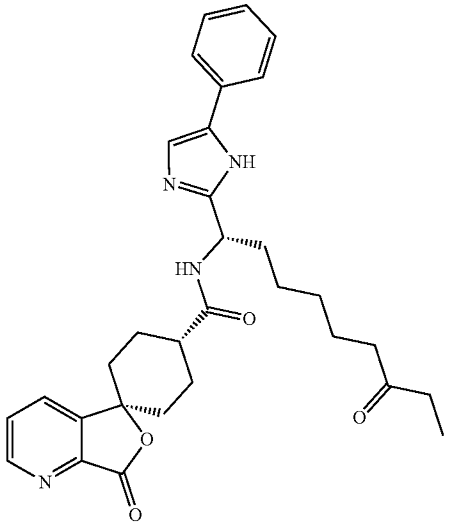 [SMILES: CCC(=O)CCCCC[C@H](NC(=O)[C@H]1CC[C@@]2(CC1)OC(=O)c1ncccc12)c1ncc(-c2ccccc2)[nH]1] | 529.35 |
| 375 | 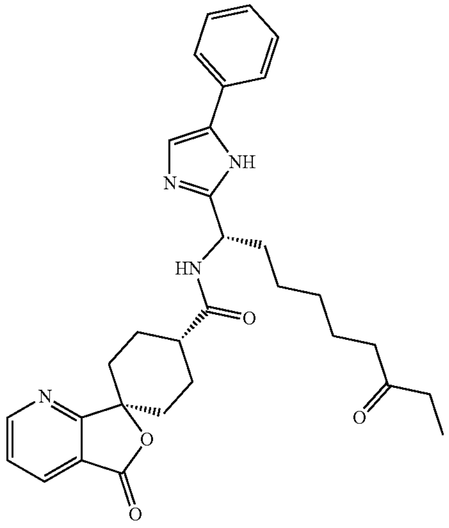 [SMILES: CCC(=O)CCCCC[C@H](NC(=O)[C@H]1CC[C@@]2(CC1)OC(=O)c1cccnc12)c1ncc(-c2ccccc2)[nH]1] | 529.29 |
| 376 | 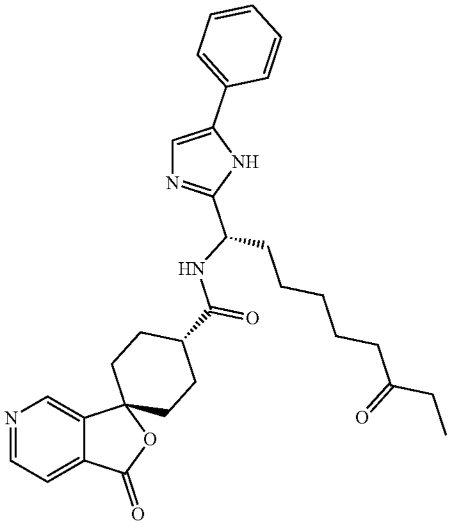 [SMILES: CCC(=O)CCCCC[C@H](NC(=O)[C@H]1CC[C@]2(CC1)OC(=O)c1ccncc12)c1ncc(-c2ccccc2)[nH]1] | 529.32 |

-continued
| ID | Structure | Observed [M + H]+ |
|---|---|---|
| 377 | 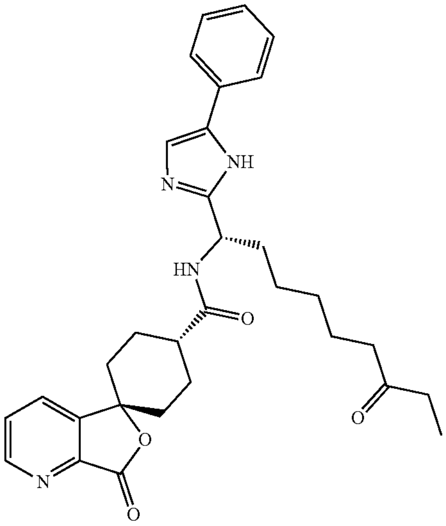 [SMILES: CCC(=O)CCCCC[C@H](NC(=O)[C@H]1CC[C@]2(CC1)OC(=O)c1ncccc12)c1ncc(-c2ccccc2)[nH]1] | 529.31 |
| 378 | 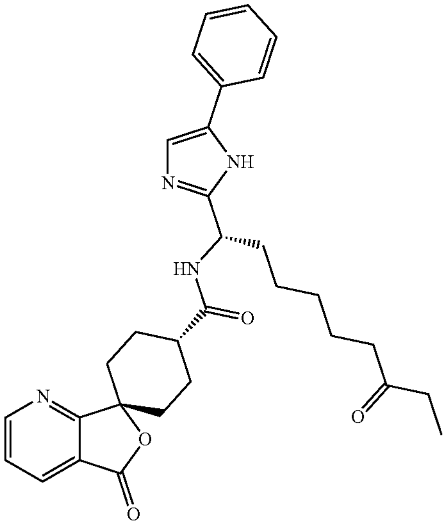 [SMILES: CCC(=O)CCCCC[C@H](NC(=O)[C@H]1CC[C@]2(CC1)OC(=O)c1cccnc12)c1ncc(-c2ccccc2)[nH]1] | 529.33 |
| 379 | 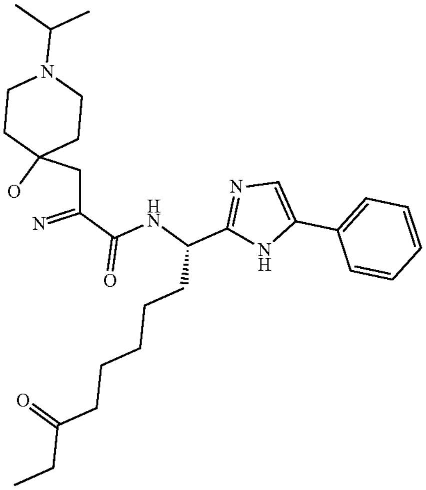 [SMILES: CCC(=O)CCCCC[C@H](NC(=O)C(=N)CC1(O)CCN(C(C)C)CC1)c1ncc(-c2ccccc2)[nH]1] | 508.36 |

-continued
| ID | Structure | Observed [M + H]+ |
|---|---|---|
| 380 | 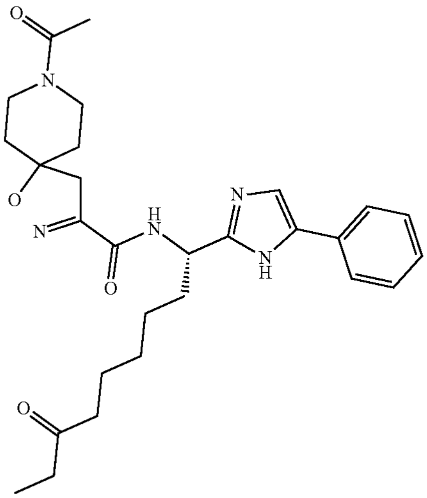 [SMILES: CCC(=O)CCCCC[C@H](NC(=O)C(=N)CC1(O)CCN(C(C)=O)CC1)c1ncc(-c2ccccc2)[nH]1] | 508.3 |
| 381 | 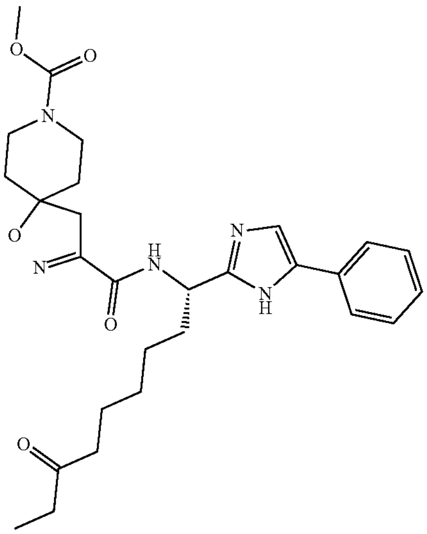 [SMILES: CCC(=O)CCCCC[C@H](NC(=O)C(=N)CC1(O)CCN(C(=O)OC)CC1)c1ncc(-c2ccccc2)[nH]1] | 524.41 |
| 382 | 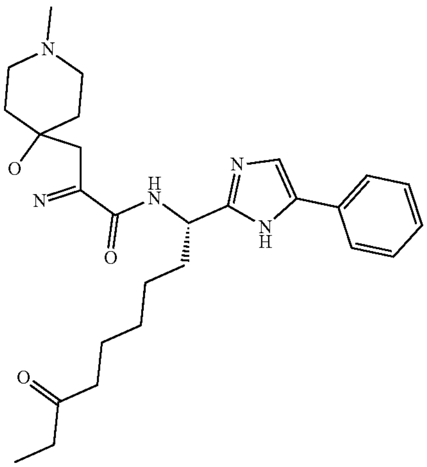 [SMILES: CCC(=O)CCCCC[C@H](NC(=O)C(=N)CC1(O)CCN(C)CC1)c1ncc(-c2ccccc2)[nH]1] | 480.31 |

-continued
| ID | Structure | Observed [M + H]+ |
|---|---|---|
| 383 | 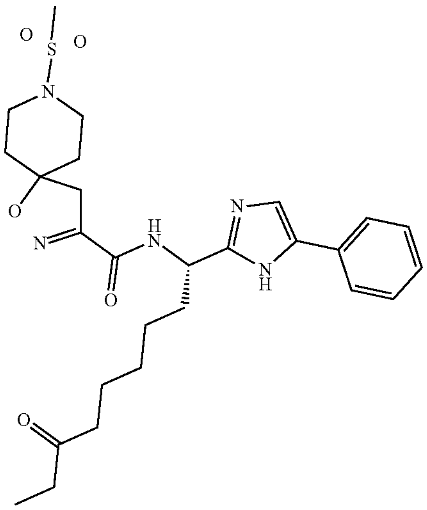 | 544.3 |
| 384 | 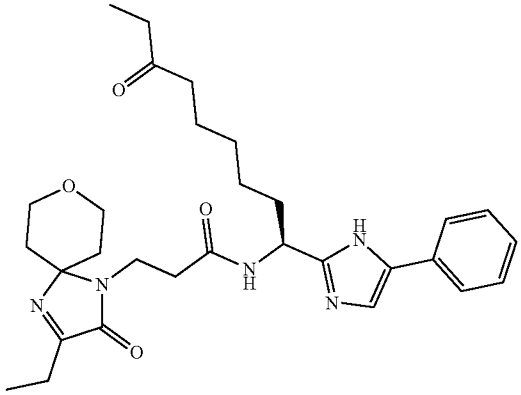 [SMILES: CCC(=O)CCCCC[C@H](NC(=O)CCN1C(=O)C(CC)=NC12CCOCC2)c1ncc(-c2ccccc2)[nH]1] | 536.44 |

Example 87

N1-((S)-1-(5-(2-methoxyquinolin-3-yl)-1H-imidazol-2-yl)-7-oxononyl)-6-azaspiro[2.5]octane-1,6-dicarboxamide (318 and 319)

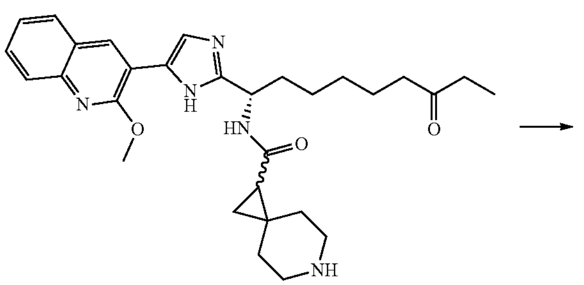

E1b

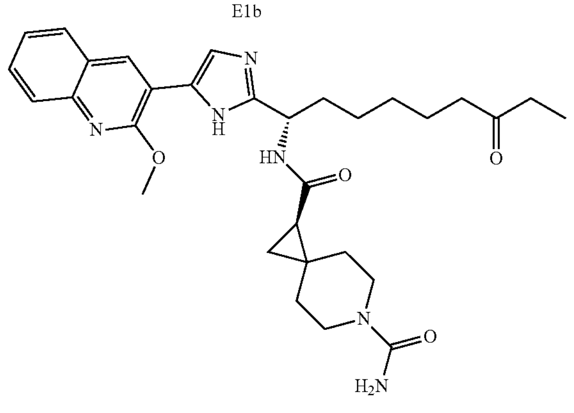

318

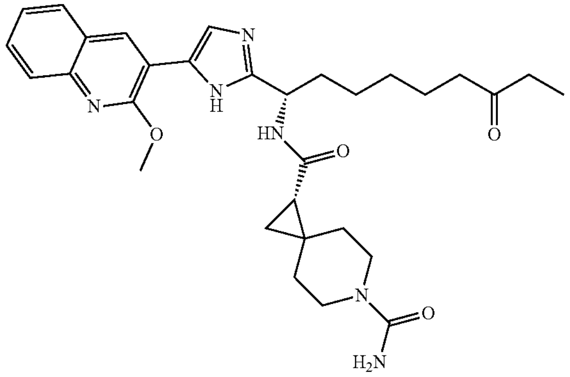

319

To a 8 mL pressure vial with a pressure release cap was added N—((S)-1-(5-(2-methoxyquinolin-3-yl)-1H-imidazol-2-yl)-7-oxononyl)-6-azaspiro[2.5]octane-1-carboxamide, 2TFA (E1b, 66 mg, 0.089 mmol), urea (10.63 mg, 0.177 mmol), iron(III) nitrate nonahydrate (2.128 µl, 8.85 µmol), and toluene (885 µl). The reaction was stirred at 110° C. for 2 hours. The toluene was removed by blowing $N_2$ and the product was purified by C18 HPLC (Gilson, $CH_3CN$ in water with 0.1% TFA: 0% to 50%) to give (R)—$N_1$—((S)-1-(5-(2-methoxyquinolin-3-yl)-1H-imidazol-2-yl)-7-oxononyl)-6-azaspiro[2.5]octane-1,6-dicarboxamide, TFA (318, 1st peak), LCMS (ESI): 561.1 $[M+H]^+$, and (S)—$N_1$—((S)-1-(5-(2-methoxyquinolin-3-yl)-1H-imidazol-2-yl)-7-oxononyl)-6-azaspiro[2.5]octane-1,6-dicarboxamide, TFA (319, 2nd peak). LCMS (ESI): 561.1 $[M+H]^+$.

Example 88

N—((S)-1-(5-(2-hydroxyquinolin-3-yl)-1H-imidazol-2-yl)-7-oxononyl)-6-methyl-6-azaspiro[2.5]octane-1-carboxamide (324 and 325)

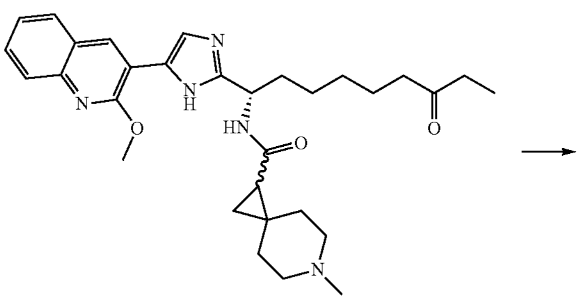

313

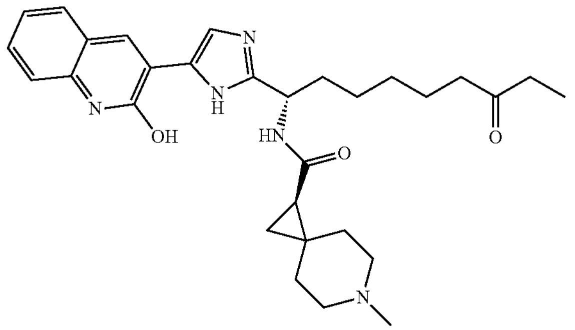

324

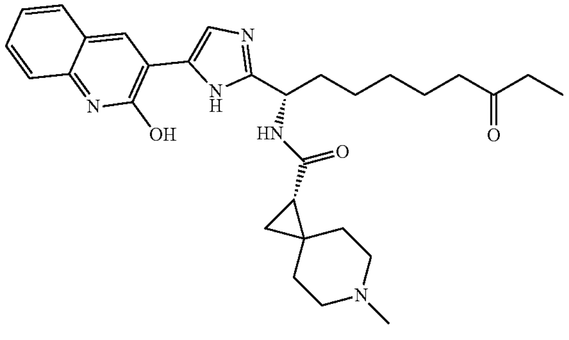

325

To a 4 mL pressure vial with a pressure release cap was added N—((S)-1-(5-(2-methoxyquinolin-3-yl)-1H-imidazol-2-yl)-7-oxononyl)-6-methyl-6-azaspiro[2.5]octane-1-carboxamide (313, 150 mg, 0.282 mmol), HCl (23.17 µl, 0.282 mmol), water (1411 µl), and THF (1411 µl). The reaction was stirred at 25° C. for 16 hours. The crude reaction mixture was checked by LCMS. The product was purified by $C_{18}$ chromatography (30 g, $CH_3CN$ in water with 0.1% TFA: 0% to 90%) to give (R)—N—((S)-1-(5-(2-hydroxyquinolin-3-yl)-1H-imidazol-2-yl)-7-oxononyl)-6-methyl-6-azaspiro[2.5]octane-1-carboxamide, 2TFA (324, first peak), LCMS (ESI): 518.4 $[M+H]^+$; and (S)—N—((S)-1-(5-(2-hydroxyquinolin-3-yl)-1H-imidazol-2-yl)-7-oxononyl)-6-methyl-6-azaspiro[2.5]octane-1-carboxamide, 2TFA (325, 2nd peak), LCMS (ESI): 518.4 $[M+H]^+$.

The following compounds were prepared using similar procedures as described for compounds 324 and 325.
| ID | Structure | Observed [M + H]+ |
|---|---|---|
| 291 | 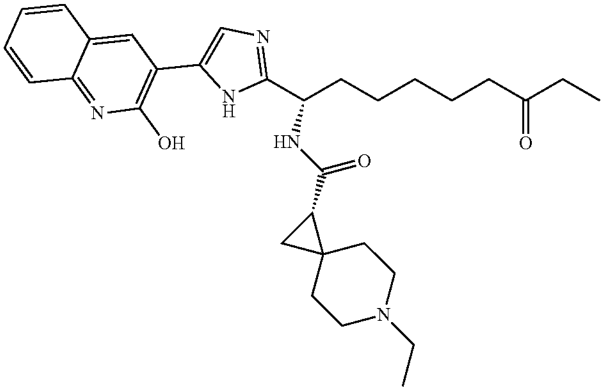 [SMILES: CCC(=O)CCCCC[C@H](NC(=O)[C@H]1CC12CCN(CC)CC2)c1ncc(-c2cc3ccccc3nc2O)[nH]1] | 532.4 |
| 292 | 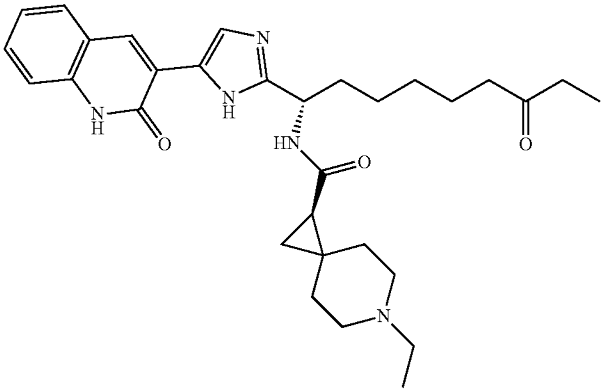 [SMILES: CCC(=O)CCCCC[C@H](NC(=O)[C@@H]1CC12CCN(CC)CC2)c1ncc(-c2cc3ccccc3[nH]c2=O)[nH]1] | 532.4 |
| 326 | 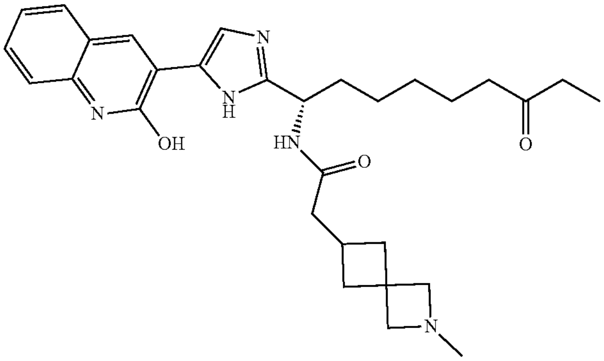 [SMILES: CCC(=O)CCCCC[C@H](NC(=O)CC1CC2(C1)CN(C)C2)c1ncc(-c2cc3ccccc3nc2O)[nH]1] | 518.1 |

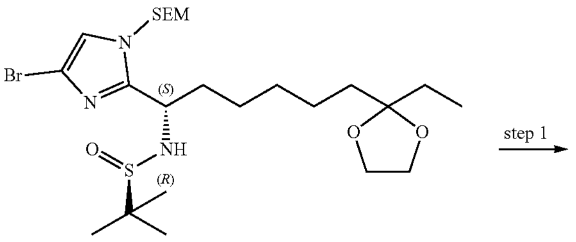

A3_C

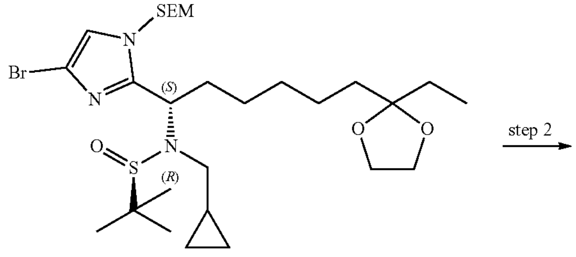

398A

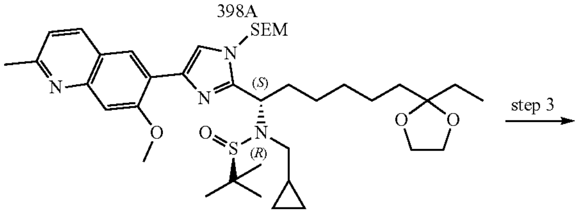

398B

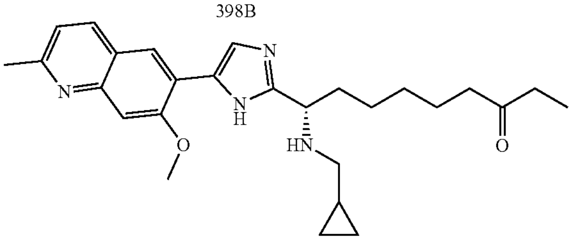

398

Step 1: (R)—N—((S)-1-(5-bromo-1-((2-(trimethylsilyl)ethoxy)methyl)-1H-imidazol-2-yl)-6-(2-ethyl-1,3-dioxolan-2-yl)hexyl)-N-(cyclopropylmethyl)-2-methylpropane-2-sulfinamide (398A): NaH (22 mg, 0.550 mmol) was added to a stirred mixture of (R)—N—((S)-1-(5-bromo-1-((2-(trimethylsilyl)ethoxy)methyl)-1H-imidazol-2-yl)-6-(2-ethyl-1,3-dioxolan-2-yl)hexyl)-2-methylpropane-2-sulfinamide (A3_C, 103 mg, 0.177 mmol) in DMF (2 mL) at 24° C. and the mixture was stirred at 24° C. for 30 mins, then (bromomethyl)cyclopropane (34 mg, 0.252 mmol) was added and the mixture was stirred at 24° C. for 3 h. The mixture was diluted with water (5 mL), and extracted with ethyl acetate (3×10 mL). The combined organic fractions were washed with water (3×8 mL), brine (saturated, 8 mL), dried ($Na_2SO_4$), filtered and the solvent was evaporated under reduced pressure. The residue was purified by silica gel column flash chromatography, eluting with EtOAc/petroleum ether=0-50% to give (R)—N—((S)-1-(5-bromo-1-((2-(trimethylsilyl)ethoxy)methyl)-1H-imidazol-2-yl)-6-(2-ethyl-1,3-dioxolan-2-yl)hexyl)-N-(cyclopropylmethyl)-2-methylpropane-2-sulfinamide (398A). LCMS (ESI) calc'd for $C_{28}H_{52}BrN_3O_4SSi$ $[M+H]^+$: 634.3, found: 634.2.

Step 2: (R)—N-(cyclopropylmethyl)-N—((S)-6-(2-ethyl-1,3-dioxolan-2-yl)-1-(5-(7-methoxy-2-methylquinolin-6-yl)-1-((2-(trimethylsilyl)ethoxy)methyl)-1H-imidazol-2-yl)hexyl)-2-methylpropane-2-sulfinamide (398B): $PdCl_2$ (DTBPF) (10 mg, 0.015 mmol) was added to a mixture of (R)—N—((S)-1-(5-bromo-1-((2-(trimethylsilyl)ethoxy)methyl)-1H-imidazol-2-yl)-6-(2-ethyl-1,3-dioxolan-2-yl)hexyl)-N-(cyclopropylmethyl)-2-methylpropane-2-sulfinamide (398A, 90 mg, 0.142 mmol), 7-methoxy-2-methyl-6-(4,4,5,5-tetramethyl-1,3,2-dioxaborolan-2-yl)quinoline (C1, 54 mg, 0.180 mmol) and $K_3PO_4$ (121 mg, 0.570 mmol) in THF (2 mL) and water (0.2 mL) at 24° C. and the mixture was stirred at 70° C. for 3 h under $N_2$ protection. The mixture was diluted with water (15 mL) and extracted with DCM (3×10 mL). The combined organic fractions were washed with brine (saturated, 10 mL), dried ($Na_2SO_4$), filtered and the solvent was evaporated under reduced pressure to give (R)—N-(cyclopropylmethyl)-N—((S)-6-(2-ethyl-1,3-dioxolan-2-yl)-1-(5-(7-methoxy-2-methylquinolin-6-yl)-1-((2-(trimethylsilyl)ethoxy)methyl)-1H-imidazol-2-yl)hexyl)-2-methylpropane-2-sulfinamide (398B) which was used to the next step without further purification. LCMS (ESI) calc'd for $C_{39}H_{62}N_4O_5SSi$ $[M+H]^+$: 727.4, found: 727.4.

Step 3: (S)-9-((cyclopropylmethyl)amino)-9-(5-(7-methoxy-2-methylquinolin-6-yl)-1H-imidazol-2-yl)nonan-3-one (398): HCl (3 mL, 36.5 mmol) was added to a mixture of (R)—N-(cyclopropylmethyl)-N—((S)-6-(2-ethyl-1,3-dioxolan-2-yl)-1-(5-(7-methoxy-2-methylquinolin-6-yl)-1-((2-(trimethylsilyl)ethoxy)methyl)-1H-imidazol-2-yl)hexyl)-2-methylpropane-2-sulfinamide (398B, 100 mg, 0.138 mmol) in MeOH (5 mL) and water (1 mL) at 24° C. and the mixture was stirred at 50° C. for 15 h. The mixture was concentrated in vacuo. The residue was purified by preparative HPLC (reverse phase C-18 column), eluting with acetonitrile/water+0.05% $NH_3 \cdot H_2O$, to give (S)-9-((cyclopropylmethyl)amino)-9-(5-(7-methoxy-2-methylquinolin-6-yl)-1H-imidazol-2-yl)nonan-3-one (398).

L-(+)-tartaric acid (8 mg, 0.053 mmol) was added to (S)-9-((cyclopropylmethyl)amino)-9-(5-(7-methoxy-2-methylquinolin-6-yl)-1H-imidazol-2-yl)nonan-3-one (398, 23 mg, 0.051 mmol) in acetonitrile (1 mL) and water (2 mL) at 24° C. and the mixture was stirred at 24° C. for 15 min. The mixture was lyophilized to give (S)-9-((cyclopropylmethyl)amino)-9-(5-(7-methoxy-2-methylquinolin-6-yl)-1H-imidazol-2-yl)nonan-3-one (2R,3R)-2,3-dihydroxysuccinate. LCMS (ESI) calc'd for $C_{27}H_{36}N_4O_2$ $[M+H]^+$: 449.3, found: 449.3. $^1H$ NMR (400 MHz, MeOD) δ 8.43 (s, 1H), 8.20 (d, J=8.6 Hz, 1H), 7.75 (s, 1H), 7.41 (s, 1H), 7.30 (d, J=8.2 Hz, 1H), 4.44-4.49 (m, 1H), 4.44 (s, 2H), 4.10 (s, 3H), 2.90 (brs, 1H), 2.61-2.74 (m, 1H), 2.61-2.73 (s, 3H), 2.32-2.42 (m, 4H), 2.24 (brs, 1H), 2.11 (brs, 1H), 1.46-1.57 (m, 2H), 1.25-1.40 (m, 3H), 1.03-1.23 (m, 2H), 0.93 (t, J=7.2 Hz, 3H), 0.66 (d, J=7.4 Hz, 2H), 0.34 (brs, 2H).

The following compounds were prepared using similar procedures as described for compound 398.

| ID | Structure | Observed [M + H]+ |
|---|---|---|
| 403 | 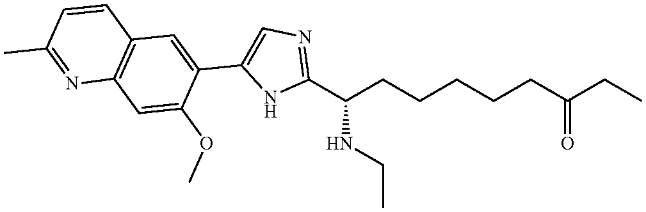 [SMILES: CCN[C@@H](CCCCCC(=O)CC)c1ncc(-c2cc3ccc(C)nc3cc2OC)[nH]1] | 423.3 |
| 404 | 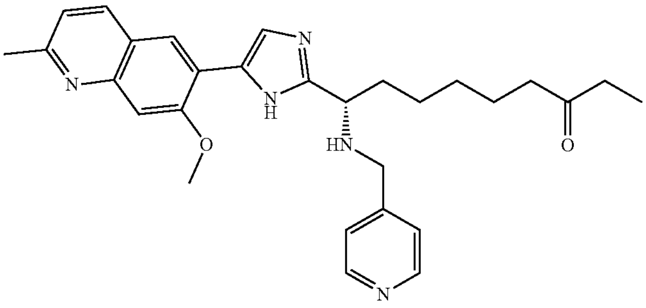 [SMILES: CCC(=O)CCCCC[C@H](NCc1ccncc1)c1ncc(-c2cc3ccc(C)nc3cc2OC)[nH]1] | 486.1 |

Example 90

(9S)-9-[5-(7-methoxy-2-methylquinolin-6-yl)-1,3-oxazol-2-yl]-9-{[(1-methylazetidin-3-yl)methyl]amino}nonan-3-one (401)

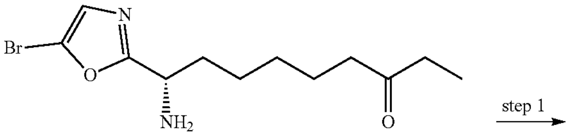

A6

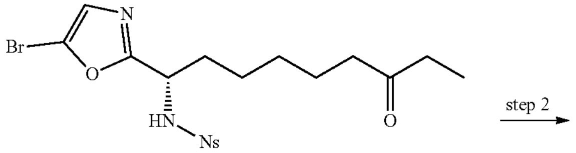

401A

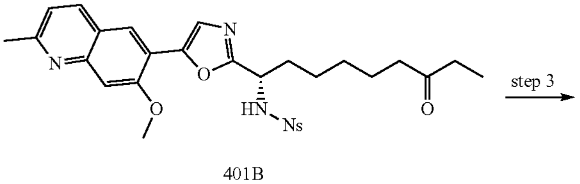

401B

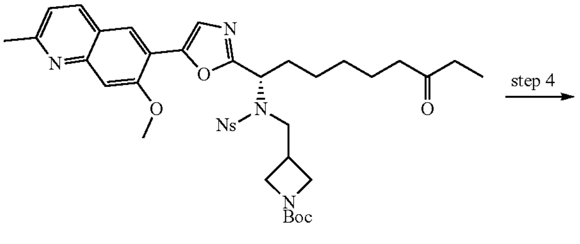

401C

-continued

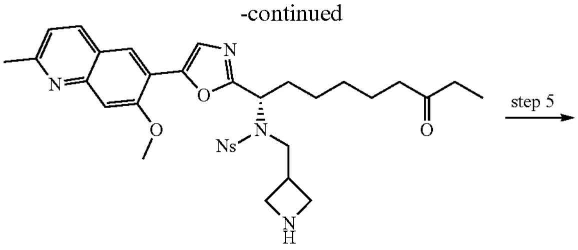

401D

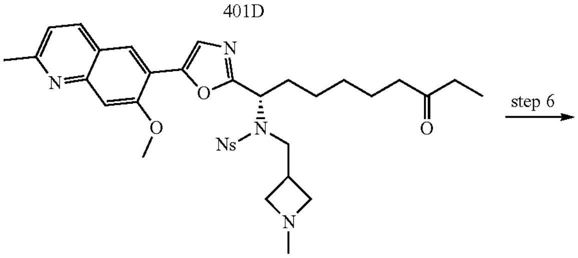

401E

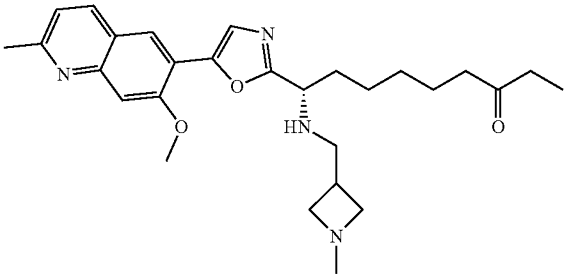

401

Step 1: Preparation of (S)—N-(1-(5-bromooxazol-2-yl)-7-oxononyl)-2-nitrobenzenesulfonamide (401A): 2-nitrobenzene-1-sulfonyl chloride (848 mg, 3.83 mmol) was added to a stirred mixture of (S)-9-amino-9-(5-bromooxazol-2-yl)nonan-3-one hydrochloride (A6, 1.0 g, 2.94 mmol) and TEA (2.0 mL, 14.35 mmol) in DCM (10 mL) at room temperature and the mixture was stirred at room temperature for 3 h. Water (5 mL) was added and the mixture was extracted with DCM (3×10 mL). The combined organic fractions were washed with brine (saturated, 1×10 mL), dried ($Na_2SO_4$), filtered and the solvent was evaporated under reduced pressure. The residue was purified by silica gel flash chromatography (ISCORF75; Sepa flash column), eluting with petroleum ether/EtOAc=0~30% to give (S)—N-(1-(5-bromooxazol-2-yl)-7-oxononyl)-2-nitrobenzenesulfonamide (401A). LCMS (ESI) calc'd for $C_{18}H_{22}BrN_3O_6S$ $[M+H]^+$: 488.0, 490.0, found: 488.1, 490.1. $^1H$ NMR (400 MHz, $CDCl_3$) δ 7.98 (dd, J=1.6, 7.43 Hz, 1H), 7.88 (dd, J=1.2, 7.8 Hz, 1H), 7.60-7.74 (m, 2H), 6.61 (s, 1H), 6.06 (d, J=9.8 Hz, 1H), 4.64-4.76 (m, 1H), 2.35-2.46 (m, 4H), 1.86-1.96 (m, 2H), 1.56 (q, J=7.3 Hz, 2H), 1.30-1.50 (m, 4H), 1.05 (t, J=7.4 Hz, 3H).

Step 2: Preparation of (S)—N-(1-(5-(7-methoxy-2-methylquinolin-6-yl)oxazol-2-yl)-7-oxononyl)-2-nitrobenzenesulfonamide (401B): $PdCl_2$(DTBPF) (133 mg, 0.204 mmol) was added to a stirred mixture of 7-methoxy-2-methyl-6-(4,4,5,5-tetramethyl-1,3,2-dioxaborolan-2-yl)quinoline (C1, 643 mg, 2.149 mmol), (S)—N-(1-(5-bromooxazol-2-yl)-7-oxononyl)-2-nitrobenzenesulfonamide (401A, 1.0 g, 2.048 mmol) and potassium phosphate (1.3 g, 6.12 mmol) in THF (10 mL)/water (1 mL) at room temperature and the mixture was heated with stirring at 70° C. for 8 h. The mixture was cooled to room temperature. Water (10 mL) was added and the mixture was extracted with ethyl acetate (3×10 mL). The combined organic fractions were washed with brine (saturated, 1×10 mL), dried ($Na_2SO_4$), filtered and the solvent was evaporated under reduced pressure. The residue was purified by silica gel column flash chromatography, eluting with petroleum ether/EtOAc=1/2 to give (S)—N-(1-(5-(7-methoxy-2-methylquinolin-6-yl)oxazol-2-yl)-7-oxononyl)-2-nitrobenzenesulfonamide (401B). LCMS (ESI) calc'd for $C_{29}H_{32}N_4O_7S$ $[M+H]^+$: 581.2, found: 581.2.

Step 3: Preparation of (S)-tert-butyl 3-((N-(1-(5-(7-methoxy-2-methylquinolin-6-yl)oxazol-2-yl)-7-oxononyl)-2-nitrophenylsulfonamido)methyl)azetidine-1-carboxylate (401C): DEAD (0.45 mL, 2.84 mmol) was added to a stirred mixture of (S)—N-(1-(5-(7-methoxy-2-methylquinolin-6-yl)oxazol-2-yl)-7-oxononyl)-2-nitrobenzenesulfonamide (401B, 500 mg, 0.861 mmol), tert-butyl 3-(hydroxymethyl) azetidine-1-carboxylate (177 mg, 0.947 mmol) and $PPh_3$ (678 mg, 2.58 mmol) in THF (5 mL) at room temperature and the mixture was stirred at room temperature for 2 h. Water (10 mL) was added and the mixture was extracted with ethyl acetate (3×10 mL). The combined organic fractions were washed with brine (saturated, 1×10 mL), dried ($Na_2SO_4$), filtered and the solvent was evaporated under reduced pressure. The residue was purified by silica gel column flash chromatography, eluting with petroleum ether/EtOAc=1/2 to give (S)-tert-butyl 3-((N-(1-(5-(7-methoxy-2-methylquinolin-6-yl)oxazol-2-yl)-7-oxononyl)-2-nitrophenylsulfonamido)methyl)azetidine-1-carboxylate (401C). LCMS (ESI) calc'd for $C_{38}H_{47}N_5O_9S$ $[M+H]^+$: 750.3, found: 750.3.

Step 4: Preparation of (S)—N-(azetidin-3-ylmethyl)-N-(1-(5-(7-methoxy-2-methylquinolin-6-yl)oxazol-2-yl)-7-oxononyl)-2-nitrobenzenesulfonamide 2,2,2-trifluoroacetate (401D): TFA (1.2 mL, 15.58 mmol) was added to a stirred mixture of (S)-tert-butyl 3-((N-(1-(5-(7-methoxy-2-methylquinolin-6-yl)oxazol-2-yl)-7-oxononyl)-2-nitrophenylsulfonamido)methyl)azetidine-1-carboxylate (401C, 600 mg, 0.800 mmol) in DCM (6 mL) at room temperature and the mixture was stirred at room temperature for 90 min. All the volatiles were removed off by evaporator to give (S)—N-(azetidin-3-ylmethyl)-N-(1-(5-(7-methoxy-2-methylquinolin-6-yl)oxazol-2-yl)-7-oxononyl)-2-nitrobenzenesulfonamide 2,2,2-trifluoroacetate (401D) which was directly used for next step. LCMS (ESI) calc'd for $C_{33}H_{39}N_5O_7S$ $[M+H]^+$: 650.3, found: 650.3.

Step 5: Preparation of (S)—N-(1-(5-(7-methoxy-2-methylquinolin-6-yl)oxazol-2-yl)-7-oxononyl)-N-((1-methylazetidin-3-yl)methyl)-2-nitrobenzenesulfonamide (401E): Formaldehyde (0.5 mL, 6.72 mmol) was added to a stirred mixture of (S)—N-(azetidin-3-ylmethyl)-N-(1-(5-(7-methoxy-2-methylquinolin-6-yl)oxazol-2-yl)-7-oxononyl)-2-nitrobenzenesulfonamide 2,2,2-trifluoroacetate (401D, 611 mg, 0.800 mmol) in MeOH (12 mL) at room temperature and the mixture was stirred at room temperature for 30 min. Then $NaBH(OAc)_3$ (509 mg, 2.400 mmol) was added and it was stirred at 26° C. for 30 min. Water (10 mL) was added then neutralized with $NaHCO_3$(sat.) and the mixture was extracted with ethyl acetate (3×10 mL). The combined organic fractions were washed with brine (saturated, 1×10 mL), dried ($Na_2SO_4$), filtered and the solvent was evaporated under reduced pressure. The residue was purified by silica gel flash chromatography (ISCORF75; Sepa flash column), eluting with DCM/MeOH=0~6% to give (S)—N-(1-(5-(7-methoxy-2-methylquinolin-6-yl)oxazol-2-yl)-7-oxononyl)-N-((1-methylazetidin-3-yl)methyl)-2-nitrobenzenesulfonamide (401E). LCMS (ESI) calc'd for $C_{34}H_{41}N_5O_7S$ $[M+H]^+$: 664.3, found: 664.3.

Step 6: Preparation of (S)-9-(5-(7-methoxy-2-methylquinolin-6-yl)oxazol-2-yl)-9-(((1-methylazetidin-3-yl)methyl)amino)nonan-3-one (401): Benzenethiol (0.2 mL, 1.948 mmol) was dissolved in 6 mL DMF, then 3.5 mL of the solution was added to a stirred mixture of (S)—N-(1-(5-(7-methoxy-2-methylquinolin-6-yl)oxazol-2-yl)-7-oxononyl)-N-((1-methylazetidin-3-yl)methyl)-2-nitrobenzenesulfonamide (401E, 350 mg, 0.527 mmol) and $K_2CO_3$ (729 mg, 5.27 mmol) in DMF (2 mL) at room temperature, and the mixture was stirred at room temperature for 2 h. The mixture was purified by preparative HPLC (reverse phase C-18 column), eluting with acetonitrile/water+0.1% TFA, to give the TFA salt of the product. The salt was dissolved in MeOH, neutralized with $NaHCO_3$(sat.), and the mixture was purified by preparative HPLC (reverse phase C-18 column), eluting with acetonitrile/water+0.05% $NH_3 \cdot H_2O$, to give (S)-9-(5-(7-methoxy-2-methylquinolin-6-yl)oxazol-2-yl)-9-(((1-methylazetidin-3-yl)methyl)amino)nonan-3-one (401).

L-(+)-tartaric acid (35 mg, 0.233 mmol) was added to a stirred mixture of (S)-9-(5-(7-methoxy-2-methylquinolin-6-yl)oxazol-2-yl)-9-(((1-methylazetidin-3-yl)methyl)amino) nonan-3-one (401, 110 mg, 0.230 mmol) in acetonitrile (2 mL) and water (2 mL) at room temperature and the mixture was made dry by lyophilization to give (S)-9-(5-(7-methoxy-2-methylquinolin-6-yl)oxazol-2-yl)-9-(((1-methylazetidin-3-yl)methyl)amino)nonan-3-one (2R,3R)-2,3-dihydroxysuccinate. LCMS (ESI) calc'd for $C_{28}H_{38}N_4O_3$ $[M+H]^+$: 479.3, found: 479.2. $^1H$ NMR (400 MHz, MeOD) δ 8.22-8.28 (m, 2H), 7.63 (s, 1H), 7.42 (s, 1H), 7.32 (d, J=8.2 Hz, 1H), 4.43 (s, 2H), 4.14-4.26 (m, 2H), 4.12 (s, 3H), 4.04 (t, J=7.0 Hz, 1H), 3.93 (brs, 2H), 2.97-3.08 (m, 1H), 2.88 (brs, 2H), 2.86 (s, 3H), 2.70 (s, 3H), 2.39 (q, J=7.7 Hz, 4H), 1.93-2.04 (m, 2H), 1.54 (q, J=7.2 Hz, 2H), 1.24-1.46 (m, 4H), 0.94 (t, J=7.4 Hz, 3H).

Example 90

N-{(1S)-1-[5-(7-methoxy-2-methylquinolin-6-yl)-1H-imidazol-2-yl]-7-oxononyl}-6-oxaspiro[2.5]octane-1-carboxamide (407 and 413)

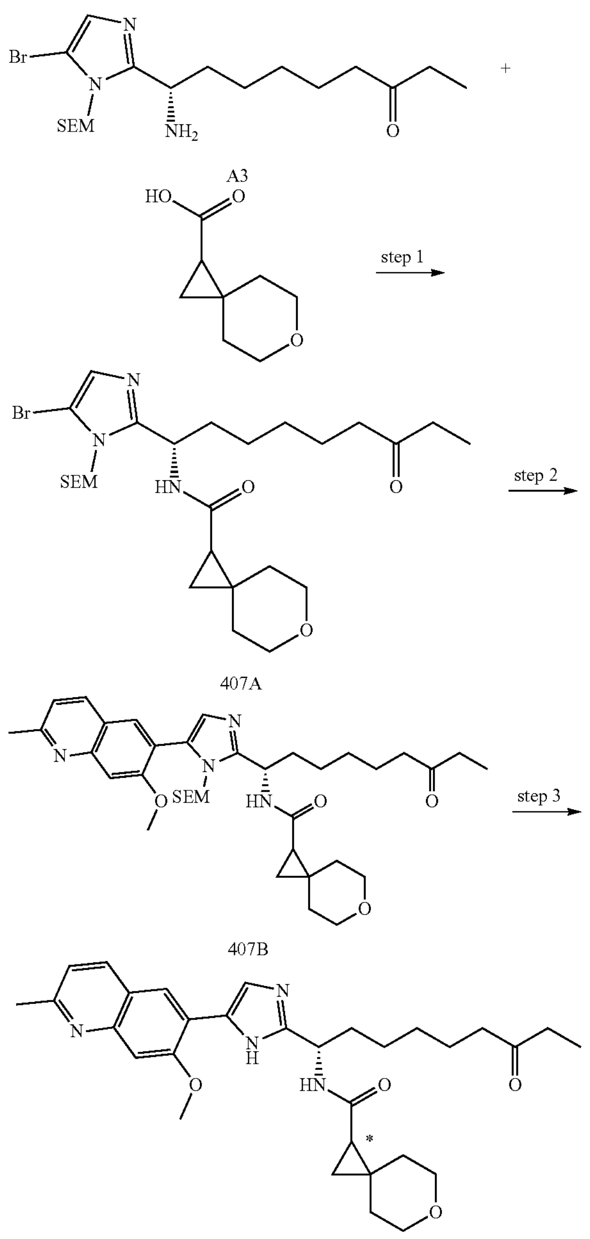

A3

407A

407B 407, 413

Step 1: Preparation of N—((S)-1-(5-bromo-1-((2-(trimethylsilyl)ethoxy)methyl)-1H-imidazol-2-yl)-7-oxononyl)-6-oxaspiro[2.5]octane-1-carboxamide (407A): EDC (277 mg, 1.445 mmol) and 1H-benzo[d][1,2,3]triazol-1-ol (195 mg, 1.445 mmol) were added to a stirred mixture of 6-oxaspiro[2.5]octane-1-carboxylic acid (90 mg, 0.578 mmol) and DIPEA (0.303 mL, 1.734 mmol) in DMF (10 mL) at room temperature. Then (S)-9-amino-9-(5-bromo-1-((2-(trimethylsilyl)ethoxy)methyl)-1H-imidazol-2-yl)nonan-3-one (A3, 250 mg, 0.578 mmol) was added. The mixture was stirred at 25° C. for 18 h. Water (10 mL) and brine (10 mL) was added to the reaction solution and it was extracted with EtOAc (50 mL×2). The organic phase was washed with brine (50 mL) and the solvent was evaporated under reduced pressure. The residue was purified by silica gel column flash chromatography, eluting with EtOAc: Petro.Ether=5:1-1:1 to give N—((S)-1-(5-bromo-1-((2-(trimethylsilyl)ethoxy)methyl)-1H-imidazol-2-yl)-7-oxononyl)-6-oxaspiro[2.5]octane-1-carboxamide (407A). LCMS (ESI) calc'd for $C_{26}H_{44}BrN_3O_4Si$ $[M+H]^+$: 570.2, found: 572.2.

Step 2: Preparation of N—((S)-1-(5-(7-methoxy-2-methylquinolin-6-yl)-1-((2-(trimethylsilyl)ethoxy)methyl)-1H-imidazol-2-yl)-7-oxononyl)-6-oxaspiro[2.5]octane-1-carboxamide (407B): 7-methoxy-2-methyl-6-(4,4,5,5-tetramethyl-1,3,2-dioxaborolan-2-yl)quinoline (C1, 182 mg, 0.610 mmol) and $K_3PO_4$ (325 mg, 1.525 mmol) were added to a stirred mixture of N—((S)-1-(5-bromo-1-((2-(trimethylsilyl)ethoxy)methyl)-1H-imidazol-2-yl)-7-oxononyl)-6-oxaspiro[2.5]octane-1-carboxamide (407A, 290 mg, 0.508 mmol) in 1,4-dioxane (6 mL) and water (1 mL). The mixture was replaced with $N_2$. Then $PdCl_2$(DTBPF) (33 mg, 0.051 mmol) was added at room temperature and the mixture was heated with stirring at 70° C. for 2 h. The mixture was cooled to room temperature. Water (10 mL) was added and the mixture was extracted with ethyl acetate (2×10 mL). The combined organic fractions were washed with brine (2×10 mL), dried ($Na_2SO_4$), filtered and the solvent was evaporated under reduced pressure. The residue was purified by silica gel column flash chromatography, eluting with petroleum ether/EtOAc=2:1-1:2 to give N—((S)-1-(5-(7-methoxy-2-methylquinolin-6-yl)-1-((2-(trimethylsilyl)ethoxy)methyl)-1H-imidazol-2-yl)-7-oxononyl)-6-oxaspiro[2.5]octane-1-carboxamide (407B). LCMS (ESI) calc'd for $C_{37}H_{54}N_4O_5Si$ $[M+H]^+$: 663.4, found: 663.4.

Step 3: Preparation of N—((S)-1-(5-(7-methoxy-2-methylquinolin-6-yl)-1H-imidazol-2-yl)-7-oxononyl)-6-oxaspiro[2.5]octane-1-carboxamide (407 and 413): TFA (4 mL, 51.9 mmol) was added to a stirred mixture of N—((S)-1-(5-(7-methoxy-2-methylquinolin-6-yl)-1-((2-(trimethylsilyl)ethoxy)methyl)-1H-imidazol-2-yl)-7-oxononyl)-6-oxaspiro[2.5]octane-1-carboxamide (407B, 300 mg, 0.453 mmol) in DCM (2 mL) at room temperature and the mixture was stirred at room temperature for 1 h. The reaction solution was concentrated to afford racemic of N—((S)-1-(5-(7-methoxy-2-methylquinolin-6-yl)-1H-imidazol-2-yl)-7-oxononyl)-6-oxaspiro[2.5]octane-1-carboxamide] which was separated by chira SFC by Chiralcel AD column, gradient: 40% of ethanol (0.1% $NH_4OH$), and then made into a tartarate by the method described previously.

407, peak 2. LCMS (ESI) calc'd for $C_{31}H_{40}N_4O_4$ $[M+H]^+$: 533.3, found: 533.1. $^1H$ NMR (400 MHz, MeOD) δ 8.36 (s, 1H), 8.29 (d, J=8.2 Hz, 1H), 7.65 (s, 1H), 7.43 (s, 1H), 7.37 (d, J=8.22 Hz, 1H), 5.10 (t, J=7.24 Hz, 1H), 4.50 (s, 2H), 4.11 (s, 3H), 3.59-3.80 (m, 4H), 2.73 (s, 3H), 2.41-2.48 (m, 4H), 1.90-2.09 (m, 2H), 1.66-1.78 (m, 3H), 1.53-1.62 (m, 3H), 1.43-1.52 (m, 2H), 1.32-1.43 (m, 3H), 1.29 (s, 1H), 1.15 (t, J=4.7 Hz, 1H), 0.99 (t, J=7.4 Hz, 3H), 0.88 (dd, J=4.3, 8.2 Hz, 1H).

413, peak 2. LCMS (ESI) calc'd for $C_{31}H_{40}N_4O_4$ $[M+H]^+$: 533.3, found: 533.1. $^1H$ NMR (400 MHz, MeOD) δ 8.39 (s, 1H), 8.31 (d, J=8.4 Hz, 1H), 7.66 (s, 1H), 7.46 (s, 1H), 7.39 (d, J=8.4 Hz, 1H), 4.93-5.13 (m, 1H), 4.51 (s, 2H), 4.14 (s, 3H), 3.71-3.82 (m, 2H), 3.44-3.58 (m, 2H), 2.76 (s, 3H), 2.43-2.50 (m, 4H), 1.95-2.07 (m, 2H), 1.54-1.70 (m, 6H), 1.30-1.51 (m, 6H), 1.17 (t, J=4.9 Hz, 1H), 1.01 (t, J=7.4 Hz, 3H), 0.90 (dd, J=4.5, 8.0 Hz, 1H).

Example 91

N-{(1S)-1-[5-(7-methoxy-2-methylquinolin-6-yl)-1,3-oxazol-2-yl]-7-oxononyl}-6-oxaspiro[2.5]octane-1-carboxamide (409 and 410)

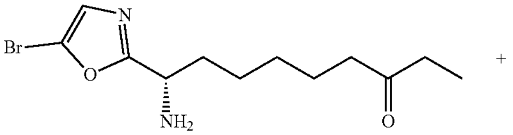

A6

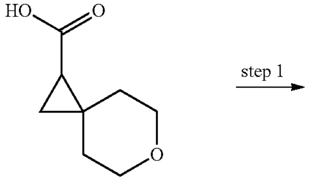

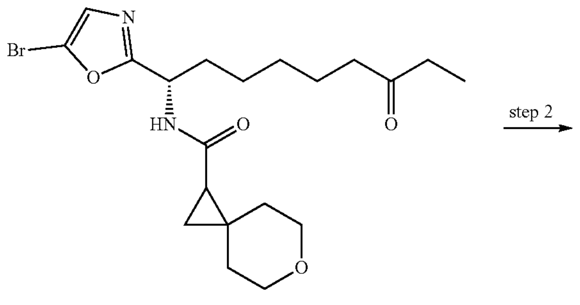

409A

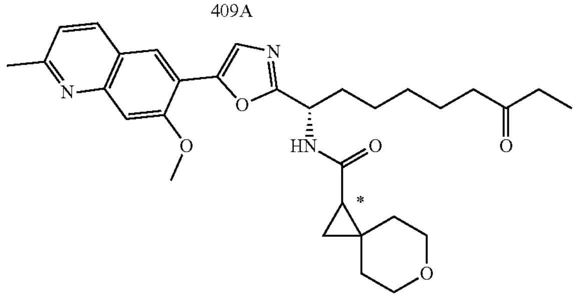

409 & 410

Step 1: Preparation of N—((S)-1-(5-bromooxazol-2-yl)-7-oxononyl)-6-oxaspiro[2.5]octane-1-carboxamide (409A): To a solution of 6-oxaspiro[2.5]octane-1-carboxylic acid (92 mg, 0.589 mmol) in DMF (10 mL) was added HOBT (198 mg, 1.295 mmol), EDC (248 mg, 1.295 mmol) and DIPEA (0.411 mL, 2.355 mmol). The mixture was stirred at rt for 15 min. (S)-9-amino-9-(5-bromooxazol-2-yl)nonan-3-one hydrochloride (A6, 200 mg, 0.589 mmol) was added. The mixture was stirred at rt for 21 h. Ethyl acetate (40 mL) was added, the solution was washed sequentially with saturated NaCl solution (40 mL). The aqueous layer was extracted with ethyl acetate (40 mL*2). The combined organic layers were washed with saturated NaCl solution (40 mL*2). The organic layer was dried over anhydrous $Na_2SO_4$, filtered, and the solvent was removed under reduced pressure. The residue was purified by column chromatography (silica, Petro. ether: ethyl acetate=2:1 to 1:1) to yield N—((S)-1-(5-bromooxazol-2-yl)-7-oxononyl)-6-oxaspiro[2.5]octane-1-carboxamide (409A). LCMS (ESI) calc'd for $C_{20}H_{30}BrN_2O_4$ $[M+H]^+$: 441.1, found: 443.1. $^1H$ NMR (400 MHz, $CDCl_3$) δ 6.89 (d, J=2.6 Hz, 1H), 6.18-6.18 (m, 1H), 6.17-6.36 (m, 1H), 5.10-5.24 (m, 1H), 3.71 (t, J=5.1 Hz, 2H), 3.54-3.67 (m, 2H), 2.31-2.46 (m, 4H), 1.85-1.96 (m, 1H), 1.76-1.82 (m, 1H), 1.70-1.76 (m, 3H), 1.51-1.58 (m, 2H), 1.41-1.48 (m, 1H), 1.35-1.38 (m, 1H), 1.27-1.34 (m, 3H), 1.18-1.24 (m, 1H), 1.02 (t, J=7.3 Hz, 3H), 0.84 (m, 1H).

Step 2: Preparation of N—((S)-1-(5-(7-methoxy-2-methylquinolin-6-yl)oxazol-2-yl)-7-oxononyl)-6-oxaspiro[2.5]octane-1-carboxamide (409 and 410): N—((S)-1-(5-bromooxazol-2-yl)-7-oxononyl)-6-oxaspiro[2.5]octane-1-carboxamide (409A, 220 mg, 0.498 mmol), 7-methoxy-2-methyl-6-(4,4,5,5-tetramethyl-1,3,2-dioxaborolan-2-yl)quinoline (C1, 179 mg, 0.598 mmol), $K_3PO_4$ (317 mg, 1.495 mmol) and $PdCl_2$(DTBPF) (33 mg, 0.051 mmol) were dissolved in a mixture of dioxane (10 mL) and water (2 mL). The reaction mixture was stirred under nitrogen at 70° C. for 2 h. After it cooled to room temperature, the mixture was concentrated under reduced pressure. The crude product was purified by column chromatography (silica, Pet. ether:EtOAc=1:2 to 1:5) to give racemic of N—((S)-1-(5-(7-methoxy-2-methylquinolin-6-yl)oxazol-2-yl)-7-oxononyl)-6-oxaspiro[2.5]octane-1-carboxamide.

The diastereoisomers were separated by chiral SFC and then made into a tartarate by previously described methods.

409, from peak 1, 79 mg, yellow solid. $^1H$ NMR (400 MHz, MeOD) δ 8.21-8.34 (m, 2H), 7.59 (s, 1H), 7.44 (s, 1H), 7.35 (d, J=8.6 Hz, 1H), 5.10-5.25 (m, 1H), 4.49 (s, 2H), 4.12 (s, 3H), 3.74-3.75 (m, 2H), 3.69 (m, 1H), 3.55-3.62 (m, 1H), 2.71 (s, 3H), 2.35-2.50 (m, 4H), 2.00-2.10 (m, 1H), 1.80-1.94 (m, 1H), 1.70-1.80 (m, 1H), 1.60-1.70 (m, 2H), 1.62-1.69 (m, 1H), 1.55-1.58 (m, 3H), 1.44-1.48 (m, 2H), 1.38-1.40 (m, 2H), 1.14-1.15 (m, 1H), 0.97 (t, J=7.3 Hz, 3H), 0.88-0.89 (m, 1H). LCMS (ESI) calc'd for $C_{31}H_{40}N_3O_5$ $[M+H]^+$: 534.3, found: 534.3.

410, peak 2, 78 mg, yellow solid. $^1H$ NMR (400 MHz, MeOD) δ 8.27 (d, J=8.2 Hz, 1H), 8.23 (s, 1H), 7.60 (s, 1H), 7.44 (s, 1H), 7.36 (d, J=8.2 Hz, 1H), 5.17 (d, J=8.2 Hz, 1H), 4.50 (s, 2H), 4.12 (s, 3H), 3.74 (t, J=5.0 Hz, 2H), 3.52 (s, 2H), 2.71 (s, 3H), 2.43 (q, J=7.8 Hz, 4H), 2.00-2.16 (m, 1H), 1.90-2.00 (m, 1H), 1.60-1.70 (m, 3H), 1.54-1.60 (m, 3H), 1.43-1.50 (m, 1H), 1.30-1.40 (m, 3H), 1.20-1.30 (m, 1H), 1.16 (t, J=4.6 Hz, 1H), 0.97 (t, J=7.1 Hz, 3H), 0.87 (dd, J=4.6, 7.7 Hz, 1H). LCMS (ESI) calc'd for $C_{31}H_{40}N_3O_5$ $[M+H]^+$: 534.3, found: 534.4.

Example 92

9-[5-(7-methoxy-2-methylquinolin-6-yl)-1H-imidazol-2-yl]-9-(6-methoxypyridin-2-yl)nonan-3-one (412)

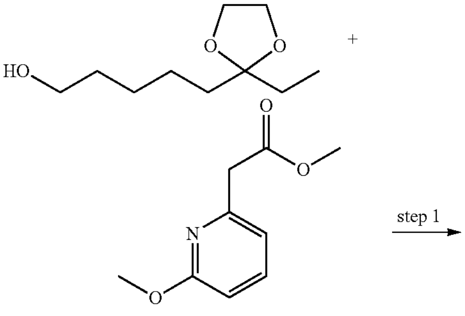

-continued

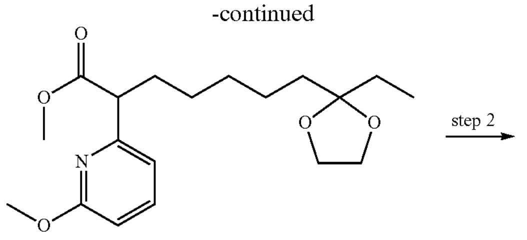

412A

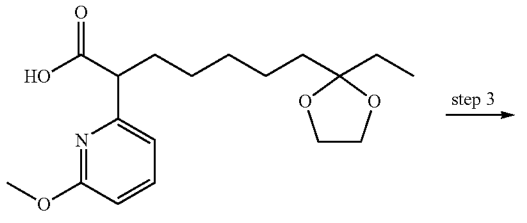

412B

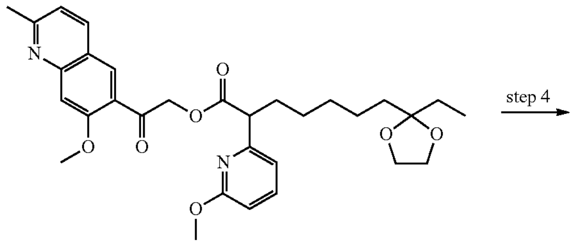

412C

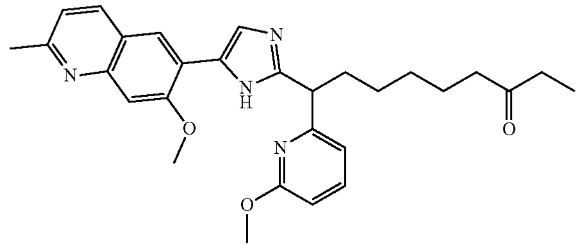

412

Step 1: Preparation of methyl 7-(2-ethyl-: LiHMDS (12 mL, 12.00 mmol) was added to a stirred mixture of methyl 2-(6-methoxypyridin-2-yl)acetate (described in WO2014/79136 A1, 1000 mg, 5.52 mmol) in THF (20 mL) at −78° C. and the mixture was stirred −78° C. for 1 h. Then 2-(5-bromopentyl)-2-ethyl-1,3-dioxolane (described in *Synthesis*, 2003, 14, 2194-2198, 1386 mg, 5.52 mmol) in THF (5 mL) was added portionwise and the reaction mixture was allowed to warm up to room temperature and left stirring overnight. The reaction mixture was quenched with $H_2O$ (50 mL) and extracted with EtOAc (50 mL×2). The organic phases were collected, dried over $Na_2SO_4$ and concentrated under reduced pressure. The residue was purified by silica gel column flash chromatography, eluting with petroleum ether/EtOAc=100:1-50:1 to give methyl 7-(2-ethyl-1,3-dioxolan-2-yl)-2-(6-methoxypyridin-2-yl)heptanoate (412A). LCMS (ESI) calc'd for $C_{19}H_{29}NO_5$ $[M+H]^+$: 352.2, found: 352.2.

Step 2: Preparation of 7-(2-ethyl-1,3-dioxolan-2-yl)-2-(6-methoxypyridin-2-yl)heptanoic acid (412B): LiOH (61 mg, 2.55 mmol) in water (2 mL) was added to a stirred mixture of methyl 7-(2-ethyl-1,3-dioxolan-2-yl)-2-(6-methoxypyridin-2-yl)heptanoate (412A, 300 mg, 0.854 mmol) in MeOH (2 mL) at room temperature and the mixture was stirred at 65° C. for 2 h. The solution was concentrated to afford 7-(2-ethyl-1,3-dioxolan-2-yl)-2-(6-methoxypyridin-2-yl) heptanoic acid (412B) was used in the next step without further purification. LCMS (ESI) calc'd for $C_{18}H_{27}NO_5$ $[M+H]^+$: 338.2, found: 337.9.

Step 3: Preparation of 2-(7-methoxy-2-methylquinolin-6-yl)-2-oxoethyl 7-(2-ethyl-1,3-dioxolan-2-yl)-2-(6-methoxypyridin-2-yl)heptanoate (412C): 2-chloro-1-(7-methoxy-2-methylquinolin-6-yl)ethanone (256 mg, 1.024 mmol) was added to a stirred mixture of 7-(2-ethyl-1,3-dioxolan-2-yl)-2-(6-methoxypyridin-2-yl)heptanoic acid (412B, 288 mg, 0.854 mmol) and $K_2CO_3$ (59 mg, 0.427 mmol) in DMF (2 mL) at 25° C. and the mixture was stirred at room temperature for 24 h. The mixture was diluted with ethyl acetate (10 mL), washed with brine (saturated, 10 mL), dried ($Na_2SO_4$), filtered and the solvent was evaporated under reduced pressure. The residue was purified by silica gel column flash chromatography, eluting with petroleum ether/EtOAc=5:1-1:2 to give 2-(7-methoxy-2-methylquinolin-6-yl)-2-oxoethyl 7-(2-ethyl-1,3-dioxolan-2-yl)-2-(6-methoxypyridin-2-yl)heptanoate (412C). LCMS (ESI) calc'd for $C_{31}H_{38}N_2O_7$ $[M+H]^+$: 551.3, found: 551.3.

Step 4: Preparation of 9-(5-(7-methoxy-2-methylquinolin-6-yl)-1H-imidazol-2-yl)-9-(6-methoxypyridin-2-yl) nonan-3-one (412): $NH_4OAc$ (574 mg, 7.45 mmol) was added to a stirred mixture of 2-(7-methoxy-2-methylquinolin-6-yl)-2-oxoethyl7-(2-ethyl-1,3-dioxolan-2-yl)-2-(6-methoxypyridin-2-yl)heptanoate (412C, 410 mg, 0.745 mmol) in toluene (20 mL) at room temperature and the mixture was heated with stirring at 110° C. for 18 h. The mixture was cooled to rt, water (10 mL) was added and the mixture was extracted with ethyl acetate (2×10 mL). The combined organic fractions were washed with water (10 mL), dried ($Na_2SO_4$), filtered and the solvent was evaporated under reduced pressure. The residue was purified by silica gel column flash chromatography, eluting with petroleum ether/EtOAc=2:1-1:2, and then further purified by preparative HPLC (reverse phase C-18 column), eluting with acetonitrile/water+0.1% TFA to give 9-(5-(7-methoxy-2-methylquinolin-6-yl)-1H-imidazol-2-yl)-9-(6-methoxypyridin-2-yl)nonan-3-one (412). LCMS (ESI) calc'd for $C_{29}H_{34}N_4O_3$ $[M+H]^+$: 487.3, found: 487.0. $^1H$ NMR (400 MHz, $CDCl_3$) δ 8.86 (brs, 1H), 8.64-8.72 (m, 1H), 8.35-8.42 (m, 1H), 7.86 (brs, 1H), 7.68 (t, J=7.8 Hz, 1H), 7.44-7.50 (m, 1H), 7.09 (d, J=7.1 Hz, 1H), 6.78 (d, J=8.4 Hz, 1H), 4.84-4.95 (m, 1H), 4.20 (s, 3H), 3.97-4.05 (m, 3H), 3.02 (s, 3H), 2.32-2.43 (m, 4H), 1.98-2.24 (m, 2H), 1.45-1.55 (m, 2H), 1.21-1.34 (m, 4H), 1.03 (t, J=7.3 Hz, 3H).

Example 93

9-amino-10-methoxy-9-[5-(7-methoxy-2-methylquinolin-6-yl)-1H-imidazol-2-yl]decan-3-one (414)

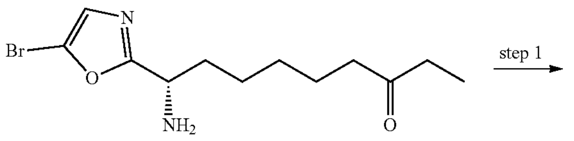

A6

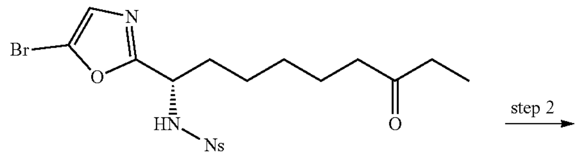

401A

-continued

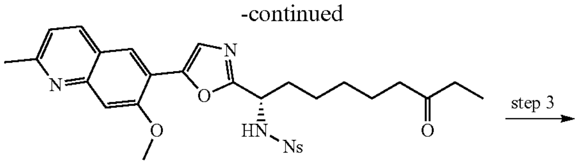

401B

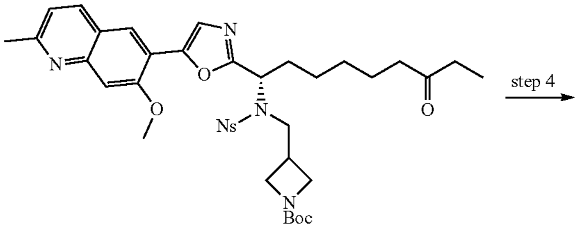

401C

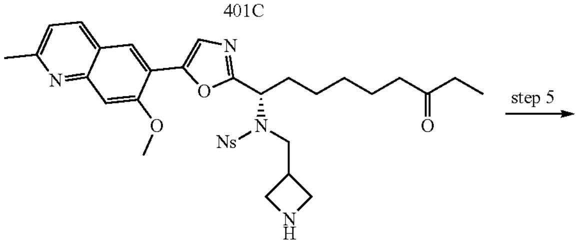

401D

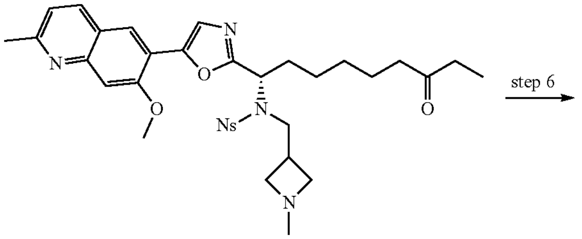

401E

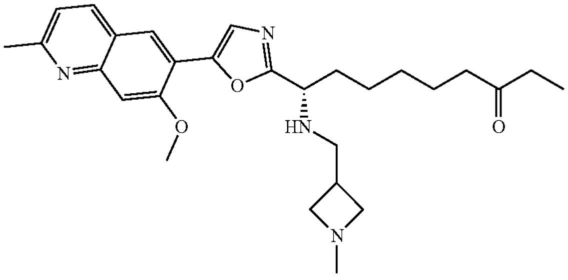

401

Step 1: (S)-methyl 2-amino-3-methoxypropanoate (414B): $SOCl_2$ (7 mL, 96 mmol) was added to a stirred mixture of (S)-2-amino-3-methoxypropanoic acid (414A, 10 g, 84 mmol) in MeOH (20 mL) at 25° C. and the mixture was heated with stirring at 80° C. for 2 h. The mixture was cooled, diluted with MeOH (20 mL) and the solvent was evaporated under reduced pressure. The residue was washed with aqueous $Na_2CO_3$ (saturated, 20 mL), extracted with EtOAc (20 mL×2), dried ($Na_2SO_4$), filtered and the solvent was evaporated under reduced pressure to give (S)-methyl 2-amino-3-methoxypropanoate (414B). LCMS (ESI) calc'd for $C_5HnNO_3$ $[M+H]^+$: 134.0, found: 134.1.

Step 2: (S,E)-methyl 2-(benzylideneamino)-3-methoxypropanoate (414C): Sodium sulfate (107 g, 751 mmol) was added to a stirred mixture of (S)-methyl 2-amino-3-methoxypropanoate (414B, 10 g, 75 mmol) and benzaldehyde (10 g, 94 mmol) in DCM (2 mL) at 25° C. and the mixture was stirred at room temperature for 8 h. The reaction was concentrated to give (S,E)-methyl 2-(benzylideneamino)-3-methoxypropanoate (414C) which was used to the next step without further purification.

Step 3: (E)-methyl 2-(benzylideneamino)-2-(methoxymethyl)pent-4-enoate (414D): 3-bromoprop-1-ene (20 g, 165 mmol) in 20 mL of acetonitrile was added to a stirred mixture of (S,E)-methyl 2-(benzylideneamino)-3-methoxypropanoate (414C, 20 g, 90 mmol), KOH (5.07 g, 90 mmol), $K_2CO_3$ (24.99 g, 181 mmol) and benzyltriethylammonium chloride (2.059 g, 9.04 mmol) in acetonitrile (300 mL) at room temperature and the mixture was stirred at room temperature for 18 h. The mixture was filtered and the filter cake was washed with $CH_3CN$ (200 mL). The filtrate was concentrated to dryness. The mixture was diluted with 500 mL of EtOAc, washed with brine (2×200 mL), dried over $Na_2SO_4$, filtered and concentrated to afford (E)-methyl 2-(benzylideneamino)-2-(methoxymethyl)pent-4-enoate (414D) which was used to the next step without purification.

Step 4: methyl 2-((tert-butoxycarbonyl)amino)-2-(methoxymethyl)pent-4-enoate (414E): HCl (10 mL, 122 mmol) was added to water (300 mL) and then it was added to a stirred mixture of (E)-methyl 2-(benzylideneamino)-2-(methoxymethyl)pent-4-enoate (414D, 20 g, 77 mmol) in toluene (300 mL) at room temperature and the mixture was stirred at room temperature for 18 h. The aqueous layer was separated and used to next step without purification.

15 mL aqueous above (~4 g of methyl 2-amino-2-(methoxymethyl)pent-4-enoate) was basified with solid $NaHCO_3$ to pH=8 and then DCM (50 mL) was added. $Boc_2O$ (6 mL, 25.8 mmol) was added. The mixture was stirred at room temperature for 18 h. The mixture was added 20 mL of EtOAc, the aqueous layer was separated and extracted with 10 mL of EtOAc. The combined organic fractions were washed with water (10 mL), brine (saturated, 1×10 mL), dried ($Na_2SO_4$), filtered and the solvent was evaporated under reduced pressure. The residue was purified by silica gel column flash chromatography, eluting with petroleum ether/EtOAc=0 to 5% to give methyl 2-((tert-butoxycarbonyl)amino)-2-(methoxymethyl)pent-4-enoate (414E). $^1H$ NMR (400 MHz, $CDCl_3$) δ 5.55-5.71 (m, 1H), 5.03-5.12 (m, 2H), 3.78-3.81 (m, 1H), 3.74 (s, 3H), 3.60-3.64 (m, 1H), 3.31-3.32 (m, 3H), 2.79-2.90 (m, 1H), 2.48-2.58 (m, 1H), 1.41 (s, 9H).

Step 5: 2-((tert-butoxycarbonyl)amino)-2-(methoxymethyl)pent-4-enoic acid (414F): Lithium hydroxide (0.526 g, 21.95 mmol) in water (2 mL) was added to a stirred solution of methyl 2-((tert-butoxycarbonyl)amino)-2-(methoxymethyl)pent-4-enoate (414E, 3 g, 10.98 mmol) in MeOH (10 mL) at room temperature and the mixture was stirred at 26° C. for 2 h. The mixture was cooled and HCl (4 M, 10 mL) was added to adjust pH=5-6 and the mixture was extracted with ethyl acetate (20 mL×3). The organic phase was concentrated to give the title compound which was used to the next step directly.

Step 6: 2-(7-methoxy-2-methylquinolin-6-yl)-2-oxoethyl 2-((tert-butoxycarbonyl)amino)-2-(methoxymethyl)pent-4-enoate (414G): 2-chloro-1-(7-methoxy-2-methylquinolin-6-yl)ethanone (289 mg, 1.157 mmol) was added to a stirred mixture DIPEA (1 mL, 5.73 mmol) and 2-((tert-butoxycarbonyl)amino)-2-(methoxymethyl)pent-4-enoic acid (414F, 300 mg, 1.157 mmol) in DMF (2 mL) at rt and the mixture was stirred at rt for 18 h. Water (20 mL) was added and the mixture was extracted with ethyl acetate (3×10 mL). The combined organic fractions were washed with brine (20 mL), dried ($Na_2SO_4$), filtered and the solvent was evaporated under reduced pressure. The residue was purified by silica gel column flash chromatography, eluting with petroleum ether/EtOAc=100:1-1:1 to give 2-(7-methoxy-2-methylquinolin-6-yl)-2-oxoethyl 2-((tert-butoxycarbonyl)amino)-2-(methoxymethyl)pent-4-enoate (414G). LCMS (ESI) calc'd for $C_{25}H_{32}N_2O_7$ $[M+H]^+$: 473.2, found: 473.1.

Step 7: tert-butyl (1-methoxy-2-(4-(7-methoxy-2-methylquinolin-6-yl)-1H-imidazol-2-yl)pent-4-en-2-yl)carbamate (414H): $NH_4OAc$ (2.94 g, 38.1 mmol) was added to a stirred mixture of 2-(7-methoxy-2-methylquinolin-6-yl)-2-oxoethyl 2-((tert-butoxycarbonyl)amino)-2-(methoxymethyl)pent-4-enoate (414G, 1.8 g, 3.81 mmol) in toluene (10 mL) at 130° C. and the mixture was stirred at 130° C. for 2 h. Water (20 mL) was added and the mixture was extracted with ethyl acetate (2×10 mL). The combined organic fractions were washed with brine (saturated, 10 mL), dried ($Na_2SO_4$), filtered and the solvent was evaporated under reduced pressure, The residue was purified by silica gel flash chromatography (ISCORF75; Sepa flash column), eluting with petroleum ether/EtOAc=100:1-1:1 to give tert-butyl (1-methoxy-2-(4-(7-methoxy-2-methylquinolin-6-yl)-1H-imidazol-2-yl)pent-4-en-2-yl)carbamate (414H). LCMS (ESI) calc'd for $C_{25}H_{32}N_4O_4$ $[M+H]^+$: 453.2, found: 453.1.

Step 8: tert-butyl 2-(2-((tert-butoxycarbonyl)amino)-1-methoxypent-4-en-2-yl)-4-(7-methoxy-2-methylquinolin-6-yl)-1H-imidazole-1-carboxylate (414I): A mixture of tert-butyl (1-methoxy-2-(4-(7-methoxy-2-methylquinolin-6-yl)-1H-imidazol-2-yl)pent-4-en-2-yl)carbamate (414H, 500 mg, 1.105 mmol), DMAP (135 mg, 1.105 mmol) and $Boc_2O$ (0.3 mL, 1.292 mmol) in DCM (10 mL) was stirred at 25° C. for 12 h. The mixture was concentrated to dryness and purified by silica gel flash chromatography (ISCORF75; Sepa flash column), eluting with petroleum ether/EtOAc=100:1-1:1 to give tert-butyl 2-(2-((tert-butoxycarbonyl)amino)-1-methoxypent-4-en-2-yl)-4-(7-methoxy-2-methylquinolin-6-yl)-1H-imidazole-1-carboxylate (414I). LCMS (ESI) calc'd for $C_{30}H_{40}N_4O_6$ $[M+H]^+$: 553.2, found: 553.1.

Step 9: (E)-tert-butyl 2-(2-((tert-butoxycarbonyl)amino)-1-methoxy-8-oxodec-4-en-2-yl)-4-(7-methoxy-2-methylquinolin-6-yl)-1H-imidazole-1-carboxylate (414J): Zhan's catalyst (50 mg, 0.068 mmol) was added to the solution of tert-butyl 2-(2-((tert-butoxycarbonyl)amino)-1-methoxypent-4-en-2-yl)-4-(7-methoxy-2-methylquinolin-6-yl)-1H-imidazole-1-carboxylate (414I, 350 mg, 0.633 mmol)) and hept-6-en-3-one (200 mg, 1.783 mmol) in degassed toluene (3 mL), the resultant mixture was stirred at 100° C. for 12 h under $N_2$ atmosphere. The residue was purified by preparative TLC on silica gel, eluting with petroleum ether/EtOAc=1:1 to give (E)-tert-butyl 2-(2-((tert-butoxycarbonyl)amino)-1-methoxy-8-oxodec-4-en-2-yl)-4-(7-methoxy-2-methylquinolin-6-yl)-1H-imidazole-1-carboxylate (414J). LCMS (ESI) calc'd for $C_{35}H_{48}N_4O_7$ $[M+H]^+$: 637.3, found: 637.5.

Step 10: tert-butyl 2-(2-((tert-butoxycarbonyl)amino)-1-methoxy-8-oxodecan-2-yl)-4-(7-methoxy-2-methylquinolin-6-yl)-1H-imidazole-1-carboxylate (414K): 10% Pd—C (50 mg, 0.047 mmol) was added to a stirred mixture of (E)-tert-butyl 2-(2-((tert-butoxycarbonyl)amino)-1-methoxy-8-oxodec-4-en-2-yl)-4-(7-methoxy-2-methylquinolin-6-yl)-1H-imidazole-1-carboxylate (414J, 100 mg, 0.157 mmol) in MeOH (3 mL) at 25° C. and The mixture was degassed and backfilled with $H_2$ (three times). The resulting mixture was stirred under 15 psi of $H_2$ at room temperature for 2 h. The mixture was filtered and the filter cake was washed with MeOH (10 mL). The filtrate was concentrated to give tert-butyl 2-(2-((tert-butoxycarbonyl)amino)-1-methoxy-8-oxodecan-2-yl)-4-(7-methoxy-2-methylquinolin-6-yl)-1H-imidazole-1-carboxylate (414K). LCMS (ESI) calc'd for $C_{35}H_{50}N_4O_7$ $[M+H]^+$: 639.3, found: 639.4.

Step 11: 9-amino-10-methoxy-9-(4-(7-methoxy-2-methylquinolin-6-yl)-1H-imidazol-2-yl)decan-3-one (414): TFA (0.2 mL, 0.055 mmol) was added to a stirred mixture of tert-butyl 2-(2-((tert-butoxycarbonyl)amino)-1-methoxy-8-oxodecan-2-yl)-4-(7-methoxy-2-methylquinolin-6-yl)-1H-imidazole-1-carboxylate (414K, 35 mg, 0.055 mmol) in DCM (1 mL) at 25° C. The resulting mixture was stirred at room temperature for 2 h. Aqueous $NaHCO_3$(saturated, 3 mL) was added and the mixture was extracted with DCM (2×4 mL). The combined organic fractions were washed with brine (saturated, 2 mL), dried ($Na_2SO_4$), filtered and the solvent was evaporated under reduced pressure. The residue was purified by preparative HPLC (reverse phase C-18 column), eluting with acetonitrile/water+0.1% TFA, to give 9-amino-10-methoxy-9-(4-(7-methoxy-2-methylquinolin-6-yl)-1H-imidazol-2-yl)decan-3-one (414). LCMS (ESI) calc'd for $C_{25}H_{34}N_4O_3$ $[M+H]^+$: 439.2, found: 439.1. $^1H$ NMR (400 MHz, MeOD) δ 8.89-8.98 (m, 1H), 8.77-8.87 (m, 1H), 7.84-7.91 (m, 1H), 7.66-7.75 (m, 1H), 7.52-7.60 (m, 1H), 4.20-4.28 (m, 3H), 3.86-3.95 (m, 1H), 3.76-3.84 (m, 1H), 3.41-3.51 (m, 1H), 2.86-2.98 (m, 3H), 2.35-2.45 (m, 4H), 1.96-2.20 (m, 2H), 1.45-1.59 (m, 2H), 1.11-1.35 (m, 4H), 0.90-1.02 (m, 3H).

Example 94

6-{1-[5-(7-methoxy-2-methylquinolin-6-yl)-1H-imidazol-2-yl]-7-oxononyl}pyridin-2(1H)-one (418&419)

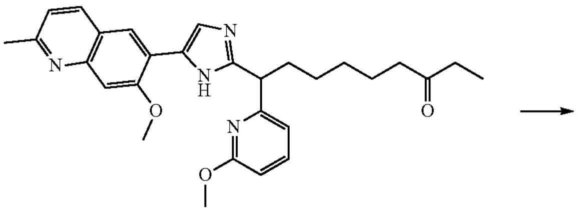

412

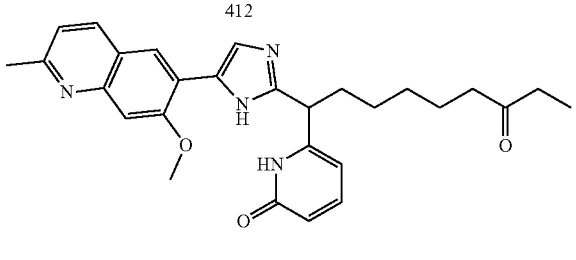

418 & 419

HCl (1 mL, 12.18 mmol) was added to a stirred mixture of 9-(5-(7-methoxy-2-methylquinolin-6-yl)-1H-imidazol-2-yl)-9-(6-methoxypyridin-2-yl)nonan-3-one (412, 94 mg, 0.193 mmol) in dioxane (1 mL) at room temperature and the mixture was stirred at 100° C. for 7 h. The reaction solution was concentrated and the residue was dissolved in DCM (10 mL) and adjusted to pH=9 with $NaHCO_3$ saturated (aqueous). The organic phase was dried over $Na_2SO_4$, filtered and concentrated to give racemic of 6-(1-(5-(7-methoxy-2-methylquinolin-6-yl)-1H-imidazol-2-yl)-7-oxononyl)pyridin-2(1H)-one which was further separated by chiral SFC on AD column, gradient with 35% EtOH (0.1% $NH_{4}OH$). It was then made into a tartarate by previously described methods.

418, from peak 1, 38 mg as a yellow solid. LCMS (ESI) calc'd for $C_{28}H_{32}N_4O_3$ $[M+H]^+$: 473.2, found: 473.1. $^1H$ NMR (400 MHz, MeOD) δ 8.52 (s, 1H), 8.42 (d, J=8.2 Hz, 1H), 7.70 (s, 1H), 7.56 (dd, J=7.2, 9.1 Hz, 1H), 7.39-7.49 (m, 2H), 6.44 (d, J=9.0 Hz, 1H), 6.35 (d, J=6.8 Hz, 1H), 4.52 (s, 2H), 4.10-4.19 (m, 4H), 2.77 (s, 3H), 2.42 (m, 4H), 2.15-2.29 (m, 1H), 2.02-2.14 (m, 1H), 1.55 (t, J=7.0 Hz, 2H), 1.27-1.43 (m, 4H), 0.97 (t, J=7.4 Hz, 3H).

419, from peak 2, 34 mg as a yellow solid. LCMS (ESI) calc'd for $C_{28}H_{32}N_4O_3$ $[M+H]^+$: 473.2, found: 473.0. $^1H$ NMR (400 MHz, MeOD) δ 8.50 (s, 1H), 8.39 (d, J=8.6 Hz, 1H), 7.69 (s, 1H), 7.56 (dd, J=7.1, 9.0 Hz, 1H), 7.38-7.46 (m, 2H), 6.44 (d, J=9.0 Hz, 1H), 6.34 (d, J=6.6 Hz, 1H), 4.51 (s, 2H), 4.11-4.17 (m, 4H), 2.76 (s, 3H), 2.42 (m, 4H), 2.21 (dd, J=4.6, 8.6 Hz, 1H), 2.04-2.12 (m, 1H), 1.51-1.59 (m, 2H), 1.29-1.40 (m, 4H), 0.97 (t, J=7.3 Hz, 3H).

Example 95

(1S)-6-(cyclopropylmethyl)-N-{3-[4-(7-methoxy-2-methylquinolin-6-yl)-1H-imidazol-2-yl]-9-oxoundecan-3-yl}-6-azaspiro[2.5]octane-1-carboxamide (420)

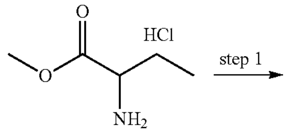

420A

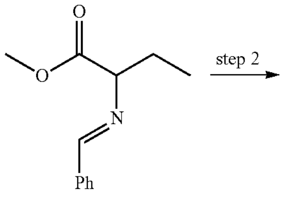

420B

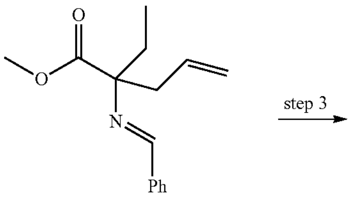

420C

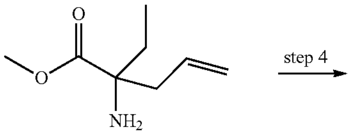

420D

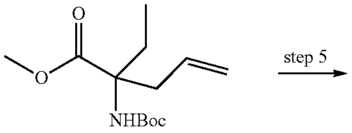

420E

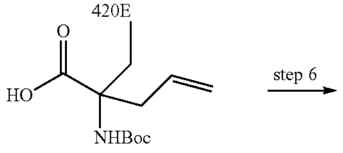

420F

-continued

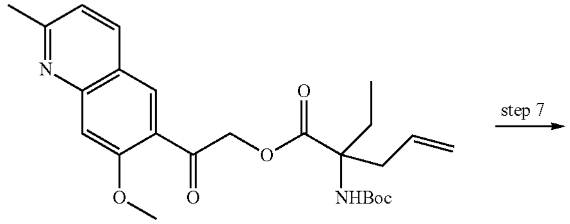

420G

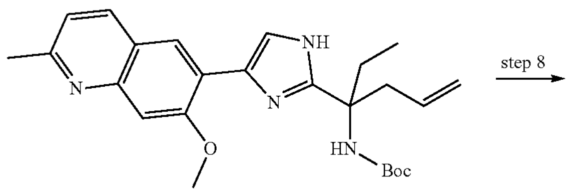

420H

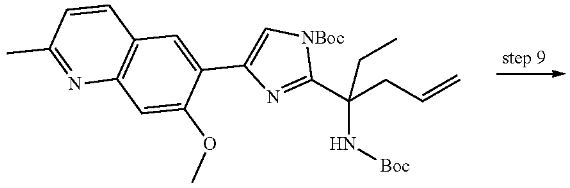

420I

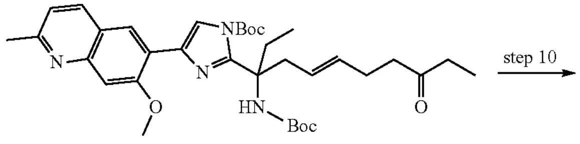

420J

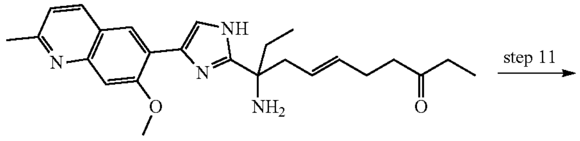

420K

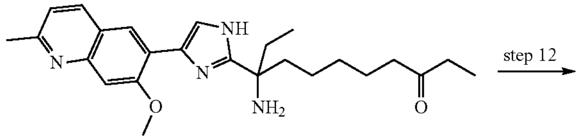

420L

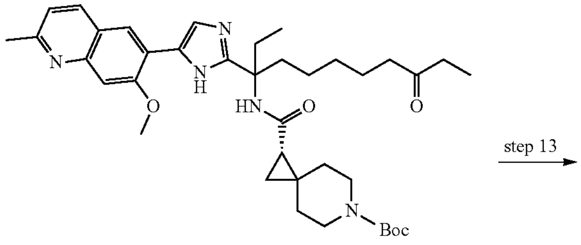

420M

-continued

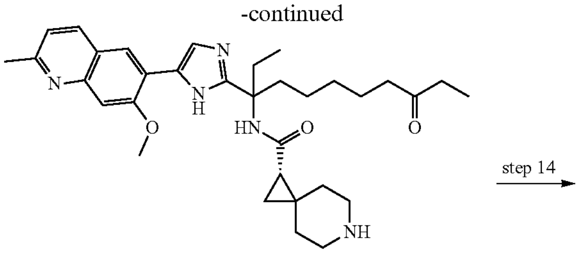

420N

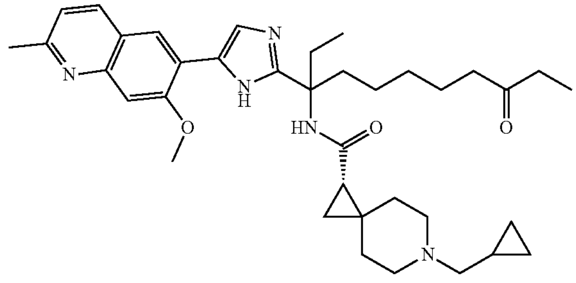

420

Step 1: Preparation of compound (E)-methyl 2-(benzylideneamino)butanoate (420B): To a solution of methyl 2-aminobutanoate hydrochloride (420A, 12.00 g, 78 mmol), benzaldehyde (9.12 g, 86 mmol) in toluene (100 mL) was added triethylamine (9.09 g, 90 mmol) drop wise 5 over 5 min at ambient temperature (<30° C.). The reaction mixture was heated to 70° C. and stirred for 4 h. Another portion of methyl 2-aminobutanoate hydrochloride (4.75 g, 31 mmol) was added, followed by additions of benzaldehyde (1.9 g, 18 mmol) and TEA (5 mL) to the reaction. The reaction was completed detected by $^1H$ NMR. The mixture was cooled and concentrated in vacuo to give (E)-methyl 2-(benzylideneamino)butanoate (420B) which was used immediately in next step without further purification. $^1H$ NMR (400 MHz, DMSO-$d_6$) δ 8.36 (s, 1H), 7.77 (dd, J=1.6, 7.4 Hz, 2H), 7.37-7.50 (m, 3H), 3.96 (dd, J=5.7, 7.6 Hz, 1H), 3.63 (s, 3H), 1.89-1.93 (m, 1H), 1.68-1.82 (m, 1H), 0.83 (t, J=7.4 Hz, 3H).

Step 2: Preparation of compound (E)-methyl 2-(benzylideneamino)-2-ethylpent-4-enoate (420C): 3-bromoprop-1-ene (21.36 g, 177 mmol) was added to a stirred mixture of (E)-methyl 2-(benzylideneamino)butanoate (420B, 30.20 g, 147 mmol), potassium hydroxide (8.26 g, 147 mmol) and potassium carbonate (61.0 g, 441 mmol) in MeCN (200 mL) at 26° C. and the mixture was stirred at room temperature for 24 h. $^1H$ NMR showed almost complete consumption of the starting compound. The mixture was filtered and the cake was washed with MeCN (10 mL), the filtrate was concentrated to dryness to give (E)-methyl 2-(benzylideneamino)-2-ethylpent-4-enoate (420C) which was used to the next step without further purification. $^1H$ NMR (400 MHz, DMSO-$d_6$) δ 8.30 (s, 1H), 7.70-7.80 (m, 2H), 7.37-7.47 (m, 3H), 5.61-5.70 (m, 1H), 4.96-5.10 (m, 2H), 3.63 (s, 3H), 2.50-2.66 (m, 2H), 1.72-1.94 (m, 2H), 0.71-0.86 (m, 3H).

Step 3: Preparation of compound methyl 2-amino-2-ethylpent-4-enoate (420D): 2M HCl (100 mL) was added to a stirred mixture of (E)-methyl 2-(benzylideneamino)-2-ethylpent-4-enoate (420C, 37.14 g, 0.151 mol)) in toluene (100 mL) at room temperature and the mixture was stirred at room temperature for 24 h. The aqueous layer was separated and basified by sat. NaOH solution. The solution was extracted with EtOAc (100 mL*2), dried over $Na_2SO_4$, filtered and concentrated to methyl 2-amino-2-ethylpent-4-enoate (420D) which was used in next step without purification.

Step 4: Preparation of compound methyl 2-((tert-butoxycarbonyl)amino)-2-ethylpent-4-enoate (420E): $Boc_2O$ (19.64 g, 90 mmol) and triethylamine (16.72 mL, 120 mmol) were added to a stirred mixture of methyl 2-amino-2-ethylpent-4-enoate (420D, 9.43 g, 60.0 mmol) in DCM (40 mL) at room temperature and the mixture was stirred at room temperature for 24 h. The mixture was diluted with $H_2O$ (40 mL), and extracted with DCM (40 mL*2). The combined organic fractions were washed with sat. NaCl (40 mL) solution, dried ($Na_2SO_4$), filtered and the solvent was evaporated under reduced pressure. The residue was purified by silica gel column flash chromatography, eluting with petroleum ether/EtOAc=0 to 5% to afford the title compound (420E). LCMS (ESI) calc'd for $C_{13}H_{24}NO_4$ $[M+H]^+$: 258.2, found: 258.2. $^1H$ NMR (400 MHz, $CDCl_3$) δ 5.55-5.78 (m, 1H), 5.03-5.10 (m, 2H), 3.74 (s, 3H), 3.00-3.02 (m, 1H), 2.44-2.56 (m, 1H), 2.16-2.34 (m, 1H), 1.69-1.88 (m, 1H), 1.42 (s, 9H), 0.77 (t, J=7.4 Hz, 3H).

Step 5: Preparation of compound 2-((tert-butoxycarbonyl)amino)-2-ethylpent-4-enoic acid (420F): Lithium hydroxide monohydrate (2.218 g, 52.9 mmol) was added to a stirred mixture of methyl 2-((tert-butoxycarbonyl)amino)-2-ethylpent-4-enoate (420E, 6.80 g, 26.4 mmol) in MeOH (60 mL) and water (20 mL) at room temperature and the mixture was stirred at 50° C. for 19 h. The mixture was cooled, the aqueous layer was separated and adjusted pH to 5 with citric acid, extracted with ethyl acetate (40 mL*3), dried ($Na_2SO_4$), filtered and evaporated under reduced pressure. The residue was purified by silica gel column flash chromatography, eluting with DCM:MeOH=10:1 to give 2-((tert-butoxycarbonyl)amino)-2-ethylpent-4-enoic acid (420F). LCMS (ESI) calc'd for $C_{12}H_{22}NO_4$ $[M+H]^+$: 244.2, found: 244.2.

Step 6: Preparation of compound 2-(7-methoxy-2-methylquinolin-6-yl)-2-oxoethyl 2-((tert-butoxycarbonyl)amino)-2-ethylpent-4-enoate (420G): 2-chloro-1-(7-methoxy-2-methylquinolin-6-yl)ethanone (1.129 g, 4.52 mmol) was added to a stirred mixture of 2-((tert-butoxycarbonyl)amino)-2-ethylpent-4-enoic acid (420F, 1.00 g, 4.11 mmol) and DIPEA (0.531 g, 4.11 mmol) in DMF (3 mL) at room temperature and the mixture was stirred at room temperature for 20 h. The temperature was raised to 50° C. and 0.1 eq. of NaI and another portion of 2-chloro-1-(7-methoxy-2-methylquinolin-6-yl)ethanone (280 mg) were added, and the mixture was stirred for 10 h. Another portion of 2-chloro-1-(7-methoxy-2-methylquinolin-6-yl)ethanone (600 mg) was added and the mixture was stirred for 16 h. The mixture was diluted with $H_2O$ (20 mL), extracted with EtOAc (30 mL*2), washed with sat. NaCl solution (40 mL), dried ($Na_2SO_4$), filtered and the solvent was evaporated under reduced pressure. The residue was purified by silica gel column flash chromatography, eluting with petroleum ether/EtOAc=3:1 to give 2-(7-methoxy-2-methylquinolin-6-yl)-2-oxoethyl 2-((tert-butoxycarbonyl)amino)-2-ethylpent-4-enoate (420G). LCMS (ESI) calc'd for $C_{25}H_{33}N_2O_6$ $[M+H]^+$: 457.2, found: 457.2.

Step 7: Preparation of compound tert-butyl (3-(4-(7-methoxy-2-methylquinolin-6-yl)-1H-imidazol-2-yl)hex-5-en-3-yl)carbamate (420H): A solution of the 2-(7-methoxy-2-methylquinolin-6-yl)-2-oxoethyl 2-((tert-butoxycarbonyl)amino)-2-ethylpent-4-enoate (420G, 900 mg, 1.971 mmol) and $NH_4OAc$ (1520 mg, 19.71 mmol) in toluene (25 mL) was maintained at 110° C. for approximately 10 h. Another $NH_4OAc$ (1.0 g) was added, and the reaction was held at 110° C. for another 10 h. The mixture was cooled and washed with water, saturated aq. $NaHCO_3$ until a basic pH was obtained, then it was washed with brine. The organic phase was then dried over $Na_2SO_4$ and concentrated under reduced pressure. Purification of the resulting residue by flash chromatography on silica gel (Pet. ether/EtOAc=2:1 to 1:1) yielded tert-butyl (3-(4-(7-methoxy-2-methylquinolin-6-yl)-1H-imidazol-2-yl)hex-5-en-3-yl)carbamate (420H). LCMS (ESI) calc'd for $C_{25}H_{33}N_4O_3$ [M+H]$^+$: 437.3, found: 437.3.

Step 8: Preparation of tert-butyl 2-(3-((tert-butoxycarbonyl)amino)hex-5-en-3-yl)-4-(7-methoxy-2-methylquinolin-6-yl)-1H-imidazole-1-carboxylate (420I): Boc-anhydride (0.287 mL, 1.237 mmol) was added to tert-butyl (3-(4-(7-methoxy-2-methylquinolin-6-yl)-1H-imidazol-2-yl)hex-5-en-3-yl)carbamate (420H, 270 mg, 0.618 mmol) and $Et_3N$ (0.345 mL, 2.474 mmol) in DCM (6 mL) at 24° C. and the mixture was stirred at rt for 18 h. The mixture was evaporated under reduced pressure. The residue was purified by silica gel column flash chromatography, eluting with EtOAc/petroleum ether=0~25% to give tert-butyl 2-(3-((tert-butoxycarbonyl)amino)hex-5-en-3-yl)-4-(7-methoxy-2-methylquinolin-6-yl)-1H-imidazole-1-carboxylate (420I). LCMS (ESI) calc'd for $C_{30}H_{40}N_4O_5$ [M+H]$^+$: 537.3, found: 537.4.

Step 9: Preparation of (E)-tert-butyl 2-(3-((tert-butoxycarbonyl)amino)-9-oxoundec-5-en-3-yl)-4-(7-methoxy-2-methylquinolin-6-yl)-1H-imidazole-1-carboxylate (420J): UMICORE M71 SIPR (18 mg, 0.022 mmol) and hept-6-en-3-one (100 mg, 0.894 mmol) were added to the degassed solution of tert-butyl 2-(3-((tert-butoxycarbonyl)amino)hex-5-en-3-yl)-4-(7-methoxy-2-methylquinolin-6-yl)-1H-imidazole-1-carboxylate (420I, 240 mg, 0.447 mmol) in toluene (3 mL), and the resultant mixture was stirred at 60° C. for 17 h. The reaction mixture was concentrated in vacuo. The residue was purified by silica gel flash chromatography (ISCORF75; Sepa flash column), eluting with petroleum ether/EtOAc=10:1-3:1 to give (E)-tert-butyl 2-(3-((tert-butoxycarbonyl)amino)-9-oxoundec-5-en-3-yl)-4-(7-methoxy-2-methylquinolin-6-yl)-1H-imidazole-1-carboxylate (420J) and recovered tert-butyl 2-(3-((tert-butoxycarbonyl)amino)hex-5-en-3-yl)-4-(7-methoxy-2-methylquinolin-6-yl)-1H-imidazole-1-carboxylate. LCMS (ESI) calc'd for $C_{35}H_{48}N_4O_6$ [M+H]$^+$: 621.4, found: 621.4.

Step 10: Preparation of (E)-9-amino-9-(4-(7-methoxy-2-methylquinolin-6-yl)-1H-imidazol-2-yl)undec-6-en-3-one (420K): TFA (1 mL, 12.98 mmol) was added to the solution of (E)-tert-butyl 2-(3-((tert-butoxycarbonyl)amino)-9-oxoundec-5-en-3-yl)-4-(7-methoxy-2-methylquinolin-6-yl)-1H-imidazole-1-carboxylate (420J, 180 mg, 0.290 mmol) in DCM (10 mL), and the resultant mixture was stirred at 24° C. for 4 h. The mixture was concentrated in vacuo to give (E)-9-amino-9-(4-(7-methoxy-2-methylquinolin-6-yl)-1H-imidazol-2-yl)undec-6-en-3-one (420K) which was used to the next step without purification. LCMS (ESI) calc'd for $C_{25}H_{32}N_4O_2$ [M+H]$^+$: 421.3, found: 421.3.

Step 11: Preparation of 9-amino-9-(4-(7-methoxy-2-methylquinolin-6-yl)-1H-imidazol-2-yl)undecan-3-one (420L): Pd/C (40 mg, 0.376 mmol) was added to the degassed solution of (E)-9-amino-9-(4-(7-methoxy-2-methylquinolin-6-yl)-1H-imidazol-2-yl)undec-6-en-3-one (420K, 122 mg, 0.290 mmol) in MeOH (5 mL), and the resultant mixture was stirred under a $H_2$ balloon at rt for 24 h. The reaction mixture was concentrated in vacuo to give 9-amino-9-(4-(7-methoxy-2-methylquinolin-6-yl)-1H-imidazol-2-yl)undecan-3-one (420L) and used directly in next step. LCMS (ESI) calc'd for $C_{25}H_{34}N_4O_2$ [M+H]$^+$: 423.4, found: 423.3.

Step 12: Preparation of (1S)-tert-butyl 1-((3-(5-(7-methoxy-2-methylquinolin-6-yl)-1H-imidazol-2-yl)-9-oxoundecan-3-yl)carbamoyl)-6-azaspiro[2.5]octane-6-carboxylate (420M): DIPEA (0.3 mL, 1.718 mmol), HOBT (91 mg, 0.592 mmol) and EDC (181 mg, 0.947 mmol) were added to the solution of (S)-6-(tert-butoxycarbonyl)-6-azaspiro[2.5]octane-1-carboxylic acid (121 mg, 0.473 mmol) and 9-amino-9-(4-(7-methoxy-2-methylquinolin-6-yl)-1H-imidazol-2-yl)undecan-3-one (420L, 100 mg, 0.237 mmol) in DMF (0.5 mL), the resultant mixture was sitrred at rt for 16 h. DMF was removed in vacuo. The residue was purified by silica gel column flash chromatography, eluting with DCM/MeOH=50:1-20:1 to give (1S)-tert-butyl 1-((3-(5-(7-methoxy-2-methylquinolin-6-yl)-1H-imidazol-2-yl)-9-oxoundecan-3-yl)carbamoyl)-6-azaspiro[2.5]octane-6-carboxylate (420M). LCMS (ESI) calc'd for $C_{38}H_{53}N_5O_5$ [M+H]$^+$: 660.4, found: 660.5.

Step 13: Preparation of (1S)—N-(3-(5-(7-methoxy-2-methylquinolin-6-yl)-1H-imidazol-2-yl)-9-oxoundecan-3-yl)-6-azaspiro[2.5]octane-1-carboxamide (420N): TFA (1.0 mL, 12.98 mmol) was added to the solution of (1S)-tert-butyl 1-((3-(5-(7-methoxy-2-methylquinolin-6-yl)-1H-imidazol-2-yl)-9-oxoundecan-3-yl)carbamoyl)-6-azaspiro[2.5]octane-6-carboxylate (420M, 150 mg, 0.227 mmol) in DCM (10 mL), and the resultant mixture was stirred at 24° C. for 3 h. The mixture was concentrated in vacuo to give (1S)—N-(3-(5-(7-methoxy-2-methylquinolin-6-yl)-1H-imidazol-2-yl)-9-oxoundecan-3-yl)-6-azaspiro[2.5]octane-1-carboxamide (420N) which was used to the next step without purification. LCMS (ESI) calc'd for $C_{33}H_{45}N_5O_3$ [M+H]$^+$: 560.4, found: 560.4.

Step 14: Preparation of (1S)-6-(cyclopropylmethyl)-N-(3-(5-(7-methoxy-2-methylquinolin-6-yl)-1H-imidazol-2-yl)-9-oxoundecan-3-yl)-6-azaspiro[2.5]octane-1-carboxamide (420): Cyclopropanecarbaldehyde (239 mg, 3.40 mmol) was added to the solution of (1S)—N-(3-(5-(7-methoxy-2-methylquinolin-6-yl)-1H-imidazol-2-yl)-9-oxoundecan-3-yl)-6-azaspiro[2.5]octane-1-carboxamide (420N, 127 mg, 0.227 mmol) in MeOH (6 mL), and the resultant mixture was stirred at rt for 16 h. Sodium triacetoxyborohydride (90 mg, 0.425 mmol) was added to the reaction mixture, and it was stirred for 3 h. The residue was purified by preparative HPLC (reverse phase C-18 column), eluting with acetonitrile/water+0.1% TFA, to give (1S)-6-(cyclopropylmethyl)-N-(3-(5-(7-methoxy-2-methylquinolin-6-yl)-1H-imidazol-2-yl)-9-oxoundecan-3-yl)-6-azaspiro[2.5]octane-1-carboxamide (420). LCMS (ESI) calc'd for $C_{37}H_{51}N_5O_3$ [M+H]$^+$: 614.4, found: 614.4.

Solid $NaHCO_3$(200 mg) was added to the solution of (1S)-6-(cyclopropylmethyl)-N-(3-(5-(7-methoxy-2-methylquinolin-6-yl)-1H-imidazol-2-yl)-9-oxoundecan-3-yl)-6-azaspiro[2.5]octane-1-carboxamide (30 mg, 0.049 mmol) (TFA salt) in MeOH (5 mL), and the bottle was shaken for a few minutes, salt was filtered off and the filtrate was concentrated to give the free base of 420. LCMS (ESI) calc'd for $C_{37}H_{51}N_5O_3$ [M+H]$^+$: 614.4, found: 614.2. $^1$H NMR (400 MHz, MeOD) δ 8.40 (brs, 1H), 8.18 (d, J=8.4 Hz, 1H), 7.45-7.61 (m, 1H), 7.39 (s, 1H), 7.27-7.35 (m, 1H), 4.08 (s, 3H), 3.34-3.50 (m, 1H), 3.16 (brs, 1H), 2.89 (brs, 2H), 2.69 (s, 3H), 2.23-2.48 (m, 6H), 1.80-2.22 (m, 4H), 1.45-1.58 (m, 2H), 1.05-1.37 (m, 6H), 0.72-1.02 (m, 8H), 0.64 (brs, 2H), 0.27 (brs, 2H).

Human HDAC Enzyme Inhibitor Fluor-De-Lys Assay

Materials

Recombinant human HDAC8 (BML-SE145-0100) and HDAC10 (BML-SE559-0050) enzymes, HDAC substrates BML-KI104 and BML-KI178, and HDAC developer solutions BML-KI105 and BML-KI176 were purchased from Enzo Life Sciences. Recombinant human HDAC5 and HDAC11 were purchased from BPS Bioscience (catalog numbers 50045 and 50021). Substrate Boc-Lys(TFA)-AMC was obtained from Bachem (catalog number I-1985). HDAC inhibitor suberoylanilide hydroxamic acid (SAHA) was obtained from Indofine and trichostatin A (TSA) was obtained from Sigma-Aldrich. D-myo inositol-1,4,5,6-tetraphosphate potassium salt ($IP_4$) was obtained from Carbosynth (catalog MI 16761). HEPES pH 8.0 was obtained from Boston BioProducts, Tween-20 from Fisher Scientific (BP337), TCEP from Calbiochem and 7.5% bovine serum albumin (BSA) from Life Technologies (Ser. No. 15/260, 037). 384-well, black assay plates were obtained from Corning (3575).

Recombinant human HDAC1, HDAC2, and HDAC3/SMRT heterodimer were prepared by Merck Research Laboratories. Full length human HDAC1-FLAG was stably expressed in HEK-293F cells and purified using an anti-FLAG affinity chromatography with FLAG peptide (100 μg/ml) elution. The final concentration of HDAC1 was 1.98 uM by Western Blot analysis and 1.39 uM by active site titration. Full length human HDAC2-FLAG was expressed in baculovirus infected Sf9 cells and purified using an anti-FLAG affinity chromatography with FLAG peptide (100 μg/ml) elution. The eluted protein was then passed over an anti-HDAC1 immunoaffinity column to remove any complexes containing HDAC1. The final concentration of HDAC2 was 16.8 uM by Western Blot analysis and 7.6 uM by active site titration. Full length human HDAC3-FLAG was expressed in HEK-293F cells along with SMRT (amino acids 1-899)-6×His; plasmid APP-0024) and purified using an anti-FLAG affinity chromatography with FLAG peptide (100 μg/ml) elution. The eluted protein was then passed over an anti-HDAC1 immunoaffinity column to remove any complexes containing HDAC1. The final concentration of the HDAC3/SMRT complex was 2.03 uM by Western Blot analysis and 1.37 uM by active site titration.

HDAC Inhibition Assays

The histone deacetylase activities of HDAC1, HDAC2, HDAC3, HDAC6, and HDAC8 were measured in modified FLUOR DE LYS assays in 384-well format. In this assay, HDAC enzymes are initially incubated with an ε-acetyl (or -trifluoroacetyl)-L-lysine-containing substrate with a C-terminal amide having aminomethylcoumarin as the amine component. HDACs cleave the ε-acetyl group, rendering the resulting product susceptible to AMC cleavage by trypsin. The released AMC is then detected by its fluorescence.

The HDAC 1, 2 assays employed buffer A, which contained 20 mM HEPES, pH 8.0, 1 mM $MgCl_2$, 137 mM NaCl, 2.7 mM KCl, 0.05% BSA. The HDAC3/SMRT assay employed buffer B, consisting of 20 mM HEPES, pH 8.0, 1 mM $MgCl_2$, 50 mM NaCl, 2.7 mM KCl, 0.05% BSA, 0.005% Tween 20, and 10 μM $IP_4$. The HDAC6 assay employed buffer C, consisting of 20 mM HEPES, pH 8.0, 1 mM $MgCl_2$, 137 mM NaCl, 2.7 mM KCl, 0.5 mM TCEP (Calbiochem) and 0.05% BSA. The HDAC8 assay employed buffer D, consisting of 20 mM HEPES, pH 8.0, 1 mM $MgCl_2$, 100 mM NaCl, 20 mM KCl, 0.10% n-octyl-β-D-glucoside (Anatrace) and 0.05% BSA. All steps were performed at room temperature (23° C.). The assay was performed by pre-incubating serial dilutions of test compounds with the target HDAC prior to initiation with substrate. Each compound was titrated in a 10-point dose response, using a 1:3 fold dilution scheme, with 0.15 ul of solution added by ECH0555 to the plate, followed by the addition of 20 μl of the appropriate HDAC isoform diluted in appropriate assay buffer. The incubation was allowed to proceed for 3 hours, then the appropriate substrate diluted in assay buffer (final substrate concentration ~$K_m$) was added and the reaction allowed to proceed for 60 min. Final conditions used for each assay were: 1. HDAC 1, 0.3 nM total enzyme, 20 μM substrate BML-KI104; 2. HDAC 2, 1.5 nM total enzyme, 40 μM substrate BML-KI104; 3. HDAC 3/SMRT, 0.3 nM total enzyme, 20 μM substrate BML-KI104; 4. HDAC 6, 1.3 nM total enzyme, 2.5 μM substrate BML-KI104; 5. HDAC 8, 1.3 nM total enzyme, 200 μM substrate BML-KI178; The final high dose of test compound was 30 μM. For potent compounds, 900 nM was used as the final high dose. The reactions were stopped and developed by addition of 30 ul of HDAC developer solution containing a saturating level of HDAC inhibitor as follows: 1. HDACs 1, 2, 3 and 6, developer BML-KI105 (stock diluted 1:125, containing 20 uM SAHA, 2. HDAC 8, developer BML-KI176 (1:100 plus 40 uM SAHA, and the plates were shaken to assure good mixing, briefly centrifuged, incubated for 30 minutes at room temperature and then the fluorescence intensity (excitation 380 nm, emission 460 nm) measured using a PHERAstar plate reader. For each assay plate, both minimal inhibition (100% DMSO; 0% inhibition) and maximal inhibition (either 10 uM SAHA or 100 uM TSA; 100% inhibition) controls were added. For data analysis, background subtracted product (fluorescence) vs. time data for each inhibitor concentration was fitted using a 4-parameter fit.

All compounds prepared were tested in the binding assays with HDAC1, 2, 3, 6 and 8.

KARN Assay

Cell Maintenance

KARN cells (Jurkat $2C_4$) were licensed from the laboratory of Dr. John Karn, Case Western Reserve University, School of Medicine. The details regarding this cell line are published (Pearson, R., Kin, Y. K., Hokello, J., Lassen, K., Friedman, J., Tyagi, M., Karn, J., 2008, *J Virol.* 82:12291-12303). The cells were grown in a T175 flask (Thermo Fisher, catalog number 159910) in RPMI 1640 containing L-glutamine and phenol red (Life Technologies, catalog number 11875-085), 5% heat inactivated fetal bovine serum (FBS; Life Technologies, catalog number 10100-147) and 100 μg/ml Penicillin-Streptomycin (Life Technologies, catalog number 15140-122) at 37° C. An atmosphere of 5% CO2 and 90% humidity was used for all culture work. Cells were split and reseeded into T175 flasks at a density of $0.2\times10^6$ cells/ml, in 40 ml of media, every 3-4 days.

KARN Assay

Day 1: After the 3-4 day growth period, the cells were transferred from the T175 flask to a 50 ml conical tube and gently pelleted at 1000 rpm for 5 minutes. The supernatant was removed and the cells gently resuspended in assay media RPMI 1640 medium containing L-glutamine but without Phenol Red (Life Technologies, catalog number 11835-030), 5% FBS and 100 μg/ml Penicillin-Streptomycin, and then reseeded such that the original flask is now divided into two T175 flasks. These flasks were returned to the incubator.

Day 2: Cell Preparation: The next day, the cells were transferred from each T175 flask to an individual 50 ml conical tube and gently pelleted at 1000 rpm for 5 minutes. The cells were gently resuspended in assay media (30 ml) and pelleted again. The cell pellets were each resuspended in 30 ml of RPMI 1640 medium containing L-glutamine but without Phenol Red, 100 μg/ml Penicillin-Streptomycin and containing either 0.1% or 5% normal human serum (NHS; Biospecialty, catalog number 115-00 Anticoagulant free). The cells were counted using the ViCell (Beckman Coulter) and diluted as necessary. A Multidrop (Combi, Thermo Scientific) with a sterile head was used to seed the cells into the wells of a 384-well solid black plate with lid (Perkin Elmer, catalog number 6007660) at 4000 cells/30 l/well for the 5% NHS assay media and 6000 cells/30 l/well for 0.1% NHS assay. The plates were covered and returned to the incubator prior to compound addition.

Compound Preparation: Solutions of control inhibitor suberoylanilide hydroxamic acid (SAHA; Sigma, catalog number SML0061) and test compounds in 100% DMSO were titrated into 384-well polypropylene plates (Labcyte, catalog number P-05525) using a 20-point dose response and 2-fold dilutions. The reference compounds, DMSO and SAHA were then added to the compound plate. Using the Access system (Labcyte), 120 nl of these inhibitor and control solutions were added to the individual wells of the plates containing the cells, and the plates were then returned to the incubator for ~20 hr (range from 18-24 hr). The final high concentration for SAHA and the test compounds in the assays was 40 μM. The final DMSO concentration in all wells was 0.4%. The minimal induction reference compound used was DMSO and the maximal induction reference compound used was SAHA (2 μM final concentration in the assay).

Day 3: The luciferase detection reagent was prepared by transferring the contents of one bottle of Steady-Glo buffer to one bottle of Steady-Glo aubstrate (Steady-Glo Luciferase Assay System, Promega, catalog number E2520), followed by gently mixing until the substrate was thoroughly dissolved and the solution was equilibrated to room temperature. The cell culture assay plates were removed from the incubator and brought to room temperature (15 min). The Steady-Glo Reagent was added to the plates (30 μl/well), which were then covered with a black lid and incubated for 10 minutes at room temperature. The plates were then read for luminescence on an Envision (Perkin Elmer) using the ultrasensitive mode (US LUM), 0.1 counts per second and 384-well aperture. Luminescence counts in the DMSO reference wells were considered as 0% induction, while those in the 2 μM SAHA reference wells were considered as 100% induction. Dose response curves were plotted as test compound concentration (X-axis) vs. percent activation (Y-axis) using a 4-parameter fit based on the Levenberg-Marquardt algorithm.

All HDAC Inhibitors were Tested

All compounds prepared were tested in the binding assays with HDAC1, 2, 3, 6 and 8 and in the KARN assays for their cell functional activity. This data is provided below:

| ID | HDAC1 $IC_{50}$ (nM) | HDAC2 $IC_{50}$ (nM) | HDAC3 $IC_{50}$ (nM) | HDAC6 $IC_{50}$ (nM) | HDAC8 $IC_{50}$ (nM) | Karn $EC_{50}$ (nM) 0.1% NHS | Karn $EC_{50}$ (nM) 5% NHS |
|---|---|---|---|---|---|---|---|
| 2 | 70.40 | 423.3 | 11.48 | 7,202 | 11,970 | 5,537 | 10,530 |
| 3 | 29.12 | 111.0 | 17.87 | 18,360 | 8,281 | 8,435 | 10,800 |
| 4 | 28.44 | 121.3 | 12.26 | 5,619 | 2,992 | 1,386 | 1,824 |
| 5 | 14.23 | 42.6 | 5.74 | 6,554 | 2,638 | 786 | 1,181 |
| 6 | 12.70 | 40.7 | 5.77 | 1,394 | 420 | 506 | 1,245 |
| 7 | 1.78 | 5.9 | <1.50 | 3,947 | 1,557 | 235 | 521 |
| 8 | <1.50 | 3.2 | <1.50 | 107 | 199 | 181 | 246 |
| 9 | 3.00 | 12.0 | 2.90 | 1,456 | 6,523 | 1,599 | 2,212 |
| 10 | 2.21 | 6.2 | <1.50 | 1,147 | 1,208 | 130 | 166 |
| 11 | 4.20 | 10.1 | 2.78 | 2,275 | 4,237 | 416 | 484 |
| 12 | 3.31 | 11.6 | <1.50 | 11,460 | 15,120 | 216 | 186 |
| 13 | 0.35 | 4.0 | 0.57 | 11,770 | 15,390 | 522 | 504 |
| 14 | 2.22 | 9.1 | <1.50 | 20,870 | 17,910 | 151 | 121 |
| 15 | 20.40 | 74.9 | 20.33 | 1,687 | 8,923 | 2,688 | 3,525 |
| 16 | 27.58 | 91.4 | 4.70 | 29,180 | 7,471 | 570 | 1,804 |
| 17 | 7.19 | 26.7 | <1.50 | 16,400 | 4,701 | 154 | 537 |
| 18 | 13.51 | 53.1 | 4.46 | >45,000 | 5,335 | 1,142 | 853 |
| 19 | 43.60 | 159.4 | 19.13 | 18,960 | 16,780 | 2,729 | 3,771 |
| 20 | 1.91 | 18.1 | 2.54 | 9,829 | 5,422 | 294 | 269 |
| 21 | 6.75 | 24.2 | 1.82 | 3,537 | 2,022 | 151 | 911 |
| 22 | 1.66 | 7.6 | <1.50 | 12,510 | 7,927 | 154 | 201 |
| 23 | <1.50 | 2.4 | <1.50 | 25,510 | 6,639 | 83 | 104 |
| 24 | 6.34 | 44.3 | 1.75 | 14,420 | 11,070 | 540 | 575 |
| 25 | 3.47 | 34.4 | 3.57 | 15,940 | 5,383 | 775 | 643 |
| 26 | 12.25 | 73.8 | 3.36 | 27,850 | 7,566 | 1,834 | 1,504 |
| 27 | 44.17 | 228.3 | 11.54 | >45,000 | 14,820 | 2,628 | 3,612 |
| 28 | 129.20 | 388.3 | 38.84 | >45,000 | 13,390 | 543 | 2,505 |
| 29 | 24.26 | 132.6 | 4.43 | 22,460 | 4,204 | 818 | 1,313 |
| 30 | 29.30 | 197.8 | 5.61 | >45,000 | 14,050 | 2,453 | 3,230 |
| 31 | 48.89 | 287.4 | 9.89 | 43,300 | 8,791 | 2,045 | 3,426 |
| 32 | 114.10 | 619.0 | 22.98 | >45,000 | 17,620 | 3,341 | 8,058 |
| 33 | 15.84 | 78.4 | 26.52 | >45,000 | 30,240 | 2,867 | 2,766 |
| 34 | 65.58 | 254.1 | 45.18 | 18,660 | >45,000 | 1,590 | 1,791 |
| 35 | 1.68 | 12.4 | 1.39 | 875 | 26,540 | 575 | 559 |
| 36 | 2.33 | 12.8 | <1.50 | 4,441 | 11,270 | 773 | 851 |
| 37 | 60.83 | 206.4 | 7.52 | >1,500 | >45,000 | 712 | 4,839 |
| 38 | 75.80 | 363.9 | 10.81 | >450 | >45,000 | 845 | 6,759 |
| 39 | 2.80 | 11.7 | 1.78 | 23,610 | 9,370 | 161 | 259 |
| 40 | 0.56 | 6.3 | 0.91 | 17,650 | 6,802 | 166 | 276 |
| 41 | 0.41 | 5.0 | 0.67 | 17,460 | 6,364 | 193 | 165 |
| 42 | 97.85 | 177.1 | 100.70 | 8,972 | >45,000 | 548 | 1,351 |
| 43 | 16.98 | 96.1 | 10.69 | 22,540 | 39,610 | 566 | 1,162 |
| 44 | 3.70 | 15.6 | 1.93 | 8,249 | 19,190 | 107 | 175 |
| 45 | 35.20 | 154.8 | 18.89 | 14,820 | 20,730 | 1,233 | 1,260 |

-continued

| ID | HDAC1 $IC_{50}$ (nM) | HDAC2 $IC_{50}$ (nM) | HDAC3 $IC_{50}$ (nM) | HDAC6 $IC_{50}$ (nM) | HDAC8 $IC_{50}$ (nM) | Karn $EC_{50}$ (nM) 0.1% NHS | Karn $EC_{50}$ (nM) 5% NHS |
|---|---|---|---|---|---|---|---|
| 46 | 58.92 | 229.2 | 34.81 | 17,060 | 38,080 | 2,112 | 1,669 |
| 47 | 0.31 | <1.5 | 0.21 | 6,301 | 9,835 | 105 | 97 |
| 48 | 0.22 | 1.7 | 0.26 | 9,466 | 12,620 | 77 | 55 |
| 49 | 27.98 | 94.9 | 22.20 | >15,000 | >15,000 | 1,060 | 1,284 |
| 50 | 0.36 | 2.1 | 0.29 | 9,044 | 12,420 | 247 | 322 |
| 51 | 25.85 | 116.9 | 13.81 | 36,930 | 19,650 | 1,564 | 2,071 |
| 52 | 6.18 | 26.9 | 3.36 | >45,000 | 6,929 | 1,731 | 2,207 |
| 53 | 47.86 | 219.3 | 26.80 | 43,320 | 29,490 | 1,605 | 3,532 |
| 54 | 10.67 | 51.3 | 3.12 | >45,000 | 12,260 | 254 | 1,111 |
| 55 | 35.55 | 164.2 | 12.11 | >45,000 | 16,190 | 558 | 2,726 |
| 56 | 5.73 | 30.5 | 2.23 | 12,590 | 12,500 | 284 | 452 |
| 57 | 4.55 | 26.6 | 2.95 | 14,910 | 7,500 | 226 | 360 |
| 61 | 5.67 | 38.5 | 6.22 | >900 | >900 | 830 | 763 |
| 62 | 49.99 | 330.8 | 111.00 | >900 | >900 | 2,871 | 3,617 |
| 63 | 7.91 | 31.3 | 2.20 | 619 | 3,089 | 234 | 1,786 |
| 64 | 21.47 | 83.2 | 5.53 | 3,580 | 6,351 | 647 | 5,036 |
| 65 | 44.91 | 306.3 | 20.55 | >45,000 | 40,050 | 2,186 | 4,388 |
| 66 | 147.10 | >900.0 | 166.60 | >450 | >1,500 | 27 | 14 |
| 67 | 19.64 | 100.8 | 14.21 | 1,283 | 2,594 | 6,483 | 6,347 |
| 68 | 8.74 | 126.2 | 8.59 | 6,805 | 4,413 | >40,000 | |
| 69 | 0.47 | 2.2 | 0.95 | 9,491 | 6,481 | 76 | 88 |
| 70 | 0.32 | 2.3 | 0.34 | 2,891 | 1,589 | 60 | 51 |
| 71 | 0.18 | 1.4 | 0.16 | >900 | >900 | 32 | 40 |
| 72 | 1.29 | 5.4 | 1.20 | >1,500 | >15,000 | 257 | 305 |
| 73 | 31.00 | 137.8 | 9.57 | 6,514 | 3,071 | 740 | 1,454 |
| 74 | 8.21 | 36.2 | 3.74 | 7,847 | 4,527 | 351 | 376 |
| 75 | 29.30 | 101.4 | 2.59 | >45,000 | 27,250 | 275 | 801 |
| 76 | 3.85 | 19.7 | 2.88 | 26,610 | 16,750 | 233 | 409 |
| 77 | 1.53 | 4.8 | <1.50 | 198 | 21,690 | 194 | 311 |
| 78 | 18.29 | 62.3 | 13.82 | 33,490 | >45,000 | 911 | 1,445 |
| 79 | 3.31 | 13.4 | 1.58 | 3,136 | 9,743 | 193 | 219 |
| 80 | 2.89 | 14.8 | 2.96 | 1,684 | >45,000 | 435 | 501 |
| 81 | 88.15 | 337.5 | 69.02 | 3,866 | 5,354 | 6,433 | 10,730 |
| 82 | 7.87 | 34.6 | 6.17 | 84 | 3,592 | 761 | 640 |
| 83 | <1.50 | <1.5 | <1.50 | 2,624 | 15,180 | 64 | 60 |
| 84 | 9.95 | 63.8 | 16.31 | 3,781 | 14,270 | 632 | 1,184 |
| 85 | 8.35 | 40.8 | 10.12 | >450 | >4,500 | 9,315 | 11,840 |
| 86 | 15.86 | 64.8 | 12.12 | 3,329 | 3,169 | 1,065 | 1,507 |
| 87 | 2.42 | 12.9 | 3.27 | 5,362 | 7,664 | 400 | 369 |
| 88 | 3.29 | 11.0 | 2.21 | 1,227 | 3,136 | 220 | 175 |
| 89 | 3.63 | 19.3 | 2.27 | 7,590 | 9,702 | 219 | 237 |
| 90 | 0.28 | 1.6 | 0.38 | 1,013 | 2,639 | 52 | 33 |
| 91 | 4.38 | 14.2 | 3.26 | 27,490 | 31,880 | 207 | 274 |
| 92 | <1.50 | <1.5 | <1.50 | 2,977 | 6,261 | 52 | 56 |
| 93 | 7.15 | 25.6 | 5.76 | 955 | 31,780 | 688 | 736 |
| 94 | 9.13 | 34.0 | 4.01 | 2,301 | 44,190 | 502 | 549 |
| 95 | 5.26 | 31.5 | 3.95 | 1,249 | 20,490 | 522 | 747 |
| 96 | 6.90 | 44.5 | 9.90 | 7,300 | >45,000 | 1,372 | 1,511 |
| 97 | 6.52 | 23.0 | 4.38 | 7,090 | >45,000 | 563 | 660 |
| 98 | 3.59 | 9.9 | 3.77 | 1,769 | 3,416 | 10,970 | 12,790 |
| 99 | 3.55 | 17.8 | 2.59 | 110 | 32,920 | 162 | 310 |
| 100 | <1.50 | <1.5 | <1.50 | 11,920 | 8,252 | 68 | 64 |
| 101 | <1.50 | <1.5 | <1.50 | 7,372 | 6,647 | 41 | 36 |
| 102 | 7.27 | 26.7 | 2.66 | 1,947 | 3,259 | 290 | 301 |
| 103 | 12.31 | 33.7 | 4.64 | 10,470 | 13,470 | 3,161 | 2,734 |
| 104 | <1.50 | <1.5 | <1.50 | 5,298 | 5,016 | 33 | 28 |
| 105 | 0.92 | 5.3 | 1.18 | 1,506 | 2,885 | 126 | 942 |
| 106 | 1.73 | 7.9 | <1.50 | 1,462 | 2,783 | 143 | 1,066 |
| 107 | 0.15 | 1.4 | 0.36 | 208 | 3,738 | 37 | 81 |
| 108 | 0.11 | 0.6 | 0.13 | 4,279 | 3,763 | 26 | 19 |
| 109 | 3.52 | 9.4 | 2.98 | 13,400 | >15,000 | 706 | 579 |
| 110 | 102.50 | 343.0 | 55.83 | 1,355 | >45,000 | 2,028 | 2,419 |
| 111 | 1.83 | 5.9 | 1.95 | 4,241 | 23,680 | 213 | 236 |
| 112 | 0.24 | 1.1 | 0.24 | 7,760 | 5,381 | 61 | 55 |
| 113 | 1.37 | 6.6 | 1.42 | >4,500 | 2,178 | 58 | 107 |
| 114 | 1.12 | 4.7 | 1.04 | 4,087 | 26,980 | 207 | 220 |
| 115 | <1.50 | 2.0 | <1.50 | 4,287 | 15,400 | 239 | 209 |
| 116 | 4.37 | 15.7 | 3.88 | 4,729 | >15,000 | 630 | 617 |
| 117 | 26.08 | 110.2 | 31.91 | 93 | 1,931 | 1,622 | 2,583 |
| 118 | 26.50 | 103.9 | 20.40 | 95 | 2,988 | 1,232 | 1,877 |
| 119 | 0.50 | 2.1 | 0.51 | >150 | >1,500 | 98 | 103 |
| 120 | 27.39 | 73.1 | 15.44 | 22,250 | 28,680 | 2,879 | 3,756 |
| 121 | 1.39 | 4.4 | 1.16 | 4,815 | 15,310 | 232 | 242 |
| 122 | 56.68 | 156.9 | 20.50 | >45,000 | 29,270 | 1,132 | 2,844 |
| 123 | 34.82 | 94.6 | 7.59 | >15,000 | >15,000 | 868 | 3,900 |

-continued

| ID | HDAC1 $IC_{50}$ (nM) | HDAC2 $IC_{50}$ (nM) | HDAC3 $IC_{50}$ (nM) | HDAC6 $IC_{50}$ (nM) | HDAC8 $IC_{50}$ (nM) | Karn $EC_{50}$ (nM) 0.1% NHS | Karn $EC_{50}$ (nM) 5% NHS |
|---|---|---|---|---|---|---|---|
| 124 | 0.92 | 4.6 | 0.63 | 137 | 16,000 | 111 | 151 |
| 125 | <1.50 | 5.6 | <1.50 | 254 | 23,440 | 154 | 256 |
| 126 | 0.19 | 1.3 | 0.19 | 18,120 | 6,478 | 53 | 33 |
| 127 | 0.24 | 1.8 | 0.34 | 364 | 76 | 37 | 60 |
| 128 | 7.09 | 22.7 | 3.71 | 759 | 5,577 | 442 | 1,144 |
| 129 | 27.04 | 89.0 | 14.22 | >15,000 | 7,721 | 828 | 1,241 |
| 130 | 5.60 | 15.3 | 2.27 | 2,123 | 6,002 | 503 | 598 |
| 131 | 0.48 | 2.5 | 0.57 | 2,275 | 2,775 | 126 | 128 |
| 132 | 2.33 | 6.5 | <1.50 | 3,681 | 8,058 | 169 | 281 |
| 133 | <1.50 | 2.1 | <1.50 | 879 | 2,057 | 89 | 81 |
| 134 | 10.46 | 51.6 | 4.00 | 1,762 | 574 | 2,414 | 2,192 |
| 135 | 14.63 | 43.5 | 10.98 | >15,000 | 18,270 | 1,119 | 1,376 |
| 136 | 10.25 | 31.2 | 6.41 | >4,500 | 4,805 | 2,500 | |
| 137 | 7.78 | 17.2 | 4.72 | 2,758 | 33,540 | 434 | 443 |
| 138 | 1.32 | 7.9 | 1.62 | 1,474 | 10,090 | 210 | 223 |
| 139 | 5.28 | 26.1 | 2.39 | 4,447 | 12,040 | 532 | 552 |
| 140 | 0.97 | 4.5 | 0.95 | 611 | 4,113 | 113 | 155 |
| 141 | 12.18 | 38.4 | 1.98 | 1,490 | 2,113 | 146 | 1,452 |
| 142 | 18.70 | 84.1 | 10.01 | 3,668 | 5,123 | 311 | 544 |
| 143 | 65.13 | 206.6 | 32.01 | 3,665 | 13,120 | 1,245 | 1,333 |
| 144 | <1.50 | 3.0 | <1.50 | >4,500 | 4,487 | 361 | 317 |
| 145 | 5.85 | 12.6 | 2.61 | 5,762 | 4,271 | 641 | 746 |
| 146 | 1.06 | 3.3 | 0.64 | 7,729 | 7,705 | 122 | 112 |
| 147 | 2.29 | 10.3 | <1.50 | 3,662 | 2,768 | 3,584 | 2,852 |
| 148 | 0.23 | 2.3 | 0.37 | 749 | 3,561 | 93 | 110 |
| 149 | 0.50 | 3.9 | 0.62 | 3,662 | 2,720 | 92 | 73 |
| 150 | 0.19 | 1.4 | 0.25 | 7,055 | 4,375 | 114 | 135 |
| 151 | 5.74 | 21.8 | 3.94 | 5,815 | 3,176 | 583 | 864 |
| 152 | 0.94 | 4.0 | 0.85 | 19,180 | 5,062 | 128 | 96 |
| 153 | 5.44 | 13.5 | 6.14 | 10,380 | >15,000 | 452 | 447 |
| 154 | 6.03 | 19.5 | 2.76 | 18,080 | 12,080 | 518 | 476 |
| 155 | 6.91 | 18.4 | 2.05 | 8,937 | 8,135 | 354 | 398 |
| 156 | 5.03 | 15.1 | 1.98 | 7,527 | 5,831 | 1,356 | 1,357 |
| 157 | 5.39 | 11.9 | 4.01 | 8,527 | 4,178 | 451 | 557 |
| 158 | 0.90 | 4.2 | 1.02 | >150 | >1,500 | 125 | 200 |
| 159 | 0.44 | 2.4 | 0.49 | 2,948 | 4,625 | 73 | 57 |
| 160 | 1.89 | 12.1 | 2.75 | 10,420 | 16,830 | 200 | 234 |
| 161 | 54.47 | 162.6 | 32.99 | 11,710 | 26,810 | 1,366 | 1,465 |
| 162 | 3.24 | 9.5 | 2.84 | 6,531 | >45,000 | 257 | 305 |
| 163 | 0.76 | 2.3 | 0.60 | 456 | >900 | 57 | 57 |
| 164 | 1.52 | 3.2 | <1.50 | 74 | 16,650 | 123 | 170 |
| 165 | 1.18 | 8.0 | 2.14 | 11,900 | 14,660 | 140 | 385 |
| 166 | 0.37 | 2.2 | 0.32 | 229 | 5,664 | 469 | 591 |
| 167 | 0.97 | 8.0 | 1.12 | 3,320 | 8,272 | 122 | 253 |
| 168 | 0.45 | 3.2 | 0.49 | 300 | 23,590 | 62 | 80 |
| 169 | <1.50 | 2.2 | <1.50 | 83 | 7,579 | 91 | 78 |
| 170 | 5.79 | 16.9 | 4.84 | 923 | 835 | 436 | 1,155 |
| 171 | 0.49 | 2.4 | 0.40 | 309 | >15,000 | 134 | 143 |
| 172 | <1.50 | <1.5 | <1.50 | 326 | 3,873 | 17 | 21 |
| 173 | <1.50 | 2.0 | <1.50 | 972 | >15,000 | 85 | 51 |
| 174 | 0.55 | 2.1 | 0.43 | 951 | 1,215 | 67 | 82 |
| 175 | 0.18 | 1.1 | 0.25 | >150 | >150 | 48 | 84 |
| 176 | 0.26 | 1.2 | 0.25 | >1,500 | >4,500 | 45 | 76 |
| 177 | 0.24 | 2.0 | 0.28 | 341 | 2,560 | 22 | 41 |
| 178 (A10) | 106.60 | 385.9 | 54.87 | >45,000 | 3,261 | 6,790 | 10,390 |
| 179 | 58.27 | 379.5 | 17.50 | 9,526 | 8,660 | 2,414 | 2,392 |
| 180 | 5.40 | 29.6 | 2.55 | 2,121 | 270 | 371 | 666 |
| 181 | <1.50 | <1.5 | <1.50 | 144 | 5,251 | 52 | 63 |
| 182 | 0.06 | 0.6 | 0.09 | 460 | 4,483 | 24 | 13 |
| 183 | <1.50 | 2.4 | <1.50 | 898 | 10,440 | 58 | 93 |
| 184 | 9.51 | 38.8 | 18.40 | 9,281 | >45,000 | 1,634 | 2,764 |
| 185 | 15.14 | 38.0 | 25.99 | 36,410 | >45,000 | 1,329 | 2,965 |
| 186 | 0.11 | 0.2 | 0.04 | 305 | >900 | 7 | 14 |
| 187 | 0.07 | 0.1 | 0.13 | 269 | >900 | 8 | 10 |
| 188 | 0.64 | 1.2 | 0.20 | >900 | >900 | 41 | 66 |
| 189 | 7.33 | 30.0 | 2.34 | 159 | 27,470 | 282 | 300 |
| 190 | 11.82 | 43.5 | 5.03 | 562 | 3,106 | 967 | 1,447 |
| 191 | 2.16 | 5.3 | 1.68 | 2,051 | 43,150 | 366 | 343 |
| 192 | 2.11 | 3.9 | 0.69 | >900 | >900 | 178 | 138 |
| 193 | 3.01 | 10.9 | 1.81 | >900 | >900 | 284 | 297 |
| 195 | 0.86 | 9.7 | 1.71 | 21,460 | 7,864 | 163 | 216 |
| 196 | 1.42 | 6.0 | 0.73 | 759 | >900 | 154 | 162 |
| 197 | 5.13 | 23.6 | 2.59 | 3,384 | 7,542 | 369 | 538 |
| 198 | 0.87 | 3.8 | 0.65 | 426 | >900 | 147 | 176 |

-continued

| ID | HDAC1 $IC_{50}$ (nM) | HDAC2 $IC_{50}$ (nM) | HDAC3 $IC_{50}$ (nM) | HDAC6 $IC_{50}$ (nM) | HDAC8 $IC_{50}$ (nM) | Karn $EC_{50}$ (nM) 0.1% NHS | Karn $EC_{50}$ (nM) 5% NHS |
|---|---|---|---|---|---|---|---|
| 199 | 0.35 | 1.3 | 0.26 | 216 | 300 | 62 | 83 |
| 200 | 1.46 | 14.2 | 1.48 | >900 | >900 | 35 | 52 |
| 201 | 7.18 | 32.6 | 8.06 | 35,760 | 14,240 | 359 | 403 |
| 202 | 1.21 | 4.9 | 0.98 | 34,930 | 8,775 | 210 | 501 |
| 204 | 0.34 | 3.9 | 0.70 | 592 | >900 | 165 | 152 |
| 205 | 4.52 | 16.3 | 2.65 | 306 | >900 | 478 | 646 |
| 206 | 0.26 | 0.7 | 0.10 | >900 | >900 | 66 | 83 |
| 207 | 0.24 | 2.1 | 0.36 | 1,346 | 1,593 | 55 | 58 |
| 208 | <1.50 | 3.2 | <1.50 | 756 | 1,449 | 53 | 63 |
| 209 (A8) | 52.94 | 150.8 | 21.60 | >900 | 144 | 1,442 | 4,946 |
| 210 | 0.26 | 2.2 | 0.54 | >900 | >900 | 30 | 39 |
| 211 | <1.50 | <1.5 | <1.50 | 328 | 6,131 | 17 | 15 |
| 215 | 0.89 | 4.0 | 1.15 | >900 | >900 | 93 | 93 |
| 216 | 7.11 | 34.8 | 13.51 | 786 | >900 | 194 | 278 |
| 217 | 4.56 | 50.3 | 10.94 | >900 | >900 | 576 | 518 |
| 218 | 0.05 | 0.7 | 0.12 | >900 | >900 | 34 | 34 |
| 219 | 0.10 | 1.8 | 0.34 | >900 | >900 | 78 | 101 |
| 220 | 29.87 | 250.8 | 33.46 | >900 | >900 | 3,809 | 3,931 |
| 221 | 8.62 | 54.5 | 13.65 | >900 | >900 | 344 | 581 |
| 222 | 1.61 | 24.5 | 4.67 | >900 | >900 | 298 | 364 |
| 223 | 1.54 | 9.7 | 2.06 | 237 | >900 | 272 | 559 |
| 224 (A13) | 38.74 | 444.5 | 92.08 | >900 | >900 | 5,001 | 6,966 |
| 225 | 0.60 | 6.2 | 1.14 | 759 | >900 | 217 | 247 |
| 226 | 1.32 | 5.1 | 1.25 | >900 | >900 | 160 | 199 |
| 228 | 0.12 | 0.6 | 0.19 | >900 | >900 | 22 | 22 |
| 229 | 0.09 | 0.7 | 0.21 | 451 | >900 | 31 | 29 |
| 230 | 0.40 | 2.7 | 0.72 | 396 | >900 | 88 | 83 |
| 231 | 1.26 | 19.2 | 3.26 | 220 | >900 | 589 | 535 |
| 232 | 1.33 | 21.4 | 4.47 | >900 | >900 | 144 | 248 |
| 233 | 3.59 | 25.2 | 8.80 | >900 | >900 | 166 | 230 |
| 234 | 0.56 | 14.1 | 2.99 | >900 | >900 | 160 | 262 |
| 235 | 0.70 | 12.4 | 2.19 | >900 | >900 | 249 | 411 |
| 236 | 0.36 | 9.9 | 1.07 | >900 | >900 | 442 | 476 |
| 237 | 2.41 | 27.2 | 6.06 | >900 | >900 | 235 | 274 |
| 238 | 0.22 | 1.9 | 0.27 | 7,780 | 6,504 | 66 | 45 |
| 239 | 13.86 | 77.4 | 15.28 | >45,000 | 20,610 | 324 | 581 |
| 240 | 5.73 | 38.1 | 2.95 | 38,410 | 26,690 | 247 | 346 |
| 241 | 0.32 | 2.0 | 0.42 | 45 | >1,500 | 65 | 32 |
| 242 | 3.94 | 16.1 | <1.50 | 133 | 5,102 | 1,686 | 2,768 |
| 243 | 0.04 | 0.4 | 0.04 | 347 | 6,262 | 6 | 10 |
| 243 | <1.50 | <1.5 | <1.50 | 990 | 2,842 | 24 | 32 |
| 244 | 0.08 | 0.7 | 0.10 | >1,500 | >4,500 | 117 | 137 |
| 245 | 0.05 | 0.5 | 0.07 | 694 | 9,012 | 18 | 22 |
| 246 | 176.80 | 769.0 | 155.00 | | | 1,944 | 3,772 |
| 247 | 38.95 | 214.4 | 35.92 | >45,000 | 21,830 | 9,635 | 10,810 |
| 248 | 5.84 | 24.1 | 3.62 | >45,000 | 22,330 | 183 | 429 |
| 249 | 17.40 | 88.3 | 20.05 | 19,340 | 31,470 | >40,000 | |
| 250 | 80.70 | 191.7 | 122.40 | 21,920 | 38,290 | 3,731 | 4,103 |
| 251 | 2.73 | 12.6 | 1.82 | 41,660 | 29,360 | 143 | 216 |
| 252 | 56.56 | 185.3 | 66.08 | 33,930 | 29,640 | 1,597 | 2,883 |
| 253 | 30.42 | 111.3 | 16.66 | >45,000 | 26,770 | 1,866 | 2,335 |
| 254 | 29.41 | 131.2 | 29.62 | >45,000 | 38,670 | 5,343 | 6,040 |
| 255 | 168.30 | 490.6 | 81.91 | 12,130 | 5,793 | 13,320 | 14,800 |
| 256 | 74.64 | 280.2 | 57.95 | 3,934 | 1,095 | 23,660 | >40,000 |
| 257 | 64.84 | 185.0 | 49.69 | 36,600 | 10,420 | 8,085 | 10,560 |
| 258 | 7.82 | 23.8 | 3.35 | 38,680 | 16,360 | 7,439 | 7,835 |
| 259 | 23.85 | 95.0 | 18.29 | 3,144 | 6,144 | 7,929 | 8,177 |
| 260 | 13.05 | 52.5 | 5.31 | 28,430 | >15,000 | 717 | 913 |
| 261 | 25.24 | 102.2 | 16.45 | 2,467 | 4,594 | 1,384 | 1,499 |
| 262 | 4.42 | 18.8 | 3.36 | 33,490 | 12,580 | 773 | 851 |
| 263 | <1.50 | <1.5 | <1.50 | 873 | 4,522 | 140 | 181 |
| 264 | 1.79 | 5.9 | <1.50 | 1,712 | 1,144 | 78 | 143 |
| 265 | 5.14 | 12.4 | 3.86 | 630 | 4,602 | 142 | 370 |
| 266 | 155.20 | 371.6 | 74.14 | 42,490 | 19,280 | 9,898 | 13,850 |
| 267 | 46.68 | 169.7 | 34.27 | 6,374 | 11,600 | | |
| 268 | 3.89 | 17.2 | 3.07 | 1,778 | 6,082 | 205 | 330 |
| 269 | 5.18 | 36.7 | 8.30 | >900 | >900 | 746 | 1,214 |
| 271 | 1.90 | 7.7 | <1.50 | 464 | 1,754 | 154 | 634 |
| 272 | 2.08 | 8.2 | <1.50 | 449 | 1,246 | 163 | 721 |
| 273 | <1.50 | 3.4 | <1.50 | 400 | 1,965 | 111 | 438 |
| 274 | 4.25 | 14.8 | 2.68 | 357 | 6,890 | 228 | 634 |
| 275 | 0.23 | <1.5 | 0.35 | 158 | 3,978 | 26 | 57 |
| 276 | 1.56 | 9.1 | 1.57 | 1,285 | 5,003 | 1,560 | 4,781 |

-continued

| ID | HDAC1 $IC_{50}$ (nM) | HDAC2 $IC_{50}$ (nM) | HDAC3 $IC_{50}$ (nM) | HDAC6 $IC_{50}$ (nM) | HDAC8 $IC_{50}$ (nM) | Karn $EC_{50}$ (nM) 0.1% NHS | Karn $EC_{50}$ (nM) 5% NHS |
|---|---|---|---|---|---|---|---|
| 277 | 1.75 | 6.1 | <1.50 | 405 | 1,921 | 140 | 708 |
| 278 | 2.06 | 7.9 | <1.50 | 479 | 980 | 166 | 1,001 |
| 279 | 1.94 | 6.7 | <1.50 | 362 | 5,116 | 160 | 860 |
| 280 | 29.98 | 122.3 | 10.63 | 11,140 | 10,800 | 1,020 | 919 |
| 281 | 22.49 | 93.1 | 10.11 | 3,725 | 20,890 | 2,138 | 2,173 |
| 282 | 1.80 | 8.1 | <1.50 | 2,195 | 10,710 | 294 | 247 |
| 283 | 0.98 | 5.8 | 1.08 | 1,458 | 8,576 | 251 | 283 |
| 284 | 18.65 | 82.1 | 6.09 | 13,450 | 14,950 | 606 | 598 |
| 285 | 5.47 | 24.6 | 2.10 | 260 | 9,186 | 257 | 1,008 |
| 286 | 1.00 | 6.1 | 1.08 | 342 | 3,870 | 116 | 406 |
| 287 | 3.66 | 18.6 | 11.86 | 351 | 2,778 | 81 | 325 |
| 288 | 7.10 | 26.5 | 2.32 | 285 | 5,280 | 295 | 1,317 |
| 289 | 63.14 | 258.7 | 21.72 | 10,430 | 3,748 | 1,064 | 1,090 |
| 290 | 15.38 | 73.5 | 4.08 | 5,988 | 5,232 | 415 | 519 |
| 291 | 0.23 | 2.0 | 0.31 | 741 | >15,000 | 192 | 295 |
| 292 | 5.85 | 23.6 | <1.50 | >1,500 | >4,500 | 992 | 1,379 |
| 293 | 2.03 | 8.2 | 2.14 | 727 | 8,197 | 75 | 175 |
| 294 | 0.46 | 3.9 | 0.78 | 415 | 4,924 | 63 | 277 |
| 295 | 6.44 | 17.4 | 1.73 | 973 | 3,231 | 113 | 180 |
| 296 | 3.68 | 13.8 | 11.99 | 41,600 | 3,606 | 232 | 6,839 |
| 297 | 27.88 | 120.3 | 9.69 | 8,172 | 8,460 | 5,842 | 15,790 |
| 298 | 36.46 | 143.7 | 10.45 | 5,066 | 1,693 | 7,009 | 11,750 |
| 299 | 12.19 | 35.8 | 6.56 | 2,364 | 27,810 | 7,001 | 9,267 |
| 300 | 199.00 | 801.6 | 38.74 | 23,180 | 11,090 | 9,206 | 10,250 |
| 301 | 24.63 | 77.6 | 15.79 | 3,479 | 29,520 | 24,250 | |
| 302 | 49.36 | 121.3 | 37.56 | 821 | >45,000 | 4,462 | 7,431 |
| 303 | 17.23 | 40.5 | 10.49 | 982 | 29,230 | 2,429 | 4,255 |
| 304 | 3.59 | 8.0 | 3.23 | 447 | 20,820 | 17,290 | |
| 305 | 47.28 | 160.0 | 21.71 | 636 | >45,000 | 2,204 | 3,089 |
| 306 | 12.86 | 58.2 | 9.93 | 1,169 | >45,000 | 690 | 691 |
| 307 | 62.93 | 617.4 | 16.95 | 12,140 | 13,490 | 3,700 | 2,571 |
| 308 | 27.31 | 97.7 | 27.35 | 1,277 | >45,000 | 2,690 | 3,699 |
| 309 | 6.91 | 19.3 | 7.19 | 529 | 23,980 | 1,353 | 1,917 |
| 310 | 33.02 | 167.2 | 10.41 | 6,048 | 6,496 | 1,493 | 1,922 |
| 311 | 0.99 | 5.4 | 1.28 | 385 | 2,657 | 131 | 841 |
| 312 | 1.62 | 7.1 | <1.50 | 299 | 2,024 | 155 | 633 |
| 313 | <1.50 | 2.3 | <1.50 | 246 | 3,018 | 57 | 272 |
| 314 | 1.03 | 5.1 | 0.86 | 405 | 2,573 | 131 | 811 |
| 315 | <1.50 | 3.7 | <1.50 | 459 | 1,947 | 86 | 688 |
| 316 | <1.50 | 5.4 | <1.50 | 387 | 1,684 | 151 | 660 |
| 317 | 0.87 | 5.0 | 0.84 | 186 | 4,890 | 591 | 1,718 |
| 318 | 6.22 | 27.3 | 2.02 | 551 | 1,195 | 861 | 4,595 |
| 319 | 20.88 | 41.4 | 2.59 | 1,169 | 2,271 | 1,560 | 9,848 |
| 320 | 6.07 | 31.4 | 1.68 | 709 | 14,650 | 339 | 1,366 |
| 321 | 0.19 | 1.4 | 0.19 | 158 | 3,379 | 27 | 83 |
| 322 | 0.72 | 3.6 | 0.80 | 219 | 2,491 | 74 | 287 |
| 323 | 4.74 | 12.4 | <1.50 | 376 | 2,295 | 284 | 1,292 |
| 324 | 4.91 | 13.5 | <1.50 | 1,444 | >4,500 | 1,172 | 1,210 |
| 325 | 0.24 | 1.7 | 0.31 | 423 | >4,500 | 154 | 216 |
| 326 | 3.27 | 9.0 | 1.58 | >1,500 | >4,500 | 2,395 | 3,816 |
| 327 | 0.76 | 5.3 | 0.93 | 187 | 3,872 | 73 | 232 |
| 328 | 1.24 | 6.5 | 1.23 | 395 | 3,309 | 73 | 322 |
| 329 | 4.76 | 18.8 | 1.87 | >150 | 7,035 | 262 | 1,142 |
| 330 | 8.28 | 31.4 | 2.87 | 632 | 13,690 | 309 | 1,149 |
| 331 | 2.24 | 10.3 | 1.69 | 490 | 2,033 | 154 | 896 |
| 332 | 2.73 | 13.1 | 3.10 | 745 | 14,090 | 78 | 343 |
| 333 | 3.46 | 9.9 | <1.50 | 1,107 | 6,093 | 113 | 719 |
| 334 | <1.50 | <1.5 | <1.50 | 552 | >4,500 | 145 | 236 |
| 335 | 0.29 | 2.3 | 0.36 | 329 | 3,279 | 31 | 63 |
| 336 | 0.09 | 0.7 | 0.09 | 189 | 3,129 | 16 | 30 |
| 337 | 0.11 | <1.5 | 0.18 | 160 | 5,664 | 32 | 57 |
| 338 | 0.27 | 2.0 | 0.28 | 405 | 2,934 | 44 | 111 |
| 339 | 1.95 | 9.3 | <1.50 | 518 | 2,328 | 162 | 720 |
| 340 | <1.50 | 2.2 | <1.50 | 184 | 3,721 | 19 | 83 |
| 341 | 0.42 | 2.5 | 0.43 | 8,970 | 11,920 | 44 | 70 |
| 342 | 0.48 | 5.0 | 0.67 | >45,000 | >45,000 | 211 | 159 |
| 344 | <1.50 | 1.6 | <1.50 | 862 | 3,416 | 37 | 54 |
| 345 | 4.14 | 22.5 | 5.24 | 260 | 2,865 | 305 | 835 |
| 346 | <1.50 | <1.5 | <1.50 | 545 | 3,161 | 46 | 57 |
| 347 | 0.40 | 2.2 | 0.41 | 4,218 | 8,301 | 42 | 59 |
| 348 | 0.24 | <1.5 | 0.33 | 1,528 | 7,183 | 27 | 29 |
| 349 | 0.28 | 3.1 | 0.46 | 7,689 | 10,060 | 51 | 46 |
| 350 | 0.31 | 2.5 | 0.45 | 4,440 | 5,548 | 19 | 29 |
| 351 | 1.57 | 7.1 | 1.32 | 1,473 | 5,829 | | |
| 352 | 0.53 | 3.1 | 0.63 | 693 | 4,359 | 115 | 97 |

-continued

| ID | HDAC1 $IC_{50}$ (nM) | HDAC2 $IC_{50}$ (nM) | HDAC3 $IC_{50}$ (nM) | HDAC6 $IC_{50}$ (nM) | HDAC8 $IC_{50}$ (nM) | Karn $EC_{50}$ (nM) 0.1% NHS | Karn $EC_{50}$ (nM) 5% NHS |
|---|---|---|---|---|---|---|---|
| 353 | 0.38 | 3.3 | 0.54 | 5,559 | 8,867 | 142 | 166 |
| 354 | 1.82 | 11.3 | 2.18 | 354 | 798 | 264 | 295 |
| 355 | 3.30 | 9.5 | <1.50 | 382 | 3,159 | 356 | 1,353 |
| 356 | <1.50 | 2.5 | <1.50 | 664 | >4,500 | | |
| 357 | 0.55 | 4.1 | 0.75 | 7,838 | 9,219 | 50 | 58 |
| 358 | 0.20 | 1.6 | 0.29 | 2,019 | 5,568 | 101 | 134 |
| 359 | <1.50 | <1.5 | <1.50 | 2,277 | 6,274 | 54 | 44 |
| 360 | <1.50 | 5.0 | <1.50 | 4,403 | 9,315 | 231 | 162 |
| 361 | 0.19 | 1.1 | 0.15 | 221 | 38,700 | 26 | 24 |
| 362 | 1.89 | 6.9 | <1.50 | 765 | 3,478 | 298 | 1,276 |
| 363 | 85.48 | 234.4 | 33.45 | 2,037 | 25,520 | 2,080 | 4,810 |
| 364 | 62.97 | 247.7 | 21.79 | 1,990 | 32,150 | 1,768 | 4,311 |
| 365 | 61.25 | 208.1 | 23.20 | 1,943 | 28,370 | 1,554 | 3,826 |
| 366 | 89.42 | 321.5 | 37.26 | 2,760 | >45,000 | 1,496 | 5,361 |
| 367 | 25.86 | 67.6 | 10.69 | 2,111 | 21,420 | 1,326 | 4,492 |
| 368 | 50.54 | 149.3 | 20.61 | 2,377 | 21,700 | 1,572 | 5,241 |
| 369 | 18.55 | 68.2 | 11.81 | 2,498 | 19,860 | 804 | 1,684 |
| 370 | 10.76 | 41.8 | 8.87 | 1,744 | 8,646 | 752 | 1,434 |
| 371 | 86.67 | 286.6 | 30.23 | 4,655 | >45,000 | 5,000 | 6,040 |
| 372 | 92.55 | 416.1 | 14.10 | 10,210 | 7,734 | 2,652 | 5,246 |
| 373 | 95.64 | 422.6 | 18.77 | 10,100 | 6,672 | 1,647 | 5,340 |
| 374 | 92.74 | 422.9 | 15.77 | 11,220 | 8,176 | 2,581 | 5,397 |
| 375 | 116.60 | 478.7 | 19.88 | 10,200 | 8,880 | 1,448 | 9,329 |
| 376 | 49.95 | 239.1 | 9.02 | 10,850 | 4,842 | 1,862 | 3,676 |
| 377 | 47.10 | 232.5 | 6.90 | 8,289 | 3,015 | | |
| 378 | 46.05 | 219.8 | 7.08 | 10,760 | 2,956 | 1,309 | 2,992 |
| 379 | 21.87 | 100.1 | 4.77 | 8,588 | 3,288 | 472 | 771 |
| 380 | 69.82 | 326.3 | 8.92 | 16,200 | 6,332 | 1,917 | 2,407 |
| 381 | 178.70 | 637.3 | 26.06 | 32,310 | 7,472 | 2,735 | 6,414 |
| 382 | 32.91 | 145.5 | 8.02 | 12,110 | 6,637 | 665 | 1,074 |
| 383 | 96.53 | 427.1 | 16.68 | 16,050 | 8,956 | 2,624 | 3,260 |
| 384 | 37.31 | 153.8 | 12.58 | 10,290 | 8,933 | 2,215 | 2,408 |
| 386 | 7.82 | 54.7 | 12.42 | >900 | >900 | 934 | 1,063 |
| 387 | 25.80 | 207.1 | 48.14 | >900 | >900 | 1,545 | 1,699 |
| 389 | 21.40 | 98.3 | 30.15 | >900 | >900 | 1,120 | 1,553 |
| 390 | 18.02 | 158.7 | 39.42 | 309 | >900 | 674 | 1,676 |
| 391 | 9.57 | 74.5 | 18.60 | >900 | >900 | 460 | 541 |
| 393 | 0.05 | 0.1 | 0.05 | 325 | >900 | 21 | 22 |
| 394 | 0.05 | 0.3 | 0.10 | 76 | >900 | 18 | 24 |
| 395 | 2.42 | 36.3 | 6.78 | >900 | >900 | 618 | 725 |
| 397 | 1.36 | 6.6 | 2.66 | >900 | >900 | 279 | 327 |
| 398 | 185.70 | 809.6 | 240.70 | >900 | >900 | 5,504 | 10,190 |
| 400 | 6.41 | 39.7 | 8.61 | >900 | >900 | 577 | 557 |
| 401 | 32.08 | 179.0 | 51.33 | >900 | >900 | 1,845 | 2,210 |
| 403 | 248.30 | >900.0 | 283.20 | >900 | >900 | 5,344 | 5,598 |
| 404 | 367.40 | >900.0 | 501.40 | >900 | >900 | >40,000 | >40,000 |
| 405 | 0.30 | 2.0 | 0.70 | 163 | >900 | 65 | 57 |
| 406 | 0.83 | 2.5 | 1.05 | >900 | 300 | 280 | 279 |
| 407 | 0.90 | 20.2 | 3.68 | >900 | >900 | 336 | 977 |
| 408 | 3.82 | 36.1 | 7.37 | 647 | >900 | 250 | 593 |
| 409 | 10.46 | 100.2 | 32.18 | >900 | >900 | 811 | 1,862 |
| 410 | 17.55 | 143.4 | 43.93 | >900 | >900 | 663 | 1,391 |
| A30 (411) | 60.59 | 304.3 | 95.60 | >900 | 542 | 1,487 | 5,610 |
| 413 | 16.21 | 155.5 | 61.85 | >900 | >900 | 348 | 1,266 |
| 414 | >900.00 | >900.0 | >900.00 | >900 | >900 | >40,000 | >40,000 |
| 415 | 3.31 | 33.1 | 7.82 | >900 | >900 | 105 | 118 |
| 416 | <1.58 | 4.5 | 1.11 | >900 | >900 | 11 | 15 |
| 420 | 484.30 | 329.9 | 327.70 | >900 | >900 | 11,850 | >40,000 |
| 422 | 0.17 | 0.7 | 0.08 | 113 | >900 | 15 | 10 |

Treatment or Prevention of HIV Infection

The Compounds of Formula I may be useful in the activation of HIV latency, the the treatment of HIV infection and/or reduction of the likelihood or severity of symptoms of HIV infection and the inhibition of HIV viral replication and/or HIV viral production in a cell-based system. For example, the Compounds of Formula I may be useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Compound of Formula I or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Compounds of Formula I are also useful in the preparation and execution of screening assays for antiviral compounds. For example the Compounds of Formula I may be useful for identifying resistant HIV cell lines harboring mutations, which are excellent screening tools for more powerful antiviral compounds. Furthermore, the Compounds of Formula I may be useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Compounds of Formula I.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: I at least one Compound of Formula I (which may include two or more different Compounds of Formula I), or a pharmaceutically acceptable salt or prodrug thereof, and (ii) at least one additional therapeutic agent that is other than a Compound of Formula I, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tricyclic Heterocycle Compound and an additional therapeutic agent may be present in fixed amounts (dosage amounts) in a single dosage unit (e.g., a capsule, a tablet and the like).

In one embodiment, at least one Compound of Formula I is administered during a time when the additional therapeutic agent(s) exert their prophylactic or therapeutic effect, or vice versa.

In another embodiment, at least one Compound of Formula I and the additional therapeutic agent(s) are administered in doses commonly employed when such agents are used as monotherapy for treating a viral infection.

In another embodiment, at least one Compound of Formula I and the additional therapeutic agent(s) are administered in doses lower than the doses commonly employed when such agents are used as monotherapy for treating a viral infection.

In still another embodiment, at least one Compound of Formula I and the additional therapeutic agent(s) act synergistically and are administered in doses lower than the doses commonly employed when such agents are used as monotherapy for treating a viral infection.

In one embodiment, at least one Compound of Formula I and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is AIDS.

The at least one Compound of Formula I and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Compound of Formula I and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Trade Name |
|---|---|
| abacavir, ABC | Ziagen ® |
| abacavir + lamivudine | Epzicom ® |
| abacavir + lamivudine + zidovudine | Trizivir ® |
| amprenavir | Agenerase ® |
| atazanavir | Reyataz ® |
| AZT, zidovudine, azidothymidine | Retrovir ® |
| darunavir | Prezista ® |
| ddC, zalcitabine, dideoxycytidine | Hivid ® |
| ddI, didanosine, dideoxyinosine | Videx ® |
| ddI (enteric coated) | Videx EC ® |
| delavirdine, DLV | Rescriptor ® |
| dolutegravir | Tivicay ® |
| doravirine | |
| efavirenz, EFV | Sustiva ®, Stocrin ® |
| efavirenz + emtricitabine + tenofovir DF | Atripla ® |
| EFdA (4'-ethynyl-2-fluoro-2'-deoxyadenosine) | |
| emtricitabine, FTC | Emtriva ® |
| emtricitabine + tenofovir DF | Truvada ® |
| emvirine | Coactinon ® |

TABLE A-continued

| Name | Trade Name |
|---|---|
| enfuvirtide | Fuzeon ® |
| enteric coated didanosine | Videx EC ® |
| etravirine, TMC-125 | Intelence ® |
| fosamprenavir calcium | Lexiva ® |
| indinavir | Crixivan ® |
| lamivudine, 3TC | Epivir ® |
| lamivudine + zidovudine | Combivir ® |
| lopinavir | |
| lopinavir + ritonavir | Kaletra ® |
| maraviroc | Selzentry ® |
| nelfinavir | Viracept ® |
| nevirapine, NVP | Viramune ® |
| raltegravir | Isentress ® |
| rilpivirine, TMC-278 | Edurant ® |
| ritonavir | Norvir ® |
| saquinavir | Invirase ®, Fortovase ® |
| stavudine, d4T, didehydrodeoxythymidine | Zerit ® |
| tenofovir DF (DF = disoproxil fumarate), TDF | Viread ® |
| tipranavir | Aptivus ® |

Some of the drugs listed in the table are used in a salt form; e.g., abacavir sulfate, indinavir sulfate, atazanavir sulfate, nelfinavir mesylate.

In one embodiment, one or more anti-HIV drugs are selected from, raltegravir, lamivudine, abacavir, ritonavir, darunavir, atazanavir, emtricitabine, tenofovir, rilpivirine, doravirine, EFdA and lopinavir.

In another embodiment, the compound of formula I is used in combination with raltegravir.

In another embodiment, the compound of formula I is used in combination with lamivudine.

In still another embodiment, the compound of formula I is used in combination atazanavir.

In another embodiment, the compound of formula I is used in combination with darunavir.

In another embodiment, the compound of formula I is used in combination with rilpivirine.

In one embodiment, the compound of formula I is used in combination with lamivudine and abacavir.

In another embodiment, the compound of formula I is used in combination with EFdA.

In another embodiment, the compound of formula I is used in combination with emtricitabine and tenofovir.

In still another embodiment, the compound of formula I is used in combination doravirine.

In another embodiment, the compound of formula I is used in combination with ritonavir and lopinavir.

In one embodiment, the compound of formula I is used in combination with abacavir and lamivudine.

In another embodiment, the compound of formula I is used in combination with lopinavir and ritonavir.

In one embodiment, the present invention provides pharmaceutical compositions comprising (i) a compound of formula I or a pharmaceutically acceptable salt or prodrug thereof; (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula I or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, $57^{th}$ edition (2003), the $58^{th}$ edition (2004), the $59^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Tricyclic Heterocycle Compound(s) and the other agent(s) may be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Compounds of Formula I may be administered as a component of a composition that comprises a pharmaceutically acceptable carrier or vehicle. The present invention provides pharmaceutical compositions comprising an effective amount of at least one Compound of Formula I and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Compounds of Formula I are administered orally.

In another embodiment, the one or more Compounds of Formula I are administered intravenously.

In one embodiment, a pharmaceutical preparation comprising at least one Compound of Formula I is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Compound(s) of Formula I by weight or volume. In various embodiments, the present compositions can contain, in one embodiment, from about 1% to about 70% or from about 5% to about 60% of the Compound(s) of Formula I by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Compounds of Formula I may be administered at varying frequencies. In one embodiment, a unit dosage of a Compound of Formula I may be administered once daily. In another embodiment, a unit dosage of a Compound of Formula I may be administered twice weekly. In another embodiment, a unit dosage of a Compound of Formula I may be administered once weekly. In still another embodiment, a unit dosage of a Compound of Formula I may be administered once biweekly. In another embodiment, a unit dosage of a Compound of Formula I may be administered once monthly. In yet another embodiment, a unit dosage of a Compound of Formula I may be administered once bimonthly.

In another embodiment, a unit dosage of a Compound of Formula I may be administered once every 3 months. In a further embodiment, a unit dosage of a Compound of Formula I may be administered once every 6 months. In another embodiment, a unit dosage of a Compound of Formula I may be administered once yearly.

The amount and frequency of administration of the Compounds of Formula I will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Compound of Formula I, or a pharmaceutically acceptable salt or prodrug of said compound and a pharmaceutically acceptable carrier, vehicle or diluent.

In another aspect the present invention provides a kit comprising an amount of at least one Compound of Formula I, or a pharmaceutically acceptable salt or prodrug of said compound and an amount of at least one additional therapeutic agent listed above, wherein the amounts of the two or more active ingredients result in a desired therapeutic effect. In one embodiment, the one or more Compounds of Formula I and the one or more additional therapeutic agents are provided in the same container. In one embodiment, the one or more Compounds of Formula I and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound being one of:

| | |
|---|---|
| (S)-N-((S)-1-(5-(2-methoxyquinolin-3-yl)-1H-imidazol-2-yl)-7-oxononyl)-6-oxaspiro[2.5]octane-1-carboxamide | 63 |
| (R)-N-((S)-1-(5-(2-methoxyquinolin-3-yl)-1H-imidazol-2-yl)-7-oxononyl)-6-oxaspiro[2.5]octane-1-carboxamide | 64 |
| (1S)-N-[(1S)-1-{5-[2-(dimethylamino)quinolin-6-yl]-1H-imidazol-2-yl}-7-oxononyl]-6-methyl-6-azaspiro[2.5]octane-1-carboxamide | 66 |
| (S)-N-((S)-1-(5-(1,5-naphthyridin-3-yl)-1H-imidazol-2-yl)-7-oxononyl)-6-methyl-6-azaspiro[2.5]octane-1-carboxamide | 67 |
| (S)-6-methyl-N-((S)-9,9,9-trifluoro-1-(5-(4-fluorophenyl)-1H-imidazol-2-yl)-7-oxononyl)-6-azaspiro[2.5]octane-1-carboxamide | 68 |
| (S)-N-((S)-1-(5-(2-ethylquinolin-6-yl)-1H-imidazol-2-yl)-7-oxononyl)-6-methyl-6-azaspiro[2.5]octane-1-carboxamide | 70 |
| (1S)-N-{(1S)-1-[5-(7-fluoro-2-methylquinolin-6-yl)-1H-imidazol-2-yl]-7-oxononyl}-6-methyl-6-azaspiro[2.5]octane-1-carboxamide | 71 |
| (S)-6-methyl-N-((S)-1-(5-(1-methyl-2-oxo-1,2-dihydroquinolin-6-yl)-1H-imidazol-2-yl)-7-oxononyl)-6-azaspiro[2.5]octane-1-carboxamide | 72 |
| (S)-6-methyl-N-((S)-7-oxo-1-(5-((1R,4S)-1,2,3,4-tetrahydro-1,4-methanonaphthalen-6-yl)-1H-imidazol-2-yl)nonyl)-6-azaspiro[2.5]octane-1-carboxamide | 74 |
| (S)-N-((S)-1-(4-fluoro-5-(2-methoxyquinolin-3-yl)-1H-imidazol-2-yl)-7-oxononyl)-6-methyl-6-azaspiro[2.5]octane-1-carboxamide | 75 |
| (S)-N-((S)-1-(4-cyano-2-(4-fluorophenyl)-1H-imidazol-5-yl)-7-oxononyl)-6-methyl-6-azaspiro[2.5]octane-1-carboxamide | 76 |
| (S)-N-((S)-1-(5-(2-methoxyquinolin-3-yl)oxazol-2-yl)-7-oxononyl)-6-methyl-6-azaspiro[2.5]octane-1-carboxamide | 77 |
| (S)-N-((S)-1-(5-(2-methoxyquinolin-3-yl)oxazol-2-yl)-7-oxononyl)-6-methyl-6-azaspiro[2.5]octane-1-carboxamide | 77 |
| (1S)-6-methyl-N-[(1S)-7-oxo-1-{5-[2-(trifluoromethyl)quinolin-6-yl]-1,3-oxazol-2-yl}nonyl]-6-azaspiro[2.5]octane-1-carboxamide | 78 |
| (S)-6-methyl-N-((S)-7-oxo-1-(5-(4-(pyridin-3-yl)phenyl)oxazol-2-yl)nonyl)-6-azaspiro[2.5]octane-1-carboxamide | 79 |
| (S)-6-methyl-N-((S)-1-(5-(2-methylquinolin-6-yl)oxazol-2-yl)-7-oxononyl)-6-azaspiro[2.5]octane-1-carboxamide | 80 |
| (1S)-N-{(1S)-1-[4-chloro-5-(2-hydroxyquinolin-3-yl)-1H-imidazol-2-yl]-7-oxononyl}-6-methyl-6-azaspiro[2.5]octane-1-carboxamide | 81 |
| (S)-6-methyl-N-((S)-7-oxo-1-(5-(quinoxalin-6-yl)-1H-imidazol-2-yl)nonyl)-6-azaspiro[2.5]octane-1-carboxamide | 82 |
| (S)-6-isopropyl-N-((S)-1-(5-(2-methylquinolin-6-yl)-1H-imidazol-2-yl)-7-oxononyl)-6-azaspiro[2.5]octane-1-carboxamide | 83 |
| (S)-N-((S)-8-cyclopropyl-1-(5-(4-fluorophenyl)-1H-imidazol-2-yl)-7-oxooctyl)-6-methyl-6-azaspiro[2.5]octane-1-carboxamide | 84 |
| (S)-6-methyl-N-((S)-7-oxo-1-(5-(4-oxo-4H-chromen-3-yl)-1H-imidazol-2-yl)nonyl)-6-azaspiro[2.5]octane-1-carboxamide | 86 |
| (S)-N-((S)-1-(5-(benzo[d]oxazol-6-yl)-1H-imidazol-2-yl)-7-oxononyl)-6-methyl-6-azaspiro[2.5]octane-1-carboxamide | 89 |
| (S)-N-((S)-1-(5-(6-cyanonaphthalen-2-yl)-1H-imidazol-2-yl)-7-oxononyl)-6-methyl-6-azaspiro[2.5]octane-1-carboxamide | 90 |
| (S)-N-((S)-1-(4-chloro-2-(4-fluorophenyl)-1H-imidazol-5-yl)-7-oxononyl)-6-methyl-6-azaspiro[2.5]octane-1-carboxamide | 91 |
| (S)-6-ethyl-N-((S)-1-(5-(2-ethyl-1-oxo-1,2-dihydroisoquinolin-6-yl)-1H-imidazol-2-yl)-7-oxononyl)-6-azaspiro[2.5]octane-1-carboxamide | 92 |
| (S)-6-ethyl-N-((S)-7-oxo-1-(5-(4-(thiazol-2-yl)phenyl)oxazol-2-yl)nonyl)-6-azaspiro[2.5]octane-1-carboxamide | 93 |
| (S)-6-ethyl-N-((S)-1-(5-(4-(oxazol-2-yl)phenyl)oxazol-2-yl)-7-oxononyl)-6-azaspiro[2.5]octane-1-carboxamide | 94 |
| (S)-N-((S)-1-(5-(4-(1H-pyrazol-1-yl)phenyl)oxazol-2-yl)-7-oxononyl)-6-ethyl-6-azaspiro[2.5]octane-1-carboxamide | 95 |
| (S)-6-isopropyl-N-((S)-1-(5-(1-methyl-2-oxo-1,2-dihydroquinolin-6-yl)oxazol-2-yl)-7-oxononyl)-6-azaspiro[2.5]octane-1-carboxamide | 96 |

-continued

| | |
|---|---|
| (S)-6-ethyl-N-((S)-1-(5-(1-methyl-2-oxo-1,2-dihydroquinolin-6-yl)oxazol-2-yl)-7-oxononyl)-6-azaspiro[2.5]octane-1-carboxamide | 97 |
| (S)-N-((S)-1-(5-(1,8-naphthyridin-3-yl)-1H-imidazol-2-yl)-7-oxononyl)-6-methyl-6-azaspiro[2.5]octane-1-carboxamide | 98 |
| (S)-6-isopropyl-N-((S)-1-(5-(2-methoxyquinolin-3-yl)oxazol-2-yl)-7-oxononyl)-6-azaspiro[2.5]octane-1-carboxamide | 99 |
| (S)-N-((S)-1-(5-(2-cyclopropylquinolin-6-yl)-1H-imidazol-2-yl)-7-oxononyl)-6-isopropyl-6-azaspiro[2.5]octane-1-carboxamide | 100 |
| (S)-6-ethyl-N-((S)-1-(5-(1-methyl-2-oxo-1,2-dihydroquinolin-6-yl)oxazol-2-yl)-7-oxononyl)-6-azaspiro[2.5]octane-1-carboxamide | 101 |
| (S)-N-((S)-1-(5-(2-methoxypyridin-3-yl)-1H-imidazol-2-yl)-7-oxononyl)-6-methyl-6-azaspiro[2.5]octane-1-carboxamide | 102 |
| (S)-N-((S)-1-(5-(cinnolin-6-yl)-1H-imidazol-2-yl)-7-oxononyl)-6-methyl-6-azaspiro[2.5]octane-1-carboxamide | 103 |
| (S)-6-(cyclopropylmethyl)-N-((S)-1-(5-(2-cyclopropylquinolin-6-yl)-1H-imidazol-2-yl)-7-oxononyl)-6-azaspiro[2.5]octane-1-carboxamide | 104 |
| (S)-N-(1-(5-(2-methoxyquinolin-3-yl)-1H-imidazol-2-yl)-7-oxononyl)-8-methyl-1-oxa-2,8-diazaspiro[4.5]dec-2-ene-3-carboxamide | 105 |
| N-{(1S)-1-[5-(2-methoxyquinolin-3-yl)-1H-imidazol-2-yl]-7-oxononyl}-8-(1-methylethyl)-1-oxa-2,8-diazaspiro[4.5]dec-2-ene-3-carboxamide | 106 |
| (S)-N-((S)-1-(5-(7-methoxyquinolin-6-yl)-1H-imidazol-2-yl)-7-oxononyl)-6-methyl-6-azaspiro[2.5]octane-1-carboxamide | 107 |
| (1S)-N-{(1S)-1-[5-(2-cyclopropyl-7-methoxyquinolin-6-yl)-1H-imidazol-2-yl]-7-oxononyl}-6-methyl-6-azaspiro[2.5]octane-1-carboxamide | 108 |
| (S)-6-methyl-N-((S)-1-(5-(1-methyl-2-oxo-1,2-dihydroquinolin-6-yl)oxazol-2-yl)-7-oxononyl)-6-azaspiro[2.5]octane-1-carboxamide | 109 |
| (1S)-N-{(1S)-1-[5-(4-chlorophenyl)-1,3-oxazol-2-yl]-7-oxononyl}-6-ethyl-6-azaspiro[2.5]octane-1-carboxamide | 110 |
| (S)-N-((S)-1-(5-(2-cyclopropyl-7-fluoroquinolin-6-yl)oxazol-2-yl)-7-oxononyl)-6-methyl-6-azaspiro[2.5]octane-1-carboxamide | 111 |
| (S)-N-((S)-1-(5-(2-cyclopropylquinolin-6-yl)-1H-imidazol-2-yl)-7-oxononyl)-6-methyl-6-azaspiro[2.5]octane-1-carboxamide | 112 |
| (S)-N-((S)-1-(5-(3-methoxyisoquinolin-6-yl)-1H-imidazol-2-yl)-7-oxononyl)-6-methyl-6-azaspiro[2.5]octane-1-carboxamide | 113 |
| (S)-N-((S)-1-(5-(2-cyclopropylquinolin-6-yl)oxazol-2-yl)-7-oxononyl)-6-ethyl-6-azaspiro[2.5]octane-1-carboxamide | 114 |
| (S)-6-(cyclopropylmethyl)-N-((S)-1-(5-(2-cyclopropylquinolin-6-yl)oxazol-2-yl)-7-oxononyl)-6-azaspiro[2.5]octane-1-carboxamide | 115 |
| (S)-N-((S)-1-(5-(2-cyclopropylquinolin-6-yl)oxazol-2-yl)-7-oxononyl)-6-isopropyl-6-azaspiro[2.5]octane-1-carboxamide | 116 |
| (S)-6-methyl-N-((S)-1-(5-(2-(oxazol-2-yl)quinolin-6-yl)-1H-imidazol-2-yl)-7-oxononyl)-6-azaspiro[2.5]octane-1-carboxamide | 119 |
| (1S)-N-[(1S)-1-{5-[4-(2-azetidin-1-ylpyrimidin-5-yl)phenyl]-1,3-oxazol-2-yl}-7-oxononyl]-6-ethyl-6-azaspiro[2.5]octane-1-carboxamide | 120 |
| (S)-N-((S)-1-(5-(2-cyclopropylquinolin-6-yl)oxazol-2-yl)-7-oxononyl)-6-methyl-6-azaspiro[2.5]octane-1-carboxamide | 121 |
| (1R,4s)-N-((S)-1-(5-(2-cyclopropylquinolin-6-yl)oxazol-2-yl)-7-oxononyl)-7'-oxo-7'H-spiro[cyclohexane-1,5'-furo[3,4-b]pyridine]-4-carboxamide | 122 |
| (1R,4s)-N-((S)-1-(5-(2-cyclopropylquinolin-6-yl)oxazol-2-yl)-7-oxononyl)-7'-oxo-7'H-spiro[cyclohexane-1,5'-furo[3,4-b]pyridine]-4-carboxamide | 123 |
| (S)-6-ethyl-N-((S)-1-(5-(2-methoxyquinolin-3-yl)oxazol-2-yl)-7-oxononyl)-6-azaspiro[2.5]octane-1-carboxamide | 124 |
| (S)-N-((S)-1-(5-(2-methoxyquinolin-3-yl)oxazol-2-yl)-7-oxononyl)-6-methyl-6-azaspiro[2.5]octane-1-carboxamide | 125 |
| (S)-6-ethyl-N-((S)-1-(5-(2-isopropyl-1-oxo-1,2-dihydroisoquinolin-6-yl)-1H-imidazol-2-yl)-7-oxononyl)-6-azaspiro[2.5]octane-1-carboxamide | 126 |
| 6-(dimethylamino)-N-{(1S)-1-[5-(2-methoxyquinolin-3-yl)-1H-imidazol-2-yl]-7-oxononyl}spiro[2.5]octane-1-carboxamide | 127 |
| (1S)-N-[(1S)-1-{5-[4-(5-cyclopropylpyrazin-2-yl)phenyl]-1,3-oxazol-2-yl}-7-oxononyl]-6-ethyl-6-azaspiro[2.5]octane-1-carboxamide | 129 |
| 5,5,6-trimethyl-N-{(1S)-1-[5-(2-methylquinolin-6-yl)-1H-imidazol-2-yl]-7-oxononyl}-6-azaspiro[2.5]octane-1-carboxamide | 130 |
| (1S)-N-{(1S)-1-[4-(4-fluorophenyl)-1H-imidazol-2-yl]-8-hydroxy-7-oxononyl}-6-methyl-6-azaspiro[2.5]octane-1-carboxamide | 134 |
| (S)-N-(1-(5-(2-cyclopropylquinolin-6-yl)oxazol-2-yl)-7-oxononyl)-8-methyl-1-oxa-2,8-diazaspiro[4.5]dec-2-ene-3-carboxamide | 135 |
| (S)-N-(1-(5-(2-cyclopropylquinolin-6-yl)oxazol-2-yl)-7-oxononyl)-8-isopropyl-1-oxa-2,8-diazaspiro[4.5]dec-2-ene-3-carboxamide | 136 |

-continued

| | |
|---|---|
| (S)-6-methyl-N-((S)-1-(5-(2-methyl-1-oxo-1,2-dihydroisoquinolin-6-yl)oxazol-2-yl)-7-oxononyl)-6-azaspiro[2.5]octane-1-carboxamide | 137 |
| (S)-6-methyl-N-((S)-7-oxo-1-(5-(2-oxo-2H-chromen-6-yl)-1H-imidazol-2-yl)nonyl)-6-azaspiro[2.5]octane-1-carboxamide | 138 |
| (S)-N-((S)-1-(5-(6-cyclopropylpyridin-3-yl)-1H-imidazol-2-yl)-7-oxononyl)-6-methyl-6-azaspiro[2.5]octane-1-carboxamide | 139 |
| (S)-N-((S)-1-(5-(3-chloroquinolin-6-yl)-1H-imidazol-2-yl)-7-oxononyl)-6-methyl-6-azaspiro[2.5]octane-1-carboxamide | 140 |
| (1R,4s)-N-((S)-1-(5-(2-methoxyquinolin-3-yl)-1H-imidazol-2-yl)-7-oxononyl)-7'-oxo-7'H-spiro[cyclohexane-1,5'-furo[3,4-b]pyridine]-4-carboxamide | 141 |
| (S)-N-((S)-1-(5-(2-methoxy-1,5-naphthyridin-3-yl)-1H-imidazol-2-yl)-7-oxononyl)-6-methyl-6-azaspiro[2.5]octane-1-carboxamide | 142 |
| (S)-N-((S)-1-(5-(4-(6-cyclopropylpyridin-3-yl)phenyl)oxazol-2-yl)-7-oxononyl)-6-methyl-6-azaspiro[2.5]octane-1-carboxamide | 143 |
| (S)-6-methyl-N-((S)-1-(5-(1-methyl-2-oxo-1,2-dihydroquinolin-6-yl)-1H-imidazol-2-yl)-7-oxononyl)-6-azaspiro[2.5]octane-1-carboxamide | 144 |
| (S)-7-methyl-N-(1-(5-(2-methyl-2H-indazol-5-yl)-1H-imidazol-2-yl)-7-oxononyl)-7-azaspiro[3.5]nonane-2-carboxamide | 145 |
| (S)-N-((S)-1-(5-(2-cyclopropylbenzo[d]thiazol-6-yl)-1H-imidazol-2-yl)-7-oxononyl)-6-methyl-6-azaspiro[2.5]octane-1-carboxamide | 146 |
| (S)-2-methyl-N-(1-(5-(2-methyl-2H-indazol-5-yl)-1H-imidazol-2-yl)-7-oxononyl)-2-azaspiro[3.3]heptane-6-carboxamide | 147 |
| (S)-N-((S)-1-(5-(2-methoxy-1,7-naphthyridin-3-yl)-1H-imidazol-2-yl)-7-oxononyl)-6-methyl-6-azaspiro[2.5]octane-1-carboxamide | 148 |
| (S)-N-((S)-1-(5-(2-ethylbenzo[d]thiazol-6-yl)-1H-imidazol-2-yl)-7-oxononyl)-6-methyl-6-azaspiro[2.5]octane-1-carboxamide | 149 |
| (S)-N-((S)-1-(5-(2-cyclopropyl-1-oxo-1,2-dihydroisoquinolin-6-yl)-1H-imidazol-2-yl)-7-oxononyl)-6-ethyl-6-azaspiro[2.5]octane-1-carboxamide | 150 |
| (1S)-1-methyl-6-(1-methylethyl)-N-{(1S)-1-[5-(2-methylquinolin-6-yl)-1H-imidazol-2-yl]-7-oxononyl}-6-azaspiro[2.5]octane-1-carboxamide | 151 |
| (1S)-1-methyl-6-(1-methylethyl)-N-{(1S)-1-[5-(2-methylquinolin-6-yl)-1H-imidazol-2-yl]-7-oxononyl}-6-azaspiro[2.5]octane-1-carboxamide | 152 |
| (S)-N-((S)-1-(5-(2-cyclopropyl-1-oxo-1,2-dihydroisoquinolin-6-yl)oxazol-2-yl)-7-oxononyl)-6-ethyl-6-azaspiro[2.5]octane-1-carboxamide | 153 |
| (S)-8-methyl-N-(1-(5-(2-methyl-2H-indazol-5-yl)-1H-imidazol-2-yl)-7-oxononyl)-1-oxa-2,8-diazaspiro[4.5]dec-2-ene-3-carboxamide | 154 |
| (S)-N-(1-(5-(2-methyl-2H-indazol-5-yl)-1H-imidazol-2-yl)-7-oxononyl)-2-(6-azaspiro[2.5]octan-6-yl)acetamide | 155 |
| (S)-2-methyl-N-(1-(5-(2-methyl-2H-indazol-5-yl)-1H-imidazol-2-yl)-7-oxononyl)-2-azaspiro[3.5]nonane-7-carboxamide | 156 |
| (S)-6-isobutyl-2-methyl-N-(1-(5-(2-methylquinolin-6-yl)-1H-imidazol-2-yl)-7-oxononyl)-2-azaspiro[3.3]heptane-6-carboxamide | 157 |
| (S)-N-((S)-1-(5-(2-(1H-pyrazol-1-yl)quinolin-6-yl)-1H-imidazol-2-yl)-7-oxononyl)-6-methyl-6-azaspiro[2.5]octane-1-carboxamide | 158 |
| (S)-N-((S)-1-(5-(1-cyclopropyl-1H-indazol-5-yl)-1H-imidazol-2-yl)-7-oxononyl)-6-ethyl-6-azaspiro[2.5]octane-1-carboxamide | 159 |
| (S)-N-((S)-1-(5-(2-cyclopropylbenzo[d]oxazol-6-yl)-1H-imidazol-2-yl)-7-oxononyl)-6-methyl-6-azaspiro[2.5]octane-1-carboxamide | 160 |
| (S)-N-((S)-1-(5-(4-(2-cyclopropylpyrimidin-5-yl)phenyl)oxazol-2-yl)-7-oxononyl)-6-ethyl-6-azaspiro[2.5]octane-1-carboxamide | 161 |
| (S)-6-ethyl-N-((S)-1-(5-(2-ethyl-1-oxo-1,2-dihydroisoquinolin-6-yl)oxazol-2-yl)-7-oxononyl)-6-azaspiro[2.5]octane-1-carboxamide | 162 |
| (1S)-N-{(1S)-1-[5-(7-methoxy-2-methylquinolin-6-yl)-1,3-oxazol-2-yl]-7-oxononyl}-6-methyl-6-azaspiro[2.5]octane-1-carboxamide | 163 |
| (S)-N-((S)-1-(5-(7-methoxyquinolin-6-yl)oxazol-2-yl)-7-oxononyl)-6-methyl-6-azaspiro[2.5]octane-1-carboxamide | 164 |
| (S)-N-((S)-8-cyclopropyl-1-(5-(7-methoxy-2-methylquinolin-6-yl)-1H-imidazol-2-yl)-7-oxooctyl)-6-ethyl-6-azaspiro[2.5]octane-1-carboxamide | 165 |
| 8-methyl-N-[(1S)-7-oxo-1-(5-quinolin-6-yl-1H-imidazol-2-yl)nonyl]-8-azaspiro[bicyclo[3.2.1]octane-3,1'-cyclopropane]-2'-carboxamide | 166 |
| (S)-N-((S)-8-cyclopropyl-1-(5-(7-methoxy-2-methylquinolin-6-yl)oxazol-2-yl)-7-oxooctyl)-6-ethyl-6-azaspiro[2.5]octane-1-carboxamide | 167 |
| (S)-6-ethyl-N-((S)-1-(5-(2-methoxy-1,7-naphthyridin-3-yl)oxazol-2-yl)-7-oxononyl)-6-azaspiro[2.5]octane-1-carboxamide | 168 |
| (S)-6-ethyl-N-((S)-1-(5-(7-methoxyquinolin-6-yl)oxazol-2-yl)-7-oxononyl)-6-azaspiro[2.5]octane-1-carboxamide | 169 |
| (S)-N-((S)-1-(5-(4-methoxyquinolin-2-yl)-1H-imidazol-2-yl)-7-oxononyl)-6-methyl-6-azaspiro[2.5]octane-1-carboxamide | 170 |

-continued

| | |
|---|---|
| (S)-6-ethyl-N-((S)-1-(5-(7-methoxy-1-methyl-2-oxo-1,2-dihydroquinolin-6-yl)oxazol-2-yl)-7-oxononyl)-6-azaspiro[2.5]octane-1-carboxamide | 171 |
| (S)-N-((S)-1-(5-(7-methoxy-2-methylquinolin-6-yl)-1H-imidazol-2-yl)-7-oxononyl)-6-methyl-6-azaspiro[2.5]octane-1-carboxamide | 172 |
| (S)-6-ethyl-N-((S)-1-(5-(2-ethyl-7-methoxy-1-oxo-1,2-dihydroisoquinolin-6-yl)oxazol-2-yl)-7-oxononyl)-6-azaspiro[2.5]octane-1-carboxamide | 173 |
| (S)-N-((S)-1-(5-(4-chloro-2-methylquinolin-6-yl)-1H-imidazol-2-yl)-7-oxononyl)-6-methyl-6-azaspiro[2.5]octane-1-carboxamide | 174 |
| (1S)-N-[(1S)-1-{5-[2-methoxy-7-(1,3-oxazol-2-yl)quinolin-3-yl]-1H-imidazol-2-yl}-7-oxononyl]-6-methyl-6-azaspiro[2.5]octane-1-carboxamide | 175 |
| (1S)-N-[(1S)-1-{5-[2-methoxy-7-(1H-pyrazol-1-yl)quinolin-3-yl]-1H-imidazol-2-yl}-7-oxononyl]-6-methyl-6-azaspiro[2.5]octane-1-carboxamide | 176 |
| (S)-N-((S)-1-(5-(7-chloro-2-methoxyquinolin-3-yl)-1H-imidazol-2-yl)-7-oxononyl)-6-methyl-6-azaspiro[2.5]octane-1-carboxamide | 177 |
| (1S)-N-{(1S)-7-oxo-1-[5-(9-prop-2-en-1-yl-1,2,3,4-tetrahydro-1,4-epiminonaphthalen-6-yl)-1H-imidazol-2-yl]nonyl}-6-prop-2-en-1-yl-6-azaspiro[2.5]octane-1-carboxamide | 179 |
| (1S)-N-{(1S)-7-oxo-1-[5-(9-prop-2-en-1-yl-1,2,3,4-tetrahydro-1,4-epiminonaphthalen-5-yl)-1H-imidazol-2-yl]nonyl}-6-prop-2-en-1-yl-6-azaspiro[2.5]octane-1-carboxamide | 180 |
| (S)-6-ethyl-N-((S)-1-(5-(7-methoxyquinolin-6-yl)-1H-imidazol-2-yl)-7-oxononyl)-6-azaspiro[2.5]octane-1-carboxamide | 181 |
| (S)-6-isopropyl-N-((S)-1-(5-(7-methoxy-2-methylquinolin-6-yl)-1H-imidazol-2-yl)-7-oxononyl)-6-azaspiro[2.5]octane-1-carboxamide | 182 |
| (S)-N-((S)-1-(5-(2,4-dimethoxyphenyl)-1H-imidazol-2-yl)-7-oxononyl)-6-ethyl-6-azaspiro[2.5]octane-1-carboxamide | 183 |
| (S)-N-((S)-8-cyclobutyl-1-(5-(7-methoxy-2-methylquinolin-6-yl)oxazol-2-yl)-7-oxooctyl)-6-ethyl-6-azaspiro[2.5]octane-1-carboxamide | 184 |
| (S)-N-((S)-8-cyclobutyl-1-(5-(7-methoxy-2-methylquinolin-6-yl)oxazol-2-yl)-7-oxooctyl)-6-methyl-6-azaspiro[2.5]octane-1-carboxamide | 185 |
| (1S)-6-cyclobutyl-N-{(1S)-1-[5-(7-methoxy-2-methylquinolin-6-yl)-1H-imidazol-2-yl]-7-oxononyl}-6-azaspiro[2.5]octane-1-carboxamide | 186 |
| (1S)-6-(cyclopropylmethyl)-N-{(1S)-1-[5-(7-methoxy-2-methylquinolin-6-yl)-1H-imidazol-2-yl]-7-oxononyl}-6-azaspiro[2.5]octane-1-carboxamide | 187 |
| (S)-N-(1-(5-(7-methoxy-2-methylquinolin-6-yl)-1H-imidazol-2-yl)-7-oxononyl)-8-methyl-1-oxa-2,8-diazaspiro[4.5]dec-2-ene-3-carboxamide | 188 |
| (S)-6-ethyl-N-((S)-1-(5-(5-methoxy-2-methyl-2H-indazol-6-yl)oxazol-2-yl)-7-oxononyl)-6-azaspiro[2.5]octane-1-carboxamide | 189 |
| (S)-6-ethyl-N-((S)-1-(5-(5-methoxy-2-methyl-2H-indazol-6-yl)-1H-imidazol-2-yl)-7-oxononyl)-6-azaspiro[2.5]octane-1-carboxamide | 190 |
| (S)-N-((S)-1-(5-(7-methoxy-2-methylquinolin-6-yl)-1,3,4-oxadiazol-2-yl)-7-oxononyl)-6-methyl-6-azaspiro[2.5]octane-1-carboxamide | 191 |
| (S)-8-(cyclopropylmethyl)-N-(1-(5-(7-methoxy-1-methyl-2-oxo-1,2-dihydroquinolin-6-yl)-1H-imidazol-2-yl)-7-oxononyl)-1-oxa-2,8-diazaspiro[4.5]dec-2-ene-3-carboxamide | 192 |
| (S)-N-(1-(5-(7-methoxy-1-methyl-2-oxo-1,2-dihydroquinolin-6-yl)oxazol-2-yl)-7-oxononyl)-8-methyl-1-oxa-2,8-diazaspiro[4.5]dec-2-ene-3-carboxamide | 193 |
| (1S)-N-{(1S)-8-cyclopropyl-1-[5-(7-methoxy-2-methylquinolin-6-yl)-1,3-oxazol-2-yl]-7-oxooctyl}-6-methyl-6-azaspiro[2.5]octane-1-carboxamide | 195 |
| (S)-N-(1-(5-(7-methoxy-2-methylquinolin-6-yl)oxazol-2-yl)-7-oxononyl)-8-methyl-1-oxa-2,8-diazaspiro[4.5]dec-2-ene-3-carboxamide | 196 |
| (S)-6-ethyl-N-((S)-1-(5-(4-fluoro-2-methoxyphenyl)-1H-imidazol-2-yl)-7-oxononyl)-6-azaspiro[2.5]octane-1-carboxamide | 197 |
| (S)-N-((S)-1-(5-(7-methoxy-1-methyl-2-oxo-1,2-dihydroquinolin-6-yl)oxazol-2-yl)-7-oxononyl)-6-methyl-6-azaspiro[2.5]octane-1-carboxamide | 198 |
| (S)-6-(cyclopropylmethyl)-N-((S)-1-(5-(7-methoxy-1-methyl-2-oxo-1,2-dihydroquinolin-6-yl)oxazol-2-yl)-7-oxononyl)-6-azaspiro[2.5]octane-1-carboxamide | 199 |
| (S)-N-((S)-1-(5-(7-chloro-2-methylquinolin-6-yl)-1H-imidazol-2-yl)-7-oxononyl)-6-methyl-6-azaspiro[2.5]octane-1-carboxamide | 200 |
| (S)-N-((S)-8-cyclopropyl-1-(5-(4-fluorophenyl)-1H-imidazol-2-yl)-7-oxooctyl)-6-ethyl-6-azaspiro[2.5]octane-1-carboxamide | 201 |

-continued

| | |
|---|---|
| (S)-N-((S)-8-cyclopropyl-1-(5-(2-methoxypyridin-3-yl)-1H-imidazol-2-yl)-7-oxooctyl)-6-ethyl-6-azaspiro[2.5]octane-1-carboxamide | 202 |
| (S)-8-ethyl-N-(1-(5-(7-methoxy-2-methylquinolin-6-yl)oxazol-2-yl)-7-oxononyl)-1-oxa-2,8-diazaspiro[4.5]dec-2-ene-3-carboxamide | 204 |
| (S)-6-ethyl-N-((S)-1-(5-(7-methoxyquinoxalin-6-yl)-1H-imidazol-2-yl)-7-oxononyl)-6-azaspiro[2.5]octane-1-carboxamide | 205 |
| (S)-6-ethyl-N-((S)-1-(5-(6-methoxy-2-methyl-2H-indazol-5-yl)-1H-imidazol-2-yl)-7-oxononyl)-6-azaspiro[2.5]octane-1-carboxamide | 206 |
| (S)-8-ethyl-N-(1-(5-(7-methoxy-2-methylquinolin-6-yl)-1H-imidazol-2-yl)-7-oxononyl)-1-oxa-2,8-diazaspiro[4.5]dec-2-ene-3-carboxamide | 207 |
| (S)-6-ethyl-N-((S)-1-(5-(2-methoxy-4-methylphenyl)-1H-imidazol-2-yl)-7-oxononyl)-6-azaspiro[2.5]octane-1-carboxamide | 208 |
| (1S)-N-{(1S)-1-[5-(7-ethyl-2-methylquinolin-6-yl)-1H-imidazol-2-yl]-7-oxononyl}-6-methyl-6-azaspiro[2.5]octane-1-carboxamide | 210 |
| (S)-6-ethyl-N-((S)-1-(5-(7-methoxy-2-methylquinolin-6-yl)-1H-imidazol-2-yl)-7-oxononyl)-6-azaspiro[2.5]octane-1-carboxamide | 211 |
| {2-[(1S)-1-({[(1S)-6-ethyl-6-azaspiro[2.5]oct-1-yl]carbonyl}amino)-7-oxononyl]-4-(7-methoxy-2-methylquinolin-6-yl)-1H-imidazol-1-yl}methyl 2,2-dimethylpropanoate | 215 |
| (S)-N-(1-(5-(2-methoxy-1,7-naphthyridin-3-yl)oxazol-2-yl)-7-oxononyl)-8-methyl-1-oxa-2,8-diazaspiro[4.5]dec-2-ene-3-carboxamide | 216 |
| (S)-N-((S)-1-(5-(2,7-dimethylquinolin-6-yl)-1H-imidazol-2-yl)-7-oxononyl)-6-methyl-6-azaspiro[2.5]octane-1-carboxamide | 218 |
| (S)-8-(cyclopropylmethyl)-N-(1-(5-(7-methoxy-2-methylquinolin-6-yl)-1H-imidazol-2-yl)-7-oxononyl)-1-oxa-2,8-diazaspiro[4.5]dec-2-ene-3-carboxamide | 219 |
| (S)-N-((S)-1-(5-(5-fluoro-2-methoxypyridin-4-yl)oxazol-2-yl)-7-oxononyl)-6-methyl-6-azaspiro[2.5]octane-1-carboxamide | 220 |
| (S)-N-(1-(5-(7-fluoro-2-methylquinolin-6-yl)oxazol-2-yl)-7-oxononyl)-8-methyl-1-oxa-2,8-diazaspiro[4.5]dec-2-ene-3-carboxamide | 221 |
| N-{(1S)-1-[5-(2-methoxy-4-pyridin-3-ylphenyl)-1,3-oxazol-2-yl]-7-oxononyl}-8-methyl-1-oxa-2,8-diazaspiro[4.5]dec-2-ene-3-carboxamide | 222 |
| (S)-N-(1-(5-(7-methoxyquinolin-6-yl)oxazol-2-yl)-7-oxononyl)-8-methyl-1-oxa-2,8-diazaspiro[4.5]dec-2-ene-3-carboxamide | 223 |
| (S)-8-(cyclopropylmethyl)-N-(1-(5-(7-methoxy-2-methylquinolin-6-yl)oxazol-2-yl)-7-oxononyl)-1-oxa-2,8-diazaspiro[4.5]dec-2-ene-3-carboxamide | 225 |
| (S)-N-((S)-1-(5-(7-fluoro-2-methylquinolin-6-yl)oxazol-2-yl)-7-oxononyl)-6-methyl-6-azaspiro[2.5]octane-1-carboxamide | 226 |
| (S)-6-(cyclopropylmethyl)-N-((S)-1-(5-(7-fluoro-2-methylquinolin-6-yl)-1H-imidazol-2-yl)-7-oxononyl)-6-azaspiro[2.5]octane-1-carboxamide | 228 |
| (S)-6-(cyclopropylmethyl)-N-((S)-1-(5-(7-methoxy-2-methyl-1-oxo-1,2-dihydroisoquinolin-6-yl)oxazol-2-yl)-7-oxononyl)-6-azaspiro[2.5]octane-1-carboxamide | 229 |
| (S)-N-((S)-1-(5-(7-methoxy-2-methylquinolin-6-yl)oxazol-2-yl)-7-oxononyl)-5-methyl-5-azaspiro[2.3]hexane-1-carboxamide | 230 |
| (R)-N-((S)-1-(5-(7-methoxy-2-methylquinolin-6-yl)oxazol-2-yl)-7-oxononyl)-5-methyl-5-azaspiro[2.3]hexane-1-carboxamide | 231 |
| (S)-N-(1-(5-(7-fluoro-2-methylquinolin-6-yl)-1H-imidazol-2-yl)-7-oxononyl)-8-methyl-1-oxa-2,8-diazaspiro[4.5]dec-2-ene-3-carboxamide | 232 |
| (S)-8-ethyl-N-(1-(5-(7-fluoro-2-methylquinolin-6-yl)-1H-imidazol-2-yl)-7-oxononyl)-1-oxa-2,8-diazaspiro[4.5]dec-2-ene-3-carboxamide | 233 |
| (S)-8-(cyclopropylmethyl)-N-(1-(5-(7-fluoro-2-methylquinolin-6-yl)-1H-imidazol-2-yl)-7-oxononyl)-1-oxa-2,8-diazaspiro[4.5]dec-2-ene-3-carboxamide | 234 |
| (S)-8-ethyl-N-(1-(5-(7-methoxy-1-methyl-2-oxo-1,2-dihydroquinolin-6-yl)oxazol-2-yl)-7-oxononyl)-1-oxa-2,8-diazaspiro[4.5]dec-2-ene-3-carboxamide | 235 |
| (S)-8-(cyclopropylmethyl)-N-(1-(5-(7-methoxy-1-methyl-2-oxo-1,2-dihydroquinolin-6-yl)oxazol-2-yl)-7-oxononyl)-1-oxa-2,8-diazaspiro[4.5]dec-2-ene-3-carboxamide | 236 |
| N-{(1S)-1-[5-(2-methoxy-4-pyrazin-2-ylphenyl)-1,3-oxazol-2-yl]-7-oxononyl}-8-methyl-1-oxa-2,8-diazaspiro[4.5]dec-2-ene-3-carboxamide | 237 |
| (S)-N-((S)-1-(5-(2-cyclopropyl-2H-indazol-5-yl)-1H-imidazol-2-yl)-7-oxononyl)-6-ethyl-6-azaspiro[2.5]octane-1-carboxamide | 238 |
| (S)-N-((S)-1-(5-(4-fluorophenyl)-1H-imidazol-2-yl)-7-oxodecyl)-6-methyl-6-azaspiro[2.5]octane-1-carboxamide | 239 |

-continued

| | |
|---|---|
| (S)-N-((S)-1-(4-chloro-2-(4-fluorophenyl)-1H-imidazol-5-yl)-7-oxononyl)-6-methyl-6-azaspiro[2.5]octane-1-carboxamide | 240 |
| (S)-6-methyl-N-((S)-7-oxo-1-(5-(2-(pyrrolidin-1-yl)quinolin-6-yl)-1H-imidazol-2-yl)nonyl)-6-azaspiro[2.5]octane-1-carboxamide | 241 |
| (S)-6-ethyl-N-((S)-1-(5-(isoquinolin-6-yl)-1H-imidazol-2-yl)-7-oxononyl)-6-azaspiro[2.5]octane-1-carboxamide | 243 |
| (S)-6-ethyl-N-((S)-1-(5-(7-methoxy-2-methylquinolin-6-yl)-1H-imidazol-2-yl)-7-oxononyl)-6-azaspiro[2.5]octane-1-carboxamide | 243 |
| (S)-6-ethyl-N-((S)-1-(5-(7-methoxy-1-methyl-2-oxo-1,2-dihydroquinolin-6-yl)-1H-imidazol-2-yl)-7-oxononyl)-6-azaspiro[2.5]octane-1-carboxamide | 244 |
| (S)-6-ethyl-N-((S)-1-(5-(2-ethyl-7-methoxy-1-oxo-1,2-dihydroisoquinolin-6-yl)-1H-imidazol-2-yl)-7-oxononyl)-6-azaspiro[2.5]octane-1-carboxamide | 245 |
| 6-ethyl-N-((S)-1-(2-(4-fluorophenyl)-5-(3-methoxyphenyl)-1H-imidazol-4-yl)-7-oxononyl)-6-azaspiro[2.5]octane-1-carboxamide | 246 |
| 6-ethyl-N-((S)-1-(2-(4-fluorophenyl)-5-(2-methoxypyrimidin-5-yl)-1H-imidazol-4-yl)-7-oxononyl)-6-azaspiro[2.5]octane-1-carboxamide | 247 |
| 6-ethyl-N-((S)-1-(2-(4-fluorophenyl)-5-(1-methyl-1H-pyrazol-4-yl)-1H-imidazol-4-yl)-7-oxononyl)-6-azaspiro[2.5]octane-1-carboxamide | 248 |
| 6-ethyl-N-((S)-1-(2-(4-fluorophenyl)-5-(1H-pyrazol-4-yl)-1H-imidazol-4-yl)-7-oxononyl)-6-azaspiro[2.5]octane-1-carboxamide | 249 |
| 6-ethyl-N-((S)-1-(2-(4-fluorophenyl)-5-(thiophen-3-yl)-1H-imidazol-4-yl)-7-oxononyl)-6-azaspiro[2.5]octane-1-carboxamide | 250 |
| 6-ethyl-N-((S)-1-(2-(4-fluorophenyl)-5-(1-methyl-1H-pyrrol-3-yl)-1H-imidazol-4-yl)-7-oxononyl)-6-azaspiro[2.5]octane-1-carboxamide | 251 |
| 6-ethyl-N-((S)-1-(2-(4-fluorophenyl)-5-(thiophen-2-yl)-1H-imidazol-4-yl)-7-oxononyl)-6-azaspiro[2.5]octane-1-carboxamide | 252 |
| 6-ethyl-N-((S)-1-(2-(4-fluorophenyl)-5-(1-methyl-1H-pyrazol-5-yl)-1H-imidazol-4-yl)-7-oxononyl)-6-azaspiro[2.5]octane-1-carboxamide | 253 |
| 6-ethyl-N-((S)-1-(2-(4-fluorophenyl)-5-(1-propyl-1H-pyrazol-4-yl)-1H-imidazol-4-yl)-7-oxononyl)-6-azaspiro[2.5]octane-1-carboxamide | 254 |
| (S)-N-((S)-1-(5-(2-methoxypyrimidin-5-yl)-1H-imidazol-2-yl)-7-oxononyl)-6-methyl-6-azaspiro[2.5]octane-1-carboxamide | 255 |
| (S)-6-methyl-N-((S)-1-(5-(3-methyl-3H-imidazo[4,5-b]pyridin-6-yl)-1H-imidazol-2-yl)-7-oxononyl)-6-azaspiro[2.5]octane-1-carboxamide | 256 |
| (S)-6-methyl-N-((S)-1-(5-(2-(4-methyl-1H-pyrazol-1-yl)pyrimidin-5-yl)-1H-imidazol-2-yl)-7-oxononyl)-6-azaspiro[2.5]octane-1-carboxamide | 257 |
| (1S)-6-methyl-N-((1S)-7-oxo-1-(5-(4-((tetrahydrofuran-3-yl)carbamoyl)phenyl)-1H-imidazol-2-yl)nonyl)-6-azaspiro[2.5]octane-1-carboxamide | 258 |
| (S)-N-((S)-1-(5-(1,5-naphthyridin-3-yl)-1H-imidazol-2-yl)-7-oxononyl)-6-methyl-6-azaspiro[2.5]octane-1-carboxamide | 259 |
| (S)-N-((S)-1-(5-(4-(3,5-dimethyl-1H-pyrazol-1-yl)phenyl)-1H-imidazol-2-yl)-7-oxononyl)-6-methyl-6-azaspiro[2.5]octane-1-carboxamide | 260 |
| (S)-N-((S)-1-(5-(3-fluoro-2-morpholinopyridin-4-yl)-1H-imidazol-2-yl)-7-oxononyl)-6-methyl-6-azaspiro[2.5]octane-1-carboxamide | 261 |
| (S)-N-((S)-1-(5-([2,3'-bipyridin]-5-yl)-1H-imidazol-2-yl)-7-oxononyl)-6-methyl-6-azaspiro[2.5]octane-1-carboxamide | 262 |
| (S)-6-methyl-N-((S)-7-oxo-1-(5-(quinolin-3-yl)-1H-imidazol-2-yl)nonyl)-6-azaspiro[2.5]octane-1-carboxamide | 263 |
| (S)-6-methyl-N-((S)-1-(5-(1-methyl-1H-indol-3-yl)-1H-imidazol-2-yl)-7-oxononyl)-6-azaspiro[2.5]octane-1-carboxamide | 264 |
| (S)-6-methyl-N-((S)-1-(5-(9-methyl-9H-carbazol-3-yl)-1H-imidazol-2-yl)-7-oxononyl)-6-azaspiro[2.5]octane-1-carboxamide | 265 |
| (S)-N-((S)-1-(5-(2-ethoxypyrimidin-5-yl)-1H-imidazol-2-yl)-7-oxononyl)-6-methyl-6-azaspiro[2.5]octane-1-carboxamide | 266 |
| (S)-N-((S)-1-(5-([1,2,4]triazolo[1,5-a]pyridin-7-yl)-1H-imidazol-2-yl)-7-oxononyl)-6-methyl-6-azaspiro[2.5]octane-1-carboxamide | 267 |
| (S)-N-((S)-1-(5-(2-methoxy-6-methylpyridin-3-yl)-1H-imidazol-2-yl)-7-oxononyl)-6-methyl-6-azaspiro[2.5]octane-1-carboxamide | 268 |
| (S)-8-ethyl-N-(1-(5-(7-fluoro-2-methylquinolin-6-yl)oxazol-2-yl)-7-oxononyl)-1-oxa-2,8-diazaspiro[4.5]dec-2-ene-3-carboxamide | 269 |
| (S)-2-ethyl-N-(1-(5-(2-methoxyquinolin-3-yl)-1H-imidazol-2-yl)-7-oxononyl)-2-azaspiro[3.5]nonane-7-carboxamide | 271 |
| (S)-N-(1-(5-(2-methoxy-4-(pyridin-2-yl)phenyl)oxazol-2-yl)-7-oxononyl)-8-methyl-1-oxa-2,8-diazaspiro[4.5]dec-2-ene-3-carboxamide | 272 |
| (S)-2-(2-isopropyl-2-azaspiro[3.3]heptan-6-yl)-N-(1-(5-(2-methoxyquinolin-3-yl)-1H-imidazol-2-yl)-7-oxononyl)acetamide | 273 |
| (S)-2-ethyl-N-(1-(5-(2-methoxyquinolin-3-yl)-1H-imidazol-2-yl)-7-oxononyl)-2-azaspiro[3.5]nonane-7-carboxamide | 274 |

-continued

| | |
|---|---|
| (S)-6-ethyl-N-((S)-1-(5-(2-methoxyquinolin-3-yl)-1H-imidazol-2-yl)-7-oxononyl)-6-azaspiro[2.5]octane-1-carboxamide | 275 |
| (S)-6-amino-N-(1-(5-(2-methoxyquinolin-3-yl)-1H-imidazol-2-yl)-7-oxononyl)-2-methyl-2-azaspiro[3.3]heptane-6-carboxamide | 276 |
| (S)-N-(1-(5-(2-methoxyquinolin-3-yl)-1H-imidazol-2-yl)-7-oxononyl)-7-methyl-7-azaspiro[3.5]nonane-2-carboxamide | 277 |
| (S)-7-ethyl-N-(1-(5-(2-methoxyquinolin-3-yl)-1H-imidazol-2-yl)-7-oxononyl)-7-azaspiro[3.5]nonane-2-carboxamide | 278 |
| (S)-2-ethyl-N-(1-(5-(2-methoxyquinolin-3-yl)-1H-imidazol-2-yl)-7-oxononyl)-2-azaspiro[3.3]heptane-6-carboxamide | 279 |
| (S)-N-((S)-1-(5-(4-fluorophenyl)-1H-imidazol-2-yl)-7-oxononyl)-6-methyl-6-azaspiro[2.5]octane-1-carboxamide | 280 |
| (R)-6-methyl-N-((S)-7-oxo-1-(5-(quinolin-6-yl)-1H-imidazol-2-yl)nonyl)-6-azaspiro[2.5]octane-1-carboxamide | 281 |
| (S)-6-methyl-N-((S)-7-oxo-1-(5-(quinolin-6-yl)-1H-imidazol-2-yl)nonyl)-6-azaspiro[2.5]octane-1-carboxamide | 282 |
| (S)-6-methyl-N-((S)-7-oxo-1-(5-(quinolin-3-yl)-1H-imidazol-2-yl)nonyl)-6-azaspiro[2.5]octane-1-carboxamide | 283 |
| (S)-6-methyl-N-((S)-7-oxo-1-(5-(4-(trifluoromethyl)phenyl)-1H-imidazol-2-yl)nonyl)-6-azaspiro[2.5]octane-1-carboxamide | 284 |
| (1R)-N-((S)-1-(5-(2-methoxyquinolin-3-yl)-1H-imidazol-2-yl)-7-oxononyl)-5-methyl-5-azaspiro[2.5]octane-1-carboxamide | 285 |
| (1S)-N-((S)-1-(5-(2-methoxyquinolin-3-yl)-1H-imidazol-2-yl)-7-oxononyl)-5-methyl-5-azaspiro[2.5]octane-1-carboxamide | 286 |
| (1S)-N-((S)-1-(5-(2-methoxyquinolin-3-yl)-1H-imidazol-2-yl)-7-oxononyl)-5-methyl-5-azaspiro[2.5]octane-1-carboxamide | 287 |
| (1R)-N-((S)-1-(5-(2-methoxyquinolin-3-yl)-1H-imidazol-2-yl)-7-oxononyl)-5-azaspiro[2.5]octane-1-carboxamide | 288 |
| (S)-N-((S)-1-(5-(2,4-difluorophenyl)-1H-imidazol-2-yl)-7-oxononyl)-6-methyl-6-azaspiro[2.5]octane-1-carboxamide | 289 |
| (S)-N-((S)-1-(5-(2-fluorophenyl)-1H-imidazol-2-yl)-7-oxononyl)-6-methyl-6-azaspiro[2.5]octane-1-carboxamide | 290 |
| (S)-6-ethyl-N-((S)-1-(5-(2-hydroxyquinolin-3-yl)-1H-imidazol-2-yl)-7-oxononyl)-6-azaspiro[2.5]octane-1-carboxamide | 291 |
| (R)-6-ethyl-N-((S)-7-oxo-1-(5-(2-oxo-1,2-dihydroquinolin-3-yl)-1H-imidazol-2-yl)nonyl)-6-azaspiro[2.5]octane-1-carboxamide | 292 |
| (S)-6-benzyl-N-((S)-1-(5-(2-methoxyquinolin-3-yl)-1H-imidazol-2-yl)-7-oxononyl)-6-azaspiro[2.5]octane-1-carboxamide | 293 |
| (S)-N-((S)-1-(5-(2-methoxyquinolin-3-yl)-1H-imidazol-2-yl)-7-oxononyl)-6-(pyridin-3-ylmethyl)-6-azaspiro[2.5]octane-1-carboxamide | 294 |
| (S)-6-(4-methoxybenzyl)-N-((S)-1-(5-(2-methoxyquinolin-3-yl)-1H-imidazol-2-yl)-7-oxononyl)-6-azaspiro[2.5]octane-1-carboxamide | 295 |
| (S)-N-(7-oxo-1-(5-phenyl-1H-imidazol-2-yl)nonyl)-2-(2-azaspiro[3.3]heptan-6-yl)acetamide | 297 |
| (R)-N-(7-oxo-1-(5-phenyl-1H-imidazol-2-yl)nonyl)-2-azaspiro[3.5]nonane-7-carboxamide | 298 |
| (S)-N-(1-(5-(2-methoxyquinolin-3-yl)-1,3,4-oxadiazol-2-yl)-7-oxononyl)-2-azaspiro[3.5]nonane-7-carboxamide | 299 |
| (S)-2-(2-acetyl-2-azaspiro[3.3]heptan-6-yl)-N-(7-oxo-1-(5-phenyl-1H-imidazol-2-yl)nonyl)acetamide | 300 |
| (S)-N-(1-(5-(2-methoxyquinolin-3-yl)-1,3,4-oxadiazol-2-yl)-7-oxononyl)-2-(2-azaspiro[3.3]heptan-6-yl)acetamide | 301 |
| tert-butyl 5-(((S)-1-(5-(2-methoxyquinolin-3-yl)-1,3,4-oxadiazol-2-yl)-7-oxononyl)carbamoyl)-7-oxo-2,6-diazaspiro[3.4]octane-2-carboxylate | 302 |
| N-((S)-1-(5-(2-methoxyquinolin-3-yl)-1,3,4-oxadiazol-2-yl)-7-oxononyl)-6-azaspiro[2.5]octane-1-carboxamide | 303 |
| N-((S)-1-(5-(2-methoxyquinolin-3-yl)-1,3,4-oxadiazol-2-yl)-7-oxononyl)-7-oxo-2,6-diazaspiro[3.4]octane-5-carboxamide | 304 |
| (R)-N-((S)-1-(5-(2-methoxyquinolin-3-yl)-1,3,4-oxadiazol-2-yl)-7-oxononyl)-6-methyl-6-azaspiro[2.5]octane-1-carboxamide | 305 |
| (S)-N-((S)-1-(5-(2-methoxyquinolin-3-yl)-1,3,4-oxadiazol-2-yl)-7-oxononyl)-6-methyl-6-azaspiro[2.5]octane-1-carboxamide | 306 |
| (S)-2-(2-methyl-2-azaspiro[3.3]heptan-6-yl)-N-(7-oxo-1-(5-phenyl-1H-imidazol-2-yl)nonyl)acetamide | 307 |
| (S)-N-(1-(5-(2-methoxyquinolin-3-yl)-1,3,4-oxadiazol-2-yl)-7-oxononyl)-2-(2-methyl-2-azaspiro[3.3]heptan-6-yl)acetamide | 308 |
| N-((S)-1-(5-(2-methoxyquinolin-3-yl)-1,3,4-oxadiazol-2-yl)-7-oxononyl)-2-methyl-7-oxo-2,6-diazaspiro[3.4]octane-5-carboxamide | 309 |
| (R)-2-methyl-N-(7-oxo-1-(5-phenyl-1H-imidazol-2-yl)nonyl)-2-azaspiro[3.5]nonane-7-carboxamide | 310 |
| (S)-N-(1-(5-(2-methoxyquinolin-3-yl)-1H-imidazol-2-yl)-7-oxononyl)-2-methyl-2-azaspiro[3.3]heptane-6-carboxamide | 311 |
| N-((S)-1-(5-(2-methoxyquinolin-3-yl)-1H-imidazol-2-yl)-7-oxononyl)-5-methyl-5-azaspiro[2.3]hexane-1-carboxamide | 312 |

-continued

| | |
|---|---|
| N-((S)-1-(5-(2-methoxyquinolin-3-yl)-1H-imidazol-2-yl)-7-oxononyl)-6-methyl-6-azaspiro[2.5]octane-1-carboxamide | 313 |
| N-((S)-1-(5-(2-methoxyquinolin-3-yl)-1H-imidazol-2-yl)-7-oxononyl)-6-methyl-6-azaspiro[2.5]octane-1-carboxamide | 313 |
| (S)-N-(1-(5-(2-methoxyquinolin-3-yl)-1H-imidazol-2-yl)-7-oxononyl)-2-(2-methyl-2-azaspiro[3.3]heptan-6-yl)acetamide | 314 |
| (S)-N-(1-(5-(2-methoxyquinolin-3-yl)-1H-imidazol-2-yl)-7-oxononyl)-2-methyl-2-azaspiro[3.5]nonane-7-carboxamide | 315 |
| (S)-N-(1-(5-(2-methoxyquinolin-3-yl)-1H-imidazol-2-yl)-7-oxononyl)-2-methyl-2-azaspiro[3.5]nonane-7-carboxamide | 316 |
| N-((S)-1-(5-(2-methoxyquinolin-3-yl)-1H-imidazol-2-yl)-7-oxononyl)-2-methyl-7-oxo-2,6-diazaspiro[3.4]octane-5-carboxamide | 317 |
| N1-((S)-1-(5-(2-methoxyquinolin-3-yl)-1H-imidazol-2-yl)-7-oxononyl)-6-azaspiro[2.5]octane-1,6-dicarboxamide | 318 |
| (R)-N-((S)-1-(5-(2-methoxyquinolin-3-yl)-1H-imidazol-2-yl)-7-oxononyl)-6-methyl-6-azaspiro[2.5]octane-1-carboxamide | 320 |
| (S)-N-((S)-1-(5-(2-methoxyquinolin-3-yl)-1H-imidazol-2-yl)-7-oxononyl)-6-methyl-6-azaspiro[2.5]octane-1-carboxamide | 321 |
| (R)-N-((S)-1-(5-(2-methoxyquinolin-3-yl)-1H-imidazol-2-yl)-7-oxononyl)-5-methyl-5-azaspiro[2.3]hexane-1-carboxamide | 322 |
| (S)-N-((S)-1-(5-(2-methoxyquinolin-3-yl)-1H-imidazol-2-yl)-7-oxononyl)-5-methyl-5-azaspiro[2.3]hexane-1-carboxamide | 323 |
| (1S,3S)-N-((S)-1-(5-(2-methoxyquinolin-3-yl)-1H-imidazol-2-yl)-7-oxononyl)-5-methyl-5-azaspiro[2.4]heptane-1-carboxamide | 324 |
| N-((S)-1-(5-(2-hydroxyquinolin-3-yl)-1H-imidazol-2-yl)-7-oxononyl)-6-methyl-6-azaspiro[2.5]octane-1-carboxamide | 324 |
| (S)-N-(1-(5-(2-hydroxyquinolin-3-yl)-1H-imidazol-2-yl)-7-oxononyl)-2-(2-methyl-2-azaspiro[3.3]heptan-6-yl)acetamide | 326 |
| (1S,3R)-N-((S)-1-(5-(2-methoxyquinolin-3-yl)-1H-imidazol-2-yl)-7-oxononyl)-5-methyl-5-azaspiro[2.4]heptane-1-carboxamide | 328 |
| (1R,3S)-N-((S)-1-(5-(2-methoxyquinolin-3-yl)-1H-imidazol-2-yl)-7-oxononyl)-5-methyl-5-azaspiro[2.4]heptane-1-carboxamide | 329 |
| (1R,3R)-N-((S)-1-(5-(2-methoxyquinolin-3-yl)-1H-imidazol-2-yl)-7-oxononyl)-5-methyl-5-azaspiro[2.4]heptane-1-carboxamide | 330 |
| (S)-N-((S)-1-(5-(2-methoxyquinolin-3-yl)-1H-imidazol-2-yl)-7-oxononyl)-6-propyl-6-azaspiro[2.5]octane-1-carboxamide | 331 |
| (S)-N-((S)-1-(5-(2-methoxyquinolin-3-yl)-1H-imidazol-2-yl)-7-oxononyl)-6-(3,3,3-trifluoropropyl)-6-azaspiro[2.5]octane-1-carboxamide | 332 |
| (S)-N-((S)-1-(5-(2-methoxyquinolin-3-yl)-1H-imidazol-2-yl)-7-oxononyl)-6-(2,2,2-trifluoroethyl)-6-azaspiro[2.5]octane-1-carboxamide | 333 |
| (S)-6-isobutyl-N-((S)-1-(5-(2-methoxyquinolin-3-yl)-1H-imidazol-2-yl)-7-oxononyl)-6-azaspiro[2.5]octane-1-carboxamide | 335 |
| (S)-6-(cyclopropylmethyl)-N-((S)-1-(5-(2-methoxyquinolin-3-yl)-1H-imidazol-2-yl)-7-oxononyl)-6-azaspiro[2.5]octane-1-carboxamide | 336 |
| (S)-6-isopropyl-N-((S)-1-(5-(2-methoxyquinolin-3-yl)-1H-imidazol-2-yl)-7-oxononyl)-6-azaspiro[2.5]octane-1-carboxamide | 337 |
| (S)-7-ethyl-N-((S)-1-(5-(2-methoxyquinolin-3-yl)-1H-imidazol-2-yl)-7-oxononyl)-7-azaspiro[3.5]nonane-1-carboxamide | 338 |
| (S)-6-ethyl-N-((S)-7-oxo-1-(5-(7-(trifluoromethyl)quinolin-3-yl)-1H-imidazol-2-yl)nonyl)-6-azaspiro[2.5]octane-1-carboxamide | 341 |
| (S)-6-ethyl-N-((S)-7-oxo-1-(5-(2-oxo-6-phenyl-1,2-dihydro-pyridin-3-yl)-1H-imidazol-2-yl)nonyl)-6-azaspiro[2.5]octane-1-carboxamide | 342 |
| (S)-6-ethyl-N-((S)-7-oxo-1-(5-(quinolin-7-yl)-1H-imidazol-2-yl)nonyl)-6-azaspiro[2.5]octane-1-carboxamide | 344 |
| (S)-6-ethyl-N-((S)-1-(5-(isoquinolin-7-yl)-1H-imidazol-2-yl)-7-oxononyl)-6-azaspiro[2.5]octane-1-carboxamide | 345 |
| (S)-6-ethyl-N-((S)-7-oxo-1-(5-(quinolin-6-yl)-1H-imidazol-2-yl)nonyl)-6-azaspiro[2.5]octane-1-carboxamide | 346 |
| (S)-N-((S)-1-(5-(2-methoxyquinolin-6-yl)-1H-imidazol-2-yl)-7-oxononyl)-6-methyl-6-azaspiro[2.5]octane-1-carboxamide | 347 |
| (S)-6-methyl-N-((S)-1-(5-(2-methylquinolin-6-yl)-1H-imidazol-2-yl)-7-oxononyl)-6-azaspiro[2.5]octane-1-carboxamide | 348 |
| (S)-6-methyl-N-((S)-7-oxo-1-(5-(4-(pyridin-4-yl)phenyl)-1H-imidazol-2-yl)nonyl)-6-azaspiro[2.5]octane-1-carboxamide | 349 |
| (S)-6-methyl-N-((S)-7-oxo-1-(5-(4-(pyridin-3-yl)phenyl)-1H-imidazol-2-yl)nonyl)-6-azaspiro[2.5]octane-1-carboxamide | 350 |
| (S)-N-((S)-1-(5-(3-chloroisoquinolin-6-yl)-1H-imidazol-2-yl)-7-oxononyl)-6-methyl-6-azaspiro[2.5]octane-1-carboxamide | 351 |
| (S)-6-methyl-N-((S)-7-oxo-1-(5-(quinolin-6-yl)-1H-imidazol-2-yl)nonyl)-6-azaspiro[2.5]octane-1-carboxamide | 352 |
| (S)-6-methyl-N-((S)-1-(5-(2-methyl-2H-indazol-5-yl)-1H-imidazol-2-yl)-7-oxononyl)-6-azaspiro[2.5]octane-1-carboxamide | 353 |
| (S)-N-((S)-1-(5-(8-fluoro-2-methylquinolin-7-yl)-1H-imidazol-2-yl)-7-oxononyl)-6-methyl-6-azaspiro[2.5]octane-1-carboxamide | 354 |

-continued

| | |
|---|---|
| (S)-6-methyl-N-((S)-1-(5-(1-methyl-2-oxo-1,2-dihydroquinolin-3-yl)-1H-imidazol-2-yl)-7-oxononyl)-6-azaspiro[2.5]octane-1-carboxamide | 356 |
| (S)-6-methyl-N-((S)-7-oxo-1-(5-(4-(pyrazin-2-yl)phenyl)-1H-imidazol-2-yl)nonyl)-6-azaspiro[2.5]octane-1-carboxamide | 357 |
| (S)-6-methyl-N-((S)-1-(5-(2-methyl-1-oxo-1,2-dihydroisoquinolin-6-yl)-1H-imidazol-2-yl)-7-oxononyl)-6-azaspiro[2.5]octane-1-carboxamide | 358 |
| (S)-6-(cyclopropylmethyl)-N-((S)-1-(5-(2-methyl-2H-indazol-5-yl)-1H-imidazol-2-yl)-7-oxononyl)-6-azaspiro[2.5]octane-1-carboxamide | 359 |
| (S)-6-isopropyl-N-((S)-1-(5-(2-methyl-2H-indazol-5-yl)-1H-imidazol-2-yl)-7-oxononyl)-6-azaspiro[2.5]octane-1-carboxamide | 360 |
| (S)-6-ethyl-N-((S)-1-(5-(7-methoxy-2-methylquinolin-6-yl)oxazol-2-yl)-7-oxononyl)-6-azaspiro[2.5]octane-1-carboxamide | 361 |
| (1S,4r)-N-((S)-1-(5-(2-methoxyquinolin-3-yl)-1,3,4-oxadiazol-2-yl)-7-oxononyl)-1'-oxo-1'H-spiro[cyclohexane-1,3'-furo[3.4-c]pyridine]-4-carboxamide | 363 |
| (1S,4r)-N-((S)-1-(5-(2-methoxyquinolin-3-yl)-1,3,4-oxadiazol-2-yl)-7-oxononyl)-1'-oxo-1'H-spiro[cyclohexane-1,3'-furo[3,4-c]pyridine]-4-carboxamide | 364 |
| (1S,4r)-N-((S)-1-(5-(2-methoxyquinolin-3-yl)-1,3,4-oxadiazol-2-yl)-7-oxononyl)-7'-oxo-7'H-spiro[cyclohexane-1,5'-furo[3,4-b]pyridine]-4-carboxamide | 365 |
| (1S,4r)-N-((S)-1-(5-(2-methoxyquinolin-3-yl)-1,3,4-oxadiazol-2-yl)-7-oxononyl)-5'-oxo-5'H-spiro[cyclohexane-1,7'-furo[3,4-b]pyridine]-4-carboxamide | 366 |
| (1R,4s)-N-((S)-1-(5-(2-methoxyquinolin-3-yl)-1,3,4-oxadiazol-2-yl)-7-oxononyl)-7'-oxo-7'H-spiro[cyclohexane-1,5'-furo[3,4-b]pyridine]-4-carboxamide | 367 |
| (1R,4s)-N-((S)-1-(5-(2-methoxyquinolin-3-yl)-1,3,4-oxadiazol-2-yl)-7-oxononyl)-5'-oxo-5'H-spiro[cyclohexane-1,7'-furo[3,4-b]pyridine]-4-carboxamide | 368 |
| (S)-8-isopropyl-N-(1-(5-(2-methoxyquinolin-3-yl)-1,3,4-oxadiazol-2-yl)-7-oxononyl)-1-oxa-2,8-diazaspiro[4.5]dec-2-ene-3-carboxamide | 369 |
| (S)-N-(1-(5-(2-methoxyquinolin-3-yl)-1,3,4-oxadiazol-2-yl)-7-oxononyl)-8-methyl-1-oxa-2,8-diazaspiro[4.5]dec-2-ene-3-carboxamide | 370 |
| (S)-N-(1-(5-(2-methoxyquinolin-3-yl)-1,3,4-oxadiazol-2-yl)-7-oxononyl)-8-(methylsulfonyl)-1-oxa-2,8-diazaspiro[4.5]dec-2-ene-3-carboxamide | 371 |
| (1S,4r)-1'-oxo-N-((S)-7-oxo-1-(5-phenyl-1H-imidazol-2-yl)nonyl)-1'H-spiro[cyclohexane-1,3'-furo[3,4-c]pyridine]-4-carboxamide | 372 |
| (1S,4r)-3'-oxo-N-((S)-7-oxo-1-(5-phenyl-1H-imidazol-2-yl)nonyl)-3'H-spiro[cyclohexane-1,1'-furo[3,4-c]pyridine]-4-carboxamide | 373 |
| (1S,4r)-7'-oxo-N-((S)-7-oxo-1-(5-phenyl-1H-imidazol-2-yl)nonyl)-7'H-spiro[cyclohexane-1,5'-furo[3,4-b]pyridine]-4-carboxamide | 374 |
| (1S,4r)-5'-oxo-N-((S)-7-oxo-1-(5-phenyl-1H-imidazol-2-yl)nonyl)-5'H-spiro[cyclohexane-1,7'-furo[3,4-b]pyridine]-4-carboxamide | 375 |
| (1R,4s)-1'-oxo-N-((S)-7-oxo-1-(5-phenyl-1H-imidazol-2-yl)nonyl)-1'H-spiro[cyclohexane-1,3'-furo[3,4-c]pyridine]-4-carboxamide | 376 |
| (1R,4s)-7'-oxo-N-((S)-7-oxo-1-(5-phenyl-1H-imidazol-2-yl)nonyl)-7'H-spiro[cyclohexane-1,5'-furo[3,4-b]pyridine]-4-carboxamide | 377 |
| (1R,4s)-5'-oxo-N-((S)-7-oxo-1-(5-phenyl-1H-imidazol-2-yl)nonyl)-5'H-spiro[cyclohexane-1,7'-furo[3,4-b]pyridine]-4-carboxamide | 378 |
| (S)-8-isopropyl-N-(7-oxo-1-(5-phenyl-1H-imidazol-2-yl)nonyl)-1-oxa-2,8-diazaspiro[4.5]dec-2-ene-3-carboxamide | 379 |
| (S)-8-acetyl-N-(7-oxo-1-(5-phenyl-1H-imidazol-2-yl)nonyl)-1-oxa-2,8-diazaspiro[4.5]dec-2-ene-3-carboxamide | 380 |
| methyl (S)-3-((7-oxo-1-(5-phenyl-1H-imidazol-2-yl)nonyl)carbamoyl)-1-oxa-2,8-diazaspiro[4.5]dec-2-ene-8-carboxylate | 381 |
| (S)-8-methyl-N-(7-oxo-1-(5-phenyl-1H-imidazol-2-yl)nonyl)-1-oxa-2,8-diazaspiro[4.5]dec-2-ene-3-carboxamide | 382 |
| (S)-8-(methylsulfonyl)-N-(7-oxo-1-(5-phenyl-1H-imidazol-2-yl)nonyl)-1-oxa-2,8-diazaspiro[4.5]dec-2-ene-3-carboxamide | 383 |

-continued

| | |
|---|---|
| (S)-3-(3-ethyl-2-oxo-8-oxa-1,4-diazaspiro[4.5]dec-3-en-1-yl)-N-(7-oxo-1-(5-phenyl-1H-imidazol-2-yl)nonyl)propanamide | 384 |
| (S)-N-(1-(5-(7-fluoro-1-methyl-2-oxo-1,2-dihydroquinolin-6-yl)oxazol-2-yl)-7-oxononyl)-8-methyl-1-oxa-2,8-diazaspiro[4.5]dec-2-ene-3-carboxamide | 386 |
| (S)-8-(cyclopropylmethyl)-N-(1-(5-(7-fluoro-1-methyl-2-oxo-1,2-dihydroquinolin-6-yl)oxazol-2-yl)-7-oxononyl)-1-oxa-2,8-diazaspiro[4.5]dec-2-ene-3-carboxamide | 387 |
| (S)-N-((S)-1-(5-(5-fluorobenzo[d]oxazol-6-yl)oxazol-2-yl)-7-oxononyl)-6-methyl-6-azaspiro[2.5]octane-1-carboxamide | 389 |
| (S)-N-(1-(5-(4-chloro-2-methoxyphenyl)oxazol-2-yl)-7-oxononyl)-8-methyl-1-oxa-2,8-diazaspiro[4.5]dec-2-ene-3-carboxamide | 390 |
| (S)-N-(1-(5-(2-methoxy-4-(pyridin-2-yl)phenyl)oxazol-2-yl)-7-oxononyl)-8-methyl-1-oxa-2,8-diazaspiro[4.5]dec-2-ene-3-carboxamide | 391 |
| (S)-6-(cyclopropylmethyl)-N-((S)-1-(5-(2-methylquinolin-6-yl)-1H-imidazol-2-yl)-7-oxononyl)-6-azaspiro[2.5]octane-1-carboxamide | 393 |
| (S)-6-(cyclopropylmethyl)-N-((S)-1-(5-(7-methoxyquinolin-6-yl)-1H-imidazol-2-yl)-7-oxononyl)-6-azaspiro[2.5]octane-1-carboxamide | 394 |
| (S)-N-(1-(5-(2-methoxy-4-(pyridin-4-yl)phenyl)oxazol-2-yl)-7-oxononyl)-8-methyl-1-oxa-2,8-diazaspiro[4.5]dec-2-ene-3-carboxamide | 395 |
| (S)-N-(1-(5-(2-(dimethylamino)-7-methoxyquinolin-6-yl)oxazol-2-yl)-7-oxononyl)-8-methyl-1-oxa-2,8-diazaspiro[4.5]dec-2-ene-3-carboxamide | 397 |
| (S)-6-(cyclopropylmethyl)-N-((S)-1-(5-(7-fluoro-1-methyl-2-oxo-1,2-dihydroquinolin-6-yl)oxazol-2-yl)-7-oxononyl)-6-azaspiro[2.5]octane-1-carboxamide | 400 |
| (S)-N-((S)-1-(5-(7-methoxyisoquinolin-6-yl)oxazol-2-yl)-7-oxononyl)-6-methyl-6-azaspiro[2.5]octane-1-carboxamide | 405 |
| (S)-N-((S)-1-(5-(2-(dimethylamino)-7-methoxyquinolin-6-yl)oxazol-2-yl)-7-oxononyl)-6-methyl-6-azaspiro[2.5]octane-1-carboxamide | 406 |
| N-{(1S)-1-[5-(7-methoxy-2-methylquinolin-6-yl)-1H-imidazol-2-yl]-7-oxononyl}-6-oxaspiro[2.5]octane-1-carboxamide | 407 |
| (S)-N-((S)-1-(5-(5-methoxybenzo[d]oxazol-6-yl)oxazol-2-yl)-7-oxononyl)-6-methyl-6-azaspiro[2.5]octane-1-carboxamide | 408 |
| N-{(1S)-1-[5-(7-methoxy-2-methylquinolin-6-yl)-1,3-oxazol-2-yl]-7-oxononyl}-6-oxaspiro[2.5]octane-1-carboxamide | 409 |
| (S)-N-(1-(5-(7-methoxyisoquinolin-6-yl)oxazol-2-yl)-7-oxononyl)-8-methyl-1-oxa-2,8-diazaspiro[4.5]dec-2-ene-3-carboxamide | 415 |
| (S)-6-(cyclopropylmethyl)-N-((S)-1-(5-(7-methoxy-2-methylquinolin-6-yl)-1H-imidazol-2-yl)-7-oxodecyl)-6-azaspiro[2.5]octane-1-carboxamide | 416 |
| (1S)-6-(cyclopropylmethyl)-N-{3-[4-(7-methoxy-2-methylquinolin-6-yl)-1H-imidazol-2-yl]-9-oxoundecan-3-yl}-6-azaspiro[2.5]octane-1-carboxamide | 420 |
| (S)-6-(cyclopropylmethyl)-N-((S)-1-(5-(7-methoxy-2-methylquinolin-6-yl)oxazol-2-yl)-7-oxononyl)-6-azaspiro[2.5]octane-1-carboxamide | 422 |

or a pharmaceutically acceptable salt thereof.

2. A method for the inhibition of HDAC in a subject in need thereof which comprises administering to the subject an effective amount of a compound of claim 1, or a pharmaceutically acceptable salt thereof.

3. A pharmaceutical composition comprising an effective amount of a compound of claim 1, or a pharmaceutically acceptable salt thereof, and a pharmaceutically acceptable carrier.

4. The pharmaceutical composition of claim 3, further comprising one or more additional therapeutic agents selected from lamivudine, abacavir, ritonavir, darunavir, atazanavir, emtricitabine, tenofovir, rilpivirine, lopinavir, doravirine and EFdA.

* * * * *